(12) United States Patent
Olson et al.

(10) Patent No.: US 11,648,290 B2
(45) Date of Patent: May 16, 2023

(54) CARTILAGE-HOMING PEPTIDES

(71) Applicants: FRED HUTCHINSON CANCER CENTER, Seattle, WA (US); BLAZE BIOSCIENCE, INC., Seattle, WA (US)

(72) Inventors: James Olson, Seattle, WA (US); Andrew David Strand, Seattle, WA (US); Emily June Girard, Renton, WA (US); Roland Strong, Seattle, WA (US); Christopher Mehlin, Seattle, WA (US); Colin Correnti, Seattle, WA (US); Natalie Nairn, Seattle, WA (US)

(73) Assignees: FRED HUTCHINSON CANCER CENTER, Seattle, WA (US); BLAZE BIOSCIENCE, INC., Seattle, WA (US)

( * ) Notice: Subject to any disclaimer, the term of this patent is extended or adjusted under 35 U.S.C. 154(b) by 10 days.

(21) Appl. No.: 17/353,447

(22) Filed: Jun. 21, 2021

(65) Prior Publication Data
US 2022/0016202 A1 Jan. 20, 2022

Related U.S. Application Data

(63) Continuation of application No. 15/758,320, filed as application No. PCT/US2016/051166 on Sep. 9, 2016, now Pat. No. 11,090,358.
(Continued)

(51) Int. Cl.
*A61K 38/17* (2006.01)
*C07K 14/435* (2006.01)
(Continued)

(52) U.S. Cl.
CPC .............. *A61K 38/17* (2013.01); *A61K 47/64* (2017.08); *A61K 47/65* (2017.08); *A61K 47/66* (2017.08);
(Continued)

(58) Field of Classification Search
CPC ........ A61K 38/17; A61K 47/64; A61K 47/66; C07K 14/435
See application file for complete search history.

(56) References Cited

U.S. PATENT DOCUMENTS

| 8,945,553 B2 | 2/2015 | Stevens et al. |
| 9,944,683 B2 | 4/2018 | Olson |

(Continued)

FOREIGN PATENT DOCUMENTS

| CA | 2993891 A1 | 1/2017 |
| CN | 101583370 A | 11/2009 |

(Continued)

OTHER PUBLICATIONS

Schwartz et al., Br. J. Pharmacol., 2009, vol. 157(3):392-403.*
(Continued)

*Primary Examiner* — Xiaozhen Xie
(74) *Attorney, Agent, or Firm* — DLA Piper LLP

(57) ABSTRACT

Peptides that home, target, migrate to, are directed to, are retained by, or accumulate in and/or binds to the cartilage of a subject are disclosed. Pharmaceutical compositions and uses for peptides or peptide-active agent complexes comprising such peptides are also disclosed. Such compositions can be formulated for targeted delivery of a drug to a target region, tissue, structure or cell in the cartilage. Targeted compositions of the disclosure can deliver peptide or peptide-active agent complexes to target regions, tissues, structures or cells targeted by the peptide.

20 Claims, 75 Drawing Sheets
Specification includes a Sequence Listing.

Related U.S. Application Data

(60) Provisional application No. 62/385,734, filed on Sep. 9, 2016, provisional application No. 62/278,929, filed on Jan. 14, 2016, provisional application No. 62/216,331, filed on Sep. 9, 2015.

(51) Int. Cl.
*A61K 47/64* (2017.01)
*A61K 47/66* (2017.01)
*A61P 19/02* (2006.01)
*A61K 49/00* (2006.01)
*A61K 51/08* (2006.01)
*A61K 47/65* (2017.01)
*A61P 19/04* (2006.01)

(52) U.S. Cl.
CPC ...... *A61K 49/0032* (2013.01); *A61K 49/0056* (2013.01); *A61K 51/08* (2013.01); *A61P 19/02* (2018.01); *A61P 19/04* (2018.01); *C07K 14/435* (2013.01)

(56) References Cited

U.S. PATENT DOCUMENTS

| | | |
|---|---|---|
| 11,013,814 B2 | 5/2021 | Novak et al. |
| 11,090,358 B2 | 8/2021 | Olson et al. |
| 11,331,393 B2 | 5/2022 | Novak et al. |
| 2003/0031669 A1 | 2/2003 | Goldenberg |
| 2006/0088899 A1 | 4/2006 | Alvarez et al. |
| 2009/0142266 A1 | 6/2009 | Ronjat et al. |
| 2010/0215575 A1 | 8/2010 | O'Neill et al. |
| 2013/0028836 A1 | 1/2013 | Sentissi et al. |
| 2013/0164220 A1 | 6/2013 | Yu et al. |
| 2013/0280281 A1 | 10/2013 | Castaigne et al. |
| 2014/0179560 A1 | 6/2014 | Olson et al. |
| 2015/0182596 A1 | 7/2015 | Lee et al. |

FOREIGN PATENT DOCUMENTS

| | | |
|---|---|---|
| JP | 2009023993 A | 2/2009 |
| JP | 2013224283 A | 10/2013 |
| WO | WO-0153342 A1 | 7/2001 |
| WO | WO-03020751 A2 | 3/2003 |
| WO | WO-03082196 A2 | 10/2003 |
| WO | WO-2008063291 A2 | 5/2008 |
| WO | WO-2012064658 A1 | 5/2012 |
| WO | WO-2013078250 A2 | 5/2013 |
| WO | WO-2014063012 A1 | 4/2014 |
| WO | WO-2014093406 A1 | 6/2014 |
| WO | 2014165422 A1 | 10/2014 |
| WO | WO-2014180534 A1 | 11/2014 |
| WO | WO-2015013330 A2 | 1/2015 |
| WO | WO-2015075699 A1 | 5/2015 |
| WO | WO-2015100370 A3 | 8/2015 |
| WO | WO-2015179635 A2 | 11/2015 |
| WO | WO-2016112176 A1 | 7/2016 |
| WO | WO-2016112208 A2 | 7/2016 |
| WO | WO-2016118859 A1 | 7/2016 |
| WO | WO-2016210376 A2 | 12/2016 |
| WO | WO-2017044894 A2 | 3/2017 |
| WO | WO-2017100700 A2 | 6/2017 |
| WO | WO-2017143259 A1 | 8/2017 |
| WO | WO-2018049285 A1 | 3/2018 |
| WO | WO-2018119001 A1 | 6/2018 |
| WO | WO-2018136614 A1 | 7/2018 |
| WO | WO-2018170480 A1 | 9/2018 |
| WO | WO-2018232122 A1 | 12/2018 |

OTHER PUBLICATIONS

Extended European Search Report for European Application 19767592.9, dated Sep. 16, 2022, 10 pages.

Moore S.J., et al., "Engineered Knottin Peptide Enables Noninvasive Optical Imaging of Intracranial Medulloblastoma," PNAS, Sep. 3, 2013, 110 (36), pp. 14598-14603.

Moore S.J., et al., "Engineering Agatoxin, a Cystine-Knot Peptide from Spider Venom, as a Molecular Probe for In Vivo Tumor Imaging," PLoS One, Apr. 2013, vol. 8 (4), p. e60498.

Cheung C.S.F., et al., "Identification of Chondrocyte-binding Peptides by Phage Display," Journal of Orthopaedic research, Jul. 2013, vol. 31, pp. 1053-1058.

Hu Q., et al., "Chondrocyte Affinity Peptide Modified PAMAM Conjugate as a Nanoplatform for Targeting and Retention in Cartilage," Nanomedicine, Mar. 12, 2018, vol. 13 (7), pp. 749-767, 20 Pages.

The Extended European Search Report for European application, No. EP18767105.2 dated Nov. 24, 2020, 13 Pages.

Akdag, et al., "The Uptake Mechanism of the Cell-Penetrating pVEC Peptide," J. Chem, 2013, Mar. 10, 2013, 10 pages.

Akhmedov D., et al., "Knock-in Luciferase Reporter Mice for in Vivo Monitoring of CREB Activity," PLoS One, vol. 11(6), Jun. 13, 2016, 13 Pages.

Almagro J.C., et al., "Progress and Challenges in the Design and Clinical Development of Antibodies for Cancer Therapy," Frontiers in immunology, Jan. 4, 2018, vol. 8, pp. 1751, doi:10.3389/fimmu.2017.01751 https://www.frontiersin.org/articles/10.3389/fimmu.2017.01751/full.

Altschul, et al., "Optimal Sequence Alignment using Affine Gap Costs," Bulletin of Mathematical Biology, Feb. 17, 1986, vol. 48(5-6), pp. 603-616.

Alves H C., et al., "Animal Models of Bone Loss in Inflammatory Arthritis: from Cytokines in the Bench to Novel Treatments for Bone Loss in the Bedside—a Comprehensive Review," Clin Rev Allergy Immunol, Aug. 2016, vol. 51(1), pp. 27-47, doi: 10.1007/s12016-015-8522-7.

Appelbaum J.S., et al., "Arginine Topology Controls Escape of Minimally Cationic Proteins from Early Endosomes to the Cytoplasm," Chem. Biol. Jul. 27, 2012, vol. 19, pp. 819-830.

Ashkenazi A., et al., "From Basic Apoptosis Discoveries to Advanced Selective BCL-2 Family Inhibitors," Nature Reviews Drug Discovery, 2017, vol. 16, pp. 273-284, Published online: Feb. 17, 2017. doi:10.1038/nrd.2016.253.

Baar M.P., et al., "Targeted Apoptosis of Senescent Cells Restores Tissue Homeostasis in Response to Chemotoxicity and Aging," Cell 169.1, Mar. 23, 2017, pp. 132-147.

Bagal S.K., et al., "Ion Channels as Therapeutic Targets: A Drug Discovery Perspective," J Med Chem, Feb. 14, 2013, vol. 56(3), pp. 593-624, doi: 10.1021/jm3011433. Epub Nov. 29, 2012.

Baik F.M., et al., "Fluorescence Identification of Head and Neck Squamous Cell Carcinoma and High-Risk Oral Dysplasia With BLZ-100, a Chlorotoxin-Indocyanine Green Conjugate," JAMA Otolaryngol Head Neck Surg, Published on line Feb. 18, 2016, vol. 142, Issue. 4, pp. 330-338, doi: 10.1001/jamaoto.2015.3617; JAMA Otolaryngol Head Neck Surg. Apr. 1, 2016.

Baker N.A., et al., "Electrostatics of Nanosystems: Application to Microtubules and the Ribosome," Proc Natl Acad Sci U S A, Aug. 28, 2001, vol. 98(18), pp. 10037-10041.

Balayssac S., et al., "Comparison of Penetratin and Other Homeodomain-Derived Cell-Penetrating Peptides: Interaction in a Membrane-Mimicking Environment and Cellular Uptake Efficiency," Biochemistry, Dec. 1, 2006, vol. 45, pp. 1408-1420.

Bandaranayake A.D., et al., "Daedalus: A Robust, Turnkey Platform for Rapid Production of Decigram Quantities of Active Recombinant Proteins in Human Cell Lines using Novel Lentiviral Vectors," Nucleic Acids Res, Nov. 2011, vol. 39(21), pp. 1-143, doi: 10.1093/nar/gkr706, Epub Sep. 12, 2011.

Bao Q., et al., "The Tripeptide Phenylalanine-(D) Glutamate-(D) Glycine Modulates Leukocyte Infiltration and Oxidative Damage in Rat injured Spinal Cord," Neuroscience, Jul. 7, 2006, vol. 140(3), pp. 1011-1022, Epub Apr. 3, 2006.

Barad M., et al., "Rolipram, a type IV-specific Phosphodiesterase Inhibitor, Facilitates the Establishment of Long-lasting Long-term Potentiation and Improves Memory," Proceedings National Academy Sciences, Oct. 13, 1998, vol. 95, pp. 15020-15025.

(56) References Cited

OTHER PUBLICATIONS

Barchetta I., et al., "Neurotensin is a Lipid-Induced Gastrointestinal Peptide Associated with Visceral Adipose Tissue Inflammation in Obesity," Nutrients, Apr. 23, 2018, vol. 10, pp. 1-526.

Bar-Or D., et al., "A Randomized Clinical Trial to Evaluate Two Doses of an Intra-articular Injection of LMWF-5A in Adults with Pain due to Osteoarthritis of the Knee," PLoS One, Feb. 3, 2014, vol. 9(2), e87910, 8 pages, doi: 10.1371/journal.pone.0087910, eCollection 2014.

Bar-Or D., et al., "Low Molecular Weight Fraction of Commercial Human Serum Albumin Induces Morphologic and Transcriptional Changes of Bone Marrow-Derived Mesenchymal Stem Cells," Stem Cells Translational Medicine, Aug. 2015, vol. 4(8), pp. 945-955.

Barton., et al., "Protein Secondary Structure Prediction," Current Opinion in Structural Biology, Jun. 1995. vol. 5(3), pp. 372-376.

Bendtsen, et al., "Improved Prediction of Signal Peptides: SignalP 3.0," Journal of molecular biology, Jul. 2004, vol. 340, pp. 783-795.

Benedek T.G., "History of the Development of Corticosteroid Therapy," Clinical and Experimental Rheumatology, Sep.-Oct. 2011, vol. 29(5 Suppl 68), S-5-12, Epub Oct. 21, 2011, 8 pages.

Berger S., et al., "Computationally designed high specificity inhibitors delineate the roles of BCL2 family proteins in cancer", Nov. 2, 2016, Elife 5, e20352, 31 pages.

Berman, et al., "The Protein Data Bank," Nucleic acids research, vol. 28, No. 1, Jan. 2000, pp. 235-242.

Bernard J.C., et al., "Identification of an lnterleukin-15alpha Receptor-binding Site on Human Interleukin-15," Journal of Biological Chemistry, Jun. 4, 2004, vol. 279(23), pp. 24313-24322.

Bernhard J.C., et al., "Should we use Cells, Biomaterials, or Tissue Engineering for Cartilage Regeneration?," Stem Cell Research & Therapy , Dec. 2016, vol. 7, Issue. 1, 9 pages, DOI: 10.1186/S13287-016-0314-3.

Beyder A., et al., "Targeting Ion Channels for the Treatment of Gastrointestinal Motility Disorders," Therapeutic Advances in Gastroenterology, Jan. 2012, vol. 5(1), pp. 5-21.

Bhardwaj, et al., "Accurate de novo Design of Hyperstable Constrained Peptides," Nature 538, Oct. 20, 2016, pp. 329-335.

Bjellqvist B., et al., "Reference Points for Comparisons of Two-dimensional Maps of Proteins from Different Human Cell types defined in a pH Scale where Isoelectric Points Correlate with Polypeptide Compositions," Electrophoresis, Mar.-Apr. 1994 , vol. 15(3-4), pp. 529-539.

Bjellqvist B., et al., "The Focusing Positions of Polypeptides in Immobilized pH Gradients can be Predicted from their Amino Acid Sequences," Electrophoresis, Oct. 1993, vol. 14(10), pp. 1023-1031.

Bodenhofer U., et al., "Msa: an R Package for Multiple Sequence Alignment," Bioinformatics, Dec. 2015, vol. 31, Issue. 24, pp. 3997-3999.

Bohlen C.J., et al., "A Bivalent Tarantula Toxin Activates the Capsaicin Receptor, TRPV1, by targeting the outer pore domain," Cell, May 28, 2010, vol. 141, pp. 834-845.

Boisseau S., et al., "Cell Penetration Properties of Maurocalcine, A Natural Venom Peptide Active on the Intracellular Ryanodine Receptr,o" Biochimica et Biophysica Acta—Biomembr, Mar. 2006, vol. 1758, pp. 308-319.

Boswell C.A., et al., "Comparative Physiology of Mice and Rats: Radiometric Measurement of Vascular Parameters in Rodent Tissues," Apr. 7, 2014, vol. 11, pp. 1591-1598.

Bouchaud, et al., "The Exon-3-encoded Domain of IL-15ralpha Contributes to IL-15 High-affinity Binding and is crucial for the IL-15 antagonistic effect of soluble IL-15Ralpha," Journal of Molecular Biology, Sep. 26, 2008, vol. 382, Issue. 1, pp. 1-12.

Boules M., et al., "Diverse Roles of Neurotensin Agonists in the Central Nervous System", Front Endocrinol (Lausanne), Mar. 22, 2013, vol. 4(36).

Brattsand R., "Overview of Newer Glucocorticosteroid Preparations for Inflammatory Bowel Disease. IDB: Trends in Medical Therapy," Canadian Journal of Gastroenterology, Nov. 7, 1990, vol. 4(7), pp. 407-414.

Brü äggemann M., et al., "Human Antibody Production in Transgenic Animals," Arch. Immunol. Ther. Exp. (Warsz), 2015, vol. 63, pp. 101-108.

Bruno B.J., et al., "Basics and Recent Advances in Peptide and Protein Drug Delivery," Ther Deliv, Nov. 4, 2013, vol. 4 (11), pp. 1443-1467.

Burns C.M., "The History of Cortisone Discovery and Development," Rheumatic Disease Clinics of North America, Feb. 2016, vol. 42 (1), pp. 1-14.

Butoescu N., et al., "Dexamethasone-Containing PLGA Superparamagnetic Microparticles as Carriers for the Local Treatment of Arthritis," Biomaterials, Mar. 2009, vol. 30, Issue. 9, pp. 1772-1780, doi: 10.1016/j.biomaterials.2008.12.017. Epub Jan. 8, 2009, 9 pages.

Butte P.V., et al., "Near-Infrared Imaging of Brain Tumors Using the Tumor Paint BLZ-100 to Achieve Near-complete Resection of Brain tumors.," Neurosurg Focus, Feb. 2014, vol. 36 (2), E1, 8 pages.

Carver T., et al., "The Design of Jemboss: A Graphical User Interface to EMBOSS," Bioinformatics, Sep. 22, 2003, vol. 19 (14), pp. 1837-1843.

Chaturvedi M., et al., "A Review on Mucoadhesive Polymer used in Nasal Drug Delivery System," Journal of Advanced Pharmaceutical Technology & Research, Oct. 2011, vol. 2 (4), pp. 215-222, doi: 10.4103/2231-4040.90876.

Chen J., et al., "Protein-protein Interactions: General Trends in the Relationship between Binding Affinity and Interfacial Buried Surface Area," Protein Science, Apr. 2013, vol. 22 (4), pp. 510-515.

Chen S., et al., "A Targeted IL-15 Fusion Protein with Potent Anti-tumor activity," Cancer biology & therapy, Sep. 2015, vol. 16 (8), pp. 1415-1421.

Chen Y., et al., "The Application of Aptamer in Apoptosis," Biochimie, Jan. 2017, vol. 132, pp. 1-8.

Chen Z., et al., "Toxin Acidic Residue Evolutionary Function-guided Design of De Novo Peptide Drugs for the Immunotherapeutic Target, the Kv1. 3 Channel," Scientific reports, May 8, 2015, vol. 5(1), 8 Pages.

Chen Z., et al., "Unusual Binding Mode of Scorpion Toxin BmKTX onto Potassium Channels Relies on its Ristribution of Acidic Residues," Biochemical and biophysical research communications, Apr. 3, 2014, vol. 447, pp. 70-76.

Choi D-K., et al., "A General Strategy for Generating Intact, Full-length IgG Antibodies that Penetrate into the Cytosol of Living Cells," MAbs, Dec. 2014, vol. 6(6), pp. 1402-1414.

Collaborative computational Project, No. 4. "The CCP4 suite: Programs for Protein Crystallography," Acta crystallographica. Section D, Biological crystallography, Sep. 1, 1994, vol. 50 (Pt 5), pp. 760-763.

Compton J.T., et al., "A Review of Osteocyte Function and the Emerging Importance of Sclerostin," Journal of Bone and Joint Surgery, Oct. 1, 2014, vol. 96 (19), pp. 1659-1668, doi: 10.2106/JBJS.M.01096.

Corbi-Verge C., et al., "Strategies to Develop Inhibitors of Motif-Mediated Protein-Protein Interactions as Drug Leads," Annual Review of Pharmacology and Toxicology, Jan. 6, 2017, vol. 57, pp. 39-60.

Cordes M,H.J., et al., "Sequence Space, Folding and Protein Design," Current Opinion in Structural Biology, Feb. 1996, vol. 6(1), pp. 3-10.

Correnti C.E., et al., "Screening, Large-scale Production, and Structure-based Classification for Cystine-dense Peptides," Nature Structural & Molecular Biology, Mar. 2018, vol. 25 (3), pp. 270-278.

Craik D.J., et al., "Potential Therapeutic Applications of the Cyclotides and Related Cystine Knot Mini-proteins," Expert Opinion on Investigational Drugs, May 2007, vol. 16 (5), pp. 595-604.

Crook Z.R., et al., "Mammalian Display Screening of Diverse Cystine-Dense Peptides for Difficult to Drug Targets", Nature Communications, Dec. 21, 2017, vol. 8 (1), 15 pages, XP055606762.

(56) References Cited

OTHER PUBLICATIONS

Crowley P. J., et al., "Bioorganic & Medicinal Chemistry the Role of Molecular Modeling in the Design of Analogues of the Fungicidal Natural Products Crocacins A and D," Bioorganic & Medicinal Chemistry, Dec. 15, 2008, vol. 16 (24), pp. 10345-10355.

Daly N.L., et al., "Bioactive Cystine Knot Proteins," Current Opinion in Chemical Biology, Jun. 2011, vol. 15(3), pp. 362-368, doi: 10.1016/j.cbpa.2011.02.008. Epub Feb. 27, 2011.

Dancevic C.M., et al., "Current and Emerging Therapeutic Strategies for Preventing Inflammation and Aggrecanase-mediated Cartilage Destruction in Arthritis," Arthritis Research & Therapy, Sep. 2014, vol. 16 (5), pp. 429.

Daniels T.R., et al., "The Transferrin Receptor and the Targeted Delivery of Therapeutic Agents against Cancer," Biochimica et Biophysica Acta—General Subjects, Mar. 2012, vol. 1820 (3), pp. 291-317.

Davis, W., et al., "MolProbity: All-atom Contacts and Structure Validation for Proteins and Nuleic Acids," Nucleic acids research,Jul. 1, 2007, vol. 35 (2), pp. W375-W383.

De Coupade., et al., "Novel Human-derived Cell-penetrating Peptides for Specific Subcellular Delivery of Therapeutic Biomolecules," Biochemical Journal, Sep. 2005, vol. 390, pp. 407-418.

De Groot., et al., "Glucocorticoid Therapy and Adrenal Suppression. 2000," South Dartmouth (MA): MDText.com, Inc, Oct. 19, 2018, 27 pages.

Derakhshankhah H., et al., "Cell Penetrating Peptides: A Concise Review with Emphasis on Biomedical Applications," Biomedicine & Pharmacotherapy, Dec. 2018, vol. 108, pp. 1090-1096.

Derendorf H., et al., "Pharmacokinetics and Pharmacodynamics of Glucocorticoid Suspensions after Intra-articular Administration," Clinical Pharmacology & Therapeutics, Mar. 1986, vol. 39(3), pp. 313-317.

Dohmen C., et al., "Multifunctional CPP Polymer System for Tumor-targeted pDNA and siRNA Delivery," Methods in Molecular Biology, 2011; vol. 683, pp. 453-463, doi: 10.1007/978-1-60761-919-2_32.

Dolinsky T.J., et al., "PDB2PQR: Expanding and Upgrading Automated Preparation of Biomolecular Structures for Molecular Simulations," Nucleic Acids Research, Jul. 2007, vol. 35(Web Server issue), pp. W522-W525.

Dou P.Q., et al., "Overview of Proteasome Inhibitor-based Anticancer Therapies: Perspective on Bortezomib and Second Generation Proteasome Inhibitors versus Future Generation Inhibitors of Ubiquitin-proteasome System," Current Cancer Drug Targets, Dec. 30, 2014, vol. 14(6), pp. 517-536.

D'Souza C., et al., "Structural Parameters Modulating the Cellular Uptake of Disulfide-rich Cyclic Cell-penetrating Peptides: MCoTI-II and SFTI-1," Eur. Journal of Medicinal Chemistry, Jun. 24, 2014, vol. 88, pp. 10-18.

Drake M.T., et al., "Bisphosphonates: Mechanism of Action and Role in Clinical Practice," Mayo Clinic Proceedings, Sep. 2008, vol. 83 (9), pp. 1032-1045.

Drin G., et al., "Physico-chemical Requirements for Cellular Uptake of pAntp Peptide: Role of lipid-binding affinity," European Journal of Biochemistry, Mar. 2001, vol. 268, pp. 1304-1314.

Drug Bank, Retrived from: [https://www.drugbank.ca/drugs/DB01248 created Jun. 13, 2005], updated Nov. 22, 2019,18 Pages.

Duchardt F., et al., "A Cell-penetrating Peptide derived from Human Lactoferrin with Conformation-dependent Uptake Efficiency," Journal of Biological Chemistry, Dec. 25, 2009, vol. 284, pp. 36099-36108.

Ducry L., et al., "Antibody-drug Conjugates: Linking Cytotoxic Payloads to Monoclonal Antibodies," Bioconjugate Chemistry. Jan. 2010, vol. 21 (1), pp. 5-13, doi: 10.1021/bc9002019.

Dulhunty A.F., et al., "Multiple Actions of Imperatoxin A on Ryanodine Receptors: Interactions with the II-III loop 'A' fragment," Journal of Biological Chemistry, Mar. 19, 2004, vol. 279, pp. 11853-11862.

Elmallah M., et al., "Marine Drugs Regulating Apoptosis Induced by Tumor Necrosis Factor-Related Apoptosis-Inducing Ligand (TRAIL)," Mar Drugs, Nov. 13, 2015, vol. 13 (11), pp. 6884-6909, doi: 10.3390/md13116884.

Emboss iep. Available at http://emboss.sourceforge.net/apps/release/6.6/emboss/apps/iep.html. Accessed on Dec. 26, 2018, 12 pages.

Emsley P., et al., "Coot: Model-building Tools for Molecular Graphics," Acta crystallographica Section D, Biological crystallography 60, Aug. 4, 2004, pp. 2126-2132.

Erazo-Oliveras A., et al., "Protein Delivery into Live Cells by Incubation with an Endosomolytic Agent," Nature Methods 11, Jun. 15, 2014, pp. 861-867.

Esteve E., et al., "Critical Amino Acid Residues Determine the Binding Affinity and the Ca 2+ Release Efficacy of Maurocalcine in Skeletal Muscle Cells," Journal of Biological Chemistry, Sep. 26, 2003, vol. 278, pp. 37822-37831.

Everts S., "Can We Hit the Snooze button on Aging?," Chemical & Engineering News 95, Mar. 6, 2017, vol. 10, pp. 31-35.

Extended European Search Report for European application, No. EP16815459.9 dated Nov. 28, 2018, 11 pages.

Farr J., et al., "Clinical Cartilage Restoration: Evolution and Overview," Clin Orthop Relat Res, Oct. 2011, vol. 469, Issue. 10, pp. 2696-2705, doi: 10.1007/s11999-010-1764-z.

Fidel J., et al., "Preclinical Validation of the Utility of BLZ-100 in Providing Fluorescence Contrast for Imaging Spontaneous Solid Tumors," Cancer Research, Oct. 15, 2015, vol. 75, No. 20, pp. 4283-4291.

Finton K.A.K., et al., "Autoreactivity and Exceptional CDR Plasticity (but Not Unusual Polyspecificity) Hinder Elicitation of the Anti-HIV Antibody 4E10," PLoS Pathog. Sep. 26, 2013, e1003639, 20 pages.

Fischer U., et al., "Apoptosis-based Therapies and Drug Targets," Cell Death Differ, Aug. 2005, vol. 12, Suppl 1, pp. 942-961.

Fu Q., et al., "Programmed Hydrolysis in Designing Paclitaxel Prodrug for Nanocarrier Assembly," Scientific Reports, Jul. 13, 2015, 5:12023, 10 pages.

Furtek S.L., et al., "Strategies and Approaches of Targeting STAT3 for Cancer Treatment," ACS Chem. Biol., Jan. 5, 2016, vol. 11, pp. 308-318.

Garcia R., et al., "Constitutive Activation of Stat3 by the Src and JAK Tyrosine Kinases Participates in Growth Regulation of Human Breast Carcinoma Cells," Oncogene, vol. 20, May 2001, pp. 2499-2513.

Gasteiger E., et al., "Protein Identification and Analysis Tools on the ExPASy Server," Excerpt, available at: http://web.expasy.org/compute_pi/pi_tool-doc.html. Accessed Nov. 7, 2018, 3 Pages.

Gasteiger E., et al., "Protein Identification and Analysis Tools on the ExPASy Server. (In) John M. Walker (ed):," The Proteomics Protocols Handbook, Humana Press, (2005, pp. 571-607.

Gautam A., et al., "Topical Delivery of Protein and Peptide Using Novel Cell Penetrating Peptide IMT-P8," Sci. Rep. 6, 2016, pp. 26278 May 18, 2016, 13 pages.

Geissler J.R, et al. American Society of Biomechanics Journal of Biomechanics Award 2013: cortical bone tissue mechanical quality and biological mechanisms possibly underlying atypical fractures. J Biomech. Apr. 13, 2015;48(6):. doi: 10.1016/j.jbiomech.2015.01.032. Epub Feb. 2, 2015, 30 pages.

Gelly J., et al., "The Knottin Website and Database: A New Information System Dedicated to the Knottin Scaffold," Nucleic Acids Research 32, 2004, suppl_1, pp. D156-D159.

Geng Q., et al., "Peptide-drug Conjugate Linked via a Disulfide Bond for Kidney Targeted Drug Delivery," Bioconjug Chem. Jun. 20, 2012, vol. 23, Issue. 6, pp. 1200-1210, doi: 10.1021/bc300020f. Epub Jun. 12, 2012.

Gibson C.J,. et al., "BCL-2 Antagonism to Target the Intrinsic Mitochondrial Pathway of Apoptosis," Clin Cancer Res. Nov. 15, 2015, vol. 21, Issue. 22, pp. 5021-5029. doi: 10.1158/1078-0432.CCR-15-0364, 9 Pages.

Goldring M.B., et al., "Emerging Targets in Osteoarthritis Therapy," Curr Opin Pharmacol, Jun. 2015, vol. 22, pp. 51-63. Published online Apr. 10, 2015. doi: 10.1016/j.coph.2015.03.004, 25 Pages.

Goodsell D., "Multidrug Resistance Transporters: Many bacteria use multidrug resistance transporters to pump drugs and poisons out

(56) References Cited

OTHER PUBLICATIONS of the cell". Molecule of the Month. Web article. Protein Data Bank (PDB-101). Nov. 2007. 3 pages. URL: https://pdb101.rcsb.org/motm/95, 3 Pages.
Gothard D., et al., "Tissue Engineered Bone using Select Growth factors: A Comprehensive Review of Animal Studies and Clinical Translation Studies in Man," Eur Cell Mate, Oct. 6, 2014, vol. 28, pp. 166-207, 43 Pages.
Gould A., et al., "Cyclotides, a Novel Ultrastable Polypeptide Scaffold for Drug Discovery," Current Pharmaceutical Design 17, Dec. 2011, vol. 38, pp. 4294-4307, 26 Pages.
Gump J.M., et al., "TAT Transduction: The Molecular Mechanism and Therapeutic Prospects," Trends Mol Med, Oct. 4, 2007, vol. 13, Issue. 10, pp. 443-448, 6 Pages.
Guo W., et al., "Protection Against Th17 Cells Differentiation by an Interleukin-23 Receptor Cytokine-Binding Homology Region," PLoS One, Sep. 19, 2012, vol. 7, Issue. 9, pp. e45625, 10 Pages.
Gurrola G.B., et al., "Imperatoxin A, a Cell-Penetrating Peptide from Scorpion Venom, as a Probe of Ca-Release Channels/Ryanodine Receptors," Pharmaceuticals (Basel). 3, Apr. 1, 2010, pp. 1093-1107, 15 Pages.
Guzman F., et al., "Mechanism of Action, Indications and Adverse Effects of: Etanercept, Infliximab and Adalimumab," Pharmacoloy Corner. Available at: http://pharmacologycorner.com/mechanism-of-action-indications-and-adverse-effects-of-etanercept-infliximab-and-adalimumab. Accessed Nov. 7, 2018, 7 Pages.
Haas M., et al., "Drug-targeting to the Kidney: Renal Delivery and Degradation of a Naproxen-lysozyme Conjugate In vivo," Kidney Int, Dec. 1997, vol. 52, Issue. 6, pp. 1693-1699, 7 Pages.
Hainer B.L., et al., "Diagnosis, treatment, and prevention of gout," Am Fam Physician, Dec. 15, 2014, vol. 90, Issue. 12, pp. 831-836, 6 Pages.
Hammaker D., et al., "Go Upstream, Young man": Lessons learned from the p38 saga, Ann Rheum Dis, Jan. 2010, 69 Suppl 1:i77-82. doi: 10.1136/ard.2009.119479, 14 Pages.
Hamman J.H., et al., "Oral Delivery of Peptide Drugs: Barriers and Developments," BioDrugs, 2005, vol. 19, Issue. 3, pp. 165-177, 13 Pages.
Han S., et al., "Structural Basis of a Potent Peptide Inhibitor Designed for Kv1. 3 Channel, A Therapeutic Target of Autoimmune Disease", Journal of Biological Chemistry, 283.27 (Jul. 4, 2008): 19058-19065, 9 Pages.
Harada H., et al., "Antitumor Protein Therapy; Application of the Protein Transduction Domain to the Development of a Protein Drug for Cancer Treatment," Breast Cancer, Jan. 2006, vol. 13, Issue. 1, pp. 16-26, 11 Pages.
Haseeb A., et al., "Immunopathogenesis of Osteoarthritis," Clin Immunol, Mar. 2013, vol. 146, Issue. 3, Epub, Jan. 6, 2013, doi: https://doi.org/10.1016/j.clim.2012.12.011, pp. 185-196.
He X.K., et al., "Low Molecular Weight Hydroxyethyl Chitosan-prednisolone Conjugate for Renal Targeting Therapy: Synthesis, Characterization and In Vivo Studies," Theranostics, 2012, vol. 2(11), pp. 1054-1063, 10 Pages.
Henikoff S., et al., "Amino Acid Substitution Matrices from Protein Blocks," PNAS USA, Nov. 1992, vol. 89 (22), pp. 10915-10919, 5 Pages.
Hermans E., et al., "Phospholipase C Activation by Neurotensin and Neuromedin N in Chinese Hamster Ovary Cells Expressing the Rat Neurotensin Receptor," Molecular Brain Research, Oct. 1992, vol. 15, pp. 332-338, 7 Pages.
Herzig V., et al., "The Cystine Knot is Responsible for the Exceptional Stability of the Insecticidal Spider Toxin ?—Hexatoxin-Hv1a," Toxins (Basel), Oct. 26, 2015, vol. 7 (10), pp. 4366-4380, 15 Pages.
Hochberg M.C., et al., "American College of Rheumatology 2012 Recommendations for the Use of Non-Pharmacologic and Pharmacologic Therapies in Osteoarthritis of the Hand, Hip and Knee," Arthritis Care Res (Hoboken), Apr. 2012, vol. 64 (4), pp. 465-474, 10 Pages.

Hockaday D.C., et al., "Imaging Glioma Extent with 131I-TM-601," J. Nuc. Med, Apr. 2005, vol. 46 (4), pp. 580-586, 7 Pages.
Hollander J L., "Intrasynovial Corticosteroid Therapy in Arthritis," Md State Med J, Mar. 1970, vol. 19 (3), pp. 62-66, 5 Pages.
Huber-Lang M., et al., "Mesenchymal Stem Cells after Polytrauma: Actor and Target," Stem Cells Int, Jun. 2016, 2016:6289825, 11 Pages.
Hunziker E.B., et al., "An Educational Review of Cartilage Repair: Precepts & Practice—Myths & Misconceptions—Progress & Prospects," Osteoarthritis Cartilage, Mar. 2015, vol. 23 (3), pp. 334-350, 17 Pages.
Hwang H.S., et al., "Chondrocyte Apoptosis in the Pathogenesis of Osteoarthritis," Int J Mol Sci, Nov. 2015, vol. 16 (11), pp. 26035-26054, 20 Pages.
"Inhaled Corticosteroids: Are Considered the most Effective Long Term usage Medication for Control and Management of Asthma," URL: https://www.aaaai.org/conditions-and-treatments/treatments/drug-guide/inhaled-corticosteroids. ©American Academy of Allergy, Asthma & Immunology, Mar. 7, 2017, 6 pages.
International Preliminary Report on Patentability for Application No. PCT/US2016/051166, dated Mar. 22, 2018, 8 Pages.
International Search Report and Written Opinion Application No. PCT/US2018/023006, dated Jul. 27, 2018, 16 pages.
International Search Report and Written Opinion Application No. PCT/US2018/037544, dated Oct. 26, 2018, 15 pages.
International Search Report and Written Opinion Application No. PCT/US2018/066337, dated Apr. 30, 2019, 13 pages.
International Search Report and Written Opinion Application No. PCT/US2019/022630, dated Jul. 5, 2019, 10 pages.
International Search Report and Written Opinion for Application No. PCT/US16/66007, dated May 24, 2017, 10 pages.
International Search Report and Written Opinion for Application No. PCT/US2016/039431, dated Jan. 13, 2017, 10 pages.
International Search Report for Application No. PCT/US2016/051166, dated Mar. 23, 2017, 5 pages.
IUPHAR/BPS. Guide to Pharmacology—"Tumour necrosis factor (TNF) receptor family," Available at: http://www.guidetopharmacology.org/GRAC/FamilyDisplayForward?familyId=334. Accessed Jul. 11, 2018, 3 pages.
Iyer S., et al., "Tying the Knot: The Cystine Signature and Molecular-Recognition Processes of the Vascular Endothelial Growth Factor Family of Angiogenic Cytokines," The FEBS journal, 2011, vol. 278(22), pp. 4304-4322.
Jain N., et al., "Current ADC Linker Chemistry," Pharmaceutical Research, 2015, vol. 32, No. 11, pp. 3526-3540.
Jang J.Y., et al., "A Nucleic Acid-Hydrolyzing Antibody Penetrates into Cells via Caveolae-Mediated Endocytosis, Localizes in the Cytosol and Exhibits Cytotoxicity," Cell Mol Life Sci, 2009, vol. 66, pp. 1985-1997.
Janzer M., et al., "Drug Conjugation Affects Pharmacokinetics and Specificity of Kidney-Targeted Peptide Carriers," Bioconjugate Chemistry, Sep. 12, 2016, vol. 27, No. 10, pp. 2441-2449.
Jeffrey D., et al., "Intra-Articular Corticosteroids are Safe and Have no Major Effect on Structural Progression of Synovitic Knee OA: A2—Year Randomized Controlled Trial of 3-Monthly Triamcinolone Hexacetonide," 2015 ACR/ARHP Annual Meeting, Sep. 29, 2015, 3 pages.
Jentoft N., et al., "Labeling of Proteins by Reductive Methylation Using Sodium Cyanoborohydride," Journal of Biological Chemistry, Jan. 17, 1979, vol. 254, pp. 4359-4365.
Jentoft N., et al., "Protein Labeling by Reductive Alkylation," Methods in Enzymology, 1983, vol. 91 (C), pp. 570-579.
Karlsson R., et al., "Analyzing a Kinetic Titration Series Using Affinity Biosensors," Analytical Biochemistry, 2006, vol. 349, pp. 136-147.
Kean W.F., et al., "Clinical Pharmacology of Gold," Inflammopharmacology, Jun. 4, 2008, vol. 16(3), pp. 112-125.
Kern H.B., et al., "Enzyme-Cleavable Polymeric Micelles for the Intracellular Delivery of Proapoptotic Peptides," Molecular Pharmaceutics, May 1, 2017, vol. 14 (5), pp. 1450-1459.
Kikuchi K., et al., "High Proteolytic Resistance of Spider-Derived Inhibitor Cystine Knots," International Journal of Peptide, 2015, 9 pages.

(56) References Cited

OTHER PUBLICATIONS

Kim H.T., et al., "Chondrocyte Apoptosis: Implications for Osteochondral Allograft Transplantation," Clin Orthop Relat Res, Aug. 2008, vol. 466 (8), pp. 1819-1825.
Kimura R.H., et al., "Engineered Cystine Knot Peptides that Bind avβ3, avβ5, and a5β1 Integrins with Low-Nanomolar Affinity," Proteins Struct. Funct. Bioinforma, Nov. 1, 2009, vol. 77 (2), pp. 359-369.
Kintizing J.R., et al., "Engineered Knottin Peptides as Diagnostics, Therapeutics, and Drug Delivery Vehicles," Current Opinion in Chemical Biology, 2016, vol. 34, pp. 143-150.
Kirkland J L., "Translating Advances from the Basic Biology of Aging into Clinical Application," Exp Gerontol, Jan. 2013, vol. 48(1), pp. 1-5.
Kirkland J.L., et al., "Clinical Strategies and Animal Models for Developing Senolytic Agents," Exp Gerontol, Aug. 2015, vol. 68, pp. 19-25.
Kirwan J.R., et al., "A Randomised Placebo Controlled 12 Week Trial of Budesonide and Prednisolone in Rheumatoid Arthritis," Annals of the Rheumatic Diseases, Jun. 2004, vol. 63 (6), pp. 688-695.
Kolmar H., "Biological Diversity and Therapeutic Potential of Natural and Engineered Cystine Knot Miniproteins," Current Opinion in Pharmacology, Jun. 10, 2009, vol. 9(5), pp. 608-614.
Kolmar H., "Natural and Engineered Cystine Knot Miniproteins for Diagnostic and Therapeutic Applications," Current Pharmaceutical Design, 2011, vol. 17(38), pp. 4329-4336.
Kozminsky-Atias A., et al., "Isolation of the First Toxin from the Scorpion Buthus Occitanus Israelis Showing Preference for Shaker Potassium Channels," FEBS Letters, 2007, vol. 581(13), pp. 2478-2484.
Krezel A.M., et al., "Solution Structure of the Potassium Channel Inhibitor Agitoxin 2: Caliper for Probing Channel Geometry," Protein Science, 1995, vol. 4(8), pp. 1478-1489.
Kumari G., et al., "Cysteine-Rich Peptide Family with Unusual Disulfide Connectivity from Jasminum Sambac," Journal of Natural Products, Nov. 25, 2015, vol. 78(11). pp. 2791-2799.
Kuyinu E.L., et al., "Animal Models of Osteoarthritis: Classification, Update and Measurement of Outcomes," Journal of Orthopaedic Surgery and Research, Feb. 2, 2016, vol. 11(19), 27 pages.
Lal M.A., et al., "Targeting the Podocyte to Treat Glomerular Kidney Disease," Drug Discovery Today, Oct. 10, 2015, vol. 20(10), pp. 1228-1234.
Lange A., et al., "Classical Nuclear Localization Signals: Definition, Function, and Interaction with Importin a*,s," Journal of Biological Chemistry, Feb. 23, 2007, vol. 282(8), pp. 5101-5105.
Larking M.A., et al., "Clustal Wand Clustal X Version 2.0," Bioinformatics Applications Note, 2007, vol. 23(21), pp. 2947-2948.
Li B., et al., "Synergistic Effects of Vascular Endothelial Growth Factor on Bone Morphogenetic Proteins Induced Bone Formation In Vivo: Influencing Factors and Future Research Directions," BioMed Research International, 2016, vol. 2016, Article ID. 2869572, 11 pages.
Li G., et al., "Three Dimensional de Novo Micro Bone Marrow and its Versatile Application in Drug Screening and Regenerative Medicine," Experimental Biology and Medicine (Maywood), Aug. 2015, vol. 240(8), pp. 1029-1038.
Li M.X., et al., "Mitochondria and Apoptosis: Emerging Concepts," F1000Prime Rep, 2015, vol. 7(42), Published online Apr. 1, 2015, 9 pages.
Li Z., et al., "Influence of Molecular Size on Tissue Distribution of Antibody Fragments," MAbs, Jan. 2016, vol. 8(1), pp. 113-119.
Lim K.J., et al., "A Cancer Specific Cell-Penetrating Peptide, BR2, for the Efficient Delivery of an scFv into Cancer Cells," PLoS One, Jun. 2013, vol. 8(6), pp. 1-11.
Ling J., et al., "Molecular Mechanism of the Sea Anemone Toxin ShK Recognizing the Kv1.3 Channel Explored by Docking and Molecular Dynamic Simulations," Journal of Chemical Information and Modeling, 2007, vol. 47, pp. 1967-1972.

Liu Q., et al., "Robust Structural Analysis of Native Biological Macromolecules from Multi-Crystal Anomalous Diffraction Data," Acta Crystallographica Section D: Biological Crystallography, 2013, vol. 69(7), pp. 1314-1332.
Liu Y., et al., "Dual Receptor Recognizing Cell Penetrating Peptide for Selective Targeting, Efficient Intratumoral Diffusion and Synthesized Anti-Glioma Therapy," Theranostics, Jan. 1, 2016, vol. 6(2), pp. 177-191.
Lv Z., et al., "HIV Protease Inhibitors: A Review of Molecular Selectivity and Toxicity," HIV AIDS (Auckland), Apr. 8, 2015, vol. 7, pp. 95-104.
Ma D.D., et al., "Engineered Nanoparticles Induce Cell Apoptosis: Potential for Cancer Therapy," Oncotarget, Jun. 28, 2016, vol. 7 (26), pp. 40882-40903.
MacMahon P.J., et al., "Injectable Corticosteroid and Local Anesthetic Preparations: A Review for Radiologists," Radiology, Sep. 2009, vol. 252 (3), pp. 647-661.
Maillere B., et al., "Immunogenicity of a Disulphide-Containing Neurotoxin: Presentation to T-cells Requires a Reduction step," Toxicon, Apr. 1995, vol. 33 (4), pp. 475-482.
Mamelak A.N., et al., "Phase I Single-Dose Study of Intracavitary-Administered Iodine-131-TM-601 in Adults with Recurrent High-Grade Glioma," Journal of Clinical Oncology, Aug. 1, 2006, vol. 24 (22), pp. 3644-3650.
McCoy A.J., et al., "Phaser Crystallographic Software," Journal of Applied Crystallography, Aug. 1, 2007, vol. 40 (pt 4), pp. 658-674.
McNulty A.L., et al., "TRPV4 as a Therapeutic Target for Joint Diseases," Naunyn-Schmiedeberg's Archives of Pharmacology, Apr. 2015, vol. 388 (4), pp. 437-450.
Mehndiratta S., et al., "Quinazolines as Apoptosis Inducers and Inhibitors: A Review of Patent Literature," Recent Patents on Anti-Cancer Drug Discovery, 2016, vol. 11 (1), pp. 2-66.
Mewar D., et al., "Treatment of Rheumatoid Arthritis with Tumour Necrosis Factor Inhibitors," British Journal of Pharmacology, Feb. 2011, vol. 162 (4), pp. 785-791.
Mitchell D.J., et al., "Polyarginine Enters Cells more Efficiently than Other Polycationic Homopolymers," Journal of Peptide Research, Nov. 2000, vol. 56 (5), pp. 318-325.
Mitragotri S., et al., "Overcoming the Challenges in Administering Biopharmaceuticals: Formulation and Delivery Strategies," Nature Reviews Drug Discovery, Sep. 2014, vol. 13(9), pp. 655-672.
Mobasheri A., et al., "Potassium Channels in Articular Chondrocytes," Channels (Austin), Nov. 1, 2012, vol. 6 (6), pp. 416-425.
Montagne M., et al al., "The Max b-HLH-LZ can Transduce into Cells and Inhibit c-Myc Transcriptional Activities," PLoS One, 2012, vol. 7 (2), p. e32172.
Moore., et al., "Knottins: Disulfide-Bonded Therapeutic and Diagnostic Peptides," Drug Discovery Today: Technologies, Spring 2012, vol. 9, Issue. 1, pp. e3-e11.
Moore S.J., et al., "Engineering Knottins as Novel Binding Agents," Methods in Enzymology, 2012, vol. 503, pp. 223-251.
Moroni G., et al., "Synthetic Pharmacotherapy for Lupus Nephritis," Expert Opinion on Pharmacotherapy, Feb. 2017, vol. 18 (2), pp. 175-186.
Moroz E., et al., "Oral Delivery of Macromolecular Drugs: Where we are after Almost 100years of Attempts," Advanced Drug Delivery Reviews, Jun. 1, 2016, vol. 101, pp. 108-121.
Mortier E., et al., "Soluble Interleukin-15 Receptor Alpha (IL-15R alpha)—Sushi as a Selective and Potent Agonist of IL-15 Action Through IL-15R Beta/Gamma, Hyperagonist IL-15 x IL-15R alpha Fusion Proteins," Journal of Biological Chemistry, Jan. 20, 2006, vol. 281 (3), pp. 1612-1619.
Mouhat S., et al., "Diversity of Folds in Animal Toxins Acting on Ion Channels," Biochemical Journal, Mar. 2004, vol. 378 (Pt 3), pp. 717-726.
Moura A., et al., "Relative Amino Acid Composition Signatures of Organisms and Environments," PloS one, Oct. 2013, vol. 8 (10), p. e77319.
Moyse E., et al., "Distribution of Neurotensin Binding Sites in Rat Brain: A Light Microscopic Radioautographic Study using Monoiodo [125I]Tyr3-Neurotensin," Neuroscience, Aug. 1987, vol. 22 (2), pp. 525-536.

(56) References Cited

OTHER PUBLICATIONS

Mullins L.J., et al., "Renal Disease Pathophysiology and Treatment: Contributions from the Rat," Disease Models & Mechanisms, Dec. 1, 2016, vol. 9 (12), pp. 1419-1433.
Munno D.O., et al., "Effects of Glucocorticoid Treatment on Focal and Systemic Bone Loss in Rheumatoid Arthritis," J Endocrinol Invest, Jul. 2008, vol. 31 (7 Suppl), pp. 43-47.
Murshudov G.N., et al., "Refinement of Macromolecular Structures by the Maximum-likelihood Method," Acta Crystallographica Section D, May 1, 1997, D53, pp. 240-255.
Mustain W.C., et al., "The Role of Neurotensin in Physiologic and Pathologic Processes," Current Opinion in Endocrinology, Diabetes and Obesity, Feb. 2011, vol. 18(1), pp. 75-82.
Musumeci G., et al., "Biomarkers of Chondrocyte Apoptosis and Autophagy in Osteoarthritis," International Journal of Molecular Sciences, Aug. 31, 2015, vol. 16(9), pp. 20560-20575.
Myszka D.G., "Improving Biosensor Analysis," Journal of Molecular Recognition, Sep.-Oct. 1999, vol. 12(5), pp. 279-284.
Nagase H., "Substrate Specificity of MMPs," Chapter 2, Matrix Metalloproteinase Inhibitors in Cancer Therapy, Cancer Drug Discovery and Development, Humana Press, Totowa, NJ, 2001, pp. 39-66.
Nayak A., et al., "In Vitro and In Vivo Study of Poly (ethylene glycol) Conjugated Ibuprofen to Extend the Duration of Action," Scientia Pharmaceutica, Apr.-Jun. 2011, vol. 79(2), pp. 359-373.
Needleman S.B., et al., "A General Method Applicable to the Search for Similarities in the Amino Acid Sequence of two Proteins," Journal of Molecular Biology, Mar. 28, 1970, vol. 48(3), pp. 443-453.
Nelson A.R., et al., "Myristoyl-Based Transport of Peptides into Living Cells," Biochemistry, Dec. 25, 2007, vol. 46(51), pp. 14771-14781.
Nicolaides N.C., et al., "Glucocorticoid Therapy and Adrenal Suppression," Endotext, South Dartmouth, MA, MDText com, Incorporated, 2000, 26 Pages.
Nielsen M., et al., "NN-Align. An Artificial Neural Network-Based Alignment Algorithm for MHC Class II Peptide Binding Prediction," BMC Bioinformatics, Sep. 18, 2009, vol. 10(296), 10 Pages.
Nielsen M., et al., "Prediction of MHC Class II Binding Affinity Using SMM-Align, A Novel Stabilization Matrix Alignment Method," BMC Bioinformatics, Jul. 4, 2007, vol. 8(238), 12 Pages.
Njiojob C.N., et al., "Tailored Near-Infrared Contrast Agents for Image Guided Surgery," Journal of Medicinal Chemistry, Mar. 26, 2015, vol. 58(6), pp. 2845-2854.
Oh C.J., et al., "Dimethylfumarate Attenuates Renal Fibrosis via NF-E2-Related Factor 2-Mediated Inhibition of Transforming Growth Factor-β/Smad Signaling," PLOS One, Oct. 2012, vol. 7(10), e45870.
Ojeda P.G., et al., "Lysine to Arginine Mutagenesis of Chlorotoxin Enhances its Cellular Uptake," Biopolymers, Sep. 2017, vol. 108(5), 10 pages.
OJEDA P.G., et al., "Review: Chlorotoxin: Structure, Activity, and Potential Uses in Cancer Therapy," Biopolymers, Jan. 1, 2016, vol. 106(1), pp. 25-36.
Otwinowski Z., et al., "Processing of X-ray Diffraction Data Collected in Oscillation Mode," Methods in Enzymology, 1997, vol. 276, pp. 307-326.
Park M.S., et al., "In Situ Recruitment of Human Bone Marrow-Derived Mesenchymal Stem Cells Using Chemokines for Articular Cartilage Regeneration," Cell Transplantation, 2015, vol. 24(6), pp. 1067-1083.
Pearson W.R., et al., "Improved Tools for Biological Sequence Comparison," Proceedings of the National Academy of Sciences of the United States of America, Apr. 1988, vol. 85(8), pp. 2444-2448.
Pearson W.R., "Rapid and Sensitive Sequence Comparison with FASTP and FASTA," Methods in Enzymology, 1990, vol. 183, pp. 63-98.
Pi Y., et al., "Targeted Delivery of Non-Viral Vectors to Cartilage in Vivo Using a Chondrocyte-Homing Peptide Identified by Phage Display," Biomaterials, Sep. 2011, vol. 32(26), pp. 6324-6332.
Pillow T.H., et al., "Site-Specific Trastuzumab Maytansinoid Antibody-Drug Conjugates with Improved Therapeutic Activity Through Linker and Antibody Engineering," Journal of Medicinal Chemistry, Oct. 9, 2014, vol. 57(19), pp. 7890-7899.
Plosker G.L., et al. "Sulfasalazine: A Review of its Use in The Management of Rheumatoid Arthritis," Drugs, Jan. 1, 2005, vol. 65(13), pp. 1825-1849.
Poillot C., et al., "Small Efficient Cell-Penetrating Peptides Derived from Scorpion Toxin Maurocalcine," Journal of Biological Chemistry, May 18, 2012, vol. 287(21), pp. 17331-17342.
Ponce A., "Expression of Voltage Dependent Potassium Currents in Freshly Dissociated Rat Articular Chondrocytes," Cellular Physiology and Biochemistry, Aug. 14, 2006, vol. 18(1-3), pp. 35-46.
Pooga M., et al., "Cell Penetration by Transportan," Faseb Journal, Jan. 1998, vol. 12(1), pp. 67-77.
Portilla D., "Apoptosis, Fibrosis and Senescence," Nephron Clinical Practice, 2014, vol. 127(1-4), pp. 65-69.
Portilla D., et al., "Metabolomic Study of Cisplatin-Induced Nephrotoxicity," Kidney International, Jun. 2006, vol. 69(12), pp. 2194-2204.
Potterton E., et al., "A Graphical User Interface to the CCP4 Program Suite," Acta Crystallographica, Jul. 2003, vol. 59(7), pp. 1131-1137.
Pouyani T., et al., "Functionalized Derivatives of Hyaluronic Acid Oligosaccharides: Drug Carriers and Novel Biomaterials," Bioconjugate Chemistry, Jul.-Aug. 1994, vol. 5(4), pp. 339-347.
Procko., et al., "A Computationally Designed Inhibitor of an Epstein-Barr Viral Bcl-2 Protein Induces Apoptosis in Infected Cells," Cell, Jun. 19, 2014, vol. 157(7), pp. 1644-1656.
Punzi L., et al., "Post-Traumatic Arthritis: Overview on Pathogenic Mechanisms and Role of Inflammation," RMD Open, Sep. 6, 2016, vol. 2(2), e000279, 9 pages.
Qian Z., et al., "Early Endosomal Escape of a Cyclic Cell-Penetrating Peptide Allows Effective Cytosolic Cargo Delivery," Biochemistry. Jun. 24, 2014, vol. 53(24), pp. 4034-4046.
Quintas-Cardama A., et al., "Molecular Pathways: JAK/STAT Pathway: Mutations, Inhibitors, and Resistance," Clinical Cancer Research, Apr. 15, 2013, vol. 19(8), pp. 1933-1940.
Ramos A.M., et al., "Designing Drugs that Combat Kidney Damage," Expert Opinion on Drug Discovery, May 2015, vol. 10(5), pp. 541-556.
Rashid M.H., et al., "A Potent and Kv1.3-Selective Analogue of the Scorpion Toxin HsTX1 as a Potential Therapeutic for Autoimmune Diseases," Scientific Reports, Mar. 28, 2014, vol. 4(4509), pp. 1-9.
Rau R., "Glucocorticoid Treatment in Rheumatoid Arthritis," Expert Opinion on Pharmacotheraphy, Aug. 2014, vol. 15(11), pp. 1575-1583.
Raynauld J-P., et al., "Safety And Efficacy of Long-Term Intraarticular Steroid Injections in Osteoarthritis of the Knee: A Randomized, Double-Blind, Placebo-Controlled Trial," Arthritis & Rheumatology, Feb. 2003, vol. 48(2), pp. 370-377.
Rees D.C., et al., "Refined Crystal Structure of the Potato Inhibitor Complex of Carboxypeptidase A at 2.5 A Resolution," Journal of Molecular Biology, Sep. 25, 1982, vol. 160(3), pp. 475-498.
Reines B.P., "Is Rheumatoid Arthritis Premature Osteoarthritis with Fetal-Like Healing?," Autoimmune Review, Jun. 2004, vol. 3(4), pp. 305-311.
Reinwarth M., et al., "Chemical Synthesis, Backbone Cyclization and Oxidative Folding of Cystine-Knot Peptides-Promising Scaffolds for Applications In Drug Design," Molecules, Oct. 24, 2012, vol. 17(11), pp. 12533-12552.
Ren J., et al., "Quercetin Inhibits Fibroblast Activation and Kidney Fibrosis Involving the Suppression of Mammalian Target of Rapamycin and Beta-Catenin Signaling," Scientific Reports, Apr. 7, 2016, vol. 6(23968), 11 pages.
Renisio J-G., et al., "Solution Structure of BmKTX, a K+ Blocker Toxin from the Chinese Scorpion *Buthus martensi*," Proteins: Structure, Function and Genetics, Jan. 1, 2000, vol. 38(1), pp. 70-78.
Rhee M., et al., "Mechanism of Uptake of C105Y, A Novel Cell-Penetrating Peptide," Journal of Biological Chemistry, Jan. 13, 2006, vol. 281(2), pp. 1233-1240.

(56) References Cited

OTHER PUBLICATIONS

Ricci M.C., et al., "Chemotherapeutic Approaches for Targeting Cell Death Pathways," Oncologist, Apr. 2006, vol. 11(4), pp. 342-357.
Rice P., et al., "Emboss: The European Molecular Biology Open Software Suite," Trends in Genetics, Jun. 2000, vol. 16(6), pp. 276-277.
Rossini M., et al., "Focal Bone Involvement in Inflammatory Arthritis: The Role of IL17," Rheumatology International, Apr. 2016, vol. 36(4), pp. 469-482.
Said E.A., et al., "The Anti-Hiv Cytokine Midkine Binds the Cell Surface-Expressed Nucleolin as a Low Affinity Receptor," Journal of Biological Chemistry, Oct. 4, 2002, vol. 277 (40), pp. 37492-37502.
Samy R.P., et al.,"Animal Venoms as Antimicrobial Agents," Biochem Pharmacology, Jun. 15, 2017, vol. 134, pp. 127-138.
Sangphukieo A., et al., "Computational Design of Hypothetical New Peptides Based on a Cyclotide Scaffold as Hiv Gp120 Inhibitor," Plos One 10, Oct. 30, 2015, vol. 10 (11), 15 Pages.
Sansone P., et al., "Targeting the Interleukin-6/Jak/Stat Pathway in Human Malignancies," Journal of Clinical Oncology , Mar. 20, 2012, vol. 30, pp. 1005-1014.
Santos S.P., et al., "Thermofluor-based Optimization Strategy for the Stabilization and Crystallization of Campylobacter Jejuni Desulforubrerythrin," Protein Expression and Purification, 2012, vol. 81, pp. 193-200.
Schmidt T.J., et al., "Reactivity of Dimethyl Fumarate and Methylhydrogen Fumarate Towards Glutathione and N-Acetyl-L-Cysteine—Preparation of S-Substituted Thiosuccinic Acid Esters," Bioorganic & Medicinal Chemistry, Jan. 1, 2007, vol. 15 (1), pp. 333-342.
Schwartz E.F., et al., "Characterization of Hadrucalcin, A Peptide from Hadrurus Gertschi Scorpion Venom With Pharmacological Activity on Ryanodine Receptors," British Journal of Pharmacology, Jun. 2009, vol. 157 (3), pp. 392-403.
Sellers P.H., et al., "On the Theory and Computation of Evolutionary Distances," Siam Journal on Applied Mathematics, Jun. 1974, vol. 26 (4), pp. 787.
Shahbazzadeh D., et al., "Hemicalcin, A New Toxin from the Iranian Scorpion *Hemiscorpius lepturus* Which is Active on Ryanodine-Sensitive Ca2+ Channels," Biochemical Journal, 2007, vol. 404, pp. 89-96.
Shao B-Z., et al., "Nlrp3 Inflammasome and its Inhibitors: A Review," Frontiers in Pharmacology, Nov. 2015, vol. 6, pp. 262.
Shen J., et al., "Nlrp3 Inflammasome Mediates Contrast Media-Induced Acute Kidney Injury by Regulating Cell Apoptosis," Scientific Reports 6, Article No. 34682, 2016, 10 Pages.
Shen X., et al., "Prolyl Hydroxylase Inhibitors Increase Neoangiogenesis and Callus formation Following Femur Fracture in Mice," Journal of Orthopaedic Research, Oct. 2009, vol. 27 (10), pp. 1298-1305.
Shimoaka T., et al., "Regulation of Osteoblast, Chondrocyte, and Osteoclast Functions by Fibroblast Growth Factor (Fgf)-18 in Comparison With Fgf-2 and Fgf-10," Journal of Biological Chemistry, Mar. 1, 2002, vol. 277 (9), pp. 7493-7500.
Shire S.J., et al., "Challenges in the Development of High Protein Concentration formulations," Journal of Pharmaceutical Sciences, 2004, vol. 93 (6), pp. 1390-1402.
Sillero A., et al., "Isoelectric Point Determination of Proteins and Other Macromolecules: Oscillating Method," Computers in Biology and Medicine, Feb. 2006, vol. 36 (2), pp. 157-166.
Sillero A., et al., "Isoelectric Points of Proteins: Theoretical Determination," Analytical Biochemistry, Jun. 1989, vol. 179 (2), pp. 319-325.
Simeon R., et al., "In Vitro-Engineered Non-Antibody Protein Therapeutics," Protein Cell, 2018, vol. 9(1), pp. 3-14.
Singh S.K., et al., "Antibody-Drug Conjugates: Design, formulation and Physicochemical Stability," Pharmaceutical Research, Nov. 2015, vol. 32 (11), pp. 3541-3571.
Sinha V.R., et al., "Oral Colon-Specific Drug Delivery of Protein and Peptide Drugs," Critical Review in Therapeutic Drug Carrier Systems, 2007, vol. 24 (1), pp. 63-92.
Sinniah R., et al., "Serum Iron, Total Iron-Binding Capacity, and Percentage Saturation in Normal Subjects," Journal of Clinical Pathology, 1968, vol. 21, pp. 603-610.
Solon E G., "Autoradiography Techniques and Quantification of Drug Distribution," Cell and Tissue Research, 2015, vol. 360 (1), pp. 87-107.
Song Y., et al., "Small-Molecule Modulators of The Ox40-Ox40 Ligand Co-Stimulatory Protein-Protein Interaction," British Journal of Pharmacology, Nov. 2014, vol. 171 (21), pp. 4955-4969.
Soroceanu L., et al., "Use of Chlorotoxin for Targeting of Primary Brain Tumors," Cancer Research, Nov. 1, 1998, vol. 58 (21), pp. 4871-4879.
Sottero T.L., et al., "Pacifastin-Derived Peptides Target Tumors for Use in In Vivo Imaging," Anticancer Research, Jan. 2018, vol. 38 (1), pp. 51-60.
Steinert A.F., et al., "Major Biological Obstacles for Persistent Cell-Based Regeneration of Articular Cartilage," Arthritis Research & Therapy, Jun. 5, 2007, vol. 9 (3), 15 pages.
Stern L.A., et al., "Alternative Non-Antibody Protein Scaffolds for Molecular Imaging of Cancer," Current Opinion in Chemical Engineering, Nov. 2013, vol. 2 (4), 15 pages.
Sudo K., et al., "Human-Derived Fusogenic Peptides for the Intracellular Delivery of Proteins," Journal of Controlled Release, Jun. 10, 2017, vol. 255, pp. 1-11.
Sugumar D., et al., "Targeted Treatments for Multiple Myeloma: Specific Role of Carfilzomib," Pharmacogenomics and Personalized Medicine, Jan. 20, 2015, vol. 8, pp. 23-33.
Sutherland R., et al., "Ubiquitous Cell-Surface Glycoprotein on Tumor Cells is Proliferation-Associated Receptor for Transferrin," Proceedings of the National Academy of Sciences of the United States of America, Jul. 1981, vol. 78 (7), pp. 4515-4519.
Swanson C.D.A., et al., "Tyrosine Kinases as Targets for the Treatment of Rheumatoid Arthritis," Nature Reviews Rheumatology, Jun. 2009, vol. 5 (6), pp. 317-324.
Tabrizi M., et al., "Biodistribution Mechanisms of Therapeutic Monoclonal Antibodies in Health and Disease," An Official Journal of the American Association of Pharmaceutical Scientists, Mar. 2010, vol. 12 (1), pp. 33-43.
Tait S.W.G., et al., "Die Another Way-Non-Apoptotic Mechanisms of Cell Death," Journal Cell Science, May 15, 2014, vol. 127 (10), pp. 2135-2144.
Takayama K., et al., "Enhanced Intracellular Delivery Using Arginine-Rich Peptides by the Addition of Penetration Accelerating Sequences (Pas)," Journal of Control Release, Sep. 1, 2009, vol. 138 (2), pp. 128-133.
Tam J.P., et al., "Antimicrobial Peptides from Plants," Pharmaceuticals, Dec. 2015, vol. 8 (4), pp. 711-757.
Tangri S., et al., "Rationally Engineered Proteins or Antibodies With Absent or Reduced Immunogenicity," Current Medicinal Chemistry, Dec. 2002, vol. 9 (24), pp. 2191-2199.
Tesmer J.J., et al., "The Structure, Catalytic Mechanism and Regulation of Adenylyl Cyclase," Current Opinion in Structural Biology, Dec. 1998, vol. 8 (6), pp. 713-719.
The Extended European Search Report for European application. No. EP16845226.6 dated Mar. 28, 2019.
The Extended European Search Report for European application. No. EP16874006.6 dated Jul. 30, 2019.
The Extended European Search Report for European application. No. EP17849695.6 dated Apr. 1, 2020.
The partial Supplemental European Search Report for European application. No. EP16874006.6 dated Apr. 24, 2019.
The Uniprot Consortium, "Uniprot: The Universal Protein Knowledgebase," Nucleic Acids Research, 2017, vol. 45, pp. D158-D169.
Trenevska I., et al., "Therapeutic Antibodies Against Intracellular Tumor Antigens," Frontiers in Immunology, Aug. 18, 2017, vol. 8 (article 1001), pp. 1001.

(56) References Cited

OTHER PUBLICATIONS

Trudeau L E., "Neurotensin Regulates Intracellular Calcium in Ventral Tegmental Area Astrocytes: Evidence for the Involvement of Multiple Receptors," Neuroscience, 2000, vol. 97 (2), pp. 293-302.
Tsunemi M., et al., "Crystallization of a Complex Between an Elastase-Specific Inhibitor Elafin and Porcine Pancreatic Elastase," Journal of Molecular Biology, Jul. 1993, vol. 232 (1), pp. 310-311.
Tundo G.R., et al., "Effect of Cisplatin on Proteasome Activity," Journal of Inorganic Biochemistry, Dec. 2015, vol. 153, pp. 253-258.
Ueda N., "Ceramide-Induced Apoptosis in Renal Tubular Cells: A Role of Mitochondria and Sphingosine-1-Phosphate," International Journal of Molecular Sciences, Mar. 5, 2015, vol. 16(3), pp. 5076-5124.
Van Den Hoven J.M., et al., "Optimizing the Therapeutic Index of Liposomal Glucocorticoids in Experimental Arthritis," International Journal of Pharmaceutics, Sep. 20, 2011, vol. 416(2), pp. 471-477.
Van Walsem A., et al., "Relative Benefit-Risk Comparing Diclofenac to Other Traditional Non-Steroidal Anti-Inflammatory Drugs and Cyclooxygenase-2 Inhibitors in Patients With Osteoarthritis or Rheumatoid Arthritis: A Network Meta-Analysis," Arthritis Research Therapy, Mar. 19, 2015, vol. 17(66), 18 Pages.
Vannucci G., et al., "Glucocorticoids in the Management of Systemic Juvenile Idiopathic Arthritis," Paediatric Drugs, Oct. 2013, vol. 15(5), pp. 343-349.
Varoga D., et al., "Human Beta-Defensin 3 Mediates Tissue Remodeling Processes in Articular Cartilage by Increasing Levels of Metalloproteinases and Reducing Levels of Their Endogenous Inhibitors," Arthritis and Rheumatism, Jun. 2005, vol. 52(6), pp. 1736-1745.
Varoga D., et al., "Production of Endogenous Antibiotics in Articular Cartilage," Arthritis and Rheumatism, Nov. 2004, vol. 50(11), pp. 3526-3534.
Vasalou C., et al., "A Mechanistic Tumor Penetration Model to Guide Antibody Drug Conjugate Design," Plos One, ADC Tumor Penetration, Mar. 18, 2015, vol. 10(3), pp. 1-20, E0118977.
Veiseh M., et al., "Tumor Paint: A Chlorotoxin:Cy5.5 Bioconjugate for Intraoperative Visualization of Cancer Foci," Cancer Research, Jul. 15, 2007, vol. 67(14), pp. 6882-6888.
Vincent J-P., et al., "Neurotensin and Neurotensin Receptors," Trends Pharmacological Science, Jul. 1, 1999, vol. 20(7), pp. 302-309.
Vitt U.A., et al., "Evolution and Classification of Cystine Knot-Containing Hormones and Related Extracellular Signaling Molecules," Molecular Endocrinology, May 1, 2001, vol. 15(5), pp. 681-694.
Vives E., et al., "A Truncated HIV-1 Tat Protein Basic Domain Rapidly Translocates Through the Plasma Membrane and Accumulates in the Cell Nucleus," The Journal of Biological Chemistry, Jun. 20, 1997, vol. 272(25), pp. 16010-16017.
Vordenbaumen S., et al., "Defensins Potential Effectors Autoimmune Rheumatic Disorders," Polymers, 2011, vol. 3, pp. 1268-1281.
Vyas S., et al. "Ketorolac-Dextran Conjugates: Synthesis, in Vitro and in Vivo Evaluation," Acta Pharmaceutica, Dec. 2007, vol. 57(4), pp. 441-450.
Wakankar A.A., et al., "Formulation Considerations for Proteins Susceptible to Asparagine Deamidation and Aspartate Isomerization," Journal of Pharmaceutical Sciences, Nov. 2006, vol. 95(11), pp. 2321-2336.
Wan L., et al., "Epo Promotes Bone Repair Through Enhanced Cartilaginous Callus formation and Angiogenesis," Plos One, EPO in Skeletal Regeneration, Jul. 2014, vol. 9(7), 10 Pages, E102010.
Wang P., et al., "Flavonoid Compound Icariin Activates Hypoxia Inducible Factor-1 Alpha in Chondrocytes and Promotes Articular Cartilage Repair," Plos One, Feb. 3, 2016, vol. 11(2), 24 Pages, E0148372.
Wang W., et al., "Annexin-Mediated Ca2+ Influx Regulates Growth Plate Chondrocyte Maturation and Apoptosis," The Journal of Biological Chemistry, Feb. 7, 2003, vol. 278(6), pp. 3762-3769.
Wang X., et al., "Characterization of Promoter Elements Regulating the Expression of the Human Neurotensin/Neuromedin N Gene," The Journal of Biological Chemistry, Jan. 7, 2011, vol. 286(1), pp. 542-554.
Ward M.M., et al., "American College of Rheumatology/Spondylitis Association of America/Spondyloarthritis Research and Treatment Network 2015 Recommendations for the Treatment of Ankylosing Spondylitis and Nonradiographic Axial Spondyloarthritis," Arthritis Rheumatol, Feb. 2016, vol. 68(2), pp. 282-298.
Weatherall K.L., et al., "Small Conductance Calcium-Activated Potassium Channels: from Structure to Function," Progress in Neurobiology, Jul. 2010, vol. 91(3), pp. 242-255.
Werle M., et al., "The Potential of Cystine-Knot Microproteins as Novel Pharmacophoric Scaffolds in Oral Peptide Drug Delivery," Journal of Drug Targeting, Apr. 2006, vol. 14(3), pp. 137-146.
Winn M.D., et al., "Overview of the CCP4 Suite and Current Developments," Acta Crystallographica Section D, Biological Crystallography, 2011, D67, pp. 235-242.
Winnard P.T., et al., "Development of Novel Chimeric Transmembrane Proteins for Multimodality Imaging of Cancer Cells," Cancer Biology and Therapy, Dec. 2007, vol. 6(12), pp. 1889-1899.
Wiranowska M., et al., "Clathrin-Mediated Entry and Cellular Localization of Chlorotoxin in Human Glioma," Cancer Cell International, Aug. 12, 2011, vol. 11:27, 13 pages.
Wischnjowa., et al., "Renal Targeting: Peptide-Based Drug Delivery to Proximal Tubule Cells," Bioconjugate Chemistry, Apr. 20, 2016, vol. 27(4), pp. 1050-1057. doi: 10.1021/acs.bioconjchem.6b00057. Epub Mar. 30, 2016.
Wojdasiewicz P., et al., "The Role of Inflammatory and Anti-Inflammatory Cytokines in the Pathogenesis of Osteoarthritis," Mediators of Inflammation. vol. 2014 (2014), Article ID 561459, 19 pages, http://dx.doi.org/10.1155/2014/561459.
Xiao Z., et al., "Mechanisms of Cyclosporine-Induced Renal Cell Apoptosis: A Systematic Review," American Journal of Nephrology, 2013, vol. 37, pp. 30-40, https://doi.org/10.1159/000345988.
Yamada., et al., "Internalization of Bacterial Redox Protein Azurin in Mammalian Cells: Entry domain and specificity," Cellular Microbiology, 2005, vol. 7(10), pp. 1418-1431.
Yang J., et al., "The I-TASSER Suite: Protein Structure and function Prediction," Nature Methods, Jan. 2015, vol. 12(1), pp. 7-8.
Yang M., et al., "Protein-peptide Interactions Analyzed with the Yeast Two-Hybrid System," Nucleic Acids Research, 1995, vol. 23 No. 7, pp. 1152-1156.
Ye F., et al., "The Scorpion Toxin Analogue BmKTX-D33H as a Potential Kv1. 3 Channel-selective Immunomodulator for Autoimmune Diseases," Toxins, 2016, vol. 8(4), pp. 115.
Yu R.Y., et al., "A Naturally Occurring, Soluble Antagonist of Human IL-23 Inhibits the Development and In vitro Function of human Th17 Cells," Journal Immunology, Dec. 15, 2010, vol. 185(12), pp. 7302-7308, doi: 10.4049/jimmunol.1002410, Epub Nov. 12, 2010.
Yurkovetskiy A.V., et al., "A Polymer-Based Antibody-Vinca Drug Conjugate Platform: Characterization and Preclinical Efficacy," Cancer Research, Aug. 15, 2015, vol. 75(16), pp. 3365-3372.
Zager R.A., "Marked Protection Against Acute Renal and Hepatic Injury after Nitrited Myoglobin+ tin Protoporphyrin Administration," Translational Research, 2015, vol. 166(5), pp. 485-501.
Zamli Z., et al., "Chondrocyte Apoptosis: A Cause or Consequence of Osteoarthritis?," International Journal of Rheumatic Diseases, May 2011, vol. 14(2), pp. 159-166, doi: 10.1111/j.1756-185X.2011.01618.x.
Zhang H., et al., "Tumor-Selective Proteotoxicity of Verteporfin Inhibits Colon Cancer Progression Independently of YAPI," Science Signaling, Oct. 6, 2015, vol. 8, Issue. 397(ra98), 13 pages.
Zhang Z., et al., "The Functions of BMP3 in Rabbit Articular Cartilage Repair," International Journal of Molecular Sciences, Oct. 29, 2015, vol. 16(11), pp. 25934-25946, doi: 10.3390/ijms161125937.

(56) References Cited

OTHER PUBLICATIONS

Zhao Y., et al., "Chemical Engineering of Cell Penetrating Antibodies," Journal of Immunological Methods, 2001, vol. 254, pp. 137-145.

Zhou Y., et al., "Kidney-targeted Drug Delivery Systems," Acta Pharmaceutica Sinica B, Feb. 2014, vol. 4(1), pp. 37-42, Published online Jan. 23, 2014, doi: 10.1016/j.apsb.2013.12.005.

Zhu Y., et al., "Evolutionary Origin of Inhibitor Cystine Knot Peptides," FASEB Journal, vol. 17, Jul. 3, 2003, pp. 1765-1767.

Zhu Y., et al., "Identification of a Novel Senolytic Agent, Navitoclax, Targeting the Bcl-2 family of Anti-apoptotic Factors," Aging Cell, Jun. 15, 2016, vol. 15(3), pp. 428-435, Epub Mar. 18, 2016.

Zhu Y., et al., "Precursor Nucleotide Sequence and Genomic Organization of BmTXKS1, A New Scorpion Toxin-like Peptide from Buthus martensii Karsch," Toxicon, Sep. 2001, vol. 39(9), pp. 1291-1296.

Zhu Y., et al., "The Achilles' Heel of Senescent Cells: from Transcriptome to Senolytic Drugs," Aging Cell, Aug. 2015, vol. 14(4), pp. 644-658, Epub Apr. 22, 2015.

Biological Science, 2/e, Pearson Prentice Hall, Inc., Figure 3-5, 2005, 1 page.

* cited by examiner

FIG. 1

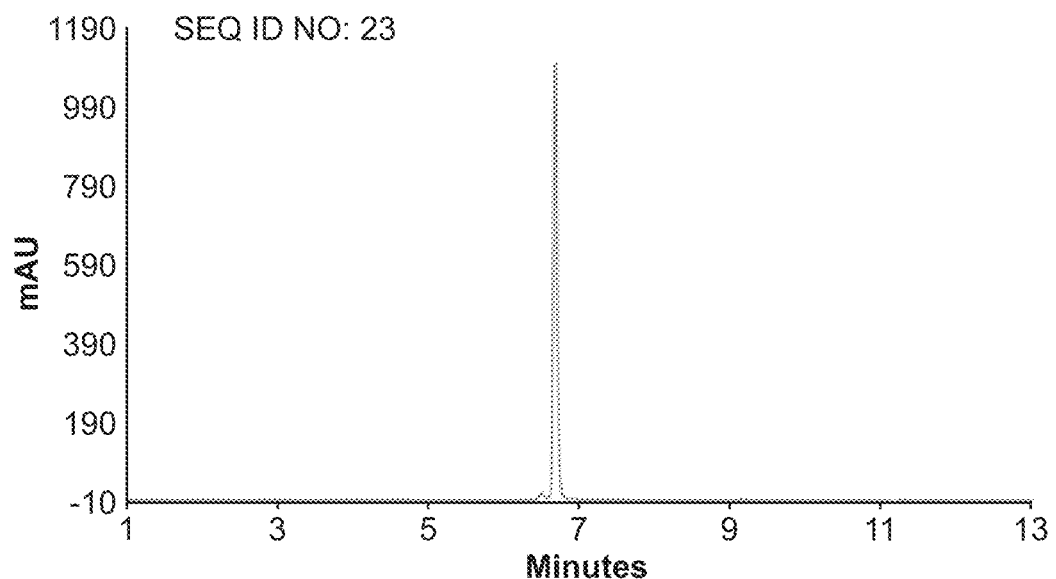
FIG. 6A
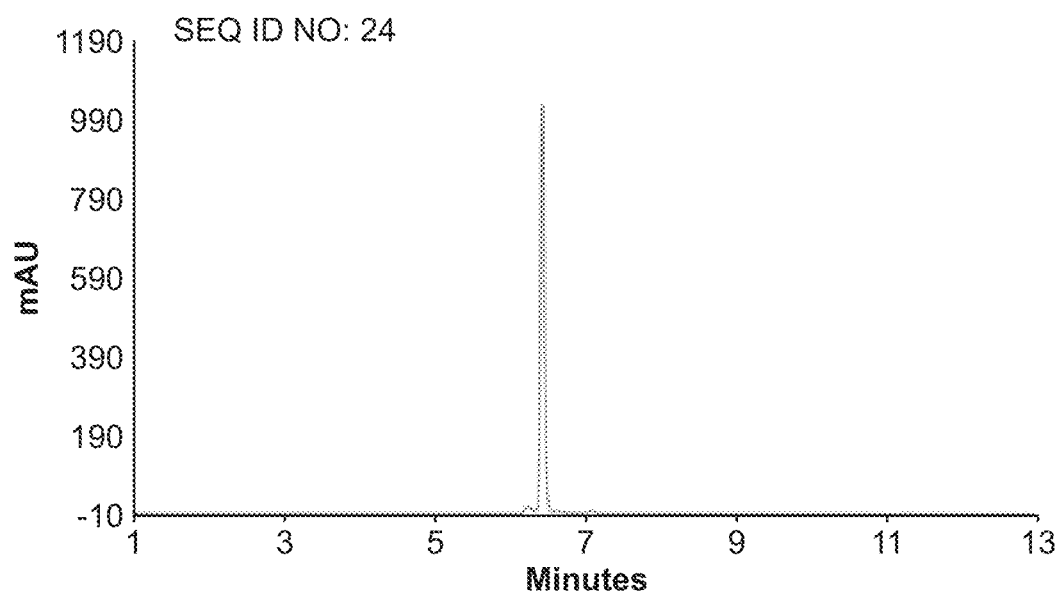
FIG. 6B
FIG. 6

Construct 1

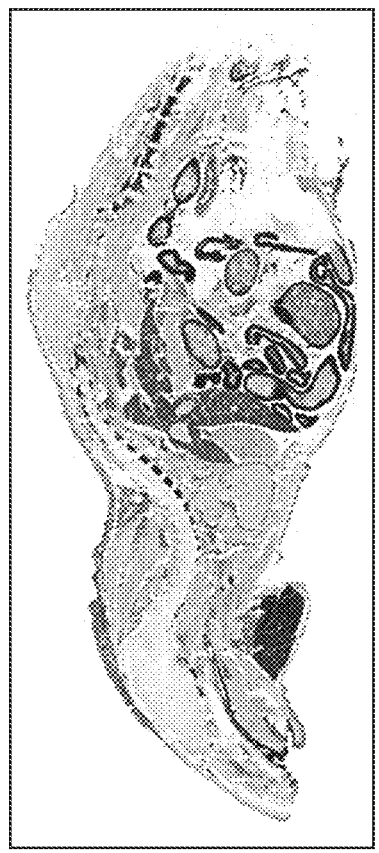
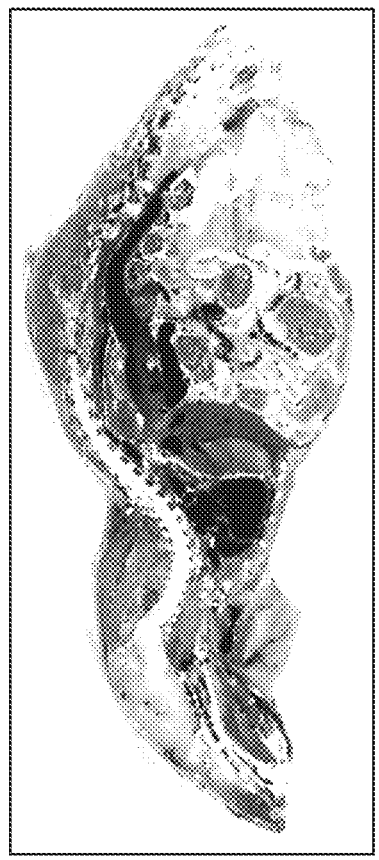
FIG. 11A
FIG. 11B
FIG. 11

```
GSXVXXXVKCXGSKQCXXPCKRXXGXRXGKCINKKXCKCYXXX    SEQ ID NO: 9
GSGVPINVKCRGSRDCLDPCKKA--GMRFGKCINSK-CHCTP---  SEQ ID NO: 24
GS-VRIPVSCKHSGQCLKPCKDA--GMRFGKCMNGK-CDCTPK--  SEQ ID NO: 23
GSQVQTNVKCQGGS-CASVCRREIGVAAGKCINGK-CVCYRN--   SEQ ID NO: 27
GS----ISCTGSKQCYDPCKRKTGCPNAKCMNKS-CKCYGCG     SEQ ID NO: 26
GSEV---IRCSGSKQCYGPCKQQTGCTNSKCMNKV-CKCYGCG    SEQ ID NO: 28
GSAVCVYRT------CDKDCKRR-GYRSGKCINNA-CKCYPYG    SEQ ID NO: 25
GS----GIVC---KVCKIICGMQ-GKKVNICKAPIKCKCKKG-    SEQ ID NO: 21
GSQIYTSKECNGSSECYSHCEGITGKRSGKCINKK-CYCYR--    SEQ ID NO: 30

GSXXXGCVXXXXKCRPGXKKXCCXPXKRCSRRFGXXXKKCKXXXXX SEQ ID NO: 10
GS---ACKGVFDACTPGKNECC-PNRVCSDK-H----KWCKWKL-- SEQ ID NO: 29
GS---GCLEFWWKCNPNDDKCCRPKLKCSKLF----KLCNFSFG-- SEQ ID NO: 31
GSSEKDCIKHLQRCR-ENKDCC---SKKCSRR-GTNPEKRCR---- SEQ ID NO: 22
GS---GCFGY--KCDYY-KGCCSGYV-CSPTW----KWCVRPGPGR SEQ ID NO: 33
```

FIG. 12

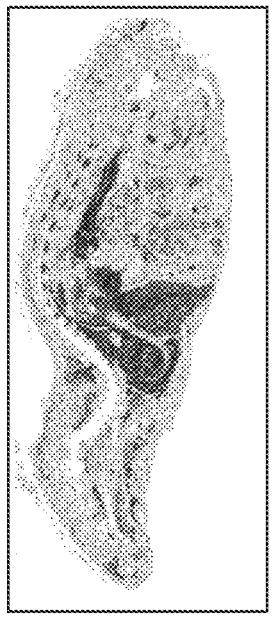
FIG. 13A
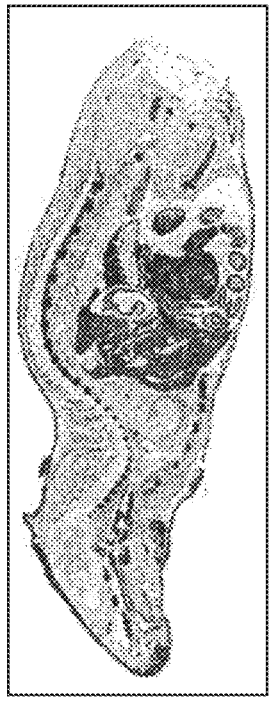
FIG. 13B
FIG. 13

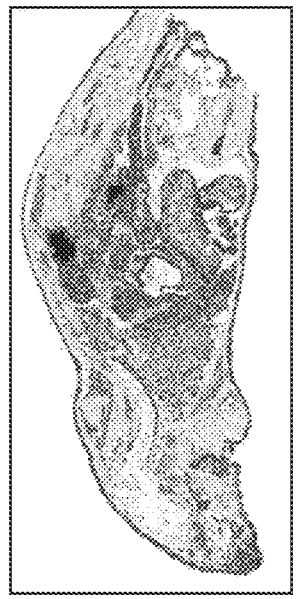
FIG. 14B
FIG. 14A
FIG. 14

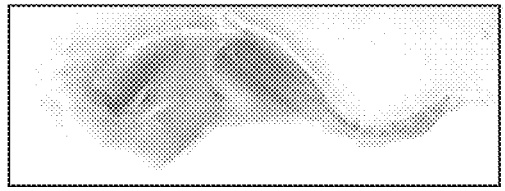
FIG. 15A
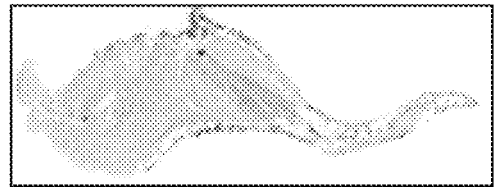
FIG. 15B
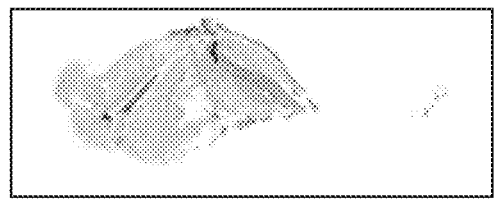
FIG. 15C
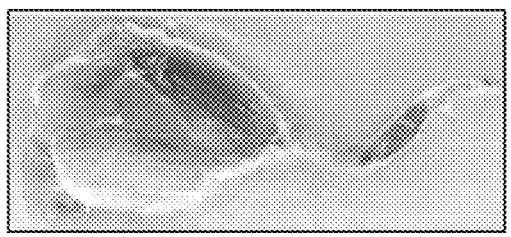
FIG. 15D
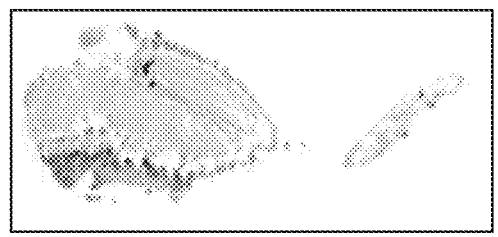
FIG. 15E
FIG. 15F
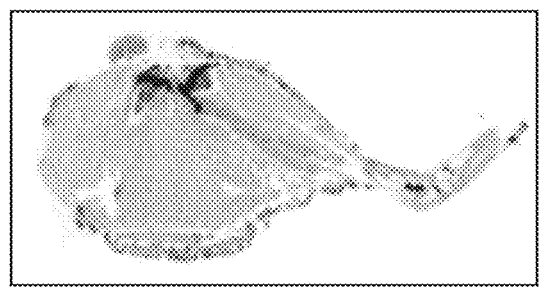
FIG. 15G
FIG. 15

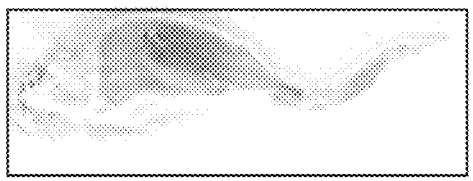
FIG. 16A
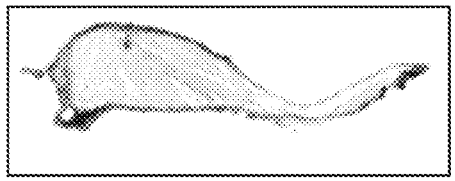
FIG. 16B
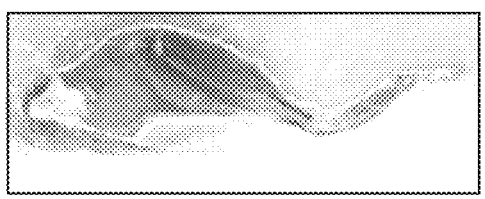
FIG. 16C
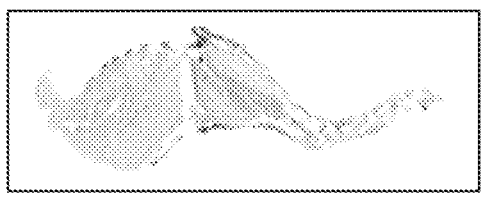
FIG. 16D
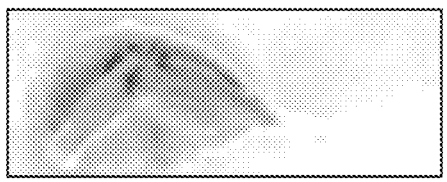
FIG. 16E
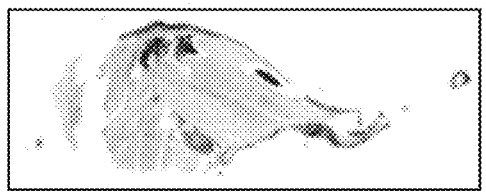
FIG. 16F
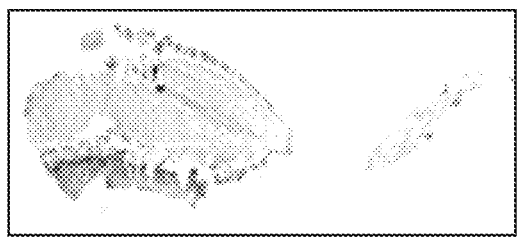
FIG. 16G
FIG. 16

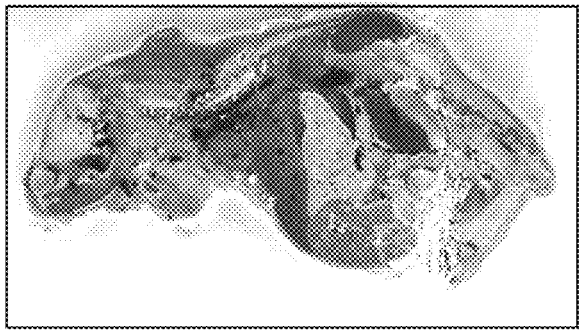
FIG. 17A
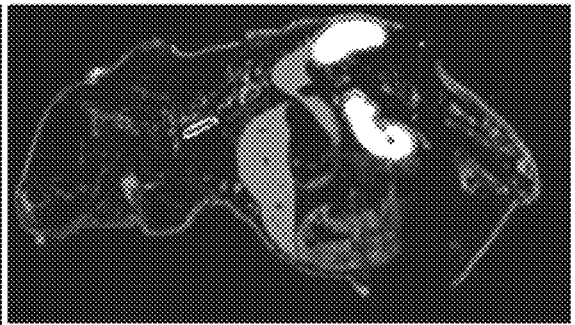
FIG. 17B
FIG. 17C
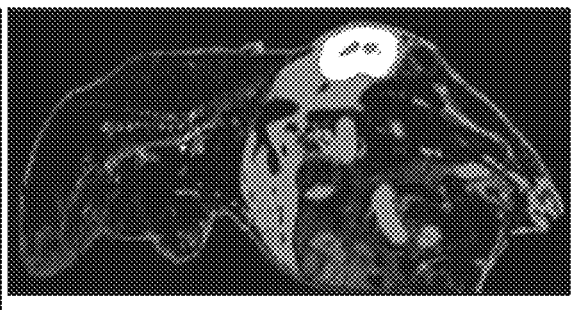
FIG. 17D
FIG. 17E
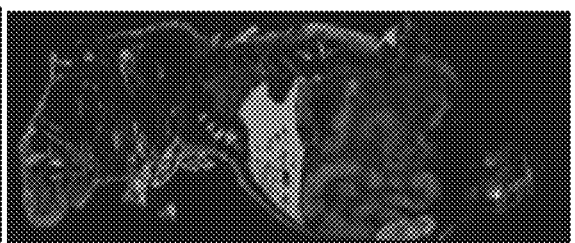
FIG. 17F
FIG. 17

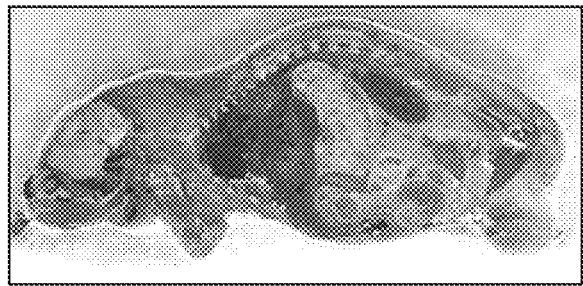
FIG. 18A
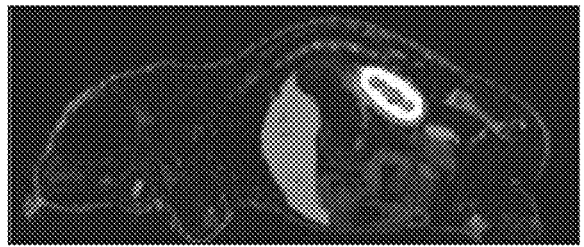
FIG. 18B
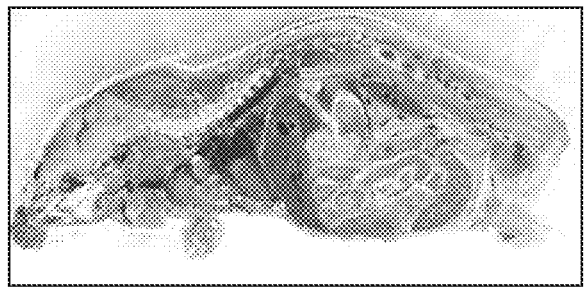
FIG. 18C
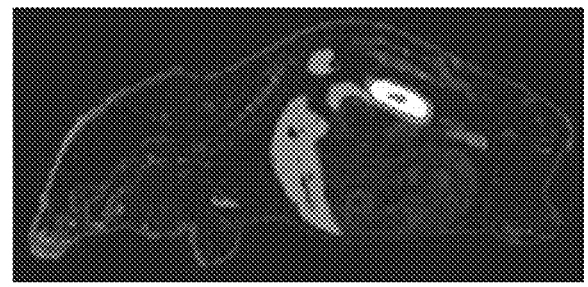
FIG. 18D
FIG. 18E
FIG. 18F
FIG. 18

FIG. 19A
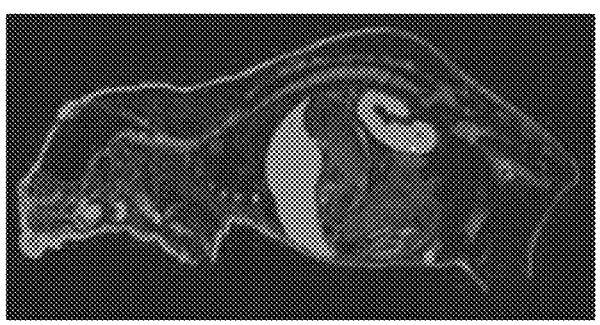
FIG. 19B
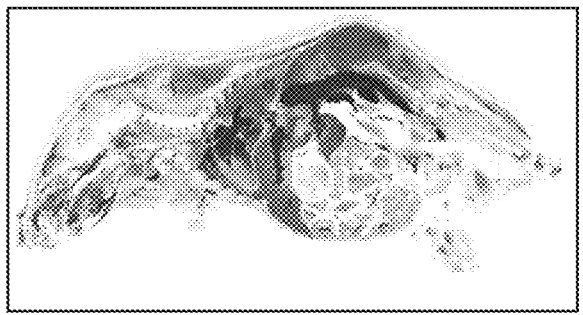
FIG. 19C
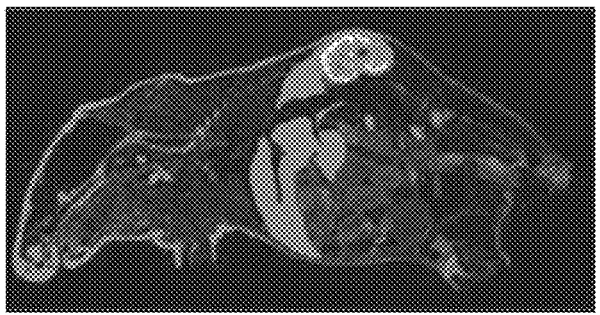
FIG. 19D
FIG. 19

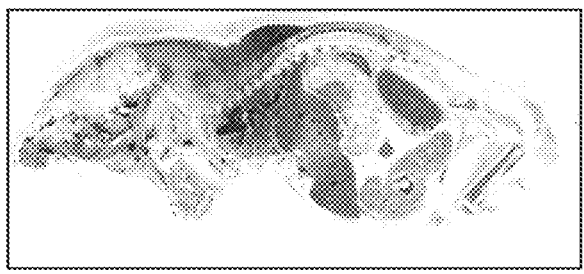
FIG. 20A
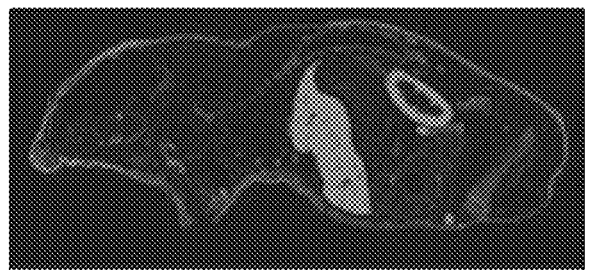
FIG. 20B
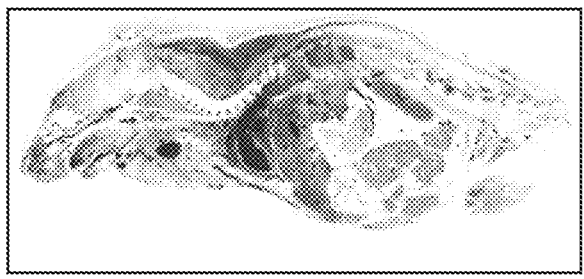
FIG. 20C
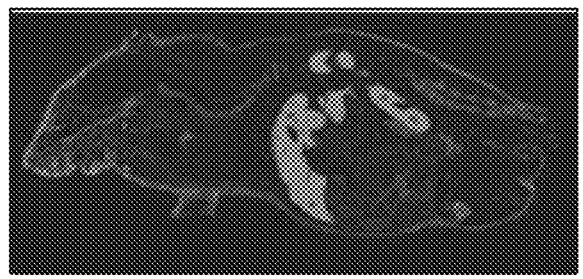
FIG. 20D
FIG. 20

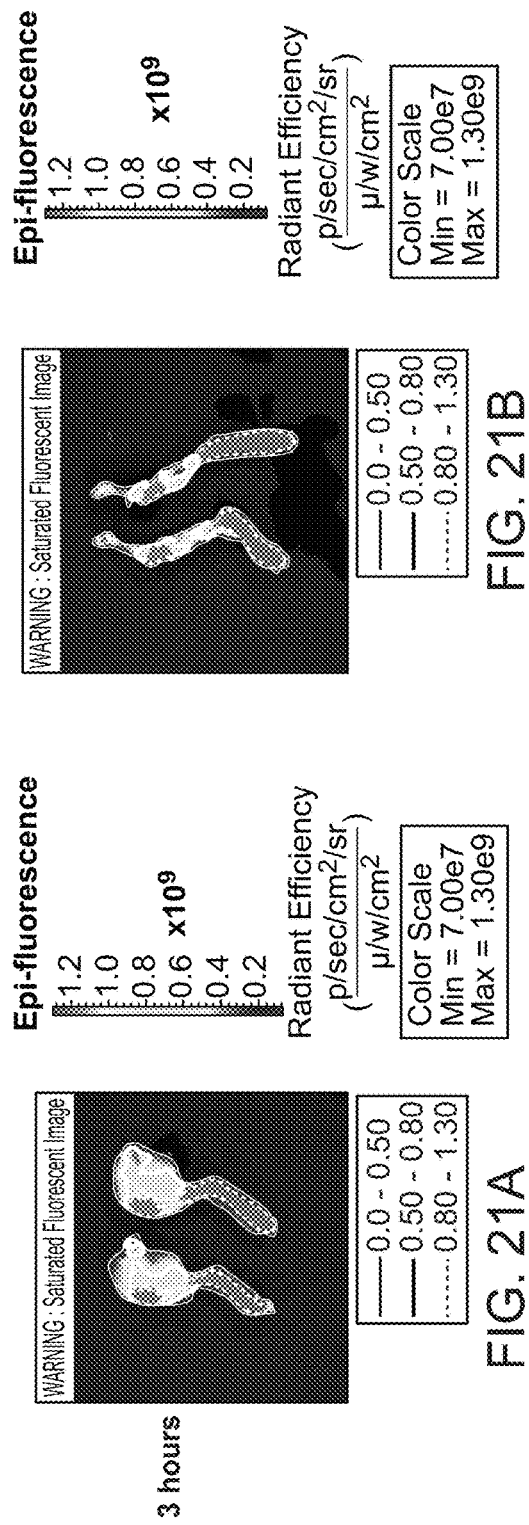
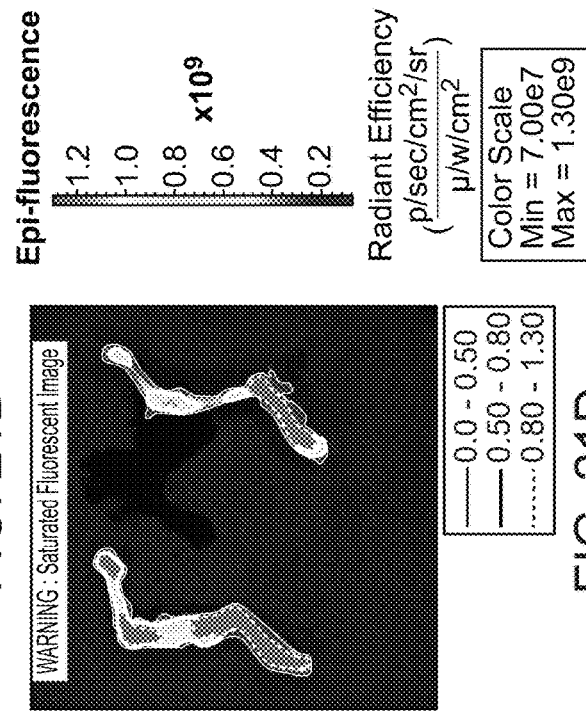
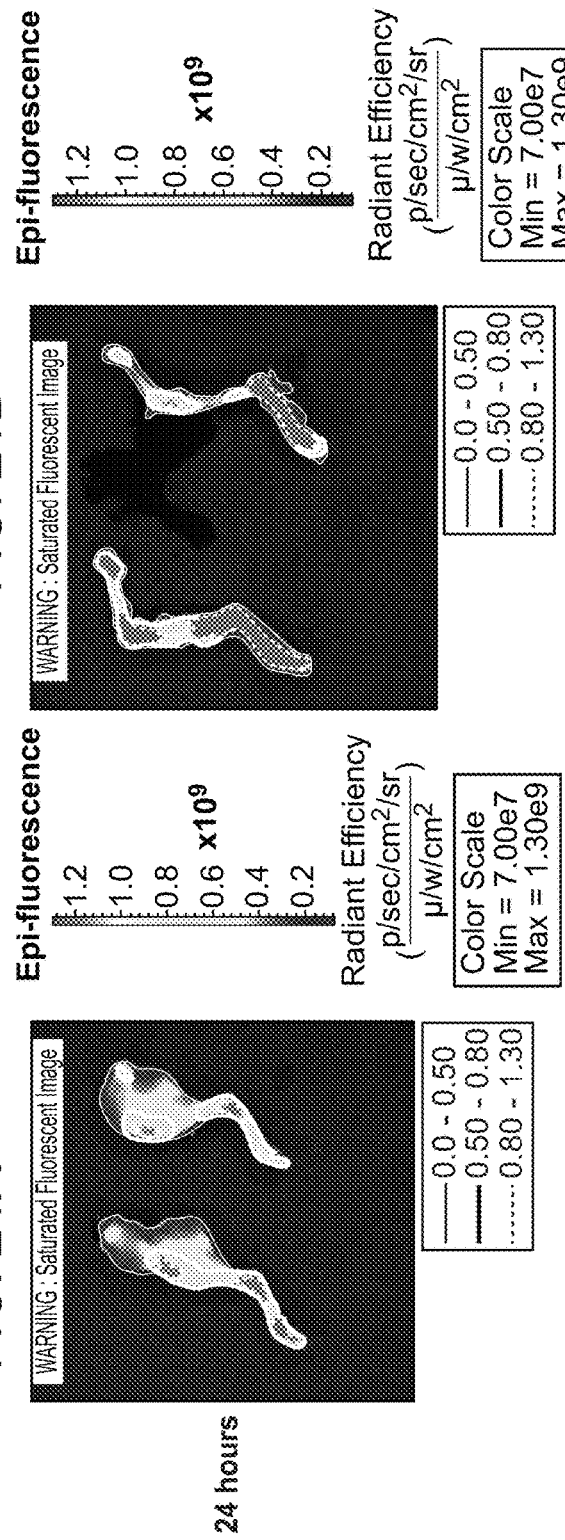
FIG. 21A  FIG. 21B  FIG. 21C  FIG. 21D
FIG. 21

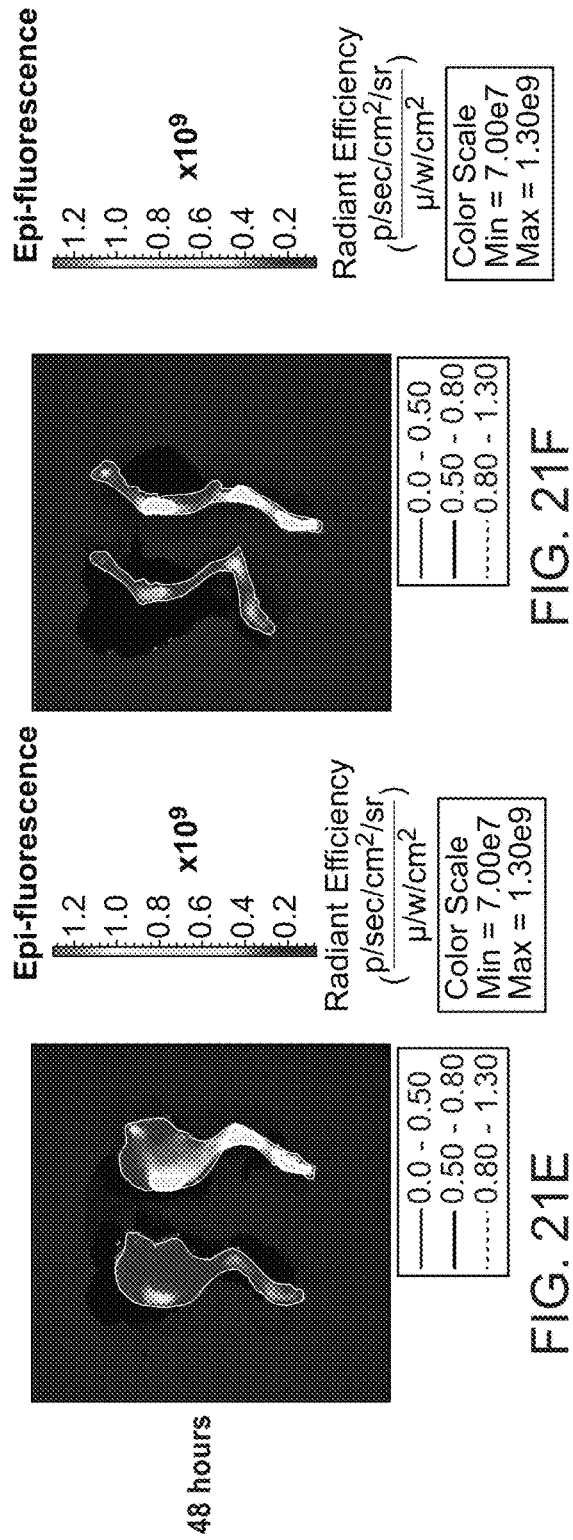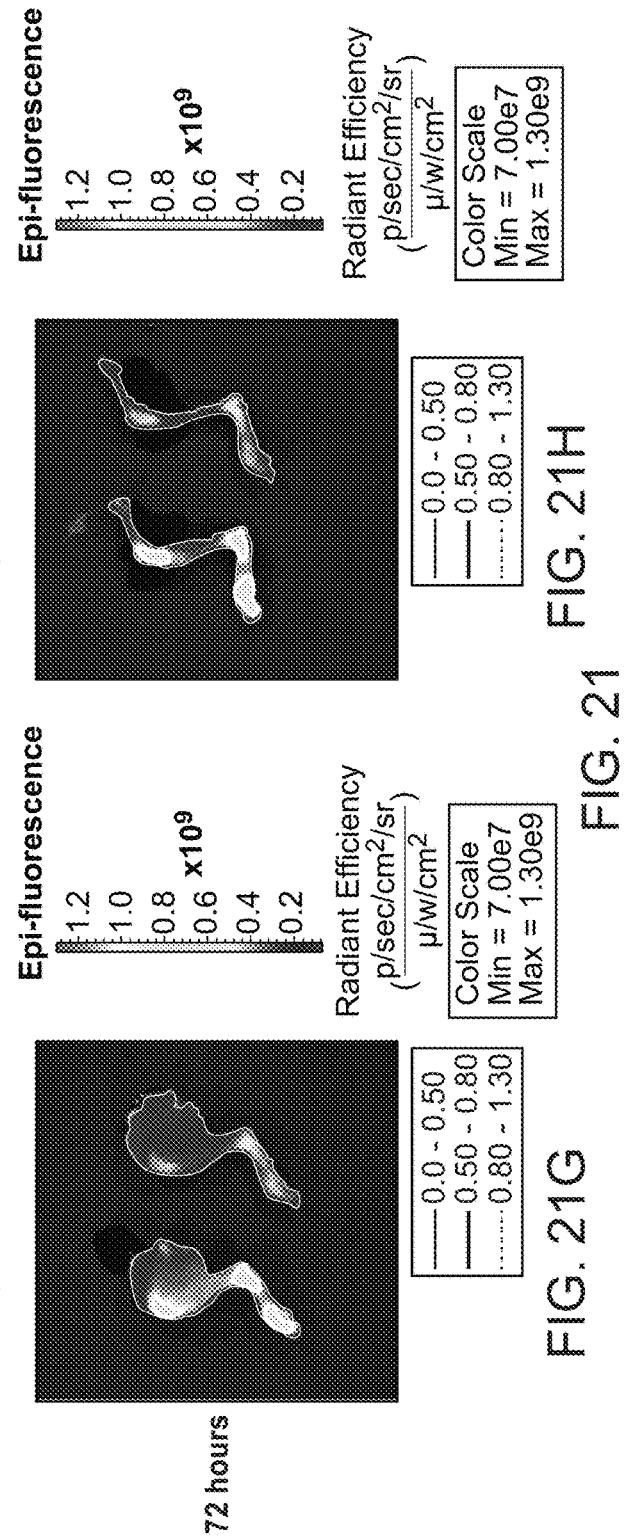
FIG. 21E  FIG. 21F  FIG. 21G  FIG. 21H  FIG. 21

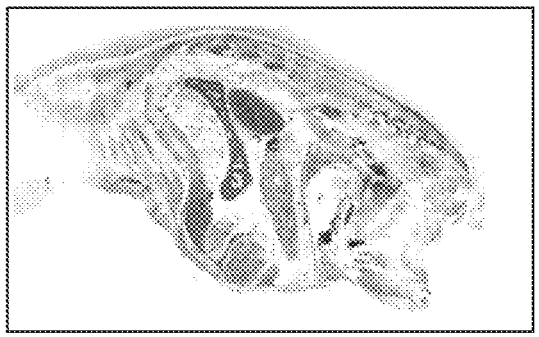
FIG. 22A
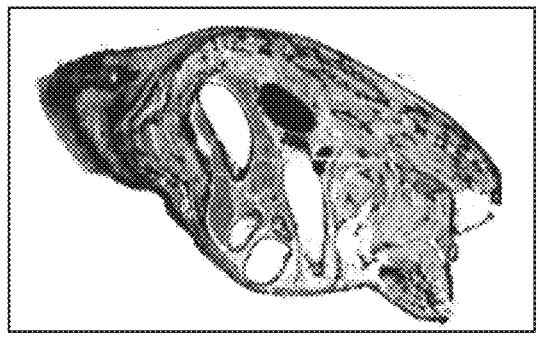
FIG. 22B
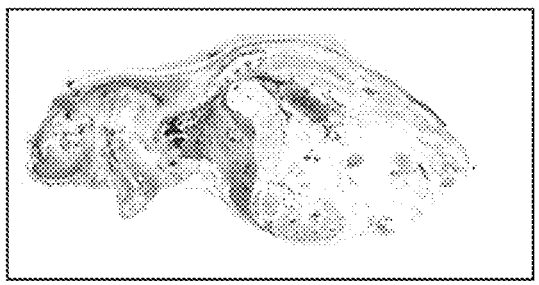
FIG. 22C
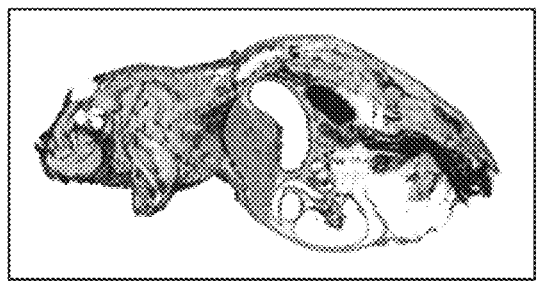
FIG. 22D
FIG. 22E
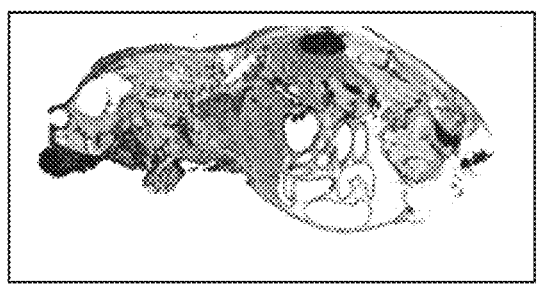
FIG. 22F
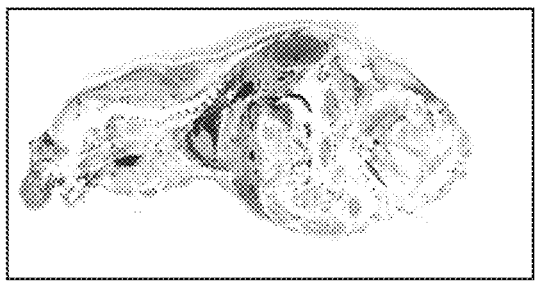
FIG. 22G
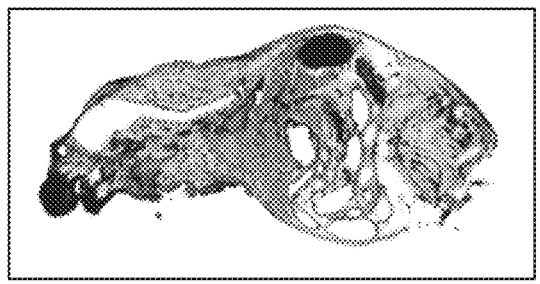
FIG. 22H
FIG. 22

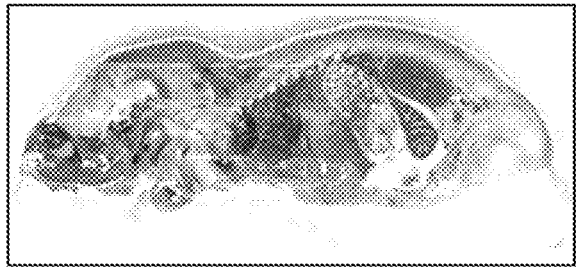
FIG. 23A
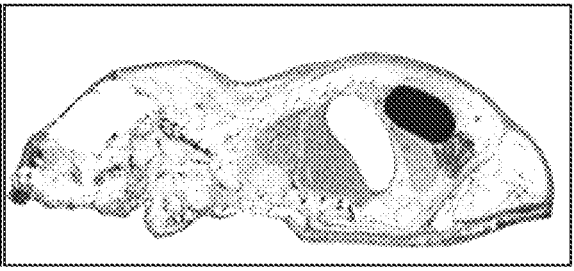
FIG. 23B
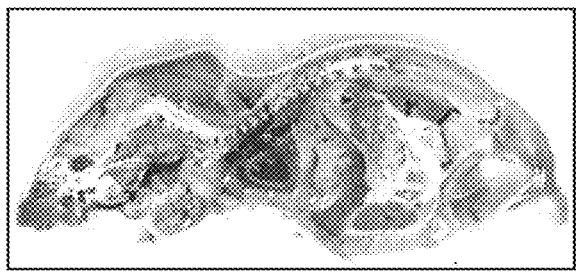
FIG. 23C
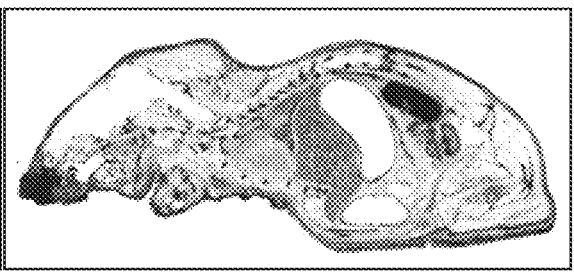
FIG. 23D
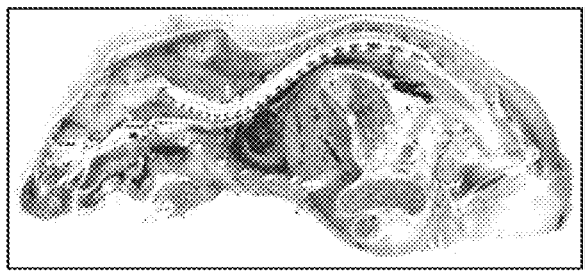
FIG. 23E
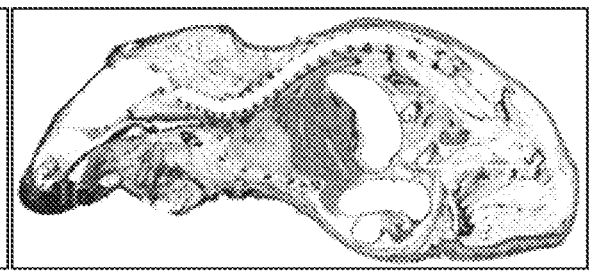
FIG. 23F
FIG. 23

FIG. 24A
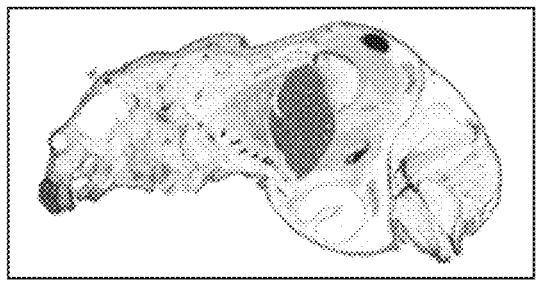
FIG. 24B
FIG. 24C
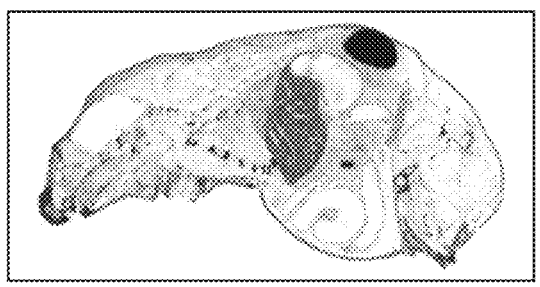
FIG. 24D
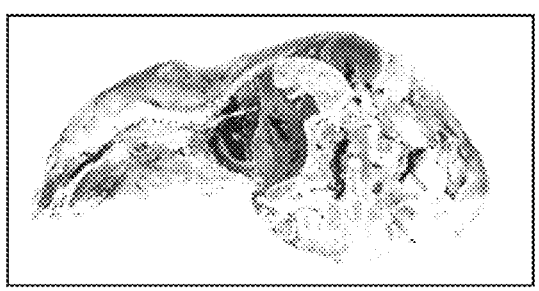
FIG. 24E
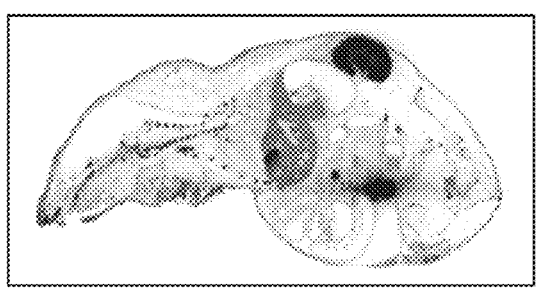
FIG. 24F
FIG. 24G
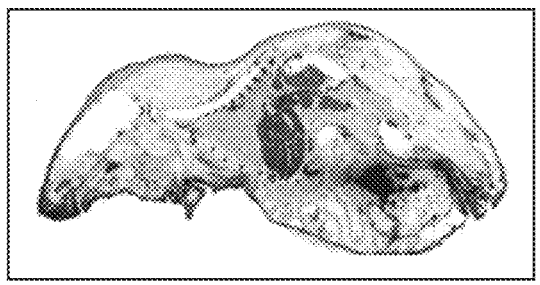
FIG. 24H
FIG. 24

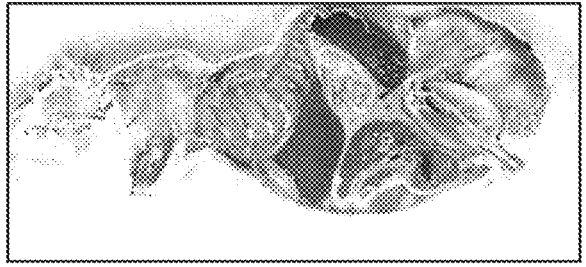
FIG. 25A
FIG. 25B
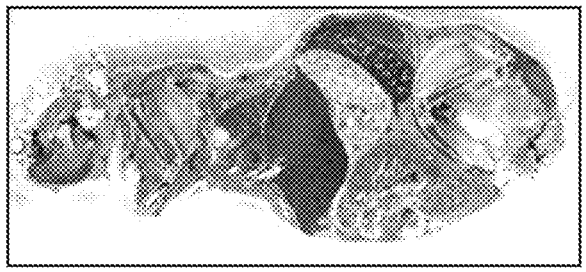
FIG. 25C
FIG. 25D
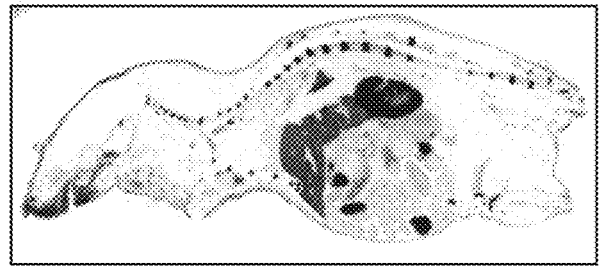
FIG. 25E
FIG. 25

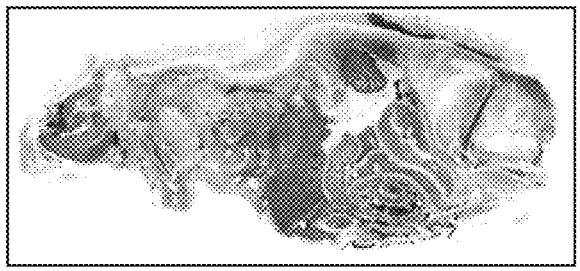
FIG. 26A
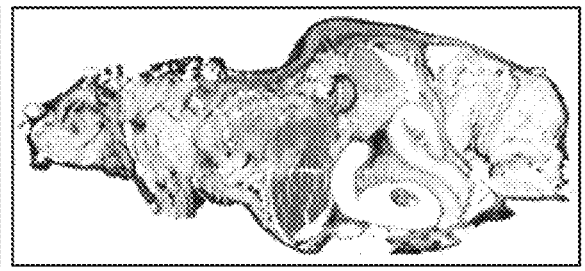
FIG. 26B
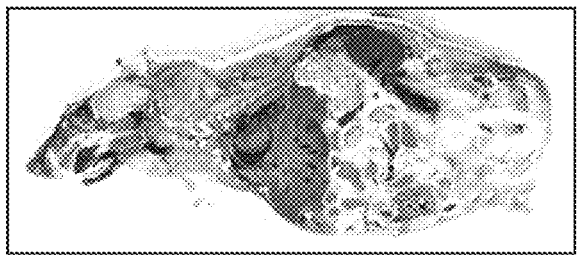
FIG. 26C
FIG. 26D
FIG. 26E
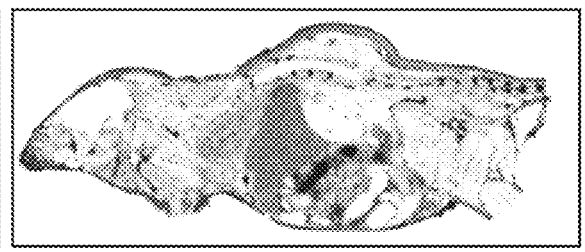
FIG. 26F
FIG. 26

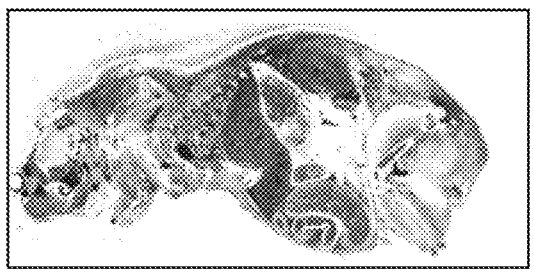
FIG. 27A
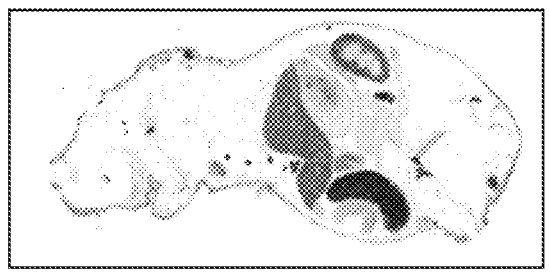
FIG. 27B
FIG. 27C
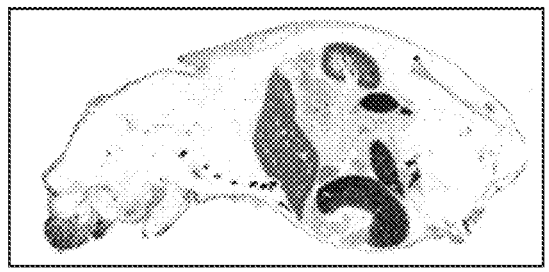
FIG. 27D
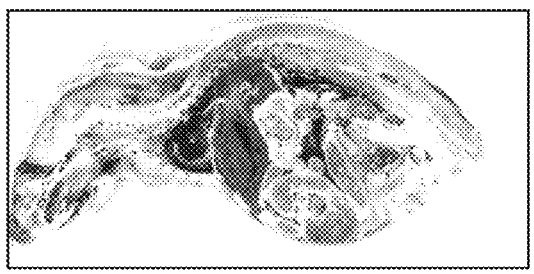
FIG. 27E
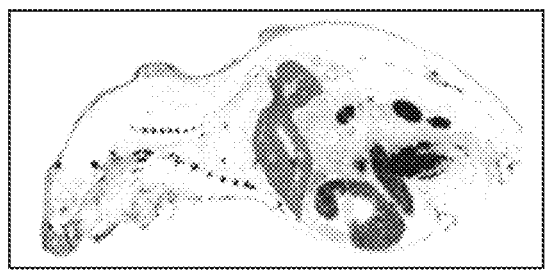
FIG. 27F
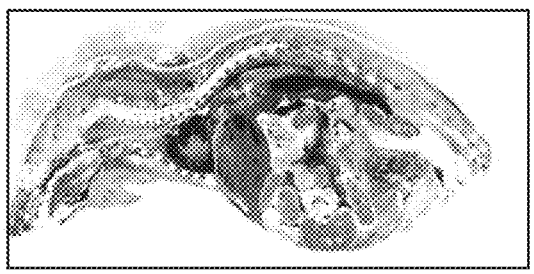
FIG. 27G
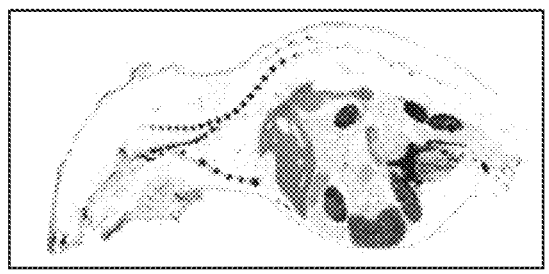
FIG. 27H
FIG. 27

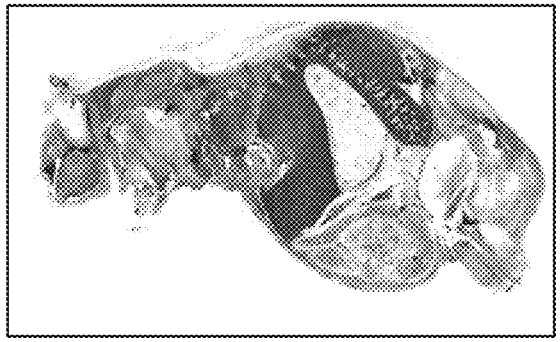
FIG. 28A
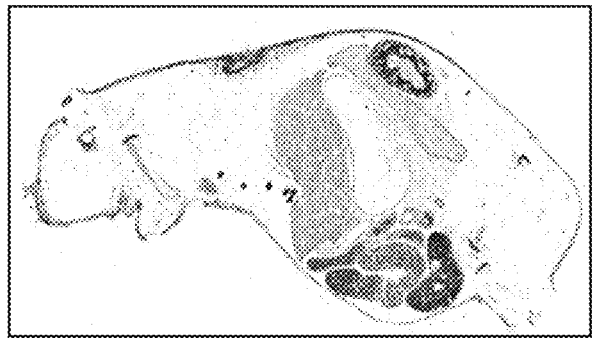
FIG. 28B
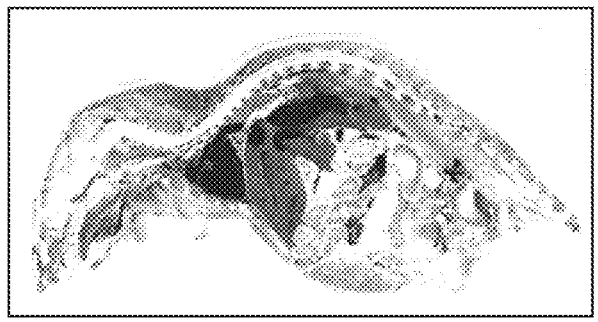
FIG. 28C
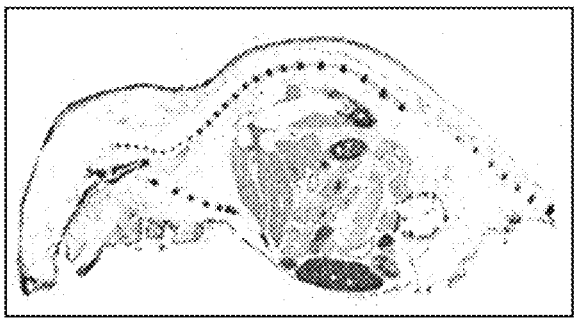
FIG. 28D
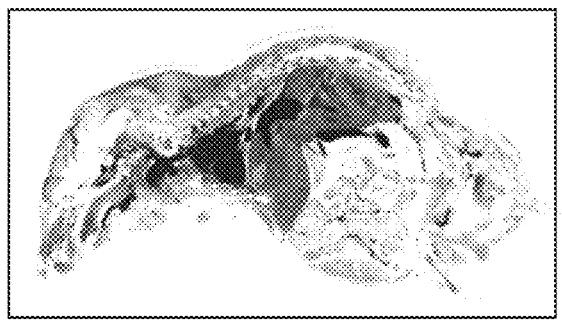
FIG. 28E
FIG. 28F
FIG. 28

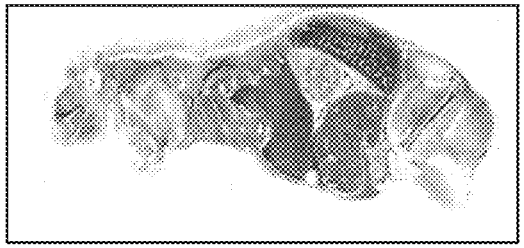
FIG. 29A
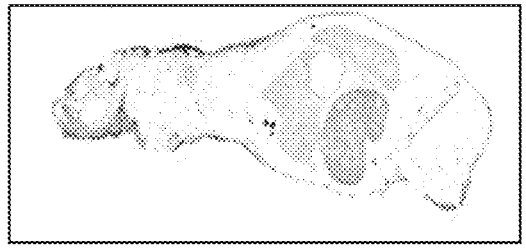
FIG. 29B
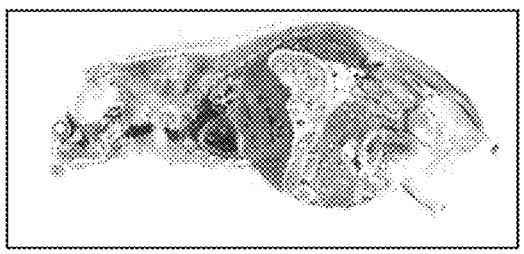
FIG. 29C
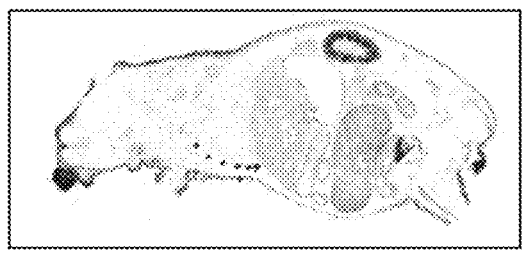
FIG. 29D
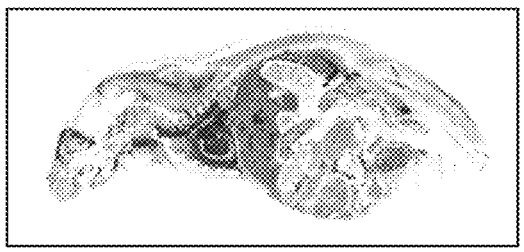
FIG. 29E
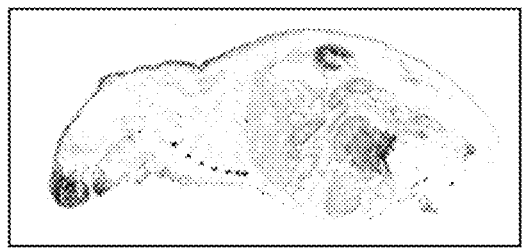
FIG. 29F
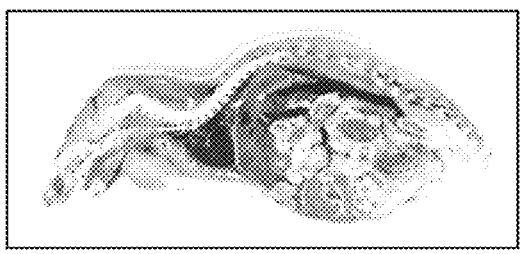
FIG. 29G
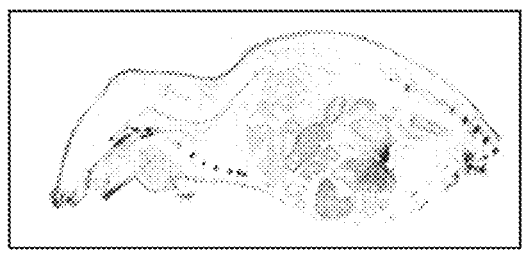
FIG. 29H
FIG. 29

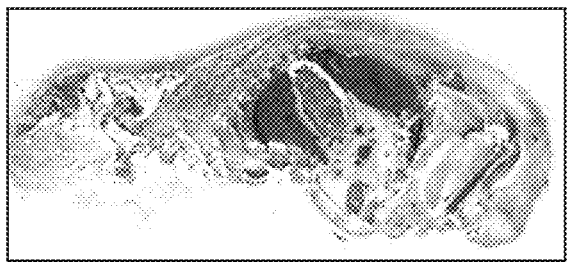
FIG. 30A
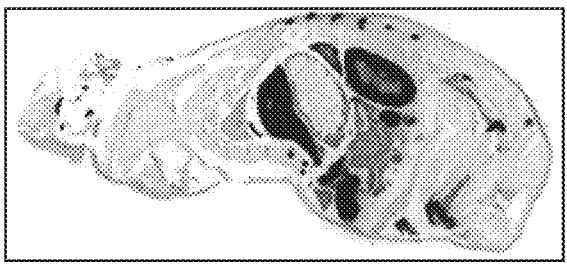
FIG. 30B
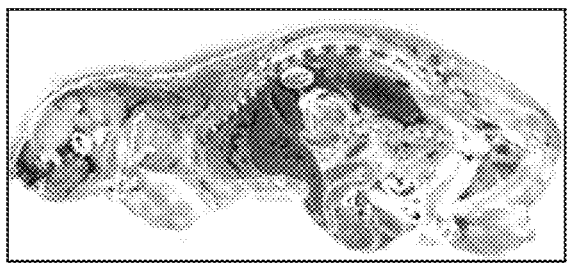
FIG. 30C
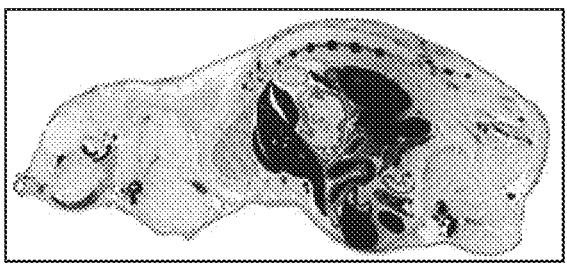
FIG. 30D
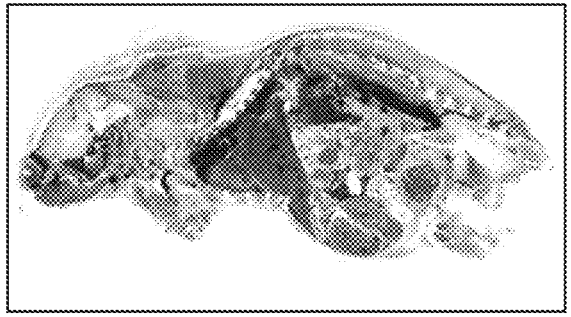
FIG. 30E
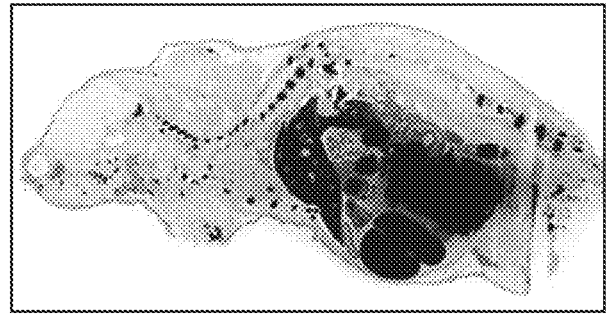
FIG. 30F
FIG. 30

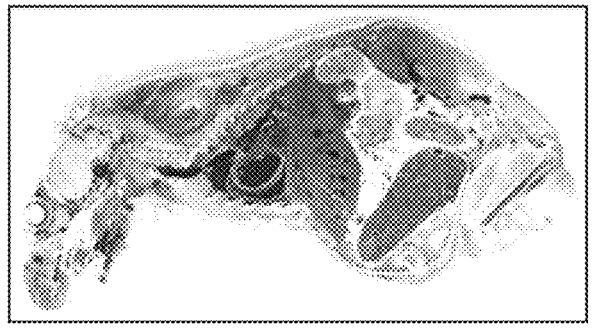
FIG. 31A
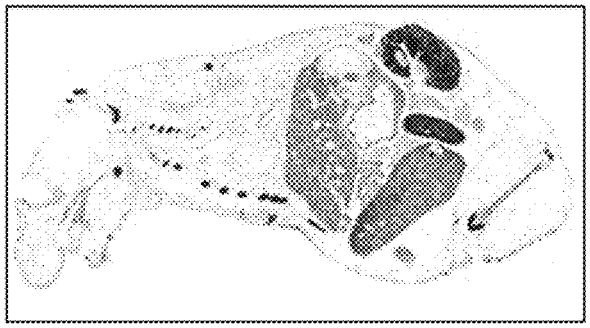
FIG. 31B
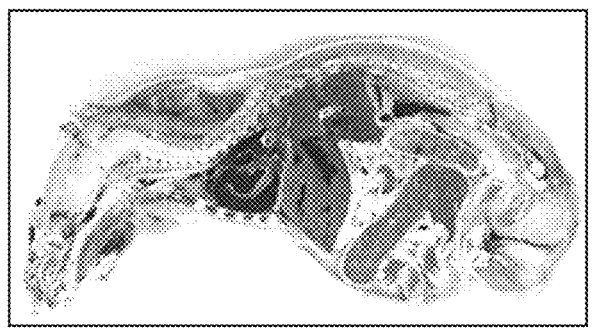
FIG. 31C
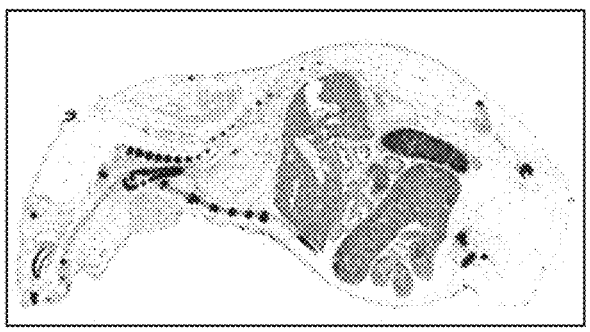
FIG. 31D
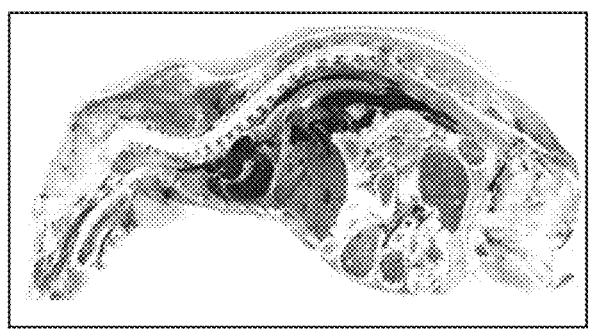
FIG. 31E
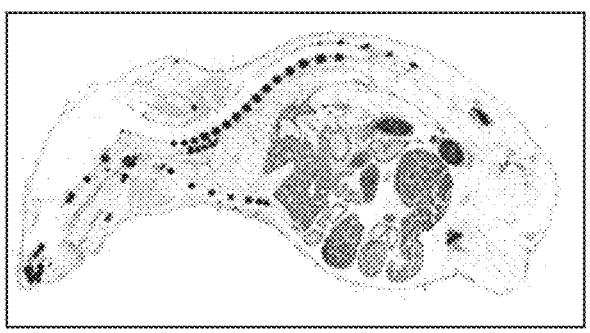
FIG. 31F
FIG. 31

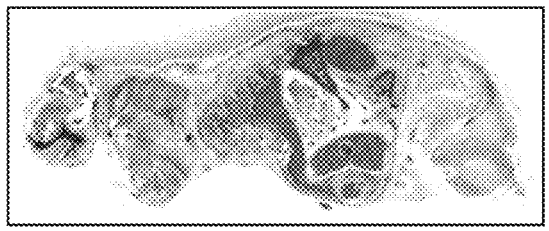
FIG. 32A
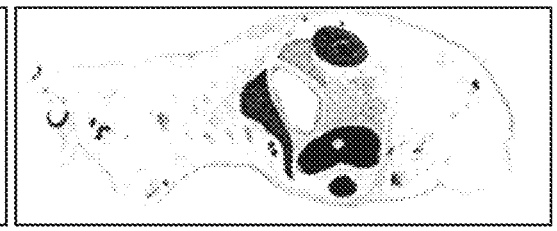
FIG. 32B
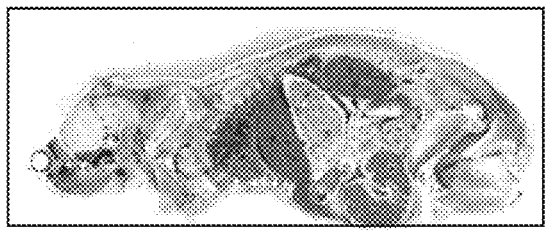
FIG. 32C
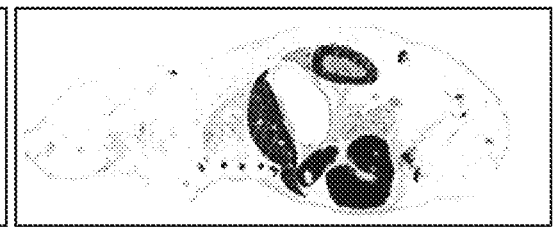
FIG. 32D
FIG. 32E
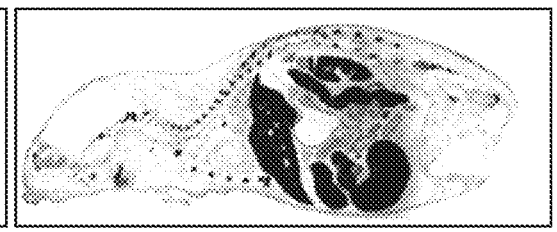
FIG. 32F
FIG. 32G
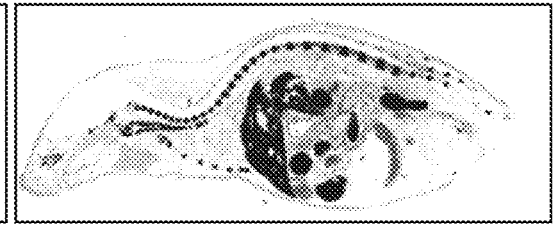
FIG. 32H
FIG. 32

FIG. 33A
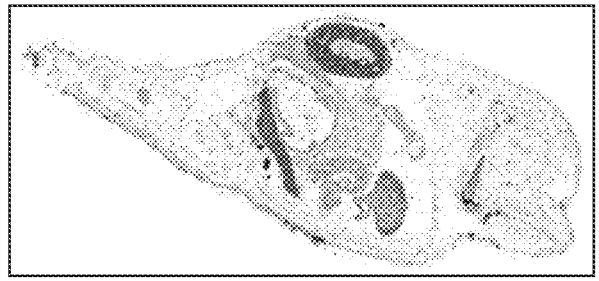
FIG. 33B
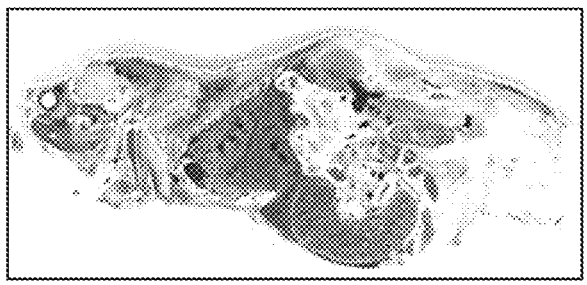
FIG. 33C
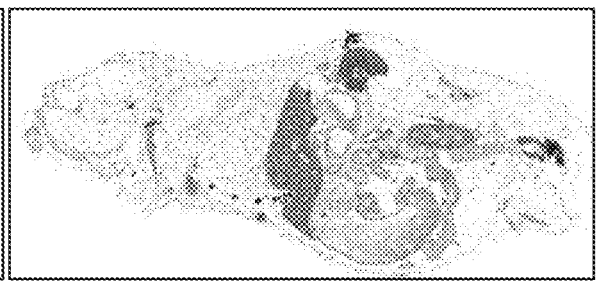
FIG. 33D
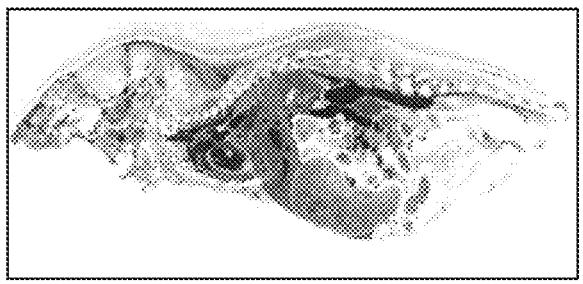
FIG. 33E
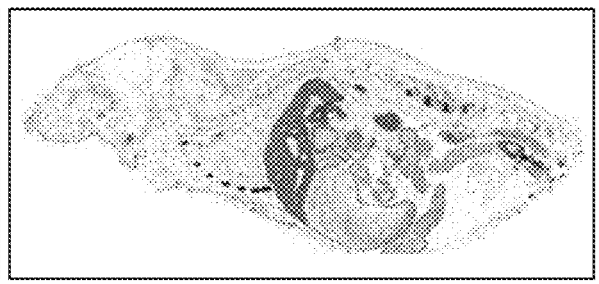
FIG. 33F
FIG. 33

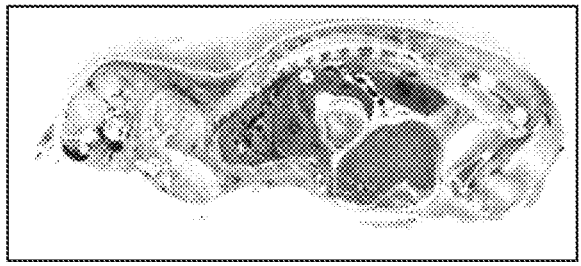
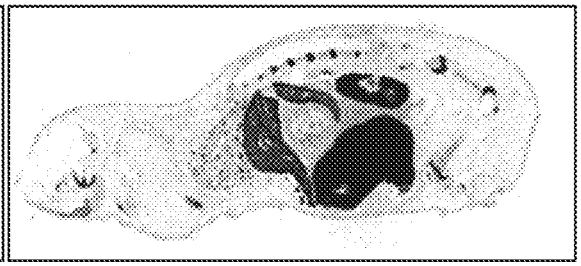
FIG. 34A  FIG. 34B
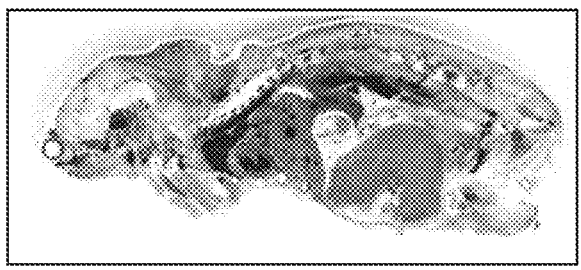
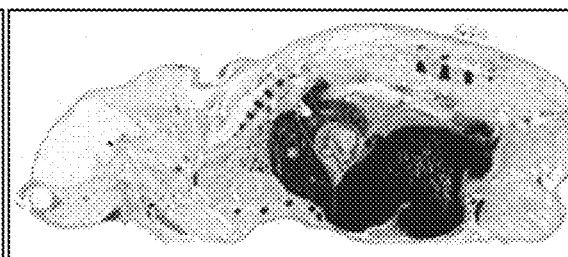
FIG. 34C  FIG. 34D
FIG. 34E  FIG. 34F
FIG. 34

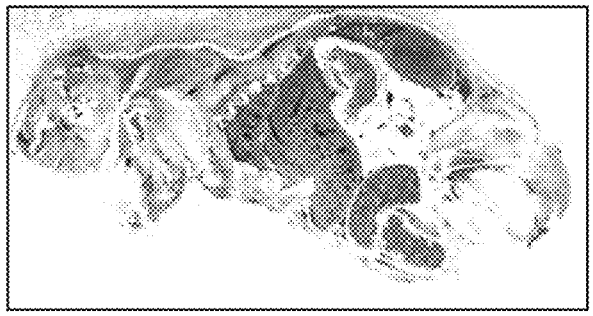
FIG. 35A
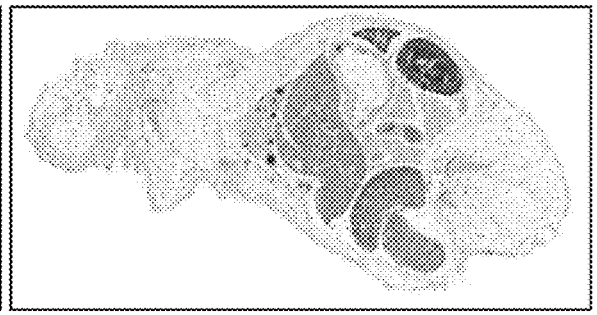
FIG. 35B
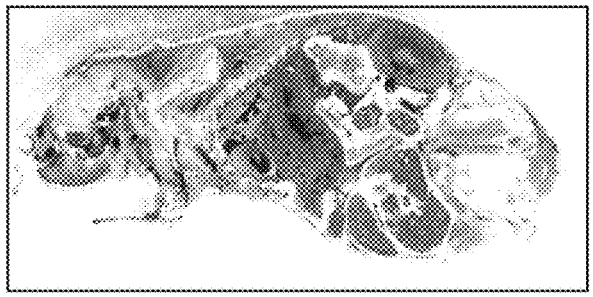
FIG. 35C
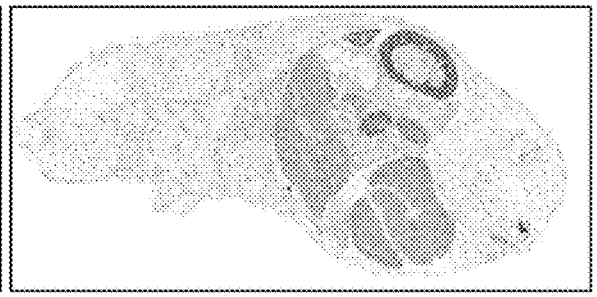
FIG. 35D
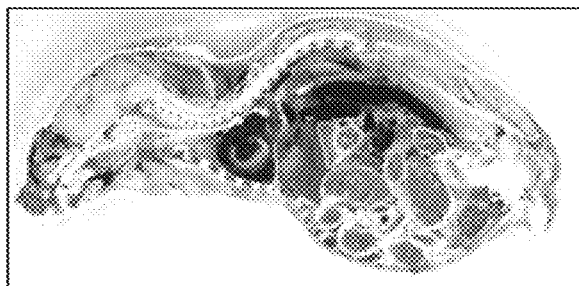
FIG. 35E
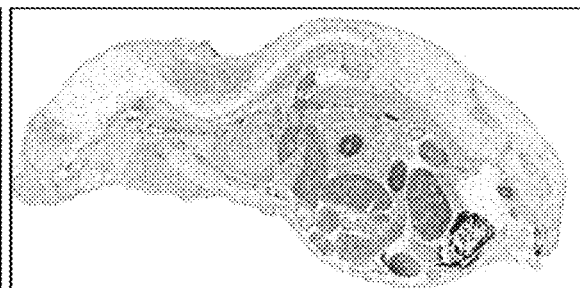
FIG. 35F
FIG. 35

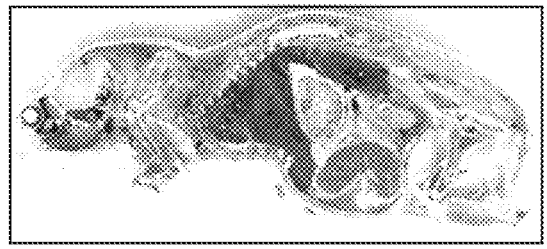
FIG. 36A
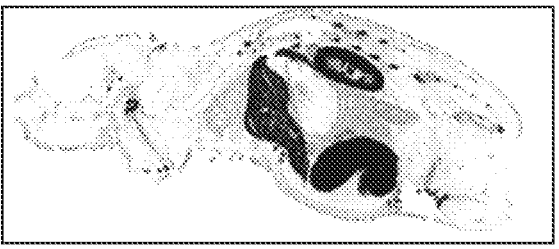
FIG. 36B
FIG. 36C
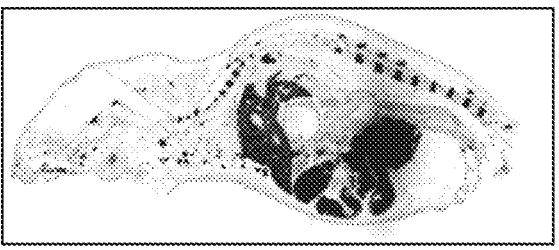
FIG. 36D
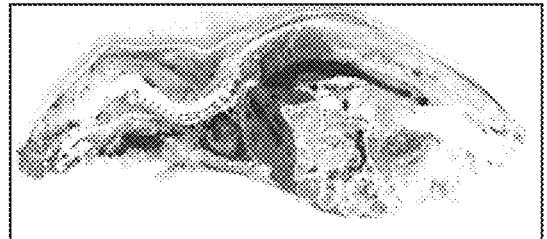
FIG. 36E
FIG. 36F
FIG. 36

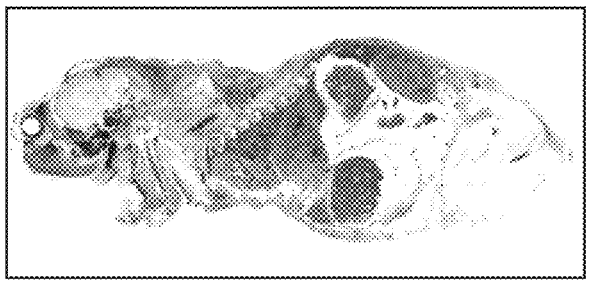
FIG. 37A
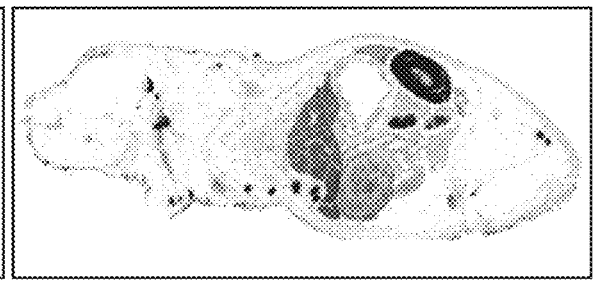
FIG. 37B
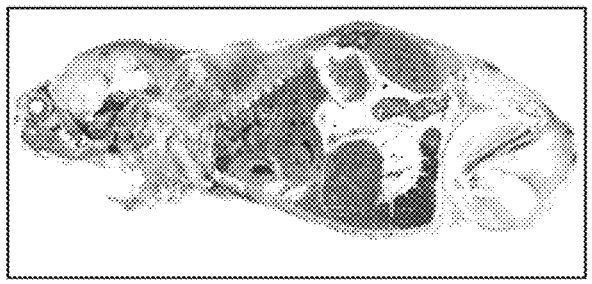
FIG. 37C
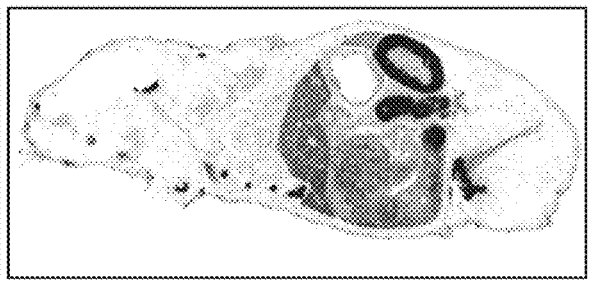
FIG. 37D
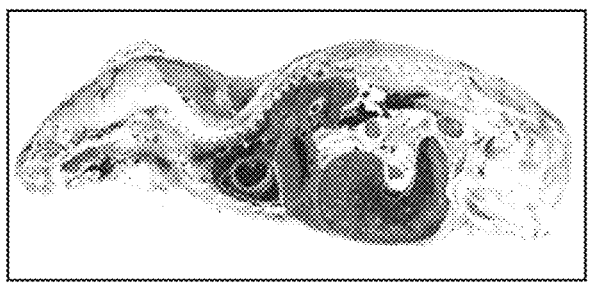
FIG. 37E
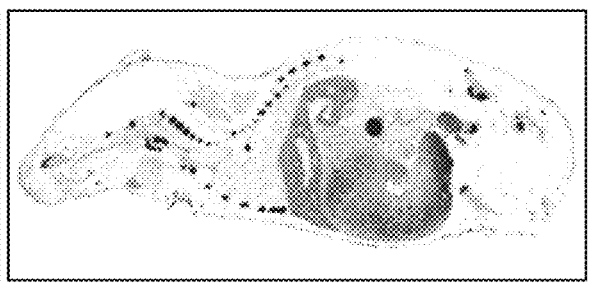
FIG. 37F
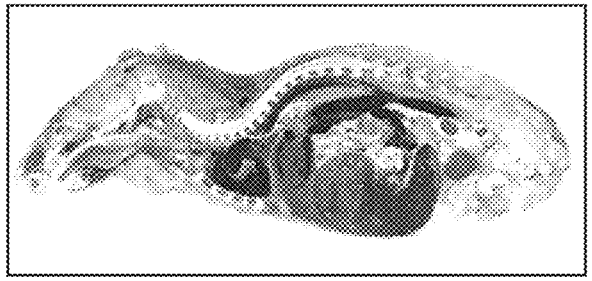
FIG. 37G
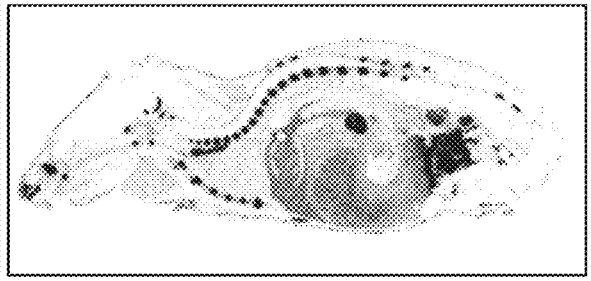
FIG. 37H
FIG. 37

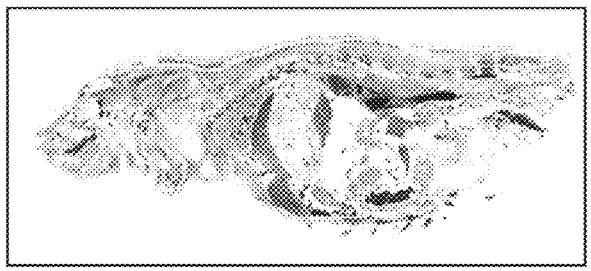
FIG. 38A
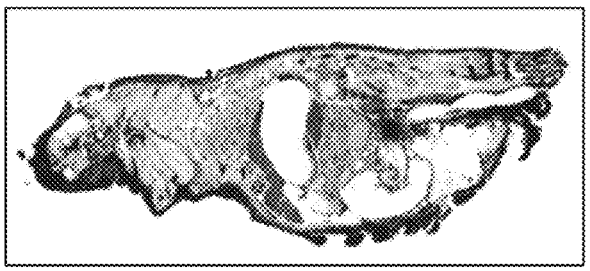
FIG. 38B
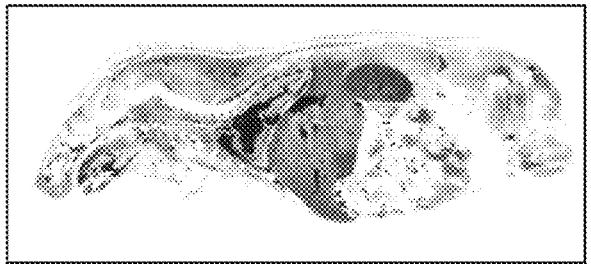
FIG. 38C
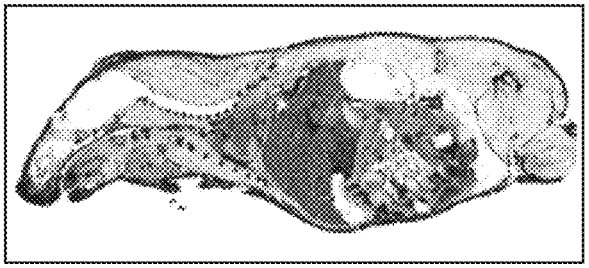
FIG. 38D
FIG. 38

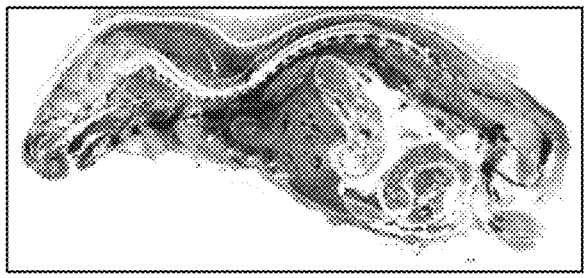
FIG. 39A
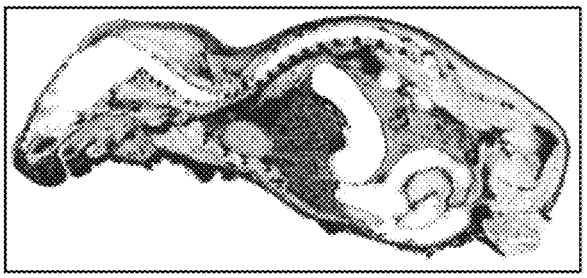
FIG. 39B
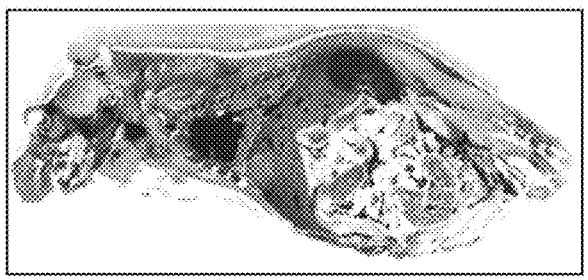
FIG. 39C
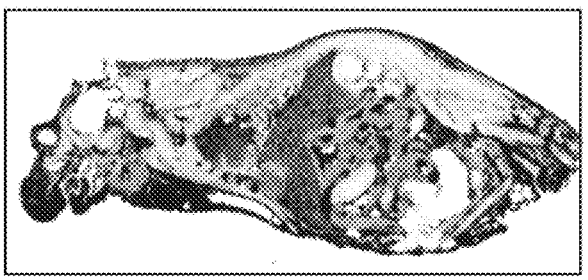
FIG. 39D
FIG. 39

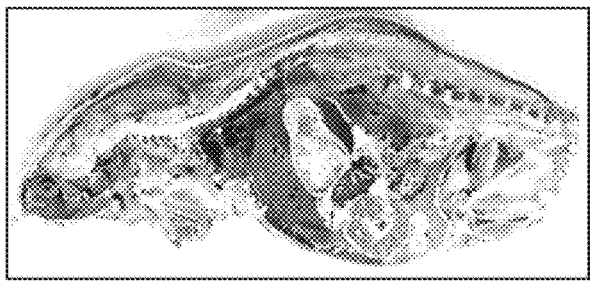
FIG. 40A
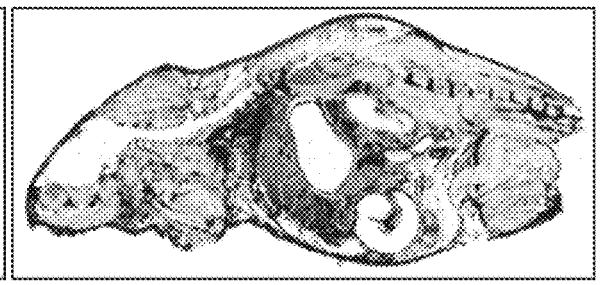
FIG. 40B
FIG. 40C
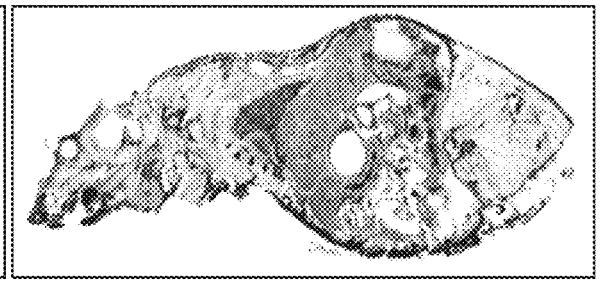
FIG. 40D
FIG. 40

FIG. 41A
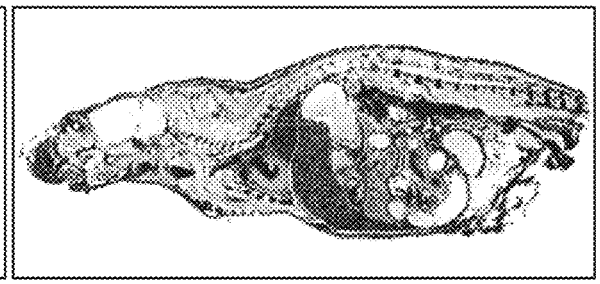
FIG. 41B
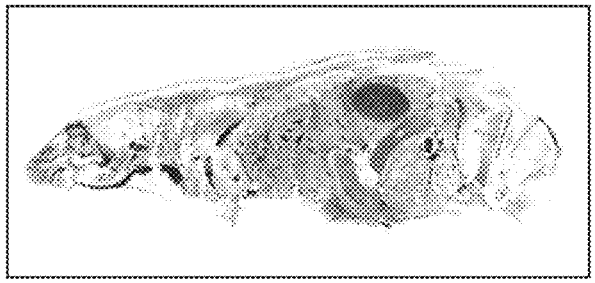
FIG. 41C
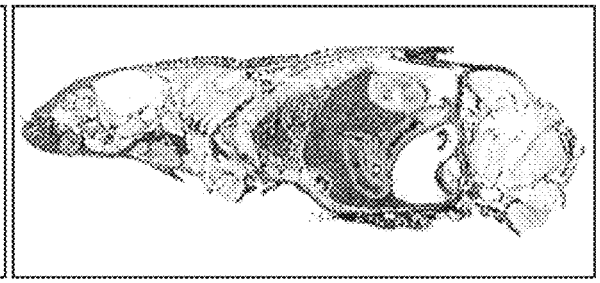
FIG. 41D
FIG. 41

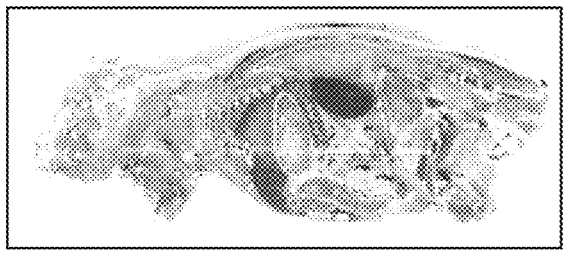
FIG. 42A
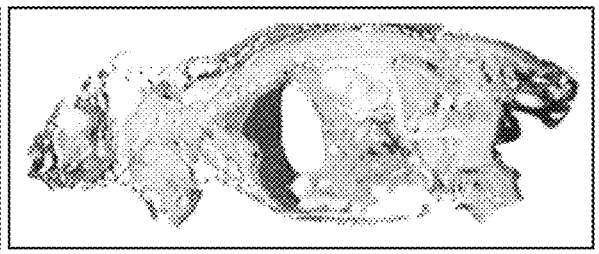
FIG. 42B
FIG. 42C
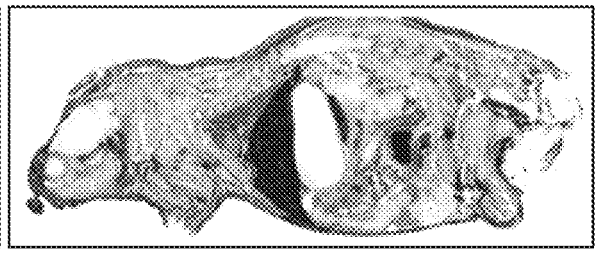
FIG. 42D
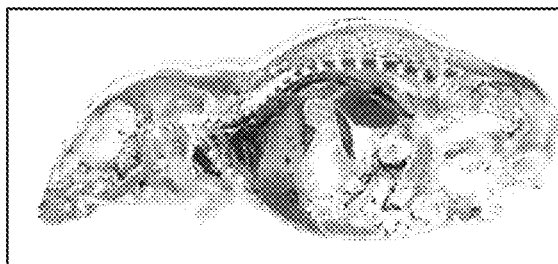
FIG. 42E
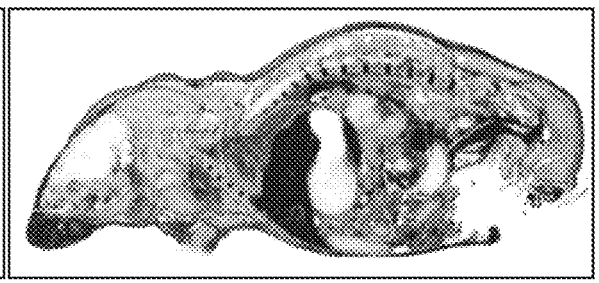
FIG. 42F
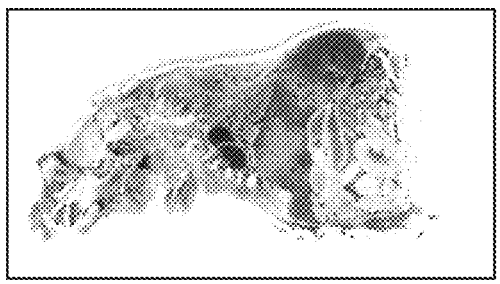
FIG. 42G
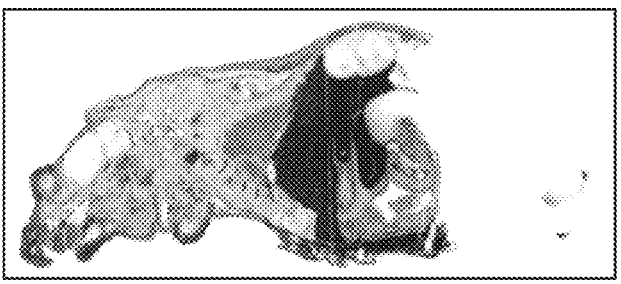
FIG. 42H
FIG. 42

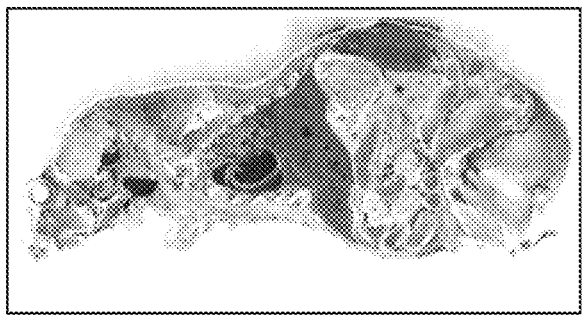
FIG. 43A
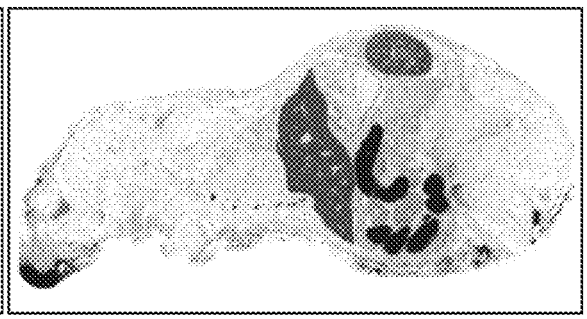
FIG. 43B
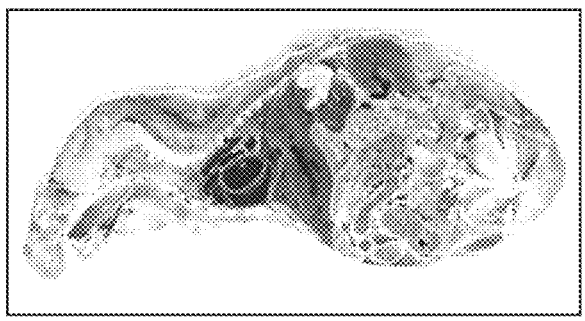
FIG. 43C
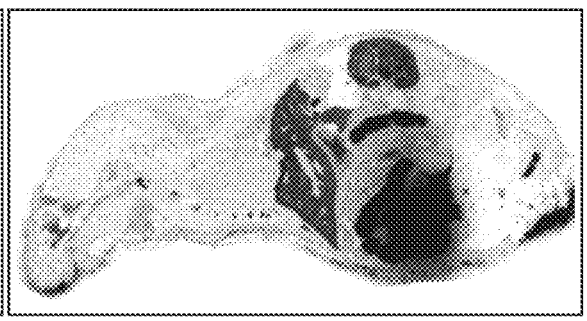
FIG. 43D
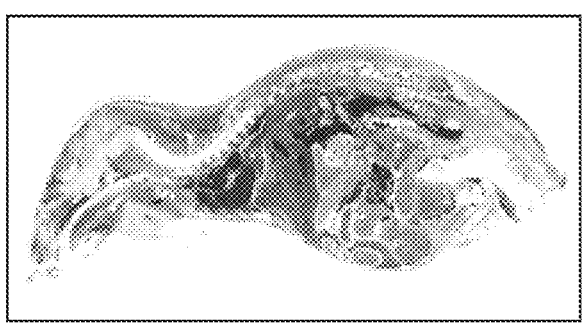
FIG. 43E
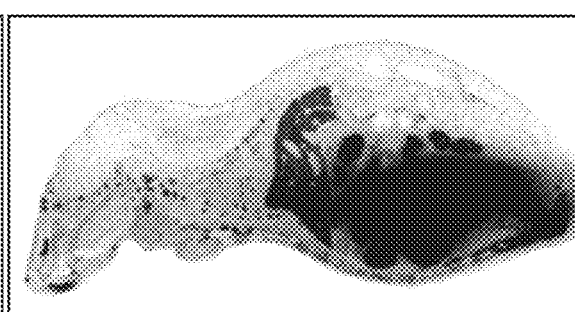
FIG. 43F
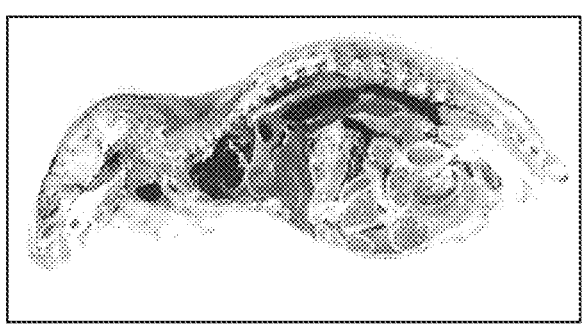
FIG. 43G
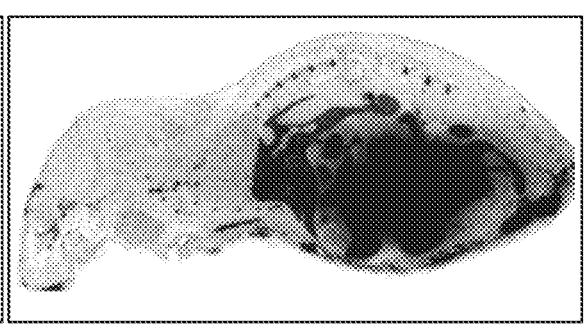
FIG. 43H
FIG. 43

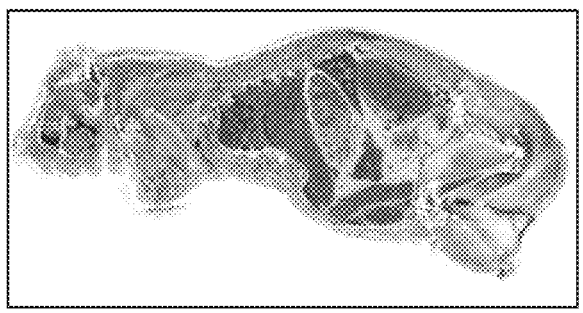
FIG. 44A
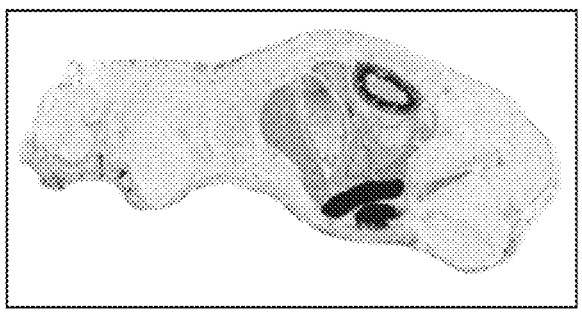
FIG. 44B
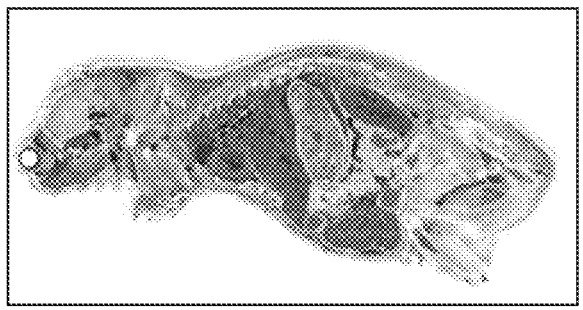
FIG. 44C
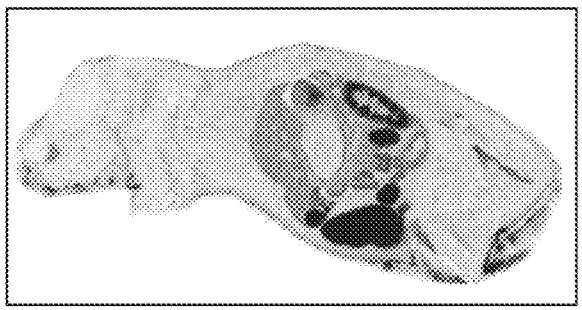
FIG. 44D
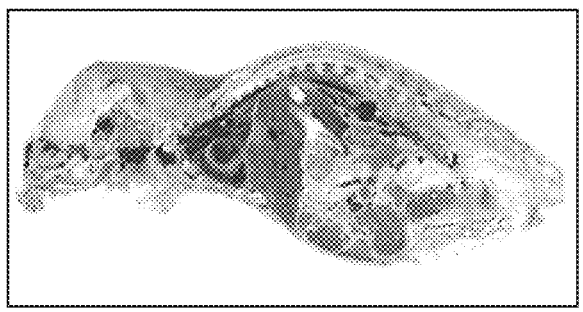
FIG. 44E
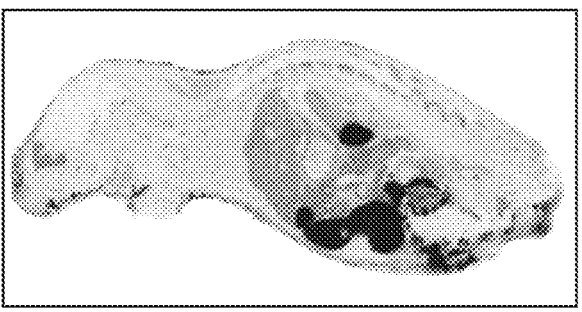
FIG. 44F
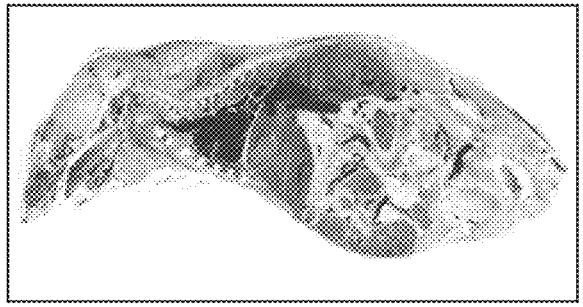
FIG. 44G
FIG. 44H
FIG. 44

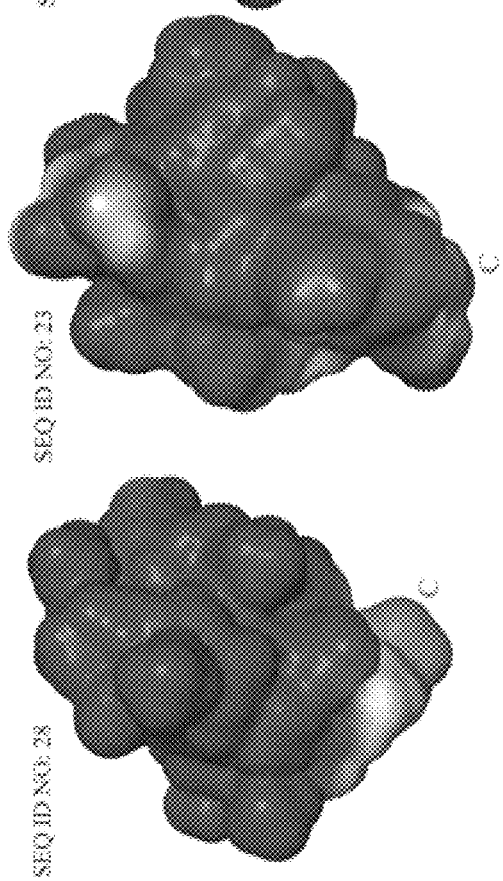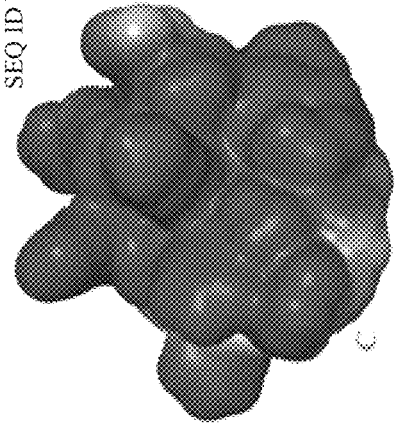
FIG. 48A  FIG. 48B  FIG. 48C  FIG. 48D
FIG. 48

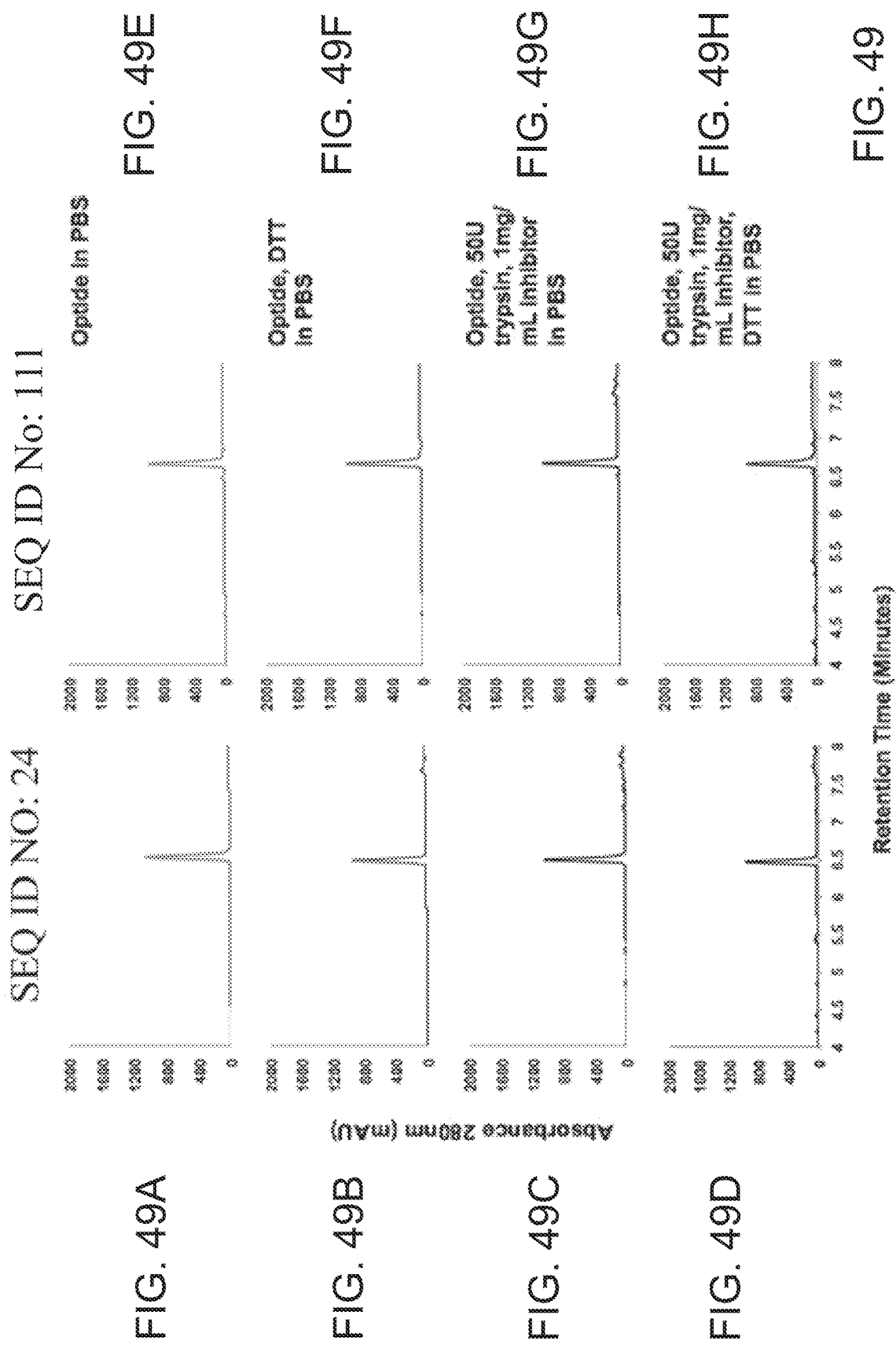

```
              *  *  *  *    *       *    * * * * * * * *  *   * *   * * *
SEQ ID NO: 486    VPINVKCRGSRDCLDPCKKAGMRFGKCINSKCHCTP
SEQ ID NO: 239    VRIPVSCKHSGQCLKPCKDAGMRFGKCMNGKCDCTPK
```

FIG. 50A

```
              *   * * * *   *        *         *        * * * * *  * *   *
SEQ ID NO: 486    VPINVKCRGSRDCLDPCKKA-GMRFGKCINSKCHCTP
SEQ ID NO: 487    VQTNVKCQGG-SCASVCRREIGVAAGKCINGKCVCYRN
```

FIG. 50B

```
              *  * * * * * * * *       * *    * *  *  *      * * *  *  * *   *  *
SEQ ID NO: 486    VPINVKCRGSRDCLDPCKKA-GMRFGKCINSKCHCTP
SEQ ID NO: 422    VFINVKCRGSPECLPKCKEAIGKSAGKCMNGKCKCYP
```

```
                          *  *  **  *     *    *    ** ***** **** **
SEQ ID NO: 243   QVQTNVKCQGGS-CASVCRREIGVAAGRCINGKCVCYRN
SEQ ID NO: 423   VFINAKCRGSPECLPKCKEAIGKAAGKCMNGKCKCYP
                                              └─────┬─────┘
                                              Predicted Dyad
```

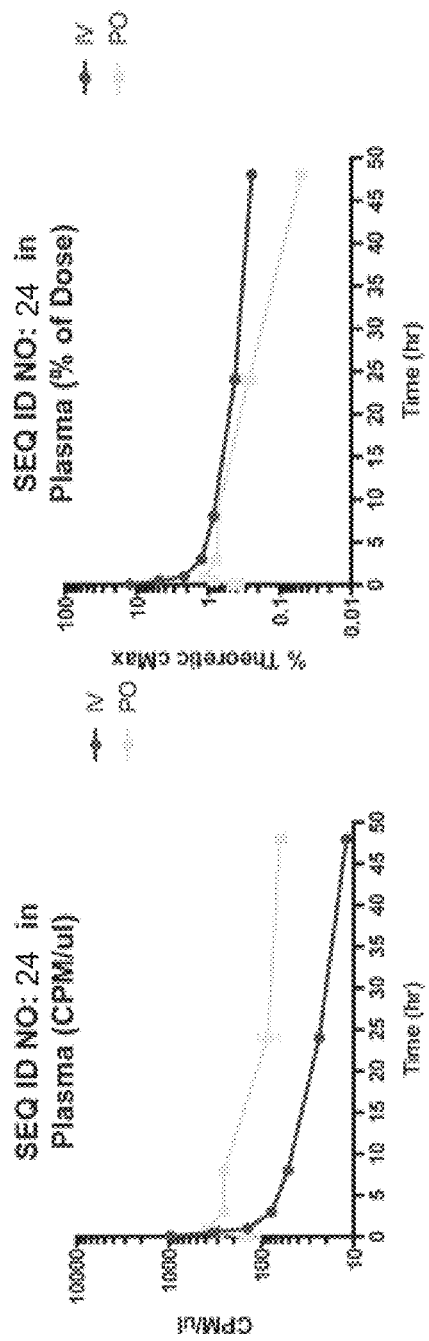
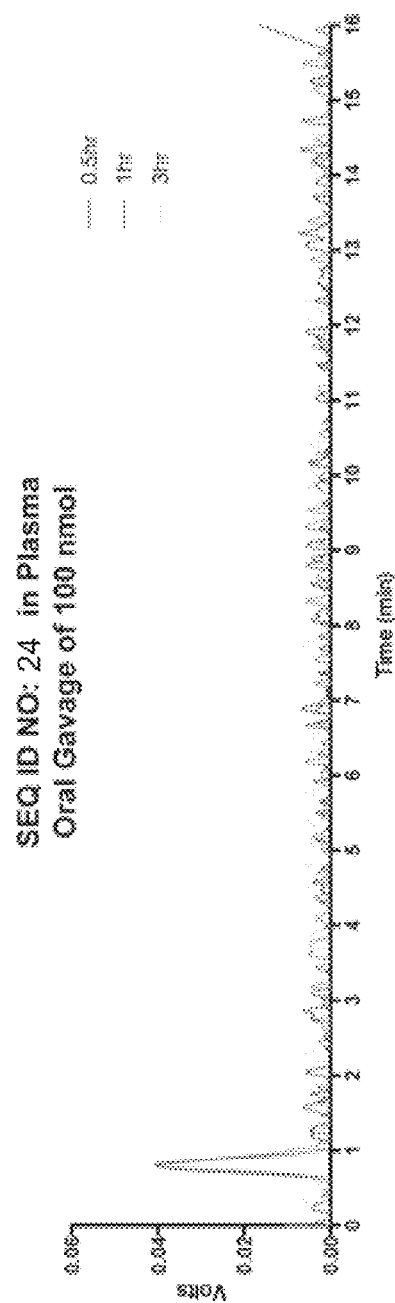
FIG. 68A
FIG. 68B
FIG. 68C
FIG. 68

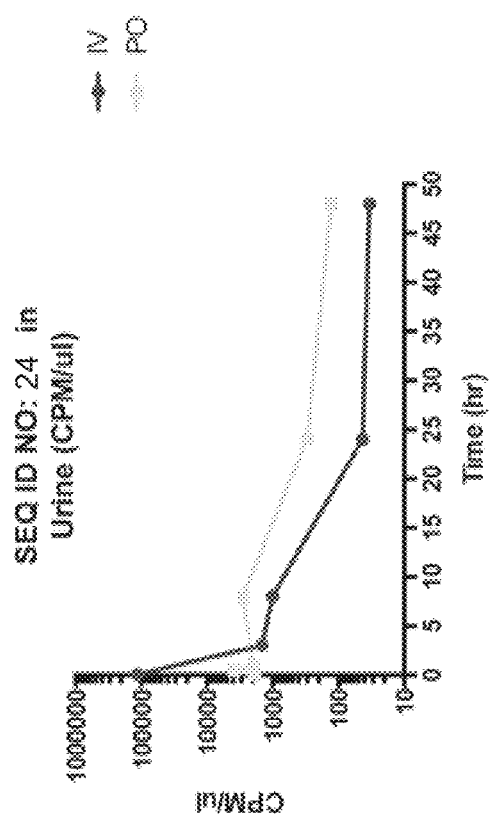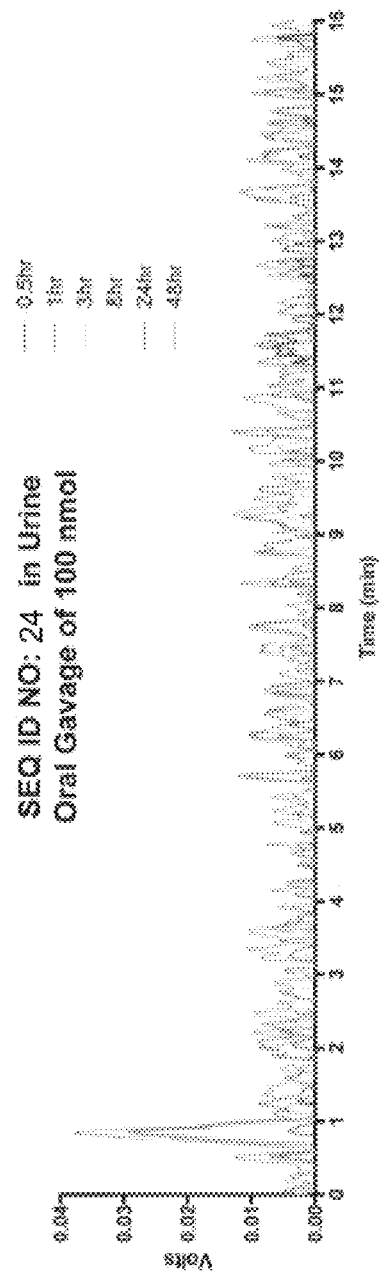
FIG. 69A
FIG. 69B
FIG. 69

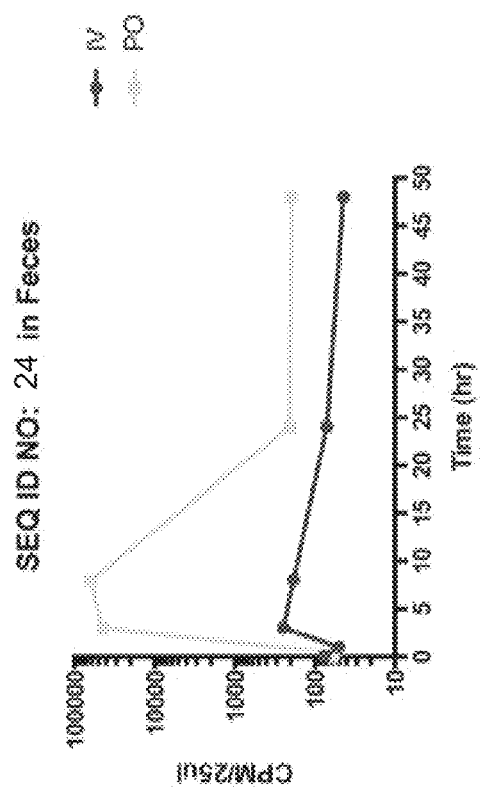
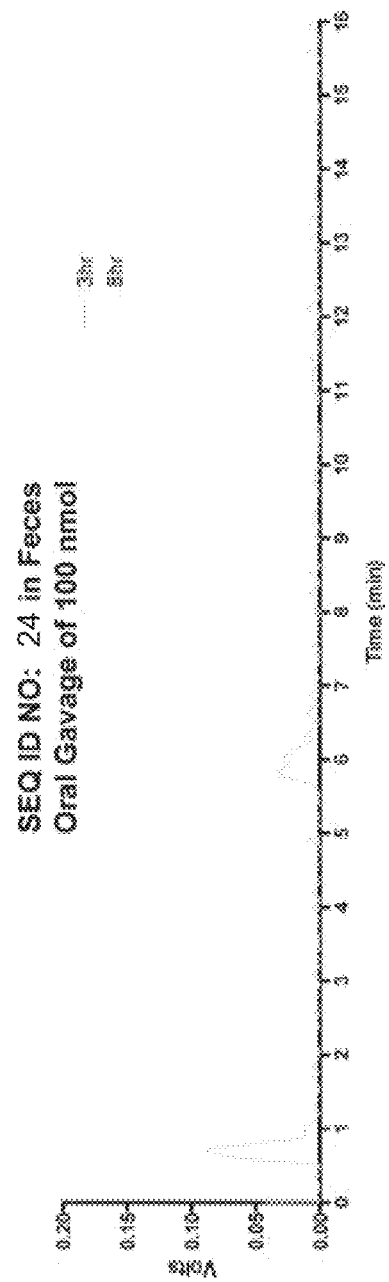
FIG. 70A
FIG. 70B
FIG. 70

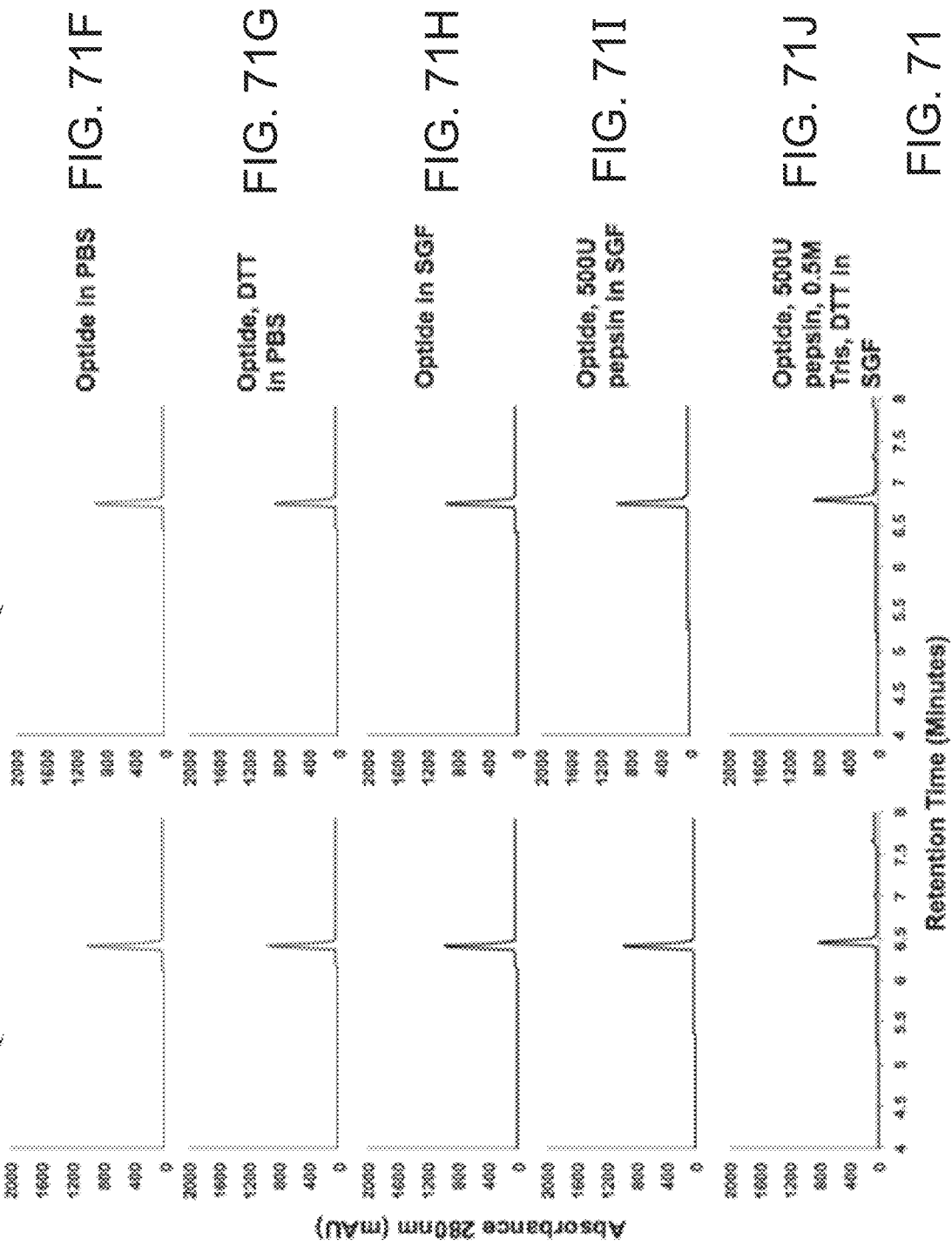

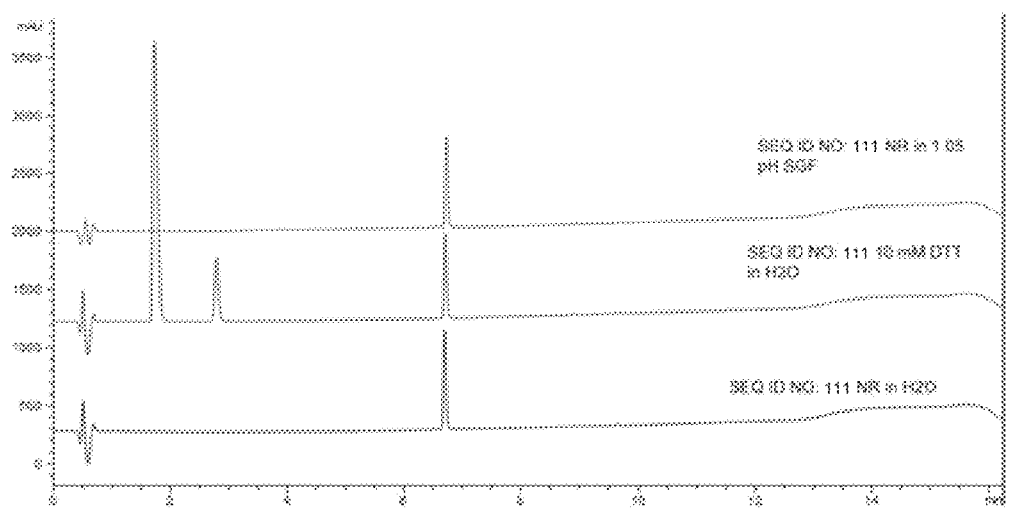
FIG. 72A
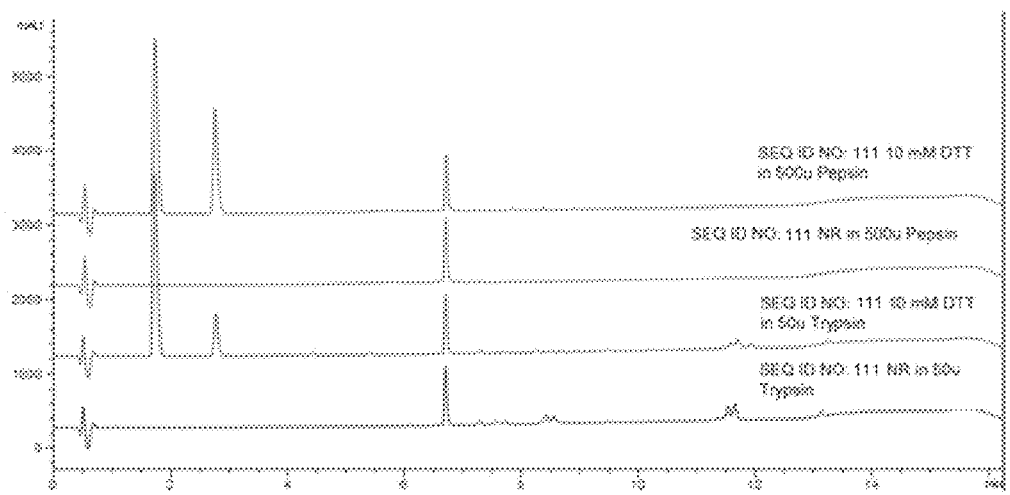
FIG. 72B
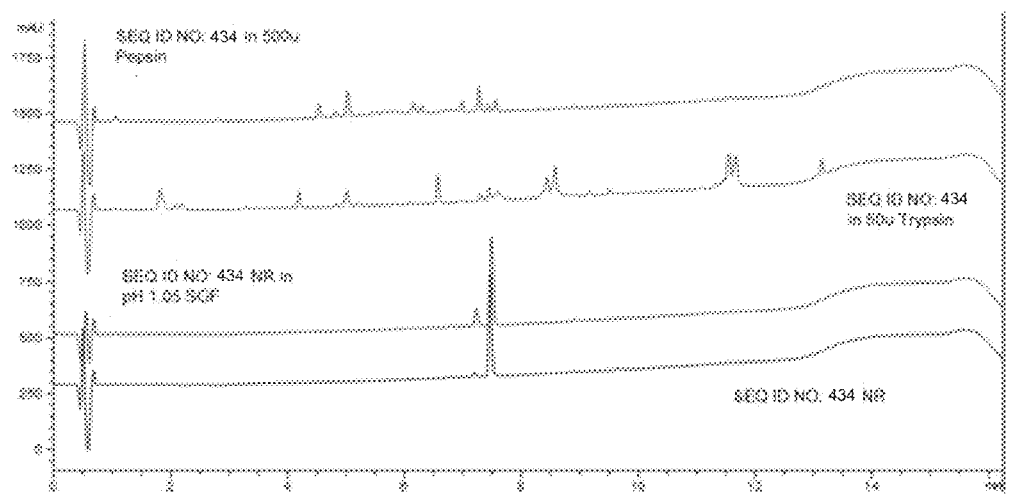
FIG. 72C
FIG. 72

```
SEQ ID NO:436    5  IKCSESYQCPVCKSRFGKTNG-RCVNGFCDCF 36
SEQ ID NO:437    5  VKCSSPQQCLKPCKAAFGISAGgKCINGKCKCY 37
SEQ ID NO:438   26  VSCSASSQCWPVCKKLFGTYRG-KCMNSKCRCY 57
SEQ ID NO:439    5  ESCTASNQCWSICKRLHNTNRG-KCMNKKCRCY 36
SEQ ID NO:440    5  VSCTTSKECWSVCEKLYNTSRG-KCMNKKCRCY 36
SEQ ID NO:441    4  MRCKSSKECLVKCKQATGRPNG-KCMNRKCKCY 35
SEQ ID NO:442    1  IKCTLSKDCYSPCKKETGCPRA-KCINRNCKCY 32
SEQ ID NO:443    1  IRCSGSRDCYSPCMKQTGCPNA-KCINKSCKCY 32
SEQ ID NO:444   27  IRCSGTRECYAPCQKLTGCLNA-KCMNKACKCY 58
SEQ ID NO:445    2  ISCTNPKQCYPHCKKETGYPNA-KCMNRKCKCF 33
SEQ ID NO:446    1  ASCRTPKDCADPCRKETGCPYG-KCMNRKCKCN 32
SEQ ID NO:447    3  TSCISPKQCTEPCRAK-GCKHG-KCMNRKCHCM 33
SEQ ID NO:448    2  KECTGPQHCTNFCRKN-KCTHG-KCMNRKCKCF 32
SEQ ID NO:449   27  IKCRTPKDCADPCRKQTGCPHA-KCMNKTCRCH 58
SEQ ID NO:450    5  VKCTTSKECWPPCKAATGKAAG-KCMNKKCKCQ 36
SEQ ID NO:451    8  LECGASRECYDPCFKAFGRAHG-KCMNNKCRCY 39
SEQ ID NO:452    5  EKCFATSQCWTPCKKAIGSLQS-KCMNGKCKCY 36
SEQ ID NO:453   27  VRCYASRECWEPCRRVTGSAQA-KCQNNQCRCY 58
SEQ ID NO:454   28  VKCSASRECWVACKKVTGSGQG-KCQNNQCRCY 59
SEQ ID NO:455    5  VKCISSQECWIACKKVTGRFEG-KCQNRQCRCY 36
SEQ ID NO:456    5  VRCYDSRQCWIACKKVTGSTQG-KCQNKQCRCY 36
SEQ ID NO:457    5  VDCTVSKECWAPCKAAFGVDRG-KCMGKKCKCY 36
SEQ ID NO:458    5  AKCRGSPECLPKCKEAIGKAAG-KCMNGKCKCY 36
SEQ ID NO:459   28  KKCQGGS-CASVCRRVIGVAAG-KCINGRCVCY 58
SEQ ID NO:460   28  KKCSNTSQCYKTCEKVVGVAAG-KCMNGKCICY 59
SEQ ID NO:461    6  VKCSGSSKCVKICIDRYNTRGA-KCINGRCTCY 37
SEQ ID NO:462   28  NRCNNSSECIPHCIRIFGTRAA-KCINRKCYCY 59
SEQ ID NO:463   28  KECNGSSECYSHCEGITGKRSG-KCINKKCYCY 59
SEQ ID NO:464    1  AFCNL-RRCELSCRSL---GLLG-KCIGEECKCV 29
SEQ ID NO:465   29  AVCNL-KRCQLSCRSL---GLLG-KCIGDKCECV 57
SEQ ID NO:466    1  AACYSS-DCRVKCVAM-GFSSG-KCINSKCKCY 30
SEQ ID NO:467   27  AICATDADCSRKCP---GNPP---CRNGFCACT 53
SEQ ID NO:468   28  TECQIKNDCQRYCQSVK------ECKYGKCYCN 54
SEQ ID NO:469    2  TQCQSVRDCQQYCLTPD------RCSYGTCYCK 28
SEQ ID NO:470   29  VSCRYGSDCAEPCKRLKCLLPS-KCINGKCTCY 60
SEQ ID NO:471   28  IKCRYPADCHIMCRKVTGRAEG-KCMNGKCTCY 59
SEQ ID NO:472   28  IKCSSSSSCYEPCRGVTGRAHG-KCMNGRCTCY 59
SEQ ID NO:473    5  VKCTGSKQCLPACKAAVGKAAG-KCMNGKCKCY 36
SEQ ID NO:474    5  VSCKHSGQCIKPCKDA-GMRFG-KCMNRKCDCT 35
SEQ ID NO:475    6  VKCRGSPQCIQPCRDA-GMRFG-KCMNGKCHCT 36
SEQ ID NO:476    5  VKCTSPKQCLPPCKAQFGIRAGaKCMNGKCKCY 37
SEQ ID NO:477    5  VKCTSPKQCSKPCKELYGSSAGaKCMNGKCKCY 37
SEQ ID NO:478    5  VKCTSPKQCLPPCKEIYGRHAGaKCMNGKCHCS 37
SEQ ID NO:479   25  VKCTGSKQCWPVCKQMFGKPNG-KCMNGKCRCY 56
SEQ ID NO:480   28  VKCRGSRDCLDPCKKA-GMRFG-KCINSKCHCT 58
SEQ ID NO:481   28  VRCVTDDDCFRKCP---GNPS---CKRGFCACK 54
SEQ ID NO:482   28  VPCNNSRPCVPVCIREVNNKNG-KCSNGKCLCY 59
```

FIG. 73

SEQ ID NO: 436   --------IKCSESYQCFPVCKSRFGKTNGRCVNGFCDCF-
SEQ ID NO: 24   GSGVPINVKCRGSRDCLDPCK-KAGMRFGKCINSKCHCTP
                :**    *  :*:   **  : *    *:*:*. *.*

FIG. 74

SEQUENCE LISTING

```
<160> NUMBER OF SEQ ID NOS: 487

<210> SEQ ID NO 1
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any amino acid or amino acid
      analogue or null
<220> FEATURE:
<221> NAME/KEY: misc_feature
<222> LOCATION: (7)..(8)
<223> OTHER INFORMATION: Xaa can be any amino acid or amino acid
      analogue or null
<220> FEATURE:
<221> NAME/KEY: misc_feature
<222> LOCATION: (11)..(11)
<223> OTHER INFORMATION: Xaa can be any amino acid or amino acid
      analogue or null
<220> FEATURE:
<221> NAME/KEY: misc_feature
<222> LOCATION: (17)..(17)
<223> OTHER INFORMATION: Xaa can be any amino acid or amino acid
      analogue or null
```

```
<220> FEATURE:
<221> NAME/KEY: misc_feature
<222> LOCATION: (22)..(24)
<223> OTHER INFORMATION: Xaa can be any amino acid or amino acid
      analogue or null
<220> FEATURE:
<221> NAME/KEY: misc_feature
<222> LOCATION: (26)..(26)
<223> OTHER INFORMATION: Xaa can be any amino acid or amino acid
      analogue or null
<220> FEATURE:
<221> NAME/KEY: misc_feature
<222> LOCATION: (28)..(28)
<223> OTHER INFORMATION: Xaa can be any amino acid or amino acid
      analogue or null
<220> FEATURE:
<221> NAME/KEY: misc_feature
<222> LOCATION: (32)..(32)
<223> OTHER INFORMATION: Xaa can be any amino acid or amino acid
      analogue or null
<220> FEATURE:
<221> NAME/KEY: misc_feature
<222> LOCATION: (39)..(42)
<223> OTHER INFORMATION: Xaa can be any amino acid or amino acid
      analogue or null

<400> SEQUENCE: 1

Gly Ser Gly Val Xaa Ile Xaa Xaa Lys Cys Xaa Gly Ser Lys Gln Cys
1               5                   10                  15

Xaa Asp Pro Cys Lys Xaa Xaa Xaa Gly Xaa Arg Xaa Gly Lys Cys Xaa
            20                  25                  30

Asn Lys Lys Cys Lys Cys Xaa Xaa Xaa Xaa
            35                  40

<210> SEQ ID NO 2
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from P or N
<220> FEATURE:
<221> NAME/KEY: misc_feature
<222> LOCATION: (8)..(8)
<223> OTHER INFORMATION: X is selected from V or I
<220> FEATURE:
<221> NAME/KEY: misc_feature
<222> LOCATION: (11)..(11)
<223> OTHER INFORMATION: X is selected from S, T, R or K
<220> FEATURE:
<221> NAME/KEY: misc_feature
<222> LOCATION: (17)..(17)
<223> OTHER INFORMATION: X is selected from Y or L
<220> FEATURE:
<221> NAME/KEY: misc_feature
<222> LOCATION: (22)..(24)
<223> OTHER INFORMATION: X is selected from Q, R or K
<220> FEATURE:
<221> NAME/KEY: misc_feature
<222> LOCATION: (23)..(23)
<223> OTHER INFORMATION: X is selected from A, K or R
<220> FEATURE:
<221> NAME/KEY: misc_feature
<222> LOCATION: (24)..(24)
<223> OTHER INFORMATION: X is selected from T or A
<220> FEATURE:
<221> NAME/KEY: misc_feature
<222> LOCATION: (26)..(26)
```

```
<223> OTHER INFORMATION: X is selected from C or M
<220> FEATURE:
<221> NAME/KEY: misc_feature
<222> LOCATION: (28)..(28)
<223> OTHER INFORMATION: X is selected from F or N
<220> FEATURE:
<221> NAME/KEY: misc_feature
<222> LOCATION: (32)..(32)
<223> OTHER INFORMATION: X is selected from M or I
<220> FEATURE:
<221> NAME/KEY: misc_feature
<222> LOCATION: (39)..(42)
<223> OTHER INFORMATION: X is selected from Y or T
<220> FEATURE:
<221> NAME/KEY: misc_feature
<222> LOCATION: (40)..(40)
<223> OTHER INFORMATION: X is selected from G or P
<220> FEATURE:
<221> NAME/KEY: misc_feature
<222> LOCATION: (41)..(41)
<223> OTHER INFORMATION: X is selected from C or null
<220> FEATURE:
<221> NAME/KEY: misc_feature
<222> LOCATION: (42)..(42)
<223> OTHER INFORMATION: X is selected from G or null

<400> SEQUENCE: 2

Gly Ser Gly Val Xaa Ile Xaa Xaa Lys Cys Xaa Gly Ser Lys Gln Cys
1               5                   10                  15

Xaa Asp Pro Cys Lys Xaa Xaa Xaa Gly Xaa Arg Xaa Gly Lys Cys Xaa
            20                  25                  30

Asn Lys Lys Cys Lys Cys Xaa Xaa Xaa Xaa
            35                  40

<210> SEQ ID NO 3
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: Xaa can be any amino acid or amino acid
      analogue or null
<220> FEATURE:
<221> NAME/KEY: misc_feature
<222> LOCATION: (6)..(6)
<223> OTHER INFORMATION: Xaa can be any amino acid or amino acid
      analogue or null
<220> FEATURE:
<221> NAME/KEY: misc_feature
<222> LOCATION: (8)..(8)
<223> OTHER INFORMATION: Xaa can be any amino acid or amino acid
      analogue or null
<220> FEATURE:
<221> NAME/KEY: misc_feature
<222> LOCATION: (15)..(15)
<223> OTHER INFORMATION: Xaa can be any amino acid or amino acid
      analogue or null
<220> FEATURE:
<221> NAME/KEY: misc_feature
<222> LOCATION: (19)..(20)
<223> OTHER INFORMATION: Xaa can be any amino acid or amino acid
      analogue or null
<220> FEATURE:
<221> NAME/KEY: misc_feature
<222> LOCATION: (24)..(26)
<223> OTHER INFORMATION: Xaa can be any amino acid or amino acid
      analogue or null
<220> FEATURE:
<221> NAME/KEY: misc_feature
<222> LOCATION: (29)..(30)
<223> OTHER INFORMATION: Xaa can be any amino acid or amino acid
      analogue or null
```

-continued

```
<220> FEATURE:
<221> NAME/KEY: misc_feature
<222> LOCATION: (32)..(32)
<223> OTHER INFORMATION: Xaa can be any amino acid or amino acid
      analogue or null

<400> SEQUENCE: 3

Xaa Xaa Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Xaa Lys Cys Xaa Xaa Lys Xaa
            20                  25                  30

Cys Lys Cys Tyr Gly Cys Gly
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from S or null
<220> FEATURE:
<221> NAME/KEY: misc_feature
<222> LOCATION: (3)..(3)
<223> OTHER INFORMATION: X is selected from E, G or null
<220> FEATURE:
<221> NAME/KEY: misc_feature
<222> LOCATION: (4)..(4)
<223> OTHER INFORMATION: X is selected from V, S, or null
<220> FEATURE:
<221> NAME/KEY: misc_feature
<222> LOCATION: (6)..(6)
<223> OTHER INFORMATION: X is selected from R or S
<220> FEATURE:
<221> NAME/KEY: misc_feature
<222> LOCATION: (8)..(8)
<223> OTHER INFORMATION: X is selected from S or T
<220> FEATURE:
<221> NAME/KEY: misc_feature
<222> LOCATION: (15)..(15)
<223> OTHER INFORMATION: X is selected from G or D
<220> FEATURE:
<221> NAME/KEY: misc_feature
<222> LOCATION: (19)..(19)
<223> OTHER INFORMATION: X is selected from Q or R
<220> FEATURE:
<221> NAME/KEY: misc_feature
<222> LOCATION: (20)..(20)
<223> OTHER INFORMATION: X is selected from Q or K
<220> FEATURE:
<221> NAME/KEY: misc_feature
<222> LOCATION: (24)..(24)
<223> OTHER INFORMATION: X is selected from T or P
<220> FEATURE:
<221> NAME/KEY: misc_feature
<222> LOCATION: (25)..(25)
<223> OTHER INFORMATION: X is selected from N or Q
<220> FEATURE:
<221> NAME/KEY: misc_feature
<222> LOCATION: (26)..(26)
<223> OTHER INFORMATION: X is selected from S or A
<220> FEATURE:
<221> NAME/KEY: misc_feature
<222> LOCATION: (29)..(29)
<223> OTHER INFORMATION: X is selected from M or L
<220> FEATURE:
<221> NAME/KEY: misc_feature
<222> LOCATION: (30)..(30)
```

```
<223> OTHER INFORMATION: X is selected from N or Q
<220> FEATURE:
<221> NAME/KEY: misc_feature
<222> LOCATION: (32)..(32)
<223> OTHER INFORMATION: X is selected from V or S

<400> SEQUENCE: 4

Xaa Xaa Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Xaa Lys Cys Xaa Xaa Lys Xaa
            20                  25                  30

Cys Lys Cys Tyr Gly Cys Gly
            35

<210> SEQ ID NO 5
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any amino acid or amino acid
      analogue or null
<220> FEATURE:
<221> NAME/KEY: misc_feature
<222> LOCATION: (5)..(5)
<223> OTHER INFORMATION: Xaa can be any amino acid or amino acid
      analogue or null
<220> FEATURE:
<221> NAME/KEY: misc_feature
<222> LOCATION: (7)..(7)
<223> OTHER INFORMATION: Xaa can be any amino acid or amino acid
      analogue or null
<220> FEATURE:
<221> NAME/KEY: misc_feature
<222> LOCATION: (9)..(9)
<223> OTHER INFORMATION: Xaa can be any amino acid or amino acid
      analogue or null
<220> FEATURE:
<221> NAME/KEY: misc_feature
<222> LOCATION: (11)..(12)
<223> OTHER INFORMATION: Xaa can be any amino acid or amino acid
      analogue or null
<220> FEATURE:
<221> NAME/KEY: misc_feature
<222> LOCATION: (14)..(15)
<223> OTHER INFORMATION: Xaa can be any amino acid or amino acid
      analogue or null
<220> FEATURE:
<221> NAME/KEY: misc_feature
<222> LOCATION: (18)..(18)
<223> OTHER INFORMATION: Xaa can be any amino acid or amino acid
      analogue or null
<220> FEATURE:
<221> NAME/KEY: misc_feature
<222> LOCATION: (22)..(22)
<223> OTHER INFORMATION: Xaa can be any amino acid or amino acid
      analogue or null
<220> FEATURE:
<221> NAME/KEY: misc_feature
<222> LOCATION: (31)..(31)
<223> OTHER INFORMATION: Xaa can be any amino acid or amino acid
      analogue or null
<220> FEATURE:
<221> NAME/KEY: misc_feature
<222> LOCATION: (33)..(33)
<223> OTHER INFORMATION: Xaa can be any amino acid or amino acid
      analogue or null
<220> FEATURE:
<221> NAME/KEY: misc_feature
<222> LOCATION: (36)..(36)
<223> OTHER INFORMATION: Xaa can be any amino acid or amino acid
      analogue or null
```

-continued

```
<220> FEATURE:
<221> NAME/KEY: misc_feature
<222> LOCATION: (40)..(40)
<223> OTHER INFORMATION: Xaa can be any amino acid or amino acid
      analogue or null

<400> SEQUENCE: 5

Xaa Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30

Xaa Lys Cys Xaa Cys Thr Pro Xaa
        35                  40

<210> SEQ ID NO 6
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from G, S or null
<220> FEATURE:
<221> NAME/KEY: misc_feature
<222> LOCATION: (3)..(3)
<223> OTHER INFORMATION: X is selected from G, S or null
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from N or P
<220> FEATURE:
<221> NAME/KEY: misc_feature
<222> LOCATION: (9)..(9)
<223> OTHER INFORMATION: X is selected from K or S
<220> FEATURE:
<221> NAME/KEY: misc_feature
<222> LOCATION: (11)..(11)
<223> OTHER INFORMATION: X is selected from R or K
<220> FEATURE:
<221> NAME/KEY: misc_feature
<222> LOCATION: (12)..(12)
<223> OTHER INFORMATION: X is selected from G or H
<220> FEATURE:
<221> NAME/KEY: misc_feature
<222> LOCATION: (14)..(14)
<223> OTHER INFORMATION: X is selected from R or G
<220> FEATURE:
<221> NAME/KEY: misc_feature
<222> LOCATION: (15)..(15)
<223> OTHER INFORMATION: X is selected from D or Q
<220> FEATURE:
<221> NAME/KEY: misc_feature
<222> LOCATION: (18)..(18)
<223> OTHER INFORMATION: X is selected from D or K
<220> FEATURE:
<221> NAME/KEY: misc_feature
<222> LOCATION: (22)..(22)
<223> OTHER INFORMATION: X is selected from K or D
<220> FEATURE:
<221> NAME/KEY: misc_feature
<222> LOCATION: (31)..(31)
<223> OTHER INFORMATION: X is selected from I or M
<220> FEATURE:
<221> NAME/KEY: misc_feature
<222> LOCATION: (33)..(33)
```

```
<223> OTHER INFORMATION: X is selected from S or G
<220> FEATURE:
<221> NAME/KEY: misc_feature
<222> LOCATION: (36)..(36)
<223> OTHER INFORMATION: X is selected from H or D
<220> FEATURE:
<221> NAME/KEY: misc_feature
<222> LOCATION: (40)..(40)
<223> OTHER INFORMATION: X is selected from K or null

<400> SEQUENCE: 6

Xaa Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30

Xaa Lys Cys Xaa Cys Thr Pro Xaa
        35                  40

<210> SEQ ID NO 7
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 7

Xaa Val Xaa Val Lys Cys Xaa Gly Ser Lys Gln Cys Xaa Pro Cys Lys
1               5                   10                  15

Arg Xaa Gly Xaa Arg Xaa Gly Lys Cys Ile Asn Lys Lys Xaa Cys Lys
            20                  25                  30

Cys Tyr Xaa
        35

<210> SEQ ID NO 8
<211> LENGTH: 32
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 8

Xaa Gly Cys Val Xaa Lys Cys Arg Pro Gly Xaa Lys Xaa Cys Cys Xaa
1               5                   10                  15

Pro Xaa Lys Arg Cys Ser Arg Arg Phe Gly Xaa Lys Lys Cys Lys Xaa
                20                  25                  30

<210> SEQ ID NO 9
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
```

-continued

```
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (41)..(43)
<223> OTHER INFORMATION: Xaa can be any naturally occurring amino acid

<400> SEQUENCE: 9

Gly Ser Xaa Val Xaa Xaa Xaa Val Lys Cys Xaa Gly Ser Lys Gln Cys
1               5                   10                  15

Xaa Xaa Pro Cys Lys Arg Xaa Xaa Gly Xaa Arg Xaa Gly Lys Cys Ile
            20                  25                  30

Asn Lys Lys Xaa Cys Lys Cys Tyr Xaa Xaa Xaa
        35                  40

<210> SEQ ID NO 10
<211> LENGTH: 47
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (42)..(47)
<223> OTHER INFORMATION: Xaa can be any naturally occurring amino acid

<400> SEQUENCE: 10

Gly Ser Xaa Xaa Xaa Gly Cys Val Xaa Xaa Xaa Xaa Lys Cys Arg Pro
1               5                   10                  15

Gly Xaa Lys Xaa Cys Cys Xaa Pro Xaa Lys Arg Cys Ser Arg Arg Phe
            20                  25                  30

Gly Xaa Xaa Xaa Xaa Lys Lys Cys Lys Xaa Xaa Xaa Xaa Xaa Xaa
        35                  40                  45

<210> SEQ ID NO 11
<211> LENGTH: 42
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (5)..(5)
<223> OTHER INFORMATION: Xaa can be any amino acid or amino acid
      analogue or null
<220> FEATURE:
<221> NAME/KEY: misc_feature
<222> LOCATION: (7)..(8)
<223> OTHER INFORMATION: Xaa can be any amino acid or amino acid
      analogue or null
<220> FEATURE:
<221> NAME/KEY: misc_feature
<222> LOCATION: (11)..(11)
<223> OTHER INFORMATION: Xaa can be any amino acid or amino acid
      analogue or null
<220> FEATURE:
<221> NAME/KEY: misc_feature
<222> LOCATION: (17)..(17)
<223> OTHER INFORMATION: Xaa can be any amino acid or amino acid
      analogue or null
<220> FEATURE:
<221> NAME/KEY: misc_feature
<222> LOCATION: (22)..(24)
<223> OTHER INFORMATION: Xaa can be any amino acid or amino acid
      analogue or null
<220> FEATURE:
<221> NAME/KEY: misc_feature
<222> LOCATION: (26)..(26)
<223> OTHER INFORMATION: Xaa can be any amino acid or amino acid
      analogue or null
<220> FEATURE:
<221> NAME/KEY: misc_feature
<222> LOCATION: (28)..(28)
<223> OTHER INFORMATION: Xaa can be any amino acid or amino acid
      analogue or null
<220> FEATURE:
<221> NAME/KEY: misc_feature
<222> LOCATION: (32)..(32)
<223> OTHER INFORMATION: Xaa can be any amino acid or amino acid
      analogue or null
<220> FEATURE:
<221> NAME/KEY: misc_feature
<222> LOCATION: (39)..(42)
<223> OTHER INFORMATION: Xaa can be any amino acid or amino acid
      analogue or null

<400> SEQUENCE: 11

Gly Ser Gly Val Xaa Ile Xaa Xaa Arg Cys Xaa Gly Ser Arg Gln Cys
1               5                   10                  15

Xaa Asp Pro Cys Arg Xaa Xaa Xaa Gly Xaa Arg Xaa Gly Arg Cys Xaa
                20                  25                  30

Asn Arg Arg Cys Arg Cys Xaa Xaa Xaa Xaa
            35                  40

<210> SEQ ID NO 12
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from P or N
<220> FEATURE:
<221> NAME/KEY: misc_feature
<222> LOCATION: (8)..(8)
<223> OTHER INFORMATION: X is selected from V or I
<220> FEATURE:
<221> NAME/KEY: misc_feature
<222> LOCATION: (11)..(11)
```

```
<223> OTHER INFORMATION: X is selected from S, T, R or K
<220> FEATURE:
<221> NAME/KEY: misc_feature
<222> LOCATION: (17)..(17)
<223> OTHER INFORMATION: X is selected from Y or L
<220> FEATURE:
<221> NAME/KEY: misc_feature
<222> LOCATION: (22)..(22)
<223> OTHER INFORMATION: X is selected from Q, R or K
<220> FEATURE:
<221> NAME/KEY: misc_feature
<222> LOCATION: (23)..(23)
<223> OTHER INFORMATION: X is selected from A, K or R
<220> FEATURE:
<221> NAME/KEY: misc_feature
<222> LOCATION: (24)..(24)
<223> OTHER INFORMATION: X is selected from T or A
<220> FEATURE:
<221> NAME/KEY: misc_feature
<222> LOCATION: (26)..(26)
<223> OTHER INFORMATION: X is selected from C or M
<220> FEATURE:
<221> NAME/KEY: misc_feature
<222> LOCATION: (28)..(28)
<223> OTHER INFORMATION: X is selected from F or N
<220> FEATURE:
<221> NAME/KEY: misc_feature
<222> LOCATION: (32)..(32)
<223> OTHER INFORMATION: X is selected from M or I
<220> FEATURE:
<221> NAME/KEY: misc_feature
<222> LOCATION: (39)..(39)
<223> OTHER INFORMATION: X is selected from Y or T
<220> FEATURE:
<221> NAME/KEY: misc_feature
<222> LOCATION: (40)..(40)
<223> OTHER INFORMATION: X is selected from G or P
<220> FEATURE:
<221> NAME/KEY: misc_feature
<222> LOCATION: (41)..(41)
<223> OTHER INFORMATION: X is selected from C or null
<220> FEATURE:
<221> NAME/KEY: misc_feature
<222> LOCATION: (42)..(42)
<223> OTHER INFORMATION: X is selected from G or null

<400> SEQUENCE: 12

Gly Ser Gly Val Xaa Ile Xaa Xaa Arg Cys Xaa Gly Ser Arg Gln Cys
1               5                   10                  15

Xaa Asp Pro Cys Arg Xaa Xaa Xaa Gly Xaa Arg Xaa Gly Arg Cys Xaa
            20                  25                  30

Asn Arg Arg Cys Arg Cys Xaa Xaa Xaa Xaa
        35                  40

<210> SEQ ID NO 13
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: Xaa can be any amino acid or amino acid
      analogue or null
<220> FEATURE:
<221> NAME/KEY: misc_feature
<222> LOCATION: (6)..(6)
<223> OTHER INFORMATION: Xaa can be any amino acid or amino acid
      analogue or null
<220> FEATURE:
<221> NAME/KEY: misc_feature
<222> LOCATION: (8)..(8)
<223> OTHER INFORMATION: Xaa can be any amino acid or amino acid
      analogue or null
```

<220> FEATURE:
<221> NAME/KEY: misc_feature
<222> LOCATION: (15)..(15)
<223> OTHER INFORMATION: Xaa can be any amino acid or amino acid analogue or null
<220> FEATURE:
<221> NAME/KEY: misc_feature
<222> LOCATION: (19)..(20)
<223> OTHER INFORMATION: Xaa can be any amino acid or amino acid analogue or null
<220> FEATURE:
<221> NAME/KEY: misc_feature
<222> LOCATION: (24)..(26)
<223> OTHER INFORMATION: Xaa can be any amino acid or amino acid analogue or null
<220> FEATURE:
<221> NAME/KEY: misc_feature
<222> LOCATION: (29)..(30)
<223> OTHER INFORMATION: Xaa can be any amino acid or amino acid analogue or null
<220> FEATURE:
<221> NAME/KEY: misc_feature
<222> LOCATION: (32)..(32)
<223> OTHER INFORMATION: Xaa can be any amino acid or amino acid analogue or null

<400> SEQUENCE: 13

```
Xaa Xaa Xaa Xaa Ile Xaa Cys Xaa Gly Ser Arg Gln Cys Tyr Xaa Pro
1               5                   10                  15

Cys Arg Xaa Xaa Thr Gly Cys Xaa Xaa Xaa Arg Cys Xaa Xaa Arg Xaa
            20                  25                  30

Cys Arg Cys Tyr Gly Cys Gly
        35
```

<210> SEQ ID NO 14
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from S or null
<220> FEATURE:
<221> NAME/KEY: misc_feature
<222> LOCATION: (3)..(3)
<223> OTHER INFORMATION: X is selected from E, G or null
<220> FEATURE:
<221> NAME/KEY: misc_feature
<222> LOCATION: (4)..(4)
<223> OTHER INFORMATION: X is selected from V, S, or null
<220> FEATURE:
<221> NAME/KEY: misc_feature
<222> LOCATION: (6)..(6)
<223> OTHER INFORMATION: X is selected from R or S
<220> FEATURE:
<221> NAME/KEY: misc_feature
<222> LOCATION: (8)..(8)
<223> OTHER INFORMATION: X is selected from S or T
<220> FEATURE:
<221> NAME/KEY: misc_feature
<222> LOCATION: (15)..(15)
<223> OTHER INFORMATION: X is selected from G or D
<220> FEATURE:
<221> NAME/KEY: misc_feature
<222> LOCATION: (19)..(19)
<223> OTHER INFORMATION: X is selected from Q or R
<220> FEATURE:
<221> NAME/KEY: misc_feature
<222> LOCATION: (20)..(20)

```
<223> OTHER INFORMATION: X is selected from Q, R, or K
<220> FEATURE:
<221> NAME/KEY: misc_feature
<222> LOCATION: (24)..(24)
<223> OTHER INFORMATION: X is selected from T or P
<220> FEATURE:
<221> NAME/KEY: misc_feature
<222> LOCATION: (25)..(25)
<223> OTHER INFORMATION: X is selected from N or Q
<220> FEATURE:
<221> NAME/KEY: misc_feature
<222> LOCATION: (26)..(26)
<223> OTHER INFORMATION: X is selected from S or A
<220> FEATURE:
<221> NAME/KEY: misc_feature
<222> LOCATION: (29)..(29)
<223> OTHER INFORMATION: X is selected from M or L
<220> FEATURE:
<221> NAME/KEY: misc_feature
<222> LOCATION: (30)..(30)
<223> OTHER INFORMATION: X is selected from N or Q
<220> FEATURE:
<221> NAME/KEY: misc_feature
<222> LOCATION: (32)..(32)
<223> OTHER INFORMATION: X is selected from V or S

<400> SEQUENCE: 14

Xaa Xaa Xaa Xaa Ile Xaa Cys Xaa Gly Ser Arg Gln Cys Tyr Xaa Pro
1               5                   10                  15

Cys Arg Xaa Xaa Thr Gly Cys Xaa Xaa Xaa Arg Cys Xaa Xaa Arg Xaa
            20                  25                  30

Cys Arg Cys Tyr Gly Cys Gly
            35

<210> SEQ ID NO 15
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: Xaa can be any amino acid or amino acid
      analogue or null
<220> FEATURE:
<221> NAME/KEY: misc_feature
<222> LOCATION: (5)..(5)
<223> OTHER INFORMATION: Xaa can be any amino acid or amino acid
      analogue or null
<220> FEATURE:
<221> NAME/KEY: misc_feature
<222> LOCATION: (7)..(7)
<223> OTHER INFORMATION: Xaa can be any amino acid or amino acid
      analogue or null
<220> FEATURE:
<221> NAME/KEY: misc_feature
<222> LOCATION: (9)..(9)
<223> OTHER INFORMATION: Xaa can be any amino acid or amino acid
      analogue or null
<220> FEATURE:
<221> NAME/KEY: misc_feature
<222> LOCATION: (11)..(12)
<223> OTHER INFORMATION: Xaa can be any amino acid or amino acid
      analogue or null
<220> FEATURE:
<221> NAME/KEY: misc_feature
<222> LOCATION: (14)..(15)
<223> OTHER INFORMATION: Xaa can be any amino acid or amino acid
      analogue or null
<220> FEATURE:
<221> NAME/KEY: misc_feature
<222> LOCATION: (18)..(18)
<223> OTHER INFORMATION: Xaa can be any amino acid or amino acid
      analogue or null
```

-continued

```
<220> FEATURE:
<221> NAME/KEY: misc_feature
<222> LOCATION: (22)..(22)
<223> OTHER INFORMATION: Xaa can be any amino acid or amino acid
      analogue or null
<220> FEATURE:
<221> NAME/KEY: misc_feature
<222> LOCATION: (31)..(31)
<223> OTHER INFORMATION: Xaa can be any amino acid or amino acid
      analogue or null
<220> FEATURE:
<221> NAME/KEY: misc_feature
<222> LOCATION: (33)..(33)
<223> OTHER INFORMATION: Xaa can be any amino acid or amino acid
      analogue or null
<220> FEATURE:
<221> NAME/KEY: misc_feature
<222> LOCATION: (36)..(36)
<223> OTHER INFORMATION: Xaa can be any amino acid or amino acid
      analogue or null
<220> FEATURE:
<221> NAME/KEY: misc_feature
<222> LOCATION: (40)..(40)
<223> OTHER INFORMATION: Xaa can be any amino acid or amino acid
      analogue or null

<400> SEQUENCE: 15

Xaa Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
            35                  40

<210> SEQ ID NO 16
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from G, S or null
<220> FEATURE:
<221> NAME/KEY: misc_feature
<222> LOCATION: (3)..(3)
<223> OTHER INFORMATION: X is selected from G, S or null
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from N or P
<220> FEATURE:
<221> NAME/KEY: misc_feature
<222> LOCATION: (9)..(9)
<223> OTHER INFORMATION: X is selected from R, K or S
<220> FEATURE:
<221> NAME/KEY: misc_feature
<222> LOCATION: (11)..(11)
<223> OTHER INFORMATION: X is selected from R or K
<220> FEATURE:
<221> NAME/KEY: misc_feature
<222> LOCATION: (12)..(12)
<223> OTHER INFORMATION: X is selected from G or H
<220> FEATURE:
<221> NAME/KEY: misc_feature
<222> LOCATION: (14)..(14)
```

```
<223> OTHER INFORMATION: X is selected from R or G
<220> FEATURE:
<221> NAME/KEY: misc_feature
<222> LOCATION: (15)..(15)
<223> OTHER INFORMATION: X is selected from D or Q
<220> FEATURE:
<221> NAME/KEY: misc_feature
<222> LOCATION: (18)..(18)
<223> OTHER INFORMATION: X is selected from D, R, or K
<220> FEATURE:
<221> NAME/KEY: misc_feature
<222> LOCATION: (22)..(22)
<223> OTHER INFORMATION: X is selected from K, R, or D
<220> FEATURE:
<221> NAME/KEY: misc_feature
<222> LOCATION: (31)..(31)
<223> OTHER INFORMATION: X is selected from I or M
<220> FEATURE:
<221> NAME/KEY: misc_feature
<222> LOCATION: (33)..(33)
<223> OTHER INFORMATION: X is selected from S or G
<220> FEATURE:
<221> NAME/KEY: misc_feature
<222> LOCATION: (36)..(36)
<223> OTHER INFORMATION: X is selected from H or D
<220> FEATURE:
<221> NAME/KEY: misc_feature
<222> LOCATION: (40)..(40)
<223> OTHER INFORMATION: X is selected from K, R, or null

<400> SEQUENCE: 16

Xaa Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
        35                  40

<210> SEQ ID NO 17
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (30)..(30)
```

```
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 17

Xaa Val Xaa Val Arg Cys Xaa Gly Ser Arg Gln Cys Xaa Pro Cys Arg
1               5                   10                  15

Arg Xaa Gly Xaa Arg Xaa Gly Arg Cys Ile Asn Arg Arg Xaa Cys Arg
            20                  25                  30

Cys Tyr Xaa
        35

<210> SEQ ID NO 18
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 18

Xaa Gly Cys Val Xaa Arg Cys Arg Pro Gly Xaa Arg Xaa Cys Cys Xaa
1               5                   10                  15

Pro Xaa Arg Arg Cys Ser Arg Arg Phe Gly Xaa Arg Arg Cys Arg Xaa
            20                  25                  30

<210> SEQ ID NO 19
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
```

-continued

```
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (41)..(43)
<223> OTHER INFORMATION: Xaa can be any naturally occurring amino acid

<400> SEQUENCE: 19

Gly Ser Xaa Val Xaa Xaa Xaa Val Arg Cys Xaa Gly Ser Arg Gln Cys
 1               5                  10                  15

Xaa Xaa Pro Cys Arg Arg Xaa Xaa Gly Xaa Arg Xaa Gly Arg Cys Ile
            20                  25                  30

Asn Arg Arg Xaa Cys Arg Cys Tyr Xaa Xaa Xaa
        35                  40

<210> SEQ ID NO 20
<211> LENGTH: 47
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (34)..(37)
<223> OTHER INFORMATION: Xaa can be any naturally occurring amino acid
<220> FEATURE:
<221> NAME/KEY: misc_feature
<222> LOCATION: (42)..(47)
```

<223> OTHER INFORMATION: Xaa can be any naturally occurring amino acid

<400> SEQUENCE: 20

Gly Ser Xaa Xaa Xaa Gly Cys Val Xaa Xaa Xaa Arg Cys Arg Pro
1               5                   10                  15

Gly Xaa Arg Xaa Cys Cys Xaa Pro Xaa Arg Arg Cys Ser Arg Arg Phe
            20                  25                  30

Gly Xaa Xaa Xaa Xaa Arg Arg Cys Arg Xaa Xaa Xaa Xaa Xaa
        35                  40                  45

<210> SEQ ID NO 21
<211> LENGTH: 34
<212> TYPE: PRT
<213> ORGANISM: Artificial Sequence
<220> FEATURE:
<223> OTHER INFORMATION: Synthetic

<400> SEQUENCE: 21

Gly Ser Gly Ile Val Cys Lys Val Cys Lys Ile Ile Cys Gly Met Gln
1               5                   10                  15

Gly Lys Lys Val Asn Ile Cys Lys Ala Pro Ile Lys Cys Lys Cys Lys
            20                  25                  30

Lys Gly

<210> SEQ ID NO 22
<211> LENGTH: 37
<212> TYPE: PRT
<213> ORGANISM: Artificial Sequence
<220> FEATURE:
<223> OTHER INFORMATION: Synthetic

<400> SEQUENCE: 22

Gly Ser Ser Glu Lys Asp Cys Ile Lys His Leu Gln Arg Cys Arg Glu
1               5                   10                  15

Asn Lys Asp Cys Cys Ser Lys Lys Cys Ser Arg Arg Gly Thr Asn Pro
            20                  25                  30

Glu Lys Arg Cys Arg
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic

<400> SEQUENCE: 23

Gly Ser Val Arg Ile Pro Val Ser Cys Lys His Ser Gly Gln Cys Leu
1               5                   10                  15

Lys Pro Cys Lys Asp Ala Gly Met Arg Phe Gly Lys Cys Met Asn Gly
            20                  25                  30

Lys Cys Asp Cys Thr Pro Lys
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic

<400> SEQUENCE: 24

```
Gly Ser Gly Val Pro Ile Asn Val Lys Cys Arg Gly Ser Arg Asp Cys
1               5                   10                  15

Leu Asp Pro Cys Lys Lys Ala Gly Met Arg Phe Gly Lys Cys Ile Asn
            20                  25                  30

Ser Lys Cys His Cys Thr Pro
        35

<210> SEQ ID NO 25
<211> LENGTH: 35
<212> TYPE: PRT
<213> ORGANISM: Artificial Sequence
<220> FEATURE:
<223> OTHER INFORMATION: Synthetic

<400> SEQUENCE: 25

Gly Ser Ala Val Cys Val Tyr Arg Thr Cys Asp Lys Asp Cys Lys Arg
1               5                   10                  15

Arg Gly Tyr Arg Ser Gly Lys Cys Ile Asn Asn Ala Cys Lys Cys Tyr
            20                  25                  30

Pro Tyr Gly
        35

<210> SEQ ID NO 26
<211> LENGTH: 37
<212> TYPE: PRT
<213> ORGANISM: Artificial Sequence
<220> FEATURE:
<223> OTHER INFORMATION: Synthetic

<400> SEQUENCE: 26

Gly Ser Ile Ser Cys Thr Gly Ser Lys Gln Cys Tyr Asp Pro Cys Lys
1               5                   10                  15

Arg Lys Thr Gly Cys Pro Asn Ala Lys Cys Met Asn Lys Ser Cys Lys
            20                  25                  30

Cys Tyr Gly Cys Gly
        35

<210> SEQ ID NO 27
<211> LENGTH: 40
<212> TYPE: PRT
<213> ORGANISM: Artificial Sequence
<220> FEATURE:
<223> OTHER INFORMATION: Synthetic

<400> SEQUENCE: 27

Gly Ser Gln Val Gln Thr Asn Val Lys Cys Gly Gly Ser Cys Ala
1               5                   10                  15

Ser Val Cys Arg Arg Glu Ile Gly Val Ala Ala Gly Lys Cys Ile Asn
            20                  25                  30

Gly Lys Cys Val Cys Tyr Arg Asn
        35                  40

<210> SEQ ID NO 28
<211> LENGTH: 39
<212> TYPE: PRT
<213> ORGANISM: Artificial Sequence
<220> FEATURE:
<223> OTHER INFORMATION: Synthetic

<400> SEQUENCE: 28

Gly Ser Glu Val Ile Arg Cys Ser Gly Ser Lys Gln Cys Tyr Gly Pro
1               5                   10                  15
```

```
Cys Lys Gln Gln Thr Gly Cys Thr Asn Ser Lys Cys Met Asn Lys Val
            20                  25                  30

Cys Lys Cys Tyr Gly Cys Gly
        35

<210> SEQ ID NO 29
<211> LENGTH: 35
<212> TYPE: PRT
<213> ORGANISM: Artificial Sequence
<220> FEATURE:
<223> OTHER INFORMATION: Synthetic

<400> SEQUENCE: 29

Gly Ser Ala Cys Lys Gly Val Phe Asp Ala Cys Thr Pro Gly Lys Asn
1               5                   10                  15

Glu Cys Cys Pro Asn Arg Val Cys Ser Asp Lys His Lys Trp Cys Lys
            20                  25                  30

Trp Lys Leu
        35

<210> SEQ ID NO 30
<211> LENGTH: 40
<212> TYPE: PRT
<213> ORGANISM: Artificial Sequence
<220> FEATURE:
<223> OTHER INFORMATION: Synthetic

<400> SEQUENCE: 30

Gly Ser Gln Ile Tyr Thr Ser Lys Glu Cys Asn Gly Ser Ser Glu Cys
1               5                   10                  15

Tyr Ser His Cys Glu Gly Ile Thr Gly Lys Arg Ser Gly Lys Cys Ile
            20                  25                  30

Asn Lys Lys Cys Tyr Cys Tyr Arg
        35                  40

<210> SEQ ID NO 31
<211> LENGTH: 37
<212> TYPE: PRT
<213> ORGANISM: Artificial Sequence
<220> FEATURE:
<223> OTHER INFORMATION: Synthetic

<400> SEQUENCE: 31

Gly Ser Gly Cys Leu Glu Phe Trp Trp Lys Cys Asn Pro Asn Asp Asp
1               5                   10                  15

Lys Cys Cys Arg Pro Lys Leu Lys Cys Ser Lys Leu Phe Lys Leu Cys
            20                  25                  30

Asn Phe Ser Phe Gly
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic

<400> SEQUENCE: 32

Gly Ser Asp Cys Val Arg Phe Trp Gly Lys Cys Ser Gln Thr Ser Asp
1               5                   10                  15

Cys Cys Pro His Leu Ala Cys Lys Ser Lys Trp Pro Arg Asn Ile Cys
            20                  25                  30
```

```
Val Trp Asp Gly Ser Val Gly
        35
```

<210> SEQ ID NO 33
<211> LENGTH: 35
<212> TYPE: PRT
<213> ORGANISM: Artificial Sequence
<220> FEATURE:
<223> OTHER INFORMATION: Synthetic

<400> SEQUENCE: 33

```
Gly Ser Gly Cys Phe Gly Tyr Lys Cys Asp Tyr Tyr Lys Gly Cys Cys
1               5                   10                  15

Ser Gly Tyr Val Cys Ser Pro Thr Trp Lys Trp Cys Val Arg Pro Gly
            20                  25                  30

Pro Gly Arg
        35
```

<210> SEQ ID NO 34
<211> LENGTH: 62
<212> TYPE: PRT
<213> ORGANISM: Artificial Sequence
<220> FEATURE:
<223> OTHER INFORMATION: Synthetic

<400> SEQUENCE: 34

```
Gly Ser Met Asn Ala Lys Phe Ile Leu Leu Val Leu Thr Thr Met
1               5                   10                  15

Met Leu Leu Pro Asp Thr Lys Gly Ala Glu Val Ile Arg Cys Ser Gly
            20                  25                  30

Ser Lys Gln Cys Tyr Gly Pro Cys Lys Gln Gln Thr Gly Cys Thr Asn
        35                  40                  45

Ser Lys Cys Met Asn Lys Val Cys Lys Cys Tyr Gly Cys Gly
    50                  55                  60
```

<210> SEQ ID NO 35
<211> LENGTH: 63
<212> TYPE: PRT
<213> ORGANISM: Artificial Sequence
<220> FEATURE:
<223> OTHER INFORMATION: Synthetic

<400> SEQUENCE: 35

```
Gly Ser Met Asn Ala Lys Leu Ile Tyr Leu Leu Val Val Thr Thr
1               5                   10                  15

Met Thr Leu Met Phe Asp Thr Ala Gln Ala Val Asp Ile Met Cys Ser
            20                  25                  30

Gly Pro Lys Gln Cys Tyr Gly Pro Cys Lys Lys Glu Thr Gly Cys Pro
        35                  40                  45

Asn Ala Lys Cys Met Asn Arg Arg Cys Lys Cys Tyr Gly Cys Val
    50                  55                  60
```

<210> SEQ ID NO 36
<211> LENGTH: 64
<212> TYPE: PRT
<213> ORGANISM: Artificial Sequence
<220> FEATURE:
<223> OTHER INFORMATION: Synthetic

<400> SEQUENCE: 36

```
Gly Ser Met Asn Ala Lys Leu Ile Tyr Leu Leu Val Val Thr Thr
1               5                   10                  15
```

Met Met Leu Thr Phe Asp Thr Thr Gln Ala Gly Asp Ile Lys Cys Ser
            20                  25                  30

Gly Thr Arg Gln Cys Trp Gly Pro Cys Lys Lys Gln Thr Thr Cys Thr
            35                  40                  45

Asn Ser Lys Cys Met Asn Gly Lys Cys Lys Cys Tyr Gly Cys Val Gly
            50                  55                  60

<210> SEQ ID NO 37
<211> LENGTH: 63
<212> TYPE: PRT
<213> ORGANISM: Artificial Sequence
<220> FEATURE:
<223> OTHER INFORMATION: Synthetic

<400> SEQUENCE: 37

Gly Ser Met Asn Thr Lys Phe Ile Phe Leu Leu Leu Val Val Thr Asn
1               5                   10                  15

Thr Met Met Leu Phe Asp Thr Lys Pro Val Glu Gly Ile Ser Cys Thr
            20                  25                  30

Gly Ser Lys Gln Cys Tyr Asp Pro Cys Lys Arg Lys Thr Gly Cys Pro
            35                  40                  45

Asn Ala Lys Cys Met Asn Lys Ser Cys Lys Cys Tyr Gly Cys Gly
            50                  55                  60

<210> SEQ ID NO 38
<211> LENGTH: 40
<212> TYPE: PRT
<213> ORGANISM: Artificial Sequence
<220> FEATURE:
<223> OTHER INFORMATION: Synthetic

<400> SEQUENCE: 38

Gly Ser Gly Val Pro Ile Asn Val Lys Cys Ser Gly Ser Arg Asp Cys
1               5                   10                  15

Leu Glu Pro Cys Lys Lys Ala Gly Met Arg Phe Gly Lys Cys Ile Asn
            20                  25                  30

Arg Lys Cys His Cys Thr Pro Lys
            35                  40

<210> SEQ ID NO 39
<211> LENGTH: 40
<212> TYPE: PRT
<213> ORGANISM: Artificial Sequence
<220> FEATURE:
<223> OTHER INFORMATION: Synthetic

<400> SEQUENCE: 39

Gly Ser Gly Val Pro Ile Asn Val Lys Cys Thr Gly Ser Pro Gln Cys
1               5                   10                  15

Leu Lys Pro Cys Lys Asp Ala Gly Met Arg Phe Gly Lys Cys Ile Asn
            20                  25                  30

Gly Lys Cys His Cys Thr Pro Lys
            35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic

<400> SEQUENCE: 40

Gly Ser Gly Val Ile Ile Asn Val Lys Cys Lys Ile Ser Arg Gln Cys
1               5                   10                  15

Leu Glu Pro Cys Lys Lys Ala Gly Met Arg Phe Gly Lys Cys Met Asn
                20                  25                  30

Gly Lys Cys His Cys Thr Pro Lys
        35                  40

<210> SEQ ID NO 41
<211> LENGTH: 40
<212> TYPE: PRT
<213> ORGANISM: Artificial Sequence
<220> FEATURE:
<223> OTHER INFORMATION: Synthetic

<400> SEQUENCE: 41

Gly Ser Gly Val Pro Ile Asn Val Lys Cys Arg Gly Ser Pro Gln Cys
1               5                   10                  15

Ile Gln Pro Cys Arg Asp Ala Gly Met Arg Phe Gly Lys Cys Met Asn
                20                  25                  30

Gly Lys Cys His Cys Thr Pro Gln
        35                  40

<210> SEQ ID NO 42
<211> LENGTH: 40
<212> TYPE: PRT
<213> ORGANISM: Artificial Sequence
<220> FEATURE:
<223> OTHER INFORMATION: Synthetic

<400> SEQUENCE: 42

Gly Ser Gly Val Glu Ile Asn Val Lys Cys Thr Gly Ser His Gln Cys
1               5                   10                  15

Ile Lys Pro Cys Lys Asp Ala Gly Met Arg Phe Gly Lys Cys Ile Asn
                20                  25                  30

Arg Lys Cys His Cys Thr Pro Lys
        35                  40

<210> SEQ ID NO 43
<211> LENGTH: 40
<212> TYPE: PRT
<213> ORGANISM: Artificial Sequence
<220> FEATURE:
<223> OTHER INFORMATION: Synthetic

<400> SEQUENCE: 43

Gly Ser Gly Val Glu Ile Asn Val Lys Cys Ser Gly Ser Pro Gln Cys
1               5                   10                  15

Leu Lys Pro Cys Lys Asp Ala Gly Met Arg Phe Gly Lys Cys Met Asn
                20                  25                  30

Arg Lys Cys His Cys Thr Pro Lys
        35                  40

<210> SEQ ID NO 44
<211> LENGTH: 40
<212> TYPE: PRT
<213> ORGANISM: Artificial Sequence
<220> FEATURE:
<223> OTHER INFORMATION: Synthetic

<400> SEQUENCE: 44

Gly Ser Gly Val Pro Thr Asp Val Lys Cys Arg Gly Ser Pro Gln Cys
1               5                   10                  15

Ile Gln Pro Cys Lys Asp Ala Gly Met Arg Phe Gly Lys Cys Met Asn
            20                  25                  30

Gly Lys Cys His Cys Thr Pro Lys
        35                  40

<210> SEQ ID NO 45
<211> LENGTH: 40
<212> TYPE: PRT
<213> ORGANISM: Artificial Sequence
<220> FEATURE:
<223> OTHER INFORMATION: Synthetic

<400> SEQUENCE: 45

Gly Ser Gly Val Pro Ile Asn Val Ser Cys Thr Gly Ser Pro Gln Cys
1               5                   10                  15

Ile Lys Pro Cys Lys Asp Ala Gly Met Arg Phe Gly Lys Cys Met Asn
            20                  25                  30

Arg Lys Cys His Cys Thr Pro Lys
        35                  40

<210> SEQ ID NO 46
<211> LENGTH: 40
<212> TYPE: PRT
<213> ORGANISM: Artificial Sequence
<220> FEATURE:
<223> OTHER INFORMATION: Synthetic

<400> SEQUENCE: 46

Gly Ser Gly Val Pro Ile Asn Val Pro Cys Thr Gly Ser Pro Gln Cys
1               5                   10                  15

Ile Lys Pro Cys Lys Asp Ala Gly Met Arg Phe Gly Lys Cys Met Asn
            20                  25                  30

Arg Lys Cys His Cys Thr Pro Lys
        35                  40

<210> SEQ ID NO 47
<211> LENGTH: 39
<212> TYPE: PRT
<213> ORGANISM: Artificial Sequence
<220> FEATURE:
<223> OTHER INFORMATION: Synthetic

<400> SEQUENCE: 47

Gly Ser Val Gly Ile Asn Val Lys Cys Lys His Ser Gly Gln Cys Leu
1               5                   10                  15

Lys Pro Cys Lys Asp Ala Gly Met Arg Phe Gly Lys Cys Ile Asn Gly
            20                  25                  30

Lys Cys Asp Cys Thr Pro Lys
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic

<400> SEQUENCE: 48

Gly Ser Val Gly Ile Asn Val Lys Cys Lys His Ser Gly Gln Cys Leu
1               5                   10                  15

Lys Pro Cys Lys Asp Ala Gly Met Arg Phe Gly Lys Cys Met Asn Gly
            20                  25                  30

-continued

Lys Cys Asp Cys Thr Pro Lys
        35

<210> SEQ ID NO 49
<211> LENGTH: 39
<212> TYPE: PRT
<213> ORGANISM: Artificial Sequence
<220> FEATURE:
<223> OTHER INFORMATION: Synthetic

<400> SEQUENCE: 49

Gly Ser Val Gly Ile Pro Val Ser Cys Lys His Ser Gly Gln Cys Ile
1               5                   10                  15

Lys Pro Cys Lys Asp Ala Gly Met Arg Phe Gly Lys Cys Met Asn Arg
            20                  25                  30

Lys Cys Asp Cys Thr Pro Lys
        35

<210> SEQ ID NO 50
<211> LENGTH: 38
<212> TYPE: PRT
<213> ORGANISM: Artificial Sequence
<220> FEATURE:
<223> OTHER INFORMATION: Synthetic

<400> SEQUENCE: 50

Gly Ser Arg Lys Gly Cys Phe Lys Glu Gly His Ser Cys Pro Lys Thr
1               5                   10                  15

Ala Pro Cys Cys Arg Pro Leu Val Cys Lys Gly Pro Ser Pro Asn Thr
            20                  25                  30

Lys Lys Cys Thr Arg Pro
        35

<210> SEQ ID NO 51
<211> LENGTH: 34
<212> TYPE: PRT
<213> ORGANISM: Artificial Sequence
<220> FEATURE:
<223> OTHER INFORMATION: Synthetic

<400> SEQUENCE: 51

Gly Ser Ser Phe Cys Ile Pro Phe Lys Pro Cys Lys Ser Asp Glu Asn
1               5                   10                  15

Cys Cys Lys Lys Phe Lys Cys Lys Thr Thr Gly Ile Val Lys Leu Cys
            20                  25                  30

Arg Trp

<210> SEQ ID NO 52
<211> LENGTH: 38
<212> TYPE: PRT
<213> ORGANISM: Artificial Sequence
<220> FEATURE:
<223> OTHER INFORMATION: Synthetic

<400> SEQUENCE: 52

Gly Ser Leu Lys Gly Cys Leu Pro Arg Asn Arg Phe Cys Asn Ala Leu
1               5                   10                  15

Ser Gly Pro Arg Cys Cys Ser Gly Leu Arg Cys Lys Glu Leu Ser Ile
            20                  25                  30

Trp Ala Ser Lys Cys Leu
        35

<210> SEQ ID NO 53
<211> LENGTH: 36
<212> TYPE: PRT
<213> ORGANISM: Artificial Sequence
<220> FEATURE:
<223> OTHER INFORMATION: Synthetic

<400> SEQUENCE: 53

Gly Ser Gly Asn Tyr Cys Leu Arg Gly Arg Cys Leu Pro Gly Gly Arg
1               5                   10                  15

Lys Cys Cys Asn Gly Arg Pro Cys Glu Cys Phe Ala Lys Ile Cys Ser
                20                  25                  30

Cys Lys Pro Lys
        35

<210> SEQ ID NO 54
<211> LENGTH: 31
<212> TYPE: PRT
<213> ORGANISM: Artificial Sequence
<220> FEATURE:
<223> OTHER INFORMATION: Synthetic

<400> SEQUENCE: 54

Gly Ser Thr Val Lys Cys Gly Gly Cys Asn Arg Lys Cys Cys Pro Gly
1               5                   10                  15

Gly Cys Arg Ser Gly Lys Cys Ile Asn Gly Lys Cys Gln Cys Tyr
                20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Synthetic

<400> SEQUENCE: 55

Gly Ser Gly Cys Met Lys Glu Tyr Cys Ala Gly Gln Cys Arg Gly Lys
1               5                   10                  15

Val Ser Gln Asp Tyr Cys Leu Lys His Cys Lys Cys Ile Pro Arg
                20                  25                  30

<210> SEQ ID NO 56
<211> LENGTH: 36
<212> TYPE: PRT
<213> ORGANISM: Artificial Sequence
<220> FEATURE:
<223> OTHER INFORMATION: Synthetic

<400> SEQUENCE: 56

Gly Ser Ala Cys Leu Gly Phe Gly Glu Lys Cys Asn Pro Ser Asn Asp
1               5                   10                  15

Lys Cys Cys Lys Ser Ser Ser Leu Val Cys Ser Gln Lys His Lys Trp
                20                  25                  30

Cys Lys Tyr Gly
        35

<210> SEQ ID NO 57
<211> LENGTH: 39
<212> TYPE: PRT
<213> ORGANISM: Artificial Sequence
<220> FEATURE:
<223> OTHER INFORMATION: Synthetic

<400> SEQUENCE: 57

```
Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Lys Glu Leu Ser Ile
                20                  25                  30

Arg Asp Ser Arg Cys Leu Gly
                35
```

<210> SEQ ID NO 58
<211> LENGTH: 38
<212> TYPE: PRT
<213> ORGANISM: Artificial Sequence
<220> FEATURE:
<223> OTHER INFORMATION: Synthetic

<400> SEQUENCE: 58

```
Gly Ser Arg Gly Gly Cys Leu Pro Arg Asn Lys Phe Cys Asn Pro Ser
1               5                   10                  15

Ser Gly Pro Arg Cys Cys Ser Gly Leu Thr Cys Lys Glu Leu Asn Ile
                20                  25                  30

Trp Ala Ser Lys Cys Leu
                35
```

<210> SEQ ID NO 59
<211> LENGTH: 35
<212> TYPE: PRT
<213> ORGANISM: Artificial Sequence
<220> FEATURE:
<223> OTHER INFORMATION: Synthetic

<400> SEQUENCE: 59

```
Gly Ser Gln Arg Ser Cys Ala Lys Pro Gly Asp Met Cys Met Gly Ile
1               5                   10                  15

Lys Cys Cys Asp Gly Gln Cys Gly Cys Asn Arg Gly Thr Gly Arg Cys
                20                  25                  30

Phe Cys Lys
        35
```

<210> SEQ ID NO 60
<211> LENGTH: 42
<212> TYPE: PRT
<213> ORGANISM: Artificial Sequence
<220> FEATURE:
<223> OTHER INFORMATION: Synthetic

<400> SEQUENCE: 60

```
Gly Ser Ala Arg Gly Cys Ala Asp Ala Tyr Lys Ser Cys Asn His Pro
1               5                   10                  15

Arg Thr Cys Cys Asp Gly Tyr Asn Gly Tyr Lys Arg Ala Cys Ile Cys
                20                  25                  30

Ser Gly Ser Asn Cys Lys Cys Lys Lys Ser
        35                  40
```

<210> SEQ ID NO 61
<211> LENGTH: 39
<212> TYPE: PRT
<213> ORGANISM: Artificial Sequence
<220> FEATURE:
<223> OTHER INFORMATION: Synthetic

<400> SEQUENCE: 61

```
Gly Ser Arg Gly Gly Cys Leu Pro His Asn Arg Phe Cys Asn Ala Leu
1               5                   10                  15
```

```
Ser Gly Pro Arg Cys Cys Ser Gly Leu Arg Cys Lys Glu Leu Ser Ile
            20                  25                  30

Trp Asp Ser Arg Cys Leu Gly
        35
```

<210> SEQ ID NO 62
<211> LENGTH: 39
<212> TYPE: PRT
<213> ORGANISM: Artificial Sequence
<220> FEATURE:
<223> OTHER INFORMATION: Synthetic

<400> SEQUENCE: 62

```
Gly Ser Arg Gly Gly Cys Leu Pro His Asn Arg Phe Cys Asn Ala Leu
1               5                   10                  15

Ser Gly Pro Arg Cys Cys Ser Gly Leu Lys Cys Lys Glu Leu Ser Ile
            20                  25                  30

Tyr Asp Ser Arg Cys Leu Gly
        35
```

<210> SEQ ID NO 63
<211> LENGTH: 39
<212> TYPE: PRT
<213> ORGANISM: Artificial Sequence
<220> FEATURE:
<223> OTHER INFORMATION: Synthetic

<400> SEQUENCE: 63

```
Gly Ser Arg Gly Gly Cys Leu Pro His Asn Arg Phe Cys Asn Ala Leu
1               5                   10                  15

Ser Gly Pro Arg Cys Cys Ser Arg Leu Lys Cys Lys Glu Leu Ser Ile
            20                  25                  30

Trp Asp Ser Arg Cys Leu Gly
        35
```

<210> SEQ ID NO 64
<211> LENGTH: 39
<212> TYPE: PRT
<213> ORGANISM: Artificial Sequence
<220> FEATURE:
<223> OTHER INFORMATION: Synthetic

<400> SEQUENCE: 64

```
Gly Ser Arg Gly Gly Cys Leu Pro His Asn Arg Phe Cys Asn Ala Leu
1               5                   10                  15

Thr Gly Pro Arg Cys Cys Ser Arg Leu Arg Cys Lys Glu Leu Ser Ile
            20                  25                  30

Trp Asp Ser Ile Cys Leu Gly
        35
```

<210> SEQ ID NO 65
<211> LENGTH: 36
<212> TYPE: PRT
<213> ORGANISM: Artificial Sequence
<220> FEATURE:
<223> OTHER INFORMATION: Synthetic

<400> SEQUENCE: 65

```
Gly Ser Ser Cys Ala Asp Ala Tyr Lys Ser Cys Asp Ser Leu Lys Cys
1               5                   10                  15

Cys Asn Asn Arg Thr Cys Met Cys Ser Met Ile Gly Thr Asn Cys Thr
            20                  25                  30
```

Cys Arg Lys Lys
        35

<210> SEQ ID NO 66
<211> LENGTH: 32
<212> TYPE: PRT
<213> ORGANISM: Artificial Sequence
<220> FEATURE:
<223> OTHER INFORMATION: Synthetic

<400> SEQUENCE: 66

Gly Ser Glu Arg Arg Cys Leu Pro Ala Gly Lys Thr Cys Val Arg Gly
1               5                   10                  15

Pro Met Arg Val Pro Cys Cys Gly Ser Cys Ser Gln Asn Lys Cys Thr
            20                  25                  30

<210> SEQ ID NO 67
<211> LENGTH: 33
<212> TYPE: PRT
<213> ORGANISM: Artificial Sequence
<220> FEATURE:
<223> OTHER INFORMATION: Synthetic

<400> SEQUENCE: 67

Gly Ser Leu Cys Ser Arg Glu Gly Glu Phe Cys Tyr Lys Leu Arg Lys
1               5                   10                  15

Cys Cys Ala Gly Phe Tyr Cys Lys Ala Phe Val Leu His Cys Tyr Arg
            20                  25                  30

Asn

<210> SEQ ID NO 68
<211> LENGTH: 25
<212> TYPE: PRT
<213> ORGANISM: Artificial Sequence
<220> FEATURE:
<223> OTHER INFORMATION: Synthetic

<400> SEQUENCE: 68

Gly Ser Ala Cys Gly Ser Cys Arg Lys Lys Cys Lys Gly Ser Gly Lys
1               5                   10                  15

Cys Ile Asn Gly Arg Cys Lys Cys Tyr
            20                  25

<210> SEQ ID NO 69
<211> LENGTH: 25
<212> TYPE: PRT
<213> ORGANISM: Artificial Sequence
<220> FEATURE:
<223> OTHER INFORMATION: Synthetic

<400> SEQUENCE: 69

Gly Ser Ala Cys Gly Ser Cys Arg Lys Lys Cys Lys Gly Pro Gly Lys
1               5                   10                  15

Cys Ile Asn Gly Arg Cys Lys Cys Tyr
            20                  25

<210> SEQ ID NO 70
<211> LENGTH: 34
<212> TYPE: PRT
<213> ORGANISM: Artificial Sequence
<220> FEATURE:
<223> OTHER INFORMATION: Synthetic

<400> SEQUENCE: 70

-continued

Gly Ser Ala Cys Gln Gly Tyr Met Arg Lys Cys Gly Arg Asp Lys Pro
1               5                   10                  15

Pro Cys Cys Lys Lys Leu Glu Cys Ser Lys Thr Trp Arg Trp Cys Val
            20                  25                  30

Trp Asn

<210> SEQ ID NO 71
<211> LENGTH: 32
<212> TYPE: PRT
<213> ORGANISM: Artificial Sequence
<220> FEATURE:
<223> OTHER INFORMATION: Synthetic

<400> SEQUENCE: 71

Gly Ser Gly Arg Tyr Cys Gln Lys Trp Met Trp Thr Cys Asp Ser Lys
1               5                   10                  15

Arg Ala Cys Cys Glu Gly Leu Arg Cys Lys Leu Trp Cys Arg Lys Ile
            20                  25                  30

<210> SEQ ID NO 72
<211> LENGTH: 36
<212> TYPE: PRT
<213> ORGANISM: Artificial Sequence
<220> FEATURE:
<223> OTHER INFORMATION: Synthetic

<400> SEQUENCE: 72

Gly Ser Asn Ala Lys Cys Arg Gly Ser Pro Glu Cys Leu Pro Lys Cys
1               5                   10                  15

Lys Glu Ala Ile Gly Lys Ala Ala Gly Lys Cys Met Asn Gly Lys Cys
            20                  25                  30

Lys Cys Tyr Pro
        35

<210> SEQ ID NO 73
<211> LENGTH: 36
<212> TYPE: PRT
<213> ORGANISM: Artificial Sequence
<220> FEATURE:
<223> OTHER INFORMATION: Synthetic

<400> SEQUENCE: 73

Gly Ser Asn Val Lys Cys Arg Gly Ser Lys Glu Cys Leu Pro Ala Cys
1               5                   10                  15

Lys Ala Ala Val Gly Lys Ala Ala Gly Lys Cys Met Asn Gly Lys Cys
            20                  25                  30

Lys Cys Tyr Pro
        35

<210> SEQ ID NO 74
<211> LENGTH: 36
<212> TYPE: PRT
<213> ORGANISM: Artificial Sequence
<220> FEATURE:
<223> OTHER INFORMATION: Synthetic

<400> SEQUENCE: 74

Gly Ser Asn Val Lys Cys Arg Gly Ser Pro Glu Cys Leu Pro Lys Cys
1               5                   10                  15

Lys Glu Ala Ile Gly Lys Ser Ala Gly Lys Cys Met Asn Gly Lys Cys
            20                  25                  30

Lys Cys Tyr Pro

<210> SEQ ID NO 75
<211> LENGTH: 36
<212> TYPE: PRT
<213> ORGANISM: Artificial Sequence
<220> FEATURE:
<223> OTHER INFORMATION: Synthetic

<400> SEQUENCE: 75

Gly Ser Asn Ala Lys Cys Arg Gly Ser Pro Glu Cys Leu Pro Lys Cys
1               5                   10                  15

Lys Gln Ala Ile Gly Lys Ala Ala Gly Lys Cys Met Asn Gly Lys Cys
            20                  25                  30

Lys Cys Tyr Pro
        35

<210> SEQ ID NO 76
<211> LENGTH: 35
<212> TYPE: PRT
<213> ORGANISM: Artificial Sequence
<220> FEATURE:
<223> OTHER INFORMATION: Synthetic

<400> SEQUENCE: 76

Gly Ser Arg Gly Tyr Cys Ala Glu Lys Gly Ile Lys Cys His Asn Ile
1               5                   10                  15

His Cys Cys Ser Gly Leu Thr Cys Lys Cys Lys Gly Ser Ser Cys Val
            20                  25                  30

Cys Arg Lys
        35

<210> SEQ ID NO 77
<211> LENGTH: 33
<212> TYPE: PRT
<213> ORGANISM: Artificial Sequence
<220> FEATURE:
<223> OTHER INFORMATION: Synthetic

<400> SEQUENCE: 77

Gly Ser Glu Arg Gly Cys Lys Leu Thr Phe Trp Lys Cys Lys Asn Lys
1               5                   10                  15

Lys Glu Cys Cys Gly Trp Asn Ala Cys Ala Leu Gly Ile Cys Met Pro
            20                  25                  30

Arg

<210> SEQ ID NO 78
<211> LENGTH: 41
<212> TYPE: PRT
<213> ORGANISM: Artificial Sequence
<220> FEATURE:
<223> OTHER INFORMATION: Synthetic

<400> SEQUENCE: 78

Gly Ser Lys Lys Cys Ile Ala Lys Asp Tyr Gly Arg Cys Lys Trp
1               5                   10                  15

Gly Gly Thr Pro Cys Cys Arg Gly Arg Gly Cys Ile Cys Ser Ile Met
            20                  25                  30

Gly Thr Asn Cys Glu Cys Lys Pro Arg
        35                  40

<210> SEQ ID NO 79

```
<211> LENGTH: 31
<212> TYPE: PRT
<213> ORGANISM: Artificial Sequence
<220> FEATURE:
<223> OTHER INFORMATION: Synthetic

<400> SEQUENCE: 79
```

Gly Ser Gly Cys Lys Leu Thr Phe Trp Lys Cys Lys Asn Lys Lys Glu
1               5                   10                  15

Cys Cys Gly Trp Asn Ala Cys Ala Leu Gly Ile Cys Met Pro Arg
            20                  25                  30

```
<210> SEQ ID NO 80
<211> LENGTH: 34
<212> TYPE: PRT
<213> ORGANISM: Artificial Sequence
<220> FEATURE:
<223> OTHER INFORMATION: Synthetic

<400> SEQUENCE: 80
```

Gly Ser Ala Cys Lys Gly Leu Phe Val Thr Cys Thr Pro Gly Lys Asp
1               5                   10                  15

Glu Cys Cys Pro Asn His Val Cys Ser Ser Lys His Lys Trp Cys Lys
            20                  25                  30

Tyr Lys

```
<210> SEQ ID NO 81
<211> LENGTH: 38
<212> TYPE: PRT
<213> ORGANISM: Artificial Sequence
<220> FEATURE:
<223> OTHER INFORMATION: Synthetic

<400> SEQUENCE: 81
```

Gly Ser Ile Ala Cys Ala Pro Arg Gly Leu Leu Cys Phe Arg Asp Lys
1               5                   10                  15

Glu Cys Cys Lys Gly Leu Thr Cys Lys Gly Arg Phe Val Asn Thr Trp
            20                  25                  30

Pro Thr Phe Cys Leu Val
            35

```
<210> SEQ ID NO 82
<211> LENGTH: 38
<212> TYPE: PRT
<213> ORGANISM: Artificial Sequence
<220> FEATURE:
<223> OTHER INFORMATION: Synthetic

<400> SEQUENCE: 82
```

Gly Ser Ala Cys Ala Gly Leu Tyr Lys Lys Cys Gly Lys Gly Val Asn
1               5                   10                  15

Thr Cys Cys Glu Asn Arg Pro Cys Lys Cys Asp Leu Ala Met Gly Asn
            20                  25                  30

Cys Ile Cys Lys Lys Lys
            35

```
<210> SEQ ID NO 83
<211> LENGTH: 40
<212> TYPE: PRT
<213> ORGANISM: Artificial Sequence
<220> FEATURE:
<223> OTHER INFORMATION: Synthetic

<400> SEQUENCE: 83
```

```
Gly Ser Phe Thr Cys Ala Ile Ser Cys Asp Ile Lys Val Asn Gly Lys
1               5                   10                  15

Pro Cys Lys Gly Ser Gly Glu Lys Cys Ser Gly Gly Trp Ser Cys
            20                  25                  30

Lys Phe Asn Val Cys Val Lys Val
            35              40
```

<210> SEQ ID NO 84
<211> LENGTH: 35
<212> TYPE: PRT
<213> ORGANISM: Artificial Sequence
<220> FEATURE:
<223> OTHER INFORMATION: Synthetic

<400> SEQUENCE: 84

```
Gly Ser Gly Phe Cys Ala Gln Lys Gly Ile Lys Cys His Asp Ile His
1               5                   10                  15

Cys Cys Thr Asn Leu Lys Cys Val Arg Glu Gly Ser Asn Arg Val Cys
            20                  25                  30

Arg Lys Ala
        35
```

<210> SEQ ID NO 85
<211> LENGTH: 44
<212> TYPE: PRT
<213> ORGANISM: Artificial Sequence
<220> FEATURE:
<223> OTHER INFORMATION: Synthetic

<400> SEQUENCE: 85

```
Gly Ser Cys Ala Lys Lys Arg Asn Trp Cys Gly Lys Asn Glu Asp Cys
1               5                   10                  15

Cys Cys Pro Met Lys Cys Ile Tyr Ala Trp Tyr Asn Gln Gln Gly Ser
            20                  25                  30

Cys Gln Ser Thr Ile Thr Gly Leu Phe Lys Lys Cys
            35                  40
```

<210> SEQ ID NO 86
<211> LENGTH: 30
<212> TYPE: PRT
<213> ORGANISM: Artificial Sequence
<220> FEATURE:
<223> OTHER INFORMATION: Synthetic

<400> SEQUENCE: 86

```
Gly Ser Tyr Cys Gln Lys Trp Met Trp Thr Cys Asp Ser Ala Arg Lys
1               5                   10                  15

Cys Cys Glu Gly Leu Val Cys Arg Leu Trp Cys Lys Lys Ile
            20                  25                  30
```

<210> SEQ ID NO 87
<211> LENGTH: 39
<212> TYPE: PRT
<213> ORGANISM: Artificial Sequence
<220> FEATURE:
<223> OTHER INFORMATION: Synthetic

<400> SEQUENCE: 87

```
Gly Ser Arg Gly Gly Cys Leu Pro His Asn Lys Phe Cys Asn Ala Leu
1               5                   10                  15

Ser Gly Pro Arg Cys Cys Ser Gly Leu Lys Cys Lys Glu Leu Thr Ile
            20                  25                  30
```

Trp Asn Thr Lys Cys Leu Glu
        35

<210> SEQ ID NO 88
<211> LENGTH: 36
<212> TYPE: PRT
<213> ORGANISM: Artificial Sequence
<220> FEATURE:
<223> OTHER INFORMATION: Synthetic

<400> SEQUENCE: 88

Gly Ser Asn Val Lys Cys Thr Gly Ser Lys Gln Cys Leu Pro Ala Cys
1               5                   10                  15

Lys Ala Ala Val Gly Lys Ala Ala Gly Lys Cys Met Asn Gly Lys Cys
            20                  25                  30

Lys Cys Tyr Thr
        35

<210> SEQ ID NO 89
<211> LENGTH: 35
<212> TYPE: PRT
<213> ORGANISM: Artificial Sequence
<220> FEATURE:
<223> OTHER INFORMATION: Synthetic

<400> SEQUENCE: 89

Gly Ser Gln Arg Ser Cys Ala Lys Pro Gly Glu Met Cys Met Arg Ile
1               5                   10                  15

Lys Cys Cys Asp Gly Gln Cys Gly Cys Asn Arg Gly Thr Gly Arg Cys
            20                  25                  30

Phe Cys Lys
        35

<210> SEQ ID NO 90
<211> LENGTH: 38
<212> TYPE: PRT
<213> ORGANISM: Artificial Sequence
<220> FEATURE:
<223> OTHER INFORMATION: Synthetic

<400> SEQUENCE: 90

Gly Ser Gly Cys Ile Pro Lys His Lys Arg Cys Thr Trp Ser Gly Pro
1               5                   10                  15

Lys Cys Cys Asn Asn Ile Ser Cys His Cys Asn Ile Ser Gly Thr Leu
            20                  25                  30

Cys Lys Cys Arg Pro Gly
        35

<210> SEQ ID NO 91
<211> LENGTH: 35
<212> TYPE: PRT
<213> ORGANISM: Artificial Sequence
<220> FEATURE:
<223> OTHER INFORMATION: Synthetic

<400> SEQUENCE: 91

Gly Ser Asn Tyr Cys Val Ala Lys Cys Arg Pro Gly Gly Arg Gln
1               5                   10                  15

Cys Cys Ser Gly Lys Pro Cys Ala Cys Val Gly Lys Val Cys Lys Cys
            20                  25                  30

Pro Arg Asp
        35

```
<210> SEQ ID NO 92
<211> LENGTH: 39
<212> TYPE: PRT
<213> ORGANISM: Artificial Sequence
<220> FEATURE:
<223> OTHER INFORMATION: Synthetic

<400> SEQUENCE: 92

Gly Ser Glu Arg Gly Cys Ser Gly Ala Tyr Lys Arg Cys Ser Ser
1               5                   10                  15

Gln Arg Cys Cys Glu Gly Arg Pro Val Cys Ser Ala Ile Asn Ser
                20                  25                  30

Asn Cys Lys Cys Arg Lys Thr
            35

<210> SEQ ID NO 93
<211> LENGTH: 38
<212> TYPE: PRT
<213> ORGANISM: Artificial Sequence
<220> FEATURE:
<223> OTHER INFORMATION: Synthetic

<400> SEQUENCE: 93

Gly Ser Arg Tyr Cys Pro Arg Asn Pro Glu Ala Cys Tyr Asn Tyr Cys
1               5                   10                  15

Leu Arg Thr Gly Arg Pro Gly Gly Tyr Cys Gly Arg Ser Arg Ile
                20                  25                  30

Thr Cys Phe Cys Phe Arg
            35

<210> SEQ ID NO 94
<211> LENGTH: 35
<212> TYPE: PRT
<213> ORGANISM: Artificial Sequence
<220> FEATURE:
<223> OTHER INFORMATION: Synthetic

<400> SEQUENCE: 94

Gly Ser Gln Arg Ser Cys Ala Lys Pro Gly Glu Met Cys Met Gly Ile
1               5                   10                  15

Lys Cys Cys Asp Gly Gln Cys Gly Cys Asn Arg Gly Thr Gly Arg Cys
                20                  25                  30

Phe Cys Lys
        35

<210> SEQ ID NO 95
<211> LENGTH: 38
<212> TYPE: PRT
<213> ORGANISM: Artificial Sequence
<220> FEATURE:
<223> OTHER INFORMATION: Synthetic

<400> SEQUENCE: 95

Gly Ser Arg Arg Gly Cys Phe Lys Glu Gly Lys Trp Cys Pro Lys Ser
1               5                   10                  15

Ala Pro Cys Cys Ala Pro Leu Lys Cys Lys Gly Pro Ser Ile Lys Gln
                20                  25                  30

Gln Lys Cys Val Arg Glu
            35

<210> SEQ ID NO 96
```

```
<211> LENGTH: 33
<212> TYPE: PRT
<213> ORGANISM: Artificial Sequence
<220> FEATURE:
<223> OTHER INFORMATION: Synthetic

<400> SEQUENCE: 96

Gly Ser Thr Val Lys Cys Gly Gly Cys Asn Arg Lys Cys Cys Ala Gly
1               5                   10                  15

Gly Cys Arg Ser Gly Lys Cys Ile Asn Gly Lys Cys Gln Cys Tyr Gly
            20                  25                  30

Arg

<210> SEQ ID NO 97
<211> LENGTH: 31
<212> TYPE: PRT
<213> ORGANISM: Artificial Sequence
<220> FEATURE:
<223> OTHER INFORMATION: Synthetic

<400> SEQUENCE: 97

Gly Ser Glu Arg Arg Cys Glu Pro Ser Gly Lys Pro Cys Arg Pro Leu
1               5                   10                  15

Met Arg Ile Pro Cys Cys Gly Ser Cys Val Arg Gly Lys Cys Ala
            20                  25                  30

<210> SEQ ID NO 98
<211> LENGTH: 38
<212> TYPE: PRT
<213> ORGANISM: Artificial Sequence
<220> FEATURE:
<223> OTHER INFORMATION: Synthetic

<400> SEQUENCE: 98

Gly Ser Arg Gly Gly Cys Leu Pro Arg Asn Lys Phe Cys Asn Pro Ser
1               5                   10                  15

Ser Gly Pro Arg Cys Cys Ser Gly Leu Thr Cys Lys Glu Leu Asn Ile
            20                  25                  30

Trp Ala Asn Lys Cys Leu
        35

<210> SEQ ID NO 99
<211> LENGTH: 44
<212> TYPE: PRT
<213> ORGANISM: Artificial Sequence
<220> FEATURE:
<223> OTHER INFORMATION: Synthetic

<400> SEQUENCE: 99

Gly Ser Cys Ala Lys Lys Arg Asn Trp Cys Gly Lys Asn Glu Asp Cys
1               5                   10                  15

Cys Cys Pro Met Lys Cys Ile Tyr Ala Trp Tyr Asn Gln Gln Gly Ser
            20                  25                  30

Cys Gln Thr Thr Ile Thr Gly Leu Phe Lys Lys Cys
        35                  40

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100
```

```
Gly Ser Gly Lys Cys Ile Asn Lys Cys Lys Cys
1               5                   10
```

<210> SEQ ID NO 101
<211> LENGTH: 6
<212> TYPE: PRT
<213> ORGANISM: Artificial Sequence
<220> FEATURE:
<223> OTHER INFORMATION: Synthetic

<400> SEQUENCE: 101

```
Gly Ser Lys Cys Ile Asn
1               5
```

<210> SEQ ID NO 102
<211> LENGTH: 6
<212> TYPE: PRT
<213> ORGANISM: Artificial Sequence
<220> FEATURE:
<223> OTHER INFORMATION: Synthetic

<400> SEQUENCE: 102

```
Gly Ser Lys Lys Cys Lys
1               5
```

<210> SEQ ID NO 103
<211> LENGTH: 6
<212> TYPE: PRT
<213> ORGANISM: Artificial Sequence
<220> FEATURE:
<223> OTHER INFORMATION: Synthetic

<400> SEQUENCE: 103

```
Gly Ser Pro Cys Lys Arg
1               5
```

<210> SEQ ID NO 104
<211> LENGTH: 8
<212> TYPE: PRT
<213> ORGANISM: Artificial Sequence
<220> FEATURE:
<223> OTHER INFORMATION: Synthetic

<400> SEQUENCE: 104

```
Gly Ser Lys Arg Cys Ser Arg Arg
1               5
```

<210> SEQ ID NO 105
<211> LENGTH: 5
<212> TYPE: PRT
<213> ORGANISM: Artificial Sequence
<220> FEATURE:
<223> OTHER INFORMATION: Synthetic

<400> SEQUENCE: 105

```
Gly Ser Lys Gln Cys
1               5
```

<210> SEQ ID NO 106
<211> LENGTH: 39
<212> TYPE: PRT
<213> ORGANISM: Artificial Sequence
<220> FEATURE:
<223> OTHER INFORMATION: Synthetic

<400> SEQUENCE: 106

```
Gly Ser Val Arg Ile Pro Val Ser Cys Lys His Ser Gly Gln Cys Leu
1               5                   10                  15

Lys Pro Cys Lys Asp Ala Gly Met Arg Thr Gly Lys Cys Met Asn Gly
                20                  25                  30

Lys Cys Asp Cys Thr Pro Lys
            35
```

<210> SEQ ID NO 107
<211> LENGTH: 22
<212> TYPE: PRT
<213> ORGANISM: Artificial Sequence
<220> FEATURE:
<223> OTHER INFORMATION: Synthetic

<400> SEQUENCE: 107

```
Gly Ser Val Lys Cys Thr Thr Ser Lys Asp Cys Trp Pro Cys Lys
1               5                   10                  15

Lys Val Thr Gly Arg Ala
            20
```

<210> SEQ ID NO 108
<211> LENGTH: 34
<212> TYPE: PRT
<213> ORGANISM: Artificial Sequence
<220> FEATURE:
<223> OTHER INFORMATION: Synthetic

<400> SEQUENCE: 108

```
Gly Ser Gly Ile Val Cys Arg Val Cys Arg Ile Ile Cys Gly Met Gln
1               5                   10                  15

Gly Arg Arg Val Asn Ile Cys Arg Ala Pro Ile Arg Cys Arg Cys Arg
                20                  25                  30

Arg Gly
```

<210> SEQ ID NO 109
<211> LENGTH: 37
<212> TYPE: PRT
<213> ORGANISM: Artificial Sequence
<220> FEATURE:
<223> OTHER INFORMATION: Synthetic

<400> SEQUENCE: 109

```
Gly Ser Ser Glu Arg Asp Cys Ile Arg His Leu Gln Arg Cys Arg Glu
1               5                   10                  15

Asn Arg Asp Cys Cys Ser Arg Arg Cys Ser Arg Arg Gly Thr Asn Pro
                20                  25                  30

Glu Arg Arg Cys Arg
            35
```

<210> SEQ ID NO 110
<211> LENGTH: 39
<212> TYPE: PRT
<213> ORGANISM: Artificial Sequence
<220> FEATURE:
<223> OTHER INFORMATION: Synthetic

<400> SEQUENCE: 110

```
Gly Ser Val Arg Ile Pro Val Ser Cys Arg His Ser Gly Gln Cys Leu
1               5                   10                  15

Arg Pro Cys Arg Asp Ala Gly Met Arg Phe Gly Arg Cys Met Asn Gly
                20                  25                  30

Arg Cys Asp Cys Thr Pro Arg
```

<210> SEQ ID NO 111
<211> LENGTH: 39
<212> TYPE: PRT
<213> ORGANISM: Artificial Sequence
<220> FEATURE:
<223> OTHER INFORMATION: Synthetic

<400> SEQUENCE: 111

Gly Ser Gly Val Pro Ile Asn Val Arg Cys Arg Gly Ser Arg Asp Cys
1               5                   10                  15

Leu Asp Pro Cys Arg Arg Ala Gly Met Arg Phe Gly Arg Cys Ile Asn
            20                  25                  30

Ser Arg Cys His Cys Thr Pro
        35

<210> SEQ ID NO 112
<211> LENGTH: 35
<212> TYPE: PRT
<213> ORGANISM: Artificial Sequence
<220> FEATURE:
<223> OTHER INFORMATION: Synthetic

<400> SEQUENCE: 112

Gly Ser Ala Val Cys Val Tyr Arg Thr Cys Asp Arg Asp Cys Arg Arg
1               5                   10                  15

Arg Gly Tyr Arg Ser Gly Arg Cys Ile Asn Asn Ala Cys Arg Cys Tyr
            20                  25                  30

Pro Tyr Gly
        35

<210> SEQ ID NO 113
<211> LENGTH: 37
<212> TYPE: PRT
<213> ORGANISM: Artificial Sequence
<220> FEATURE:
<223> OTHER INFORMATION: Synthetic

<400> SEQUENCE: 113

Gly Ser Ile Ser Cys Thr Gly Ser Arg Gln Cys Tyr Asp Pro Cys Arg
1               5                   10                  15

Arg Arg Thr Gly Cys Pro Asn Ala Arg Cys Met Asn Arg Ser Cys Arg
            20                  25                  30

Cys Tyr Gly Cys Gly
        35

<210> SEQ ID NO 114
<211> LENGTH: 40
<212> TYPE: PRT
<213> ORGANISM: Artificial Sequence
<220> FEATURE:
<223> OTHER INFORMATION: Synthetic

<400> SEQUENCE: 114

Gly Ser Gln Val Gln Thr Asn Val Arg Cys Gln Gly Gly Ser Cys Ala
1               5                   10                  15

Ser Val Cys Arg Arg Glu Ile Gly Val Ala Ala Gly Arg Cys Ile Asn
            20                  25                  30

Gly Arg Cys Val Cys Tyr Arg Asn
        35                  40

```
<210> SEQ ID NO 115
<211> LENGTH: 39
<212> TYPE: PRT
<213> ORGANISM: Artificial Sequence
<220> FEATURE:
<223> OTHER INFORMATION: Synthetic

<400> SEQUENCE: 115

Gly Ser Glu Val Ile Arg Cys Ser Gly Ser Arg Gln Cys Tyr Gly Pro
1               5                   10                  15

Cys Arg Gln Gln Thr Gly Cys Thr Asn Ser Arg Cys Met Asn Arg Val
                20                  25                  30

Cys Arg Cys Tyr Gly Cys Gly
        35

<210> SEQ ID NO 116
<211> LENGTH: 35
<212> TYPE: PRT
<213> ORGANISM: Artificial Sequence
<220> FEATURE:
<223> OTHER INFORMATION: Synthetic

<400> SEQUENCE: 116

Gly Ser Ala Cys Arg Gly Val Phe Asp Ala Cys Thr Pro Gly Arg Asn
1               5                   10                  15

Glu Cys Cys Pro Asn Arg Val Cys Ser Asp Arg His Arg Trp Cys Arg
                20                  25                  30

Trp Arg Leu
        35

<210> SEQ ID NO 117
<211> LENGTH: 40
<212> TYPE: PRT
<213> ORGANISM: Artificial Sequence
<220> FEATURE:
<223> OTHER INFORMATION: Synthetic

<400> SEQUENCE: 117

Gly Ser Gln Ile Tyr Thr Ser Arg Glu Cys Asn Gly Ser Ser Glu Cys
1               5                   10                  15

Tyr Ser His Cys Glu Gly Ile Thr Gly Arg Arg Ser Gly Arg Cys Ile
                20                  25                  30

Asn Arg Arg Cys Tyr Cys Tyr Arg
        35                  40

<210> SEQ ID NO 118
<211> LENGTH: 37
<212> TYPE: PRT
<213> ORGANISM: Artificial Sequence
<220> FEATURE:
<223> OTHER INFORMATION: Synthetic

<400> SEQUENCE: 118

Gly Ser Gly Cys Leu Glu Phe Trp Trp Arg Cys Asn Pro Asn Asp Asp
1               5                   10                  15

Arg Cys Cys Arg Pro Arg Leu Arg Cys Ser Arg Leu Phe Arg Leu Cys
                20                  25                  30

Asn Phe Ser Phe Gly
        35

<210> SEQ ID NO 119
<211> LENGTH: 39
<212> TYPE: PRT
```

```
<213> ORGANISM: Artificial Sequence
<220> FEATURE:
<223> OTHER INFORMATION: Synthetic

<400> SEQUENCE: 119

Gly Ser Asp Cys Val Arg Phe Trp Gly Arg Cys Ser Gln Thr Ser Asp
1               5                   10                  15

Cys Cys Pro His Leu Ala Cys Arg Ser Arg Trp Pro Arg Asn Ile Cys
                20                  25                  30

Val Trp Asp Gly Ser Val Gly
            35

<210> SEQ ID NO 120
<211> LENGTH: 35
<212> TYPE: PRT
<213> ORGANISM: Artificial Sequence
<220> FEATURE:
<223> OTHER INFORMATION: Synthetic

<400> SEQUENCE: 120

Gly Ser Gly Cys Phe Gly Tyr Arg Cys Asp Tyr Tyr Arg Gly Cys Cys
1               5                   10                  15

Ser Gly Tyr Val Cys Ser Pro Thr Trp Arg Trp Cys Val Arg Pro Gly
                20                  25                  30

Pro Gly Arg
        35

<210> SEQ ID NO 121
<211> LENGTH: 62
<212> TYPE: PRT
<213> ORGANISM: Artificial Sequence
<220> FEATURE:
<223> OTHER INFORMATION: Synthetic

<400> SEQUENCE: 121

Gly Ser Met Asn Ala Arg Phe Ile Leu Leu Val Leu Thr Thr Met
1               5                   10                  15

Met Leu Leu Pro Asp Thr Arg Gly Ala Glu Val Ile Arg Cys Ser Gly
                20                  25                  30

Ser Arg Gln Cys Tyr Gly Pro Cys Arg Gln Gln Thr Gly Cys Thr Asn
            35                  40                  45

Ser Arg Cys Met Asn Arg Val Cys Arg Cys Tyr Gly Cys Gly
        50                  55                  60

<210> SEQ ID NO 122
<211> LENGTH: 63
<212> TYPE: PRT
<213> ORGANISM: Artificial Sequence
<220> FEATURE:
<223> OTHER INFORMATION: Synthetic

<400> SEQUENCE: 122

Gly Ser Met Asn Ala Arg Leu Ile Tyr Leu Leu Val Val Thr Thr
1               5                   10                  15

Met Thr Leu Met Phe Asp Thr Ala Gln Ala Val Asp Ile Met Cys Ser
                20                  25                  30

Gly Pro Arg Gln Cys Tyr Gly Pro Cys Arg Arg Glu Thr Gly Cys Pro
            35                  40                  45

Asn Ala Arg Cys Met Asn Arg Arg Cys Arg Cys Tyr Gly Cys Val
        50                  55                  60
```

```
<210> SEQ ID NO 123
<211> LENGTH: 64
<212> TYPE: PRT
<213> ORGANISM: Artificial Sequence
<220> FEATURE:
<223> OTHER INFORMATION: Synthetic

<400> SEQUENCE: 123

Gly Ser Met Asn Ala Arg Leu Ile Tyr Leu Leu Val Val Thr Thr
1               5                   10                  15

Met Met Leu Thr Phe Asp Thr Thr Gln Ala Gly Asp Ile Arg Cys Ser
            20                  25                  30

Gly Thr Arg Gln Cys Trp Gly Pro Cys Arg Arg Gln Thr Thr Cys Thr
        35                  40                  45

Asn Ser Arg Cys Met Asn Gly Arg Cys Arg Cys Tyr Gly Cys Val Gly
    50                  55                  60

<210> SEQ ID NO 124
<211> LENGTH: 63
<212> TYPE: PRT
<213> ORGANISM: Artificial Sequence
<220> FEATURE:
<223> OTHER INFORMATION: Synthetic

<400> SEQUENCE: 124

Gly Ser Met Asn Thr Arg Phe Ile Phe Leu Leu Val Val Thr Asn
1               5                   10                  15

Thr Met Met Leu Phe Asp Thr Arg Pro Val Glu Gly Ile Ser Cys Thr
            20                  25                  30

Gly Ser Arg Gln Cys Tyr Asp Pro Cys Arg Arg Arg Thr Gly Cys Pro
        35                  40                  45

Asn Ala Arg Cys Met Asn Arg Ser Cys Arg Cys Tyr Gly Cys Gly
    50                  55                  60

<210> SEQ ID NO 125
<211> LENGTH: 40
<212> TYPE: PRT
<213> ORGANISM: Artificial Sequence
<220> FEATURE:
<223> OTHER INFORMATION: Synthetic

<400> SEQUENCE: 125

Gly Ser Gly Val Pro Ile Asn Val Arg Cys Ser Gly Ser Arg Asp Cys
1               5                   10                  15

Leu Glu Pro Cys Arg Arg Ala Gly Met Arg Phe Gly Arg Cys Ile Asn
            20                  25                  30

Arg Arg Cys His Cys Thr Pro Arg
        35                  40

<210> SEQ ID NO 126
<211> LENGTH: 40
<212> TYPE: PRT
<213> ORGANISM: Artificial Sequence
<220> FEATURE:
<223> OTHER INFORMATION: Synthetic

<400> SEQUENCE: 126

Gly Ser Gly Val Pro Ile Asn Val Arg Cys Thr Gly Ser Pro Gln Cys
1               5                   10                  15

Leu Arg Pro Cys Arg Asp Ala Gly Met Arg Phe Gly Arg Cys Ile Asn
            20                  25                  30

Gly Arg Cys His Cys Thr Pro Arg
```

-continued

```
              35                  40
```

<210> SEQ ID NO 127
<211> LENGTH: 40
<212> TYPE: PRT
<213> ORGANISM: Artificial Sequence
<220> FEATURE:
<223> OTHER INFORMATION: Synthetic

<400> SEQUENCE: 127

```
Gly Ser Gly Val Ile Ile Asn Val Arg Cys Arg Ile Ser Arg Gln Cys
1               5                   10                  15

Leu Glu Pro Cys Arg Arg Ala Gly Met Arg Phe Gly Arg Cys Met Asn
            20                  25                  30

Gly Arg Cys His Cys Thr Pro Arg
        35                  40
```

<210> SEQ ID NO 128
<211> LENGTH: 40
<212> TYPE: PRT
<213> ORGANISM: Artificial Sequence
<220> FEATURE:
<223> OTHER INFORMATION: Synthetic

<400> SEQUENCE: 128

```
Gly Ser Gly Val Pro Ile Asn Val Arg Cys Arg Gly Ser Pro Gln Cys
1               5                   10                  15

Ile Gln Pro Cys Arg Asp Ala Gly Met Arg Phe Gly Arg Cys Met Asn
            20                  25                  30

Gly Arg Cys His Cys Thr Pro Gln
        35                  40
```

<210> SEQ ID NO 129
<211> LENGTH: 40
<212> TYPE: PRT
<213> ORGANISM: Artificial Sequence
<220> FEATURE:
<223> OTHER INFORMATION: Synthetic

<400> SEQUENCE: 129

```
Gly Ser Gly Val Glu Ile Asn Val Arg Cys Thr Gly Ser His Gln Cys
1               5                   10                  15

Ile Arg Pro Cys Arg Asp Ala Gly Met Arg Phe Gly Arg Cys Ile Asn
            20                  25                  30

Arg Arg Cys His Cys Thr Pro Arg
        35                  40
```

<210> SEQ ID NO 130
<211> LENGTH: 40
<212> TYPE: PRT
<213> ORGANISM: Artificial Sequence
<220> FEATURE:
<223> OTHER INFORMATION: Synthetic

<400> SEQUENCE: 130

```
Gly Ser Gly Val Glu Ile Asn Val Arg Cys Ser Gly Ser Pro Gln Cys
1               5                   10                  15

Leu Arg Pro Cys Arg Asp Ala Gly Met Arg Phe Gly Arg Cys Met Asn
            20                  25                  30

Arg Arg Cys His Cys Thr Pro Arg
        35                  40
```

<210> SEQ ID NO 131
<211> LENGTH: 40
<212> TYPE: PRT
<213> ORGANISM: Artificial Sequence
<220> FEATURE:
<223> OTHER INFORMATION: Synthetic

<400> SEQUENCE: 131

Gly Ser Gly Val Pro Thr Asp Val Arg Cys Arg Gly Ser Pro Gln Cys
1               5                   10                  15

Ile Gln Pro Cys Arg Asp Ala Gly Met Arg Phe Gly Arg Cys Met Asn
            20                  25                  30

Gly Arg Cys His Cys Thr Pro Arg
        35                  40

<210> SEQ ID NO 132
<211> LENGTH: 40
<212> TYPE: PRT
<213> ORGANISM: Artificial Sequence
<220> FEATURE:
<223> OTHER INFORMATION: Synthetic

<400> SEQUENCE: 132

Gly Ser Gly Val Pro Ile Asn Val Ser Cys Thr Gly Ser Pro Gln Cys
1               5                   10                  15

Ile Arg Pro Cys Arg Asp Ala Gly Met Arg Phe Gly Arg Cys Met Asn
            20                  25                  30

Arg Arg Cys His Cys Thr Pro Arg
        35                  40

<210> SEQ ID NO 133
<211> LENGTH: 40
<212> TYPE: PRT
<213> ORGANISM: Artificial Sequence
<220> FEATURE:
<223> OTHER INFORMATION: Synthetic

<400> SEQUENCE: 133

Gly Ser Gly Val Pro Ile Asn Val Pro Cys Thr Gly Ser Pro Gln Cys
1               5                   10                  15

Ile Arg Pro Cys Arg Asp Ala Gly Met Arg Phe Gly Arg Cys Met Asn
            20                  25                  30

Arg Arg Cys His Cys Thr Pro Arg
        35                  40

<210> SEQ ID NO 134
<211> LENGTH: 39
<212> TYPE: PRT
<213> ORGANISM: Artificial Sequence
<220> FEATURE:
<223> OTHER INFORMATION: Synthetic

<400> SEQUENCE: 134

Gly Ser Val Gly Ile Asn Val Arg Cys Arg His Ser Gly Gln Cys Leu
1               5                   10                  15

Arg Pro Cys Arg Asp Ala Gly Met Arg Phe Gly Arg Cys Ile Asn Gly
            20                  25                  30

Arg Cys Asp Cys Thr Pro Arg
        35

<210> SEQ ID NO 135
<211> LENGTH: 39
<212> TYPE: PRT

<213> ORGANISM: Artificial Sequence
<220> FEATURE:
<223> OTHER INFORMATION: Synthetic

<400> SEQUENCE: 135

Gly Ser Val Gly Ile Asn Val Arg Cys Arg His Ser Gly Gln Cys Leu
1               5                   10                  15

Arg Pro Cys Arg Asp Ala Gly Met Arg Phe Gly Arg Cys Met Asn Gly
                20                  25                  30

Arg Cys Asp Cys Thr Pro Arg
            35

<210> SEQ ID NO 136
<211> LENGTH: 39
<212> TYPE: PRT
<213> ORGANISM: Artificial Sequence
<220> FEATURE:
<223> OTHER INFORMATION: Synthetic

<400> SEQUENCE: 136

Gly Ser Val Gly Ile Pro Val Ser Cys Arg His Ser Gly Gln Cys Ile
1               5                   10                  15

Arg Pro Cys Arg Asp Ala Gly Met Arg Phe Gly Arg Cys Met Asn Arg
                20                  25                  30

Arg Cys Asp Cys Thr Pro Arg
            35

<210> SEQ ID NO 137
<211> LENGTH: 38
<212> TYPE: PRT
<213> ORGANISM: Artificial Sequence
<220> FEATURE:
<223> OTHER INFORMATION: Synthetic

<400> SEQUENCE: 137

Gly Ser Arg Arg Gly Cys Phe Arg Glu Gly His Ser Cys Pro Arg Thr
1               5                   10                  15

Ala Pro Cys Cys Arg Pro Leu Val Cys Arg Gly Pro Ser Pro Asn Thr
                20                  25                  30

Arg Arg Cys Thr Arg Pro
            35

<210> SEQ ID NO 138
<211> LENGTH: 34
<212> TYPE: PRT
<213> ORGANISM: Artificial Sequence
<220> FEATURE:
<223> OTHER INFORMATION: Synthetic

<400> SEQUENCE: 138

Gly Ser Ser Phe Cys Ile Pro Phe Arg Pro Cys Arg Ser Asp Glu Asn
1               5                   10                  15

Cys Cys Arg Arg Phe Arg Cys Arg Thr Thr Gly Ile Val Arg Leu Cys
                20                  25                  30

Arg Trp

<210> SEQ ID NO 139
<211> LENGTH: 38
<212> TYPE: PRT
<213> ORGANISM: Artificial Sequence
<220> FEATURE:
<223> OTHER INFORMATION: Synthetic

```
<400> SEQUENCE: 139

Gly Ser Leu Arg Gly Cys Leu Pro Arg Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Trp Ala Ser Arg Cys Leu
            35

<210> SEQ ID NO 140
<211> LENGTH: 36
<212> TYPE: PRT
<213> ORGANISM: Artificial Sequence
<220> FEATURE:
<223> OTHER INFORMATION: Synthetic

<400> SEQUENCE: 140

Gly Ser Gly Asn Tyr Cys Leu Arg Gly Arg Cys Leu Pro Gly Gly Arg
1               5                   10                  15

Arg Cys Cys Asn Gly Arg Pro Cys Glu Cys Phe Ala Arg Ile Cys Ser
            20                  25                  30

Cys Arg Pro Arg
            35

<210> SEQ ID NO 141
<211> LENGTH: 31
<212> TYPE: PRT
<213> ORGANISM: Artificial Sequence
<220> FEATURE:
<223> OTHER INFORMATION: Synthetic

<400> SEQUENCE: 141

Gly Ser Thr Val Arg Cys Gly Gly Cys Asn Arg Cys Cys Pro Gly
1               5                   10                  15

Gly Cys Arg Ser Gly Arg Cys Ile Asn Gly Arg Cys Gln Cys Tyr
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Synthetic

<400> SEQUENCE: 142

Gly Ser Gly Cys Met Arg Glu Tyr Cys Ala Gly Gln Cys Arg Gly Arg
1               5                   10                  15

Val Ser Gln Asp Tyr Cys Leu Arg His Cys Arg Cys Ile Pro Arg
            20                  25                  30

<210> SEQ ID NO 143
<211> LENGTH: 36
<212> TYPE: PRT
<213> ORGANISM: Artificial Sequence
<220> FEATURE:
<223> OTHER INFORMATION: Synthetic

<400> SEQUENCE: 143

Gly Ser Ala Cys Leu Gly Phe Gly Glu Arg Cys Asn Pro Ser Asn Asp
1               5                   10                  15

Arg Cys Cys Arg Ser Ser Ser Leu Val Cys Ser Gln Arg His Arg Trp
            20                  25                  30

Cys Arg Tyr Gly
```

<210> SEQ ID NO 144
<211> LENGTH: 39
<212> TYPE: PRT
<213> ORGANISM: Artificial Sequence
<220> FEATURE:
<223> OTHER INFORMATION: Synthetic

<400> SEQUENCE: 144

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Arg Asp Ser Arg Cys Leu Gly
        35

<210> SEQ ID NO 145
<211> LENGTH: 38
<212> TYPE: PRT
<213> ORGANISM: Artificial Sequence
<220> FEATURE:
<223> OTHER INFORMATION: Synthetic

<400> SEQUENCE: 145

Gly Ser Arg Gly Gly Cys Leu Pro Arg Asn Arg Phe Cys Asn Pro Ser
1               5                   10                  15

Ser Gly Pro Arg Cys Cys Ser Gly Leu Thr Cys Arg Glu Leu Asn Ile
            20                  25                  30

Trp Ala Ser Arg Cys Leu
        35

<210> SEQ ID NO 146
<211> LENGTH: 35
<212> TYPE: PRT
<213> ORGANISM: Artificial Sequence
<220> FEATURE:
<223> OTHER INFORMATION: Synthetic

<400> SEQUENCE: 146

Gly Ser Gln Arg Ser Cys Ala Arg Pro Gly Asp Met Cys Met Gly Ile
1               5                   10                  15

Arg Cys Cys Asp Gly Gln Cys Gly Cys Asn Arg Gly Thr Gly Arg Cys
            20                  25                  30

Phe Cys Arg
        35

<210> SEQ ID NO 147
<211> LENGTH: 42
<212> TYPE: PRT
<213> ORGANISM: Artificial Sequence
<220> FEATURE:
<223> OTHER INFORMATION: Synthetic

<400> SEQUENCE: 147

Gly Ser Ala Arg Gly Cys Ala Asp Ala Tyr Arg Ser Cys Asn His Pro
1               5                   10                  15

Arg Thr Cys Cys Asp Gly Tyr Asn Gly Tyr Arg Arg Ala Cys Ile Cys
            20                  25                  30

Ser Gly Ser Asn Cys Arg Cys Arg Arg Ser
        35                  40

```
<210> SEQ ID NO 148
<211> LENGTH: 39
<212> TYPE: PRT
<213> ORGANISM: Artificial Sequence
<220> FEATURE:
<223> OTHER INFORMATION: Synthetic

<400> SEQUENCE: 148

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Trp Asp Ser Arg Cys Leu Gly
        35

<210> SEQ ID NO 149
<211> LENGTH: 39
<212> TYPE: PRT
<213> ORGANISM: Artificial Sequence
<220> FEATURE:
<223> OTHER INFORMATION: Synthetic

<400> SEQUENCE: 149

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Ser Ile
            20                  25                  30

Tyr Asp Ser Arg Cys Leu Gly
        35

<210> SEQ ID NO 150
<211> LENGTH: 39
<212> TYPE: PRT
<213> ORGANISM: Artificial Sequence
<220> FEATURE:
<223> OTHER INFORMATION: Synthetic

<400> SEQUENCE: 150

Gly Ser Arg Gly Gly Cys Leu Pro His Asn Arg Phe Cys Asn Ala Leu
1               5                   10                  15

Ser Gly Pro Arg Cys Cys Ser Arg Leu Arg Cys Arg Glu Leu Ser Ile
            20                  25                  30

Trp Asp Ser Arg Cys Leu Gly
        35

<210> SEQ ID NO 151
<211> LENGTH: 39
<212> TYPE: PRT
<213> ORGANISM: Artificial Sequence
<220> FEATURE:
<223> OTHER INFORMATION: Synthetic

<400> SEQUENCE: 151

Gly Ser Arg Gly Gly Cys Leu Pro His Asn Arg Phe Cys Asn Ala Leu
1               5                   10                  15

Thr Gly Pro Arg Cys Cys Ser Arg Leu Arg Cys Arg Glu Leu Ser Ile
            20                  25                  30

Trp Asp Ser Ile Cys Leu Gly
        35

<210> SEQ ID NO 152
<211> LENGTH: 36
<212> TYPE: PRT
```

```
<213> ORGANISM: Artificial Sequence
<220> FEATURE:
<223> OTHER INFORMATION: Synthetic

<400> SEQUENCE: 152

Gly Ser Ser Cys Ala Asp Ala Tyr Lys Ser Cys Asp Ser Leu Arg Cys
1               5                   10                  15

Cys Asn Asn Arg Thr Cys Met Cys Ser Met Ile Gly Thr Asn Cys Thr
                20                  25                  30

Cys Arg Arg Arg
        35

<210> SEQ ID NO 153
<211> LENGTH: 32
<212> TYPE: PRT
<213> ORGANISM: Artificial Sequence
<220> FEATURE:
<223> OTHER INFORMATION: Synthetic

<400> SEQUENCE: 153

Gly Ser Glu Arg Arg Cys Leu Pro Ala Gly Arg Thr Cys Val Arg Gly
1               5                   10                  15

Pro Met Arg Val Pro Cys Cys Gly Ser Cys Ser Gln Asn Arg Cys Thr
                20                  25                  30

<210> SEQ ID NO 154
<211> LENGTH: 33
<212> TYPE: PRT
<213> ORGANISM: Artificial Sequence
<220> FEATURE:
<223> OTHER INFORMATION: Synthetic

<400> SEQUENCE: 154

Gly Ser Leu Cys Ser Arg Glu Gly Glu Phe Cys Tyr Arg Leu Arg Arg
1               5                   10                  15

Cys Cys Ala Gly Phe Tyr Cys Arg Ala Phe Val Leu His Cys Tyr Arg
                20                  25                  30

Asn

<210> SEQ ID NO 155
<211> LENGTH: 25
<212> TYPE: PRT
<213> ORGANISM: Artificial Sequence
<220> FEATURE:
<223> OTHER INFORMATION: Synthetic

<400> SEQUENCE: 155

Gly Ser Ala Cys Gly Ser Cys Arg Arg Cys Arg Gly Ser Gly Arg
1               5                   10                  15

Cys Ile Asn Gly Arg Cys Arg Cys Tyr
                20                  25

<210> SEQ ID NO 156
<211> LENGTH: 25
<212> TYPE: PRT
<213> ORGANISM: Artificial Sequence
<220> FEATURE:
<223> OTHER INFORMATION: Synthetic

<400> SEQUENCE: 156

Gly Ser Ala Cys Gly Ser Cys Arg Arg Cys Arg Gly Pro Gly Arg
1               5                   10                  15

Cys Ile Asn Gly Arg Cys Arg Cys Tyr
```

```
                    20                  25

<210> SEQ ID NO 157
<211> LENGTH: 34
<212> TYPE: PRT
<213> ORGANISM: Artificial Sequence
<220> FEATURE:
<223> OTHER INFORMATION: Synthetic

<400> SEQUENCE: 157

Gly Ser Ala Cys Gln Gly Tyr Met Arg Arg Cys Gly Arg Asp Arg Pro
1               5                   10                  15

Pro Cys Cys Arg Arg Leu Glu Cys Ser Arg Thr Trp Arg Trp Cys Val
            20                  25                  30

Trp Asn

<210> SEQ ID NO 158
<211> LENGTH: 32
<212> TYPE: PRT
<213> ORGANISM: Artificial Sequence
<220> FEATURE:
<223> OTHER INFORMATION: Synthetic

<400> SEQUENCE: 158

Gly Ser Gly Arg Tyr Cys Gln Arg Trp Met Trp Thr Cys Asp Ser Arg
1               5                   10                  15

Arg Ala Cys Cys Glu Gly Leu Arg Cys Arg Leu Trp Cys Arg Arg Ile
            20                  25                  30

<210> SEQ ID NO 159
<211> LENGTH: 36
<212> TYPE: PRT
<213> ORGANISM: Artificial Sequence
<220> FEATURE:
<223> OTHER INFORMATION: Synthetic

<400> SEQUENCE: 159

Gly Ser Asn Ala Arg Cys Arg Gly Ser Pro Glu Cys Leu Pro Arg Cys
1               5                   10                  15

Arg Glu Ala Ile Gly Arg Ala Ala Gly Arg Cys Met Asn Gly Arg Cys
            20                  25                  30

Arg Cys Tyr Pro
        35

<210> SEQ ID NO 160
<211> LENGTH: 36
<212> TYPE: PRT
<213> ORGANISM: Artificial Sequence
<220> FEATURE:
<223> OTHER INFORMATION: Synthetic

<400> SEQUENCE: 160

Gly Ser Asn Val Arg Cys Arg Gly Ser Arg Glu Cys Leu Pro Ala Cys
1               5                   10                  15

Arg Ala Ala Val Gly Arg Ala Ala Gly Arg Cys Met Asn Gly Arg Cys
            20                  25                  30

Arg Cys Tyr Pro
        35

<210> SEQ ID NO 161
<211> LENGTH: 36
<212> TYPE: PRT
<213> ORGANISM: Artificial Sequence
```

```
<220> FEATURE:
<223> OTHER INFORMATION: Synthetic

<400> SEQUENCE: 161

Gly Ser Asn Val Arg Cys Arg Gly Ser Pro Glu Cys Leu Pro Arg Cys
1               5                   10                  15

Arg Glu Ala Ile Gly Arg Ser Ala Gly Arg Cys Met Asn Gly Arg Cys
            20                  25                  30

Arg Cys Tyr Pro
        35

<210> SEQ ID NO 162
<211> LENGTH: 36
<212> TYPE: PRT
<213> ORGANISM: Artificial Sequence
<220> FEATURE:
<223> OTHER INFORMATION: Synthetic

<400> SEQUENCE: 162

Gly Ser Asn Ala Arg Cys Arg Gly Ser Pro Glu Cys Leu Pro Arg Cys
1               5                   10                  15

Arg Gln Ala Ile Gly Arg Ala Ala Gly Arg Cys Met Asn Gly Arg Cys
            20                  25                  30

Arg Cys Tyr Pro
        35

<210> SEQ ID NO 163
<211> LENGTH: 35
<212> TYPE: PRT
<213> ORGANISM: Artificial Sequence
<220> FEATURE:
<223> OTHER INFORMATION: Synthetic

<400> SEQUENCE: 163

Gly Ser Arg Gly Tyr Cys Ala Glu Arg Gly Ile Arg Cys His Asn Ile
1               5                   10                  15

His Cys Cys Ser Gly Leu Thr Cys Arg Cys Arg Gly Ser Ser Cys Val
            20                  25                  30

Cys Arg Arg
        35

<210> SEQ ID NO 164
<211> LENGTH: 33
<212> TYPE: PRT
<213> ORGANISM: Artificial Sequence
<220> FEATURE:
<223> OTHER INFORMATION: Synthetic

<400> SEQUENCE: 164

Gly Ser Glu Arg Gly Cys Arg Leu Thr Phe Trp Arg Cys Arg Asn Arg
1               5                   10                  15

Arg Glu Cys Cys Gly Trp Asn Ala Cys Ala Leu Gly Ile Cys Met Pro
            20                  25                  30

Arg

<210> SEQ ID NO 165
<211> LENGTH: 41
<212> TYPE: PRT
<213> ORGANISM: Artificial Sequence
<220> FEATURE:
<223> OTHER INFORMATION: Synthetic

<400> SEQUENCE: 165
```

```
Gly Ser Arg Arg Cys Ile Ala Arg Asp Tyr Gly Arg Cys Arg Trp
1               5                   10                  15

Gly Gly Thr Pro Cys Cys Arg Gly Arg Gly Cys Ile Cys Ser Ile Met
                20                  25                  30

Gly Thr Asn Cys Glu Cys Arg Pro Arg
            35                  40

<210> SEQ ID NO 166
<211> LENGTH: 31
<212> TYPE: PRT
<213> ORGANISM: Artificial Sequence
<220> FEATURE:
<223> OTHER INFORMATION: Synthetic

<400> SEQUENCE: 166

Gly Ser Gly Cys Arg Leu Thr Phe Trp Arg Cys Arg Asn Arg Arg Glu
1               5                   10                  15

Cys Cys Gly Trp Asn Ala Cys Ala Leu Gly Ile Cys Met Pro Arg
                20                  25                  30

<210> SEQ ID NO 167
<211> LENGTH: 34
<212> TYPE: PRT
<213> ORGANISM: Artificial Sequence
<220> FEATURE:
<223> OTHER INFORMATION: Synthetic

<400> SEQUENCE: 167

Gly Ser Ala Cys Arg Gly Leu Phe Val Thr Cys Thr Pro Gly Arg Asp
1               5                   10                  15

Glu Cys Cys Pro Asn His Val Cys Ser Ser Arg His Arg Trp Cys Arg
                20                  25                  30

Tyr Arg

<210> SEQ ID NO 168
<211> LENGTH: 38
<212> TYPE: PRT
<213> ORGANISM: Artificial Sequence
<220> FEATURE:
<223> OTHER INFORMATION: Synthetic

<400> SEQUENCE: 168

Gly Ser Ile Ala Cys Ala Pro Arg Gly Leu Leu Cys Phe Arg Asp Arg
1               5                   10                  15

Glu Cys Cys Arg Gly Leu Thr Cys Arg Gly Arg Phe Val Asn Thr Trp
                20                  25                  30

Pro Thr Phe Cys Leu Val
            35

<210> SEQ ID NO 169
<211> LENGTH: 38
<212> TYPE: PRT
<213> ORGANISM: Artificial Sequence
<220> FEATURE:
<223> OTHER INFORMATION: Synthetic

<400> SEQUENCE: 169

Gly Ser Ala Cys Ala Gly Leu Tyr Arg Arg Cys Gly Arg Gly Val Asn
1               5                   10                  15

Thr Cys Cys Glu Asn Arg Pro Cys Arg Cys Asp Leu Ala Met Gly Asn
                20                  25                  30
```

Cys Ile Cys Arg Arg Arg
        35

<210> SEQ ID NO 170
<211> LENGTH: 40
<212> TYPE: PRT
<213> ORGANISM: Artificial Sequence
<220> FEATURE:
<223> OTHER INFORMATION: Synthetic

<400> SEQUENCE: 170

Gly Ser Phe Thr Cys Ala Ile Ser Cys Asp Ile Arg Val Asn Gly Arg
1               5                   10                  15

Pro Cys Arg Gly Ser Gly Glu Arg Cys Ser Gly Gly Trp Ser Cys
            20                  25                  30

Arg Phe Asn Val Cys Val Arg Val
        35                  40

<210> SEQ ID NO 171
<211> LENGTH: 35
<212> TYPE: PRT
<213> ORGANISM: Artificial Sequence
<220> FEATURE:
<223> OTHER INFORMATION: Synthetic

<400> SEQUENCE: 171

Gly Ser Gly Phe Cys Ala Gln Arg Gly Ile Arg Cys His Asp Ile His
1               5                   10                  15

Cys Cys Thr Asn Leu Arg Cys Val Arg Glu Gly Ser Asn Arg Val Cys
            20                  25                  30

Arg Arg Ala
        35

<210> SEQ ID NO 172
<211> LENGTH: 44
<212> TYPE: PRT
<213> ORGANISM: Artificial Sequence
<220> FEATURE:
<223> OTHER INFORMATION: Synthetic

<400> SEQUENCE: 172

Gly Ser Cys Ala Arg Arg Asn Trp Cys Gly Arg Asn Glu Asp Cys
1               5                   10                  15

Cys Cys Pro Met Arg Cys Ile Tyr Ala Trp Tyr Asn Gln Gln Gly Ser
            20                  25                  30

Cys Gln Ser Thr Ile Thr Gly Leu Phe Arg Arg Cys
        35                  40

<210> SEQ ID NO 173
<211> LENGTH: 30
<212> TYPE: PRT
<213> ORGANISM: Artificial Sequence
<220> FEATURE:
<223> OTHER INFORMATION: Synthetic

<400> SEQUENCE: 173

Gly Ser Tyr Cys Gln Arg Trp Met Trp Thr Cys Asp Ser Ala Arg Arg
1               5                   10                  15

Cys Cys Glu Gly Leu Val Cys Arg Leu Trp Cys Arg Arg Ile
            20                  25                  30

<210> SEQ ID NO 174
<211> LENGTH: 39

```
<212> TYPE: PRT
<213> ORGANISM: Artificial Sequence
<220> FEATURE:
<223> OTHER INFORMATION: Synthetic

<400> SEQUENCE: 174

Gly Ser Arg Gly Gly Cys Leu Pro His Asn Arg Phe Cys Asn Ala Leu
1               5                   10                  15

Ser Gly Pro Arg Cys Cys Ser Gly Leu Arg Cys Arg Glu Leu Thr Ile
            20                  25                  30

Trp Asn Thr Arg Cys Leu Glu
        35

<210> SEQ ID NO 175
<211> LENGTH: 36
<212> TYPE: PRT
<213> ORGANISM: Artificial Sequence
<220> FEATURE:
<223> OTHER INFORMATION: Synthetic

<400> SEQUENCE: 175

Gly Ser Asn Val Arg Cys Thr Gly Ser Arg Gln Cys Leu Pro Ala Cys
1               5                   10                  15

Arg Ala Ala Val Gly Arg Ala Ala Gly Arg Cys Met Asn Gly Arg Cys
            20                  25                  30

Arg Cys Tyr Thr
        35

<210> SEQ ID NO 176
<211> LENGTH: 35
<212> TYPE: PRT
<213> ORGANISM: Artificial Sequence
<220> FEATURE:
<223> OTHER INFORMATION: Synthetic

<400> SEQUENCE: 176

Gly Ser Gln Arg Ser Cys Ala Arg Pro Gly Glu Met Cys Met Arg Ile
1               5                   10                  15

Arg Cys Cys Asp Gly Gln Cys Gly Cys Asn Arg Gly Thr Gly Arg Cys
            20                  25                  30

Phe Cys Arg
        35

<210> SEQ ID NO 177
<211> LENGTH: 38
<212> TYPE: PRT
<213> ORGANISM: Artificial Sequence
<220> FEATURE:
<223> OTHER INFORMATION: Synthetic

<400> SEQUENCE: 177

Gly Ser Gly Cys Ile Pro Arg His Arg Cys Thr Trp Ser Gly Pro
1               5                   10                  15

Arg Cys Cys Asn Asn Ile Ser Cys His Cys Asn Ile Ser Gly Thr Leu
            20                  25                  30

Cys Arg Cys Arg Pro Gly
        35

<210> SEQ ID NO 178
<211> LENGTH: 35
<212> TYPE: PRT
<213> ORGANISM: Artificial Sequence
<220> FEATURE:
```

<223> OTHER INFORMATION: Synthetic

<400> SEQUENCE: 178

Gly Ser Asn Tyr Cys Val Ala Arg Arg Cys Arg Pro Gly Gly Arg Gln
1               5                   10                  15

Cys Cys Ser Gly Arg Pro Cys Ala Cys Val Gly Arg Val Cys Arg Cys
            20                  25                  30

Pro Arg Asp
        35

<210> SEQ ID NO 179
<211> LENGTH: 39
<212> TYPE: PRT
<213> ORGANISM: Artificial Sequence
<220> FEATURE:
<223> OTHER INFORMATION: Synthetic

<400> SEQUENCE: 179

Gly Ser Glu Arg Gly Cys Ser Gly Ala Tyr Arg Arg Cys Ser Ser Ser
1               5                   10                  15

Gln Arg Cys Cys Glu Gly Arg Pro Cys Val Cys Ser Ala Ile Asn Ser
            20                  25                  30

Asn Cys Arg Cys Arg Arg Thr
        35

<210> SEQ ID NO 180
<211> LENGTH: 35
<212> TYPE: PRT
<213> ORGANISM: Artificial Sequence
<220> FEATURE:
<223> OTHER INFORMATION: Synthetic

<400> SEQUENCE: 180

Gly Ser Gln Arg Ser Cys Ala Arg Pro Gly Glu Met Cys Met Gly Ile
1               5                   10                  15

Arg Cys Cys Asp Gly Gln Cys Gly Cys Asn Arg Gly Thr Gly Arg Cys
            20                  25                  30

Phe Cys Arg
        35

<210> SEQ ID NO 181
<211> LENGTH: 38
<212> TYPE: PRT
<213> ORGANISM: Artificial Sequence
<220> FEATURE:
<223> OTHER INFORMATION: Synthetic

<400> SEQUENCE: 181

Gly Ser Arg Arg Gly Cys Phe Arg Glu Gly Arg Trp Cys Pro Arg Ser
1               5                   10                  15

Ala Pro Cys Cys Ala Pro Leu Arg Cys Arg Gly Pro Ser Ile Arg Gln
            20                  25                  30

Gln Arg Cys Val Arg Glu
        35

<210> SEQ ID NO 182
<211> LENGTH: 33
<212> TYPE: PRT
<213> ORGANISM: Artificial Sequence
<220> FEATURE:
<223> OTHER INFORMATION: Synthetic

<400> SEQUENCE: 182

Gly Ser Thr Val Arg Cys Gly Gly Cys Asn Arg Arg Cys Cys Ala Gly
1               5                   10                  15

Gly Cys Arg Ser Gly Arg Cys Ile Asn Gly Arg Cys Gln Cys Tyr Gly
                20                  25                  30

Arg

<210> SEQ ID NO 183
<211> LENGTH: 31
<212> TYPE: PRT
<213> ORGANISM: Artificial Sequence
<220> FEATURE:
<223> OTHER INFORMATION: Synthetic

<400> SEQUENCE: 183

Gly Ser Glu Arg Arg Cys Glu Pro Ser Gly Arg Pro Cys Arg Pro Leu
1               5                   10                  15

Met Arg Ile Pro Cys Cys Gly Ser Cys Val Arg Gly Arg Cys Ala
                20                  25                  30

<210> SEQ ID NO 184
<211> LENGTH: 38
<212> TYPE: PRT
<213> ORGANISM: Artificial Sequence
<220> FEATURE:
<223> OTHER INFORMATION: Synthetic

<400> SEQUENCE: 184

Gly Ser Arg Gly Gly Cys Leu Pro Arg Asn Arg Phe Cys Asn Pro Ser
1               5                   10                  15

Ser Gly Pro Arg Cys Cys Ser Gly Leu Thr Cys Arg Glu Leu Asn Ile
                20                  25                  30

Trp Ala Asn Arg Cys Leu
            35

<210> SEQ ID NO 185
<211> LENGTH: 44
<212> TYPE: PRT
<213> ORGANISM: Artificial Sequence
<220> FEATURE:
<223> OTHER INFORMATION: Synthetic

<400> SEQUENCE: 185

Gly Ser Cys Ala Arg Arg Arg Asn Trp Cys Gly Arg Asn Glu Asp Cys
1               5                   10                  15

Cys Cys Pro Met Arg Cys Ile Tyr Ala Trp Tyr Asn Gln Gln Gly Ser
                20                  25                  30

Cys Gln Thr Thr Ile Thr Gly Leu Phe Arg Arg Cys
            35                  40

<210> SEQ ID NO 186
<211> LENGTH: 12
<212> TYPE: PRT
<213> ORGANISM: Artificial Sequence
<220> FEATURE:
<223> OTHER INFORMATION: Synthetic

<400> SEQUENCE: 186

Gly Ser Gly Arg Cys Ile Asn Arg Arg Cys Arg Cys
1               5                   10

<210> SEQ ID NO 187
<211> LENGTH: 6

```
<212> TYPE: PRT
<213> ORGANISM: Artificial Sequence
<220> FEATURE:
<223> OTHER INFORMATION: Synthetic

<400> SEQUENCE: 187

Gly Ser Arg Cys Ile Asn
1               5

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gly Ser Arg Arg Cys Arg
1               5

<210> SEQ ID NO 189
<211> LENGTH: 6
<212> TYPE: PRT
<213> ORGANISM: Artificial Sequence
<220> FEATURE:
<223> OTHER INFORMATION: Synthetic

<400> SEQUENCE: 189

Gly Ser Pro Cys Arg Arg
1               5

<210> SEQ ID NO 190
<211> LENGTH: 8
<212> TYPE: PRT
<213> ORGANISM: Artificial Sequence
<220> FEATURE:
<223> OTHER INFORMATION: Synthetic

<400> SEQUENCE: 190

Gly Ser Arg Arg Cys Ser Arg Arg
1               5

<210> SEQ ID NO 191
<211> LENGTH: 5
<212> TYPE: PRT
<213> ORGANISM: Artificial Sequence
<220> FEATURE:
<223> OTHER INFORMATION: Synthetic

<400> SEQUENCE: 191

Gly Ser Arg Gln Cys
1               5

<210> SEQ ID NO 192
<211> LENGTH: 39
<212> TYPE: PRT
<213> ORGANISM: Artificial Sequence
<220> FEATURE:
<223> OTHER INFORMATION: Synthetic

<400> SEQUENCE: 192

Gly Ser Val Arg Ile Pro Val Ser Cys Arg His Ser Gly Gln Cys Leu
1               5                   10                  15

Arg Pro Cys Arg Asp Ala Gly Met Arg Thr Gly Arg Cys Met Asn Gly
            20                  25                  30

Arg Cys Asp Cys Thr Pro Arg
```

<210> SEQ ID NO 193
<211> LENGTH: 6
<212> TYPE: PRT
<213> ORGANISM: Artificial Sequence
<220> FEATURE:
<223> OTHER INFORMATION: Synthetic

<400> SEQUENCE: 193

Gly Ser Pro Cys Lys Lys
1               5

<210> SEQ ID NO 194
<211> LENGTH: 8
<212> TYPE: PRT
<213> ORGANISM: Artificial Sequence
<220> FEATURE:
<223> OTHER INFORMATION: Synthetic

<400> SEQUENCE: 194

Gly Ser Lys Lys Cys Ser Lys Lys
1               5

<210> SEQ ID NO 195
<211> LENGTH: 37
<212> TYPE: PRT
<213> ORGANISM: Artificial Sequence
<220> FEATURE:
<223> OTHER INFORMATION: Synthetic

<400> SEQUENCE: 195

Gly Ser Asn Phe Lys Val Glu Gly Ala Cys Ser Lys Pro Cys Arg Lys
1               5                   10                  15

Tyr Cys Ile Asp Lys Gly Ala Arg Asn Gly Lys Cys Ile Asn Gly Arg
            20                  25                  30

Cys His Cys Tyr Tyr
        35

<210> SEQ ID NO 196
<211> LENGTH: 40
<212> TYPE: PRT
<213> ORGANISM: Artificial Sequence
<220> FEATURE:
<223> OTHER INFORMATION: Synthetic

<400> SEQUENCE: 196

Gly Ser Gln Lys Ile Leu Ser Asn Arg Cys Asn Asn Ser Ser Glu Cys
1               5                   10                  15

Ile Pro His Cys Ile Arg Ile Phe Gly Thr Arg Ala Ala Lys Cys Ile
            20                  25                  30

Asn Arg Lys Cys Tyr Cys Tyr Pro
        35                  40

<210> SEQ ID NO 197
<211> LENGTH: 44
<212> TYPE: PRT
<213> ORGANISM: Artificial Sequence
<220> FEATURE:
<223> OTHER INFORMATION: Synthetic

<400> SEQUENCE: 197

Gly Ser Asp Arg Asp Ser Cys Ile Asp Lys Ser Arg Cys Ser Lys Tyr
1               5                   10                  15

```
Gly Tyr Tyr Gln Glu Cys Gln Asp Cys Cys Lys Lys Ala Gly His Asn
            20                  25                  30

Gly Gly Thr Cys Met Phe Phe Lys Cys Lys Cys Ala
        35                  40
```

<210> SEQ ID NO 198
<211> LENGTH: 34
<212> TYPE: PRT
<213> ORGANISM: Artificial Sequence
<220> FEATURE:
<223> OTHER INFORMATION: Synthetic

<400> SEQUENCE: 198

```
Gly Ser Ala Val Cys Asn Leu Lys Arg Cys Gln Leu Ser Cys Arg Ser
1               5                   10                  15

Leu Gly Leu Leu Gly Lys Cys Ile Gly Asp Lys Cys Glu Cys Val Lys
            20                  25                  30

His Gly
```

<210> SEQ ID NO 199
<211> LENGTH: 39
<212> TYPE: PRT
<213> ORGANISM: Artificial Sequence
<220> FEATURE:
<223> OTHER INFORMATION: Synthetic

<400> SEQUENCE: 199

```
Gly Ser Ile Ser Ile Gly Ile Arg Cys Ser Pro Ser Ile Asp Leu Cys
1               5                   10                  15

Glu Gly Gln Cys Arg Ile Arg Arg Tyr Phe Thr Gly Tyr Cys Ser Gly
            20                  25                  30

Asp Thr Cys His Cys Ser Gly
            35
```

<210> SEQ ID NO 200
<211> LENGTH: 35
<212> TYPE: PRT
<213> ORGANISM: Artificial Sequence
<220> FEATURE:
<223> OTHER INFORMATION: Synthetic

<400> SEQUENCE: 200

```
Gly Ser Gly Asp Cys Leu Pro His Leu Arg Arg Cys Arg Glu Asn Asn
1               5                   10                  15

Asp Cys Cys Ser Arg Arg Cys Arg Arg Gly Ala Asn Pro Glu Arg
            20                  25                  30

Arg Cys Arg
        35
```

<210> SEQ ID NO 201
<211> LENGTH: 36
<212> TYPE: PRT
<213> ORGANISM: Artificial Sequence
<220> FEATURE:
<223> OTHER INFORMATION: Synthetic

<400> SEQUENCE: 201

```
Gly Ser Ser Cys Glu Pro Gly Arg Thr Phe Arg Asp Arg Cys Asn Thr
1               5                   10                  15

Cys Lys Cys Gly Ala Asp Gly Arg Ser Ala Ala Cys Thr Leu Arg Ala
            20                  25                  30

Cys Pro Asn Gln
```

<210> SEQ ID NO 202
<211> LENGTH: 35
<212> TYPE: PRT
<213> ORGANISM: Artificial Sequence
<220> FEATURE:
<223> OTHER INFORMATION: Synthetic

<400> SEQUENCE: 202

Gly Ser Gly Asp Cys Leu Pro His Leu Lys Arg Cys Lys Ala Asp Asn
1               5                   10                  15
Asp Cys Cys Gly Lys Lys Cys Lys Arg Arg Gly Thr Asn Ala Glu Lys
            20                  25                  30
Arg Cys Arg
        35

<210> SEQ ID NO 203
<211> LENGTH: 35
<212> TYPE: PRT
<213> ORGANISM: Artificial Sequence
<220> FEATURE:
<223> OTHER INFORMATION: Synthetic

<400> SEQUENCE: 203

Gly Ser Gly Asp Cys Leu Pro His Leu Lys Arg Cys Lys Glu Asn Asn
1               5                   10                  15
Asp Cys Cys Ser Lys Lys Cys Lys Arg Arg Gly Thr Asn Pro Glu Lys
            20                  25                  30
Arg Cys Arg
        35

<210> SEQ ID NO 204
<211> LENGTH: 35
<212> TYPE: PRT
<213> ORGANISM: Artificial Sequence
<220> FEATURE:
<223> OTHER INFORMATION: Synthetic

<400> SEQUENCE: 204

Gly Ser Lys Asp Cys Leu Lys Lys Leu Lys Leu Cys Lys Glu Asn Lys
1               5                   10                  15
Asp Cys Cys Ser Lys Ser Cys Lys Arg Arg Gly Thr Asn Ile Glu Lys
            20                  25                  30
Arg Cys Arg
        35

<210> SEQ ID NO 205
<211> LENGTH: 35
<212> TYPE: PRT
<213> ORGANISM: Artificial Sequence
<220> FEATURE:
<223> OTHER INFORMATION: Synthetic

<400> SEQUENCE: 205

Gly Ser Gly Asp Cys Leu Pro His Leu Lys Arg Cys Lys Glu Asn Asn
1               5                   10                  15
Asp Cys Cys Ser Lys Lys Cys Lys Arg Arg Gly Ala Asn Pro Glu Lys
            20                  25                  30
Arg Cys Arg
        35

```
<210> SEQ ID NO 206
<211> LENGTH: 39
<212> TYPE: PRT
<213> ORGANISM: Artificial Sequence
<220> FEATURE:
<223> OTHER INFORMATION: Synthetic

<400> SEQUENCE: 206

Gly Ser Val Phe Ile Asn Val Lys Cys Arg Gly Ser Pro Glu Cys Leu
1               5                   10                  15

Pro Lys Cys Lys Glu Ala Ile Gly Lys Ser Ala Gly Lys Cys Met Asn
            20                  25                  30

Gly Lys Cys Lys Cys Tyr Pro
        35

<210> SEQ ID NO 207
<211> LENGTH: 39
<212> TYPE: PRT
<213> ORGANISM: Artificial Sequence
<220> FEATURE:
<223> OTHER INFORMATION: Synthetic

<400> SEQUENCE: 207

Gly Ser Val Phe Ile Asn Ala Lys Cys Arg Gly Ser Pro Glu Cys Leu
1               5                   10                  15

Pro Lys Cys Lys Glu Ala Ile Gly Lys Ala Ala Gly Lys Cys Met Asn
            20                  25                  30

Gly Lys Cys Lys Cys Tyr Pro
        35

<210> SEQ ID NO 208
<211> LENGTH: 38
<212> TYPE: PRT
<213> ORGANISM: Artificial Sequence
<220> FEATURE:
<223> OTHER INFORMATION: Synthetic

<400> SEQUENCE: 208

Gly Ser Val Ile Ile Asn Val Lys Cys Lys Ile Ser Arg Gln Cys Leu
1               5                   10                  15

Glu Pro Cys Lys Lys Ala Gly Met Arg Phe Gly Lys Cys Met Asn Gly
            20                  25                  30

Lys Cys His Cys Thr Pro
        35

<210> SEQ ID NO 209
<211> LENGTH: 38
<212> TYPE: PRT
<213> ORGANISM: Artificial Sequence
<220> FEATURE:
<223> OTHER INFORMATION: Synthetic

<400> SEQUENCE: 209

Gly Ser Val Pro Thr Asp Val Lys Cys Arg Gly Ser Pro Gln Cys Ile
1               5                   10                  15

Gln Pro Cys Lys Asp Ala Gly Met Arg Phe Gly Lys Cys Met Asn Gly
            20                  25                  30

Lys Cys His Cys Thr Pro
        35

<210> SEQ ID NO 210
<211> LENGTH: 38
<212> TYPE: PRT
```

```
<213> ORGANISM: Artificial Sequence
<220> FEATURE:
<223> OTHER INFORMATION: Synthetic

<400> SEQUENCE: 210

Gly Ser Val Arg Ile Pro Val Ser Cys Lys His Ser Gly Gln Cys Leu
1               5                   10                  15

Lys Pro Cys Lys Asp Ala Gly Met Arg Phe Gly Lys Cys Met Asn Gly
            20                  25                  30

Lys Cys Asp Cys Thr Pro
        35

<210> SEQ ID NO 211
<211> LENGTH: 38
<212> TYPE: PRT
<213> ORGANISM: Artificial Sequence
<220> FEATURE:
<223> OTHER INFORMATION: Synthetic

<400> SEQUENCE: 211

Gly Ser Val Arg Ile Pro Val Ser Cys Arg His Ser Gly Gln Cys Leu
1               5                   10                  15

Arg Pro Cys Arg Asp Ala Gly Met Arg Phe Gly Arg Cys Met Asn Gly
            20                  25                  30

Arg Cys Asp Cys Thr Pro
        35

<210> SEQ ID NO 212
<211> LENGTH: 35
<212> TYPE: PRT
<213> ORGANISM: Artificial Sequence
<220> FEATURE:
<223> OTHER INFORMATION: Synthetic

<400> SEQUENCE: 212

Gly Ser Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys
        35

<210> SEQ ID NO 213
<211> LENGTH: 34
<212> TYPE: PRT
<213> ORGANISM: Artificial Sequence
<220> FEATURE:
<223> OTHER INFORMATION: Synthetic

<400> SEQUENCE: 213

Gly Ser Asn Val Lys Cys Thr Gly Ser Lys Gln Cys Leu Pro Ala Cys
1               5                   10                  15

Lys Ala Ala Val Gly Lys Ala Ala Gly Lys Cys Met Asn Gly Lys Cys
            20                  25                  30

Lys Cys

<210> SEQ ID NO 214
<211> LENGTH: 39
<212> TYPE: PRT
<213> ORGANISM: Artificial Sequence
<220> FEATURE:
<223> OTHER INFORMATION: Synthetic
```

<400> SEQUENCE: 214

Gly Ser Gly Val Pro Ile Asn Val Arg Cys Arg Gly Ser Arg Asp Cys
1               5                   10                  15

Leu Asp Pro Cys Arg Gly Ala Gly Glu Arg His Gly Arg Cys Gly Asn
            20                  25                  30

Ser Arg Cys His Cys Thr Pro
            35

<210> SEQ ID NO 215
<211> LENGTH: 39
<212> TYPE: PRT
<213> ORGANISM: Artificial Sequence
<220> FEATURE:
<223> OTHER INFORMATION: Synthetic

<400> SEQUENCE: 215

Gly Ser Val Arg Ile Pro Val Ser Cys Arg His Ser Gly Gln Cys Leu
1               5                   10                  15

Arg Pro Cys Arg Asp Ala Gly Glu Arg His Gly Arg Cys Gly Gly Gly
            20                  25                  30

Arg Cys Asp Cys Thr Pro Arg
            35

<210> SEQ ID NO 216
<211> LENGTH: 40
<212> TYPE: PRT
<213> ORGANISM: Artificial Sequence
<220> FEATURE:
<223> OTHER INFORMATION: Synthetic

<400> SEQUENCE: 216

Gly Ser Gln Val Gln Thr Asn Val Arg Cys Gln Gly Gly Ser Cys Gly
1               5                   10                  15

Ser Val Cys Arg Arg Glu Gly Gly Ala Gly Gly Cys Gly Asn
            20                  25                  30

Gly Arg Cys Gly Cys Tyr Arg Asn
            35                  40

<210> SEQ ID NO 217
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is any amino acid or amino acid analogue or
      null
<220> FEATURE:
<221> NAME/KEY: misc_feature
<222> LOCATION: (5)..(6)
<223> OTHER INFORMATION: X is any amino acid or amino acid analogue or
      null
<220> FEATURE:
<221> NAME/KEY: misc_feature
<222> LOCATION: (9)..(9)
<223> OTHER INFORMATION: X is any amino acid or amino acid analogue or
      null
<220> FEATURE:
<221> NAME/KEY: misc_feature
<222> LOCATION: (15)..(15)
<223> OTHER INFORMATION: X is any amino acid or amino acid analogue or
      null
<220> FEATURE:
<221> NAME/KEY: misc_feature
<222> LOCATION: (20)..(22)

-continued

```
<223> OTHER INFORMATION: X is any amino acid or amino acid analogue or
      null
<220> FEATURE:
<221> NAME/KEY: misc_feature
<222> LOCATION: (24)..(24)
<223> OTHER INFORMATION: X is any amino acid or amino acid analogue or
      null
<220> FEATURE:
<221> NAME/KEY: misc_feature
<222> LOCATION: (26)..(26)
<223> OTHER INFORMATION: X is any amino acid or amino acid analogue or
      null
<220> FEATURE:
<221> NAME/KEY: misc_feature
<222> LOCATION: (30)..(30)
<223> OTHER INFORMATION: X is any amino acid or amino acid analogue or
      null
<220> FEATURE:
<221> NAME/KEY: misc_feature
<222> LOCATION: (37)..(40)
<223> OTHER INFORMATION: X is any amino acid or amino acid analogue or
      null

<400> SEQUENCE: 217

Gly Val Xaa Ile Xaa Xaa Lys Cys Xaa Gly Ser Lys Gln Cys Xaa Asp
1               5                   10                  15

Pro Cys Lys Xaa Xaa Xaa Gly Xaa Arg Xaa Gly Lys Cys Xaa Asn Lys
                20                  25                  30

Lys Cys Lys Cys Xaa Xaa Xaa Xaa
            35                  40

<210> SEQ ID NO 218
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is selected from P or R
<220> FEATURE:
<221> NAME/KEY: misc_feature
<222> LOCATION: (5)..(5)
<223> OTHER INFORMATION: X is selected from P or N
<220> FEATURE:
<221> NAME/KEY: misc_feature
<222> LOCATION: (6)..(6)
<223> OTHER INFORMATION: X is selected from V or I
<220> FEATURE:
<221> NAME/KEY: misc_feature
<222> LOCATION: (9)..(9)
<223> OTHER INFORMATION: X is selected from S, T, R or K
<220> FEATURE:
<221> NAME/KEY: misc_feature
<222> LOCATION: (15)..(15)
<223> OTHER INFORMATION: X is selected from Y or L
<220> FEATURE:
<221> NAME/KEY: misc_feature
<222> LOCATION: (20)..(20)
<223> OTHER INFORMATION: X is selected from Q, R or K
<220> FEATURE:
<221> NAME/KEY: misc_feature
<222> LOCATION: (21)..(21)
<223> OTHER INFORMATION: X is selected from A, K or R
<220> FEATURE:
<221> NAME/KEY: misc_feature
<222> LOCATION: (22)..(22)
<223> OTHER INFORMATION: X is selected from T or A
<220> FEATURE:
<221> NAME/KEY: misc_feature
<222> LOCATION: (24)..(24)
<223> OTHER INFORMATION: X is selected from C or M
<220> FEATURE:
<221> NAME/KEY: misc_feature
```

```
<222> LOCATION: (26)..(26)
<223> OTHER INFORMATION: X is selected from F or N
<220> FEATURE:
<221> NAME/KEY: misc_feature
<222> LOCATION: (30)..(30)
<223> OTHER INFORMATION: X is selected from M or I
<220> FEATURE:
<221> NAME/KEY: misc_feature
<222> LOCATION: (37)..(37)
<223> OTHER INFORMATION: X is selected from Y or T
<220> FEATURE:
<221> NAME/KEY: misc_feature
<222> LOCATION: (38)..(38)
<223> OTHER INFORMATION: X is selected from G or P
<220> FEATURE:
<221> NAME/KEY: misc_feature
<222> LOCATION: (39)..(39)
<223> OTHER INFORMATION: X is selected from C or null
<220> FEATURE:
<221> NAME/KEY: misc_feature
<222> LOCATION: (40)..(40)
<223> OTHER INFORMATION: X is selected from G or null

<400> SEQUENCE: 218

Gly Val Xaa Ile Xaa Xaa Lys Cys Xaa Gly Ser Lys Gln Cys Xaa Asp
1               5                   10                  15

Pro Cys Lys Xaa Xaa Xaa Gly Xaa Arg Xaa Gly Lys Cys Xaa Asn Lys
            20                  25                  30

Lys Cys Lys Cys Xaa Xaa Xaa Xaa
        35                  40

<210> SEQ ID NO 219
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: X is any amino acid or amino acid analogue or
      null
<220> FEATURE:
<221> NAME/KEY: misc_feature
<222> LOCATION: (6)..(6)
<223> OTHER INFORMATION: X is any amino acid or amino acid analogue or
      null
<220> FEATURE:
<221> NAME/KEY: misc_feature
<222> LOCATION: (8)..(8)
<223> OTHER INFORMATION: X is any amino acid or amino acid analogue or
      null
<220> FEATURE:
<221> NAME/KEY: misc_feature
<222> LOCATION: (15)..(15)
<223> OTHER INFORMATION: X is any amino acid or amino acid analogue or
      null
<220> FEATURE:
<221> NAME/KEY: misc_feature
<222> LOCATION: (19)..(20)
<223> OTHER INFORMATION: X is any amino acid or amino acid analogue or
      null
<220> FEATURE:
<221> NAME/KEY: misc_feature
<222> LOCATION: (24)..(26)
<223> OTHER INFORMATION: X is any amino acid or amino acid analogue or
      null
<220> FEATURE:
<221> NAME/KEY: misc_feature
<222> LOCATION: (29)..(30)
<223> OTHER INFORMATION: X is any amino acid or amino acid analogue or
      null
<220> FEATURE:
<221> NAME/KEY: misc_feature
<222> LOCATION: (32)..(32)
```

-continued

```
<223> OTHER INFORMATION: X is any amino acid or amino acid analogue or
      null

<400> SEQUENCE: 219

Xaa Xaa Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Xaa Lys Cys Xaa Xaa Lys Xaa
            20                  25                  30

Cys Lys Cys Tyr Gly Cys Gly
        35

<210> SEQ ID NO 220
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from S or null
<220> FEATURE:
<221> NAME/KEY: misc_feature
<222> LOCATION: (3)..(3)
<223> OTHER INFORMATION: X is selected from E, G or null
<220> FEATURE:
<221> NAME/KEY: misc_feature
<222> LOCATION: (4)..(4)
<223> OTHER INFORMATION: X is selected from V, S, or null
<220> FEATURE:
<221> NAME/KEY: misc_feature
<222> LOCATION: (6)..(6)
<223> OTHER INFORMATION: X is selected from R or S
<220> FEATURE:
<221> NAME/KEY: misc_feature
<222> LOCATION: (8)..(8)
<223> OTHER INFORMATION: X is selected from S or T
<220> FEATURE:
<221> NAME/KEY: misc_feature
<222> LOCATION: (15)..(15)
<223> OTHER INFORMATION: X is selected from G or D
<220> FEATURE:
<221> NAME/KEY: misc_feature
<222> LOCATION: (19)..(19)
<223> OTHER INFORMATION: X is selected from Q or R
<220> FEATURE:
<221> NAME/KEY: misc_feature
<222> LOCATION: (20)..(20)
<223> OTHER INFORMATION: X is selected from Q or K
<220> FEATURE:
<221> NAME/KEY: misc_feature
<222> LOCATION: (24)..(24)
<223> OTHER INFORMATION: X is selected from T or P
<220> FEATURE:
<221> NAME/KEY: misc_feature
<222> LOCATION: (25)..(25)
<223> OTHER INFORMATION: X is selected from N or Q
<220> FEATURE:
<221> NAME/KEY: misc_feature
<222> LOCATION: (26)..(26)
<223> OTHER INFORMATION: X is selected from S or A
<220> FEATURE:
<221> NAME/KEY: misc_feature
<222> LOCATION: (29)..(29)
<223> OTHER INFORMATION: X is selected from M or L
<220> FEATURE:
<221> NAME/KEY: misc_feature
<222> LOCATION: (30)..(30)
<223> OTHER INFORMATION: X is selected from N or Q
<220> FEATURE:
<221> NAME/KEY: misc_feature
```

<222> LOCATION: (32)..(32)
<223> OTHER INFORMATION: X is selected from V or S

<400> SEQUENCE: 220

Xaa Xaa Xaa Xaa Ile Xaa Cys Xaa Gly Ser Lys Gln Cys Tyr Xaa Pro
1               5                   10                  15

Cys Lys Xaa Xaa Thr Gly Cys Xaa Xaa Xaa Lys Cys Xaa Xaa Lys Xaa
            20                  25                  30

Cys Lys Cys Tyr Gly Cys Gly
        35

<210> SEQ ID NO 221
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: X is any amino acid or amino acid analogue or
      null
<220> FEATURE:
<221> NAME/KEY: misc_feature
<222> LOCATION: (5)..(5)
<223> OTHER INFORMATION: X is any amino acid or amino acid analogue or
      null
<220> FEATURE:
<221> NAME/KEY: misc_feature
<222> LOCATION: (7)..(7)
<223> OTHER INFORMATION: X is any amino acid or amino acid analogue or
      null
<220> FEATURE:
<221> NAME/KEY: misc_feature
<222> LOCATION: (9)..(9)
<223> OTHER INFORMATION: X is any amino acid or amino acid analogue or
      null
<220> FEATURE:
<221> NAME/KEY: misc_feature
<222> LOCATION: (11)..(12)
<223> OTHER INFORMATION: X is any amino acid or amino acid analogue or
      null
<220> FEATURE:
<221> NAME/KEY: misc_feature
<222> LOCATION: (14)..(15)
<223> OTHER INFORMATION: X is any amino acid or amino acid analogue or
      null
<220> FEATURE:
<221> NAME/KEY: misc_feature
<222> LOCATION: (18)..(18)
<223> OTHER INFORMATION: X is any amino acid or amino acid analogue or
      null
<220> FEATURE:
<221> NAME/KEY: misc_feature
<222> LOCATION: (22)..(22)
<223> OTHER INFORMATION: X is any amino acid or amino acid analogue or
      null
<220> FEATURE:
<221> NAME/KEY: misc_feature
<222> LOCATION: (31)..(31)
<223> OTHER INFORMATION: X is any amino acid or amino acid analogue or
      null
<220> FEATURE:
<221> NAME/KEY: misc_feature
<222> LOCATION: (33)..(33)
<223> OTHER INFORMATION: X is any amino acid or amino acid analogue or
      null
<220> FEATURE:
<221> NAME/KEY: misc_feature
<222> LOCATION: (36)..(36)
<223> OTHER INFORMATION: X is any amino acid or amino acid analogue or
      null
<220> FEATURE:
<221> NAME/KEY: misc_feature
<222> LOCATION: (40)..(40)

```
<223> OTHER INFORMATION: X is any amino acid or amino acid analogue or
      null

<400> SEQUENCE: 221

Xaa Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30

Xaa Lys Cys Xaa Cys Thr Pro Xaa
            35                  40

<210> SEQ ID NO 222
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from G, S or null
<220> FEATURE:
<221> NAME/KEY: misc_feature
<222> LOCATION: (3)..(3)
<223> OTHER INFORMATION: X is selected from G, S or null
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from N or P
<220> FEATURE:
<221> NAME/KEY: misc_feature
<222> LOCATION: (9)..(9)
<223> OTHER INFORMATION: X is selected from K or S
<220> FEATURE:
<221> NAME/KEY: misc_feature
<222> LOCATION: (11)..(11)
<223> OTHER INFORMATION: X is selected from R or K
<220> FEATURE:
<221> NAME/KEY: misc_feature
<222> LOCATION: (12)..(12)
<223> OTHER INFORMATION: X is selected from G or H
<220> FEATURE:
<221> NAME/KEY: misc_feature
<222> LOCATION: (14)..(14)
<223> OTHER INFORMATION: X is selected from R or G
<220> FEATURE:
<221> NAME/KEY: misc_feature
<222> LOCATION: (15)..(15)
<223> OTHER INFORMATION: X is selected from D or Q
<220> FEATURE:
<221> NAME/KEY: misc_feature
<222> LOCATION: (18)..(18)
<223> OTHER INFORMATION: X is selected from D or K
<220> FEATURE:
<221> NAME/KEY: misc_feature
<222> LOCATION: (22)..(22)
<223> OTHER INFORMATION: X is selected from K or D
<220> FEATURE:
<221> NAME/KEY: misc_feature
<222> LOCATION: (31)..(31)
<223> OTHER INFORMATION: X is selected from I or M
<220> FEATURE:
<221> NAME/KEY: misc_feature
<222> LOCATION: (33)..(33)
<223> OTHER INFORMATION: X is selected from S or G
<220> FEATURE:
<221> NAME/KEY: misc_feature
```

<222> LOCATION: (36)..(36)
<223> OTHER INFORMATION: X is selected from H or D
<220> FEATURE:
<221> NAME/KEY: misc_feature
<222> LOCATION: (40)..(40)
<223> OTHER INFORMATION: X is selected from K or null

<400> SEQUENCE: 222

Xaa Xaa Xaa Val Xaa Ile Xaa Val Xaa Cys Xaa Xaa Ser Xaa Xaa Cys
1               5                   10                  15

Leu Xaa Pro Cys Lys Xaa Ala Gly Met Arg Phe Gly Lys Cys Xaa Asn
            20                  25                  30

Xaa Lys Cys Xaa Cys Thr Pro Xaa
        35                  40

<210> SEQ ID NO 223
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: all X may be absent, or any amino acid or amino
      acid analogue
<220> FEATURE:
<221> NAME/KEY: misc_feature
<222> LOCATION: (12)..(21)
<223> OTHER INFORMATION: all X may be absent, or any amino acid or amino
      acid analogue
<220> FEATURE:
<221> NAME/KEY: misc_feature
<222> LOCATION: (25)..(34)
<223> OTHER INFORMATION: all X may be absent, or any amino acid or amino
      acid analogue
<220> FEATURE:
<221> NAME/KEY: misc_feature
<222> LOCATION: (40)..(49)
<223> OTHER INFORMATION: all X may be absent, or any amino acid or amino
      acid analogue
<220> FEATURE:
<221> NAME/KEY: misc_feature
<222> LOCATION: (54)..(63)
<223> OTHER INFORMATION: all X may be absent, or any amino acid or amino
      acid analogue
<220> FEATURE:
<221> NAME/KEY: misc_feature
<222> LOCATION: (65)..(74)
<223> OTHER INFORMATION: all X may be absent, or any amino acid or amino
      acid analogue
<220> FEATURE:
<221> NAME/KEY: misc_feature
<222> LOCATION: (76)..(85)
<223> OTHER INFORMATION: all X may be absent, or any amino acid or amino
      acid analogue
<220> FEATURE:
<221> NAME/KEY: misc_feature
<222> LOCATION: (93)..(102)
<223> OTHER INFORMATION: all X may be absent, or any amino acid or amino
      acid analogue
<220> FEATURE:
<221> NAME/KEY: misc_feature
<222> LOCATION: (107)..(116)
<223> OTHER INFORMATION: all X may be absent, or any amino acid or amino
      acid analogue

<400> SEQUENCE: 223

Xaa Xaa Xaa Xaa Xaa Xaa Xaa Xaa Xaa Xaa Val Xaa Xaa Xaa Xaa Xaa
1               5                   10                  15

Xaa Xaa Xaa Xaa Xaa Val Lys Cys Xaa Xaa Xaa Xaa Xaa Xaa Xaa Xaa
            20                  25                  30

```
Xaa Xaa Gly Ser Lys Gln Cys Xaa Xaa Xaa Xaa Xaa Xaa Xaa
         35                  40                  45

Xaa Pro Cys Lys Arg Xaa Xaa Xaa Xaa Xaa Xaa Xaa Xaa Xaa Gly
 50                      55                  60

Xaa Xaa Xaa Xaa Xaa Xaa Xaa Xaa Xaa Arg Xaa Xaa Xaa Xaa
 65                  70                  75                  80

Xaa Xaa Xaa Xaa Xaa Gly Lys Cys Ile Asn Lys Lys Xaa Xaa Xaa
                 85                  90                  95

Xaa Xaa Xaa Xaa Xaa Cys Lys Cys Tyr Xaa Xaa Xaa Xaa Xaa
             100                 105                 110

Xaa Xaa Xaa Xaa
        115

<210> SEQ ID NO 224
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: all X may be absent, or any amino acid or amino
      acid analogue
<220> FEATURE:
<221> NAME/KEY: misc_feature
<222> LOCATION: (14)..(23)
<223> OTHER INFORMATION: all X may be absent, or any amino acid or amino
      acid analogue
<220> FEATURE:
<221> NAME/KEY: misc_feature
<222> LOCATION: (29)..(38)
<223> OTHER INFORMATION: all X may be absent, or any amino acid or amino
      acid analogue
<220> FEATURE:
<221> NAME/KEY: misc_feature
<222> LOCATION: (40)..(49)
<223> OTHER INFORMATION: all X may be absent, or any amino acid or amino
      acid analogue
<220> FEATURE:
<221> NAME/KEY: misc_feature
<222> LOCATION: (52)..(61)
<223> OTHER INFORMATION: all X may be absent, or any amino acid or amino
      acid analogue
<220> FEATURE:
<221> NAME/KEY: misc_feature
<222> LOCATION: (63)..(72)
<223> OTHER INFORMATION: all X may be absent, or any amino acid or amino
      acid analogue
<220> FEATURE:
<221> NAME/KEY: misc_feature
<222> LOCATION: (81)..(90)
<223> OTHER INFORMATION: all X may be absent, or any amino acid or amino
      acid analogue
<220> FEATURE:
<221> NAME/KEY: misc_feature
<222> LOCATION: (95)..(104)
<223> OTHER INFORMATION: all X may be absent, or any amino acid or amino
      acid analogue

<400> SEQUENCE: 224

Xaa Xaa Xaa Xaa Xaa Xaa Xaa Xaa Xaa Xaa Gly Cys Val Xaa Xaa
 1               5                  10                  15

Xaa Xaa Xaa Xaa Xaa Xaa Xaa Lys Cys Arg Pro Gly Xaa Xaa Xaa Xaa
                 20                  25                  30

Xaa Xaa Xaa Xaa Xaa Xaa Lys Xaa Xaa Xaa Xaa Xaa Xaa Xaa Xaa
         35                  40                  45

Xaa Cys Cys Xaa Xaa Xaa Xaa Xaa Xaa Xaa Xaa Xaa Pro Xaa Xaa
 50                  55                  60
```

Xaa Xaa Xaa Xaa Xaa Xaa Xaa Xaa Lys Arg Cys Ser Arg Arg Phe Gly
65                  70                  75                  80

Xaa Xaa Xaa Xaa Xaa Xaa Xaa Xaa Lys Lys Cys Lys Xaa Xaa
                85                  90                  95

Xaa Xaa Xaa Xaa Xaa Xaa Xaa Xaa
            100

<210> SEQ ID NO 225
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: all X may be absent, or any amino acid or amino
      acid analogue
<220> FEATURE:
<221> NAME/KEY: misc_feature
<222> LOCATION: (3)..(5)
<223> OTHER INFORMATION: all X may be absent, or any amino acid or amino
      acid analogue
<220> FEATURE:
<221> NAME/KEY: misc_feature
<222> LOCATION: (9)..(9)
<223> OTHER INFORMATION: all X may be absent, or any amino acid or amino
      acid analogue
<220> FEATURE:
<221> NAME/KEY: misc_feature
<222> LOCATION: (15)..(16)
<223> OTHER INFORMATION: all X may be absent, or any amino acid or amino
      acid analogue
<220> FEATURE:
<221> NAME/KEY: misc_feature
<222> LOCATION: (21)..(22)
<223> OTHER INFORMATION: all X may be absent, or any amino acid or amino
      acid analogue
<220> FEATURE:
<221> NAME/KEY: misc_feature
<222> LOCATION: (24)..(24)
<223> OTHER INFORMATION: all X may be absent, or any amino acid or amino
      acid analogue
<220> FEATURE:
<221> NAME/KEY: misc_feature
<222> LOCATION: (26)..(26)
<223> OTHER INFORMATION: all X may be absent, or any amino acid or amino
      acid analogue
<220> FEATURE:
<221> NAME/KEY: misc_feature
<222> LOCATION: (34)..(34)
<223> OTHER INFORMATION: all X may be absent, or any amino acid or amino
      acid analogue
<220> FEATURE:
<221> NAME/KEY: misc_feature
<222> LOCATION: (39)..(41)
<223> OTHER INFORMATION: all X may be absent, or any amino acid or amino
      acid analogue

<400> SEQUENCE: 225

Xaa Val Xaa Xaa Xaa Val Lys Cys Xaa Gly Ser Lys Gln Cys Xaa Xaa
1               5                   10                  15

Pro Cys Lys Arg Xaa Xaa Gly Xaa Arg Xaa Gly Lys Cys Ile Asn Lys
            20                  25                  30

Lys Xaa Cys Lys Cys Tyr Xaa Xaa Xaa
            35                  40

<210> SEQ ID NO 226
<211> LENGTH: 45
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(3)
<223> OTHER INFORMATION: all X may be absent, or any amino acid or amino
      acid analogue
<220> FEATURE:
<221> NAME/KEY: misc_feature
<222> LOCATION: (7)..(10)
<223> OTHER INFORMATION: all X may be absent, or any amino acid or amino
      acid analogue
<220> FEATURE:
<221> NAME/KEY: misc_feature
<222> LOCATION: (16)..(16)
<223> OTHER INFORMATION: all X may be absent, or any amino acid or amino
      acid analogue
<220> FEATURE:
<221> NAME/KEY: misc_feature
<222> LOCATION: (18)..(18)
<223> OTHER INFORMATION: all X may be absent, or any amino acid or amino
      acid analogue
<220> FEATURE:
<221> NAME/KEY: misc_feature
<222> LOCATION: (21)..(21)
<223> OTHER INFORMATION: all X may be absent, or any amino acid or amino
      acid analogue
<220> FEATURE:
<221> NAME/KEY: misc_feature
<222> LOCATION: (23)..(23)
<223> OTHER INFORMATION: all X may be absent, or any amino acid or amino
      acid analogue
<220> FEATURE:
<221> NAME/KEY: misc_feature
<222> LOCATION: (32)..(35)
<223> OTHER INFORMATION: all X may be absent, or any amino acid or amino
      acid analogue
<220> FEATURE:
<221> NAME/KEY: misc_feature
<222> LOCATION: (40)..(45)
<223> OTHER INFORMATION: all X may be absent, or any amino acid or amino
      acid analogue

<400> SEQUENCE: 226

Xaa Xaa Xaa Gly Cys Val Xaa Xaa Xaa Xaa Lys Cys Arg Pro Gly Xaa
1               5                   10                  15

Lys Xaa Cys Cys Xaa Pro Xaa Lys Arg Cys Ser Arg Arg Phe Gly Xaa
            20                  25                  30

Xaa Xaa Xaa Lys Lys Cys Lys Xaa Xaa Xaa Xaa Xaa Xaa
        35                  40                  45

<210> SEQ ID NO 227
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is any amino acid or amino acid analogue or
      null
<220> FEATURE:
<221> NAME/KEY: misc_feature
<222> LOCATION: (5)..(6)
<223> OTHER INFORMATION: X is any amino acid or amino acid analogue or
      null
<220> FEATURE:
<221> NAME/KEY: misc_feature
<222> LOCATION: (9)..(9)
<223> OTHER INFORMATION: X is any amino acid or amino acid analogue or
      null
<220> FEATURE:
<221> NAME/KEY: misc_feature
<222> LOCATION: (15)..(15)
```

```
<223> OTHER INFORMATION: X is any amino acid or amino acid analogue or
      null
<220> FEATURE:
<221> NAME/KEY: misc_feature
<222> LOCATION: (20)..(22)
<223> OTHER INFORMATION: X is any amino acid or amino acid analogue or
      null
<220> FEATURE:
<221> NAME/KEY: misc_feature
<222> LOCATION: (24)..(24)
<223> OTHER INFORMATION: X is any amino acid or amino acid analogue or
      null
<220> FEATURE:
<221> NAME/KEY: misc_feature
<222> LOCATION: (26)..(26)
<223> OTHER INFORMATION: X is any amino acid or amino acid analogue or
      null
<220> FEATURE:
<221> NAME/KEY: misc_feature
<222> LOCATION: (30)..(30)
<223> OTHER INFORMATION: X is any amino acid or amino acid analogue or
      null
<220> FEATURE:
<221> NAME/KEY: misc_feature
<222> LOCATION: (37)..(40)
<223> OTHER INFORMATION: X is any amino acid or amino acid analogue or
      null

<400> SEQUENCE: 227

Gly Val Xaa Ile Xaa Xaa Arg Cys Xaa Gly Ser Arg Gln Cys Xaa Asp
1               5                   10                  15

Pro Cys Arg Xaa Xaa Xaa Gly Xaa Arg Xaa Gly Arg Cys Xaa Asn Arg
                20                  25                  30

Arg Cys Arg Cys Xaa Xaa Xaa Xaa
            35                  40

<210> SEQ ID NO 228
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: X is selected from P or R
<220> FEATURE:
<221> NAME/KEY: misc_feature
<222> LOCATION: (5)..(5)
<223> OTHER INFORMATION: X is selected from P or N
<220> FEATURE:
<221> NAME/KEY: misc_feature
<222> LOCATION: (6)..(6)
<223> OTHER INFORMATION: X is selected from V or I
<220> FEATURE:
<221> NAME/KEY: misc_feature
<222> LOCATION: (9)..(9)
<223> OTHER INFORMATION: X is selected from S, T, R or K
<220> FEATURE:
<221> NAME/KEY: misc_feature
<222> LOCATION: (15)..(15)
<223> OTHER INFORMATION: X is selected from Y or L
<220> FEATURE:
<221> NAME/KEY: misc_feature
<222> LOCATION: (20)..(20)
<223> OTHER INFORMATION: X is selected from Q, R or K
<220> FEATURE:
<221> NAME/KEY: misc_feature
<222> LOCATION: (21)..(21)
<223> OTHER INFORMATION: X is selected from A, K or R
<220> FEATURE:
<221> NAME/KEY: misc_feature
<222> LOCATION: (22)..(22)
<223> OTHER INFORMATION: X is selected from T or A
<220> FEATURE:
```

```
<221> NAME/KEY: misc_feature
<222> LOCATION: (24)..(24)
<223> OTHER INFORMATION: X is selected from C or M
<220> FEATURE:
<221> NAME/KEY: misc_feature
<222> LOCATION: (26)..(26)
<223> OTHER INFORMATION: X is selected from F or N
<220> FEATURE:
<221> NAME/KEY: misc_feature
<222> LOCATION: (30)..(30)
<223> OTHER INFORMATION: X is selected from M or I
<220> FEATURE:
<221> NAME/KEY: misc_feature
<222> LOCATION: (37)..(37)
<223> OTHER INFORMATION: X is selected from Y or T
<220> FEATURE:
<221> NAME/KEY: misc_feature
<222> LOCATION: (38)..(38)
<223> OTHER INFORMATION: X is selected from G or P
<220> FEATURE:
<221> NAME/KEY: misc_feature
<222> LOCATION: (39)..(39)
<223> OTHER INFORMATION: X is selected from C or null
<220> FEATURE:
<221> NAME/KEY: misc_feature
<222> LOCATION: (40)..(40)
<223> OTHER INFORMATION: X is selected from G or null

<400> SEQUENCE: 228

Gly Val Xaa Ile Xaa Xaa Arg Cys Xaa Gly Ser Arg Gln Cys Xaa Asp
1               5                   10                  15

Pro Cys Arg Xaa Xaa Xaa Gly Xaa Arg Xaa Gly Arg Cys Xaa Asn Arg
                20                  25                  30

Arg Cys Arg Cys Xaa Xaa Xaa Xaa
            35                  40

<210> SEQ ID NO 229
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: X is any amino acid or amino acid analogue or
      null
<220> FEATURE:
<221> NAME/KEY: misc_feature
<222> LOCATION: (6)..(6)
<223> OTHER INFORMATION: X is any amino acid or amino acid analogue or
      null
<220> FEATURE:
<221> NAME/KEY: misc_feature
<222> LOCATION: (8)..(8)
<223> OTHER INFORMATION: X is any amino acid or amino acid analogue or
      null
<220> FEATURE:
<221> NAME/KEY: misc_feature
<222> LOCATION: (15)..(15)
<223> OTHER INFORMATION: X is any amino acid or amino acid analogue or
      null
<220> FEATURE:
<221> NAME/KEY: misc_feature
<222> LOCATION: (19)..(20)
<223> OTHER INFORMATION: X is any amino acid or amino acid analogue or
      null
<220> FEATURE:
<221> NAME/KEY: misc_feature
<222> LOCATION: (24)..(26)
<223> OTHER INFORMATION: X is any amino acid or amino acid analogue or
      null
<220> FEATURE:
<221> NAME/KEY: misc_feature
<222> LOCATION: (29)..(30)
```

```
<223> OTHER INFORMATION: X is any amino acid or amino acid analogue or
      null
<220> FEATURE:
<221> NAME/KEY: misc_feature
<222> LOCATION: (32)..(32)
<223> OTHER INFORMATION: X is any amino acid or amino acid analogue or
      null

<400> SEQUENCE: 229

Xaa Xaa Xaa Xaa Ile Xaa Cys Xaa Gly Ser Arg Gln Cys Tyr Xaa Pro
1               5                   10                  15

Cys Arg Xaa Xaa Thr Gly Cys Xaa Xaa Xaa Arg Cys Xaa Xaa Arg Xaa
                20                  25                  30

Cys Arg Cys Tyr Gly Cys Gly
        35

<210> SEQ ID NO 230
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from S or null
<220> FEATURE:
<221> NAME/KEY: misc_feature
<222> LOCATION: (3)..(3)
<223> OTHER INFORMATION: X is selected from E, G or null
<220> FEATURE:
<221> NAME/KEY: misc_feature
<222> LOCATION: (4)..(4)
<223> OTHER INFORMATION: X is selected from V, S, or null
<220> FEATURE:
<221> NAME/KEY: misc_feature
<222> LOCATION: (6)..(6)
<223> OTHER INFORMATION: X is selected from R or S
<220> FEATURE:
<221> NAME/KEY: misc_feature
<222> LOCATION: (8)..(8)
<223> OTHER INFORMATION: X is selected from S or T
<220> FEATURE:
<221> NAME/KEY: misc_feature
<222> LOCATION: (15)..(15)
<223> OTHER INFORMATION: X is selected from G or D
<220> FEATURE:
<221> NAME/KEY: misc_feature
<222> LOCATION: (19)..(19)
<223> OTHER INFORMATION: X is selected from Q or R
<220> FEATURE:
<221> NAME/KEY: misc_feature
<222> LOCATION: (20)..(20)
<223> OTHER INFORMATION: X is selected from Q, R, or K
<220> FEATURE:
<221> NAME/KEY: misc_feature
<222> LOCATION: (24)..(24)
<223> OTHER INFORMATION: X is selected from T or P
<220> FEATURE:
<221> NAME/KEY: misc_feature
<222> LOCATION: (25)..(25)
<223> OTHER INFORMATION: X is selected from N or Q
<220> FEATURE:
<221> NAME/KEY: misc_feature
<222> LOCATION: (26)..(26)
<223> OTHER INFORMATION: X is selected from S or A
<220> FEATURE:
<221> NAME/KEY: misc_feature
<222> LOCATION: (29)..(29)
<223> OTHER INFORMATION: X is selected from M or L
<220> FEATURE:
```

```
<221> NAME/KEY: misc_feature
<222> LOCATION: (30)..(30)
<223> OTHER INFORMATION: X is selected from N or Q
<220> FEATURE:
<221> NAME/KEY: misc_feature
<222> LOCATION: (32)..(32)
<223> OTHER INFORMATION: X is selected from V or S

<400> SEQUENCE: 230
```

Xaa Xaa Xaa Xaa Ile Xaa Cys Xaa Gly Ser Arg Gln Cys Tyr Xaa Pro
1               5                   10                  15

Cys Arg Xaa Xaa Thr Gly Cys Xaa Xaa Xaa Arg Cys Xaa Xaa Arg Xaa
            20                  25                  30

Cys Arg Cys Tyr Gly Cys Gly
        35

```
<210> SEQ ID NO 231
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: X is any amino acid or amino acid analogue or
      null
<220> FEATURE:
<221> NAME/KEY: misc_feature
<222> LOCATION: (5)..(5)
<223> OTHER INFORMATION: X is any amino acid or amino acid analogue or
      null
<220> FEATURE:
<221> NAME/KEY: misc_feature
<222> LOCATION: (7)..(7)
<223> OTHER INFORMATION: X is any amino acid or amino acid analogue or
      null
<220> FEATURE:
<221> NAME/KEY: misc_feature
<222> LOCATION: (9)..(9)
<223> OTHER INFORMATION: X is any amino acid or amino acid analogue or
      null
<220> FEATURE:
<221> NAME/KEY: misc_feature
<222> LOCATION: (11)..(12)
<223> OTHER INFORMATION: X is any amino acid or amino acid analogue or
      null
<220> FEATURE:
<221> NAME/KEY: misc_feature
<222> LOCATION: (14)..(15)
<223> OTHER INFORMATION: X is any amino acid or amino acid analogue or
      null
<220> FEATURE:
<221> NAME/KEY: misc_feature
<222> LOCATION: (18)..(18)
<223> OTHER INFORMATION: X is any amino acid or amino acid analogue or
      null
<220> FEATURE:
<221> NAME/KEY: misc_feature
<222> LOCATION: (22)..(22)
<223> OTHER INFORMATION: X is any amino acid or amino acid analogue or
      null
<220> FEATURE:
<221> NAME/KEY: misc_feature
<222> LOCATION: (31)..(31)
<223> OTHER INFORMATION: X is any amino acid or amino acid analogue or
      null
<220> FEATURE:
<221> NAME/KEY: misc_feature
<222> LOCATION: (33)..(33)
<223> OTHER INFORMATION: X is any amino acid or amino acid analogue or
      null
<220> FEATURE:
<221> NAME/KEY: misc_feature
<222> LOCATION: (36)..(36)
```

-continued

```
<223> OTHER INFORMATION: X is any amino acid or amino acid analogue or
      null
<220> FEATURE:
<221> NAME/KEY: misc_feature
<222> LOCATION: (40)..(40)
<223> OTHER INFORMATION: X is any amino acid or amino acid analogue or
      null

<400> SEQUENCE: 231

Xaa Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
            35                  40

<210> SEQ ID NO 232
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: X is selected from G or null
<220> FEATURE:
<221> NAME/KEY: misc_feature
<222> LOCATION: (2)..(2)
<223> OTHER INFORMATION: X is selected from G, S or null
<220> FEATURE:
<221> NAME/KEY: misc_feature
<222> LOCATION: (3)..(3)
<223> OTHER INFORMATION: X is selected from G, S or null
<220> FEATURE:
<221> NAME/KEY: misc_feature
<222> LOCATION: (5)..(5)
<223> OTHER INFORMATION: X is selected from P or R
<220> FEATURE:
<221> NAME/KEY: misc_feature
<222> LOCATION: (7)..(7)
<223> OTHER INFORMATION: X is selected from N or P
<220> FEATURE:
<221> NAME/KEY: misc_feature
<222> LOCATION: (9)..(9)
<223> OTHER INFORMATION: X is selected from R, K or S
<220> FEATURE:
<221> NAME/KEY: misc_feature
<222> LOCATION: (11)..(11)
<223> OTHER INFORMATION: X is selected from R or K
<220> FEATURE:
<221> NAME/KEY: misc_feature
<222> LOCATION: (12)..(12)
<223> OTHER INFORMATION: X is selected from G or H
<220> FEATURE:
<221> NAME/KEY: misc_feature
<222> LOCATION: (14)..(14)
<223> OTHER INFORMATION: X is selected from R or G
<220> FEATURE:
<221> NAME/KEY: misc_feature
<222> LOCATION: (15)..(15)
<223> OTHER INFORMATION: X is selected from D or Q
<220> FEATURE:
<221> NAME/KEY: misc_feature
<222> LOCATION: (18)..(18)
<223> OTHER INFORMATION: X is selected from D, R, or K
<220> FEATURE:
<221> NAME/KEY: misc_feature
<222> LOCATION: (22)..(22)
<223> OTHER INFORMATION: X is selected from K, R, or D
<220> FEATURE:
<221> NAME/KEY: misc_feature
<222> LOCATION: (31)..(31)
<223> OTHER INFORMATION: X is selected from I or M
<220> FEATURE:
```

```
<221> NAME/KEY: misc_feature
<222> LOCATION: (33)..(33)
<223> OTHER INFORMATION: X is selected from S or G
<220> FEATURE:
<221> NAME/KEY: misc_feature
<222> LOCATION: (36)..(36)
<223> OTHER INFORMATION: X is selected from H or D
<220> FEATURE:
<221> NAME/KEY: misc_feature
<222> LOCATION: (40)..(40)
<223> OTHER INFORMATION: X is selected from K, R, or null

<400> SEQUENCE: 232

Xaa Xaa Xaa Val Xaa Ile Xaa Val Xaa Cys Xaa Xaa Ser Xaa Xaa Cys
1               5                   10                  15

Leu Xaa Pro Cys Arg Xaa Ala Gly Met Arg Phe Gly Arg Cys Xaa Asn
            20                  25                  30

Xaa Arg Cys Xaa Cys Thr Pro Xaa
        35                  40

<210> SEQ ID NO 233
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: all X may be absent, or any amino acid or amino
      acid analogue
<220> FEATURE:
<221> NAME/KEY: misc_feature
<222> LOCATION: (12)..(21)
<223> OTHER INFORMATION: all X may be absent, or any amino acid or amino
      acid analogue
<220> FEATURE:
<221> NAME/KEY: misc_feature
<222> LOCATION: (25)..(34)
<223> OTHER INFORMATION: all X may be absent, or any amino acid or amino
      acid analogue
<220> FEATURE:
<221> NAME/KEY: misc_feature
<222> LOCATION: (40)..(49)
<223> OTHER INFORMATION: all X may be absent, or any amino acid or amino
      acid analogue
<220> FEATURE:
<221> NAME/KEY: misc_feature
<222> LOCATION: (54)..(63)
<223> OTHER INFORMATION: all X may be absent, or any amino acid or amino
      acid analogue
<220> FEATURE:
<221> NAME/KEY: misc_feature
<222> LOCATION: (65)..(74)
<223> OTHER INFORMATION: all X may be absent, or any amino acid or amino
      acid analogue
<220> FEATURE:
<221> NAME/KEY: misc_feature
<222> LOCATION: (76)..(85)
<223> OTHER INFORMATION: all X may be absent, or any amino acid or amino
      acid analogue
<220> FEATURE:
<221> NAME/KEY: misc_feature
<222> LOCATION: (93)..(102)
<223> OTHER INFORMATION: all X may be absent, or any amino acid or amino
      acid analogue
<220> FEATURE:
<221> NAME/KEY: misc_feature
<222> LOCATION: (107)..(116)
<223> OTHER INFORMATION: all X may be absent, or any amino acid or amino
      acid analogue

<400> SEQUENCE: 233

Xaa Xaa Xaa Xaa Xaa Xaa Xaa Xaa Xaa Xaa Val Xaa Xaa Xaa Xaa Xaa
```

```
              1               5                  10                 15
Xaa Xaa Xaa Xaa Xaa Val Arg Cys Xaa Xaa Xaa Xaa Xaa Xaa
                    20                  25                 30
Xaa Xaa Gly Ser Arg Gln Cys Xaa Xaa Xaa Xaa Xaa Xaa Xaa
            35                  40                 45
Xaa Pro Cys Arg Arg Xaa Xaa Xaa Xaa Xaa Xaa Xaa Xaa Gly
50                      55                 60
Xaa Xaa Xaa Xaa Xaa Xaa Xaa Xaa Arg Xaa Xaa Xaa Xaa
65                  70                  75                 80
Xaa Xaa Xaa Xaa Xaa Gly Arg Cys Ile Asn Arg Arg Xaa Xaa Xaa
                    85                  90                 95
Xaa Xaa Xaa Xaa Xaa Xaa Cys Arg Cys Tyr Xaa Xaa Xaa Xaa Xaa
                    100                 105                110
Xaa Xaa Xaa Xaa
        115

<210> SEQ ID NO 234
<211> LENGTH: 104
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: all X may be absent, or any amino acid or amino
      acid analogue
<220> FEATURE:
<221> NAME/KEY: misc_feature
<222> LOCATION: (14)..(23)
<223> OTHER INFORMATION: all X may be absent, or any amino acid or amino
      acid analogue
<220> FEATURE:
<221> NAME/KEY: misc_feature
<222> LOCATION: (29)..(38)
<223> OTHER INFORMATION: all X may be absent, or any amino acid or amino
      acid analogue
<220> FEATURE:
<221> NAME/KEY: misc_feature
<222> LOCATION: (40)..(49)
<223> OTHER INFORMATION: all X may be absent, or any amino acid or amino
      acid analogue
<220> FEATURE:
<221> NAME/KEY: misc_feature
<222> LOCATION: (52)..(61)
<223> OTHER INFORMATION: all X may be absent, or any amino acid or amino
      acid analogue
<220> FEATURE:
<221> NAME/KEY: misc_feature
<222> LOCATION: (63)..(72)
<223> OTHER INFORMATION: all X may be absent, or any amino acid or amino
      acid analogue
<220> FEATURE:
<221> NAME/KEY: misc_feature
<222> LOCATION: (81)..(90)
<223> OTHER INFORMATION: all X may be absent, or any amino acid or amino
      acid analogue
<220> FEATURE:
<221> NAME/KEY: misc_feature
<222> LOCATION: (95)..(104)
<223> OTHER INFORMATION: all X may be absent, or any amino acid or amino
      acid analogue

<400> SEQUENCE: 234

Xaa Xaa Xaa Xaa Xaa Xaa Xaa Xaa Xaa Xaa Gly Cys Val Xaa Xaa Xaa
1               5                   10                  15
Xaa Xaa Xaa Xaa Xaa Xaa Xaa Arg Cys Arg Pro Gly Xaa Xaa Xaa Xaa
                20                  25                  30
```

```
Xaa Xaa Xaa Xaa Xaa Arg Xaa Xaa Xaa Xaa Xaa Xaa Xaa
            35                  40                  45

Xaa Cys Cys Xaa Xaa Xaa Xaa Xaa Xaa Xaa Xaa Pro Xaa Xaa
 50                  55                  60

Xaa Xaa Xaa Xaa Xaa Xaa Xaa Arg Arg Cys Ser Arg Arg Phe Gly
 65                  70                  75                  80

Xaa Xaa Xaa Xaa Xaa Xaa Xaa Xaa Xaa Arg Arg Cys Arg Xaa Xaa
                85                  90                  95

Xaa Xaa Xaa Xaa Xaa Xaa Xaa Xaa
            100

<210> SEQ ID NO 235
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: all X may be absent, or any amino acid or amino
      acid analogue
<220> FEATURE:
<221> NAME/KEY: misc_feature
<222> LOCATION: (3)..(5)
<223> OTHER INFORMATION: all X may be absent, or any amino acid or amino
      acid analogue
<220> FEATURE:
<221> NAME/KEY: misc_feature
<222> LOCATION: (9)..(9)
<223> OTHER INFORMATION: all X may be absent, or any amino acid or amino
      acid analogue
<220> FEATURE:
<221> NAME/KEY: misc_feature
<222> LOCATION: (15)..(16)
<223> OTHER INFORMATION: all X may be absent, or any amino acid or amino
      acid analogue
<220> FEATURE:
<221> NAME/KEY: misc_feature
<222> LOCATION: (21)..(22)
<223> OTHER INFORMATION: all X may be absent, or any amino acid or amino
      acid analogue
<220> FEATURE:
<221> NAME/KEY: misc_feature
<222> LOCATION: (24)..(24)
<223> OTHER INFORMATION: all X may be absent, or any amino acid or amino
      acid analogue
<220> FEATURE:
<221> NAME/KEY: misc_feature
<222> LOCATION: (26)..(26)
<223> OTHER INFORMATION: all X may be absent, or any amino acid or amino
      acid analogue
<220> FEATURE:
<221> NAME/KEY: misc_feature
<222> LOCATION: (34)..(34)
<223> OTHER INFORMATION: all X may be absent, or any amino acid or amino
      acid analogue
<220> FEATURE:
<221> NAME/KEY: misc_feature
<222> LOCATION: (39)..(41)
<223> OTHER INFORMATION: all X may be absent, or any amino acid or amino
      acid analogue

<400> SEQUENCE: 235

Xaa Val Xaa Xaa Xaa Val Arg Cys Xaa Gly Ser Arg Gln Cys Xaa Xaa
 1               5                  10                  15

Pro Cys Arg Arg Xaa Xaa Gly Xaa Arg Xaa Gly Arg Cys Ile Asn Arg
                20                  25                  30

Arg Xaa Cys Arg Cys Tyr Xaa Xaa Xaa
            35                  40
```

```
<210> SEQ ID NO 236
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: all X may be absent, or any amino acid or amino
      acid analogue
<220> FEATURE:
<221> NAME/KEY: misc_feature
<222> LOCATION: (7)..(10)
<223> OTHER INFORMATION: all X may be absent, or any amino acid or amino
      acid analogue
<220> FEATURE:
<221> NAME/KEY: misc_feature
<222> LOCATION: (16)..(16)
<223> OTHER INFORMATION: all X may be absent, or any amino acid or amino
      acid analogue
<220> FEATURE:
<221> NAME/KEY: misc_feature
<222> LOCATION: (18)..(18)
<223> OTHER INFORMATION: all X may be absent, or any amino acid or amino
      acid analogue
<220> FEATURE:
<221> NAME/KEY: misc_feature
<222> LOCATION: (21)..(21)
<223> OTHER INFORMATION: all X may be absent, or any amino acid or amino
      acid analogue
<220> FEATURE:
<221> NAME/KEY: misc_feature
<222> LOCATION: (23)..(23)
<223> OTHER INFORMATION: all X may be absent, or any amino acid or amino
      acid analogue
<220> FEATURE:
<221> NAME/KEY: misc_feature
<222> LOCATION: (32)..(35)
<223> OTHER INFORMATION: all X may be absent, or any amino acid or amino
      acid analogue
<220> FEATURE:
<221> NAME/KEY: misc_feature
<222> LOCATION: (40)..(45)
<223> OTHER INFORMATION: all X may be absent, or any amino acid or amino
      acid analogue

<400> SEQUENCE: 236

Xaa Xaa Xaa Gly Cys Val Xaa Xaa Xaa Xaa Arg Cys Arg Pro Gly Xaa
1               5                   10                  15

Arg Xaa Cys Cys Xaa Pro Xaa Arg Arg Cys Ser Arg Arg Phe Gly Xaa
            20                  25                  30

Xaa Xaa Xaa Arg Arg Cys Arg Xaa Xaa Xaa Xaa Xaa Xaa
        35                  40                  45

<210> SEQ ID NO 237
<211> LENGTH: 32
<212> TYPE: PRT
<213> ORGANISM: Artificial Sequence
<220> FEATURE:
<223> OTHER INFORMATION: Synthetic

<400> SEQUENCE: 237

Gly Ile Val Cys Lys Val Cys Lys Ile Ile Cys Gly Met Gln Gly Lys
1               5                   10                  15

Lys Val Asn Ile Cys Lys Ala Pro Ile Lys Cys Lys Cys Lys Lys Gly
            20                  25                  30

<210> SEQ ID NO 238
<211> LENGTH: 35
<212> TYPE: PRT
```

<213> ORGANISM: Artificial Sequence
<220> FEATURE:
<223> OTHER INFORMATION: Synthetic

<400> SEQUENCE: 238

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg
        35

<210> SEQ ID NO 239
<211> LENGTH: 37
<212> TYPE: PRT
<213> ORGANISM: Artificial Sequence
<220> FEATURE:
<223> OTHER INFORMATION: Synthetic

<400> SEQUENCE: 239

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 240
<211> LENGTH: 37
<212> TYPE: PRT
<213> ORGANISM: Artificial Sequence
<220> FEATURE:
<223> OTHER INFORMATION: Synthetic

<400> SEQUENCE: 240

Gly Val Pro Ile Asn Val Lys Cys Arg Gly Ser Arg Asp Cys Leu Asp
1               5                   10                  15

Pro Cys Lys Lys Ala Gly Met Arg Phe Gly Lys Cys Ile Asn Ser Lys
            20                  25                  30

Cys His Cys Thr Pro
        35

<210> SEQ ID NO 241
<211> LENGTH: 33
<212> TYPE: PRT
<213> ORGANISM: Artificial Sequence
<220> FEATURE:
<223> OTHER INFORMATION: Synthetic

<400> SEQUENCE: 241

Ala Val Cys Val Tyr Arg Thr Cys Asp Lys Asp Cys Lys Arg Arg Gly
1               5                   10                  15

Tyr Arg Ser Gly Lys Cys Ile Asn Asn Ala Cys Lys Cys Tyr Pro Tyr
            20                  25                  30

Gly

<210> SEQ ID NO 242
<211> LENGTH: 35
<212> TYPE: PRT
<213> ORGANISM: Artificial Sequence
<220> FEATURE:
<223> OTHER INFORMATION: Synthetic -continued

```
<400> SEQUENCE: 242

Ile Ser Cys Thr Gly Ser Lys Gln Cys Tyr Asp Pro Cys Lys Arg Lys
1               5                   10                  15

Thr Gly Cys Pro Asn Ala Lys Cys Met Asn Lys Ser Cys Lys Cys Tyr
            20                  25                  30

Gly Cys Gly
        35

<210> SEQ ID NO 243
<211> LENGTH: 38
<212> TYPE: PRT
<213> ORGANISM: Artificial Sequence
<220> FEATURE:
<223> OTHER INFORMATION: Synthetic

<400> SEQUENCE: 243

Gln Val Gln Thr Asn Val Lys Cys Gln Gly Gly Ser Cys Ala Ser Val
1               5                   10                  15

Cys Arg Arg Glu Ile Gly Val Ala Ala Gly Lys Cys Ile Asn Gly Lys
            20                  25                  30

Cys Val Cys Tyr Arg Asn
        35

<210> SEQ ID NO 244
<211> LENGTH: 37
<212> TYPE: PRT
<213> ORGANISM: Artificial Sequence
<220> FEATURE:
<223> OTHER INFORMATION: Synthetic

<400> SEQUENCE: 244

Glu Val Ile Arg Cys Ser Gly Ser Lys Gln Cys Tyr Gly Pro Cys Lys
1               5                   10                  15

Gln Gln Thr Gly Cys Thr Asn Ser Lys Cys Met Asn Lys Val Cys Lys
            20                  25                  30

Cys Tyr Gly Cys Gly
        35

<210> SEQ ID NO 245
<211> LENGTH: 33
<212> TYPE: PRT
<213> ORGANISM: Artificial Sequence
<220> FEATURE:
<223> OTHER INFORMATION: Synthetic

<400> SEQUENCE: 245

Ala Cys Lys Gly Val Phe Asp Ala Cys Thr Pro Gly Lys Asn Glu Cys
1               5                   10                  15

Cys Pro Asn Arg Val Cys Ser Asp Lys His Lys Trp Cys Lys Trp Lys
            20                  25                  30

Leu

<210> SEQ ID NO 246
<211> LENGTH: 38
<212> TYPE: PRT
<213> ORGANISM: Artificial Sequence
<220> FEATURE:
<223> OTHER INFORMATION: Synthetic

<400> SEQUENCE: 246

Gln Ile Tyr Thr Ser Lys Glu Cys Asn Gly Ser Ser Glu Cys Tyr Ser
1               5                   10                  15
```

```
His Cys Glu Gly Ile Thr Gly Lys Arg Ser Gly Lys Cys Ile Asn Lys
            20                  25                  30

Lys Cys Tyr Cys Tyr Arg
        35
```

<210> SEQ ID NO 247
<211> LENGTH: 35
<212> TYPE: PRT
<213> ORGANISM: Artificial Sequence
<220> FEATURE:
<223> OTHER INFORMATION: Synthetic

<400> SEQUENCE: 247

```
Gly Cys Leu Glu Phe Trp Trp Lys Cys Asn Pro Asn Asp Lys Cys
1               5                   10                  15

Cys Arg Pro Lys Leu Lys Cys Ser Lys Leu Phe Lys Leu Cys Asn Phe
            20                  25                  30

Ser Phe Gly
        35
```

<210> SEQ ID NO 248
<211> LENGTH: 37
<212> TYPE: PRT
<213> ORGANISM: Artificial Sequence
<220> FEATURE:
<223> OTHER INFORMATION: Synthetic

<400> SEQUENCE: 248

```
Asp Cys Val Arg Phe Trp Gly Lys Cys Ser Gln Thr Ser Asp Cys Cys
1               5                   10                  15

Pro His Leu Ala Cys Lys Ser Lys Trp Pro Arg Asn Ile Cys Val Trp
            20                  25                  30

Asp Gly Ser Val Gly
        35
```

<210> SEQ ID NO 249
<211> LENGTH: 33
<212> TYPE: PRT
<213> ORGANISM: Artificial Sequence
<220> FEATURE:
<223> OTHER INFORMATION: Synthetic

<400> SEQUENCE: 249

```
Gly Cys Phe Gly Tyr Lys Cys Asp Tyr Tyr Lys Gly Cys Cys Ser Gly
1               5                   10                  15

Tyr Val Cys Ser Pro Thr Trp Lys Trp Cys Val Arg Pro Gly Pro Gly
            20                  25                  30

Arg
```

<210> SEQ ID NO 250
<211> LENGTH: 60
<212> TYPE: PRT
<213> ORGANISM: Artificial Sequence
<220> FEATURE:
<223> OTHER INFORMATION: Synthetic

<400> SEQUENCE: 250

```
Met Asn Ala Lys Phe Ile Leu Leu Val Leu Thr Thr Met Met Leu
1               5                   10                  15

Leu Pro Asp Thr Lys Gly Ala Glu Val Ile Arg Cys Ser Gly Ser Lys
            20                  25                  30
```

-continued

Gln Cys Tyr Gly Pro Cys Lys Gln Gln Thr Gly Cys Thr Asn Ser Lys
          35                  40                  45

Cys Met Asn Lys Val Cys Lys Cys Tyr Gly Cys Gly
 50                  55                  60

<210> SEQ ID NO 251
<211> LENGTH: 61
<212> TYPE: PRT
<213> ORGANISM: Artificial Sequence
<220> FEATURE:
<223> OTHER INFORMATION: Synthetic

<400> SEQUENCE: 251

Met Asn Ala Lys Leu Ile Tyr Leu Leu Val Val Thr Thr Met Thr
 1               5                  10                  15

Leu Met Phe Asp Thr Ala Gln Ala Val Asp Ile Met Cys Ser Gly Pro
              20                  25                  30

Lys Gln Cys Tyr Gly Pro Cys Lys Lys Glu Thr Gly Cys Pro Asn Ala
          35                  40                  45

Lys Cys Met Asn Arg Arg Cys Lys Cys Tyr Gly Cys Val
 50                  55                  60

<210> SEQ ID NO 252
<211> LENGTH: 62
<212> TYPE: PRT
<213> ORGANISM: Artificial Sequence
<220> FEATURE:
<223> OTHER INFORMATION: Synthetic

<400> SEQUENCE: 252

Met Asn Ala Lys Leu Ile Tyr Leu Leu Leu Val Val Thr Thr Met Met
 1               5                  10                  15

Leu Thr Phe Asp Thr Thr Gln Ala Gly Asp Ile Lys Cys Ser Gly Thr
              20                  25                  30

Arg Gln Cys Trp Gly Pro Cys Lys Lys Gln Thr Thr Cys Thr Asn Ser
          35                  40                  45

Lys Cys Met Asn Gly Lys Cys Lys Cys Tyr Gly Cys Val Gly
 50                  55                  60

<210> SEQ ID NO 253
<211> LENGTH: 61
<212> TYPE: PRT
<213> ORGANISM: Artificial Sequence
<220> FEATURE:
<223> OTHER INFORMATION: Synthetic

<400> SEQUENCE: 253

Met Asn Thr Lys Phe Ile Phe Leu Leu Val Val Thr Asn Thr Met
 1               5                  10                  15

Met Leu Phe Asp Thr Lys Pro Val Glu Gly Ile Ser Cys Thr Gly Ser
              20                  25                  30

Lys Gln Cys Tyr Asp Pro Cys Lys Arg Lys Thr Gly Cys Pro Asn Ala
          35                  40                  45

Lys Cys Met Asn Lys Ser Cys Lys Cys Tyr Gly Cys Gly
 50                  55                  60

<210> SEQ ID NO 254
<211> LENGTH: 38
<212> TYPE: PRT
<213> ORGANISM: Artificial Sequence
<220> FEATURE:
<223> OTHER INFORMATION: Synthetic

```
<400> SEQUENCE: 254

Gly Val Pro Ile Asn Val Lys Cys Ser Gly Ser Arg Asp Cys Leu Glu
1               5                   10                  15

Pro Cys Lys Lys Ala Gly Met Arg Phe Gly Lys Cys Ile Asn Arg Lys
            20                  25                  30

Cys His Cys Thr Pro Lys
        35

<210> SEQ ID NO 255
<211> LENGTH: 38
<212> TYPE: PRT
<213> ORGANISM: Artificial Sequence
<220> FEATURE:
<223> OTHER INFORMATION: Synthetic

<400> SEQUENCE: 255

Gly Val Pro Ile Asn Val Lys Cys Thr Gly Ser Pro Gln Cys Leu Lys
1               5                   10                  15

Pro Cys Lys Asp Ala Gly Met Arg Phe Gly Lys Cys Ile Asn Gly Lys
            20                  25                  30

Cys His Cys Thr Pro Lys
        35

<210> SEQ ID NO 256
<211> LENGTH: 38
<212> TYPE: PRT
<213> ORGANISM: Artificial Sequence
<220> FEATURE:
<223> OTHER INFORMATION: Synthetic

<400> SEQUENCE: 256

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
        35

<210> SEQ ID NO 257
<211> LENGTH: 38
<212> TYPE: PRT
<213> ORGANISM: Artificial Sequence
<220> FEATURE:
<223> OTHER INFORMATION: Synthetic

<400> SEQUENCE: 257

Gly Val Pro Ile Asn Val Lys Cys Arg Gly Ser Pro Gln Cys Ile Gln
1               5                   10                  15

Pro Cys Arg Asp Ala Gly Met Arg Phe Gly Lys Cys Met Asn Gly Lys
            20                  25                  30

Cys His Cys Thr Pro Gln
        35

<210> SEQ ID NO 258
<211> LENGTH: 38
<212> TYPE: PRT
<213> ORGANISM: Artificial Sequence
<220> FEATURE:
<223> OTHER INFORMATION: Synthetic

<400> SEQUENCE: 258
```

Gly Val Glu Ile Asn Val Lys Cys Thr Gly Ser His Gln Cys Ile Lys
1               5                   10                  15

Pro Cys Lys Asp Ala Gly Met Arg Phe Gly Lys Cys Ile Asn Arg Lys
            20                  25                  30

Cys His Cys Thr Pro Lys
        35

<210> SEQ ID NO 259
<211> LENGTH: 38
<212> TYPE: PRT
<213> ORGANISM: Artificial Sequence
<220> FEATURE:
<223> OTHER INFORMATION: Synthetic

<400> SEQUENCE: 259

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 260
<211> LENGTH: 38
<212> TYPE: PRT
<213> ORGANISM: Artificial Sequence
<220> FEATURE:
<223> OTHER INFORMATION: Synthetic

<400> SEQUENCE: 260

Gly Val Pro Thr Asp Val Lys Cys Arg Gly Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 261
<211> LENGTH: 38
<212> TYPE: PRT
<213> ORGANISM: Artificial Sequence
<220> FEATURE:
<223> OTHER INFORMATION: Synthetic

<400> SEQUENCE: 261

Gly Val Pro Ile Asn Val Ser Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 262
<211> LENGTH: 38
<212> TYPE: PRT
<213> ORGANISM: Artificial Sequence
<220> FEATURE:
<223> OTHER INFORMATION: Synthetic

<400> SEQUENCE: 262

Gly Val Pro Ile Asn Val Pro Cys Thr Gly Ser Pro Gln Cys Ile Lys
1               5                   10                  15

-continued

```
Pro Cys Lys Asp Ala Gly Met Arg Phe Gly Lys Cys Met Asn Arg Lys
            20                  25                  30

Cys His Cys Thr Pro Lys
        35

<210> SEQ ID NO 263
<211> LENGTH: 37
<212> TYPE: PRT
<213> ORGANISM: Artificial Sequence
<220> FEATURE:
<223> OTHER INFORMATION: Synthetic

<400> SEQUENCE: 263

Val Gly Ile Asn Val Lys Cys Lys His Ser Gly Gln Cys Leu Lys Pro
1               5                   10                  15

Cys Lys Asp Ala Gly Met Arg Phe Gly Lys Cys Ile Asn Gly Lys Cys
            20                  25                  30

Asp Cys Thr Pro Lys
        35

<210> SEQ ID NO 264
<211> LENGTH: 37
<212> TYPE: PRT
<213> ORGANISM: Artificial Sequence
<220> FEATURE:
<223> OTHER INFORMATION: Synthetic

<400> SEQUENCE: 264

Val Gly Ile Asn Val Lys Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 265
<211> LENGTH: 37
<212> TYPE: PRT
<213> ORGANISM: Artificial Sequence
<220> FEATURE:
<223> OTHER INFORMATION: Synthetic

<400> SEQUENCE: 265

Val Gly Ile Pro Val Ser Cys Lys His Ser Gly Gln Cys Ile Lys Pro
1               5                   10                  15

Cys Lys Asp Ala Gly Met Arg Phe Gly Lys Cys Met Asn Arg Lys Cys
            20                  25                  30

Asp Cys Thr Pro Lys
        35

<210> SEQ ID NO 266
<211> LENGTH: 36
<212> TYPE: PRT
<213> ORGANISM: Artificial Sequence
<220> FEATURE:
<223> OTHER INFORMATION: Synthetic

<400> SEQUENCE: 266

Arg Lys Gly Cys Phe Lys Glu Gly His Ser Cys Pro Lys Thr Ala Pro
1               5                   10                  15

Cys Cys Arg Pro Leu Val Cys Lys Gly Pro Ser Pro Asn Thr Lys Lys
            20                  25                  30
```

Cys Thr Arg Pro
        35

<210> SEQ ID NO 267
<211> LENGTH: 32
<212> TYPE: PRT
<213> ORGANISM: Artificial Sequence
<220> FEATURE:
<223> OTHER INFORMATION: Synthetic

<400> SEQUENCE: 267

Ser Phe Cys Ile Pro Phe Lys Pro Cys Lys Ser Asp Glu Asn Cys Cys
1               5                   10                  15

Lys Lys Phe Lys Cys Lys Thr Thr Gly Ile Val Lys Leu Cys Arg Trp
            20                  25                  30

<210> SEQ ID NO 268
<211> LENGTH: 36
<212> TYPE: PRT
<213> ORGANISM: Artificial Sequence
<220> FEATURE:
<223> OTHER INFORMATION: Synthetic

<400> SEQUENCE: 268

Leu Lys Gly Cys Leu Pro Arg Asn Arg Phe Cys Asn Ala Leu Ser Gly
1               5                   10                  15

Pro Arg Cys Cys Ser Gly Leu Arg Cys Lys Glu Leu Ser Ile Trp Ala
            20                  25                  30

Ser Lys Cys Leu
        35

<210> SEQ ID NO 269
<211> LENGTH: 34
<212> TYPE: PRT
<213> ORGANISM: Artificial Sequence
<220> FEATURE:
<223> OTHER INFORMATION: Synthetic

<400> SEQUENCE: 269

Gly Asn Tyr Cys Leu Arg Gly Arg Cys Leu Pro Gly Gly Arg Lys Cys
1               5                   10                  15

Cys Asn Gly Arg Pro Cys Glu Cys Phe Ala Lys Ile Cys Ser Cys Lys
            20                  25                  30

Pro Lys

<210> SEQ ID NO 270
<211> LENGTH: 29
<212> TYPE: PRT
<213> ORGANISM: Artificial Sequence
<220> FEATURE:
<223> OTHER INFORMATION: Synthetic

<400> SEQUENCE: 270

Thr Val Lys Cys Gly Gly Cys Asn Arg Lys Cys Cys Pro Gly Gly Cys
1               5                   10                  15

Arg Ser Gly Lys Cys Ile Asn Gly Lys Cys Gln Cys Tyr
            20                  25

<210> SEQ ID NO 271
<211> LENGTH: 29
<212> TYPE: PRT
<213> ORGANISM: Artificial Sequence
<220> FEATURE:
<223> OTHER INFORMATION: Synthetic

<400> SEQUENCE: 271

Gly Cys Met Lys Glu Tyr Cys Ala Gly Gln Cys Arg Gly Lys Val Ser
1               5                   10                  15

Gln Asp Tyr Cys Leu Lys His Cys Lys Cys Ile Pro Arg
            20                  25

<210> SEQ ID NO 272
<211> LENGTH: 34
<212> TYPE: PRT
<213> ORGANISM: Artificial Sequence
<220> FEATURE:
<223> OTHER INFORMATION: Synthetic

<400> SEQUENCE: 272

Ala Cys Leu Gly Phe Gly Glu Lys Cys Asn Pro Ser Asn Asp Lys Cys
1               5                   10                  15

Cys Lys Ser Ser Ser Leu Val Cys Ser Gln Lys His Lys Trp Cys Lys
            20                  25                  30

Tyr Gly

<210> SEQ ID NO 273
<211> LENGTH: 37
<212> TYPE: PRT
<213> ORGANISM: Artificial Sequence
<220> FEATURE:
<223> OTHER INFORMATION: Synthetic

<400> SEQUENCE: 273

Arg Gly Gly Cys Leu Pro His Asn Arg Phe Cys Asn Ala Leu Ser Gly
1               5                   10                  15

Pro Arg Cys Cys Ser Gly Leu Arg Cys Lys Glu Leu Ser Ile Arg Asp
            20                  25                  30

Ser Arg Cys Leu Gly
        35

<210> SEQ ID NO 274
<211> LENGTH: 36
<212> TYPE: PRT
<213> ORGANISM: Artificial Sequence
<220> FEATURE:
<223> OTHER INFORMATION: Synthetic

<400> SEQUENCE: 274

Arg Gly Gly Cys Leu Pro Arg Asn Lys Phe Cys Asn Pro Ser Ser Gly
1               5                   10                  15

Pro Arg Cys Cys Ser Gly Leu Thr Cys Lys Glu Leu Asn Ile Trp Ala
            20                  25                  30

Ser Lys Cys Leu
        35

<210> SEQ ID NO 275
<211> LENGTH: 33
<212> TYPE: PRT
<213> ORGANISM: Artificial Sequence
<220> FEATURE:
<223> OTHER INFORMATION: Synthetic

<400> SEQUENCE: 275

Gln Arg Ser Cys Ala Lys Pro Gly Asp Met Cys Met Gly Ile Lys Cys
1               5                   10                  15

Cys Asp Gly Gln Cys Gly Cys Asn Arg Gly Thr Gly Arg Cys Phe Cys

```
            20                  25                  30

Lys

<210> SEQ ID NO 276
<211> LENGTH: 40
<212> TYPE: PRT
<213> ORGANISM: Artificial Sequence
<220> FEATURE:
<223> OTHER INFORMATION: Synthetic

<400> SEQUENCE: 276

Ala Arg Gly Cys Ala Asp Ala Tyr Lys Ser Cys Asn His Pro Arg Thr
1               5                   10                  15

Cys Cys Asp Gly Tyr Asn Gly Tyr Lys Arg Ala Cys Ile Cys Ser Gly
            20                  25                  30

Ser Asn Cys Lys Cys Lys Lys Ser
        35                  40

<210> SEQ ID NO 277
<211> LENGTH: 37
<212> TYPE: PRT
<213> ORGANISM: Artificial Sequence
<220> FEATURE:
<223> OTHER INFORMATION: Synthetic

<400> SEQUENCE: 277

Arg Gly Gly Cys Leu Pro His Asn Arg Phe Cys Asn Ala Leu Ser Gly
1               5                   10                  15

Pro Arg Cys Cys Ser Gly Leu Arg Cys Lys Glu Leu Ser Ile Trp Asp
            20                  25                  30

Ser Arg Cys Leu Gly
        35

<210> SEQ ID NO 278
<211> LENGTH: 37
<212> TYPE: PRT
<213> ORGANISM: Artificial Sequence
<220> FEATURE:
<223> OTHER INFORMATION: Synthetic

<400> SEQUENCE: 278

Arg Gly Gly Cys Leu Pro His Asn Arg Phe Cys Asn Ala Leu Ser Gly
1               5                   10                  15

Pro Arg Cys Cys Ser Gly Leu Lys Cys Lys Glu Leu Ser Ile Tyr Asp
            20                  25                  30

Ser Arg Cys Leu Gly
        35

<210> SEQ ID NO 279
<211> LENGTH: 37
<212> TYPE: PRT
<213> ORGANISM: Artificial Sequence
<220> FEATURE:
<223> OTHER INFORMATION: Synthetic

<400> SEQUENCE: 279

Arg Gly Gly Cys Leu Pro His Asn Arg Phe Cys Asn Ala Leu Ser Gly
1               5                   10                  15

Pro Arg Cys Cys Ser Arg Leu Lys Cys Lys Glu Leu Ser Ile Trp Asp
            20                  25                  30

Ser Arg Cys Leu Gly
        35
```

<210> SEQ ID NO 280
<211> LENGTH: 37
<212> TYPE: PRT
<213> ORGANISM: Artificial Sequence
<220> FEATURE:
<223> OTHER INFORMATION: Synthetic

<400> SEQUENCE: 280

Arg Gly Gly Cys Leu Pro His Asn Arg Phe Cys Asn Ala Leu Thr Gly
1               5                   10                  15

Pro Arg Cys Cys Ser Arg Leu Arg Cys Lys Glu Leu Ser Ile Trp Asp
            20                  25                  30

Ser Ile Cys Leu Gly
        35

<210> SEQ ID NO 281
<211> LENGTH: 34
<212> TYPE: PRT
<213> ORGANISM: Artificial Sequence
<220> FEATURE:
<223> OTHER INFORMATION: Synthetic

<400> SEQUENCE: 281

Ser Cys Ala Asp Ala Tyr Lys Ser Cys Asp Ser Leu Lys Cys Cys Asn
1               5                   10                  15

Asn Arg Thr Cys Met Cys Ser Met Ile Gly Thr Asn Cys Thr Cys Arg
            20                  25                  30

Lys Lys

<210> SEQ ID NO 282
<211> LENGTH: 30
<212> TYPE: PRT
<213> ORGANISM: Artificial Sequence
<220> FEATURE:
<223> OTHER INFORMATION: Synthetic

<400> SEQUENCE: 282

Glu Arg Arg Cys Leu Pro Ala Gly Lys Thr Cys Val Arg Gly Pro Met
1               5                   10                  15

Arg Val Pro Cys Cys Gly Ser Cys Ser Gln Asn Lys Cys Thr
            20                  25                  30

<210> SEQ ID NO 283
<211> LENGTH: 31
<212> TYPE: PRT
<213> ORGANISM: Artificial Sequence
<220> FEATURE:
<223> OTHER INFORMATION: Synthetic

<400> SEQUENCE: 283

Leu Cys Ser Arg Glu Gly Glu Phe Cys Tyr Lys Leu Arg Lys Cys Cys
1               5                   10                  15

Ala Gly Phe Tyr Cys Lys Ala Phe Val Leu His Cys Tyr Arg Asn
            20                  25                  30

<210> SEQ ID NO 284
<211> LENGTH: 23
<212> TYPE: PRT
<213> ORGANISM: Artificial Sequence
<220> FEATURE:
<223> OTHER INFORMATION: Synthetic

<400> SEQUENCE: 284

```
Ala Cys Gly Ser Cys Arg Lys Lys Cys Lys Gly Ser Gly Lys Cys Ile
1               5                   10                  15

Asn Gly Arg Cys Lys Cys Tyr
            20
```

<210> SEQ ID NO 285
<211> LENGTH: 23
<212> TYPE: PRT
<213> ORGANISM: Artificial Sequence
<220> FEATURE:
<223> OTHER INFORMATION: Synthetic

<400> SEQUENCE: 285

```
Ala Cys Gly Ser Cys Arg Lys Lys Cys Lys Gly Pro Gly Lys Cys Ile
1               5                   10                  15

Asn Gly Arg Cys Lys Cys Tyr
            20
```

<210> SEQ ID NO 286
<211> LENGTH: 32
<212> TYPE: PRT
<213> ORGANISM: Artificial Sequence
<220> FEATURE:
<223> OTHER INFORMATION: Synthetic

<400> SEQUENCE: 286

```
Ala Cys Gln Gly Tyr Met Arg Lys Cys Gly Arg Asp Lys Pro Pro Cys
1               5                   10                  15

Cys Lys Lys Leu Glu Cys Ser Lys Thr Trp Arg Trp Cys Val Trp Asn
            20                  25                  30
```

<210> SEQ ID NO 287
<211> LENGTH: 30
<212> TYPE: PRT
<213> ORGANISM: Artificial Sequence
<220> FEATURE:
<223> OTHER INFORMATION: Synthetic

<400> SEQUENCE: 287

```
Gly Arg Tyr Cys Gln Lys Trp Met Trp Thr Cys Asp Ser Lys Arg Ala
1               5                   10                  15

Cys Cys Glu Gly Leu Arg Cys Lys Leu Trp Cys Arg Lys Ile
            20                  25                  30
```

<210> SEQ ID NO 288
<211> LENGTH: 34
<212> TYPE: PRT
<213> ORGANISM: Artificial Sequence
<220> FEATURE:
<223> OTHER INFORMATION: Synthetic

<400> SEQUENCE: 288

```
Asn Ala Lys Cys Arg Gly Ser Pro Glu Cys Leu Pro Lys Cys Lys Glu
1               5                   10                  15

Ala Ile Gly Lys Ala Ala Gly Lys Cys Met Asn Gly Lys Cys Lys Cys
            20                  25                  30

Tyr Pro
```

<210> SEQ ID NO 289
<211> LENGTH: 34
<212> TYPE: PRT
<213> ORGANISM: Artificial Sequence
<220> FEATURE:

-continued

<223> OTHER INFORMATION: Synthetic

<400> SEQUENCE: 289

Asn Val Lys Cys Arg Gly Ser Lys Glu Cys Leu Pro Ala Cys Lys Ala
1               5                   10                  15

Ala Val Gly Lys Ala Ala Gly Lys Cys Met Asn Gly Lys Cys Lys Cys
            20                  25                  30

Tyr Pro

<210> SEQ ID NO 290
<211> LENGTH: 34
<212> TYPE: PRT
<213> ORGANISM: Artificial Sequence
<220> FEATURE:
<223> OTHER INFORMATION: Synthetic

<400> SEQUENCE: 290

Asn Val Lys Cys Arg Gly Ser Pro Glu Cys Leu Pro Lys Cys Lys Glu
1               5                   10                  15

Ala Ile Gly Lys Ser Ala Gly Lys Cys Met Asn Gly Lys Cys Lys Cys
            20                  25                  30

Tyr Pro

<210> SEQ ID NO 291
<211> LENGTH: 34
<212> TYPE: PRT
<213> ORGANISM: Artificial Sequence
<220> FEATURE:
<223> OTHER INFORMATION: Synthetic

<400> SEQUENCE: 291

Asn Ala Lys Cys Arg Gly Ser Pro Glu Cys Leu Pro Lys Cys Lys Gln
1               5                   10                  15

Ala Ile Gly Lys Ala Ala Gly Lys Cys Met Asn Gly Lys Cys Lys Cys
            20                  25                  30

Tyr Pro

<210> SEQ ID NO 292
<211> LENGTH: 33
<212> TYPE: PRT
<213> ORGANISM: Artificial Sequence
<220> FEATURE:
<223> OTHER INFORMATION: Synthetic

<400> SEQUENCE: 292

Arg Gly Tyr Cys Ala Glu Lys Gly Ile Lys Cys His Asn Ile His Cys
1               5                   10                  15

Cys Ser Gly Leu Thr Cys Lys Cys Lys Gly Ser Ser Cys Val Cys Arg
            20                  25                  30

Lys

<210> SEQ ID NO 293
<211> LENGTH: 31
<212> TYPE: PRT
<213> ORGANISM: Artificial Sequence
<220> FEATURE:
<223> OTHER INFORMATION: Synthetic

<400> SEQUENCE: 293

Glu Arg Gly Cys Lys Leu Thr Phe Trp Lys Cys Lys Asn Lys Lys Glu
1               5                   10                  15

Cys Cys Gly Trp Asn Ala Cys Ala Leu Gly Ile Cys Met Pro Arg
            20                  25                  30

<210> SEQ ID NO 294
<211> LENGTH: 39
<212> TYPE: PRT
<213> ORGANISM: Artificial Sequence
<220> FEATURE:
<223> OTHER INFORMATION: Synthetic

<400> SEQUENCE: 294

Lys Lys Lys Cys Ile Ala Lys Asp Tyr Gly Arg Cys Lys Trp Gly Gly
1               5                   10                  15

Thr Pro Cys Cys Arg Gly Arg Gly Cys Ile Cys Ser Ile Met Gly Thr
            20                  25                  30

Asn Cys Glu Cys Lys Pro Arg
        35

<210> SEQ ID NO 295
<211> LENGTH: 29
<212> TYPE: PRT
<213> ORGANISM: Artificial Sequence
<220> FEATURE:
<223> OTHER INFORMATION: Synthetic

<400> SEQUENCE: 295

Gly Cys Lys Leu Thr Phe Trp Lys Cys Lys Asn Lys Lys Glu Cys Cys
1               5                   10                  15

Gly Trp Asn Ala Cys Ala Leu Gly Ile Cys Met Pro Arg
            20                  25

<210> SEQ ID NO 296
<211> LENGTH: 32
<212> TYPE: PRT
<213> ORGANISM: Artificial Sequence
<220> FEATURE:
<223> OTHER INFORMATION: Synthetic

<400> SEQUENCE: 296

Ala Cys Lys Gly Leu Phe Val Thr Cys Thr Pro Gly Lys Asp Glu Cys
1               5                   10                  15

Cys Pro Asn His Val Cys Ser Ser Lys His Lys Trp Cys Lys Tyr Lys
            20                  25                  30

<210> SEQ ID NO 297
<211> LENGTH: 36
<212> TYPE: PRT
<213> ORGANISM: Artificial Sequence
<220> FEATURE:
<223> OTHER INFORMATION: Synthetic

<400> SEQUENCE: 297

Ile Ala Cys Ala Pro Arg Gly Leu Leu Cys Phe Arg Asp Lys Glu Cys
1               5                   10                  15

Cys Lys Gly Leu Thr Cys Lys Gly Arg Phe Val Asn Thr Trp Pro Thr
            20                  25                  30

Phe Cys Leu Val
        35

<210> SEQ ID NO 298
<211> LENGTH: 36
<212> TYPE: PRT
<213> ORGANISM: Artificial Sequence
<220> FEATURE:

<223> OTHER INFORMATION: Synthetic

<400> SEQUENCE: 298

Ala Cys Ala Gly Leu Tyr Lys Lys Cys Gly Lys Gly Val Asn Thr Cys
1               5                   10                  15

Cys Glu Asn Arg Pro Cys Lys Cys Asp Leu Ala Met Gly Asn Cys Ile
                20                  25                  30

Cys Lys Lys Lys
        35

<210> SEQ ID NO 299
<211> LENGTH: 38
<212> TYPE: PRT
<213> ORGANISM: Artificial Sequence
<220> FEATURE:
<223> OTHER INFORMATION: Synthetic

<400> SEQUENCE: 299

Phe Thr Cys Ala Ile Ser Cys Asp Ile Lys Val Asn Gly Lys Pro Cys
1               5                   10                  15

Lys Gly Ser Gly Glu Lys Lys Cys Ser Gly Gly Trp Ser Cys Lys Phe
                20                  25                  30

Asn Val Cys Val Lys Val
        35

<210> SEQ ID NO 300
<211> LENGTH: 33
<212> TYPE: PRT
<213> ORGANISM: Artificial Sequence
<220> FEATURE:
<223> OTHER INFORMATION: Synthetic

<400> SEQUENCE: 300

Gly Phe Cys Ala Gln Lys Gly Ile Lys Cys His Asp Ile His Cys Cys
1               5                   10                  15

Thr Asn Leu Lys Cys Val Arg Glu Gly Ser Asn Arg Val Cys Arg Lys
                20                  25                  30

Ala

<210> SEQ ID NO 301
<211> LENGTH: 42
<212> TYPE: PRT
<213> ORGANISM: Artificial Sequence
<220> FEATURE:
<223> OTHER INFORMATION: Synthetic

<400> SEQUENCE: 301

Cys Ala Lys Lys Arg Asn Trp Cys Gly Lys Asn Glu Asp Cys Cys Cys
1               5                   10                  15

Pro Met Lys Cys Ile Tyr Ala Trp Tyr Asn Gln Gln Gly Ser Cys Gln
                20                  25                  30

Ser Thr Ile Thr Gly Leu Phe Lys Lys Cys
        35                  40

<210> SEQ ID NO 302
<211> LENGTH: 28
<212> TYPE: PRT
<213> ORGANISM: Artificial Sequence
<220> FEATURE:
<223> OTHER INFORMATION: Synthetic

<400> SEQUENCE: 302

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile
                20                  25

<210> SEQ ID NO 303
<211> LENGTH: 37
<212> TYPE: PRT
<213> ORGANISM: Artificial Sequence
<220> FEATURE:
<223> OTHER INFORMATION: Synthetic

<400> SEQUENCE: 303

Arg Gly Gly Cys Leu Pro His Asn Lys Phe Cys Asn Ala Leu Ser Gly
1               5                   10                  15

Pro Arg Cys Cys Ser Gly Leu Lys Cys Lys Glu Leu Thr Ile Trp Asn
                20                  25                  30

Thr Lys Cys Leu Glu
        35

<210> SEQ ID NO 304
<211> LENGTH: 34
<212> TYPE: PRT
<213> ORGANISM: Artificial Sequence
<220> FEATURE:
<223> OTHER INFORMATION: Synthetic

<400> SEQUENCE: 304

Asn Val Lys Cys Thr Gly Ser Lys Gln Cys Leu Pro Ala Cys Lys Ala
1               5                   10                  15

Ala Val Gly Lys Ala Ala Gly Lys Cys Met Asn Gly Lys Cys Lys Cys
                20                  25                  30

Tyr Thr

<210> SEQ ID NO 305
<211> LENGTH: 33
<212> TYPE: PRT
<213> ORGANISM: Artificial Sequence
<220> FEATURE:
<223> OTHER INFORMATION: Synthetic

<400> SEQUENCE: 305

Gln Arg Ser Cys Ala Lys Pro Gly Glu Met Cys Met Arg Ile Lys Cys
1               5                   10                  15

Cys Asp Gly Gln Cys Gly Cys Asn Arg Gly Thr Gly Arg Cys Phe Cys
                20                  25                  30

Lys

<210> SEQ ID NO 306
<211> LENGTH: 36
<212> TYPE: PRT
<213> ORGANISM: Artificial Sequence
<220> FEATURE:
<223> OTHER INFORMATION: Synthetic

<400> SEQUENCE: 306

Gly Cys Ile Pro Lys His Lys Arg Cys Thr Trp Ser Gly Pro Lys Cys
1               5                   10                  15

Cys Asn Asn Ile Ser Cys His Cys Asn Ile Ser Gly Thr Leu Cys Lys
                20                  25                  30

Cys Arg Pro Gly
        35

<210> SEQ ID NO 307
<211> LENGTH: 33
<212> TYPE: PRT
<213> ORGANISM: Artificial Sequence
<220> FEATURE:
<223> OTHER INFORMATION: Synthetic

<400> SEQUENCE: 307

Asn Tyr Cys Val Ala Lys Arg Cys Arg Pro Gly Gly Arg Gln Cys Cys
1               5                   10                  15

Ser Gly Lys Pro Cys Ala Cys Val Gly Lys Val Cys Lys Cys Pro Arg
            20                  25                  30

Asp

<210> SEQ ID NO 308
<211> LENGTH: 37
<212> TYPE: PRT
<213> ORGANISM: Artificial Sequence
<220> FEATURE:
<223> OTHER INFORMATION: Synthetic

<400> SEQUENCE: 308

Glu Arg Gly Cys Ser Gly Ala Tyr Lys Arg Cys Ser Ser Gln Arg
1               5                   10                  15

Cys Cys Glu Gly Arg Pro Cys Val Cys Ser Ala Ile Asn Ser Asn Cys
            20                  25                  30

Lys Cys Arg Lys Thr
        35

<210> SEQ ID NO 309
<211> LENGTH: 36
<212> TYPE: PRT
<213> ORGANISM: Artificial Sequence
<220> FEATURE:
<223> OTHER INFORMATION: Synthetic

<400> SEQUENCE: 309

Arg Tyr Cys Pro Arg Asn Pro Glu Ala Cys Tyr Asn Tyr Cys Leu Arg
1               5                   10                  15

Thr Gly Arg Pro Gly Gly Tyr Cys Gly Arg Ser Arg Ile Thr Cys
            20                  25                  30

Phe Cys Phe Arg
        35

<210> SEQ ID NO 310
<211> LENGTH: 33
<212> TYPE: PRT
<213> ORGANISM: Artificial Sequence
<220> FEATURE:
<223> OTHER INFORMATION: Synthetic

<400> SEQUENCE: 310

Gln Arg Ser Cys Ala Lys Pro Gly Glu Met Cys Met Gly Ile Lys Cys
1               5                   10                  15

Cys Asp Gly Gln Cys Gly Cys Asn Arg Gly Thr Gly Arg Cys Phe Cys
            20                  25                  30

Lys

<210> SEQ ID NO 311
<211> LENGTH: 36
<212> TYPE: PRT

```
<213> ORGANISM: Artificial Sequence
<220> FEATURE:
<223> OTHER INFORMATION: Synthetic

<400> SEQUENCE: 311

Arg Arg Gly Cys Phe Lys Glu Gly Lys Trp Cys Pro Lys Ser Ala Pro
1               5                   10                  15

Cys Cys Ala Pro Leu Lys Cys Lys Gly Pro Ser Ile Lys Gln Gln Lys
            20                  25                  30

Cys Val Arg Glu
        35

<210> SEQ ID NO 312
<211> LENGTH: 31
<212> TYPE: PRT
<213> ORGANISM: Artificial Sequence
<220> FEATURE:
<223> OTHER INFORMATION: Synthetic

<400> SEQUENCE: 312

Thr Val Lys Cys Gly Gly Cys Asn Arg Lys Cys Cys Ala Gly Gly Cys
1               5                   10                  15

Arg Ser Gly Lys Cys Ile Asn Gly Lys Cys Gln Cys Tyr Gly Arg
            20                  25                  30

<210> SEQ ID NO 313
<211> LENGTH: 29
<212> TYPE: PRT
<213> ORGANISM: Artificial Sequence
<220> FEATURE:
<223> OTHER INFORMATION: Synthetic

<400> SEQUENCE: 313

Glu Arg Arg Cys Glu Pro Ser Gly Lys Pro Cys Arg Pro Leu Met Arg
1               5                   10                  15

Ile Pro Cys Cys Gly Ser Cys Val Arg Gly Lys Cys Ala
            20                  25

<210> SEQ ID NO 314
<211> LENGTH: 36
<212> TYPE: PRT
<213> ORGANISM: Artificial Sequence
<220> FEATURE:
<223> OTHER INFORMATION: Synthetic

<400> SEQUENCE: 314

Arg Gly Gly Cys Leu Pro Arg Asn Lys Phe Cys Asn Pro Ser Ser Gly
1               5                   10                  15

Pro Arg Cys Cys Ser Gly Leu Thr Cys Lys Glu Leu Asn Ile Trp Ala
            20                  25                  30

Asn Lys Cys Leu
        35

<210> SEQ ID NO 315
<211> LENGTH: 42
<212> TYPE: PRT
<213> ORGANISM: Artificial Sequence
<220> FEATURE:
<223> OTHER INFORMATION: Synthetic

<400> SEQUENCE: 315

Cys Ala Lys Lys Arg Asn Trp Cys Gly Lys Asn Glu Asp Cys Cys Cys
1               5                   10                  15
```

```
Pro Met Lys Cys Ile Tyr Ala Trp Tyr Asn Gln Gln Gly Ser Cys Gln
            20                  25                  30

Thr Thr Ile Thr Gly Leu Phe Lys Lys Cys
        35                  40
```

<210> SEQ ID NO 316
<211> LENGTH: 10
<212> TYPE: PRT
<213> ORGANISM: Artificial Sequence
<220> FEATURE:
<223> OTHER INFORMATION: Synthetic

<400> SEQUENCE: 316

```
Gly Lys Cys Ile Asn Lys Cys Lys Cys
1               5                   10
```

<210> SEQ ID NO 317
<211> LENGTH: 4
<212> TYPE: PRT
<213> ORGANISM: Artificial Sequence
<220> FEATURE:
<223> OTHER INFORMATION: Synthetic

<400> SEQUENCE: 317

```
Lys Cys Ile Asn
1
```

<210> SEQ ID NO 318
<211> LENGTH: 4
<212> TYPE: PRT
<213> ORGANISM: Artificial Sequence
<220> FEATURE:
<223> OTHER INFORMATION: Synthetic

<400> SEQUENCE: 318

```
Lys Lys Cys Lys
1
```

<210> SEQ ID NO 319
<211> LENGTH: 4
<212> TYPE: PRT
<213> ORGANISM: Artificial Sequence
<220> FEATURE:
<223> OTHER INFORMATION: Synthetic

<400> SEQUENCE: 319

```
Pro Cys Lys Arg
1
```

<210> SEQ ID NO 320
<211> LENGTH: 6
<212> TYPE: PRT
<213> ORGANISM: Artificial Sequence
<220> FEATURE:
<223> OTHER INFORMATION: Synthetic

<400> SEQUENCE: 320

```
Lys Arg Cys Ser Arg Arg
1               5
```

<210> SEQ ID NO 321
<211> LENGTH: 3
<212> TYPE: PRT
<213> ORGANISM: Artificial Sequence
<220> FEATURE:
<223> OTHER INFORMATION: Synthetic

```
<400> SEQUENCE: 321

Lys Gln Cys
1

<210> SEQ ID NO 322
<211> LENGTH: 37
<212> TYPE: PRT
<213> ORGANISM: Artificial Sequence
<220> FEATURE:
<223> OTHER INFORMATION: Synthetic

<400> SEQUENCE: 322

Val Arg Ile Pro Val Ser Cys Lys His Ser Gly Gln Cys Leu Lys Pro
1               5                   10                  15

Cys Lys Asp Ala Gly Met Arg Thr Gly Lys Cys Met Asn Gly Lys Cys
            20                  25                  30

Asp Cys Thr Pro Lys
        35

<210> SEQ ID NO 323
<211> LENGTH: 20
<212> TYPE: PRT
<213> ORGANISM: Artificial Sequence
<220> FEATURE:
<223> OTHER INFORMATION: Synthetic

<400> SEQUENCE: 323

Val Lys Cys Thr Thr Ser Lys Asp Cys Trp Pro Pro Cys Lys Lys Val
1               5                   10                  15

Thr Gly Arg Ala
        20

<210> SEQ ID NO 324
<211> LENGTH: 32
<212> TYPE: PRT
<213> ORGANISM: Artificial Sequence
<220> FEATURE:
<223> OTHER INFORMATION: Synthetic

<400> SEQUENCE: 324

Gly Ile Val Cys Arg Val Cys Arg Ile Cys Gly Met Gln Gly Arg
1               5                   10                  15

Arg Val Asn Ile Cys Arg Ala Pro Ile Arg Cys Arg Cys Arg Arg Gly
            20                  25                  30

<210> SEQ ID NO 325
<211> LENGTH: 35
<212> TYPE: PRT
<213> ORGANISM: Artificial Sequence
<220> FEATURE:
<223> OTHER INFORMATION: Synthetic

<400> SEQUENCE: 325

Ser Glu Arg Asp Cys Ile Arg His Leu Gln Arg Cys Arg Glu Asn Arg
1               5                   10                  15

Asp Cys Cys Ser Arg Arg Cys Ser Arg Arg Gly Thr Asn Pro Glu Arg
            20                  25                  30

Arg Cys Arg
        35

<210> SEQ ID NO 326
<211> LENGTH: 37
<212> TYPE: PRT
```

```
<213> ORGANISM: Artificial Sequence
<220> FEATURE:
<223> OTHER INFORMATION: Synthetic

<400> SEQUENCE: 326

Val Arg Ile Pro Val Ser Cys Arg His Ser Gly Gln Cys Leu Arg Pro
1               5                   10                  15

Cys Arg Asp Ala Gly Met Arg Phe Gly Arg Cys Met Asn Gly Arg Cys
            20                  25                  30

Asp Cys Thr Pro Arg
        35

<210> SEQ ID NO 327
<211> LENGTH: 37
<212> TYPE: PRT
<213> ORGANISM: Artificial Sequence
<220> FEATURE:
<223> OTHER INFORMATION: Synthetic

<400> SEQUENCE: 327

Gly Val Pro Ile Asn Val Arg Cys Arg Gly Ser Arg Asp Cys Leu Asp
1               5                   10                  15

Pro Cys Arg Arg Ala Gly Met Arg Phe Gly Arg Cys Ile Asn Ser Arg
            20                  25                  30

Cys His Cys Thr Pro
        35

<210> SEQ ID NO 328
<211> LENGTH: 33
<212> TYPE: PRT
<213> ORGANISM: Artificial Sequence
<220> FEATURE:
<223> OTHER INFORMATION: Synthetic

<400> SEQUENCE: 328

Ala Val Cys Val Tyr Arg Thr Cys Asp Arg Cys Arg Arg Gly
1               5                   10                  15

Tyr Arg Ser Gly Arg Cys Ile Asn Asn Ala Cys Arg Cys Tyr Pro Tyr
            20                  25                  30

Gly

<210> SEQ ID NO 329
<211> LENGTH: 35
<212> TYPE: PRT
<213> ORGANISM: Artificial Sequence
<220> FEATURE:
<223> OTHER INFORMATION: Synthetic

<400> SEQUENCE: 329

Ile Ser Cys Thr Gly Ser Arg Gln Cys Tyr Asp Pro Cys Arg Arg Arg
1               5                   10                  15

Thr Gly Cys Pro Asn Ala Arg Cys Met Asn Arg Ser Cys Arg Cys Tyr
            20                  25                  30

Gly Cys Gly
        35

<210> SEQ ID NO 330
<211> LENGTH: 38
<212> TYPE: PRT
<213> ORGANISM: Artificial Sequence
<220> FEATURE:
<223> OTHER INFORMATION: Synthetic
```

```
<400> SEQUENCE: 330

Gln Val Gln Thr Asn Val Arg Cys Gln Gly Gly Ser Cys Ala Ser Val
1               5                   10                  15

Cys Arg Arg Glu Ile Gly Val Ala Ala Gly Arg Cys Ile Asn Gly Arg
            20                  25                  30

Cys Val Cys Tyr Arg Asn
        35

<210> SEQ ID NO 331
<211> LENGTH: 37
<212> TYPE: PRT
<213> ORGANISM: Artificial Sequence
<220> FEATURE:
<223> OTHER INFORMATION: Synthetic

<400> SEQUENCE: 331

Glu Val Ile Arg Cys Ser Gly Ser Arg Gln Cys Tyr Gly Pro Cys Arg
1               5                   10                  15

Gln Gln Thr Gly Cys Thr Asn Ser Arg Cys Met Asn Arg Val Cys Arg
            20                  25                  30

Cys Tyr Gly Cys Gly
        35

<210> SEQ ID NO 332
<211> LENGTH: 33
<212> TYPE: PRT
<213> ORGANISM: Artificial Sequence
<220> FEATURE:
<223> OTHER INFORMATION: Synthetic

<400> SEQUENCE: 332

Ala Cys Arg Gly Val Phe Asp Ala Cys Thr Pro Gly Arg Asn Glu Cys
1               5                   10                  15

Cys Pro Asn Arg Val Cys Ser Asp Arg His Arg Trp Cys Arg Trp Arg
            20                  25                  30

Leu

<210> SEQ ID NO 333
<211> LENGTH: 38
<212> TYPE: PRT
<213> ORGANISM: Artificial Sequence
<220> FEATURE:
<223> OTHER INFORMATION: Synthetic

<400> SEQUENCE: 333

Gln Ile Tyr Thr Ser Arg Glu Cys Asn Gly Ser Ser Glu Cys Tyr Ser
1               5                   10                  15

His Cys Glu Gly Ile Thr Gly Arg Arg Ser Gly Arg Cys Ile Asn Arg
            20                  25                  30

Arg Cys Tyr Cys Tyr Arg
        35

<210> SEQ ID NO 334
<211> LENGTH: 35
<212> TYPE: PRT
<213> ORGANISM: Artificial Sequence
<220> FEATURE:
<223> OTHER INFORMATION: Synthetic

<400> SEQUENCE: 334

Gly Cys Leu Glu Phe Trp Trp Arg Cys Asn Pro Asn Asp Asp Arg Cys
1               5                   10                  15
```

```
Cys Arg Pro Arg Leu Arg Cys Ser Arg Leu Phe Arg Leu Cys Asn Phe
            20                  25                  30

Ser Phe Gly
        35

<210> SEQ ID NO 335
<211> LENGTH: 37
<212> TYPE: PRT
<213> ORGANISM: Artificial Sequence
<220> FEATURE:
<223> OTHER INFORMATION: Synthetic

<400> SEQUENCE: 335

Asp Cys Val Arg Phe Trp Gly Arg Cys Ser Gln Thr Ser Asp Cys Cys
1               5                   10                  15

Pro His Leu Ala Cys Arg Ser Arg Trp Pro Arg Asn Ile Cys Val Trp
            20                  25                  30

Asp Gly Ser Val Gly
        35

<210> SEQ ID NO 336
<211> LENGTH: 33
<212> TYPE: PRT
<213> ORGANISM: Artificial Sequence
<220> FEATURE:
<223> OTHER INFORMATION: Synthetic

<400> SEQUENCE: 336

Gly Cys Phe Gly Tyr Arg Cys Asp Tyr Tyr Arg Gly Cys Cys Ser Gly
1               5                   10                  15

Tyr Val Cys Ser Pro Thr Trp Arg Trp Cys Val Arg Pro Gly Pro Gly
            20                  25                  30

Arg

<210> SEQ ID NO 337
<211> LENGTH: 60
<212> TYPE: PRT
<213> ORGANISM: Artificial Sequence
<220> FEATURE:
<223> OTHER INFORMATION: Synthetic

<400> SEQUENCE: 337

Met Asn Ala Arg Phe Ile Leu Leu Val Leu Thr Thr Met Met Leu
1               5                   10                  15

Leu Pro Asp Thr Arg Gly Ala Glu Val Ile Arg Cys Ser Gly Ser Arg
            20                  25                  30

Gln Cys Tyr Gly Pro Cys Arg Gln Gln Thr Gly Cys Thr Asn Ser Arg
        35                  40                  45

Cys Met Asn Arg Val Cys Arg Cys Tyr Gly Cys Gly
    50                  55                  60

<210> SEQ ID NO 338
<211> LENGTH: 61
<212> TYPE: PRT
<213> ORGANISM: Artificial Sequence
<220> FEATURE:
<223> OTHER INFORMATION: Synthetic

<400> SEQUENCE: 338

Met Asn Ala Arg Leu Ile Tyr Leu Leu Leu Val Val Thr Thr Met Thr
1               5                   10                  15
```

```
Leu Met Phe Asp Thr Ala Gln Ala Val Asp Ile Met Cys Ser Gly Pro
             20                  25                  30

Arg Gln Cys Tyr Gly Pro Cys Arg Arg Glu Thr Gly Cys Pro Asn Ala
         35                  40                  45

Arg Cys Met Asn Arg Arg Cys Arg Cys Tyr Gly Cys Val
 50                  55                  60

<210> SEQ ID NO 339
<211> LENGTH: 62
<212> TYPE: PRT
<213> ORGANISM: Artificial Sequence
<220> FEATURE:
<223> OTHER INFORMATION: Synthetic

<400> SEQUENCE: 339

Met Asn Ala Arg Leu Ile Tyr Leu Leu Val Val Thr Thr Met Met
 1               5                  10                  15

Leu Thr Phe Asp Thr Thr Gln Ala Gly Asp Ile Arg Cys Ser Gly Thr
             20                  25                  30

Arg Gln Cys Trp Gly Pro Cys Arg Gln Thr Thr Cys Thr Asn Ser
         35                  40                  45

Arg Cys Met Asn Gly Arg Cys Arg Cys Tyr Gly Cys Val Gly
 50                  55                  60

<210> SEQ ID NO 340
<211> LENGTH: 61
<212> TYPE: PRT
<213> ORGANISM: Artificial Sequence
<220> FEATURE:
<223> OTHER INFORMATION: Synthetic

<400> SEQUENCE: 340

Met Asn Thr Arg Phe Ile Phe Leu Leu Val Val Thr Asn Thr Met
 1               5                  10                  15

Met Leu Phe Asp Thr Arg Pro Val Glu Gly Ile Ser Cys Thr Gly Ser
             20                  25                  30

Arg Gln Cys Tyr Asp Pro Cys Arg Arg Thr Gly Cys Pro Asn Ala
         35                  40                  45

Arg Cys Met Asn Arg Ser Cys Arg Cys Tyr Gly Cys Gly
 50                  55                  60

<210> SEQ ID NO 341
<211> LENGTH: 38
<212> TYPE: PRT
<213> ORGANISM: Artificial Sequence
<220> FEATURE:
<223> OTHER INFORMATION: Synthetic

<400> SEQUENCE: 341

Gly Val Pro Ile Asn Val Arg Cys Ser Gly Ser Arg Asp Cys Leu Glu
 1               5                  10                  15

Pro Cys Arg Arg Ala Gly Met Arg Phe Gly Arg Cys Ile Asn Arg Arg
             20                  25                  30

Cys His Cys Thr Pro Arg
         35

<210> SEQ ID NO 342
<211> LENGTH: 38
<212> TYPE: PRT
<213> ORGANISM: Artificial Sequence
<220> FEATURE:
<223> OTHER INFORMATION: Synthetic
```

-continued

<400> SEQUENCE: 342

Gly Val Pro Ile Asn Val Arg Cys Thr Gly Ser Pro Gln Cys Leu Arg
1               5                   10                  15

Pro Cys Arg Asp Ala Gly Met Arg Phe Gly Arg Cys Ile Asn Gly Arg
            20                  25                  30

Cys His Cys Thr Pro Arg
        35

<210> SEQ ID NO 343
<211> LENGTH: 38
<212> TYPE: PRT
<213> ORGANISM: Artificial Sequence
<220> FEATURE:
<223> OTHER INFORMATION: Synthetic

<400> SEQUENCE: 343

Gly Val Ile Ile Asn Val Arg Cys Arg Ile Ser Arg Gln Cys Leu Glu
1               5                   10                  15

Pro Cys Arg Arg Ala Gly Met Arg Phe Gly Arg Cys Met Asn Gly Arg
            20                  25                  30

Cys His Cys Thr Pro Arg
        35

<210> SEQ ID NO 344
<211> LENGTH: 38
<212> TYPE: PRT
<213> ORGANISM: Artificial Sequence
<220> FEATURE:
<223> OTHER INFORMATION: Synthetic

<400> SEQUENCE: 344

Gly Val Pro Ile Asn Val Arg Cys Arg Gly Ser Pro Gln Cys Ile Gln
1               5                   10                  15

Pro Cys Arg Asp Ala Gly Met Arg Phe Gly Arg Cys Met Asn Gly Arg
            20                  25                  30

Cys His Cys Thr Pro Gln
        35

<210> SEQ ID NO 345
<211> LENGTH: 38
<212> TYPE: PRT
<213> ORGANISM: Artificial Sequence
<220> FEATURE:
<223> OTHER INFORMATION: Synthetic

<400> SEQUENCE: 345

Gly Val Glu Ile Asn Val Arg Cys Thr Gly Ser His Gln Cys Ile Arg
1               5                   10                  15

Pro Cys Arg Asp Ala Gly Met Arg Phe Gly Arg Cys Ile Asn Arg Arg
            20                  25                  30

Cys His Cys Thr Pro Arg
        35

<210> SEQ ID NO 346
<211> LENGTH: 38
<212> TYPE: PRT
<213> ORGANISM: Artificial Sequence
<220> FEATURE:
<223> OTHER INFORMATION: Synthetic

<400> SEQUENCE: 346

Gly Val Glu Ile Asn Val Arg Cys Ser Gly Ser Pro Gln Cys Leu Arg
1               5                   10                  15

Pro Cys Arg Asp Ala Gly Met Arg Phe Gly Arg Cys Met Asn Arg Arg
                20                  25                  30

Cys His Cys Thr Pro Arg
            35

<210> SEQ ID NO 347
<211> LENGTH: 38
<212> TYPE: PRT
<213> ORGANISM: Artificial Sequence
<220> FEATURE:
<223> OTHER INFORMATION: Synthetic

<400> SEQUENCE: 347

Gly Val Pro Thr Asp Val Arg Cys Arg Gly Ser Pro Gln Cys Ile Gln
1               5                   10                  15

Pro Cys Arg Asp Ala Gly Met Arg Phe Gly Arg Cys Met Asn Gly Arg
                20                  25                  30

Cys His Cys Thr Pro Arg
            35

<210> SEQ ID NO 348
<211> LENGTH: 38
<212> TYPE: PRT
<213> ORGANISM: Artificial Sequence
<220> FEATURE:
<223> OTHER INFORMATION: Synthetic

<400> SEQUENCE: 348

Gly Val Pro Ile Asn Val Ser Cys Thr Gly Ser Pro Gln Cys Ile Arg
1               5                   10                  15

Pro Cys Arg Asp Ala Gly Met Arg Phe Gly Arg Cys Met Asn Arg Arg
                20                  25                  30

Cys His Cys Thr Pro Arg
            35

<210> SEQ ID NO 349
<211> LENGTH: 38
<212> TYPE: PRT
<213> ORGANISM: Artificial Sequence
<220> FEATURE:
<223> OTHER INFORMATION: Synthetic

<400> SEQUENCE: 349

Gly Val Pro Ile Asn Val Pro Cys Thr Gly Ser Pro Gln Cys Ile Arg
1               5                   10                  15

Pro Cys Arg Asp Ala Gly Met Arg Phe Gly Arg Cys Met Asn Arg Arg
                20                  25                  30

Cys His Cys Thr Pro Arg
            35

<210> SEQ ID NO 350
<211> LENGTH: 37
<212> TYPE: PRT
<213> ORGANISM: Artificial Sequence
<220> FEATURE:
<223> OTHER INFORMATION: Synthetic

<400> SEQUENCE: 350

Val Gly Ile Asn Val Arg Cys Arg His Ser Gly Gln Cys Leu Arg Pro
1               5                   10                  15

Cys Arg Asp Ala Gly Met Arg Phe Gly Arg Cys Ile Asn Gly Arg Cys
            20                  25                  30

Asp Cys Thr Pro Arg
        35

<210> SEQ ID NO 351
<211> LENGTH: 37
<212> TYPE: PRT
<213> ORGANISM: Artificial Sequence
<220> FEATURE:
<223> OTHER INFORMATION: Synthetic

<400> SEQUENCE: 351

Val Gly Ile Asn Val Arg Cys Arg His Ser Gly Gln Cys Leu Arg Pro
1               5                   10                  15

Cys Arg Asp Ala Gly Met Arg Phe Gly Arg Cys Met Asn Gly Arg Cys
            20                  25                  30

Asp Cys Thr Pro Arg
        35

<210> SEQ ID NO 352
<211> LENGTH: 37
<212> TYPE: PRT
<213> ORGANISM: Artificial Sequence
<220> FEATURE:
<223> OTHER INFORMATION: Synthetic

<400> SEQUENCE: 352

Val Gly Ile Pro Val Ser Cys Arg His Ser Gly Gln Cys Ile Arg Pro
1               5                   10                  15

Cys Arg Asp Ala Gly Met Arg Phe Gly Arg Cys Met Asn Arg Arg Cys
            20                  25                  30

Asp Cys Thr Pro Arg
        35

<210> SEQ ID NO 353
<211> LENGTH: 36
<212> TYPE: PRT
<213> ORGANISM: Artificial Sequence
<220> FEATURE:
<223> OTHER INFORMATION: Synthetic

<400> SEQUENCE: 353

Arg Arg Gly Cys Phe Arg Glu Gly His Ser Cys Pro Arg Thr Ala Pro
1               5                   10                  15

Cys Cys Arg Pro Leu Val Cys Arg Gly Pro Ser Pro Asn Thr Arg Arg
            20                  25                  30

Cys Thr Arg Pro
        35

<210> SEQ ID NO 354
<211> LENGTH: 32
<212> TYPE: PRT
<213> ORGANISM: Artificial Sequence
<220> FEATURE:
<223> OTHER INFORMATION: Synthetic

<400> SEQUENCE: 354

Ser Phe Cys Ile Pro Phe Arg Pro Cys Arg Ser Asp Glu Asn Cys Cys
1               5                   10                  15

Arg Arg Phe Arg Cys Arg Thr Thr Gly Ile Val Arg Leu Cys Arg Trp
            20                  25                  30

<210> SEQ ID NO 355
<211> LENGTH: 36
<212> TYPE: PRT
<213> ORGANISM: Artificial Sequence
<220> FEATURE:
<223> OTHER INFORMATION: Synthetic

<400> SEQUENCE: 355

Leu Arg Gly Cys Leu Pro Arg Asn Arg Phe Cys Asn Ala Leu Ser Gly
1               5                   10                  15

Pro Arg Cys Cys Ser Gly Leu Arg Cys Arg Glu Leu Ser Ile Trp Ala
            20                  25                  30

Ser Arg Cys Leu
        35

<210> SEQ ID NO 356
<211> LENGTH: 34
<212> TYPE: PRT
<213> ORGANISM: Artificial Sequence
<220> FEATURE:
<223> OTHER INFORMATION: Synthetic

<400> SEQUENCE: 356

Gly Asn Tyr Cys Leu Arg Gly Arg Cys Leu Pro Gly Gly Arg Arg Cys
1               5                   10                  15

Cys Asn Gly Arg Pro Cys Glu Cys Phe Ala Arg Ile Cys Ser Cys Arg
            20                  25                  30

Pro Arg

<210> SEQ ID NO 357
<211> LENGTH: 29
<212> TYPE: PRT
<213> ORGANISM: Artificial Sequence
<220> FEATURE:
<223> OTHER INFORMATION: Synthetic

<400> SEQUENCE: 357

Thr Val Arg Cys Gly Gly Cys Asn Arg Arg Cys Cys Pro Gly Gly Cys
1               5                   10                  15

Arg Ser Gly Arg Cys Ile Asn Gly Arg Cys Gln Cys Tyr
            20                  25

<210> SEQ ID NO 358
<211> LENGTH: 29
<212> TYPE: PRT
<213> ORGANISM: Artificial Sequence
<220> FEATURE:
<223> OTHER INFORMATION: Synthetic

<400> SEQUENCE: 358

Gly Cys Met Arg Glu Tyr Cys Ala Gly Gln Cys Arg Gly Arg Val Ser
1               5                   10                  15

Gln Asp Tyr Cys Leu Arg His Cys Arg Cys Ile Pro Arg
            20                  25

<210> SEQ ID NO 359
<211> LENGTH: 34
<212> TYPE: PRT
<213> ORGANISM: Artificial Sequence
<220> FEATURE:
<223> OTHER INFORMATION: Synthetic

<400> SEQUENCE: 359

```
Ala Cys Leu Gly Phe Gly Glu Arg Cys Asn Pro Ser Asn Asp Arg Cys
1               5                   10                  15

Cys Arg Ser Ser Ser Leu Val Cys Ser Gln Arg His Arg Trp Cys Arg
            20                  25                  30

Tyr Gly

<210> SEQ ID NO 360
<211> LENGTH: 37
<212> TYPE: PRT
<213> ORGANISM: Artificial Sequence
<220> FEATURE:
<223> OTHER INFORMATION: Synthetic

<400> SEQUENCE: 360

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Arg Asp
            20                  25                  30

Ser Arg Cys Leu Gly
        35

<210> SEQ ID NO 361
<211> LENGTH: 36
<212> TYPE: PRT
<213> ORGANISM: Artificial Sequence
<220> FEATURE:
<223> OTHER INFORMATION: Synthetic

<400> SEQUENCE: 361

Arg Gly Gly Cys Leu Pro Arg Asn Arg Phe Cys Asn Pro Ser Ser Gly
1               5                   10                  15

Pro Arg Cys Cys Ser Gly Leu Thr Cys Arg Glu Leu Asn Ile Trp Ala
            20                  25                  30

Ser Arg Cys Leu
        35

<210> SEQ ID NO 362
<211> LENGTH: 33
<212> TYPE: PRT
<213> ORGANISM: Artificial Sequence
<220> FEATURE:
<223> OTHER INFORMATION: Synthetic

<400> SEQUENCE: 362

Gln Arg Ser Cys Ala Arg Pro Gly Asp Met Cys Met Gly Ile Arg Cys
1               5                   10                  15

Cys Asp Gly Gln Cys Gly Cys Asn Arg Gly Thr Gly Arg Cys Phe Cys
            20                  25                  30

Arg

<210> SEQ ID NO 363
<211> LENGTH: 40
<212> TYPE: PRT
<213> ORGANISM: Artificial Sequence
<220> FEATURE:
<223> OTHER INFORMATION: Synthetic

<400> SEQUENCE: 363

Ala Arg Gly Cys Ala Asp Ala Tyr Arg Ser Cys Asn His Pro Arg Thr
1               5                   10                  15

Cys Cys Asp Gly Tyr Asn Gly Tyr Arg Arg Ala Cys Ile Cys Ser Gly
            20                  25                  30
```

Ser Asn Cys Arg Cys Arg Arg Ser
        35                  40

<210> SEQ ID NO 364
<211> LENGTH: 37
<212> TYPE: PRT
<213> ORGANISM: Artificial Sequence
<220> FEATURE:
<223> OTHER INFORMATION: Synthetic

<400> SEQUENCE: 364

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Trp Asp
            20                  25                  30

Ser Arg Cys Leu Gly
        35

<210> SEQ ID NO 365
<211> LENGTH: 37
<212> TYPE: PRT
<213> ORGANISM: Artificial Sequence
<220> FEATURE:
<223> OTHER INFORMATION: Synthetic

<400> SEQUENCE: 365

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Ser Ile Tyr Asp
            20                  25                  30

Ser Arg Cys Leu Gly
        35

<210> SEQ ID NO 366
<211> LENGTH: 37
<212> TYPE: PRT
<213> ORGANISM: Artificial Sequence
<220> FEATURE:
<223> OTHER INFORMATION: Synthetic

<400> SEQUENCE: 366

Arg Gly Gly Cys Leu Pro His Asn Arg Phe Cys Asn Ala Leu Ser Gly
1               5                   10                  15

Pro Arg Cys Cys Ser Arg Leu Arg Cys Arg Glu Leu Ser Ile Trp Asp
            20                  25                  30

Ser Arg Cys Leu Gly
        35

<210> SEQ ID NO 367
<211> LENGTH: 37
<212> TYPE: PRT
<213> ORGANISM: Artificial Sequence
<220> FEATURE:
<223> OTHER INFORMATION: Synthetic

<400> SEQUENCE: 367

Arg Gly Gly Cys Leu Pro His Asn Arg Phe Cys Asn Ala Leu Thr Gly
1               5                   10                  15

Pro Arg Cys Cys Ser Arg Leu Arg Cys Arg Glu Leu Ser Ile Trp Asp
            20                  25                  30

Ser Ile Cys Leu Gly
        35

<210> SEQ ID NO 368
<211> LENGTH: 34
<212> TYPE: PRT
<213> ORGANISM: Artificial Sequence
<220> FEATURE:
<223> OTHER INFORMATION: Synthetic

<400> SEQUENCE: 368

Ser Cys Ala Asp Ala Tyr Lys Ser Cys Asp Ser Leu Arg Cys Cys Asn
1               5                   10                  15

Asn Arg Thr Cys Met Cys Ser Met Ile Gly Thr Asn Cys Thr Cys Arg
            20                  25                  30

Arg Arg

<210> SEQ ID NO 369
<211> LENGTH: 30
<212> TYPE: PRT
<213> ORGANISM: Artificial Sequence
<220> FEATURE:
<223> OTHER INFORMATION: Synthetic

<400> SEQUENCE: 369

Glu Arg Arg Cys Leu Pro Ala Gly Arg Thr Cys Val Arg Gly Pro Met
1               5                   10                  15

Arg Val Pro Cys Cys Gly Ser Cys Ser Gln Asn Arg Cys Thr
            20                  25                  30

<210> SEQ ID NO 370
<211> LENGTH: 31
<212> TYPE: PRT
<213> ORGANISM: Artificial Sequence
<220> FEATURE:
<223> OTHER INFORMATION: Synthetic

<400> SEQUENCE: 370

Leu Cys Ser Arg Glu Gly Glu Phe Cys Tyr Arg Leu Arg Cys Cys
1               5                   10                  15

Ala Gly Phe Tyr Cys Arg Ala Phe Val Leu His Cys Tyr Arg Asn
            20                  25                  30

<210> SEQ ID NO 371
<211> LENGTH: 23
<212> TYPE: PRT
<213> ORGANISM: Artificial Sequence
<220> FEATURE:
<223> OTHER INFORMATION: Synthetic

<400> SEQUENCE: 371

Ala Cys Gly Ser Cys Arg Arg Arg Cys Arg Gly Ser Gly Arg Cys Ile
1               5                   10                  15

Asn Gly Arg Cys Arg Cys Tyr
            20

<210> SEQ ID NO 372
<211> LENGTH: 23
<212> TYPE: PRT
<213> ORGANISM: Artificial Sequence
<220> FEATURE:
<223> OTHER INFORMATION: Synthetic

<400> SEQUENCE: 372

Ala Cys Gly Ser Cys Arg Arg Arg Cys Arg Gly Pro Gly Arg Cys Ile
1               5                   10                  15

Asn Gly Arg Cys Arg Cys Tyr
            20

<210> SEQ ID NO 373
<211> LENGTH: 32
<212> TYPE: PRT
<213> ORGANISM: Artificial Sequence
<220> FEATURE:
<223> OTHER INFORMATION: Synthetic

<400> SEQUENCE: 373

Ala Cys Gln Gly Tyr Met Arg Arg Cys Gly Arg Asp Arg Pro Pro Cys
1               5                   10                  15

Cys Arg Arg Leu Glu Cys Ser Arg Thr Trp Arg Trp Cys Val Trp Asn
            20                  25                  30

<210> SEQ ID NO 374
<211> LENGTH: 30
<212> TYPE: PRT
<213> ORGANISM: Artificial Sequence
<220> FEATURE:
<223> OTHER INFORMATION: Synthetic

<400> SEQUENCE: 374

Gly Arg Tyr Cys Gln Arg Trp Met Trp Thr Cys Asp Ser Arg Arg Ala
1               5                   10                  15

Cys Cys Glu Gly Leu Arg Cys Arg Leu Trp Cys Arg Arg Ile
            20                  25                  30

<210> SEQ ID NO 375
<211> LENGTH: 34
<212> TYPE: PRT
<213> ORGANISM: Artificial Sequence
<220> FEATURE:
<223> OTHER INFORMATION: Synthetic

<400> SEQUENCE: 375

Asn Ala Arg Cys Arg Gly Ser Pro Glu Cys Leu Pro Arg Cys Arg Glu
1               5                   10                  15

Ala Ile Gly Arg Ala Ala Gly Arg Cys Met Asn Gly Arg Cys Arg Cys
            20                  25                  30

Tyr Pro

<210> SEQ ID NO 376
<211> LENGTH: 34
<212> TYPE: PRT
<213> ORGANISM: Artificial Sequence
<220> FEATURE:
<223> OTHER INFORMATION: Synthetic

<400> SEQUENCE: 376

Asn Val Arg Cys Arg Gly Ser Arg Glu Cys Leu Pro Ala Cys Arg Ala
1               5                   10                  15

Ala Val Gly Arg Ala Ala Gly Arg Cys Met Asn Gly Arg Cys Arg Cys
            20                  25                  30

Tyr Pro

<210> SEQ ID NO 377
<211> LENGTH: 34
<212> TYPE: PRT
<213> ORGANISM: Artificial Sequence
<220> FEATURE:
<223> OTHER INFORMATION: Synthetic

```
<400> SEQUENCE: 377

Asn Val Arg Cys Arg Gly Ser Pro Glu Cys Leu Pro Arg Cys Arg Glu
1               5                   10                  15

Ala Ile Gly Arg Ser Ala Gly Arg Cys Met Asn Gly Arg Cys Arg Cys
            20                  25                  30

Tyr Pro

<210> SEQ ID NO 378
<211> LENGTH: 34
<212> TYPE: PRT
<213> ORGANISM: Artificial Sequence
<220> FEATURE:
<223> OTHER INFORMATION: Synthetic

<400> SEQUENCE: 378

Asn Ala Arg Cys Arg Gly Ser Pro Glu Cys Leu Pro Arg Cys Arg Gln
1               5                   10                  15

Ala Ile Gly Arg Ala Ala Gly Arg Cys Met Asn Gly Arg Cys Arg Cys
            20                  25                  30

Tyr Pro

<210> SEQ ID NO 379
<211> LENGTH: 33
<212> TYPE: PRT
<213> ORGANISM: Artificial Sequence
<220> FEATURE:
<223> OTHER INFORMATION: Synthetic

<400> SEQUENCE: 379

Arg Gly Tyr Cys Ala Glu Arg Gly Ile Arg Cys His Asn Ile His Cys
1               5                   10                  15

Cys Ser Gly Leu Thr Cys Arg Cys Arg Gly Ser Ser Cys Val Cys Arg
            20                  25                  30

Arg

<210> SEQ ID NO 380
<211> LENGTH: 31
<212> TYPE: PRT
<213> ORGANISM: Artificial Sequence
<220> FEATURE:
<223> OTHER INFORMATION: Synthetic

<400> SEQUENCE: 380

Glu Arg Gly Cys Arg Leu Thr Phe Trp Arg Cys Arg Asn Arg Arg Glu
1               5                   10                  15

Cys Cys Gly Trp Asn Ala Cys Ala Leu Gly Ile Cys Met Pro Arg
            20                  25                  30

<210> SEQ ID NO 381
<211> LENGTH: 39
<212> TYPE: PRT
<213> ORGANISM: Artificial Sequence
<220> FEATURE:
<223> OTHER INFORMATION: Synthetic

<400> SEQUENCE: 381

Arg Arg Arg Cys Ile Ala Arg Asp Tyr Gly Arg Cys Arg Trp Gly Gly
1               5                   10                  15

Thr Pro Cys Cys Arg Gly Arg Gly Cys Ile Cys Ser Ile Met Gly Thr
            20                  25                  30
```

```
Asn Cys Glu Cys Arg Pro Arg
        35

<210> SEQ ID NO 382
<211> LENGTH: 29
<212> TYPE: PRT
<213> ORGANISM: Artificial Sequence
<220> FEATURE:
<223> OTHER INFORMATION: Synthetic

<400> SEQUENCE: 382

Gly Cys Arg Leu Thr Phe Trp Arg Cys Arg Asn Arg Glu Cys Cys
1               5                   10                  15

Gly Trp Asn Ala Cys Ala Leu Gly Ile Cys Met Pro Arg
            20                  25

<210> SEQ ID NO 383
<211> LENGTH: 32
<212> TYPE: PRT
<213> ORGANISM: Artificial Sequence
<220> FEATURE:
<223> OTHER INFORMATION: Synthetic

<400> SEQUENCE: 383

Ala Cys Arg Gly Leu Phe Val Thr Cys Thr Pro Gly Arg Asp Glu Cys
1               5                   10                  15

Cys Pro Asn His Val Cys Ser Ser Arg His Arg Trp Cys Arg Tyr Arg
            20                  25                  30

<210> SEQ ID NO 384
<211> LENGTH: 36
<212> TYPE: PRT
<213> ORGANISM: Artificial Sequence
<220> FEATURE:
<223> OTHER INFORMATION: Synthetic

<400> SEQUENCE: 384

Ile Ala Cys Ala Pro Arg Gly Leu Leu Cys Phe Arg Asp Arg Glu Cys
1               5                   10                  15

Cys Arg Gly Leu Thr Cys Arg Gly Arg Phe Val Asn Thr Trp Pro Thr
            20                  25                  30

Phe Cys Leu Val
        35

<210> SEQ ID NO 385
<211> LENGTH: 36
<212> TYPE: PRT
<213> ORGANISM: Artificial Sequence
<220> FEATURE:
<223> OTHER INFORMATION: Synthetic

<400> SEQUENCE: 385

Ala Cys Ala Gly Leu Tyr Arg Arg Cys Gly Arg Gly Val Asn Thr Cys
1               5                   10                  15

Cys Glu Asn Arg Pro Cys Arg Cys Asp Leu Ala Met Gly Asn Cys Ile
            20                  25                  30

Cys Arg Arg Arg
        35

<210> SEQ ID NO 386
<211> LENGTH: 38
<212> TYPE: PRT
<213> ORGANISM: Artificial Sequence
<220> FEATURE:
```

<223> OTHER INFORMATION: Synthetic

<400> SEQUENCE: 386

Phe Thr Cys Ala Ile Ser Cys Asp Ile Arg Val Asn Gly Arg Pro Cys
1               5                   10                  15

Arg Gly Ser Gly Glu Arg Arg Cys Ser Gly Gly Trp Ser Cys Arg Phe
            20                  25                  30

Asn Val Cys Val Arg Val
        35

<210> SEQ ID NO 387
<211> LENGTH: 33
<212> TYPE: PRT
<213> ORGANISM: Artificial Sequence
<220> FEATURE:
<223> OTHER INFORMATION: Synthetic

<400> SEQUENCE: 387

Gly Phe Cys Ala Gln Arg Gly Ile Arg Cys His Asp Ile His Cys Cys
1               5                   10                  15

Thr Asn Leu Arg Cys Val Arg Glu Gly Ser Asn Arg Val Cys Arg Arg
            20                  25                  30

Ala

<210> SEQ ID NO 388
<211> LENGTH: 42
<212> TYPE: PRT
<213> ORGANISM: Artificial Sequence
<220> FEATURE:
<223> OTHER INFORMATION: Synthetic

<400> SEQUENCE: 388

Cys Ala Arg Arg Arg Asn Trp Cys Gly Arg Asn Glu Asp Cys Cys Cys
1               5                   10                  15

Pro Met Arg Cys Ile Tyr Ala Trp Tyr Asn Gln Gln Gly Ser Cys Gln
            20                  25                  30

Ser Thr Ile Thr Gly Leu Phe Arg Arg Cys
        35                  40

<210> SEQ ID NO 389
<211> LENGTH: 28
<212> TYPE: PRT
<213> ORGANISM: Artificial Sequence
<220> FEATURE:
<223> OTHER INFORMATION: Synthetic

<400> SEQUENCE: 389

Tyr Cys Gln Arg Trp Met Trp Thr Cys Asp Ser Ala Arg Arg Cys Cys
1               5                   10                  15

Glu Gly Leu Val Cys Arg Leu Trp Cys Arg Arg Ile
            20                  25

<210> SEQ ID NO 390
<211> LENGTH: 37
<212> TYPE: PRT
<213> ORGANISM: Artificial Sequence
<220> FEATURE:
<223> OTHER INFORMATION: Synthetic

<400> SEQUENCE: 390

Arg Gly Gly Cys Leu Pro His Asn Arg Phe Cys Asn Ala Leu Ser Gly
1               5                   10                  15

Pro Arg Cys Cys Ser Gly Leu Arg Cys Arg Glu Leu Thr Ile Trp Asn
            20                  25                  30

Thr Arg Cys Leu Glu
        35

<210> SEQ ID NO 391
<211> LENGTH: 34
<212> TYPE: PRT
<213> ORGANISM: Artificial Sequence
<220> FEATURE:
<223> OTHER INFORMATION: Synthetic

<400> SEQUENCE: 391

Asn Val Arg Cys Thr Gly Ser Arg Gln Cys Leu Pro Ala Cys Arg Ala
1               5                   10                  15

Ala Val Gly Arg Ala Ala Gly Arg Cys Met Asn Gly Arg Cys Arg Cys
            20                  25                  30

Tyr Thr

<210> SEQ ID NO 392
<211> LENGTH: 33
<212> TYPE: PRT
<213> ORGANISM: Artificial Sequence
<220> FEATURE:
<223> OTHER INFORMATION: Synthetic

<400> SEQUENCE: 392

Gln Arg Ser Cys Ala Arg Pro Gly Glu Met Cys Met Arg Ile Arg Cys
1               5                   10                  15

Cys Asp Gly Gln Cys Gly Cys Asn Arg Gly Thr Gly Arg Cys Phe Cys
            20                  25                  30

Arg

<210> SEQ ID NO 393
<211> LENGTH: 36
<212> TYPE: PRT
<213> ORGANISM: Artificial Sequence
<220> FEATURE:
<223> OTHER INFORMATION: Synthetic

<400> SEQUENCE: 393

Gly Cys Ile Pro Arg His Arg Arg Cys Thr Trp Ser Gly Pro Arg Cys
1               5                   10                  15

Cys Asn Asn Ile Ser Cys His Cys Asn Ile Ser Gly Thr Leu Cys Arg
            20                  25                  30

Cys Arg Pro Gly
        35

<210> SEQ ID NO 394
<211> LENGTH: 33
<212> TYPE: PRT
<213> ORGANISM: Artificial Sequence
<220> FEATURE:
<223> OTHER INFORMATION: Synthetic

<400> SEQUENCE: 394

Asn Tyr Cys Val Ala Arg Arg Cys Arg Pro Gly Gly Arg Gln Cys Cys
1               5                   10                  15

Ser Gly Arg Pro Cys Ala Cys Val Gly Arg Val Cys Arg Cys Pro Arg
            20                  25                  30

Asp

```
<210> SEQ ID NO 395
<211> LENGTH: 37
<212> TYPE: PRT
<213> ORGANISM: Artificial Sequence
<220> FEATURE:
<223> OTHER INFORMATION: Synthetic

<400> SEQUENCE: 395

Glu Arg Gly Cys Ser Gly Ala Tyr Arg Arg Cys Ser Ser Ser Gln Arg
1               5                   10                  15

Cys Cys Glu Gly Arg Pro Cys Val Cys Ser Ala Ile Asn Ser Asn Cys
            20                  25                  30

Arg Cys Arg Arg Thr
        35

<210> SEQ ID NO 396
<211> LENGTH: 33
<212> TYPE: PRT
<213> ORGANISM: Artificial Sequence
<220> FEATURE:
<223> OTHER INFORMATION: Synthetic

<400> SEQUENCE: 396

Gln Arg Ser Cys Ala Arg Pro Gly Glu Met Cys Met Gly Ile Arg Cys
1               5                   10                  15

Cys Asp Gly Gln Cys Gly Cys Asn Arg Gly Thr Gly Arg Cys Phe Cys
            20                  25                  30

Arg

<210> SEQ ID NO 397
<211> LENGTH: 36
<212> TYPE: PRT
<213> ORGANISM: Artificial Sequence
<220> FEATURE:
<223> OTHER INFORMATION: Synthetic

<400> SEQUENCE: 397

Arg Arg Gly Cys Phe Arg Glu Gly Arg Trp Cys Pro Arg Ser Ala Pro
1               5                   10                  15

Cys Cys Ala Pro Leu Arg Cys Arg Gly Pro Ser Ile Arg Gln Gln Arg
            20                  25                  30

Cys Val Arg Glu
        35

<210> SEQ ID NO 398
<211> LENGTH: 31
<212> TYPE: PRT
<213> ORGANISM: Artificial Sequence
<220> FEATURE:
<223> OTHER INFORMATION: Synthetic

<400> SEQUENCE: 398

Thr Val Arg Cys Gly Gly Cys Asn Arg Arg Cys Cys Ala Gly Gly Cys
1               5                   10                  15

Arg Ser Gly Arg Cys Ile Asn Gly Arg Cys Gln Cys Tyr Gly Arg
            20                  25                  30

<210> SEQ ID NO 399
<211> LENGTH: 29
<212> TYPE: PRT
<213> ORGANISM: Artificial Sequence
<220> FEATURE:
<223> OTHER INFORMATION: Synthetic
```

-continued

<400> SEQUENCE: 399

Glu Arg Arg Cys Glu Pro Ser Gly Arg Pro Cys Arg Pro Leu Met Arg
1               5                   10                  15

Ile Pro Cys Cys Gly Ser Cys Val Arg Gly Arg Cys Ala
            20                  25

<210> SEQ ID NO 400
<211> LENGTH: 36
<212> TYPE: PRT
<213> ORGANISM: Artificial Sequence
<220> FEATURE:
<223> OTHER INFORMATION: Synthetic

<400> SEQUENCE: 400

Arg Gly Gly Cys Leu Pro Arg Asn Arg Phe Cys Asn Pro Ser Ser Gly
1               5                   10                  15

Pro Arg Cys Cys Ser Gly Leu Thr Cys Arg Glu Leu Asn Ile Trp Ala
            20                  25                  30

Asn Arg Cys Leu
        35

<210> SEQ ID NO 401
<211> LENGTH: 42
<212> TYPE: PRT
<213> ORGANISM: Artificial Sequence
<220> FEATURE:
<223> OTHER INFORMATION: Synthetic

<400> SEQUENCE: 401

Cys Ala Arg Arg Arg Asn Trp Cys Gly Arg Asn Glu Asp Cys Cys Cys
1               5                   10                  15

Pro Met Arg Cys Ile Tyr Ala Trp Tyr Asn Gln Gln Gly Ser Cys Gln
            20                  25                  30

Thr Thr Ile Thr Gly Leu Phe Arg Arg Cys
        35                  40

<210> SEQ ID NO 402
<211> LENGTH: 10
<212> TYPE: PRT
<213> ORGANISM: Artificial Sequence
<220> FEATURE:
<223> OTHER INFORMATION: Synthetic

<400> SEQUENCE: 402

Gly Arg Cys Ile Asn Arg Arg Cys Arg Cys
1               5                   10

<210> SEQ ID NO 403
<211> LENGTH: 4
<212> TYPE: PRT
<213> ORGANISM: Artificial Sequence
<220> FEATURE:
<223> OTHER INFORMATION: Synthetic

<400> SEQUENCE: 403

Arg Cys Ile Asn
1

<210> SEQ ID NO 404
<211> LENGTH: 4
<212> TYPE: PRT
<213> ORGANISM: Artificial Sequence
<220> FEATURE:

<223> OTHER INFORMATION: Synthetic

<400> SEQUENCE: 404

Arg Arg Cys Arg
1

<210> SEQ ID NO 405
<211> LENGTH: 4
<212> TYPE: PRT
<213> ORGANISM: Artificial Sequence
<220> FEATURE:
<223> OTHER INFORMATION: Synthetic

<400> SEQUENCE: 405

Pro Cys Arg Arg
1

<210> SEQ ID NO 406
<211> LENGTH: 6
<212> TYPE: PRT
<213> ORGANISM: Artificial Sequence
<220> FEATURE:
<223> OTHER INFORMATION: Synthetic

<400> SEQUENCE: 406

Arg Arg Cys Ser Arg Arg
1               5

<210> SEQ ID NO 407
<211> LENGTH: 3
<212> TYPE: PRT
<213> ORGANISM: Artificial Sequence
<220> FEATURE:
<223> OTHER INFORMATION: Synthetic

<400> SEQUENCE: 407

Arg Gln Cys
1

<210> SEQ ID NO 408
<211> LENGTH: 37
<212> TYPE: PRT
<213> ORGANISM: Artificial Sequence
<220> FEATURE:
<223> OTHER INFORMATION: Synthetic

<400> SEQUENCE: 408

Val Arg Ile Pro Val Ser Cys Arg His Ser Gly Gln Cys Leu Arg Pro
1               5                   10                  15

Cys Arg Asp Ala Gly Met Arg Thr Gly Arg Cys Met Asn Gly Arg Cys
                20                  25                  30

Asp Cys Thr Pro Arg
        35

<210> SEQ ID NO 409
<211> LENGTH: 4
<212> TYPE: PRT
<213> ORGANISM: Artificial Sequence
<220> FEATURE:
<223> OTHER INFORMATION: Synthetic

<400> SEQUENCE: 409

Pro Cys Lys Lys
1

```
<210> SEQ ID NO 410
<211> LENGTH: 6
<212> TYPE: PRT
<213> ORGANISM: Artificial Sequence
<220> FEATURE:
<223> OTHER INFORMATION: Synthetic

<400> SEQUENCE: 410

Lys Lys Cys Ser Lys Lys
1               5

<210> SEQ ID NO 411

<400> SEQUENCE: 411

000

<210> SEQ ID NO 412
<211> LENGTH: 38
<212> TYPE: PRT
<213> ORGANISM: Artificial Sequence
<220> FEATURE:
<223> OTHER INFORMATION: Synthetic

<400> SEQUENCE: 412

Gln Lys Ile Leu Ser Asn Arg Cys Asn Asn Ser Ser Glu Cys Ile Pro
1               5                   10                  15

His Cys Ile Arg Ile Phe Gly Thr Arg Ala Ala Lys Cys Ile Asn Arg
            20                  25                  30

Lys Cys Tyr Cys Tyr Pro
        35

<210> SEQ ID NO 413

<400> SEQUENCE: 413

000

<210> SEQ ID NO 414
<211> LENGTH: 32
<212> TYPE: PRT
<213> ORGANISM: Artificial Sequence
<220> FEATURE:
<223> OTHER INFORMATION: Synthetic

<400> SEQUENCE: 414

Ala Val Cys Asn Leu Lys Arg Cys Gln Leu Ser Cys Arg Ser Leu Gly
1               5                   10                  15

Leu Leu Gly Lys Cys Ile Gly Asp Lys Cys Glu Cys Val Lys His Gly
            20                  25                  30

<210> SEQ ID NO 415
<211> LENGTH: 37
<212> TYPE: PRT
<213> ORGANISM: Artificial Sequence
<220> FEATURE:
<223> OTHER INFORMATION: Synthetic

<400> SEQUENCE: 415

Ile Ser Ile Gly Ile Arg Cys Ser Pro Ser Ile Asp Leu Cys Glu Gly
1               5                   10                  15

Gln Cys Arg Ile Arg Arg Tyr Phe Thr Gly Tyr Cys Ser Gly Asp Thr
            20                  25                  30

Cys His Cys Ser Gly
        35
```

<210> SEQ ID NO 416
<211> LENGTH: 33
<212> TYPE: PRT
<213> ORGANISM: Artificial Sequence
<220> FEATURE:
<223> OTHER INFORMATION: Synthetic

<400> SEQUENCE: 416

Gly Asp Cys Leu Pro His Leu Arg Arg Cys Arg Glu Asn Asn Asp Cys
1               5                   10                  15

Cys Ser Arg Arg Cys Arg Arg Arg Gly Ala Asn Pro Glu Arg Arg Cys
            20                  25                  30

Arg

<210> SEQ ID NO 417
<211> LENGTH: 34
<212> TYPE: PRT
<213> ORGANISM: Artificial Sequence
<220> FEATURE:
<223> OTHER INFORMATION: Synthetic

<400> SEQUENCE: 417

Ser Cys Glu Pro Gly Arg Thr Phe Arg Asp Arg Cys Asn Thr Cys Lys
1               5                   10                  15

Cys Gly Ala Asp Gly Arg Ser Ala Ala Cys Thr Leu Arg Ala Cys Pro
            20                  25                  30

Asn Gln

<210> SEQ ID NO 418
<211> LENGTH: 33
<212> TYPE: PRT
<213> ORGANISM: Artificial Sequence
<220> FEATURE:
<223> OTHER INFORMATION: Synthetic

<400> SEQUENCE: 418

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg

<210> SEQ ID NO 419
<211> LENGTH: 33
<212> TYPE: PRT
<213> ORGANISM: Artificial Sequence
<220> FEATURE:
<223> OTHER INFORMATION: Synthetic

<400> SEQUENCE: 419

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg

<210> SEQ ID NO 420
<211> LENGTH: 33
<212> TYPE: PRT
<213> ORGANISM: Artificial Sequence
<220> FEATURE:

<223> OTHER INFORMATION: Synthetic

<400> SEQUENCE: 420

Lys Asp Cys Leu Lys Leu Lys Leu Cys Lys Glu Asn Lys Asp Cys
1               5                   10                  15

Cys Ser Lys Ser Cys Lys Arg Arg Gly Thr Asn Ile Glu Lys Arg Cys
            20                  25                  30

Arg

<210> SEQ ID NO 421
<211> LENGTH: 33
<212> TYPE: PRT
<213> ORGANISM: Artificial Sequence
<220> FEATURE:
<223> OTHER INFORMATION: Synthetic

<400> SEQUENCE: 421

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg

<210> SEQ ID NO 422
<211> LENGTH: 37
<212> TYPE: PRT
<213> ORGANISM: Artificial Sequence
<220> FEATURE:
<223> OTHER INFORMATION: Synthetic

<400> SEQUENCE: 422

Val Phe Ile Asn Val Lys Cys Arg Gly Ser Pro Glu Cys Leu Pro Lys
1               5                   10                  15

Cys Lys Glu Ala Ile Gly Lys Ser Ala Gly Lys Cys Met Asn Gly Lys
            20                  25                  30

Cys Lys Cys Tyr Pro
        35

<210> SEQ ID NO 423
<211> LENGTH: 37
<212> TYPE: PRT
<213> ORGANISM: Artificial Sequence
<220> FEATURE:
<223> OTHER INFORMATION: Synthetic

<400> SEQUENCE: 423

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
            20                  25                  30

Cys Lys Cys Tyr Pro
        35

<210> SEQ ID NO 424
<211> LENGTH: 36
<212> TYPE: PRT
<213> ORGANISM: Artificial Sequence
<220> FEATURE:
<223> OTHER INFORMATION: Synthetic

<400> SEQUENCE: 424

Val Ile Ile Asn Val Lys Cys Lys Ile Ser Arg Gln Cys Leu Glu Pro

```
                1               5                  10                  15
Cys Lys Lys Ala Gly Met Arg Phe Gly Lys Cys Met Asn Gly Lys Cys
                20                  25                  30

His Cys Thr Pro
            35

<210> SEQ ID NO 425
<211> LENGTH: 36
<212> TYPE: PRT
<213> ORGANISM: Artificial Sequence
<220> FEATURE:
<223> OTHER INFORMATION: Synthetic

<400> SEQUENCE: 425

Val Pro Thr Asp Val Lys Cys Arg Gly Ser Pro Gln Cys Ile Gln Pro
1               5                   10                  15

Cys Lys Asp Ala Gly Met Arg Phe Gly Lys Cys Met Asn Gly Lys Cys
                20                  25                  30

His Cys Thr Pro
            35

<210> SEQ ID NO 426
<211> LENGTH: 36
<212> TYPE: PRT
<213> ORGANISM: Artificial Sequence
<220> FEATURE:
<223> OTHER INFORMATION: Synthetic

<400> SEQUENCE: 426

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
                20                  25                  30

Asp Cys Thr Pro
            35

<210> SEQ ID NO 427
<211> LENGTH: 36
<212> TYPE: PRT
<213> ORGANISM: Artificial Sequence
<220> FEATURE:
<223> OTHER INFORMATION: Synthetic

<400> SEQUENCE: 427

Val Arg Ile Pro Val Ser Cys Arg His Ser Gly Gln Cys Leu Arg Pro
1               5                   10                  15

Cys Arg Asp Ala Gly Met Arg Phe Gly Arg Cys Met Asn Gly Arg Cys
                20                  25                  30

Asp Cys Thr Pro
            35

<210> SEQ ID NO 428
<211> LENGTH: 33
<212> TYPE: PRT
<213> ORGANISM: Artificial Sequence
<220> FEATURE:
<223> OTHER INFORMATION: Synthetic

<400> SEQUENCE: 428

Thr Asn Val Ser Cys Thr Thr Ser Lys Glu Cys Trp Ser Val Cys Gln
1               5                   10                  15

Arg Leu His Asn Thr Ser Arg Gly Lys Cys Met Asn Lys Lys Cys Arg
```

```
                 20                  25                  30

Cys

<210> SEQ ID NO 429
<211> LENGTH: 32
<212> TYPE: PRT
<213> ORGANISM: Artificial Sequence
<220> FEATURE:
<223> OTHER INFORMATION: Synthetic

<400> SEQUENCE: 429

Asn Val Lys Cys Thr Gly Ser Lys Gln Cys Leu Pro Ala Cys Lys Ala
1               5                   10                  15

Ala Val Gly Lys Ala Ala Gly Lys Cys Met Asn Gly Lys Cys Lys Cys
                20                  25                  30

<210> SEQ ID NO 430
<211> LENGTH: 37
<212> TYPE: PRT
<213> ORGANISM: Artificial Sequence
<220> FEATURE:
<223> OTHER INFORMATION: Synthetic

<400> SEQUENCE: 430

Gly Val Pro Ile Asn Val Arg Cys Arg Gly Ser Arg Asp Cys Leu Asp
1               5                   10                  15

Pro Cys Arg Gly Ala Gly Glu Arg His Gly Arg Cys Gly Asn Ser Arg
                20                  25                  30

Cys His Cys Thr Pro
        35

<210> SEQ ID NO 431
<211> LENGTH: 37
<212> TYPE: PRT
<213> ORGANISM: Artificial Sequence
<220> FEATURE:
<223> OTHER INFORMATION: Synthetic

<400> SEQUENCE: 431

Val Arg Ile Pro Val Ser Cys Arg His Ser Gly Gln Cys Leu Arg Pro
1               5                   10                  15

Cys Arg Asp Ala Gly Glu Arg His Gly Arg Cys Gly Gly Arg Cys
                20                  25                  30

Asp Cys Thr Pro Arg
        35

<210> SEQ ID NO 432
<211> LENGTH: 38
<212> TYPE: PRT
<213> ORGANISM: Artificial Sequence
<220> FEATURE:
<223> OTHER INFORMATION: Synthetic

<400> SEQUENCE: 432

Gln Val Gln Thr Asn Val Arg Cys Gln Gly Gly Ser Cys Gly Ser Val
1               5                   10                  15

Cys Arg Arg Glu Gly Gly Ala Gly Gly Cys Gly Asn Gly Arg
                20                  25                  30

Cys Gly Cys Tyr Arg Asn
        35

<210> SEQ ID NO 433
```

```
<211> LENGTH: 30
<212> TYPE: PRT
<213> ORGANISM: Artificial Sequence
<220> FEATURE:
<223> OTHER INFORMATION: Synthetic

<400> SEQUENCE: 433

Gly Ser Lys Cys Leu Pro Pro Gly Lys Pro Cys Tyr Gly Ala Thr Gln
1               5                   10                  15

Lys Ile Pro Cys Cys Gly Val Cys Ser His Asn Asn Cys Thr
            20                  25                  30

<210> SEQ ID NO 434
<211> LENGTH: 39
<212> TYPE: PRT
<213> ORGANISM: Artificial Sequence
<220> FEATURE:
<223> OTHER INFORMATION: Synthetic

<400> SEQUENCE: 434

Gly Ser Gly Val Pro Ile Asn Val Arg Ser Arg Gly Ser Arg Asp Ser
1               5                   10                  15

Leu Asp Pro Ser Arg Arg Ala Gly Met Arg Phe Gly Arg Ser Ile Asn
            20                  25                  30

Ser Arg Ser His Ser Thr Pro
        35

<210> SEQ ID NO 435
<211> LENGTH: 292
<212> TYPE: PRT
<213> ORGANISM: Artificial Sequence
<220> FEATURE:
<223> OTHER INFORMATION: Synthetic

<400> SEQUENCE: 435

Met Glu Thr Asp Thr Leu Leu Leu Trp Val Leu Leu Leu Trp Val Pro
1               5                   10                  15

Gly Ser Thr Gly Gly Ser Gly Val Pro Ile Asn Val Arg Cys Arg Gly
            20                  25                  30

Ser Arg Asp Cys Leu Asp Pro Cys Arg Arg Ala Gly Met Arg Phe Gly
        35                  40                  45

Arg Cys Ile Asn Ser Arg Cys His Cys Thr Pro Gly Gly Ser Gly Gly
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190
```

Val Tyr Thr Leu Pro Pro Ser Arg Asp Glu Leu Thr Lys Asn Gln Val
            195                 200                 205

Ser Leu Thr Cys Leu Val Lys Gly Phe Tyr Pro Ser Asp Ile Ala Val
210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
            245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
            275                 280                 285

Ser Pro Gly Lys
        290

<210> SEQ ID NO 436
<211> LENGTH: 32
<212> TYPE: PRT
<213> ORGANISM: Artificial Sequence
<220> FEATURE:
<223> OTHER INFORMATION: Synthetic

<400> SEQUENCE: 436

Ile Lys Cys Ser Glu Ser Tyr Gln Cys Phe Pro Val Cys Lys Ser Arg
1               5                   10                  15

Phe Gly Lys Thr Asn Gly Arg Cys Val Asn Gly Phe Cys Asp Cys Phe
                20                  25                  30

<210> SEQ ID NO 437
<211> LENGTH: 33
<212> TYPE: PRT
<213> ORGANISM: Artificial Sequence
<220> FEATURE:
<223> OTHER INFORMATION: Synthetic

<400> SEQUENCE: 437

Val Lys Cys Ser Ser Pro Gln Gln Cys Leu Lys Pro Cys Lys Ala Ala
1               5                   10                  15

Phe Gly Ile Ser Ala Gly Gly Lys Cys Ile Asn Gly Lys Cys Lys Cys
                20                  25                  30

Tyr

<210> SEQ ID NO 438
<211> LENGTH: 32
<212> TYPE: PRT
<213> ORGANISM: Artificial Sequence
<220> FEATURE:
<223> OTHER INFORMATION: Synthetic

<400> SEQUENCE: 438

Val Ser Cys Ser Ala Ser Ser Gln Cys Trp Pro Val Cys Lys Lys Leu
1               5                   10                  15

Phe Gly Thr Tyr Arg Gly Lys Cys Met Asn Ser Lys Cys Arg Cys Tyr
                20                  25                  30

<210> SEQ ID NO 439
<211> LENGTH: 32
<212> TYPE: PRT
<213> ORGANISM: Artificial Sequence
<220> FEATURE:
<223> OTHER INFORMATION: Synthetic

<400> SEQUENCE: 439

Glu Ser Cys Thr Ala Ser Asn Gln Cys Trp Ser Ile Cys Lys Arg Leu
1               5                   10                  15

His Asn Thr Asn Arg Gly Lys Cys Met Asn Lys Lys Cys Arg Cys Tyr
            20                  25                  30

<210> SEQ ID NO 440
<211> LENGTH: 32
<212> TYPE: PRT
<213> ORGANISM: Artificial Sequence
<220> FEATURE:
<223> OTHER INFORMATION: Synthetic

<400> SEQUENCE: 440

Val Ser Cys Thr Thr Ser Lys Glu Cys Trp Ser Val Cys Glu Lys Leu
1               5                   10                  15

Tyr Asn Thr Ser Arg Gly Lys Cys Met Asn Lys Lys Cys Arg Cys Tyr
            20                  25                  30

<210> SEQ ID NO 441
<211> LENGTH: 32
<212> TYPE: PRT
<213> ORGANISM: Artificial Sequence
<220> FEATURE:
<223> OTHER INFORMATION: Synthetic

<400> SEQUENCE: 441

Met Arg Cys Lys Ser Ser Lys Glu Cys Leu Val Lys Cys Lys Gln Ala
1               5                   10                  15

Thr Gly Arg Pro Asn Gly Lys Cys Met Asn Arg Lys Cys Lys Cys Tyr
            20                  25                  30

<210> SEQ ID NO 442
<211> LENGTH: 32
<212> TYPE: PRT
<213> ORGANISM: Artificial Sequence
<220> FEATURE:
<223> OTHER INFORMATION: Synthetic

<400> SEQUENCE: 442

Ile Lys Cys Thr Leu Ser Lys Asp Cys Tyr Ser Pro Cys Lys Lys Glu
1               5                   10                  15

Thr Gly Cys Pro Arg Ala Lys Cys Ile Asn Arg Asn Cys Lys Cys Tyr
            20                  25                  30

<210> SEQ ID NO 443
<211> LENGTH: 32
<212> TYPE: PRT
<213> ORGANISM: Artificial Sequence
<220> FEATURE:
<223> OTHER INFORMATION: Synthetic

<400> SEQUENCE: 443

Ile Arg Cys Ser Gly Ser Arg Asp Cys Tyr Ser Pro Cys Met Lys Gln
1               5                   10                  15

Thr Gly Cys Pro Asn Ala Lys Cys Ile Asn Lys Ser Cys Lys Cys Tyr
            20                  25                  30

<210> SEQ ID NO 444
<211> LENGTH: 32
<212> TYPE: PRT
<213> ORGANISM: Artificial Sequence
<220> FEATURE:
<223> OTHER INFORMATION: Synthetic -continued

```
<400> SEQUENCE: 444

Ile Arg Cys Ser Gly Thr Arg Glu Cys Tyr Ala Pro Cys Gln Lys Leu
1               5                   10                  15

Thr Gly Cys Leu Asn Ala Lys Cys Met Asn Lys Ala Cys Lys Cys Tyr
            20                  25                  30

<210> SEQ ID NO 445
<211> LENGTH: 32
<212> TYPE: PRT
<213> ORGANISM: Artificial Sequence
<220> FEATURE:
<223> OTHER INFORMATION: Synthetic

<400> SEQUENCE: 445

Ile Ser Cys Thr Asn Pro Lys Gln Cys Tyr Pro His Cys Lys Lys Glu
1               5                   10                  15

Thr Gly Tyr Pro Asn Ala Lys Cys Met Asn Arg Lys Cys Lys Cys Phe
            20                  25                  30

<210> SEQ ID NO 446
<211> LENGTH: 32
<212> TYPE: PRT
<213> ORGANISM: Artificial Sequence
<220> FEATURE:
<223> OTHER INFORMATION: Synthetic

<400> SEQUENCE: 446

Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

<210> SEQ ID NO 447
<211> LENGTH: 31
<212> TYPE: PRT
<213> ORGANISM: Artificial Sequence
<220> FEATURE:
<223> OTHER INFORMATION: Synthetic

<400> SEQUENCE: 447

Thr Ser Cys Ile Ser Pro Lys Gln Cys Thr Glu Pro Cys Arg Ala Lys
1               5                   10                  15

Gly Cys Lys His Gly Lys Cys Met Asn Arg Lys Cys His Cys Met
            20                  25                  30

<210> SEQ ID NO 448
<211> LENGTH: 31
<212> TYPE: PRT
<213> ORGANISM: Artificial Sequence
<220> FEATURE:
<223> OTHER INFORMATION: Synthetic

<400> SEQUENCE: 448

Lys Glu Cys Thr Gly Pro Gln His Cys Thr Asn Phe Cys Arg Lys Asn
1               5                   10                  15

Lys Cys Thr His Gly Lys Cys Met Asn Arg Lys Cys Lys Cys Phe
            20                  25                  30

<210> SEQ ID NO 449
<211> LENGTH: 32
<212> TYPE: PRT
<213> ORGANISM: Artificial Sequence
<220> FEATURE:
```

<223> OTHER INFORMATION: Synthetic

<400> SEQUENCE: 449

Ile Lys Cys Arg Thr Pro Lys Asp Cys Ala Asp Pro Cys Arg Lys Gln
1               5                   10                  15

Thr Gly Cys Pro His Ala Lys Cys Met Asn Lys Thr Cys Arg Cys His
            20                  25                  30

<210> SEQ ID NO 450
<211> LENGTH: 32
<212> TYPE: PRT
<213> ORGANISM: Artificial Sequence
<220> FEATURE:
<223> OTHER INFORMATION: Synthetic

<400> SEQUENCE: 450

Val Lys Cys Thr Thr Ser Lys Glu Cys Trp Pro Pro Cys Lys Ala Ala
1               5                   10                  15

Thr Gly Lys Ala Ala Gly Lys Cys Met Asn Lys Lys Cys Lys Cys Gln
            20                  25                  30

<210> SEQ ID NO 451
<211> LENGTH: 32
<212> TYPE: PRT
<213> ORGANISM: Artificial Sequence
<220> FEATURE:
<223> OTHER INFORMATION: Synthetic

<400> SEQUENCE: 451

Leu Glu Cys Gly Ala Ser Arg Glu Cys Tyr Asp Pro Cys Phe Lys Ala
1               5                   10                  15

Phe Gly Arg Ala His Gly Lys Cys Met Asn Asn Lys Cys Arg Cys Tyr
            20                  25                  30

<210> SEQ ID NO 452
<211> LENGTH: 32
<212> TYPE: PRT
<213> ORGANISM: Artificial Sequence
<220> FEATURE:
<223> OTHER INFORMATION: Synthetic

<400> SEQUENCE: 452

Glu Lys Cys Phe Ala Thr Ser Gln Cys Trp Thr Pro Cys Lys Lys Ala
1               5                   10                  15

Ile Gly Ser Leu Gln Ser Lys Cys Met Asn Gly Lys Cys Lys Cys Tyr
            20                  25                  30

<210> SEQ ID NO 453
<211> LENGTH: 32
<212> TYPE: PRT
<213> ORGANISM: Artificial Sequence
<220> FEATURE:
<223> OTHER INFORMATION: Synthetic

<400> SEQUENCE: 453

Val Arg Cys Tyr Ala Ser Arg Glu Cys Trp Glu Pro Cys Arg Arg Val
1               5                   10                  15

Thr Gly Ser Ala Gln Ala Lys Cys Gln Asn Asn Gln Cys Arg Cys Tyr
            20                  25                  30

<210> SEQ ID NO 454
<211> LENGTH: 32
<212> TYPE: PRT
<213> ORGANISM: Artificial Sequence
<220> FEATURE:
<223> OTHER INFORMATION: Synthetic

<400> SEQUENCE: 454

Val Lys Cys Ser Ala Ser Arg Glu Cys Trp Val Ala Cys Lys Lys Val
1               5                   10                  15

Thr Gly Ser Gly Gln Gly Lys Cys Gln Asn Asn Gln Cys Arg Cys Tyr
            20                  25                  30

<210> SEQ ID NO 455
<211> LENGTH: 32
<212> TYPE: PRT
<213> ORGANISM: Artificial Sequence
<220> FEATURE:
<223> OTHER INFORMATION: Synthetic

<400> SEQUENCE: 455

Val Lys Cys Ile Ser Ser Gln Glu Cys Trp Ile Ala Cys Lys Lys Val
1               5                   10                  15

Thr Gly Arg Phe Glu Gly Lys Cys Gln Asn Arg Gln Cys Arg Cys Tyr
            20                  25                  30

<210> SEQ ID NO 456
<211> LENGTH: 32
<212> TYPE: PRT
<213> ORGANISM: Artificial Sequence
<220> FEATURE:
<223> OTHER INFORMATION: Synthetic

<400> SEQUENCE: 456

Val Arg Cys Tyr Asp Ser Arg Gln Cys Trp Ile Ala Cys Lys Lys Val
1               5                   10                  15

Thr Gly Ser Thr Gln Gly Lys Cys Gln Asn Lys Gln Cys Arg Cys Tyr
            20                  25                  30

<210> SEQ ID NO 457
<211> LENGTH: 32
<212> TYPE: PRT
<213> ORGANISM: Artificial Sequence
<220> FEATURE:
<223> OTHER INFORMATION: Synthetic

<400> SEQUENCE: 457

Val Asp Cys Thr Val Ser Lys Glu Cys Trp Ala Pro Cys Lys Ala Ala
1               5                   10                  15

Phe Gly Val Asp Arg Gly Lys Cys Met Gly Lys Lys Cys Lys Cys Tyr
            20                  25                  30

<210> SEQ ID NO 458
<211> LENGTH: 32
<212> TYPE: PRT
<213> ORGANISM: Artificial Sequence
<220> FEATURE:
<223> OTHER INFORMATION: Synthetic

<400> SEQUENCE: 458

Ala Lys Cys Arg Gly Ser Pro Glu Cys Leu Pro Lys Cys Lys Glu Ala
1               5                   10                  15

Ile Gly Lys Ala Ala Gly Lys Cys Met Asn Gly Lys Cys Lys Cys Tyr
            20                  25                  30

<210> SEQ ID NO 459
<211> LENGTH: 31
<212> TYPE: PRT

<213> ORGANISM: Artificial Sequence
<220> FEATURE:
<223> OTHER INFORMATION: Synthetic

<400> SEQUENCE: 459

Lys Lys Cys Gln Gly Gly Ser Cys Ala Ser Val Cys Arg Arg Val Ile
1               5                   10                  15

Gly Val Ala Ala Gly Lys Cys Ile Asn Gly Arg Cys Val Cys Tyr
            20                  25                  30

<210> SEQ ID NO 460
<211> LENGTH: 32
<212> TYPE: PRT
<213> ORGANISM: Artificial Sequence
<220> FEATURE:
<223> OTHER INFORMATION: Synthetic

<400> SEQUENCE: 460

Lys Lys Cys Ser Asn Thr Ser Gln Cys Tyr Lys Thr Cys Glu Lys Val
1               5                   10                  15

Val Gly Val Ala Ala Gly Lys Cys Met Asn Gly Lys Cys Ile Cys Tyr
            20                  25                  30

<210> SEQ ID NO 461
<211> LENGTH: 32
<212> TYPE: PRT
<213> ORGANISM: Artificial Sequence
<220> FEATURE:
<223> OTHER INFORMATION: Synthetic

<400> SEQUENCE: 461

Val Lys Cys Ser Gly Ser Ser Lys Cys Val Lys Ile Cys Ile Asp Arg
1               5                   10                  15

Tyr Asn Thr Arg Gly Ala Lys Cys Ile Asn Gly Arg Cys Thr Cys Tyr
            20                  25                  30

<210> SEQ ID NO 462
<211> LENGTH: 32
<212> TYPE: PRT
<213> ORGANISM: Artificial Sequence
<220> FEATURE:
<223> OTHER INFORMATION: Synthetic

<400> SEQUENCE: 462

Asn Arg Cys Asn Asn Ser Ser Glu Cys Ile Pro His Cys Ile Arg Ile
1               5                   10                  15

Phe Gly Thr Arg Ala Ala Lys Cys Ile Asn Arg Lys Cys Tyr Cys Tyr
            20                  25                  30

<210> SEQ ID NO 463
<211> LENGTH: 32
<212> TYPE: PRT
<213> ORGANISM: Artificial Sequence
<220> FEATURE:
<223> OTHER INFORMATION: Synthetic

<400> SEQUENCE: 463

Lys Glu Cys Asn Gly Ser Ser Glu Cys Tyr Ser His Cys Glu Gly Ile
1               5                   10                  15

Thr Gly Lys Arg Ser Gly Lys Cys Ile Asn Lys Lys Cys Tyr Cys Tyr
            20                  25                  30

<210> SEQ ID NO 464
<211> LENGTH: 29

```
<212> TYPE: PRT
<213> ORGANISM: Artificial Sequence
<220> FEATURE:
<223> OTHER INFORMATION: Synthetic

<400> SEQUENCE: 464

Ala Phe Cys Asn Leu Arg Arg Cys Glu Leu Ser Cys Arg Ser Leu Gly
1               5                   10                  15
Leu Leu Gly Lys Cys Ile Gly Glu Cys Lys Cys Val
            20                  25

<210> SEQ ID NO 465
<211> LENGTH: 29
<212> TYPE: PRT
<213> ORGANISM: Artificial Sequence
<220> FEATURE:
<223> OTHER INFORMATION: Synthetic

<400> SEQUENCE: 465

Ala Val Cys Asn Leu Lys Arg Cys Gln Leu Ser Cys Arg Ser Leu Gly
1               5                   10                  15
Leu Leu Gly Lys Cys Ile Gly Asp Lys Cys Glu Cys Val
            20                  25

<210> SEQ ID NO 466
<211> LENGTH: 30
<212> TYPE: PRT
<213> ORGANISM: Artificial Sequence
<220> FEATURE:
<223> OTHER INFORMATION: Synthetic

<400> SEQUENCE: 466

Ala Ala Cys Tyr Ser Ser Asp Cys Arg Val Lys Cys Val Ala Met Gly
1               5                   10                  15
Phe Ser Ser Gly Lys Cys Ile Asn Ser Lys Cys Lys Cys Tyr
            20                  25                  30

<210> SEQ ID NO 467
<211> LENGTH: 27
<212> TYPE: PRT
<213> ORGANISM: Artificial Sequence
<220> FEATURE:
<223> OTHER INFORMATION: Synthetic

<400> SEQUENCE: 467

Ala Ile Cys Ala Thr Asp Ala Asp Cys Ser Arg Lys Cys Pro Gly Asn
1               5                   10                  15
Pro Pro Cys Arg Asn Gly Phe Cys Ala Cys Thr
            20                  25

<210> SEQ ID NO 468
<211> LENGTH: 27
<212> TYPE: PRT
<213> ORGANISM: Artificial Sequence
<220> FEATURE:
<223> OTHER INFORMATION: Synthetic

<400> SEQUENCE: 468

Thr Glu Cys Gln Ile Lys Asn Asp Cys Gln Arg Tyr Cys Gln Ser Val
1               5                   10                  15
Lys Glu Cys Lys Tyr Gly Lys Cys Tyr Cys Asn
            20                  25

<210> SEQ ID NO 469
```

```
<211> LENGTH: 27
<212> TYPE: PRT
<213> ORGANISM: Artificial Sequence
<220> FEATURE:
<223> OTHER INFORMATION: Synthetic

<400> SEQUENCE: 469

Thr Gln Cys Gln Ser Val Arg Asp Cys Gln Gln Tyr Cys Leu Thr Pro
1               5                   10                  15

Asp Arg Cys Ser Tyr Gly Thr Cys Tyr Cys Lys
            20                  25

<210> SEQ ID NO 470
<211> LENGTH: 32
<212> TYPE: PRT
<213> ORGANISM: Artificial Sequence
<220> FEATURE:
<223> OTHER INFORMATION: Synthetic

<400> SEQUENCE: 470

Val Ser Cys Arg Tyr Gly Ser Asp Cys Ala Glu Pro Cys Lys Arg Leu
1               5                   10                  15

Lys Cys Leu Leu Pro Ser Lys Cys Ile Asn Gly Lys Cys Thr Cys Tyr
            20                  25                  30

<210> SEQ ID NO 471
<211> LENGTH: 32
<212> TYPE: PRT
<213> ORGANISM: Artificial Sequence
<220> FEATURE:
<223> OTHER INFORMATION: Synthetic

<400> SEQUENCE: 471

Ile Lys Cys Arg Tyr Pro Ala Asp Cys His Ile Met Cys Arg Lys Val
1               5                   10                  15

Thr Gly Arg Ala Glu Gly Lys Cys Met Asn Gly Lys Cys Thr Cys Tyr
            20                  25                  30

<210> SEQ ID NO 472
<211> LENGTH: 32
<212> TYPE: PRT
<213> ORGANISM: Artificial Sequence
<220> FEATURE:
<223> OTHER INFORMATION: Synthetic

<400> SEQUENCE: 472

Ile Lys Cys Ser Ser Ser Ser Cys Tyr Glu Pro Cys Arg Gly Val
1               5                   10                  15

Thr Gly Arg Ala His Gly Lys Cys Met Asn Gly Arg Cys Thr Cys Tyr
            20                  25                  30

<210> SEQ ID NO 473
<211> LENGTH: 32
<212> TYPE: PRT
<213> ORGANISM: Artificial Sequence
<220> FEATURE:
<223> OTHER INFORMATION: Synthetic

<400> SEQUENCE: 473

Val Lys Cys Thr Gly Ser Lys Gln Cys Leu Pro Ala Cys Lys Ala Ala
1               5                   10                  15

Val Gly Lys Ala Ala Gly Lys Cys Met Asn Gly Lys Cys Lys Cys Tyr
            20                  25                  30
```

```
<210> SEQ ID NO 474
<211> LENGTH: 31
<212> TYPE: PRT
<213> ORGANISM: Artificial Sequence
<220> FEATURE:
<223> OTHER INFORMATION: Synthetic

<400> SEQUENCE: 474

Val Ser Cys Lys His Ser Gly Gln Cys Ile Lys Pro Cys Lys Asp Ala
1               5                   10                  15

Gly Met Arg Phe Gly Lys Cys Met Asn Arg Lys Cys Asp Cys Thr
            20                  25                  30

<210> SEQ ID NO 475
<211> LENGTH: 31
<212> TYPE: PRT
<213> ORGANISM: Artificial Sequence
<220> FEATURE:
<223> OTHER INFORMATION: Synthetic

<400> SEQUENCE: 475

Val Lys Cys Arg Gly Ser Pro Gln Cys Ile Gln Pro Cys Arg Asp Ala
1               5                   10                  15

Gly Met Arg Phe Gly Lys Cys Met Asn Gly Lys Cys His Cys Thr
            20                  25                  30

<210> SEQ ID NO 476
<211> LENGTH: 33
<212> TYPE: PRT
<213> ORGANISM: Artificial Sequence
<220> FEATURE:
<223> OTHER INFORMATION: Synthetic

<400> SEQUENCE: 476

Val Lys Cys Thr Ser Pro Lys Gln Cys Leu Pro Pro Cys Lys Ala Gln
1               5                   10                  15

Phe Gly Ile Arg Ala Gly Ala Lys Cys Met Asn Gly Lys Cys Lys Cys
            20                  25                  30

Tyr

<210> SEQ ID NO 477
<211> LENGTH: 33
<212> TYPE: PRT
<213> ORGANISM: Artificial Sequence
<220> FEATURE:
<223> OTHER INFORMATION: Synthetic

<400> SEQUENCE: 477

Val Lys Cys Thr Ser Pro Lys Gln Cys Ser Lys Pro Cys Lys Glu Leu
1               5                   10                  15

Tyr Gly Ser Ser Ala Gly Ala Lys Cys Met Asn Gly Lys Cys Lys Cys
            20                  25                  30

Tyr

<210> SEQ ID NO 478
<211> LENGTH: 33
<212> TYPE: PRT
<213> ORGANISM: Artificial Sequence
<220> FEATURE:
<223> OTHER INFORMATION: Synthetic

<400> SEQUENCE: 478

Val Lys Cys Thr Ser Pro Lys Gln Cys Leu Pro Pro Cys Lys Glu Ile
1               5                   10                  15
```

```
Tyr Gly Arg His Ala Gly Ala Lys Cys Met Asn Gly Lys Cys His Cys
            20                  25                  30

Ser

<210> SEQ ID NO 479
<211> LENGTH: 32
<212> TYPE: PRT
<213> ORGANISM: Artificial Sequence
<220> FEATURE:
<223> OTHER INFORMATION: Synthetic

<400> SEQUENCE: 479

Val Lys Cys Thr Gly Ser Lys Gln Cys Trp Pro Val Cys Lys Gln Met
1               5                   10                  15

Phe Gly Lys Pro Asn Gly Lys Cys Met Asn Gly Lys Cys Arg Cys Tyr
            20                  25                  30

<210> SEQ ID NO 480
<211> LENGTH: 31
<212> TYPE: PRT
<213> ORGANISM: Artificial Sequence
<220> FEATURE:
<223> OTHER INFORMATION: Synthetic

<400> SEQUENCE: 480

Val Lys Cys Arg Gly Ser Arg Asp Cys Leu Asp Pro Cys Lys Lys Ala
1               5                   10                  15

Gly Met Arg Phe Gly Lys Cys Ile Asn Ser Lys Cys His Cys Thr
            20                  25                  30

<210> SEQ ID NO 481
<211> LENGTH: 27
<212> TYPE: PRT
<213> ORGANISM: Artificial Sequence
<220> FEATURE:
<223> OTHER INFORMATION: Synthetic

<400> SEQUENCE: 481

Val Arg Cys Val Thr Asp Asp Cys Phe Arg Lys Cys Pro Gly Asn
1               5                   10                  15

Pro Ser Cys Lys Arg Gly Phe Cys Ala Cys Lys
            20                  25

<210> SEQ ID NO 482
<211> LENGTH: 32
<212> TYPE: PRT
<213> ORGANISM: Artificial Sequence
<220> FEATURE:
<223> OTHER INFORMATION: Synthetic

<400> SEQUENCE: 482

Val Pro Cys Asn Asn Ser Arg Pro Cys Val Pro Val Cys Ile Arg Glu
1               5                   10                  15

Val Asn Asn Lys Asn Gly Lys Cys Ser Asn Gly Lys Cys Leu Cys Tyr
            20                  25                  30

<210> SEQ ID NO 483
<211> LENGTH: 39
<212> TYPE: PRT
<213> ORGANISM: Artificial Sequence
<220> FEATURE:
<223> OTHER INFORMATION: Synthetic

<400> SEQUENCE: 483
```

Gly Ser Ile Ser Ile Gly Ile Lys Cys Ser Pro Ser Ile Asp Leu Cys
1               5                   10                  15

Glu Gly Gln Cys Arg Ile Arg Lys Tyr Phe Thr Gly Tyr Cys Ser Gly
                20                  25                  30

Asp Thr Cys His Cys Ser Gly
            35

<210> SEQ ID NO 484
<211> LENGTH: 39
<212> TYPE: PRT
<213> ORGANISM: Artificial Sequence
<220> FEATURE:
<223> OTHER INFORMATION: Synthetic

<400> SEQUENCE: 484

Gly Ser Glu Cys Leu Gly Phe Gly Lys Gly Cys Asn Pro Ser Asn Asp
1               5                   10                  15

Gln Cys Cys Lys Ser Ser Asn Leu Val Cys Ser Arg Lys His Arg Trp
                20                  25                  30

Cys Lys Tyr Glu Ile Gly Lys
            35

<210> SEQ ID NO 485
<211> LENGTH: 20
<212> TYPE: PRT
<213> ORGANISM: Artificial Sequence
<220> FEATURE:
<223> OTHER INFORMATION: Synthetic

<400> SEQUENCE: 485

Met Glu Thr Asp Thr Leu Leu Leu Trp Val Leu Leu Leu Trp Val Pro
1               5                   10                  15

Gly Ser Thr Gly
            20

<210> SEQ ID NO 486
<211> LENGTH: 36
<212> TYPE: PRT
<213> ORGANISM: Artificial Sequence
<220> FEATURE:
<223> OTHER INFORMATION: Synthetic

<400> SEQUENCE: 486

Val Pro Ile Asn Val Lys Cys Arg Gly Ser Arg Asp Cys Leu Asp Pro
1               5                   10                  15

Cys Lys Lys Ala Gly Met Arg Phe Gly Lys Cys Ile Asn Ser Lys Cys
                20                  25                  30

His Cys Thr Pro
            35

<210> SEQ ID NO 487
<211> LENGTH: 37
<212> TYPE: PRT
<213> ORGANISM: Artificial Sequence
<220> FEATURE:
<223> OTHER INFORMATION: Synthetic

```
<400> SEQUENCE: 487

Val Gln Thr Asn Val Lys Cys Gln Gly Gly Ser Cys Ala Ser Val Cys
1               5                   10                  15

Arg Arg Glu Ile Gly Val Ala Ala Gly Lys Cys Ile Asn Gly Lys Cys
            20                  25                  30

Val Cys Tyr Arg Asn
            35
```

CARTILAGE-HOMING PEPTIDES

CROSS-REFERENCE TO RELATED APPLICATIONS

This application is a continuation of U.S. application Ser. No. 15/758,320, filed Mar. 7, 2018, now U.S. Pat. No. 11,090,358, which is a U.S. National Phase Application under 35 U.S.C. § 371 of International Application No. PCT/US2016/051166, filed Sep. 9, 2016, which claims priority to U.S. provisional patent application No. 62/385,734, filed Sep. 9, 2016; U.S. provisional patent application No. 62/278,929, filed Jan. 14, 2016; and U.S. provisional patent application No. 62/216,331, filed Sep. 9, 2015, each of which are herein incorporated by reference in their entireties.

SEQUENCE LISTING

This application includes an electronically submitted sequence listing in .txt format. The .txt file contains a sequence listing entitled "2016-11-18_44189-710601_ST25.txt" created on Nov. 18, 2016, and is 240 kilobytes in size. The sequence listing contained in this .txt file is part of the specification and is hereby incorporated by reference herein in its entirety.

BACKGROUND

Cartilage comprises chondrocytes, a specialized cell-type which produces components of the extracellular matrix, mainly including collagen, proteoglycans (e.g., aggrecan), and elastic fibers. The extracellular matrix proteins provide support, cushion, and durability to cartilage-rich portions of the body such as joints, ears, nose and windpipe. Cartilage is one of few tissues in the body which does not contain blood vessels and is considered an avascular tissue. Unlike many cells in the body which rely on a combination of blood flow and diffusion, chondrocytes rely on diffusion. Because it does not have a direct blood supply, compared to other connective tissues, cartilage grows and repairs much more slowly. As a result, cartilage disorders are particularly difficult to treat.

SUMMARY

The present disclosure relates to compositions and methods for treatment of cartilage disorders. Described herein are peptides that home to, migrate to, accumulate in, bind to, are retained by, or are directed to, and/or bind in cartilage following administration in a subject. In some embodiments, the homing peptides of the present disclosure are used to deliver a detection agent to image and/or diagnose cartilage. In other embodiments, the homing peptides of the present disclosure are used to deliver an active agent to a region, tissue, structure, or cell thereof.

In various aspects, the present disclosure provides a knotted peptide, wherein upon administration to a subject the knotted peptide homes, targets, migrates to, accumulates in, binds to, is retained by, or is directed to a cartilage of the subject.

In some aspects, the knotted peptide comprises a sequence of any one of SEQ ID NO: 21-SEQ ID NO: 194, SEQ ID NO: 196, SEQ ID NO: 198-SEQ ID NO: 216 or a fragment thereof. In other aspects, the knotted peptide comprises a sequence that has at least 80% sequence identity with any one of SEQ ID NO: 21-SEQ ID NO: 194, SEQ ID NO: 196, SEQ ID NO: 198-SEQ ID NO: 216 or a fragment thereof. In still other aspects, the knotted peptide comprises a sequence that has at least 85%, at least 90%, or at least 95% sequence identity with any one of SEQ ID NO: 21-SEQ ID NO: 194, SEQ ID NO: 196, SEQ ID NO: 198-SEQ ID NO: 216 or a fragment thereof.

In some aspects, the knotted peptide comprises a sequence of any one of SEQ ID NO: 237-SEQ ID NO: 410, SEQ ID NO: 412, SEQ ID NO: 414-SEQ ID NO: 432 or a fragment thereof. In other aspects, the knotted peptide comprises a sequence that has at least 80% sequence identity with any one of SEQ ID NO: 237-SEQ ID NO: 410, SEQ ID NO: 412, SEQ ID NO: 414-SEQ ID NO: 432 or a fragment thereof. In still other aspects, the knotted peptide comprises a sequence that has at least 85%, at least 90%, or at least 95% sequence identity with any one of SEQ ID NO: 237-SEQ ID NO: 410, SEQ ID NO: 412, SEQ ID NO: 414-SEQ ID NO: 432 or a fragment thereof.

In some aspects, the knotted peptide comprises a sequence of any one of SEQ ID NO: 1-SEQ ID NO: 20 or a fragment thereof. In other aspects, the knotted peptide comprises a sequence of any one of SEQ ID NO: 217-SEQ ID NO: 236 or a fragment thereof.

In other aspects, the knotted peptide is at least 30%, 40%, 50%, 60%, 70%, 80%, 90%, or 95% identical to any one of SEQ ID NO: 436-SEQ ID NO: 482. In further aspects, the knotted peptide of claim 10, wherein the knotted peptide is SEQ ID NO: 24. In other aspects, the knotted peptide is SEQ ID NO: 111.

In some aspects, the knotted peptide comprises 4 or more cysteine residues. In further aspects, the knotted peptide comprises three or more disulfide bridges formed between cysteine residues, wherein one of the disulfide bridges passes through a loop formed by two other disulfide bridges. In still further aspects, the knotted peptide comprises a plurality of disulfide bridges formed between cysteine residues. In other aspects, the knotted peptide comprises a disulfide through a disulfide knot.

In some aspects, at least one amino acid residue of the knotted peptide is in an L configuration or, wherein at least one amino acid residue of the knotted peptide is in a D configuration.

In some aspects, the sequence comprises at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58 residues, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 residues.

In some aspects, any one or more K residues are replaced by an R residue or wherein any one or more R residues are replaced by for a K residue. In other aspects, any one or more M residues are replaced by any one of the I, L, or V residues. In still other aspects, any one or more L residues are replaced by any one of the V, I, or M residues.

In other aspects, any one or more I residues are replaced by any of the M, L, or V residues. In still other aspects, any one or more V residues are replaced by any of the M, I, or L residues. In some aspects, any one or more G residues are replaced by an A residue or wherein any one or more A residues are replaced by a G residue. In other aspects, any one or more S residues are replaced by a T residue or wherein any one or more T residues are replaced by for an S residue.

In still other aspects, any one or more Q residues are replaced by an N residue or wherein any one or more N residues are replaced by a Q residue. In some aspects, any one or more D residues are replaced by an E residue or wherein any one or more E residues are replaced by a D residue.

In some aspects, the knotted peptide has a charge distribution comprising an acidic region and a basic region. In further aspects, the acidic region is a nub. In other aspects, the basic region is a patch. In some aspects, the knotted peptide comprises 6 or more basic residues and 2 or fewer acidic residues. In some aspects, the knotted peptide comprises a 4-19 amino acid residue fragment containing at least 2 cysteine residues, and at least 2 positively charged amino acid residues.

In other aspects, the knotted peptide comprises a 20-70 amino acid residue fragment containing at least 2 cysteine residues, no more than 2 basic residues and at least 2 positively charged amino acid residues. In still other aspects, the knotted peptide comprises at least 3 positively charged amino acid residues. In some aspects, the positively charged amino acid residues are selected from K, R, or a combination thereof.

In some aspects, the knotted peptide has a charge greater than 2 at physiological pH. In other aspects, the knotted peptide has a charge greater than 3.5 at physiological pH. In still other aspects, the knotted peptide has a charge greater than 4.5 at physiological pH. In some aspects, the knotted peptide has a charge greater than 5.5 at physiological pH. In other aspects, the knotted peptide has a charge greater than 6.5 at physiological pH. In other aspects, the knotted peptide has a charge greater than 7.5 at physiological pH.

In some aspects, the knotted peptide is selected from a potassium channel agonist, a potassium channel antagonist, a portion of a potassium channel, a sodium channel agonist, a sodium channel antagonist, a calcium channel agonist, a calcium channel antagonist, a hadrucalcin, a theraphotoxin, a huwentoxin, a kaliotoxin, a cobatoxin or a lectin.

In further aspects, the lectin is SHL-Ib2. In some aspects, the knotted peptide is arranged in a multimeric structure with at least one other knotted peptide.

In some aspects, at least one residue of the knotted peptide comprises a chemical modification. In further aspects, the chemical modification is blocking the N-terminus of the knotted peptide. In still further aspects, the chemical modification is methylation, acetylation, or acylation. In other aspects, the chemical modification is: methylation of one or more lysine residues or analogue thereof; methylation of the N-terminus; or methylation of one or more lysine residue or analogue thereof and methylation of the N-terminus. In some aspects, the knotted peptide is linked to an acyl adduct.

In some aspects, the knotted peptide is linked to an active agent. In further aspects, the active agent is fused with the knotted peptide at an N-terminus or a C-terminus of the knotted peptide. In some aspects, the active agent is an antibody. In other aspects, the active agent is an Fc domain. In still other aspects, the knotted peptide fused with an Fc domain comprises a contiguous sequence.

In further aspects, 1, 2, 3, 4, 5, 6, 7, 8, 9, or 10 active agents are linked to the knotted peptide. In still further aspects, the knotted peptide is linked to the active agent via a cleavable linker. In some aspects, the knotted peptide is linked to the active agent at an N-terminus, at the epsilon amine of an internal lysine residue, at the carboxylic acid of an aspartic acid or glutamic acid residue, or a C-terminus of the knotted peptide by a linker. In some aspects, the knotted peptide further comprises a non-natural amino acid, wherein the non-natural amino acid is an insertion, appendage, or substitution for another amino acid.

In some aspects, the knotted peptide is linked to the active agent at the non-natural amino acid by a linker. In some aspects, the linker comprises an amide bond, an ester bond, a carbamate bond, a carbonate bond, a hydrazone bond, an oxime bond, a disulfide bond, a thioester bond, or a carbon-nitrogen bond. In further aspects, the cleavable linker comprises a cleavage site for matrix metalloproteinases, thrombin, cathepsins, or beta-glucuronidase. In other aspects, the linker is a hydrolytically labile linker. In still other aspects, the knotted peptide is linked to the active agent via a noncleavable linker.

In some aspects, the active agent is: a peptide, an oligopeptide, a polypeptide, a polynucleotide, a polyribonucleotide, a DNA, a cDNA, a ssDNA, a RNA, a dsRNA, a micro RNA, an oligonucleotide, an antibody, an antibody fragment, an aptamer, a cytokine, an enzyme, a growth factor, a chemokine, a neurotransmitter, a chemical agent, a fluorophore, a metal, a metal chelate, an X-ray contrast agent, a PET agent, a radioisotope, a photosensitizer, a radiosensitizer, a radionuclide chelator, a therapeutic small molecule, a steroid, a corticosteroid, an anti-inflammatory agent, an immune modulator, a protease inhibitor, an amino sugar, a chemotherapeutic agent, a cytotoxic chemical, a toxin, a tyrosine kinase inhibitor, an anti-infective agent, an antibiotic, an anti-viral agent, an anti-fungal agent, an aminoglycoside, a nonsteroidal anti-inflammatory drug (NSAID), a statin, a nanoparticle, a liposome, a polymer, a biopolymer, a polysaccharide, a proteoglycan, a glycosaminoglycan, a glucocorticoid, an anti-cytokine agent, a pain-reducing agent, a dendrimer, a fatty acid, an Fc region, or a combination thereof.

In some aspects, the NSAID is ketorolac. In other aspects, the NSAID is ibuprofen. In some aspects, the steroid is dexamethasone. In other aspects, the steroid is budesonide. In some aspects, the active agent induces programmed cell death. In further aspects, the programmed cell death is apoptosis. In some aspects, the active agent is a tumor necrosis factor alpha inhibitor. In further aspects, the active agent is a TNF receptor family activator. In still further aspects, the active agent is a TNF alpha antibody. In some aspects, the protease inhibitor is a collagenase inhibitor, elastase inhibitor, or a matrix metalloprotease inhibitor. In further aspects, the matrix metalloprotease is MMP13.

In some aspects, the knotted peptide is linked to a detectable agent. In further aspects, the detectable agent is fused with the knotted peptide at an N-terminus or a C-terminus of the knotted peptide. In still further aspects, 1, 2, 3, 4, 5, 6, 7, 8, 9, or 10 detectable agents are linked to the knotted peptide. In some aspects, the knotted peptide is linked to the detectable agent via a cleavable linker.

In some aspects, the knotted peptide is linked to the detectable agent at an N-terminus, at the epsilon amine of an internal lysine residue, or a C-terminus of the knotted peptide by a linker. In further aspects, the peptide further comprises a non-natural amino acid, wherein the non-natural amino acid is an insertion, appendage, or substitution for another amino acid. In still further aspects, the knotted peptide is linked to the active agent at the non-natural amino acid by a linker.

In still further aspects, the linker comprises an amide bond, an ester bond, a carbamate bond, a hydrazone bond, an oxime bond, or a carbon-nitrogen bond. In some aspects, the cleavable linker comprises a cleavage site for matrix metalloproteinases, thrombin, cathepsins, or beta-glucuronidase. In other aspects, the knotted peptide is linked to the detectable agent via a noncleavable linker.

In some aspects, the detectable agent is a fluorophore, a near-infrared dye, a contrast agent, a nanoparticle, a metal-containing nanoparticle, a metal chelate, an X-ray contrast agent, a PET agent, a radioisotope, or a radionuclide chelator. In further aspects, the detectable agent is a fluorescent dye. In some aspects, the knotted peptide has an isoelectric point of about 9.

In some aspects, the knotted peptide is SEQ ID NO: 24. In other aspects, the knotted peptide is SEQ ID NO: 111.

In various aspects, the present disclosure provides a pharmaceutical composition comprising any of the above compositions or a salt thereof, and a pharmaceutically acceptable carrier.

In further aspects, the pharmaceutical composition is formulated for administration to a subject. In still further aspects, the pharmaceutical composition is formulated for inhalation, intranasal administration, oral administration, topical administration, intravenous administration, subcutaneous administration, intra-articular administration, intramuscular administration, intraperitoneal administration, or a combination thereof.

In various aspects, the present disclosure provides a method of treating a condition in a subject in need thereof, the method comprising: administering to the subject a knotted peptide comprising any of the above compositions or any of the above pharmaceutical compositions.

In some aspects, the composition is administered by inhalation, intranasally, orally, topically, intravenously, subcutaneously, intra-articularly, intramuscularly administration, intraperitoneally, or a combination thereof. In further aspects, the composition homes, targets, or migrates to cartilage of the subject following administration.

In some aspects, the condition is associated with a function of cartilage. In some aspects, the condition is an inflammation, a cancer, a degradation, a growth disturbance, genetic, a tear, an infection, or an injury. In other aspects, the condition is a chondrodystrophy. In still other aspects, the condition is a traumatic rupture or detachment. In some aspects, the condition is a costochondritis. In other aspects, the condition is a herniation. In still other aspects, the condition is a polychondritis.

In other aspects, the condition is a chordoma. In some aspects, the condition is a type of arthritis. In further aspects, the type of arthritis is rheumatoid arthritis. In other aspects, the type of arthritis is osteoarthritis. In some aspects, the condition is achondroplasia. In some aspects, the cancer is benign chondroma or malignant chondrosarcoma. In other aspects, the condition is bursitis, tendinitis, gout, pseudogout, an arthropathy, or an infection.

In some aspects, the composition is administered to treat the injury, to repair a tissue damaged by the injury, or to treat a pain caused by the injury. In further aspects, the composition is administered to treat the tear or to repair a tissue damaged by the tear.

In various aspects, the present disclosure provides a method of imaging an organ or body region of a subject, the method comprising: administering to the subject composition of any one of knotted peptide previously described or a pharmaceutical composition as previously described; and imaging the subject.

In some aspects, the method further comprises detecting a cancer or diseased region, tissue, structure or cell. In further aspects, the method further comprises performing surgery on the subject. In some aspects, the method further comprises treating the cancer.

In other aspects, the surgery comprises removing the cancer or the diseased region, tissue, structure or cell of the subject. In still other aspects, the method further comprises imaging the cancer or diseased region, tissue, structure, or cell of the subject after surgical removal.

INCORPORATION BY REFERENCE

All publications, patents, and patent applications mentioned, disclosed or referenced in this specification are herein incorporated by reference in their entirety and to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates the $^{14}$C signal in the cartilage of animals treated with various peptides of this disclosure.

FIG. 6 illustrates the High Performance Liquid Chromatography (HPLC) profiles of peptides of this disclosure. FIG. 6A illustrates the HPLC profile of a peptide of FIG. 1D and SEQ ID NO: 23. FIG. 6B illustrates the HPLC profile of a peptide of FIG. 1C and SEQ ID NO: 24.

FIG. 11 shows a white light image and corresponding autoradiographic image from a section of a mouse 24 hours after administration of 100 nmol of radiolabeled GS-Hainantoxin (GSKCLPPGKPCYGATQKIPCCGVCSHNNCT) (SEQ ID NO: 433) peptide, which does not home to cartilage. FIG. 11A illustrates a white light image of a frozen section of a mouse 24 hours after administration of 100 nmol of SEQ ID NO: 433. FIG. 11B shows an autoradiographic image corresponding to FIG. 11A in which the $^{14}C$ signal identifies the radiolabeled SEQ ID NO: 433 peptide.

FIG. 12 illustrates alignment of cartilage homers as depicted by the examples and of SEQ ID NO: 9, SEQ ID NO: 24, SEQ ID NO: 23, SEQ ID NO: 27, SEQ ID NO: 26, SEQ ID NO: 28, SEQ ID NO: 25, SEQ ID NO: 21, SEQ ID NO: 30, SEQ ID NO: 10, SEQ ID NO: 29, SEQ ID NO: 31, SEQ ID NO: 22 and SEQ ID NO: 33.

FIG. 13 shows a white light image and corresponding autoradiographic image of a frozen section of a mouse 4 hours after administration of 100 nmol of radiolabeled SEQ ID NO: 24 peptide. FIG. 13A illustrates a white light image of a frozen section of the mouse 4 hours after administration 100 nmol of radiolabeled SEQ ID NO: 24 peptide. FIG. 13B illustrates an autoradiographic image corresponding to FIG. 13A in which the $^{14}C$ signal identifies the radiolabeled SEQ ID NO: 24 peptide distribution in the cartilage of the mouse 4 hours after administration of 100 nmol.

FIG. 14 shows a white light image and corresponding autoradiographic image of a frozen section of a mouse 24 hours after administration of 100 nmol of radiolabeled SEQ ID NO: 24 peptide. FIG. 14A illustrates a white light image of a frozen section of the mouse 24 hours after administration 100 nmol of radiolabeled SEQ ID NO: 24 peptide. FIG. 14B illustrates an autoradiographic image corresponding to FIG. 14A in which the $^{14}C$ signal identifies the radiolabeled SEQ ID NO: 24 peptide distribution in the cartilage of the mouse 24 hours after administration of 100 nmol.

FIG. 15 shows white light images and corresponding autoradiographic images of frozen hind limb sections of a mouse 4 hours after administration of 100 nmol of radiolabeled SEQ ID NO: 24 peptide. FIG. 15A illustrates a white light image of a frozen section of a hind limb of a mouse 4 hours after administration 100 nmol of radiolabeled SEQ ID NO: 24 peptide. FIG. 15B illustrates an autoradiographic image corresponding to FIG. 15A in which the $^{14}C$ signal identifies the radiolabeled SEQ ID NO: 24 peptide distribution in the ankle and digit cartilage of a mouse 4 hours after administration of 100 nmol. FIG. 15C illustrates an autoradiographic image in which the $^{14}C$ signal identifies the radiolabeled SEQ ID NO: 24 peptide distribution in the ankle and digit cartilage of a mouse 4 hours after administration of 100 nmol.

FIG. 15D illustrates a white light image of a frozen section of a hind limb of a mouse 4 hours after administration 100 nmol of radiolabeled SEQ ID NO: 24 peptide. FIG. 15E illustrates an autoradiographic image corresponding to FIG. 15D in which the $^{14}C$ signal identifies the radiolabeled SEQ ID NO: 24 peptide distribution in the ankle and digit cartilage of a mouse 4 hours after administration of 100 nmol. FIG. 15F illustrates a white light image of a frozen section of a hind limb of a mouse 4 hours after administration 100 nmol of radiolabeled SEQ ID NO: 24 peptide. FIG. 15G illustrates an autoradiographic image corresponding to FIG. 15F in which the $^{14}C$ signal identifies the radiolabeled SEQ ID NO: 24 peptide distribution in the ankle and digit cartilage of a mouse 4 hours after administration of 100 nmol.

FIG. 16 shows white light images and corresponding autoradiographic images of frozen hind limb sections of a mouse 24 hours after administration of 100 nmol of radiolabeled SEQ ID NO: 24 peptide. FIG. 16A illustrates a white light image of a frozen section of a hind limb of a mouse 24 hours after administration 100 nmol of radiolabeled SEQ ID NO: 24 peptide. FIG. 16B illustrates an autoradiographic image corresponding to FIG. 16A in which the $^{14}C$ signal identifies the radiolabeled SEQ ID NO: 24 peptide distribution in the ankle and digit cartilage of a mouse 24 hours after administration of 100 nmol. FIG. 16C illustrates a white light image of a frozen section of a hind limb of a mouse 24 hours after administration 100 nmol of radiolabeled SEQ ID NO: 24 peptide. FIG. 16D illustrates an autoradiographic image corresponding to FIG. 16C in which the $^{14}C$ signal identifies the radiolabeled SEQ ID NO: 24 peptide distribution in the ankle and digit cartilage of a mouse 24 hours after administration of 100 nmol. FIG. 16E illustrates a white light image of a frozen section of a hind limb of a mouse 24 hours after administration 100 nmol of radiolabeled SEQ ID NO: 24 peptide. FIG. 16F illustrates an autoradiographic image corresponding to FIG. 16E in which the $^{14}C$ signal identifies the radiolabeled SEQ ID NO: 24 peptide distribution in the ankle and digit cartilage of a mouse 24 hours after administration of 100 nmol. FIG. 16G illustrates an autoradiographic image in which the $^{14}C$ signal identifies the radiolabeled SEQ ID NO: 24 peptide distribution in the ankle and digit cartilage of a mouse 24 hours after administration of 100 nmol.

FIG. 17 shows white light images and corresponding whole body fluorescence images of a mouse 3 hours after administration of 10 nmol SEQ ID NO: 111 peptide conjugated to a Cy5.5 fluorophore (SEQ ID NO: 111A). FIG. 17A illustrates a white light image of a frozen section of a mouse 3 hours after administration of 10 nmol SEQ ID NO: 111 peptide conjugated to a Cy5.5 fluorophore (SEQ ID NO: 111A). FIG. 17B illustrates a whole body fluorescence image corresponding to the section shown in FIG. 17A showing the fluorescence signal in the mouse 3 hours after administration of 10 nmol SEQ ID NO: 111 peptide conjugated to a Cy5.5 fluorophore (SEQ ID NO: 111A). FIG. 17C illustrates a white light image of a different frozen section of the mouse, 3 hours after administration of 10 nmol SEQ ID NO: 111 peptide conjugated to a Cy5.5 fluorophore (SEQ ID NO: 111A). FIG. 17D illustrates a whole body fluorescence image corresponding to the section shown in FIG. 17C showing the fluorescence signal in the mouse 3 hours after administration of 10 nmol SEQ ID NO: 111 peptide conjugated to a Cy5.5 fluorophore (SEQ ID NO: 111A). FIG. 17E illustrates a white light image of a different frozen section of the mouse, 3 hours after administration of 10 nmol SEQ ID NO: 111 peptide conjugated to a Cy5.5 fluorophore (SEQ ID NO: 111A). FIG. 17F illustrates a whole body fluorescence image corresponding to the section shown in FIG. 17E showing the fluorescence signal in the mouse 3 hours after administration of 10 nmol SEQ ID NO: 111 peptide conjugated to a Cy5.5 fluorophore (SEQ ID NO: 111A).

FIG. 18 shows white light images and corresponding whole body fluorescence images of a mouse administered 10 nmol of a peptide of SEQ ID NO: 111 conjugated to a Cy5.5 fluorophore (SEQ ID NO: 111A) at 24 hours post-administration. FIG. 18A illustrates an image of a frozen section of a mouse, 24 hours after administration of 10 nmol of a peptide of SEQ ID NO: 111 conjugated to a Cy5.5 fluorophore (SEQ ID NO: 111A). FIG. 18B illustrates the fluorescence signal in the mouse, corresponding to the section shown in FIG. 18A, 24 hours after administration of 10 nmol of a peptide of SEQ ID NO: 111 conjugated to a Cy5.5 fluorophore (SEQ ID NO: 111A). FIG. 18C illustrates an image of a different frozen section of the mouse, 24 hours after administration of 10 nmol of a peptide of SEQ ID NO: 111 conjugated to a Cy5.5 fluorophore (SEQ ID NO: 111A). FIG. 18D illustrates the fluorescence signal in the mouse, corresponding to the section shown in FIG. 18C, 24 hours after administration of 10 nmol of a peptide of SEQ ID NO: 111 conjugated to a Cy5.5 fluorophore (SEQ ID NO: 111A). FIG. 18E illustrates an image of a different frozen section of the mouse, 24 hours after administration of 10 nmol of a peptide of SEQ ID NO: 111 conjugated to a Cy5.5 fluorophore (SEQ ID NO: 111A). FIG. 18F illustrates a fluorescence signal in the mouse, corresponding to the section shown in FIG. 18E, 24 hours after administration of 10 nmol of a peptide of SEQ ID NO: 111 conjugated to a Cy5.5 fluorophore (SEQ ID NO: 111A).

FIG. 19 shows white light images and corresponding whole body fluorescence images of a mouse administered 10 nmol of a peptide of SEQ ID NO: 111 conjugated to a Cy5.5 fluorophore (SEQ ID NO: 111A) at 48 hours post-administration. FIG. 19A illustrates an image of a frozen section of a mouse, 48 hours after administration of 10 nmol of a peptide of SEQ ID NO: 111 conjugated to a Cy5.5 fluorophore (SEQ ID NO: 111A). FIG. 19B illustrates the fluorescence signal in the mouse, corresponding to the section shown in FIG. 19A, 48 hours after administration of 10 nmol of a peptide of SEQ ID NO: 111 conjugated to a Cy5.5 fluorophore (SEQ ID NO: 111A). FIG. 19C illustrates an image of a different frozen section of the mouse, 48 hours after administration of 10 nmol of a peptide of SEQ ID NO: 111 conjugated to a Cy5.5 fluorophore (SEQ ID NO: 111A). FIG. 19D illustrates the fluorescence signal in the mouse, corresponding to the section shown in FIG. 19C, 48 hours after administration of 10 nmol of a peptide of SEQ ID NO: 111 conjugated to a Cy5.5 fluorophore (SEQ ID NO: 111A).

FIG. 20 shows white light images and corresponding whole body fluorescence images of a mouse administered 10 nmol of a peptide of a peptide of SEQ ID NO: 111 conjugated to a Cy5.5 fluorophore (SEQ ID NO: 111A) at 72 hours post-administration. FIG. 20A illustrates an image of a frozen section of a mouse, 72 hours after administration of 10 nmol of a peptide of SEQ ID NO: 111 conjugated to a Cy5.5 fluorophore (SEQ ID NO: 111A). FIG. 20B illustrates the fluorescence signal in the mouse, corresponding to the section shown in FIG. 20A, 72 hours after administration of 10 nmol of a peptide of SEQ ID NO: 111 conjugated to a Cy5.5 fluorophore (SEQ ID NO: 111A). FIG. 20C illustrates an image of a different frozen section of the mouse, 72 hours after administration of 10 nmol of a peptide of SEQ ID NO: 111 conjugated to a Cy5.5 fluorophore (SEQ ID NO: 111A). FIG. 20D illustrates the fluorescence signal in the mouse, corresponding to the section shown in FIG. 20C, 72 hours after administration of 10 nmol of a peptide of SEQ ID NO: 111 conjugated to a Cy5.5 fluorophore (SEQ ID NO: 111A).

FIG. 21 shows IVIS fluorescence imaging of an isolated hind limb from a first mouse and an isolated hind limb from a second mouse after administration of 10 nmol SEQ ID NO: 111 peptide conjugated to a Cy5.5 fluorophore (SEQ ID NO: 111A). Areas of low signal intensity are shown in a thin solid line, areas of medium signal intensity are shown in a thick sold line, and areas of high signal intensity are shown in a thin dotted line. FIG. 21A shows the right hind limb with skin removed from a first mouse and from a second mouse 3 hours after peptide administration. FIG. 21B shows the right hind limb with muscle removed from a first mouse and from a second mouse 3 hours after peptide administration of 10 nmol SEQ ID NO: 111 peptide conjugated to a Cy5.5 fluorophore (SEQ ID NO: 111A). FIG. 21C shows the right hind limb with skin removed from a first mouse and from a second mouse 24 hours after peptide administration of 10 nmol SEQ ID NO: 111 peptide conjugated to a Cy5.5 fluorophore (SEQ ID NO: 111A). FIG. 21D shows the right hind limb with muscle removed from a first mouse and from a second mouse 24 hours after peptide administration of 10 nmol SEQ ID NO: 111 peptide conjugated to a Cy5.5 fluorophore (SEQ ID NO: 111A). FIG. 21E shows the right hind limb with skin removed from a first mouse and from a second mouse 48 hours after administration of 10 nmol SEQ ID NO: 111 peptide conjugated to a Cy5.5 fluorophore (SEQ ID NO: 111A). FIG. 21F shows the right hind limb with muscle removed from a first mouse and from a second mouse 48 hours after administration of 10 nmol SEQ ID NO: 111 peptide conjugated to a Cy5.5 fluorophore (SEQ ID NO: 111A). FIG. 21G shows the right hind limb with skin removed from a first mouse and from a second mouse 72 hours after peptide administration of 10 nmol SEQ ID NO: 111 peptide conjugated to a Cy5.5 fluorophore (SEQ ID NO: 111A). FIG. 21H shows the right hind limb with muscle removed from a first mouse and from a second mouse 72 hours after administration of 10 nmol SEQ ID NO: 111 peptide conjugated to a Cy5.5 fluorophore (SEQ ID NO: 111A).

FIG. 22 illustrates white light images and corresponding autoradiography images of frozen sections of a mouse, 5 minutes after administration of 100 nmol of a radiolabeled peptide of SEQ ID NO: 111. FIG. 22A illustrates a white light image of a frozen section of a mouse, 5 minutes after administration of 100 nmol of a radiolabeled peptide of SEQ ID NO: 111. FIG. 22B illustrates the $^{14}$C signal in a frozen section of a mouse, corresponding to the section shown in FIG. 22A, 5 minutes after administration of 100 nmol of a radiolabeled peptide of SEQ ID NO: 111. FIG. 22C illustrates a white light image of a different frozen section of a mouse, 5 minutes after administration of 100 nmol of a radiolabeled peptide of SEQ ID NO: 111. FIG. 22D illustrates the $^{14}$C signal in a frozen section of a mouse, corresponding to the section shown in FIG. 22C, 5 minutes after administration of 100 nmol of a radiolabeled peptide of SEQ ID NO: 111. FIG. 22E illustrates a white light image of a different frozen section of a mouse, 5 minutes after administration of 100 nmol of a radiolabeled SEQ ID NO: 111. FIG. 22F illustrates the $^{14}$C signal in a frozen section of a mouse, corresponding to the section shown in FIG. 22E, 5 minutes after administration of 100 nmol of a radiolabeled peptide of SEQ ID NO: 111. FIG. 22G illustrates a white light image of a different frozen section of a mouse, 5 minutes after administration of 100 nmol of a radiolabeled peptide of a SEQ ID NO: 111. FIG. 22H illustrates the $^{14}$C signal in a frozen section of a mouse, corresponding to the section shown in FIG. 22G, 5 minutes after administration of 100 nmol of a radiolabeled peptide of a SEQ ID NO: 111.

FIG. 23 illustrates white light images and corresponding autoradiography images of frozen sections of a mouse, 30 minutes after administration of 100 nmol of a radiolabeled peptide of SEQ ID NO: 111. FIG. 23A illustrates a white light image of a frozen section of a mouse, 30 minutes after administration of 100 nmol of a radiolabeled peptide of SEQ ID NO: 111. FIG. 23B illustrates the $^{14}$C signal in a frozen section of a mouse, corresponding to the section shown in FIG. 23A, 30 minutes after administration of 100 nmol of a radiolabeled peptide of SEQ ID NO: 111. FIG. 23C illustrates a white light image of a different frozen section of a mouse, 30 minutes after administration of 100 nmol of a radiolabeled peptide of SEQ ID NO: 111. FIG. 23D illustrates the $^{14}$C signal in a frozen section of a mouse, corresponding to the section shown in FIG. 23C, 30 minutes after administration of 100 nmol of a radiolabeled peptide of SEQ ID NO: 111. FIG. 23E illustrates a white light image of a different frozen section of the mouse, 30 minutes after administration of 100 nmol of a radiolabeled peptide of SEQ ID NO: 111. FIG. 23F illustrates the $^{14}$C signal in a frozen section of the mouse, corresponding to the section shown in FIG. 23E, 30 minutes after administration of 100 nmol of a radiolabeled peptide of SEQ ID NO: 111.

FIG. 24 illustrates white light images and corresponding autoradiography images of frozen sections from a mouse, 1 hour after administration of 100 nmol of a radiolabeled peptide of SEQ ID NO: 111. FIG. 24A illustrates a white light image of a frozen section of a mouse, 1 hour after administration of 100 nmol of a radiolabeled peptide of SEQ ID NO: 111. FIG. 24B illustrates the $^{14}$C signal in a frozen section of a mouse, corresponding to the section shown in FIG. 24A, 1 hour after administration of 100 nmol of a radiolabeled peptide of SEQ ID NO: 111. FIG. 24C illustrates a white light image of a different frozen section of a mouse, 1 hour after administration of 100 nmol of a radiolabeled peptide of SEQ ID NO: 111. FIG. 24D illustrates the $^{14}$C signal in a frozen section of a mouse, corresponding to the section shown in FIG. 24C, 1 hour after administration of 100 nmol of a radiolabeled peptide of SEQ ID NO: 111. FIG. 24E illustrates a white light image of a different frozen section of the mouse, 1 hour after administration of 100 nmol of a radiolabeled peptide of SEQ ID NO: 111. FIG. 24F illustrates the $^{14}$C signal in a frozen section of a mouse, corresponding to the section shown in FIG. 24E, 1 hour after administration of 100 nmol of a radiolabeled peptide of SEQ ID NO: 111. FIG. 24G illustrates a white light image of a different frozen section of the mouse, 1 hour after administration of 100 nmol of a radiolabeled peptide of SEQ ID NO: 111. FIG. 24H illustrates the $^{14}$C signal in a frozen section of a mouse, corresponding to the section shown in FIG. 24G, 1 hour after administration of 100 nmol of a radiolabeled peptide of SEQ ID NO: 111.

FIG. 25 illustrates white light images and corresponding autoradiography images of frozen sections from a mouse, 3 hours after administration of 100 nmol of a radiolabeled peptide of SEQ ID NO: 111. FIG. 25A illustrates a white light image of a frozen section of a mouse, 3 hours after administration of 100 nmol of a radiolabeled peptide of SEQ ID NO: 111. FIG. 25B illustrates the $^{14}$C signal in a frozen section of the mouse, corresponding to the section shown in FIG. 25A, 3 hours after administration of 100 nmol of a radiolabeled peptide of SEQ ID NO: 111. FIG. 25C illustrates a white light image of a different frozen section of a mouse, 3 hours after administration of 100 nmol of a radiolabeled peptide of SEQ ID NO: 111. FIG. 25D illustrates the $^{14}$C signal in a different frozen section of the mouse, corresponding to the section shown in FIG. 25C, 3 hours after administration of 100 nmol of a radiolabeled peptide of SEQ ID NO: 111. FIG. 25E illustrates the $^{14}$C signal in a different frozen section of a mouse, 3 hours after administration of 100 nmol of a radiolabeled peptide of SEQ ID NO: 111.

FIG. 26 illustrates white light images and corresponding autoradiography images of frozen sections from a mouse with ligated kidneys, 3 hours after administration of 100 nmol of a radiolabeled peptide of SEQ ID NO: 111. FIG. 26A illustrates a white light image of a frozen section of a mouse with ligated kidneys, 3 hours after administration of 100 nmol of a radiolabeled peptide of SEQ ID NO: 111. FIG. 26B illustrates the $^{14}$C signal in a frozen section of the mouse with ligated kidneys, corresponding to the section shown in FIG. 26A, 3 hours after administration of 100 nmol of a radiolabeled peptide of SEQ ID NO: 111. FIG. 26C illustrates a white light image of a different frozen section of the mouse with ligated kidneys, 3 hours after administration of 100 nmol of a radiolabeled peptide of SEQ ID NO: 111. FIG. 26D illustrates the $^{14}$C signal in a frozen section of the mouse with ligated kidneys, corresponding to the section shown in FIG. 26C, 3 hours after administration of 100 nmol of a radiolabeled peptide of SEQ ID NO: 111. FIG. 26E illustrates a white light image of a different frozen section of a mouse with ligated kidneys, 3 hours after administration of 100 nmol of a radiolabeled peptide of SEQ ID NO: 111. FIG. 26F illustrates the $^{14}$C signal in a frozen section of the mouse with ligated kidneys, corresponding to section shown in FIG. 26E, 3 hours after administration of 100 nmol of a radiolabeled peptide of SEQ ID NO: 111.

FIG. 27 illustrates white light images and corresponding autoradiography images of frozen sections from a mouse, 8 hours after administration of 100 nmol of a radiolabeled peptide of SEQ ID NO: 111. FIG. 27A illustrates a white light image of a frozen section of a mouse, 8 hours after administration of 100 nmol of a radiolabeled peptide of SEQ ID NO: 111. FIG. 27B illustrates the $^{14}$C signal in a frozen section of the mouse, corresponding to the section shown in FIG. 27A, 8 hours after administration of 100 nmol of a radiolabeled peptide of SEQ ID NO: 111. FIG. 27C illustrates an image of a different frozen section of a mouse, 8 hours after administration of 100 nmol of a radiolabeled peptide of SEQ ID NO: 111. FIG. 27D illustrates the $^{14}$C signal in a frozen section of the mouse, corresponding to the section shown in FIG. 27C, 8 hours after administration of 100 nmol of a radiolabeled peptide of SEQ ID NO: 111. FIG. 27E illustrates an image of a different frozen section of a mouse, 8 hours after administration of 100 nmol of a radiolabeled peptide of SEQ ID NO: 111. FIG. 27F illustrates the $^{14}$C signal in a frozen section of the mouse, corresponding to the section shown in FIG. 27E, 8 hours after administration of 100 nmol of a radiolabeled peptide of SEQ ID NO: 111. FIG. 27G illustrates a white light image of a different frozen section of a mouse, 8 hours after administration of 100 nmol of a radiolabeled peptide of SEQ ID NO: 111. FIG. 27H illustrates the $^{14}$C signal in a frozen section of a mouse, corresponding to the section shown in FIG. 27G, 8 hours after administration of 100 nmol of a radiolabeled peptide of SEQ ID NO: 111.

FIG. 28 illustrates white light images and corresponding autoradiography images of frozen sections from a mouse, 24 hours after administration of 100 nmol of a radiolabeled peptide of SEQ ID NO: 111. FIG. 28A illustrates a white light image of a frozen section of a mouse, 24 hours after administration of 100 nmol of a radiolabeled peptide of SEQ ID NO: 111. FIG. 28B illustrates the $^{14}$C signal in a frozen section of the mouse, corresponding to the section shown in FIG. 28A, 24 hours after administration of 100 nmol of a radiolabeled peptide of SEQ ID NO: 111. FIG. 28C illustrates a white light image of a different frozen section of a mouse, 24 hours after administration of 100 nmol of a radiolabeled peptide of SEQ ID NO: 111. FIG. 28D illustrates the $^{14}$C signal in a frozen section of the mouse, corresponding to the section shown in FIG. 28C, 24 hours after administration of 100 nmol of a radiolabeled peptide of SEQ ID NO: 111. FIG. 28E illustrates a white light image of a different frozen section of a mouse, 24 hours after administration of 100 nmol of a radiolabeled peptide of SEQ ID NO: 111. FIG. 28F illustrates the $^{14}$C signal in a frozen section of the mouse, corresponding to the section shown in FIG. 28E, 24 hours after administration of 100 nmol of a radiolabeled peptide of SEQ ID NO: 111.

FIG. 29 illustrates white light images and corresponding autoradiography images of frozen sections from a mouse, 48 hours after administration of 100 nmol of a radiolabeled peptide of SEQ ID NO: 111. FIG. 29A illustrates a white light image of a frozen section of a mouse, 48 hours after administration of 100 nmol of a radiolabeled peptide of SEQ ID NO: 111. FIG. 29B illustrates the $^{14}$C signal in a frozen section of the mouse, corresponding to the section shown in FIG. 29A, 48 hours after administration of 100 nmol of a radiolabeled peptide of SEQ ID NO: 111. FIG. 29C illustrates a white light image of a different frozen section of a mouse, 48 hours after administration of 100 nmol of a radiolabeled peptide of SEQ ID NO: 111. FIG. 29D illustrates the $^{14}$C signal in a frozen section of the mouse, corresponding to the section shown in FIG. 29C, 48 hours after administration of 100 nmol of a radiolabeled peptide of SEQ ID NO: 111. FIG. 29E illustrates a white light image of a different frozen section of the mouse, 48 hours after administration of 100 nmol of a radiolabeled peptide of SEQ ID NO: 111. FIG. 29F illustrates the $^{14}$C signal in a frozen section of the mouse, corresponding to the section shown in FIG. 29E, 48 hours after administration of 100 nmol of a radiolabeled peptide of SEQ ID NO: 111. FIG. 29G illustrates a white light image of a different frozen section of a mouse, 48 hours after administration of 100 nmol of a radiolabeled peptide of SEQ ID NO: 111. FIG. 29H illustrates the $^{14}$C signal in a frozen section of the mouse, corresponding to the section shown in FIG. 29G, 48 hours after administration of 100 nmol of a radiolabeled peptide of SEQ ID NO: 111.

FIG. 30 illustrates white light images and corresponding autoradiography images of frozen sections from a mouse, 3 hours after administration of 100 nmol of a radiolabeled peptide of SEQ ID NO: 109. FIG. 30A illustrates a white light image of a frozen section of a mouse, 3 hours after administration of 100 nmol of a radiolabeled peptide of SEQ ID NO: 109. FIG. 30B illustrates the $^{14}$C signal in a frozen section of a mouse, corresponding to the section shown in FIG. 30A, 3 hours after administration of 100 nmol of a radiolabeled peptide of SEQ ID NO: 109. FIG. 30C illustrates a white light image of a different frozen section of a mouse, 3 hours after administration of 100 nmol of a radiolabeled peptide of SEQ ID NO: 109. FIG. 30D illustrates the $^{14}$C signal in a frozen section of the mouse, corresponding to the section shown in FIG. 30C, 3 hours after administration of 100 nmol of a radiolabeled peptide of SEQ ID NO: 109. FIG. 30E illustrates a white light image of a different frozen section of a mouse, 3 hours after administration of 100 nmol of a radiolabeled peptide of SEQ ID NO: 109. FIG. 30F illustrates the $^{14}$C signal in a frozen section of the mouse, corresponding to the section shown in FIG. 30E, 3 hours after administration of 100 nmol of a radiolabeled peptide of SEQ ID NO: 109.

FIG. 31 illustrates white light images and a corresponding autoradiography images of frozen sections from a mouse, 24 hours after administration of 100 nmol of a radiolabeled peptide of SEQ ID NO: 109. FIG. 31A illustrates a white light image of a frozen section of a mouse, 24 hours after administration of 100 nmol of a radiolabeled peptide of SEQ ID NO: 109. FIG. 31B illustrates the $^{14}$C signal in a frozen section of the mouse, corresponding to the section shown in FIG. 31A, 24 hours after administration of 100 nmol of a radiolabeled peptide of SEQ ID NO: 109. FIG. 31C illustrates a white light image of a different frozen section of the mouse, 24 hours after administration of 100 nmol of a radiolabeled peptide of SEQ ID NO: 109. FIG. 31D illustrates the $^{14}$C signal in a frozen section of the mouse, corresponding to the section shown in FIG. 31C, 24 hours after administration of 100 nmol of a radiolabeled peptide of SEQ ID NO: 109. FIG. 31E illustrates a white light image of a different frozen section of the mouse, 24 hours after administration of 100 nmol of a radiolabeled peptide of SEQ ID NO: 109. FIG. 31F illustrates the $^{14}$C signal in a frozen section of the mouse, corresponding to the section shown in FIG. 31E, 24 hours after administration of 100 nmol of a radiolabeled peptide of SEQ ID NO: 109.

FIG. 32 illustrates white light images and corresponding autoradiography images of frozen sections from a mouse 3 hours after administration of 100 nmol of a radiolabeled peptide of SEQ ID NO: 110. FIG. 32A illustrates a white light image of a frozen section of a mouse, 3 hours after administration of 100 nmol of a radiolabeled peptide of SEQ ID NO: 110. FIG. 32B illustrates the $^{14}$C signal in a frozen section of the mouse, corresponding to the section shown in FIG. 32A, 3 hours after administration of 100 nmol of a radiolabeled peptide of SEQ ID NO: 110. FIG. 32C illustrates a white light image of a different frozen section of a mouse, 3 hours after administration of 100 nmol of a radiolabeled peptide of SEQ ID NO: 110. FIG. 32D illustrates the $^{14}$C signal in a frozen section of the mouse, corresponding to the section shown in FIG. 32C, 3 hours after administration of 100 nmol of a radiolabeled peptide of SEQ ID NO: 110. FIG. 32E illustrates a white light image of a different frozen section of a mouse, 3 hours after administration of 100 nmol of a radiolabeled peptide of SEQ ID NO: 110. FIG. 32F illustrates the $^{14}$C signal in a frozen section of the mouse, corresponding to the section shown in FIG. 32E, 3 hours after administration of 100 nmol of a radiolabeled peptide of SEQ ID NO: 110. FIG. 32G illustrates a white light image of a different frozen section of a mouse, 3 hours after administration of 100 nmol of a radiolabeled peptide of SEQ ID NO: 110. FIG. 32H illustrates the $^{14}$C signal in a frozen section of the mouse, corresponding to the section shown in FIG. 32G, 3 hours after administration of 100 nmol of a radiolabeled peptide of SEQ ID NO: 110.

FIG. 33 illustrates white light images and a corresponding autoradiography images of frozen sections from a mouse, 24 hours after administration of 100 nmol of a radiolabeled peptide of SEQ ID NO: 110. FIG. 33A illustrates a white light image of a frozen section of a mouse, 24 hours after administration of 100 nmol of a radiolabeled peptide of SEQ ID NO: 110. FIG. 33B illustrates the $^{14}$C signal in a frozen section of the mouse, corresponding to the section shown in FIG. 33A, 24 hours after administration of 100 nmol of a radiolabeled peptide of SEQ ID NO: 110. FIG. 33C illustrates a white light image of a different frozen section of the mouse, 24 hours after administration of 100 nmol of a radiolabeled peptide of SEQ ID NO: 110. FIG. 33D illustrates the $^{14}$C signal in a frozen section of the mouse, corresponding to the section shown in FIG. 33C, 24 hours after administration of 100 nmol of a radiolabeled peptide of SEQ ID NO: 110. FIG. 33E illustrates a white light image of a different frozen section of the mouse, 24 hours after administration of 100 nmol of a radiolabeled peptide of SEQ ID NO: 110. FIG. 33F illustrates the $^{14}$C signal in a frozen section of the mouse, corresponding to the section shown in FIG. 33E, 24 hours after administration of 100 nmol of a radiolabeled peptide of SEQ ID NO: 110.

FIG. 34 illustrates white light images and corresponding autoradiography images of frozen sections from a mouse 3 hours after administration of 100 nmol of a radiolabeled peptide of SEQ ID NO: 114. FIG. 34A illustrates a white light image of a frozen section of a mouse, 3 hours after administration of 100 nmol of a radiolabeled peptide of SEQ ID NO: 114. FIG. 34B illustrates the $^{14}$C signal in a frozen section of the mouse, corresponding to the section shown in FIG. 34A, 3 hours after administration of 100 nmol of a radiolabeled peptide of SEQ ID NO: 114. FIG. 34C illustrates a white light image of a different frozen section of a mouse, 3 hours after administration of 100 nmol of a radiolabeled peptide of SEQ ID NO: 114. FIG. 34D illustrates the $^{14}$C signal in a frozen section of a mouse, corresponding to the section shown in FIG. 34C, 3 hours after administration of 100 nmol of a radiolabeled peptide of SEQ ID NO: 114. FIG. 34E illustrates a white light image of a different frozen section of a mouse, 3 hours after administration of 100 nmol of a radiolabeled peptide of SEQ ID NO: 114. FIG. 34F illustrates the $^{14}$C signal in a frozen section of the mouse, corresponding to the section shown in FIG. 34E, 3 hours after administration of 100 nmol of a radiolabeled peptide of SEQ ID NO: 114.

FIG. 35 illustrates white light images and corresponding autoradiography images of frozen sections from a mouse, 24 hours after administration of 100 nmol of a radiolabeled peptide of SEQ ID NO: 114. FIG. 35A illustrates a white light image of a frozen section of a mouse, 24 hours after administration of 100 nmol of a radiolabeled peptide of SEQ ID NO: 114. FIG. 35B illustrates the $^{14}$C signal in a frozen section of the mouse, corresponding to the section shown in FIG. 35A, 24 hours after administration of 100 nmol of a radiolabeled peptide of SEQ ID NO: 114. FIG. 35C illustrates a white light image of a different frozen section of a mouse, 24 hours after administration of 100 nmol of a radiolabeled peptide of SEQ ID NO: 114. FIG. 35D illustrates the $^{14}$C signal in a frozen section of the mouse, corresponding to the section shown in FIG. 35C, 24 hours after administration of 100 nmol of a radiolabeled peptide of SEQ ID NO: 114. FIG. 35E illustrates a white light image of a different frozen section of a mouse, 24 hours after administration of 100 nmol of a radiolabeled peptide of SEQ ID NO: 114. FIG. 35F illustrates the $^{14}$C signal in a frozen section of the mouse, corresponding to the section shown in FIG. 35E, 24 hours after administration of 100 nmol of a radiolabeled peptide of SEQ ID NO: 114.

FIG. 36 illustrates white light images and corresponding autoradiography images of frozen sections from a mouse, 3 hours after administration of 100 nmol of a radiolabeled peptide of SEQ ID NO: 200. FIG. 36A illustrates a white light image of a frozen section of a mouse, 3 hours after administration of 100 nmol of a radiolabeled peptide of SEQ ID NO: 200. FIG. 36B illustrates the $^{14}$C signal in a frozen section of the mouse, corresponding to the section shown in FIG. 36A, 3 hours after administration of 100 nmol of a radiolabeled peptide of SEQ ID NO: 200. FIG. 36C illustrates a white light image of a different frozen section of a mouse, 3 hours after administration of 100 nmol of a radiolabeled peptide of SEQ ID NO: 200. FIG. 36D illustrates the $^{14}$C signal in a frozen section of the mouse, corresponding to the section shown in FIG. 36C, 3 hours after administration of 100 nmol of a radiolabeled peptide of SEQ ID NO: 200. FIG. 36E illustrates a white light image of a different frozen section of a mouse, 3 hours after administration of 100 nmol of a radiolabeled peptide of SEQ ID NO: 200. FIG. 36F illustrates the $^{14}$C signal in a frozen section of the mouse, corresponding to the section shown in FIG. 36E, 3 hours after administration of 100 nmol of a radiolabeled peptide of SEQ ID NO: 200.

FIG. 37 illustrates white light images and corresponding autoradiography images of frozen sections from a mouse, 24 hours after administration of 100 nmol of a radiolabeled peptide of SEQ ID NO: 200. FIG. 37A illustrates a white light image of a frozen section of a mouse, 24 hours after administration of 100 nmol of a radiolabeled peptide of SEQ ID NO: 200. FIG. 37B illustrates the $^{14}$C signal in a frozen section of the mouse, corresponding to the section shown in FIG. 37A, 24 hours after administration of 100 nmol of a radiolabeled peptide of SEQ ID NO: 200. FIG. 37C illustrates a white light image of a different frozen section of the mouse, 24 hours after administration of 100 nmol of a radiolabeled peptide of SEQ ID NO: 200. FIG. 37D illustrates the $^{14}$C signal in a frozen section of the mouse, corresponding to the section shown in FIG. 37C, 24 hours after administration of 100 nmol of a radiolabeled peptide of SEQ ID NO: 200. FIG. 37E illustrates a white light image of a different frozen section of the mouse, 24 hours after administration of 100 nmol of a radiolabeled peptide of SEQ ID NO: 200. FIG. 37F illustrates the $^{14}$C signal in a frozen section of the mouse, corresponding to the section shown in FIG. 37E, 24 hours after administration of 100 nmol of a radiolabeled peptide of SEQ ID NO: 200. FIG. 37G illustrates a white light image of a different frozen section of the mouse, 24 hours after administration of 100 nmol of a radiolabeled peptide of SEQ ID NO: 200. FIG. 37H illustrates the $^{14}$C signal in a frozen section of a mouse, corresponding to the section shown in FIG. 37G, 24 hours after administration of 100 nmol of a radiolabeled peptide of SEQ ID NO: 200.

FIG. 38 illustrates white light images and corresponding autoradiography images of frozen sections a mouse with ligated kidneys, 3 hours after administration of 100 nmol a radiolabeled peptide of SEQ ID NO: 195 (GSNFKVEG-ACSKPCRKYCIDKGARNGKCINGRCHCYY). FIG. 38A illustrates a white light image of a frozen section of a mouse with ligated kidneys, 3 hours after administration of 100 nmol a radiolabeled peptide of SEQ ID NO: 195. FIG. 38B illustrates the $^{14}$C signal in a frozen section of a mouse with ligated kidneys, corresponding to the section shown in FIG. 38A, 3 hours after administration of 100 nmol a radiolabeled peptide of SEQ ID NO: 195. FIG. 38C illustrates a white light image of a different frozen section of the mouse with ligated kidneys, 3 hours after administration of 100 nmol a radiolabeled peptide of SEQ ID NO: 195. FIG. 38D illustrates the $^{14}$C signal in a frozen section of the mouse with ligated kidneys, corresponding to the section shown in FIG. 38C, 3 hours after administration of 100 nmol a radiolabeled peptide of SEQ ID NO: 195.

FIG. 39 illustrates white light images and corresponding autoradiography images of frozen sections from a mouse with ligated kidneys, 3 hours after administration of 100 nmol a radiolabeled peptide of SEQ ID NO: 196. FIG. 39A illustrates a white light image of a frozen section of a mouse with ligated kidneys, 3 hours after administration of 100 nmol a radiolabeled peptide of SEQ ID NO: 196. FIG. 39B illustrates the $^{14}$C signal in a frozen section of the mouse with ligated kidneys, corresponding to the section shown in FIG. 39A, 3 hours after administration of 100 nmol a radiolabeled peptide of SEQ ID NO: 196. FIG. 39C illustrates a white light image of a different frozen section of a mouse with ligated kidneys, 3 hours after administration of 100 nmol a radiolabeled peptide of SEQ ID NO: 196. FIG. 39D illustrates the $^{14}$C signal in a frozen section of the mouse with ligated kidneys, corresponding to the section shown in FIG. 39C, 3 hours after administration of 100 nmol a radiolabeled peptide of SEQ ID NO: 196.

FIG. 40 illustrates white light images and corresponding autoradiography images of frozen sections from a mouse with ligated kidneys, 3 hours after administration of 100 nmol a radiolabeled peptide of SEQ ID NO: 197 (GSDRDSCIDKSRCSKYGYYQECQDCCKK-AGHNGGTCMFFKCKCA). FIG. 40A illustrates a white light image of a frozen section of a mouse with ligated kidneys, 3 hours after administration of 100 nmol a radiolabeled peptide of SEQ ID NO: 197. FIG. 40B illustrates the $^{14}$C signal in a frozen section of a mouse with ligated kidneys, corresponding to the section shown in FIG. 40A, 3 hours after administration of 100 nmol a radiolabeled peptide of SEQ ID NO: 197. FIG. 40C illustrates a white light image of a different frozen section of the mouse with ligated kidneys, 3 hours after administration of 100 nmol a radiolabeled peptide of SEQ ID NO: 197. FIG. 40D illustrates the $^{14}$C signal in a frozen section of a mouse with ligated kidneys, corresponding to the section shown in FIG. 40C, 3 hours after administration of 100 nmol a radiolabeled peptide of SEQ ID NO: 197.

FIG. 41 illustrates white light images and corresponding autoradiography images of frozen sections from a mouse with ligated kidneys, 3 hours after administration of 100 nmol a radiolabeled peptide of SEQ ID NO: 198. FIG. 41A illustrates a white light image of a frozen section of a mouse with ligated kidneys, 3 hours after administration of 100 nmol a radiolabeled peptide of SEQ ID NO: 198. FIG. 41B illustrates the $^{14}$C signal in a frozen section of the mouse with ligated kidneys, corresponding to the section shown in FIG. 41A, 3 hours after administration of 100 nmol a radiolabeled peptide of SEQ ID NO: 198. FIG. 41C illustrates a white light image of a different frozen section of a mouse with ligated kidneys, 3 hours after administration of 100 nmol a radiolabeled peptide of SEQ ID NO: 198. FIG. 41D illustrates the $^{14}$C signal in a frozen section of a mouse with ligated kidneys, corresponding to the section shown in FIG. 41C, 3 hours after administration of 100 nmol a radiolabeled peptide of SEQ ID NO: 198.

FIG. 42 illustrates white light images and corresponding autoradiography images of frozen sections from a mouse with ligated kidneys, 3 hours after administration of 100 nmol a radiolabeled linearized peptide of SEQ ID NO: 434 (GSGVPINVRSRGSRDSLDPSRRAGMRGRSINSRSH-STP). FIG. 42A illustrates a white light image of a frozen section of a mouse with ligated kidneys, 3 hours after administration of 100 nmol a radiolabeled linearized peptide of SEQ ID NO: 434. FIG. 42B illustrates the $^{14}$C signal in a frozen section of the mouse with ligated kidneys, corresponding to the section shown in FIG. 42A, 24 hours after administration of 100 nmol a radiolabeled linearized peptide of SEQ ID NO: 434. FIG. 42C illustrates a white light image of a different frozen section of the mouse with ligated kidneys, 3 hours after administration of 100 nmol a radiolabeled linearized peptide of SEQ ID NO: 434. FIG. 42D illustrates the $^{14}$C signal in a frozen section of the mouse with ligated kidneys, corresponding to the section shown in FIG. 42C, 3 hours after administration of 100 nmol a radiolabeled linearized peptide of SEQ ID NO: 434. FIG. 42E illustrates a white light image of a different frozen section of a mouse with ligated kidneys, 3 hours after administration of 100 nmol a radiolabeled linearized peptide of SEQ ID NO: 434. FIG. 42F illustrates the $^{14}$C signal in a frozen section of the mouse with ligated kidneys, corresponding to the section shown in FIG. 42E, 3 hours after administration of 100 nmol a radiolabeled linearized peptide of SEQ ID NO: 434. FIG. 42G illustrates a white light image of a different frozen section of the mouse with ligated kidneys, 3 hours after administration of 100 nmol a radiolabeled linearized peptide of SEQ ID NO: 434. FIG. 42H illustrates the $^{14}$C signal in a frozen section of the mouse with ligated kidneys, corresponding to the section shown in FIG. 42G, 3 hours after administration of 100 nmol a radiolabeled linearized peptide of SEQ ID NO: 434.

FIG. 43 illustrates white light images and corresponding autoradiography images of frozen sections from a mouse, 3 hours after administration of 100 nmol a radiolabeled linearized peptide of SEQ ID NO: 434. FIG. 43A illustrates a white light image of a frozen section of a mouse, 3 hours after administration of 100 nmol a radiolabeled linearized peptide of SEQ ID NO: 434. FIG. 43B illustrates the $^{14}$C signal in a frozen section of the mouse, corresponding to the section shown in FIG. 43A, 3 hours after administration of 100 nmol a radiolabeled linearized peptide of SEQ ID NO: 434. FIG. 43C illustrates a white light image of a different frozen section of a mouse, 3 hours after administration of 100 nmol a radiolabeled linearized peptide of SEQ ID NO: 434. FIG. 43D illustrates the $^{14}$C signal in a frozen section of the mouse, corresponding to the section shown in FIG. 43C, 3 hours after administration of 100 nmol a radiolabeled linearized peptide of SEQ ID NO: 434. FIG. 43E illustrates a white light image of a different frozen section of the mouse, 3 hours after administration of 100 nmol a radiolabeled linearized peptide of SEQ ID NO: 434. FIG. 43F illustrates the $^{14}$C signal in a frozen section of the mouse, corresponding to the section shown in FIG. 43E, 3 hours after administration of 100 nmol a radiolabeled linearized peptide of SEQ ID NO: 434. FIG. 43G illustrates a white light image of a different frozen section of a mouse, 3 hours after administration of 100 nmol a radiolabeled linearized peptide of SEQ ID NO: 434. FIG. 43H illustrates the $^{14}$C signal in a frozen section of a mouse, corresponding to the section shown in FIG. 43G, 3 hours after administration of 100 nmol a radiolabeled linearized peptide of SEQ ID NO: 434.

FIG. 44 illustrates white light images and corresponding autoradiography images of frozen sections from a mouse, 24 hours after administration of 100 nmol a radiolabeled linearized peptide of SEQ ID NO: 434. FIG. 44A illustrates a white light image of a frozen section of a mouse, 24 hours after administration of 100 nmol a radiolabeled linearized peptide of SEQ ID NO: 434. FIG. 44B illustrates the $^{14}$C signal in a frozen section of the mouse, corresponding to the section shown in FIG. 44A, 24 hours after administration of 100 nmol a radiolabeled linearized peptide of SEQ ID NO: 434. FIG. 44C illustrates a white light image of a different frozen section of a mouse, 24 hours after administration of 100 nmol a radiolabeled linearized peptide of SEQ ID NO: 434. FIG. 44D illustrates the $^{14}$C signal in a frozen section of the mouse, corresponding to the section shown in FIG.

44C, 24 hours after administration of 100 nmol a radiolabeled linearized peptide of SEQ ID NO: 434. FIG. 44E illustrates an image of a different frozen section of the mouse, 24 hours after administration of 100 nmol a radiolabeled linearized peptide of SEQ ID NO: 434. FIG. 44F illustrates the $^{14}$C signal in a frozen section of the mouse, corresponding to the section shown in FIG. 44E, 24 hours after administration of 100 nmol a radiolabeled linearized peptide of SEQ ID NO: 434. FIG. 44G illustrates a white light image of a different frozen section of a mouse, 24 hours after administration of 100 nmol a radiolabeled linearized peptide of SEQ ID NO: 434. FIG. 44H illustrates the $^{14}$C signal in a frozen section of the mouse, corresponding to the section shown in FIG. 44G, 24 hours after administration of 100 nmol a radiolabeled linearized peptide of SEQ ID NO: 434.

FIG. 48 illustrates structural analysis of peptides of SEQ ID NO: 28, SEQ ID NO: 23, and SEQ ID NO: 27. FIG. 48A illustrates the structural analysis of a peptide of SEQ ID NO: 28 and displays the contiguous surface of positive charge and the position of positively charged residues. FIG. 48B illustrates the structural analysis of a peptide of SEQ ID NO: 23 and displays the contiguous surface of positive charge and the position of positively charged residues. FIG. 48C illustrates the structural analysis of a peptide of SEQ ID NO: 27 and displays the contiguous surface of positive charge and the position of positively charged residues. FIG. 48D illustrates the structural analysis of a peptide of SEQ ID NO: 111 and displays the contiguous surface of positive charge and the position of positively charged residues.

FIG. 49 illustrates HPLC chromatograms of peptides of SEQ ID NO: 24 and SEQ ID NO: 111 in different buffer conditions. FIG. 49A illustrates the HPLC trace of a peptide of SEQ ID NO: 24 in PBS. FIG. 49B illustrates the HPLC trace of a peptide of SEQ ID NO: 24 in DTT in PBS. FIG. 49C illustrates the HPLC trace of a peptide of SEQ ID NO: 24 in 50 U trypsin and 1 mg/ml inhibitor in PBS. FIG. 49D illustrates the HPLC trace of a peptide of SEQ ID NO: 24 in 50 U trypsin, 1 mg/ml inhibitor, and DTT in PBS. FIG. 49E illustrates the HPLC trace of a peptide of SEQ ID NO: 111 in PBS. FIG. 49F illustrates the HPLC trace of a peptide of SEQ ID NO: 111 in DTT in PBS. FIG. 49G illustrates the HPLC trace of a peptide of SEQ ID NO: 111 in 50 U trypsin and 1 mg/ml inhibitor in PBS. FIG. 49H illustrates the HPLC trace of a peptide of SEQ ID NO: 111 in 50 U trypsin, 1 mg/ml inhibitor, and DTT in PBS.

FIG. 50 illustrates alignment of SEQ ID NO: 486 with SEQ ID NO: 239, SEQ ID NO: 486 with SEQ ID NO: 487, and SEQ ID NO: 486 with SEQ ID NO: 422. FIG. 50A illustrates the alignment of the peptide of SEQ ID NO: 486 with the peptide of SEQ ID NO: 239. Boxes delineate conserved positively charged residues. FIG. 50B illustrates the alignment of the peptide of SEQ ID NO: 486 with the peptide of SEQ ID NO: 487. Boxes delineate conserved positively charged residues. FIG. 50C illustrates the alignment of the peptide of SEQ ID NO: 486 with the peptide of SEQ ID NO: 422. Boxes delineate conserved positively charged residues.

FIG. 51 illustrates the alignment of the peptide of SEQ ID NO: 243 with the peptide of SEQ ID NO: 423. Boxes delineate conserved positively charged residues.

FIG. 67 shows the HPLC chromatograms of various peptides and the mass spectrometry results of various peptides after direct-infusion electrospray mass spectrometry. All peptides tested are shown under reducing and non-reducing conditions.

FIG. 68 shows the concentration of a radiolabeled peptide of SEQ ID NO: 24 in plasma after administration of the peptide to a mouse. FIG. 68A shows the concentration of peptide in plasma after intravenous (IV) administration of 20 nmol of a radiolabeled peptide of SEQ ID NO: 24 and oral (PO) administration of 100 nmol the radiolabeled peptide of SEQ ID NO: 24, as quantified by measuring the $^{14}C$ signal using liquid scintillation counting. The delivered dose of $^{14}C$ was 4.8 µCi for intravenous administration and 24 µCi for oral administration. Time points examined included 0.08, 0.5, 1, 3, 8, 24, 48 hours and three mice were examined per time point. FIG. 68B shows the percent of administered peptide dose recovered in plasma after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 for intravenous administration and 24 µCi for oral administration. Time points examined included 0.08, 0.5, 1, 3, 8, 24, 48 hours and three mice were examined per time point. FIG. 68C shows the intensity of peptide and peptide fragment peaks in plasma as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 0.5, 1, and 3 hours.

FIG. 69 shows the concentration of a radiolabeled peptide of SEQ ID NO: 24 in urine after administration of the peptide to a mouse. FIG. 69A shows the concentration of peptide in urine after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 µCi for intravenous administration and 24 µCi for oral administration. Time points examined included 0.08, 0.5, 1, 3, 8, 24, 48 hours and three mice were examined per time point. FIG. 69B shows the intensity of peptide and peptide fragment peaks in urine as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 0.5, 1, 3, 8, 24, and 48 hours.

FIG. 70 shows the concentration of a radiolabeled peptide of SEQ ID NO: 24 in urine after administration of the peptide to a mouse. FIG. 70A shows the concentration of peptide in feces after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 µCi for intravenous administration and 24 µCi for oral administration. Time points examined included 0.08, 0.5, 1, 3, 8, 24, 48 hours and three mice were examined per time point. FIG. 70B shows the intensity of peptide and peptide fragment peaks in feces as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 3 and 8 hours.

FIG. 71 illustrates HPLC chromatograms of two peptides after exposure to reducing agents, proteinases, and/or simulated gastric fluid conditions. FIG. 71A illustrates the HPLC trace of a peptide of SEQ ID NO: 24 incubated in PBS. FIG. 71B illustrates the HPLC trace of a peptide of SEQ ID NO: 24 incubated in DTT in PBS. FIG. 71C illustrates the HPLC trace of a peptide of SEQ ID NO: 24 incubated in simulated gastric fluid (SGF). FIG. 71D illustrates the HPLC trace of a peptide of SEQ ID NO: 24 incubated in 500 U pepsin in SGF. FIG. 71E illustrates the HPLC trace of a peptide of SEQ ID NO: 24 incubated in 500 U pepsin, 0.5 M Tris, and DTT in SGF. FIG. 71F illustrates the HPLC trace of a peptide of SEQ ID NO: 111 incubated in PBS. FIG. 71G illustrates the HPLC trace of a peptide of SEQ ID NO: 111 incubated in DTT in PBS. FIG. 71H illustrates the HPLC trace of a peptide of SEQ ID NO: 111 incubated in simulated gastric fluid (SGF). FIG. 71I illustrates the HPLC trace of a peptide of SEQ ID NO: 111 incubated in 500 U pepsin in SGF. FIG. 71J illustrates the HPLC trace of a peptide of SEQ ID NO: 111 incubated in 500 U pepsin, 0.5 M Tris, and DTT in SGF.

FIG. 72 illustrates HPLC chromatograms of peptides of SEQ ID NO: 111 and SEQ ID NO: 434 after exposure to a range of conditions including oxidative, reductive, and acidic conditions as well as after exposure to proteinases. FIG. 72A illustrates the HPLC trace of a peptide of SEQ ID NO: 111 under reducing and acidic conditions. FIG. 72B illustrates the HPLC trace of a peptide of SEQ ID NO: 111 under various combinations of reducing agents and proteases including 10 mM DTT in 500 U pepsin, 500 U pepsin, 10 mM DTT in 50 U trypsin, and 50 U trypsin. FIG. 72C illustrates the HPLC trace of a peptide of SEQ ID NO: 434 under various protease conditions including in 500 U pepsin, in 50 U trypsin, non-reducing (NR, oxidized conditions) in simulated gastric fluid (SGF) at pH 1.05, and NR.

FIG. 73 illustrates alignment of peptides within the pfam00451:toxin_2 structural class family of SEQ ID NO: 436-SEQ ID NO: 482. Boxed and bolded residues indicate relative conservation of sequence while non-boxed and non-bolded residues indicate areas of higher sequence variability.

FIG. 74 illustrates alignment of a peptide of SEQ ID NO: 436 from the pfam00451:toxin 2 structural class family with a cartilage homing peptide of this disclosure of SEQ ID NO: 24. Asterisks indicate positions with a single, fully conserved residue, a colon indicates conservation between groups of strongly similar properties (scoring >0.5 in the Gonnet point accepted mutation (PAM) 250 matrix), and a period indicates conservation between groups of weakly similar properties (scoring ≤0.5 in the Gonnet PAM 250 matrix).

DETAILED DESCRIPTION

Figure 1I:
FIG. 1I illustrates the $^{14}$C signal in the cartilage of an animal treated with a peptide of SEQ ID NO: 21.
Figure 1J:
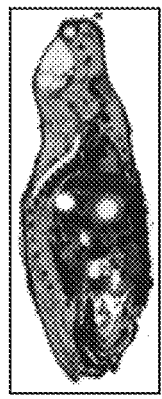
FIG. 1J illustrates the $^{14}$C signal in the cartilage of an animal treated with a peptide of SEQ ID NO: 29.
Figure 1K:
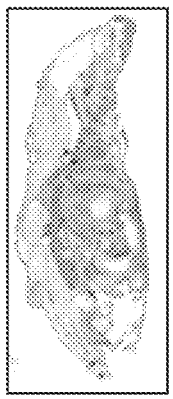
FIG. 1K illustrates the $^{14}$C signal in the cartilage of an animal treated with a peptide of SEQ ID NO: 30.
Figure 1L:
FIG. 1L illustrates the $^{14}$C signal in the cartilage of an animal treated with a peptide of SEQ ID NO: 32.
Figure 1M:
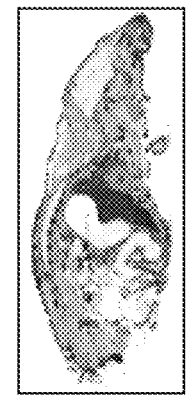
FIG. 1M illustrates the $^{14}$C signal in the cartilage of an animal treated with a peptide of SEQ ID NO: 27.
Figure 1E:
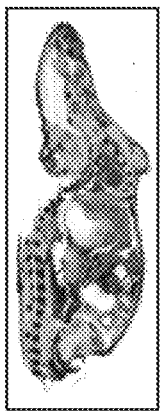
FIG. 1E illustrates the $^{14}$C signal in the cartilage of an animal treated with a peptide of SEQ ID NO: 27.
Figure 1F:
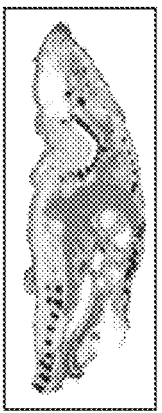
FIG. 1F illustrates the $^{14}$C signal in the cartilage of an animal treated with a peptide of SEQ ID NO: 25.
Figure 1G:
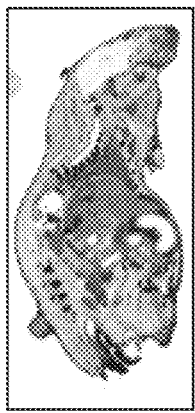
FIG. 1G illustrates the $^{14}$C signal in the cartilage of an animal treated with a peptide of SEQ ID NO: 22.
Figure 1H:
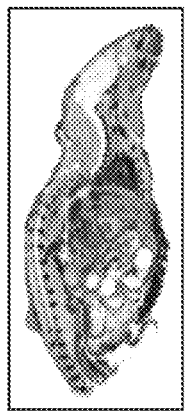
FIG. 1H illustrates the $^{14}$C signal in the cartilage of an animal treated with a peptide of SEQ ID NO: 31.
Figure 1A:
FIG. 1A illustrates the $^{14}$C signal in the cartilage of an animal treated with a peptide of SEQ ID NO: 26.
Figure 1B:
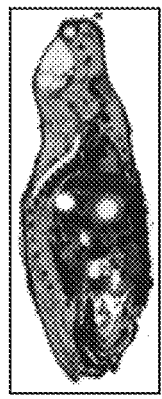
FIG. 1B illustrates the $^{14}$C signal in the cartilage of an animal treated with a peptide of SEQ ID NO: 28.
Figure 1C:
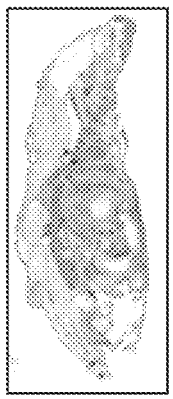
FIG. 1C illustrates the $^{14}$C signal in the cartilage of an animal treated with a peptide of SEQ ID NO: 24.
Figure 1D:
FIG. 1D illustrates the $^{14}$C signal in the cartilage of an animal treated with a peptide of SEQ ID NO: 23.

The present disclosure relates generally to compositions and methods for cartilage therapy. In some embodiments, the compositions and methods herein utilize peptides that home, target, are directed to, are retained by, accumulate in, migrate to, and/or bind to cartilage following administration to a subject. In some embodiments, the cartilage homing peptides of the present disclosure are used to deliver an active agent to cartilage or tissue or cell thereof. The active agent can exert a therapeutic effect on cartilage or tissue or cell thereof. For example, in certain embodiments, the active agent allows for localized delivery of an anti-inflammatory agent to cartilage or tissue or cell thereof. As another example, the active agent is a fluorophore that can be used for imaging of cartilage. In certain embodiments, the peptide itself induces therapeutic responses.

Cartilage disorders are particularly difficult to treat. A direct route for drug administration can be intravenously, intra-articularly, or orally. However, cartilage can be avascular thus intravenous administration of drugs can fail to reach the cartilage. Drugs for cartilage diseases, such as osteoarthritis, can be injected directly locally into the affected area, for example, directly injected into the joint. Few drugs aimed at treating cartilage disorders have proved therapeutically viable with lack of access to target tissue being a primary reason for failure. The lack of access to the target tissue can also lead to administration of doses that are higher than would be necessary if a drug could home, target, or be directed to, is retained by, and/or binds to a target region, tissue, structure or cell. Thus, treatment of cartilage conditions often requires the use of high concentrations of non-specific drugs. In addition, a number of therapeutics are of interest in treating joint disorders, but are problematic because of the level of side effects caused by systemic administration of the drug (Dancevic and McCulloch, Arthritis Research & Therapy 16:429 (2014)).

Specific and potent drugs that are capable of contacting the cartilage can counteract the non-specificity of many treatments by selectively targeting and delivering compounds to specific regions, tissues, cells and structures. Such drugs can also be useful to modulate ion channels, protein-protein interactions, extracellular matrix remodeling (i.e., protease inhibition), and the like. Such targeted therapy can allow for lower dosing, reduced side effects, improved patient compliance, and improvement in therapeutic outcomes, which would be advantageous not only in acute disease of the cartilage, but in chronic conditions as well.

The present disclosure describes a class of peptides derived from knottins that can effectively contact cartilage and be used either directly or as carriers of active drugs, peptides, or molecules to treat a cartilage condition. For instance, osteoarthritis is a cartilage condition that is associated with the thinning of cartilage covering the ends of bones resulting in bone directly contacting bone within the joint. Over time, the ends of the bones are subjected to increased levels of friction which causes erosion of the end of the bone. Individuals suffering from osteoarthritis experience reduced motion and increased pain. A therapeutic peptide that could contact the cartilage at the joint and ends of the bone to interact with the chondrocytes and induce increased expression of extracellular matrix proteins could be used in the treatment and prevention of osteoarthritis by increasing expression of collagen through, for example, the rate of production, amount of production, inhibition of proteins which degrade collagen, promote expression of other proteins which maintain the integrity of existing collagen proteins, or other mechanism. A peptide could also affect nearby tissues or cells such as the bone, osteoclasts, osteoblasts, ligaments, muscle, tendons, and bursa. The peptides of the disclosure can be used to treat the symptoms of various conditions. The peptides of the disclosure can bind to chondrocytes, to cartilage, to extracellular matrix, to collagen, hyaluronan, aggrecan (also known as cartilage-specific proteoglycan core protein (CSPCP)), or other components of the extracellular matrix, or to other components in joints and cartilaginous tissues.

Also described herein are peptides that selectively home, target, are directed to, migrate to, are retained by, or accumulate in and/or bind to specific regions, tissues, structures or cells of the cartilage that aid in managing, decreasing, ablating or reducing pain (e.g., joint pain) due to chronic disease or cartilage injury or other therapeutic indications as described herein. A peptide that homes, targets, migrates to, is directed to, is retained by, or accumulates in and/or binds to one or more specific regions, tissues, structures or cells of the cartilage can have fewer off-target and potentially negative effects, for example, side effects that often limit use and efficacy of pain drugs. In addition, such peptides can reduce dosage and increase the efficacy of existing drugs by directly targeting them to a specific region, tissue, structure or cell of the cartilage and helping the contact the cartilage or increasing the local concentration of agent. The peptide itself can modulate pain or it can be conjugated to an agent that modulates pain. Such pain modulation may operate by various mechanisms such as modulating inflammation, autoimmune responses, direct or indirect action on pain receptors, cell killing, or programmed cell death (whether via an apoptotic and/or non-apoptotic pathway of diseased cells or tissues, and the like (Tait et al. J Cell Sci 127(Pt 10):2135-44 (2014)).

Peptides of this disclosure that home, target, are directed to, migrate to, are retained by, accumulate in, or bind to specific regions, tissues, structures or cells of the cartilage can do so with different degrees of efficiency. Peptides can have a higher concentration in cartilage than in other locations, such as blood or muscle. Peptides can be recorded as having a signal in cartilage as a percentage of signal in blood. For example, a cartilage signal of 200% indicates that the signal in cartilage is twice as high as the signal in blood. In some embodiments, peptides that have cartilage homing properties can have a cartilage signal of >170% by radio densitometry measurements. In other embodiments, peptides that are cartilage homers can have a cartilage signal of >200% by radio densitometry measurements. In other embodiments, peptides that are more efficient cartilage homers can have a cartilage signal of >300% by radio densitometry measurements. In other embodiments, peptides that are more efficient cartilage homers can have a cartilage signal of >400% by radio densitometry measurements. In other embodiments, peptides that are strongest cartilage homers of highest interest can have a cartilage signal of >500% by radio densitometry measurements.

Peptides that selectively home, target, are directed to, migrate to, are retained by, or accumulate in and/or bind to specific regions, tissues, structures or cells of the cartilage can occur after administration of the peptide to a subject. A subject can be a human or a non-human animal.

The peptides disclosed herein can be used as active agents such a fluorophores for imaging or to carry agents such as anti-inflammatory agents to the joint to treat inflammation.

The peptides disclosed herein can be used to bind cartilage explants ex vivo. Cartilage explants can be from any subject, such as a human or an animal. Assessment of peptide binding to cartilage explants can be used to screen peptides that may efficiently home to cartilage in vivo.

Additional aspects and advantages of the present disclosure will become apparent to those skilled in this art from the following detailed description, wherein illustrative embodiments of the present disclosure are shown and described. As will be realized, the present disclosure is capable of other and different embodiments, and its several details are capable of modifications in various respects, all without departing from the disclosure. Accordingly, the drawings and description are to be regarded as illustrative in nature, and not as restrictive.

As used herein, the abbreviations for the natural L-enantiomeric amino acids are conventional and are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Typically, Xaa can indicate any amino acid. In some embodiments, X can be asparagine (N), glutamine (Q), histidine (H), lysine (K), or arginine (R).

Some embodiments of the disclosure contemplate D-amino acid residues of any standard or non-standard amino acid or analogue thereof. When an amino acid sequence is represented as a series of three-letter or one-letter amino acid abbreviations, the left-hand direction is the amino terminal direction and the right-hand direction is the carboxy terminal direction, in accordance with standard usage and convention.

Peptides

Knottins are a class of peptides, usually ranging from about 20 to about 80 amino acids in length that are often folded into a compact structure. Knottins are typically assembled into a complex tertiary structure that is characterized by a number of intramolecular disulfide crosslinks and may contain beta strands and other secondary structures. The presence of the disulfide bonds gives knottins remarkable environmental stability, allowing them to withstand extremes of temperature and pH and to resist the proteolytic enzymes of the blood stream.

A wider examination of the sequence structure and homology of knottins reveals that they have arisen by convergent evolution in all kinds of animals and plants. In animals, they are typically found in venoms, for example, the venoms of spiders and scorpions and have been implicated in the modulation of ion channels. Many of this class of peptide can be protease inhibitors, and as such can both home to cartilage and inhibit collagenase or a matrix metalloprotease that breaks down cartilage (e.g., matrix metalloprotease 13 (MMP13)). The knottin proteins of plants can inhibit the proteolytic enzymes of animals or have antimicrobial activity, suggesting that knottins can function in the native defense of plants. Many of this class of peptides can have antimicrobial activity, and as such one of these can both home to cartilage and treat microbial infections. Therefore, knottin peptides can interact with ion channels, and as such can home to cartilage and interact (bind, block, activate) with ion channels such as those in chondrocytes that are known to effect proliferation, mechanotransduction, and other functions (Potassium Ion Channels in Articular Chondrocytes, Ali Mobasheri, in Mechanosensitive Ion Channels Mechanosensitivity in Cells and Tissues Volume 1, 2008, pp 157-178).

The knotted peptides of the present disclosure provide certain advantages. For instance, the presence of the disulfide bonds gives knotted peptides remarkable environmental stability, allowing them to withstand extremes of temperature and pH and to resist the proteolytic enzymes of the blood stream, the gastrointestinal tract, and elsewhere in the body. The resistance of knotted peptides to degradation can be beneficial in terms of reducing immunogenicity. The rigidity of knotted peptides also allows them to bind to targets without paying the "entropic penalty" that a floppy peptide accrues upon binding a target. The knotted peptides can bind targets with antibody-like affinity. The knotted peptides can modulate the activity of a plurality of cartilage regions, tissues, structures or cells. Some of the cartilage regions, tissues, structures include: (a) elastic cartilage; (b) hyaline cartilage, such as articular cartilage and physeal cartilage; (c) fibrocartilage; and (d) any cells or cell types in (a)-(c) above. Some of the areas where the knottin peptide can home to cartilage include joints such as knees, hips, or digits, nasal cartilage, spinal cartilage, tracheal cartilage, and rib cartilage. In various aspects, cartilage components include aggrecan and type II collagen. Additionally, in some embodiments, knotted peptides can penetrate into cells. In other embodiments, knotted peptides exhibit more rapid clearance and cellular uptake compared to other types of molecules.

The present disclosure provides peptides that comprise or are derived from these knotted peptides (or knottins). As used herein, the term "knotted peptide" is considered to be interchangeable with the terms "knottin" and "optide."

The peptides of the present disclosure can comprise cysteine amino acid residues. In some cases, the peptide has at least 4 cysteine amino acid residues. In some cases, the peptide has at least 6 cysteine amino acid residues. In other cases, the peptide has at least 8 cysteine amino acid residues, at least 10 cysteine amino acid residues, at least 12 cysteine amino acid residues, at least 14 cysteine amino acid residues or at least 16 cysteine amino acid residues.

A knotted peptide can comprise disulfide bridges. A knotted peptide can be a peptide wherein 5% or more of the residues are cysteines forming intramolecular disulfide bonds. A disulfide-linked peptide can be a drug scaffold. In some embodiments, the disulfide bridges form an inhibitor knot. A disulfide bridge can be formed between cysteine residues, for example, between cysteines 1 and 4, 2 and 5, or, 3 and 6. In some cases, one disulfide bridge passes through a loop formed by the other two disulfide bridges, for example, to form the inhibitor knot. In other cases, the disulfide bridges can be formed between any two cysteine residues.

The present disclosure further includes peptide scaffolds that, e.g., can be used as a starting point for generating additional peptides that can target and home to cartilage. In some embodiments, these scaffolds can be derived from a variety of knotted peptides (or knottins). In certain embodiments, knotted peptides are assembled into a complex tertiary structure that is characterized by a number of intramolecular disulfide crosslinks, and optionally contain beta strands and other secondary structures such as an alpha helix. For example, knotted peptides include, in some embodiments, small disulfide-rich proteins characterized by a disulfide through disulfide knot. This knot can be, e.g., obtained when one disulfide bridge crosses the macrocycle formed by two other disulfides and the interconnecting backbone. In some embodiments, the knotted peptides can include growth factor cysteine knots or inhibitor cysteine knots. Other possible peptide structures can include peptide having two parallel helices linked by two disulfide bridges without β-sheets (e.g., hefutoxin).

A knotted peptide can comprise at least one amino acid residue in an L configuration. A knotted peptide can comprise at least one amino acid residue in a D configuration. In some embodiments, a knotted peptide is 15-40 amino acid residues long. In other embodiments, a knotted peptide is 11-57 amino acid residues long. In further embodiments, a knotted peptide is at least 20 amino acid residues long.

These kinds of peptides can be derived from a class of proteins known to be present or associated with toxins or venoms. In some cases, the peptide can be derived from toxins or venoms associated with scorpions or spiders. The peptide can be derived from venoms and toxins of spiders and scorpions of various genus and species. For example, the peptide can be derived from a venom or toxin of the *Leiurus quinquestriatus hebraeus, Buthus occitanus tunetanus, Hottentotta judaicus, Mesobuthus eupeus, Buthus occitanus israelis, Hadrurus gertschi, Androctonus australis, Centruroides noxius, Heterometrus laoticus, Opistophthalmus carinatus, Haplopelma schmidti, Isometrus maculatus, Grammostola rosea* or another suitable genus or species of scorpion. In some cases, a peptide can be derived from a *Buthus martensii* Karsh (scorpion) toxin.

In some embodiments, the peptides are members of the pfam00451:toxin_2 family. The pfam00451:toxin_2 structural class family can include a peptide of any one of SEQ ID NO: 436-SEQ ID NO: 482. A cartilage homing peptide of this disclosure can be a variant of any peptide members of the pfam00451:toxin_2 family. In some embodiments, an exemplary cartilage homing peptide of this disclosure that is a variant of the pfam00451:toxin_2 structural class family is a peptide of SEQ ID NO: 24. In other embodiments, an exemplary cartilage homing peptide of this disclosure that is a variant of the pfam00451:toxin_2 structural class family is a peptide of SEQ ID NO: 111. In other embodiments, the variant peptides are at least 30% identical to a peptide of the structural class pfam00451:toxin_2 family. In some embodiments, the variant peptides are 30%, 40%, 50%, 60%, 80%, 90% or 95% identical to a peptide of the structural class pfam00451:toxin_2 family. In some embodiments, the variant peptides are at least 30%, at least 40%, at least 50%, at least 60%, at least 80%, at least 90% or at least 95% identical to a peptide of the structural class pfam00451:toxin_2 family. The pfam00451:toxin_2 family comprises peptide family members found as portions of various scorpion toxins, often functioning to block potassium channels. Features of the pfam00451:toxin_2 family include, but are not limited to, a features associated with members of a knottin 1 (CL0054) clan, which has at least 120 family members. For example, the average family member amino acid residue lengths is 31.4 amino acid residues, the average identity of family member sequence homology to the consensus sequence is 46%, and family members are derived from at least the following organisms: *Tityus costatus, Centruroides noxius, Tityus serrulatus, Mesobuthus gibbosus, Centruroides elegans, Hottentotta judaicus, Mesobuthus eupeus, Parabuthus transvaalicus, Isometroides vescus, Hottentotta tamulus sindicus, Centruroides margaritatus, Centruroides suffusus suffusus, Buthus occitanus israelis, Centruroides limpidus limpidus, Leiurus quinquestriatus hebraeus, Odontobuthus doriae, Mesobuthus tamulus, Tityus stigmurus, Lychas mucronatus, Androctonus australis, Orthochirus scrobiculosus, Mesobuthus martensii, Androctonus mauretanicus mauretanicus, Centruroides limbatus, Isometrus maculatus, Tityus discrepans, Androctonus amoreuxi, Buthus occitanus tunetanus, Tityus trivittatus* and *Tityus obscurus* (Amazonian scorpion).

In some embodiments, cartilage homing peptides are members of family with the sequence GSXVXXXVKCXG-SKQCXXPCKRXXGXRXGKCINKKXCKCYXXX (SEQ ID NO: 9), in which this sequence is based on the most common elements found in the following sequences:

GSGVPINVKCRGSRDCLDPCKKA-GMRFGKCINSK-CHCTP-- (SEQ ID NO: 24), GS-VRIPVSCK-HSGQCLKPCKDA-GMRFGKCMNGK-CDCTPK- (SEQ ID NO: 23), GSQVQTNVKCQGGS-CASVCR-REIGVAAGKCINGK-CVCYRN- (SEQ ID NO: 27), GS-----ISCTGSKQCYDPCKRKTGCPNAKCMNKS-CK-CYGCG (SEQ ID NO: 26), GSEV---IRCSG-SKQCYGPCKQQTGCTNSKCMNKV-CKCYGCG (SEQ ID NO: 28), GSAVCVYRT------CDKDCKRR-GYRSGK-CINNA-CKCYPYG (SEQ ID NO: 25), GS----GIVC---KVCKIICGMQ-GKKVNICKAPIKCKCKKG- (SEQ ID NO: 21), and GSQIYTSKECNGSSECYSHCE-GITGKRSGKCINKK-CYCYR-- (SEQ ID NO: 30), where the following residues may be independently interchanged in the sequences: K and R; M, I, L, and V; G and A; S and T; Q and N; and X can independently be any number of any amino acid or no amino acid. The N-terminal GS sequence can be included or excluded between the peptides of the present disclosure.

In other embodiments, peptides are members of family with the sequence GSXXXGCVXXXXKCRPGXKXCCXPXKRCSRRFGXXXXKKCKXXXXXX (SEQ ID NO: 10), in which the sequence is based on the most common elements found in the following sequences: GS---ACKGVFDACTPGK-NECC-PNRVCSDK-H----KWCKWKL--- (SEQ ID NO: 29), GS---GCLEFWWKCNPNDDKC-CRPKLKCSKLF-----KLCNFSFG-- (SEQ ID NO: 31), GSSEKDCIKHLQRCR-ENKDCC--SKKCSRR-GTN-PEKRCR------ (SEQ ID NO: 22), and GS---GCFGY--KCDYY-KGCCSGYV-CSPTW-----KWCVRPGPGR (SEQ ID NO: 33), where the following residues may be independently interchanged in the sequences: K and R; M, I, L, and V; G and A; S and T; Q and N; and X can independently be any number of any amino acid or no amino acid. The N-terminal GS sequence can be included or excluded between the peptides of the present disclosure.

In some embodiments, a peptide comprises the sequence GSGVX$^1$IX$^2$X$^3$KCX$^4$GSKQCX$^5$DPCKX$^6$X$^7$X$^8$GX$^9$RX$^{10}$GKCX$^{11}$NKKCKCX$^{12}$X$^{13}$X$^{14}$X$^{15}$ (SEQ ID NO: 1), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$ and X$^{15}$ are each individually any amino acid or amino acid analogue or null. In some cases, the peptide comprises the sequence GSGVX$^1$IX$^2$X$^3$KCX$^4$GSKQCX$^5$DPCKX$^6$X$^7$X$^8$GX$^9$RX$^{10}$GKCX$^{11}$NKKCKCX$^{12}$X$^{13}$X$^{14}$X$^{15}$ (SEQ ID NO: 2), where X$^1$ is selected from P or R, wherein X$^2$ is selected from P or N, wherein X$^3$ is selected from V or I, wherein X$^4$ is selected from S, T, R or K, wherein X$^5$ is selected from Y or L, wherein X$^6$ is selected from Q, R or K, wherein X$^7$ is selected from A, K or R, wherein X$^8$ is selected from T or A, wherein X$^9$ is selected from C or M, wherein X$^{10}$ is selected from F or N, wherein X$^{11}$ is selected from M or I, wherein X$^{12}$ is selected from Y or T, wherein X$^{13}$ is selected from G or P, wherein X$^{14}$ is selected from C or null, and wherein X$^{15}$ is selected from G or null.

In some embodiments, a peptide comprises the sequence X$^1$X$^2$X$^3$X$^4$IX$^5$CX$^6$GSKQCYX$^7$PCKX$^8$X$^9$X$^{10}$X$^{11}$X$^{12}$X$^{13}$X$^{14}$X$^{15}$CKCYGCG (SEQ ID NO: 3), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, and X$^{15}$ are each individually any amino acid or amino acid analogue or null. In some cases, the peptide comprises the sequence X$^1$X$^2$X$^3$X$^4$IX$^5$CX$^6$GSKQCYX$^7$PCKX$^8$X$^9$X$^{10}$X$^{11}$X$^{12}$X$^{13}$X$^{14}$X$^{15}$CKCYGCG, (SEQ ID NO: 4), where X$^1$ is selected from G or null, wherein X$^2$ is selected from S or null, wherein X$^3$ is selected from E, G or null, wherein X$^4$ is selected from V, S, or null, wherein X$^5$ is selected from R or S, wherein X$^6$ is selected from S or T, wherein X$^7$ is selected from G or D, wherein X$^8$ is selected from Q or R, wherein X$^9$ is selected from Q or K, wherein X$^{10}$ is selected from T or P, wherein X$^{11}$ is selected from N or Q, wherein X$^{12}$ is selected from S or A, wherein X$^{13}$ is selected from M or L, wherein X$^{14}$ is selected from N or Q, and wherein X$^{15}$ is selected from V or S.

In some embodiments, a peptide comprises the sequence X$^1$X$^2$X$^3$X$^4$IX$^5$CX$^6$X$^7$X$^8$SX$^9$X$^{10}$CLX$^{11}$PCKX$^{12}$AGMRFGKCX$^{13}$NX$^{14}$KCX$^{15}$CTPX$^{16}$ (SEQ ID NO: 5), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$ are each individually any amino acid or amino acid analogue or null. In some cases, the peptide comprises the sequence X$^1$X$^2$X$^3$VX$^4$IX$^5$VX$^6$CX$^7$X$^8$SX$^9$X$^{10}$CLX$^{11}$PCKX$^{12}$AGMRFGKCX$^{13}$NX$^{14}$KCX$^{15}$CTPX$^{16}$ (SEQ ID NO: 6), where X$^1$ is selected from G or null, wherein X$^2$ is selected from G, S or null, wherein X$^3$ is selected from G, S or null, wherein X$^4$ is selected from P or R, wherein X$^5$ is selected from N or P, wherein X$^6$ is selected from K or S, wherein X$^7$ is selected from R or K, wherein X$^8$ is selected from G or H, wherein X$^9$ is selected from R or G, wherein X$^{10}$ is selected from D or Q, wherein X$^{11}$ is selected from D or K, wherein X$^{12}$ is selected from K or D, wherein X$^{13}$ is selected from I or M, wherein X$^{14}$ is selected from S or G, wherein X$^{15}$ is selected from H or D, and wherein X$^{16}$ is selected from K or null.

In some embodiments, a peptide comprises the sequence XVXVKCXGSKQCXPCKRXGXRXGKCINKKXCK-CYX (SEQ ID NO: 7) or XGCVXKCRPGXKXCCXPXKRCSRRFGXKKCKX (SEQ ID NO: 8), wherein each letter is each individually any amino acid or amino acid analogue and where X is no amino acid or a 1-10 amino acid long peptide fragment wherein each amino acid within such peptide fragment can in each case be any amino acid or amino acid analogue.

In some embodiments, a peptide comprises the sequence GSGVX$^1$IX$^2$X$^3$RCX$^4$GSRQCX$^5$DPCRX$^6$X$^7$X$^8$GX$^9$RX$^{10}$GRCX$^{11}$NRRCRCX$^{12}$X$^{13}$X$^{14}$X$^{15}$ (SEQ ID NO: 11), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$ and X$^{15}$ are each individually any amino acid or amino acid analogue or null. In some cases, the peptide comprises the sequence GSGVX$^1$IX$^2$X$^3$RCX$^4$GSRQCX$^5$DPCRX$^6$X$^7$X$^8$GX$^9$RX$^{10}$GRCX$^{11}$NRRCRCX$^{12}$X$^{13}$X$^{14}$X$^{15}$ (SEQ ID NO: 12), where X$^1$ is selected from P or R, wherein X$^2$ is selected from P or N, wherein X$^3$ is selected from V or I, wherein X$^4$ is selected from S, T, R or K, wherein X$^5$ is selected from Y or L, wherein X$^6$ is selected from Q, R or K, wherein X$^7$ is selected from A, K or R, wherein X$^8$ is selected from T or A, wherein X$^9$ is selected from C or M, wherein X$^{10}$ is selected from F or N, wherein X$^{11}$ is selected from M or I, wherein X$^{12}$ is selected from Y or T, wherein X$^{13}$ is selected from G or P, wherein X$^{14}$ is selected from C or null, and wherein X$^{15}$ is selected from G or null.

In some embodiments, a peptide comprises the sequence X$^1$X$^2$X$^3$X$^4$IX$^5$CX$^6$GSRQCYX$^7$PCRX$^8$X$^9$TGCX$^{10}$X$^{11}$X$^{12}$RCX$^{13}$X$^{14}$RX$^{15}$CRCYGCG (SEQ ID NO: 13), wherein X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$ and X$^{15}$ are each individually any amino acid or amino acid analogue or null. In some cases, the peptide comprises the sequence X$^1$X$^2$X$^3$X$^4$IX$^5$CX$^6$GSRQCYX$^7$PCRX$^8$X$^9$TGCX$^{10}$X$^{11}$X$^{12}$RCX$^{13}$X$^{14}$RX$^{15}$CRCYGCG, (SEQ ID NO: 14), where X$^1$ is selected from G or null, wherein X$^2$ is selected from S or null, wherein X$^3$ is selected from E, G or null, wherein X$^4$ is selected from V, S, or null, wherein X$^5$ is selected from R or S, wherein X$^6$ is selected from S or T, wherein X$^7$ is selected from G or D, wherein X$^8$ is selected from Q or R, wherein $X^9$ is selected from Q, R, or K, wherein $X^{10}$ is selected from T or P, wherein $X^{11}$ is selected from N or Q, wherein $X^{12}$ is selected from S or A, wherein $X^{13}$ is selected from M or L, wherein $X^{14}$ is selected from N or Q, and wherein $X^{15}$ is selected from V or S.

In some embodiments, a peptide comprises the sequence $X^1X^2X^3VX^4IX^5VX^6CX^7X^8SX^9X^{10}CLX^{11}PCRX^{12}AGMRFGRCX^{13}NX^{14}RCX^{15}CTPX^{16}$ (SEQ ID NO: 15), wherein $X^1, X^2, X^3, X^4, X^5, X^6, X^7, X^8, X^9, X^{10}, X^{11}, X^{12}, X^{13}, X^{14}$ and $X^{15}$ are each individually any amino acid or amino acid analogue or null. In some cases, the peptide comprises the sequence $X^1X^2X^3VX^4IX^5VX^6CX^7X^8SX^9X^{10}CLX^{11}PCRX^{12}AGMRFGRCX^{13}NX^{14}RCX^{15}CTPX^{16}$ (SEQ ID NO: 16), where $X^1$ is selected from G or null, wherein $X^2$ is selected from G, S or null, wherein $X^3$ is selected from G, S or null, wherein $X^4$ is selected from P or R, wherein $X^5$ is selected from N or P, wherein $X^6$ is selected from R, K or S, wherein $X^7$ is selected from R or K, wherein $X^8$ is selected from G or H, wherein $X^9$ is selected from R or G, wherein $X^{10}$ is selected from D or Q, wherein $X^{11}$ is selected from D, R, or K, wherein $X^{12}$ is selected from K, R, or D, wherein $X^{13}$ is selected from I or M, wherein $X^{14}$ is selected from S or G, wherein $X^{15}$ is selected from H or D, and wherein $X^{16}$ is selected from K, R, or null.

In some embodiments, a peptide comprises the sequence XVXVRCXGSRQCXPCRRXGXRXGRCINRRXCRCYX (SEQ ID NO: 17) or XGCVXRCRPGXRXCCXPXRRCSRRFGXRRCRX (SEQ ID NO: 18), wherein each letter is each individually any amino acid or amino acid analogue and where X is no amino acid or a 1-10 amino acid long peptide fragment wherein each amino acid within such peptide fragment can in each case be any amino acid or amino acid analogue.

In some embodiments, a peptide comprises one or more of the following peptide fragments: SEQ ID NO: 100, SEQ ID NO: 101, SEQ ID NO: 102, SEQ ID NO: 103, SEQ ID NO: 104, SEQ ID NO: 105, SEQ ID NO: 186, SEQ ID NO: 187, SEQ ID NO: 188, SEQ ID NO: 189, SEQ ID NO: 190, SEQ ID NO: 191, SEQ ID NO: 193, and SEQ ID NO: 194.

TABLE 1 lists some exemplary peptides according to the present disclosure.

TABLE 1

| SEQ ID NO | Amino Acid Sequence |
|---|---|
| SEQ ID NO: 21 | GSGIVCKVCKIICGMQGKKVNICKAPIKCKCKKG |
| SEQ ID NO: 22 | GSSEKDCIKHLQRCRENKDCCSKKCSRRGTNPEKRCR |
| SEQ ID NO: 23 | GSVRIPVSCKHSGQCLKPCKDAGIVIRFGKCMNGKCDCTPK |
| SEQ ID NO: 24 | GSGVPINVKCRGSRDCLDPCKKAGMRFGKCINSKCHCTP |
| SEQ ID NO: 25 | GSAVCVYRTCDKDCKRRGYRSGKCINNACKCYPYG |
| SEQ ID NO: 26 | GSISCTGSKQCYDPCKRKTGCPNAKCMNKSCKCYGCG |
| SEQ ID NO: 27 | GSQVQTNVKCQGGSCASVCRREIGVAAGKCINGKCVCRN |
| SEQ ID NO: 28 | GSEVIRCSGSKQCYGPCKQQTGCTNSKCMNKVCKCYGCG |

TABLE 1-continued

| SEQ ID NO | Amino Acid Sequence |
|---|---|
| SEQ ID NO: 29 | GSACKGVFDACTPGKNECCPNRVCSDKHKWCKWKL |
| SEQ ID NO: 30 | GSQIYTSKECNGSSECYSHCEGITGKRSGKCINKKCYCYR |
| SEQ ID NO: 31 | GSGCLEFWWKCNPNDDKCCRPKLKCSKLFKLCNFSFG |
| SEQ ID NO: 32 | GSDCVRFWGKCSQTSDCCPHLACKSKWPRNICVWDGSVG |
| SEQ ID NO: 33 | GSGCFGYKCDYYKGCCSGYVCSPTWKWCVRPGPGR |
| SEQ ID NO: 34 | GSMNAKFILLLVLTTMMLLPDTKGAEVIRCSGSKQCYGPCKQQTGCTNSKCMNKVCKCYGCG |
| SEQ ID NO: 35 | GSMNAKLIYLLLVVTTMTLMFDTAQAVDEVICSGPKQCYGPCKKETGCPNAKCMNRRCKCYGCV |
| SEQ ID NO: 36 | GSMNAKLIYLLLVVTTMMLTFDTTQAGDIKCSGTRQCWGPCKKQTTCTNSKCMNGKCKCYGCVG |
| SEQ ID NO: 37 | GSMNTKFIFLLLVVTNTMMLFDTKPVEGISCTGSKQCYDPCKRKTGCPNAKCMNKSCKCYGCG |
| SEQ ID NO: 38 | GSGVPINVKCSGSRDCLEPCKKAGMRFGKCINRKCHCTPK |
| SEQ ID NO: 39 | GSGVPINVKCTGSPQCLKPCKDAGMRFGKCINGKCHCTPK |
| SEQ ID NO: 40 | GSGVIINVKCKISRQCLEPCKKAGMRFGKCMNGKCHCTPK |
| SEQ ID NO: 41 | GSGVPINVKCRGSPQCIQPCRDAGMRFGKCMNGKCHCTPQ |
| SEQ ID NO: 42 | GSGVEINVKCTGSHQCIKPCKDAGMRFGKCINRKCHCTPK |
| SEQ ID NO: 43 | GSGVEINVKCSGSPQCLKPCKDAGMRFGKCMNRKCHCTPK |
| SEQ ID NO: 44 | GSGVPTDVKCRGSPQCIQPCKDAGMRFGKCMNGKCHCTPK |
| SEQ ID NO: 45 | GSGVPINVSCTGSPQCIKPCKDAGMRFGKCMNRKCHCTPK |
| SEQ ID NO: 46 | GSGVPINVPCTGSPQCIKPCKDAGMRFGKCMNRKCHCTPK |
| SEQ ID NO: 47 | GSVGINVKCKHSGQCLKPCKDAGMRFGKCINGKCDCTPK |
| SEQ ID NO: 48 | GSVGINVKCKHSGQCLKPCKDAGMRFGKCMNGKCDCTPK |
| SEQ ID NO: 49 | GSVGIPVSCKHSGQCIKPCKDAGMRFGKCMNRKCDCTPK |
| SEQ ID NO: 50 | GSRKGCFKEGHSCPKTAPCCRPLVCKGPSPNTKKCTRP |
| SEQ ID NO: 51 | GSSFCIPFKPCKSDENCCKKFKCKTTGIVKLCRW |
| SEQ ID NO: 52 | GSLKGCLPRNRFCNALSGPRCCSGLRCKELSIWASKCL |

TABLE 1-continued

| SEQ ID NO | Amino Acid Sequence |
|---|---|
| SEQ ID NO: 53 | GSGNYCLRGRCLPGGRKCCNGRPCECFAKICSCKPK |
| SEQ ID NO: 54 | GSTVKCGGCNRKCCPGGCRSGKCINGKCQCY |
| SEQ ID NO: 55 | GSGCMKEYCAGQCRGKVSQDYCLKHCKCIPR |
| SEQ ID NO: 56 | GSACLGFGEKCNPSNDKCCKSSSLVCSQKHKWCKYG |
| SEQ ID NO: 57 | GSRGGCLPHNRFCNALSGPRCCSGLRCKELSIRDSRCLG |
| SEQ ID NO: 58 | GSRGGCLPRNKFCNPSSGPRCCSGLTCKELNIWASKCL |
| SEQ ID NO: 59 | GSQRSCAKPGDMCMGIKCCDGQCGCNRGTGRCFCK |
| SEQ ID NO: 60 | GSARGCADAYKSCNHPRTCCDGYNGYKRACICSGSNCKCKKS |
| SEQ ID NO: 61 | GSRGGCLPHNRFCNALSGPRCCSGLRCKELSIWDSRCLG |
| SEQ ID NO: 62 | GSRGGCLPHNRFCNALSGPRCCSGLKCKELSIYDSRCLG |
| SEQ ID NO: 63 | GSRGGCLPHNRFCNALSGPRCCSRLKCKELSIWDSRCLG |
| SEQ ID NO: 64 | GSRGGCLPHNRFCNALTGPRCCSRLRCKELSIWDSICLG |
| SEQ ID NO: 65 | GSSCADAYKSCDSLKCCNNRTCMCSMIGTNCTCRKK |
| SEQ ID NO: 66 | GSERRCLPAGKTCVRGPMRVPCCGSCSQNKCT |
| SEQ ID NO: 67 | GSLCSREGEFCYKLRKCCAGFYCKAFVLHCYRN |
| SEQ ID NO: 68 | GSACGSCRKKCKGSGKCINGRCKCY |
| SEQ ID NO: 69 | GSACGSCRKKCKGPGKCINGRCKCY |
| SEQ ID NO: 70 | GSACQGYMRKCGRDKPPCCKKLECSKTWRWCVWN |
| SEQ ID NO: 71 | GSGRYCQKWMWTCDSKRACCEGLRCKLWCRKI |
| SEQ ID NO: 72 | GSNAKCRGSPECLPKCKEAIGKAAGKCMNGKCKCYP |
| SEQ ID NO: 73 | GSNVKCRGSKECLPACKAAVGKAAGKCMNGKCKCYP |
| SEQ ID NO: 74 | GSNVKCRGSPECLPKCKEAIGKSAGKCMNGKCKCYP |
| SEQ ID NO: 75 | GSNAKCRGSPECLPKCKQAIGKAAGKCMNGKCKCYP |
| SEQ ID NO: 76 | GSRGYCAEKGIKCHNIHCCSGLTCKCKGSSCVCRK |
| SEQ ID NO: 77 | GSERGCKLTFWKCKNKKECCGWNACALGICMPR |
| SEQ ID NO: 78 | GSKKKCIAKDYGRCKWGGTPCCRGRGCICSIMGTNCECKPR |
| SEQ ID NO: 79 | GSGCKLTFWKCKNKKECCGWNACALGICMPR |
| SEQ ID NO: 80 | GSACKGLFVTCTPGKDECCPNHVCSSKHKWCKYK |
| SEQ ID NO: 81 | GSIACAPRGLLCFRDKECCKGLTCKGRFVNTWPTFCLV |
| SEQ ID NO: 82 | GSACAGLYKKCGKGVNTCCENRPCKCDLAMGNCICKKK |
| SEQ ID NO: 83 | GSFTCAISCDIKVNGKPCKGSGEKKCSGGWSCKFNVCVKV |
| SEQ ID NO: 84 | GSGFCAQKGIKCHDIHCCTNLKCVREGSNRVCRKA |
| SEQ ID NO: 85 | GSCAKKRNWCGKNEDCCCPMKCIYAWYNQQGSCQSTITGLFKKC |
| SEQ ID NO: 86 | GSYCQKWMWTCDSARKCCEGLVCRLWCKKI |
| SEQ ID NO: 87 | GSRGGCLPHNKFCNALSGPRCCSGLKCKELTIWNTKCLE |
| SEQ ID NO: 88 | GSNVKCTGSKQCLPACKAAVGKAAGKCMNGKCKCYT |
| SEQ ID NO: 89 | GSQRSCAKPGEMCMRIKCCDGQCGCNRGTGRCFCK |
| SEQ ID NO: 90 | GSGCIPKHKRCTWSGPKCCNNISCHCNISGTLCKCRPG |
| SEQ ID NO: 91 | GSNYCVAKRCRPGGRQCCSGKPCACVGKVCKCPRD |
| SEQ ID NO: 92 | GSERGCSGAYKRCSSSQRCCEGRPCVCSAINSNCKCRKT |
| SEQ ID NO: 93 | GSRYCPRNPEACYNYCLRTGRPGGYCGGRSRITCFCFR |
| SEQ ID NO: 94 | GSQRSCAKPGEMCMGIKCCDGQCGCNRGTGRCFCK |
| SEQ ID NO: 95 | GSRRGCFKEGKWCPKSAPCCAPLKCKGPSIKQQKCVRE |
| SEQ ID NO: 96 | GSTVKCGGCNRKCCAGGCRSGKCINGKCQCYGR |
| SEQ ID NO: 97 | GSERRCEPSGKPCRPLMRIPCCGSCVRGKCA |
| SEQ ID NO: 98 | GSRGGCLPRNKFCNPSSGPRCCSGLTCKELNIWANKCL |
| SEQ ID NO: 99 | GSCAKKRNWCGKNEDCCCPMKCIYAWYNQQGSCQTTITGLFKKC |
| SEQ ID NO: 100 | GSGKCINKKCKC |
| SEQ ID NO: 101 | GSKCIN |
| SEQ ID NO: 102 | GSKKCK |

TABLE 1-continued

| SEQ ID NO | Amino Acid Sequence |
|---|---|
| SEQ ID NO: 103 | GSPCKR |
| SEQ ID NO: 104 | GSKRCSRR |
| SEQ ID NO: 105 | GSKQC |
| SEQ ID NO: 106 | GSVRIPVSCKHSGQCLKPCKDAGIVIRTGKCMNGKCDCTPK |
| SEQ ID NO: 107 | GSVKCTTSKDCWPPCKKVTGRA |
| SEQ ID NO: 108 | GSGIVCRVCRIICGMQGRRVNICRAPIRCRCRRG |
| SEQ ID NO: 109 | GSSERDCIRHLQRCRENRDCCSRRCSRRGTNPERRCR |
| SEQ ID NO: 110 | GSVRIPVSCRHSGQCLRPCRDAGIVIRFGRCMNGRCDCTPR |
| SEQ ID NO: 111 | GSGVPINVRCRGSRDCLDPCRRAGMRFGRCINSRCHCTP |
| SEQ ID NO: 112 | GSAVCVYRTCDRDCRRGYRSGRCINNACRCYPYG |
| SEQ ID NO: 113 | GSISCTGSRQCYDPCRRRTGCPNARCMNRSCRCYGCG |
| SEQ ID NO: 114 | GSQVQTNVRCQGGSCASVCRREIGVAAGRCINGRCVCYRN |
| SEQ ID NO: 115 | GSEVIRCSGSRQCYGPCRQQTGCTNSRCMNRVCRCYGCG |
| SEQ ID NO: 116 | GSACRGVFDACTPGRNECCPNRVCSDRHRWCRWRL |
| SEQ ID NO: 117 | GSQIYTSRECNGSSECYSHCEGITGRRSGRCINRRCYCYR |
| SEQ ID NO: 118 | GSGCLEFWWRCNPNDDRCCRPRLRCSRLFRLCNFSFG |
| SEQ ID NO: 119 | GSDCVRFWGRCSQTSDCCPHLACRSRWPRNICVWDGSVG |
| SEQ ID NO: 120 | GSGCFGYRCDYYRGCCSGYVCSPTWRWCVRPGPGR |
| SEQ ID NO: 121 | GSMNARFILLLVLTTMMLLPDTRGAEVIRCSGSRQCYGPCRQQTGCTNSRCMNRVCRCYGCG |
| SEQ ID NO: 122 | GSMNARLIYLLLVVTTMTLMFDTAQAVDEVICSGPRQCYGPCRRETGCPNARCMNRRCRCYGCV |
| SEQ ID NO: 123 | GSMNARLIYLLLVVTTMMLTFDTTQAGDIRCSGTRQCWGPCRRQTTCTNSRCMNGRCRCYGCVG |
| SEQ ID NO: 124 | GSMNTRFIFLLLVVTNTMMLFDTRPVEGISCTGSRQCYDPCRRRTGCPNARCMNRSCRCYGCG |
| SEQ ID NO: 125 | GSGVPINVRCSGSRDCLEPCRRAGMRFGRCINRRCHCTPR |
| SEQ ID NO: 126 | GSGVPINVRCTGSPQCLRPCRDAGIVIRFGRCINGRCHCTPR |
| SEQ ID NO: 127 | GSGVIINVRCRISRQCLEPCRRAGIVIRFGRCMNGRCHCTPR |
| SEQ ID NO: 128 | GSGVPINVRCRGSPQCIQPCRDAGIVIRFGRCMNGRCHCTPQ |
| SEQ ID NO: 129 | GSGVEINVRCTGSHQCIRPCRDAGMRFGRCINRRCHCTPR |
| SEQ ID NO: 130 | GSGVEINVRCSGSPQCLRPCRDAGMRFGRCMNRRCHCTPR |
| SEQ ID NO: 131 | GSGVPTDVRCRGSPQCIQPCRDAGMRFGRCMNGRCHCTPR |
| SEQ ID NO: 132 | GSGVPINVSCTGSPQCIRPCRDAGMRFGRCMNRRCHCTPR |
| SEQ ID NO: 133 | GSGVPINVPCTGSPQCIRPCRDAGMRFGRCMNRRCHCTPR |
| SEQ ID NO: 134 | GSVGINVRCRHSGQCLRPCRDAGMRFGRCINGRCDCTPR |
| SEQ ID NO: 135 | GSVGINVRCHSGQCLRPCRDAGMRFGRCMNGRCDCTPR |
| SEQ ID NO: 136 | GSVGIPVSCRHSGQCIRPCRDAGMRFGRCMNRRCDCTPR |
| SEQ ID NO: 137 | GSRRGCFREGHSCPRTAPCCRPLVCRGPSPNTRRCTRP |
| SEQ ID NO: 138 | GSSFCIPFRPCRSDENCCRRFRCRTTGIVRLCRW |
| SEQ ID NO: 139 | GSLRGCLPRNRFCNALSGPRCCSGLRCRELSIWASRCL |
| SEQ ID NO: 140 | GSGNYCLRGRCLPGGRRCCNGRPCECFARICSCRPR |
| SEQ ID NO: 141 | GSTVRCGGCNRRCCPGGCRSGRCINGRCQCY |
| SEQ ID NO: 142 | GSGCMREYCAGQCRGRVSQDYCLRHCRCIPR |
| SEQ ID NO: 143 | GSACLGFGERCNPSNDRCCRSSSLVCSQRHRWCRYG |
| SEQ ID NO: 144 | GSRGGCLPHNRFCNALSGPRCCSGLRCRELSIRDSRCLG |
| SEQ ID NO: 145 | GSRGGCLPRNRFCNPSSGPRCCSGLTCRELNIWASRCL |
| SEQ ID NO: 146 | GSQRSCARPGDMCMGIRCCDGQCGCNRGTGRCFCR |
| SEQ ID NO: 147 | GSARGCADAYRSCNHPRTCCDGYNGYRRACICSGSNCRCRRS |
| SEQ ID NO: 148 | GSRGGCLPHNRFCNALSGPRCCSGLRCRELSIWDSRCLG |
| SEQ ID NO: 149 | GSRGGCLPHNRFCNALSGPRCCSGLRCRELSIYDSRCLG |
| SEQ ID NO: 150 | GSRGGCLPHNRFCNALSGPRCCSRLRCRELSIWDSRCLG |
| SEQ ID NO: 151 | GSRGGCLPHNRFCNALTGPRCCSRLRCRELSIWDSICLG |
| SEQ ID NO: 152 | GSSCADAYKSCDSLRCCNNRTCMCSMIGTNCTCRRR |

TABLE 1-continued

| SEQ ID NO | Amino Acid Sequence |
|---|---|
| SEQ ID NO: 153 | GSERRCLPAGRTCVRGPMRVPCCGSCSQNRCT |
| SEQ ID NO: 154 | GSLCSREGEFCYRLRRCCAGFYCRAFVLHCYRN |
| SEQ ID NO: 155 | GSACGSCRRRCRGSGRCINGRCRCY |
| SEQ ID NO: 156 | GSACGSCRRRCRGPGRCINGRCRCY |
| SEQ ID NO: 157 | GSACQGYMRRCGRDRPPCCRRLECSRTWRWCVWN |
| SEQ ID NO: 158 | GSGRYCQRWMWTCDSRRACCEGLRCRLWCRRI |
| SEQ ID NO: 159 | GSNARCRGSPECLPRCREAIGRAAGRCMNGRCRCYP |
| SEQ ID NO: 160 | GSNVRCRGSRECLPACRAAVGRAAGRCMNGRCRCYP |
| SEQ ID NO: 161 | GSNVRCRGSPECLPRCREAIGRSAGRCMNGRCRCYP |
| SEQ ID NO: 162 | GSNARCRGSPECLPRCRQAIGRAAGRCMNGRCRCYP |
| SEQ ID NO: 163 | GSRGYCAERGIRCHNIHCCSGLTCRCRGSSCVCRR |
| SEQ ID NO: 164 | GSERGCRLTFWRCRNRRECCGWNACALGICMPR |
| SEQ ID NO: 165 | GSRRRCIARDYGRCRWGGTPCCRGRGCICSIIVIGTNCECRPR |
| SEQ ID NO: 166 | GSGCRLTFWRCRNRRECCGWNACALGICMPR |
| SEQ ID NO: 167 | GSACRGLFVTCTPGRDECCPNHVCSSRHRWCRYR |
| SEQ ID NO: 168 | GSIACAPRGLLCFRDRECCRGLTCRGRFVNTWPTFCLV |
| SEQ ID NO: 169 | GSACAGLYRRCGRGVNTCCENRPCRCDLAMGNCICRRR |
| SEQ ID NO: 170 | GSFTCAISCDIRVNGRPCRGSGERRCSGGWSCRFNVCVRV |
| SEQ ID NO: 171 | GSGFCAQRGIRCHDIHCCTNLRCVREGSNRVCRRA |
| SEQ ID NO: 172 | GSCARRRNWCGRNEDCCCPMRCIYAWYNQQGSCQSTITGLFRRC |
| SEQ ID NO: 173 | GSYCQRWMWTCDSARRCCEGLVCRLWCRRI |
| SEQ ID NO: 174 | GSRGGCLPHNRFCNALSGPRCCSGLRCRELTIWNTRCLE |
| SEQ ID NO: 175 | GSNVRCTGSRQCLPACRAAVGRAAGRCMNGRCRCYT |
| SEQ ID NO: 176 | GSQRSCARPGEMCMRIRCCDGQCGCNRGTGRCFCR |
| SEQ ID NO: 177 | GSGCIPRHRRCTWSGPRCCNNISCHCNISGTLCRCRPG |
| SEQ ID NO: 178 | GSNYCVARRCRPGGRQCCSGRPCACVGRVCRCPRD |
| SEQ ID NO: 179 | GSERGCSGAYRRCSSSQRCCEGRPCVCSAINSNCRCRRT |
| SEQ ID NO: 180 | GSQRSCARPGEMCMGIRCCDGQCGCNRGTGRCFCR |
| SEQ ID NO: 181 | GSRRGCFREGRWCPRSAPCCAPLRCRGPSIRQQRCVRE |
| SEQ ID NO: 182 | GSTVRCGGCNRRCCAGGCRSGRCINGRCQCYGR |
| SEQ ID NO: 183 | GSERRCEPSGRPCRPLMRIPCCGSCVRGRCA |
| SEQ ID NO: 184 | GSRGGCLPRNRFCNPSSGPRCCSGLTCRELNIWANRCL |
| SEQ ID NO: 185 | GSCARRRNWCGRNEDCCCPMRCIYAWYNQQGSCQTTITGLFRRC |
| SEQ ID NO: 186 | GSGRCINRRCRC |
| SEQ ID NO: 187 | GSRCIN |
| SEQ ID NO: 188 | GSRRCR |
| SEQ ID NO: 189 | GSPCRR |
| SEQ ID NO: 190 | GSRRCSRR |
| SEQ ID NO: 191 | GSRQC |
| SEQ ID NO: 192 | GSVRIPVSCRHSGQCLRPCRDAGMRTGRCMNGRCDCTPR |
| SEQ ID NO: 193 | GSPCKK |
| SEQ ID NO: 194 | GSKKCSKK |
| SEQ ID NO: 196 | GSQKILSNRCNNSSECIPHCIRIFGTRAAKCINRKCYCYP |
| SEQ ID NO: 198 | GSAVCNLKRCQLSCRSLGLLGKCIGDKCECVKHG |
| SEQ ID NO: 199 | GSISIGIRCSPSIDLCEGQCRIRRYFTGYCSGDTCHCSG |
| SEQ ID NO: 200 | GSGDCLPHLRRCRENNDCCSRRCRRRGANPERRCR |
| SEQ ID NO: 201 | GSSCEPGRTFRDRCNTCKCGADGRSAACTLRACPNQ |
| SEQ ID NO: 202 | GSGDCLPHLKRCKADNDCCGKKCKRRGTNAEKRCR |
| SEQ ID NO: 203 | GSGDCLPHLKRCKENNDCCSKKCKRRGTNPEKRCR |
| SEQ ID NO: 204 | GSKDCLKKLKLCKENKDCCSKSCKRRGTNIEKRCR |

TABLE 1-continued

| SEQ ID NO | Amino Acid Sequence |
|---|---|
| SEQ ID NO: 205 | GSGDCLPHLKRCKENNDCCSKKCKRRGANPEKRCR |
| SEQ ID NO: 206 | GSVFINVKCRGSPECLPKCKEAIGKSAGKCMNGKCKCYP |
| SEQ ID NO: 207 | GSVFINAKCRGSPECLPKCKEAIGKAAGKCMNGKCKCYP |
| SEQ ID NO: 208 | GSVIINVKCKISRQCLEPCKKAGMRFGKCMNGKCHCTP |
| SEQ ID NO: 209 | GSVPTDVKCRGSPQCIQPCKDAGMRFGKCMNGKCHCTP |
| SEQ ID NO: 210 | GSVRIPVSCKHSGQCLKPCKDAGMRFGKCMNGKCDCTP |
| SEQ ID NO: 211 | GSVRIPVSCRHSGQCLRPCRDAGMRFGRCMNGRCDCTP |
| SEQ ID NO: 212 | GSTNVSCTTSKECWSVCQRLHNTSRGKCMNKKCRC |
| SEQ ID NO: 213 | GSNVKCTGSKQCLPACKAAVGKAAGKCMNGKCKC |
| SEQ ID NO: 214 | GSGVPINVRCRGSRDCLDPCRGAGERHGRCGNSRCHCTP |
| SEQ ID NO: 215 | GSVRIPVSCRHSGQCLRPCRDAGERHGRCGGGRCDCTPR |
| SEQ ID NO: 216 | GSQVQTNVRCQGGSCGSVCRREGGGAGGGCGNGRCGCYRN |
| SEQ ID NO: 237 | GIVCKVCKIICGMQGKKVNICKAPIKCKCKKG |
| SEQ ID NO: 238 | SEKDCIKHLQRCRENKDCCSKKCSRRGTNPEKRCR |
| SEQ ID NO: 239 | VRIPVSCKHSGQCLKPCKDAGMRFGKCMNGKCDCTPK |
| SEQ ID NO: 240 | GVPINVKCRGSRDCLDPCKKAGMRFGKCINSKCHCTP |
| SEQ ID NO: 241 | AVCVYRTCDKDCKRRGYRSGKCINNACKCYPYG |
| SEQ ID NO: 242 | ISCTGSKQCYDPCKRKTGCPNAKCMNKSCKCYGCG |
| SEQ ID NO: 243 | QVQTNVKCQGGSCASVCRREIGVAAGKCINGKCVCYRN |
| SEQ ID NO: 244 | EVIRCSGSKQCYGPCKQQTGCTNSKCMNKVCKCYGCG |
| SEQ ID NO: 245 | ACKGVPDACTPGKNECCPNRVCSDKHKWCKWKL |
| SEQ ID NO: 246 | QIYTSKECNGSSECYSHCEGITGKRSGKCINKKCYCR |
| SEQ ID NO: 247 | GCLEFWWKCNPNDDKCCRPKLKCSKLFKLCNFSFG |
| SEQ ID NO: 248 | DCVRFWGKCSQTSDCCPHLACKSKWPRNICVWDGSVG |
| SEQ ID NO: 249 | GCFGYKCDYYKGCCSGYVCSPTWKWCVRPGPGR |
| SEQ ID NO: 250 | MNAKFILLLVLTTMMLLPDTKGAEVIRCSGSKQCYGPCKQQTGCTNSKCMNKVCKCYGCG |
| SEQ ID NO: 251 | MNAKLIYLLLVVTTMTLMFDTAQAVDIMCSGPKQCYGPCKKETGCPNAKCMNRRCKCYGCV |
| SEQ ID NO: 252 | MNAKLIYLLLVVTTMMLTFDTTQAGDIKCSGTRQCWGPCKKQTTCTNSKCMNGKCKCYGCVG |
| SEQ ID NO: 253 | MNTKFIFLLLVVTNTMMLFDTKPVEGISCTGSKQCYDPCKRKTGCPNAKCMNKSCKCYGCG |
| SEQ ID NO: 254 | GVPINVKCSGSRDCLEPCKKAGMRFGKCINRKCHCTPK |
| SEQ ID NO: 255 | GVPINVKCTGSPQCLKPCKDAGMRFGKCINGKCHCTPK |
| SEQ ID NO: 256 | GVIINVKCKISRQCLEPCKKAGMRFGKCMNGKCHCTPK |
| SEQ ID NO: 257 | GVPINVKCRGSPQCIQPCRDAGMRFGKCMNGKCHCTPQ |
| SEQ ID NO: 258 | GVEINVKCTGSHQCIKPCKDAGMRFGKCINRKCHCTPK |
| SEQ ID NO: 259 | GVEINVKCSGSPQCLKPCKDAGMRFGKCMNRKCHCTPK |
| SEQ ID NO: 260 | GVPTDVKCRGSPQCIQPCKDAGMRFGKCMNGKCHCTPK |
| SEQ ID NO: 261 | GVPINVSCTGSPQCIKPCKDAGMRFGKCMNRKCHCTPK |
| SEQ ID NO: 262 | GVPINVPCTGSPQCIKPCKDAGMRFGKCMNRKCHCTPK |
| SEQ ID NO: 263 | VGINVKCKHSGQCLKPCKDAGMRFGKCINGKCDCTPK |
| SEQ ID NO: 264 | VGINVKCKHSGQCLKPCKDAGMRFGKCMNGKCDCTPK |
| SEQ ID NO: 265 | VGIPVSCKHSGQCIKPCKDAGMRFGKCMNRKCDCTPK |
| SEQ ID NO: 266 | RKGCFKEGHSCPKTAPCCRPLVCKGPSPNTKKCTRP |
| SEQ ID NO: 267 | SFCIPFKPCKSDENCCKKFKCKTTGIVKLCRW |
| SEQ ID NO: 268 | LKGCLPRNRFCNALSGPRCCSGLRCKELSIWASKCL |
| SEQ ID NO: 269 | GNYCLRGRCLPGGRKCCNGRPCECFAKICSCKPK |
| SEQ ID NO: 270 | TVKCGGCNRKCCPGGCRSGKCINGKCQCY |
| SEQ ID NO: 271 | GCMKEYCAGQCRGKVSQDYCLKHCKCIPR |
| SEQ ID NO: 272 | ACLGFGEKCNPSNDKCCKSSSLVCSQKHKWCKYG |
| SEQ ID NO: 273 | RGGCLPHNRFCNALSGPRCCSGLRCKELSIRDSRCLG |

TABLE 1-continued

| SEQ ID NO | Amino Acid Sequence |
|---|---|
| SEQ ID NO: 274 | RGGCLPRNKFCNPSSGPRCCSGLTCKELNIWASKCL |
| SEQ ID NO: 275 | QRSCAKPGDMCMGIKCCDGQCGCNRGTGRCFCK |
| SEQ ID NO: 276 | ARGCADAYKSCNHPRTCCDGYNGYKRACICSGSNCKCKKS |
| SEQ ID NO: 277 | RGGCLPHNRFCNALSGPRCCSGLRCKELSIWDSRCLG |
| SEQ ID NO: 278 | RGGCLPHNRFCNALSGPRCCSGLKCKELSIYDSRCLG |
| SEQ ID NO: 279 | RGGCLPHNRFCNALSGPRCCSRLKCKELSIWDSRCLG |
| SEQ ID NO: 280 | RGGCLPHNRFCNALTGPRCCSRLRCKELSIWDSICLG |
| SEQ ID NO: 281 | SCADAYKSCDSLKCCNNRTCMCSMIGTNCTCRKK |
| SEQ ID NO: 282 | ERRCLPAGKTCVRGPMRVPCCGSCSQNKCT |
| SEQ ID NO: 283 | LCSREGEFCYKLRKCCAGFYCKAFVLHCYRN |
| SEQ ID NO: 284 | ACGSCRKKCKGSGKCINGRCKCY |
| SEQ ID NO: 285 | ACGSCRKKCKGPGKCINGRCKCY |
| SEQ ID NO: 286 | ACQGYMRKCGRDKPPCCKKLECSKTWRWCVWN |
| SEQ ID NO: 287 | GRYCQKWMWTCDSKRACCEGLRCKLWCRKI |
| SEQ ID NO: 288 | NAKCRGSPECLPKCKEAIGKAAGKCMNGKCKCYP |
| SEQ ID NO: 289 | NVKCRGSKECLPACKAAVGKAAGKCMNGKCKCYP |
| SEQ ID NO: 290 | NVKCRGSPECLPKCKEAIGKSAGKCMNGKCKCYP |
| SEQ ID NO: 291 | NAKCRGSPECLPKCKQAIGKAAGKCMNGKCKCYP |
| SEQ ID NO: 292 | RGYCAEKGIKCHNIHCCSGLTCKCKGSSCVCRK |
| SEQ ID NO: 293 | ERGCKLTFWKCKNKKECCGWNACALGICMPR |
| SEQ ID NO: 294 | KKKCIAKDYGRCKWGGTPCCRGRGCICSIIVIGTNCECKPR |
| SEQ ID NO: 295 | GCKLTFWKCKNKKECCGWNACALGICMPR |
| SEQ ID NO: 296 | ACKGLFVTCTPGKDECCPNHVCSSKHKWCKYK |
| SEQ ID NO: 297 | IACAPRGLLCFRDKECCKGLTCKGRFVNTWPTFCLV |
| SEQ ID NO: 298 | ACAGLYKKCGKGVNTCCENRPCKCDLAMGNCICKKK |
| SEQ ID NO: 299 | FTCAISCDIKVNGKPCKGSGEKKCSGGWSCKFNVCVKV |
| SEQ ID NO: 300 | GFCAQKGIKCHDIHCCTNLKCVREGSNRVCRKA |
| SEQ ID NO: 301 | CAKKRNWCGKNEDCCCPMKCIYAWYNQQGSCQSTITGLFKKC |
| SEQ ID NO: 302 | YCQKWMWTCDSARKCCEGLVCRLWCKKI |
| SEQ ID NO: 303 | RGGCLPHNKFCNALSGPRCCSGLKCKELTIWNTKCLE |
| SEQ ID NO: 304 | NVKCTGSKQCLPACKAAVGKAAGKCMNGKCKCYT |
| SEQ ID NO: 305 | QRSCAKPGEMCMRIKCCDGQCGCNRGTGRCFCK |
| SEQ ID NO: 306 | GCIPKHKRCTWSGPKCCNNISCHCNISGTLCKCRPG |
| SEQ ID NO: 307 | NYCVAKRCRPGGRQCCSGKPCACVGKVCKCPRD |
| SEQ ID NO: 308 | ERGCSGAYKRCSSSQRCCEGRPCVCSAINSNCKCRKT |
| SEQ ID NO: 309 | RYCPRNPEACYNYCLRTGRPGGYCGGRSRITCFCFR |
| SEQ ID NO: 310 | QRSCAKPGEMCMGIKCCDGQCGCNRGTGRCFCK |
| SEQ ID NO: 311 | RRGCFKEGKWCPKSAPCCAPLKCKGPSIKQQKCVRE |
| SEQ ID NO: 312 | TVKCGGCNRKCCAGGCRSGKCINGKCQCYGR |
| SEQ ID NO: 313 | ERRCEPSGKPCRPLMRIPCCGSCVRGKCA |
| SEQ ID NO: 314 | RGGCLPRNKFCNPSSGPRCCSGLTCKELNIWANKCL |
| SEQ ID NO: 315 | CAKKRNWCGKNEDCCCPMKCIYAWYNQQGSCQTTITGLFKKC |
| SEQ ID NO: 316 | GKCINKKCKC |
| SEQ ID NO: 317 | KCIN |
| SEQ ID NO: 318 | KKCK |
| SEQ ID NO: 319 | PCKR |
| SEQ ID NO: 320 | KRCSRR |
| SEQ ID NO: 321 | KQC |
| SEQ ID NO: 322 | VRIPVSCKHSGQCLKPCKDAGMRTGKCMNGKCDCTPK |
| SEQ ID NO: 323 | VKCTTSKDCWPPCKKVTGRA |
| SEQ ID NO: 324 | GIVCRVCRIICGMQGRRVNICRAPIRCRCRRG |

TABLE 1-continued

| SEQ ID NO | Amino Acid Sequence |
|---|---|
| SEQ ID NO: 325 | SERDCIRHLQRCRENRDCCSRRCSRRGTNPERRCR |
| SEQ ID NO: 326 | VRIPVSCRHSGQCLRPCRDAGMRFGRCMNGRCDCTPR |
| SEQ ID NO: 327 | GVPINVRCRGSRDCLDPCRRAGMRFGRCINSRCHCTP |
| SEQ ID NO: 328 | AVCVYRTCDRDCRRRGYRSGRCINNACRCYPYG |
| SEQ ID NO: 329 | ISCTGSRQCYDPCRRRTGCPNARCMNRSCRCYGCG |
| SEQ ID NO: 330 | QVQTNVRCQGGSCASVCRREIGVAAGRCINGRCVCYRN |
| SEQ ID NO: 331 | EVIRCSGSRQCYGPCRQQTGCTNSRCMNRVCRCYGCG |
| SEQ ID NO: 332 | ACRGVFDACTPGRNECCPNRVCSDRHRWCRWRL |
| SEQ ID NO: 333 | QIYTSRECNGSSECYSHCEGITGRRSGRCINRRCYCYR |
| SEQ ID NO: 334 | GCLEFWWRCNPNDDRCCRPRLRCSRLFRLCNFSFG |
| SEQ ID NO: 335 | DCVRFWGRCSQTSDCCPHLACRSRWPRNICVWDGSVG |
| SEQ ID NO: 336 | GCFGYRCDYYRGCCSGYVCSPTWRWCVRPGPGR |
| SEQ ID NO: 337 | MNARFILLLVLTTMMLLPDTRGAEVIRCSGSRQCYGPCRQQTGCTNSRCMNRVCRCYGCG |
| SEQ ID NO: 338 | MNARLIYLLLVVTTMTLMFDTAQAVDIMCSGPRQCYGPCRRETGCPNARCMNRRCRCYGCV |
| SEQ ID NO: 339 | MNARLIYLLLVVTTMMLTFDTTQAGDIRCSGTRQCWGPCRRQTTCTNSRCMNGRCRCYGCVG |
| SEQ ID NO: 340 | MNTRFIFLLLVVTNTMMLFDTRPVEGISCTGSRQCYDPCRRRTGCPNARCMNRSCRCYGCG |
| SEQ ID NO: 341 | GVPINVRCSGSRDCLEPCRRAGMRFGRCINRRCHCTPR |
| SEQ ID NO: 342 | GVPINVRCTGSPQCLRPCRDAGMRFGRCINGRCHCTPR |
| SEQ ID NO: 343 | GVIINVRCRISRQCLEPCRRAGMRFGRCMNGRCHCTPR |
| SEQ ID NO: 344 | GVPINVRCRGSPQCIQPCRDAGMRFGRCMNGRCHCTPQ |
| SEQ ID NO: 345 | GVEINVRCTGSHQCIRPCRDAGMRFGRCINRRCHCTPR |
| SEQ ID NO: 346 | GVEINVRCSGSPQCLRPCRDAGMRFGRCMNRRCHCTPR |
| SEQ ID NO: 347 | GVPTDVRCRGSPQCIQPCRDAGMRFGRCMNGRCHCTPR |
| SEQ ID NO: 348 | GVPINVSCTGSPQCIRPCRDAGMRFGRCMNRRCHCTPR |
| SEQ ID NO: 349 | GVPINVPCTGSPQCIRPCRDAGMRFGRCMNRRCHCTPR |
| SEQ ID NO: 350 | VGINVRCRHSGQCLRPCRDAGMRFGRCINGRCDCTPR |
| SEQ ID NO: 351 | VGINVRCRHSGQCLRPCRDAGMRFGRCMNGRCDCTPR |
| SEQ ID NO: 352 | VGIPVSCRHSGQCIRPCRDAGMRFGRCMNRRCDCTPR |
| SEQ ID NO: 353 | RRGCFREGHSCPRTAPCCRPLVCRGPSPNTRRCTRP |
| SEQ ID NO: 354 | SFCIPFRPCRSDENCCRRFRCRTTGIVRLCRW |
| SEQ ID NO: 355 | LRGCLPRNRFCNALSGPRCCSGLRCRELSIWASRCL |
| SEQ ID NO: 356 | GNYCLRGRCLPGGRRCCNGRPCECFARICSCRPR |
| SEQ ID NO: 357 | TVRCGGCNRRCCPGGCRSGRCINGRCQCY |
| SEQ ID NO: 358 | GCMREYCAGQCRGRVSQDYCLRHCRCIPR |
| SEQ ID NO: 359 | ACLGFGERCNPSNDRCCRSSSLVCSQRHRWCRYG |
| SEQ ID NO: 360 | RGGCLPHNRFCNALSGPRCCSGLRCRELSIRDSRCLG |
| SEQ ID NO: 361 | RGGCLPRNRFCNPSSGPRCCSGLTCRELNIWASRCL |
| SEQ ID NO: 362 | QRSCARPGDMCMGIRCCDGQCGCNRGTGRCFCR |
| SEQ ID NO: 363 | ARGCADAYRSCNHPRTCCDGYNGYRRACICSGSNCRCRRS |
| SEQ ID NO: 364 | RGGCLPHNRFCNALSGPRCCSGLRCRELSIWDSRCLG |
| SEQ ID NO: 365 | RGGCLPHNRFCNALSGPRCCSGLRCRELSIYDSRCLG |
| SEQ ID NO: 366 | RGGCLPHNRFCNALSGPRCCSRLRCRELSIWDSRCLG |
| SEQ ID NO: 367 | RGGCLPHNRFCNALTGPRCCSRLRCRELSIWDSICLG |
| SEQ ID NO: 368 | SCADAYKSCDSLRCCNNRTCMCSMIGTNCTCRRR |
| SEQ ID NO: 369 | ERRCLPAGRTCVRGPMRVPCCGSCSQNRCT |
| SEQ ID NO: 370 | LCSREGEFCYRLRRCCAGFYCRAFVLHCYRN |
| SEQ ID NO: 371 | ACGSCRRRCRGSGRCINGRCRCY |
| SEQ ID NO: 372 | ACGSCRRRCRGPGRCINGRCRCY |
| SEQ ID NO: 373 | ACQGYMRRCGRDRPPCCRRLECSRTWRWCVWN |
| SEQ ID NO: 374 | GRYCQRWMWTCDSRRACCEGLRCRLWCRRI |

TABLE 1-continued

| SEQ ID NO | Amino Acid Sequence |
|---|---|
| SEQ ID NO: 375 | NARCRGSPECLPRCREAIGRAAGRCMNGRCRCYP |
| SEQ ID NO: 376 | NVRCRGSRECLPACRAAVGRAAGRCMNGRCRCYP |
| SEQ ID NO: 377 | NVRCRGSPECLPRCREAIGRSAGRCMNGRCRCYP |
| SEQ ID NO: 378 | NARCRGSPECLPRCRQAIGRAAGRCMNGRCRCYP |
| SEQ ID NO: 379 | RGYCAERGIRCHNIHCCSGLTCRCRGSSCVCRR |
| SEQ ID NO: 380 | ERGCRLTFWRCRNRRECCGWNACALGICMPR |
| SEQ ID NO: 381 | RRRCIARDYGRCRWGGTPCCRGRGCICSIIVIGTNCECRPR |
| SEQ ID NO: 382 | GCRLTFWRCRNRRECCGWNACALGICMPR |
| SEQ ID NO: 383 | ACRGLFVTCTPGRDECCPNHVCSSRHRWCRYR |
| SEQ ID NO: 384 | IACAPRGLLCFRDRECCRGLTCRGRFVNTWPTFCLV |
| SEQ ID NO: 385 | ACAGLYRRCGRGVNTCCENRPCRCDLAMGNCICRRR |
| SEQ ID NO: 386 | FTCAISCDIRVNGRPCRGSGERRCSGGWSCRFNVCVRV |
| SEQ ID NO: 387 | GFCAQRGIRCHDIHCCTNLRCVREGSNRVCRRA |
| SEQ ID NO: 388 | CARRRNWCGRNEDCCCPMRCIYAWYNQQGSCQSTITGLFRRC |
| SEQ ID NO: 389 | YCQRWMWTCDSARRCCEGLVCRLWCRRI |
| SEQ ID NO: 390 | RGGCLPHNRFCNALSGPRCCSGLRCRELTIWNTRCLE |
| SEQ ID NO: 391 | NVRCTGSRQCLPACRAAVGRAAGRCMNGRCRCYT |
| SEQ ID NO: 392 | QRSCARPGEMCMRIRCCDGQCGCNRGTGRCFCR |
| SEQ ID NO: 393 | GCIPRHRRCTWSGPRCCNNISCHCNISGTLCRCRPG |
| SEQ ID NO: 394 | NYCVARRCRPGGRQCCSGRPCACVGRVCRCPRD |
| SEQ ID NO: 395 | ERGCSGAYRRCSSSQRCCEGRPCVCSAINSNCRCRRT |
| SEQ ID NO: 396 | QRSCARPGEMCMGIRCCDGQCGCNRGTGRCFCR |
| SEQ ID NO: 397 | RRGCFREGRWCPRSAPCCAPLRCRGPSIRQQRCVRE |
| SEQ ID NO: 398 | TVRCGGCNRRCCAGGCRSGRCINGRCQCYGR |
| SEQ ID NO: 399 | ERRCEPSGRPCRPLMRIPCCGSCVRGRCA |
| SEQ ID NO: 400 | RGGCLPRNRFCNPSSGPRCCSGLTCRELNIWANRCL |
| SEQ ID NO: 401 | CARRRNWCGRNEDCCCPMRCIYAWYNQQGSCQTTITGLFRRC |
| SEQ ID NO: 402 | GRCINRRCRC |
| SEQ ID NO: 403 | RCIN |
| SEQ ID NO: 404 | RRCR |
| SEQ ID NO: 405 | PCRR |
| SEQ ID NO: 406 | RRCSRR |
| SEQ ID NO: 407 | RQC |
| SEQ ID NO: 408 | VRIPVSCRHSGQCLRPCRDAGMRTGRCMNGRCDCTPR |
| SEQ ID NO: 409 | PCKK |
| SEQ ID NO: 410 | KKCSKK |
| SEQ ID NO: 412 | QKILSNRCNNSSECIPHCIRIFGTRAAKCINRKCYCYP |
| SEQ ID NO: 414 | AVCNLKRCQLSCRSLGLLGKCIGDKCECVKHG |
| SEQ ID NO: 415 | ISIGIRCSPSIDLCEGQCRIRRYFTGYCSGDTCHCSG |
| SEQ ID NO: 416 | GDCLPHLRRCRENNDCCSRRCRRRGANPERRCR |
| SEQ ID NO: 417 | SCEPGRTFRDRCNTCKCGADGRSAACTLRACPNQ |
| SEQ ID NO: 418 | GDCLPHLKRCKADNDCCGKKCKRRGTNAEKRCR |
| SEQ ID NO: 419 | GDCLPHLKRCKENNDCCSKKCKRRGTNPEKRCR |
| SEQ ID NO: 420 | KDCLKKLKLCKENKDCCSKSCKRRGTNIEKRCR |
| SEQ ID NO: 421 | GDCLPHLKRCKENNDCCSKKCKRRGANPEKRCR |
| SEQ ID NO: 422 | VFINVKCRGSPECLPKCKEAIGKSAGKCMNGKCKCYP |
| SEQ ID NO: 423 | VFINAKCRGSPECLPKCKEAIGKAAGKCMNGKCKCYP |
| SEQ ID NO: 424 | VIINVKCKISRQCLEPCKKAGMRFGKCMNGKCHCTP |
| SEQ ID NO: 425 | VPTDVKCRGSPQCIQPCKDAGMRFGKCMNGKCHCTP |
| SEQ ID NO: 426 | VRIPVSCKHSGQCLKPCKDAGMRFGKCMNGKCDCTP |

TABLE 1-continued

| SEQ ID NO | Amino Acid Sequence |
| --- | --- |
| SEQ ID NO: 427 | VRIPVSCRHSGQCLRPCRDAGMRFGRCMN GRCDCTP |
| SEQ ID NO: 428 | TNVSCTTSKECWSVCQRLHNTSRGKCMNK KCRC |
| SEQ ID NO: 429 | NVKCTGSKQCLPACKAAVGKAAGKCMNGK CKC |
| SEQ ID NO: 430 | GVPINVRCRGSRDCLDPCRGAGERHGRCG NSRCHCTP |
| SEQ ID NO: 431 | VRIPVSCRHSGQCLRPCRDAGERHGRCGG GRCDCTPR |
| SEQ ID NO: 432 | QVQTNVRCQGGSCGSVCRREGGGAGGGCG NGRCGCYRN |

In any of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 or fragment thereof, any one or more K residues can be replaced by an R residue or any one or more R residues can be replaced by a K residue. In any of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 or any fragment thereof, any one or more M residues can be replaced by any one of I, L, or V residues, any one or more L residues can be replaced by any one of V, I, or M residues, any one or more I residues can be replaced by any one of M, L, or V residues, or any one or more V residues can be replaced by any one of I, L, or M residues. In any embodiment, at least one of the amino acids alone or in combination can be interchanged in the peptides or peptide fragments as follows: K/R, M/I/L/V, G/A, S/T, Q/N, and D/E wherein each letter is each individually any amino acid or amino acid analogue. In some instances, the peptide can contain only one lysine residue, or no lysine residue. In any of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 or any fragment thereof, X can independently be any number of any amino acid or no amino acid. In some cases, a peptide can include the first two N-terminal amino acids GS, as with peptides of SEQ ID NO: 1-SEQ ID NO: 194, SEQ ID NO: 196, and SEQ ID NO: 198-SEQ ID NO: 216, or such N-terminal amino acids (GS) can be substituted by any other one or two amino acids. In other cases, a peptide does not include the first two N-terminal amino acids GS, as with peptides of SEQ ID NO: 217-SEQ ID NO: 410, SEQ ID NO: 412, and SEQ ID NO: 414-SEQ ID NO: 432. In some cases, the N-terminus of the peptide is blocked, such as by an acetyl group; in other instances the C-terminus of the peptide is block, such as by an amide group.

In some instances, the peptide is any one of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 or a functional fragment thereof. In other embodiments, the peptide of the disclosure further comprises a peptide with 99%, 95%, 90%, 85%, or 80% homology to any one of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432. In further embodiments, the peptide fragment comprises a contiguous fragment of any one of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 that is at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46 residues long, wherein the peptide fragment is selected from any portion of the peptide. In some embodiments, such peptide fragments contact the cartilage and exhibit properties of those described herein for peptide and peptide-active agent conjugates.

The peptides of the present disclosure can further comprise negative amino acid residues. In some cases, the peptide has 2 or fewer negative amino acid residues. In other cases, the peptide has 4 or fewer negative amino acid residues, 3 or fewer negative amino acid residues, or 1 or fewer negative amino acid residues. The negative amino acid residues can be selected from any negative charged amino acid residues. The negative amino acid residues can selected from either E or D, or a combination of both E and D.

The peptides of the present disclosure can further comprise basic amino acid residues. In some embodiments, basic residues are added to the peptide sequence to increase the charge at physiological pH. The added basic residues can be any basic amino acid. The added basic residues can be selected from K or R, or a combination of K or R.

In some embodiments, the peptide has a charge distribution comprising an acidic region and a basic region. An acidic region can be a nub. A nub is a portion of a peptide extending out of the peptide's three-dimensional structure. A basic region can be a patch. A patch is a portion of a peptide that does not designate any specific topology characteristic of the peptide's three-dimensional structure. In further embodiments, a knotted peptide can be 6 or more basic residues and 2 or fewer acidic residues.

The peptides of the present disclosure can further comprise positively charged amino acid residues. In some cases, the peptide has at least 2 positively charged residues. In other cases, the peptide has at least 3 positively charged residues, at least 4 positively charged residues, at least 5 positively charged residues, at least 6 positively charged residues, at least 7 positively charged residues, at least 8 positively charged residues or at least 9 positively charged residues. The positively charged residues can be selected from any positively charged amino acid residues. The positively charged residues can be selected from either K or R, or a combination of K and R.

In addition, the peptides herein can comprise a 4-19 amino acid residue fragment of any of the above sequences containing at least 2 cysteine residues, and at least 2 or 3 positively charged amino acid residues (for example, arginine, lysine or histidine, or any combination of arginine, lysine or histidine). In other embodiments, the peptides herein is a 20-70 amino acid residue fragment of any of the above sequences containing at least 2 cysteine residues, no more than 2 basic residues, and at least 2 or 3 positively charged amino acid residues (for example, arginine, lysine or histidine, or any combination of arginine, lysine or histidine). In some embodiments, such peptide fragments contact the cartilage and exhibit properties of those described herein for peptide and peptide-active agent conjugates.

In some embodiments, the peptide contains one or more disulfide bonds and has a positive net charge at neutral pH. At physiological pH, peptides can have a net charge, for example, of −5, −4, −3, −2, −1, 0, +1, +2, +3, +4, or +5. When the net charge is zero, the peptide can be uncharged or zwitterionic. In some instances, the peptide can have a positive charge at physiological pH. In some instances, the peptide can have a charge ≥+2 at physiological pH, ≥+3.5 at physiological pH, ≥+4.5 at physiological pH. In some embodiments, the peptide contains one or more disulfide bonds and has a positive net charge at neutral pH where the net charge can be +0.5 or less than +0.5, +1 or less than +1, +1.5 or less than +1.5, +2 or less than +2, +2.5 or less than +2.5, +3 or less than +3, +3.5 or less than +3.5, +4 or less than +4, +4.5 or less than +4.5, +5 or less than +5, +5.5 or less than +5.5, +6 or less than +6, +6.5 or less than +6.5, +7 or less than +7, +7.5 or less than +7.5, +8 or less than +8, +8.5 or less than +8.5, +9 or less than +9.5, +10 or less than +10. In some embodiments, the peptide has a negative net charge at physiological pH where the net charge can be −0.5 or less than −0.5, −1 or less than −1, −1.5 or less than −1.5, −2 or less than −2, −2.5 or less than −2.5, −3 or less than −3, −3.5 or less than −3.5, −4 or less than −4, −4.5 or less than −4.5, −5 or less than −5, −5.5 or less than −5.5, −6 or less than −6, −6.5 or less than −6.5, −7 or less than −7, −7.5 or less than −7.5, −8 or less than −8, −8.5 or less than −8.5, −9 or less than −9.5, −10 or less than −10. In some cases, the engineering of one or more mutations within a peptide yields a peptide with an altered isoelectric point, charge, surface charge, or rheology at physiological pH. Such engineering of a mutation to a peptide derived from a scorpion or spider can change the net charge of the complex, for example, by decreasing the net charge by 1, 2, 3, 4, or 5, or by increasing the net charge by 1, 2, 3, 4, or 5. In such cases, the engineered mutation may facilitate the ability of the peptide to contact the cartilage. Suitable amino acid modifications for improving the rheology and potency of a peptide can include conservative or non-conservative mutations. A peptide can comprises at most 1 amino acid mutation, at most 2 amino acid mutations, at most 3 amino acid mutations, at most 4 amino acid mutations, at most 5 amino acid mutations, at most 6 amino acid mutations, at most 7 amino acid mutations, at most 8 amino acid mutations, at most 9 amino acid mutations, at most 10 amino acid mutations, or another suitable number as compared to the sequence of the venom or toxin that the peptide is derived from. In other cases, a peptide, or a functional fragment thereof, comprises at least 1 amino acid mutation, at least 2 amino acid mutations, at least 3 amino acid mutations, at least 4 amino acid mutations, at least 5 amino acid mutations, at least 6 amino acid mutations, at least 7 amino acid mutations, at least 8 amino acid mutations, at least 9 amino acid mutations, at least 10 amino acid mutations, or another suitable number as compared to the sequence of the venom or toxin that the peptide is derived from. In some embodiments, mutations can be engineered within a peptide to provide a peptide that has a desired charge or stability at physiological pH.

In some embodiments, charge can play a role in cartilage homing. The interaction of a peptide of this disclosure in solution and in vivo can be influenced by the isoelectric point (pI) of the knottin peptide and/or the pH of the solution or the local environment it is in. The charge of a peptide in solution can impact the solubility of the protein as well as parameters such as biodistribution, bioavailability, and overall pharmacokinetics. Additionally, positively charged molecules can interact with negatively charged molecules. Positively charged molecules such as the peptides disclosed herein can interact and bind with negatively charged molecules such as the negatively charged extracellular matrix molecules in the cartilage including hyaluranon and aggrecan. Positively charged residues can also interact with specific regions of other proteins and molecules, such as negatively charged residues of receptors or electronegative regions of an ion channel pore on cell surfaces. As such, the pI of a peptide can influence whether a peptide of this disclosure can efficiently home to cartilage. Identifying a correlation between pI and cartilage homing can be an important strategy in identifying lead peptide candidates of the present disclosure. The pI of a peptide can be calculated using a number of different methods including the Expasy pI calculator and the Sillero method. The Expasy pI can be determined by calculating pKa values of amino acids as described in Bjellqvist et al., which were defined by examining polypeptide migration between pH 4.5 to pH 7.3 in an immobilized pH gradient gel environment with 9.2M and 9.8M urea at 15° C. or 25° C. (Bjellqvist et al. Electrophoresis. 14(10):1023-31 (1993)). The Sillero method of calculating pI can involve the solution of a polynomial equation and the individual pKas of each amino acid. This method does not use denaturing conditions (urea) (Sillero et al. 179(2): 319-35 (1989)) Using these pI calculation methods and quantifying the cartilage to blood ratio of peptide signal after administration to a subject can be a strategy for identifying a trend or correlation in charge and cartilage homing. In some embodiments, a peptide with a pI above biological pH (~pH 7.4) can exhibit efficient homing to cartilage. In some embodiments, a peptide with a pI of at least 8, at least 9, at least 10, or at least 11 can efficiently home to cartilage. In other embodiments, a peptide with a pI of 11-12 can home most efficiently to cartilage. In certain embodiments, a peptide can have a pI of about 9. In other embodiments, a peptide can have a pI of 8-10. In some embodiments, more basic peptides can home more efficiently to cartilage. In other embodiments, a high pI alone may not be sufficient to cause cartilage homing of a peptides.

In some embodiments, the tertiary structure and electrostatics of a peptide of the disclosure can impact cartilage homing. Structural analysis or analysis of charge distribution can be a strategy to predict residues important in biological function, such as cartilage homing. For example, several peptides of this disclosure that home to cartilage can be grouped into a structural class defined herein as "hitchins," and can share the properties of disulfide linkages between C1-C4, C2-C5, and C3-C6. The folding topologies of peptides knotted through three disulfide linkages (C1-C4, C2-C5, and C3-C6), can be broken down into structural families based on the three-dimensional arrangement of the disulfides. Knottins have the C3-C6 disulfide linkage passing through the macrocycle formed by the C1-C4 and C2-C5 disulfide linkages, hitchins have the C2-C5 disulfide linkage passing through the macrocycle formed by the C1-C4 and C3-C6 disulfide linkages, and yet other structural families have the C1-C4 disulfide linkage passing through the macrocycle formed by the C2-C5 and C3-C6 disulfide linkages. Variants of "hitchin" class peptides with preserved disulfide linkages at these cysteine residues, primary sequence identity, and/or structural homology can be a method of identifying or predicting other potential knottin peptide candidates that can home to cartilage. Additionally, members and related members of the calcin family of peptides can also home to cartilage, despite having a distinct tertiary structure from the "hitchin" class of peptides. Calcin peptides are structurally a subset of the knottin peptides, with knottin disulfide connectivity and topology, but are further classified on the basis of functioning to bind and activate ryanodine receptors (RyRs). These receptors are calcium channels that act to regulate the influx and efflux of calcium in muscle (Schwartz et al. Br J Pharmacol 157(3):392-403. (2009)). Variants of the calcin family of peptides with preserved key residues can be one way to predict promising candidates that can home to cartilage. In some embodiments, structural analysis of a peptide of this disclosure can be determined by evaluating peptides for resistance to degradation in buffers with various proteases or reducing agents. Structural analysis of the distribution of charge density on the surface of a peptide can also be a strategy for predicting promising candidates that can home to cartilage. Peptides with large patches of positive surface charge (when at pH 7.5) can home to cartilage.

The NMR solution structures, x-ray crystallography, or crystal structures of related structural homologs can be used to inform mutational strategies that can improve the folding, stability, and manufacturability, while maintaining the ability of a peptide to home to cartilage. They can be used to predict the 3D pharmacophore of a group of structurally homologous scaffolds, as well as to predict possible graft regions of related proteins to create chimeras with improved properties. For example, this strategy can be used to identify critical amino acid positions and loops that can be used to design drugs with improved properties or to correct deleterious mutations that complicate folding and manufacturability for the peptides. These key amino acid positions and loops can be retained while other residues in the peptide sequences can be mutated to improve, change, remove, or otherwise modify function, homing, and activity of the peptide.

Additionally, the comparison of the primary sequences and the tertiary sequences of two or more peptides can be used to reveal sequence and 3D folding patterns that can be leveraged to improve the peptides and parse out the biological activity of these peptides. For example, comparing two different peptide scaffolds that home to cartilage can lead to the identification of conserved pharmacophores that can guide engineering strategies, such as designing variants with improved folding properties. Important pharmacophore, for example, can comprise aromatic residues or basic residues, which can be important for binding.

Improved peptides can also be engineered based upon immunogenicity information, such as immunogenicity information predicted by TEPITOPE and TEPITOPEpan. TEPITOPE is a computational approach which uses position specific scoring matrix to provide prediction rules for whether a peptide will bind to 51 different HLA-DR alleles, and TEPITOPEpan is method that uses TEPITOPE to extrapolate from HLA-DR molecules with known binding specificities to HLA-DR molecules with unknown binding specificities based on pocket similarity. For example, TEPITOPE and TEPITOPEpan can be used to determine immunogenicity of peptides that home to cartilage. Comparison of peptides with high immunogenicity to peptides with low immunogenicity can guide engineering strategies for designing variants with decreased immunogenicity.

A peptide of this disclosure can bind to sodium channels. The peptide can bind to calcium channels. The peptide can block potassium channels and/or sodium channels. The peptide can block calcium channels. In some embodiments, the peptide can activate potassium channels and/or sodium channels. In other embodiments, the peptide can activate calcium channels. In still other embodiments, the peptide can be a potassium channel agonist, a potassium channel antagonist, a portion of a potassium channel, a sodium channel agonist, a sodium channel antagonist, a calcium channel agonist, a calcium channel antagonist, a hadrucalcin, a theraphotoxin, a huwentoxin, a kaliotoxin, a cobatoxin or a lectin. In some embodiments, the lectin can be SHL-Ib2. In some embodiments, the peptide can interact with, binds, inhibits, inactivates, or alters expression of ion channels or chloride channels. In some embodiments, the peptide can interact with an Nav1.7 ion channel. In some embodiments, the peptide can interact with a Kv 1.3 ion channel. In still other embodiments, the peptide interacts with proteases, matrix metalloproteinase, inhibits cancer cell migration or metastases, has antimicrobial activity, or has antitumor activity. In addition to acting on matrix metalloproteinases, the peptide can interact with other possible proteases (e.g., elastases).

In some embodiments, the peptide has other therapeutic effects on the cartilage or structures thereof or nearby. Beta defensin expression in articular cartilage can be correlated with immunomodulatory functions as we well as osteoarthritis, autoimmune rheumatic disorders such as systemic lupus erythematosus and rheumatoid arthritis (Vordenbaumen and Schneider 2011, Varoga 2004 and Varoga 2005). In some embodiments, the peptides or their mutants inhibit beta defensins, supplement beta defensins, are competitive inhibitors of beta defensins, active or block activation of beta defensin targets, and are used as immune modulators, or to treat autoimmune, arthritis, infections, and other articular disorders.

The present disclosure can also encompass multimers of the various peptides described herein. Examples of multimers include dimers, trimers, tetramers, pentamers, hexamers, heptamers, and so on. A multimer can be a homomer formed from a plurality of identical subunits or a heteromer formed from a plurality of different subunits. In some embodiments, a peptide of the present disclosure is arranged in a multimeric structure with at least one other peptide, or two, three, four, five, six, seven, eight, nine, ten, or more other peptides. In certain embodiments, the peptides of a multimeric structure each have the same sequence. In alternative embodiments, some or all of the peptides of a multimeric structure have different sequences.

The present disclosure further includes peptide scaffolds that, e.g., can be used as a starting point for generating additional peptides. In some embodiments, these scaffolds can be derived from a variety of knotted peptides or knottins. Some suitable peptides for scaffolds can include, but are not limited to, chlorotoxin, brazzein, circulin, stecrisp, hanatoxin, midkine, hefutoxin, potato carboxypeptidase inhibitor, bubble protein, attractin, α-GI, α-GID, ω-MVIIA, ω-CVID, χ-MrIA, ρ-TIA, conantokin G, contulakin G, GsMTx4, margatoxin, shK, toxin K, chymotrypsin inhibitor (CTI), and EGF epiregulin core.

In some embodiments, the peptide sequences of the disclosure are flanked by additional amino acids. One or more additional amino acids can, for example, confer a desired in vivo charge, isoelectric point, chemical conjugation site, stability, or physiologic property to a peptide.

Identifying sequence homology can be important for determining key residues that preserve cartilage homing function. For example, in some embodiments identification of conserved positively charged residues can be important in preserving cartilage homing in any homologous variants that are made. In other embodiments, identification of basic or aromatic dyads, can be important in preserving interaction and activity with Kv ion channels in homologous variants.

Two or more peptides can share a degree of homology and share similar properties in vivo. For instance, a peptide can share a degree of homology with a peptide of the present disclosure. In some cases, a peptide of the disclosure can have up to about 20% pairwise homology, up to about 25% pairwise homology, up to about 30% pairwise homology, up to about 35% pairwise homology, up to about 40% pairwise homology, up to about 45% pairwise homology, up to about 50% pairwise homology, up to about 55% pairwise homology, up to about 60% pairwise homology, up to about 65% pairwise homology, up to about 70% pairwise homology, up to about 75% pairwise homology, up to about 80% pairwise homology, up to about 85% pairwise homology, up to about 90% pairwise homology, up to about 95% pairwise homology, up to about 96% pairwise homology, up to about 97% pairwise homology, up to about 98% pairwise homology, up to about 99% pairwise homology, up to about 99.5% pairwise homology, or up to about 99.9% pairwise homology with a second peptide. In some cases, a peptide of the disclosure can have at least about 20% pairwise homology, at least about 25% pairwise homology, at least about 30% pairwise homology, at least about 35% pairwise homology, at least about 40% pairwise homology, at least about 45% pairwise homology, at least about 50% pairwise homology, at least about 55% pairwise homology, at least about 60% pairwise homology, at least about 65% pairwise homology, at least about 70% pairwise homology, at least about 75% pairwise homology, at least about 80% pairwise homology, at least about 85% pairwise homology, at least about 90% pairwise homology, at least about 95% pairwise homology, at least about 96% pairwise homology, at least about 97% pairwise homology, at least about 98% pairwise homology, at least about 99% pairwise homology, at least about 99.5% pairwise homology, at least about 99.9% pairwise homology with a second peptide. Various methods and software programs can be used to determine the homology between two or more peptides, such as NCBI BLAST, Clustal W, MAFFT, Clustal Omega, AlignMe, Praline, or another suitable method or algorithm.

In still other instances, the variant nucleic acid molecules of a peptide of any one of SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432 can be identified by either a determination of the sequence identity or homology of the encoded peptide amino acid sequence with the amino acid sequence of any one of SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432, or by a nucleic acid hybridization assay. Such peptide variants can include nucleic acid molecules (1) that remain hybridized with a nucleic acid molecule having the nucleotide sequence of any one of SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432 (or any complement of the previous sequences) under stringent washing conditions, in which the wash stringency is equivalent to 0.5×-2×SSC with 0.1% SDS at 55-65° C., and (2) that encode a peptide having at least 70%, at least 80%, at least 90%, at least 95% or greater than 95% sequence identity or homology to the amino acid sequence of any one SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432. Alternatively, peptide variants of any one SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432 can be characterized as nucleic acid molecules (1) that remain hybridized with a nucleic acid molecule having the nucleotide sequence of any one SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432 (or any complement of the previous sequences) under highly stringent washing conditions, in which the wash stringency is equivalent to 0.1×-0.2×SSC with 0.1% SDS at 50-65° C., and (2) that encode a peptide having at least 70%, at least 80%, at least 90%, at least 95% or greater than 95% sequence identity or homology to the amino acid sequence of any one of SEQ ID NO: 21-SEQ ID NO: 194, SEQ ID NO: 196, SEQ ID NO: 198-216, SEQ ID NO: 237-SEQ ID NO: 410, SEQ ID NO: 412, or SEQ ID NO: 414-SEQ ID NO: 432.

Percent sequence identity or homology can be determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (Id.). The sequence identity or homology is then calculated as: ([Total number of identical matches]/[length of the longer sequence plus the number of gaps introduced into the longer sequence in order to align the two sequences])(100).

Additionally, there are many established algorithms available to align two amino acid sequences. For example, the "FASTA" similarity search algorithm of Pearson and Lipman is a suitable protein alignment method for examining the level of sequence identity or homology shared by an amino acid sequence of a peptide disclosed herein and the amino acid sequence of a peptide variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 1) and a test sequence that has either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *Siam J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity or homology of nucleic acid molecules using a ratio as disclosed above. For nucleotide sequence comparisons, the ktup value can range between one to six, preferably from three to six, most preferably three, with other parameters set as described above.

Some examples of common amino acids that are a "conservative amino acid substitution" are illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Determination of amino acid residues that are within regions or domains that are critical to maintaining structural integrity can be determined. Within these regions one can determine specific residues that can be more or less tolerant of change and maintain the overall tertiary structure of the molecule. Methods for analyzing sequence structure include, but are not limited to, alignment of multiple sequences with high amino acid or nucleotide identity or homology and computer analysis using available software (e.g., the Insight II® viewer and homology modeling tools; MSI, San Diego, Calif.), secondary structure propensities, binary patterns, complementary packing and buried polar interactions (Barton, G. J., Current Opin. Struct. Biol. 5:372-6 (1995) and Cordes, M. H. et al., Current Opin. Struct. Biol. 6:3-10 (1996)). In general, when designing modifications to molecules or identifying specific fragments determination of structure can typically be accompanied by evaluating activity of modified molecules.

Pairwise sequence alignment is used to identify regions of similarity that may indicate functional, structural and/or evolutionary relationships between two biological sequences (protein or nucleic acid). By contrast, multiple sequence alignment (MSA) is the alignment of three or more biological sequences. From the output of MSA applications, homology can be inferred and the evolutionary relationship between the sequences assessed. One of skill in the art would recognize as used herein, "sequence homology" and "sequence identity" and "percent (%) sequence identity" and "percent (%) sequence homology" have been used interchangeably to mean the sequence relatedness or variation, as appropriate to a reference polynucleotide or amino acid sequence.

Chemical Modifications

A peptide can be chemically modified one or more of a variety of ways. In some embodiments, the peptide can be mutated to add function, delete function, or modify the in vivo behavior. One or more loops between the disulfide linkages can be modified or replaced to include active elements from other peptides (such as described in Moore and Cochran, Methods in Enzymology, 503, p. 223-251, 2012). Amino acids can also be mutated, such as to increase half-life, modify, add or delete binding behavior in vivo, add new targeting function, modify surface charge and hydrophobicity, or allow conjugation sites. N-methylation is one example of methylation that can occur in a peptide of the disclosure. In some embodiments, the peptide can be modified by methylation on free amines. For example, full methylation can be accomplished through the use of reductive methylation with formaldehyde and sodium cyanoborohydride.

A chemical modification can, for instance, extend the half-life of a peptide or change the biodistribution or pharmacokinetic profile. A chemical modification can comprise a polymer, a polyether, polyethylene glycol, a biopolymer, a polyamino acid, a fatty acid, a dendrimer, an Fc region, a simple saturated carbon chain such as palmitate or myristolate, or albumin. The chemical modification of a peptide with an Fc region can be a fusion Fc-peptide. A polyamino acid can include, for example, a polyamino acid sequence with repeated single amino acids (e.g., polyglycine), and a polyamino acid sequence with mixed polyamino acid sequences (e.g., gly-ala-gly-ala) that can or can not follow a pattern, or any combination of the foregoing.

In some embodiments, the peptides of the present disclosure may be modified such that the modification increases the stability and/or the half-life of the peptides. In some embodiments, the attachment of a hydrophobic moiety, such as to the N-terminus, the C-terminus, or an internal amino acid, can be used to extend half-life of a peptide of the present disclosure. In other embodiments, the peptide of the present disclosure can include post-translational modifications (e.g., methylation and/or amidation), which can affect, e.g., serum half-life. In some embodiments, simple carbon chains (e.g., by myristoylation and/or palmitylation) can be conjugated to the fusion proteins or peptides. In some embodiments, the simple carbon chains may render the fusion proteins or peptides easily separable from the unconjugated material. For example, methods that may be used to separate the fusion proteins or peptides from the unconjugated material include, but are not limited to, solvent extraction and reverse phase chromatography. The lipophilic moieties can extend half-life through reversible binding to serum albumin. The conjugated moieties can, e.g., be lipophilic moieties that extend half-life of the peptides through reversible binding to serum albumin. In some embodiments, the lipophilic moiety can be cholesterol or a cholesterol derivative including cholestenes, cholestanes, cholestadienes and oxysterols. In some embodiments, the peptides can be conjugated to myristic acid (tetradecanoic acid) or a derivative thereof. In other embodiments, the peptides of the present disclosure are coupled (e.g., conjugated) to a half-life modifying agent. Examples of half-life modifying agents include but are not limited to: a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, or a molecule that binds to albumin.

In some embodiments, the first two N-terminal amino acids (GS) of SEQ ID NO: 1-SEQ ID NO: 194, SEQ ID NO: 196, or SEQ ID NO: 198-SEQ ID NO: 216 can serve as a spacer or linker in order to facilitate conjugation or fusion to another molecule, as well as to facilitate cleavage of the peptide from such conjugated or fused molecules. In some embodiments, the fusion proteins or peptides of the present disclosure can be conjugated to other moieties that, e.g., can modify or effect changes to the properties of the peptides.

Active Agent Conjugates

Peptides according to the present disclosure can be conjugated or fused to an agent for use in the treatment of cartilage diseases, disorders, or injuries. For example, in certain embodiments, a peptide as described herein can be fused to another molecule, such as an active agent that provides a functional capability. A peptide can be fused with an active agent through expression of a vector containing the sequence of the peptide with the sequence of the active agent. In various embodiments, the sequence of the peptide and the sequence of the active agent are expressed from the same Open Reading Frame (ORF). In various embodiments, the sequence of the peptide and the sequence of the active agent can comprise a contiguous sequence. The peptide and the active agent can each retain similar functional capabilities in the fusion peptide compared with their functional capabilities when expressed separately.

Furthermore, for example, in certain embodiments, the peptides described herein are attached to another molecule, such as an active agent that provides a functional capability. In some embodiments, 1, 2, 3, 4, 5, 6, 7, 8, 9, or 10 active agents can be linked to a peptide. Multiple active agents can be attached by methods such as conjugating to multiple lysine residues and/or the N-terminus, or by linking the multiple active agents to a scaffold, such as a polymer or dendrimer and then attaching that agent-scaffold to the peptide (such as described in Yurkovetskiy, A. V., *Cancer Res* 75(16): 3365-72 (2015). Examples of active agents include but are not limited to: a peptide, an oligopeptide, a polypeptide, a peptidomimetic, a polynucleotide, a polyribonucleotide, a DNA, a cDNA, a ssDNA, a RNA, a dsRNA, a micro RNA, an oligonucleotide, an antibody, a single chain variable fragment (scFv), an antibody fragment, an aptamer, a cytokine, an interferon, a hormone, an enzyme, a growth factor, a checkpoint inhibitor, a PD-1 inhibitor, a PD-L1 inhibitor, a CTLA4 inhibitor, a CD antigen, aa chemokine, a neurotransmitter, an ion channel inhibitor, a G-protein coupled receptor inhibitor, a G-protein coupled receptor activator, a chemical agent, a radiosensitizer, a radioprotectant, a radionuclide, a therapeutic small molecule, a steroid, a corticosteroid, an anti-inflammatory agent, an immune modulator, a complement fixing peptide or protein, a tumor necrosis factor inhibitor, a tumor necrosis factor activator, a tumor necrosis factor receptor family agonist, a tumor necrosis receptor antagonist, a tumor necrosis factor (TNF) soluble receptor or antibody, caspase protease activator or inhibitor, an NF-κB a RIPK1 and/or RIPK3 inhibitor or activator (e.g., through Toll-like receptors (TLRs) TLR-3 and/or TLR-4, or T-cell receptor (TCR) and the like), a death-receptor ligand (E.g., Fas ligand) activator or inhibitor, TNF receptor family (e.g., TNFR1, TNFR2, lymphotoxin β receptor/TNFRS3, OX40/TNFRSF4, CD40/TNFRSF5, Fas/TNFRSF6, decoy receptor 3/TNFRSF6B, CD27/TNFRSF7, CD30/TNFRSF8, 4-1BB/TNFRSF9, DR4 (death receptor 4/TNFRS10A), DR5 (death receptor 5/TNFRSF10B), decoy receptor 1/TNFRSF10C, decoy receptor 2/TNFRSF10D, RANK (receptor activator of NF-kappa B/TNFRSF11A), OPG (osteoprotegerin/TNFRSF11B), DR3 (death receptor 3/TNFRSF25), TWEAK receptor/TNFRSF12A, TAC1/TNFRSF13B, BAFF-R (BAFF receptor/TNFRSF13C), HVEM (herpes virus entry mediator/TNFRSF14), nerve growth factor receptor/TNFRSF16, BCMA (B cell maturation antigen/TNFRSF17), GITR (glucocorticoid-induced TNF receptor/TNFRSF18), TAJ (toxicity and JNK inducer/TNFRSF19), RELT/TNFRSF19L, DR6 (death receptor 6/TNFRSF21), TNFRSF22, TNFRSF23, ectodysplasin A2 isoform receptor/TNFRS27, ectodysplasin 1, and anhidrotic receptor, a TNF receptor superfamily ligand including—TNF alpha, lymphotoxin-α, tumor necrosis factor membrane form, tumor necrosis factor shed form, LIGHT, lymphotoxin $β_2α_1$ heterotrimer, OX-40 ligand, compound 1 [PMID: 24930776], CD40 ligand, Fas ligand, TL1A, CD70, CD30 ligand, TRAF1, TRAF2, TRAF3, TRAIL, RANK ligand, APRIL, BAFF, B and T lymphocyte attenuator, NGF, BDNF, neurotrophin-3, neurotrophin-4, TL6, ectodysplasin A2, ectodysplasin A1-a TIMP-3 inhibitor, a BCL-2 family inhibitor, an IAP disruptor, a protease inhibitor, an amino sugar, a chemotherapeutic (whether acting through an apoptotic or non-apoptotic pathway) (Ricci et al. Oncologist 11(4):342-57 (2006)), a cytotoxic chemical, a toxin, a tyrosine kinase inhibitor (e.g. imatinib mesylate), protons, bevacuzimab (antivascular agent), erlotinib (EGFR inhibitor), an anti-infective agent, an antibiotic, an anti-viral agent, an anti-fungal agent, an aminoglycoside, a nonsteroidal anti-inflammatory drug (NSAID), a statin, a nanoparticle, a liposome, a polymer, a biopolymer, a polysaccharide, a proteoglycan, a glycosaminoglycan, polyethylene glycol, a lipid, a dendrimer, a fatty acid, or an Fc domain or an Fc region, or an active fragment or a modification thereof. Any combination of the above active agents can be co-delivered with peptides or peptide conjugates of this disclosure. Additionally, in some embodiments, other co-therapies such as proton therapy or ablative radiotherapy can be administered to a subject in need thereof along with peptides or peptide conjugates of this disclosure. In some embodiments, the peptide is covalently or non-covalently linked to an active agent, e.g., directly or via a linker. TNF blockers suppress the immune system by blocking the activity of TNF, a substance in the body that can cause inflammation and lead to immune-system diseases, such as Crohn's disease, ulcerative colitis, rheumatoid arthritis, ankylosing spondylitis, psoriatic arthritis and plaque psoriasis. The drugs in this class include Remicade (infliximab), Enbrel (etanercept), Humira (adalimumab), Cimzia (certolizumab pegol) and Simponi (golimumab). The peptide disclosed herein can be used to home, distribute to, target, directed to, is retained by, accumulate in, migrate to, and/or bind to cartilage, and thus also be used for localizing the attached or fused active agent. Furthermore, knotted chlorotoxin peptide can be internalized in cells (Wiranowska, M., *Cancer Cell Int.*, 11: 27 (2011)). Therefore, cellular internalization, subcellular localization, and intracellular trafficking after internalization of the active agent peptide conjugate or fusion peptide can be important factors in the efficacy of an active agent conjugate or fusion. (Ducry, L., *Antibody Drug Conjugates* (2013); and Singh, S. K., *Pharm Res.* 32(11): 3541-3571 (2015)). Exemplary linkers suitable for use with the embodiments herein are discussed in further detail below.

The peptides or fusion peptides of the present disclosure can also be conjugated to other moieties that can serve other roles, such as providing an affinity handle (e.g., biotin) for retrieval of the peptides from tissues or fluids. For example, peptides or fusion peptides of the present disclosure can also be conjugated to biotin. In addition to extension of half-life, biotin could also act as an affinity handle for retrieval of peptides or fusion peptides from tissues or other locations. In some embodiments, fluorescent biotin conjugates that can act both as a detectable label and an affinity handle can be used. Non limiting examples of commercially available fluorescent biotin conjugates include Atto 425-Biotin, Atto 488-Biotin, Atto 520-Biotin, Atto-550 Biotin, Atto 565-

Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, fluorescein-4-fluorescein, biotin-(5-fluorescein) conjugate, and biotin-B-phycoerythrin, Alexa fluor 488 biocytin, Alexa flour 546, Alexa Fluor 549, lucifer yellow cadaverine biotin-X, Lucifer yellow biocytin, Oregon green 488 biocytin, biotin-rhodamine and tetramethylrhodamine biocytin. In some other examples, the conjugates could include chemiluminescent compounds, colloidal metals, luminescent compounds, enzymes, radioisotopes, and paramagnetic labels. In some embodiments, the peptide described herein can be attached to another molecule. For example, the peptide sequence also can be attached to another active agent (e.g., small molecule, peptide, polypeptide, polynucleotide, antibody, aptamer, cytokine, growth factor, neurotransmitter, an active fragment or modification of any of the preceding, fluorophore, radioisotope, radionuclide chelator, acyl adduct, chemical linker, or sugar, etc.). In some embodiments, the peptide can be fused with, or covalently or non-covalently linked to an active agent.

Additionally, more than one peptide sequence derived from a toxin or venom can be present on or fused with a particular peptide. A peptide can be incorporated into a biomolecule by various techniques. A peptide can be incorporated by a chemical transformation, such as the formation of a covalent bond, such as an amide bond. A peptide can be incorporated, for example, by solid phase or solution phase peptide synthesis. A peptide can be incorporated by preparing a nucleic acid sequence encoding the biomolecule, wherein the nucleic acid sequence includes a subsequence that encodes the peptide. The subsequence can be in addition to the sequence that encodes the biomolecule, or can substitute for a subsequence of the sequence that encodes the biomolecule.

Detectable Agent Conjugates

A peptide can be conjugated to an agent used in imaging, research, therapeutics, theranostics, pharmaceuticals, chemotherapy, chelation therapy, targeted drug delivery, and radiotherapy. The agent can be a detectable agent. In some embodiments, a knottin peptide is conjugated to detectable agents, such as a metal, a radioisotope, a dye, fluorophore, or another suitable material that can be used in imaging. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212. In some embodiments, the fluorophore is a fluorescent agent emitting electromagnetic radiation at a wavelength between 650 nm and 4000 nm, such emissions being used to detect such agent. In some embodiments the fluorophore is a fluorescent agent is selected from the group consisting of Non-limiting examples of fluorescent dyes that could be used as a conjugating molecule in the present disclosure include DyLight-680, DyLight-750, VivoTag-750, DyLight-800, IRDye-800, VivoTag-680, Cy5.5, or indocyanine green (ICG). In some embodiments, near infrared dyes often include cyanine dyes. Additional non-limiting examples of fluorescent dyes for use as a conjugating molecule in the present disclosure include acradine orange or yellow, Alexa Fluors and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naphthacene, bisbenzimide, brainb ow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as for example mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, mercocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR and any derivative thereof, synaptopHluorin, tetraphenyl butadiene, tetrasodium tris, Texas Red, Titan Yellow, TSQ, umbelliferone, violanthrone, yellow fluroescent protein and YOYO-1. Other Suitable fluorescent dyes include, but are not limited to, fluorescein and fluorescein dyes (e.g., fluorescein isothiocyanine or FITC, naphthofluorescein, 4', 5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514., etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. Additional suitable detectable agents are described in PCT/US14/56177. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212.

Other embodiments of the present disclosure provide peptides conjugated to a radiosensitizer or photosensitizer. Examples of radiosensitizers include but are not limited to:

ABT-263, ABT-199, WEHI-539, paclitaxel, carboplatin, cisplatin, oxaliplatin, gemcitabine, etanidazole, misonidazole, tirapazamine, and nucleic acid base derivatives (e.g., halogenated purines or pyrimidines, such as 5-fluorodeoxyuridine). Examples of photosensitizers include but are not limited to: fluorescent molecules or beads that generate heat when illuminated, porphyrins and porphyrin derivatives (e.g., chlorins, bacteriochlorins, isobacteriochlorins, phthalocyanines, and naphthalocyanines), metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid. Advantageously, this approach allows for highly specific targeting of diseased cells (e.g., cancer cells) using both a therapeutic agent (e.g., drug) and electromagnetic energy (e.g., radiation or light) concurrently. In some embodiments, the peptide is covalently or non-covalently linked to the agent, e.g., directly or via a linker. Exemplary linkers suitable for use with the embodiments herein are discussed in further detail below Linkers Peptides according to the present disclosure that home, target, migrate to, are retained by, accumulate in, and/or bind to, or are directed to the cartilage can be attached to another moiety (e.g., an active agent), such as a small molecule, a second peptide, a protein, an antibody, an antibody fragment, an aptamer, polypeptide, polynucleotide, a fluorophore, a radioisotope, a radionuclide chelator, a polymer, a biopolymer, a fatty acid, an acyl adduct, a chemical linker, or sugar or other active agent described herein through a linker, or directly in the absence of a linker.

A peptide can be directly attached to another molecule by a covalent attachment. For example, the peptide is attached to a terminus of the amino acid sequence of a larger polypeptide or peptide molecule, or is attached to a side chain, such as the side chain of a lysine, serine, threonine, cysteine, tyrosine, aspartic acid, a non-natural amino acid residue, or glutamic acid residue. The attachment can be via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond. In some embodiments, similar regions of the disclosed peptide(s) itself (such as a terminus of the amino acid sequence, an amino acid side chain, such as the side chain of a lysine, serine, threonine, cysteine, tyrosine, aspartic acid, a non-natural amino acid residue, or glutamic acid residue, via an amide bond, an ester bond, an ether bond, a carbamate bond, a carbon-nitrogen bond, a triazole, a macrocycle, an oxime bond, a hydrazone bond, a carbon-carbon single double or triple bond, a disulfide bond, or a thioether bond, or linker as described herein) can be used to link other molecules.

Attachment via a linker can involve incorporation of a linker moiety between the other molecule and the peptide. The peptide and the other molecule can both be covalently attached to the linker. The linker can be cleavable, non-cleavable, self-immolating, hydrophilic, or hydrophobic. The linker can have at least two functional groups with one bonded to the peptide, the other bonded to the other molecule, and a linking portion between the two functional groups.

Non-limiting examples of the functional groups for attachment can include functional groups capable of forming an amide bond, an ester bond, an ether bond, a carbonate bond, a carbamate bond, or a thioether bond. Non-limiting examples of functional groups capable of forming such bonds can include amino groups; carboxyl groups; hydroxyl groups; aldehyde groups; azide groups; alkyne and alkene groups; ketones; hydrazides; acid halides such as acid fluorides, chlorides, bromides, and iodides; acid anhydrides, including symmetrical, mixed, and cyclic anhydrides; carbonates; carbonyl functionalities bonded to leaving groups such as cyano, succinimidyl, and N-hydroxysuccinimidyl; hydroxyl groups; sulfhydryl groups; and molecules possessing, for example, alkyl, alkenyl, alkynyl, allylic, or benzylic leaving groups, such as halides, mesylates, tosylates, triflates, epoxides, phosphate esters, sulfate esters, and besylates.

Non-limiting examples of the linking portion can include alkylene, alkenylene, alkynylene, polyether, such as polyethylene glycol (PEG), hydroxy carboxylic acids, polyester, polyamide, polyamino acids, polypeptides, cleavable peptides, valine-citrulline, aminobenzylcarbamates, D-amino acids, and polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, epoxides, and ester groups.

Non-limiting examples of linkers include:

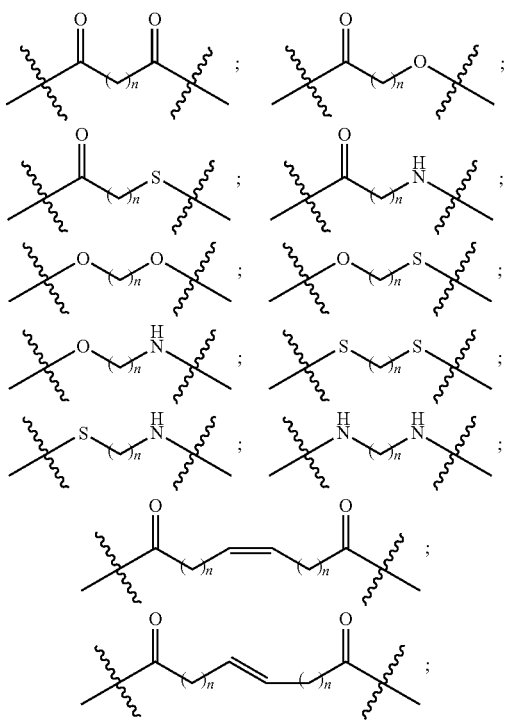

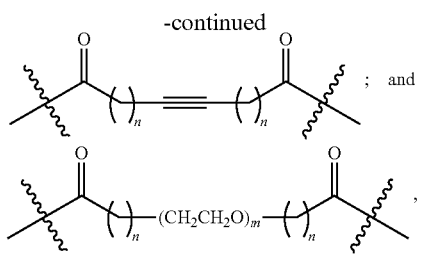

wherein each n is independently 0 to about 1,000; 1 to about 1,000; 0 to about 500; 1 to about 500; 0 to about 250; 1 to about 250; 0 to about 200; 1 to about 200; 0 to about 150; 1 to about 150; 0 to about 100; 1 to about 100; 0 to about 50; 1 to about 50; 0 to about 40; 1 to about 40; 0 to about 30; 1 to about 30; 0 to about 25; 1 to about 25; 0 to about 20; 1 to about 20; 0 to about 15; 1 to about 15; 0 to about 10; 1 to about 10; 0 to about 5; or 1 to about 5. In some embodiments, each n is independently 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50. In some embodiments, m is 1 to about 1,000; 1 to about 500; 1 to about 250; 1 to about 200; 1 to about 150; 1 to about 100; 1 to about 50; 1 to about 40; 1 to about 30; 1 to about 25; 1 to about 20; 1 to about 15; 1 to about 10; or 1 to about 5. In some embodiments, m is 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50.

In some cases a linker can be a succinic linker, and a drug can be attached to a peptide via an ester bond or an amide bond with two methylene carbons in between. In other cases, a linker can be any linker with both a hydroxyl group and a carboxylic acid, such as hydroxy hexanoic acid or lactic acid.

The linker can be a cleavable or a noncleavable linker. The use of a cleavable linker permits release of the conjugated moiety (e.g., a therapeutic agent) from the peptide, e.g., after targeting to the cartilage. In some cases the linker is enzyme cleavable, e.g., a valine-citrulline linker. In some embodiments, the linker contains a self-immolating portion. In other embodiments, the linker includes one or more cleavage sites for a specific protease, such as a cleavage site for matrix metalloproteases (MMPs), thrombin, or cathepsin. Alternatively or in combination, the linker is cleavable by other mechanisms, such as via pH, reduction, or hydrolysis. A hydrolytically labile linker, (amongst other cleavable linkers described herein) can be advantageous in terms of releasing active agents from the peptide. For example, an active agent in a conjugate form with the peptide may not be active, but upon release from the conjugate after targeting to the cartilage, the active agent is active.

The rate of hydrolysis of the linker can be tuned. For example, the rate of hydrolysis of linkers with unhindered esters is faster compared to the hydrolysis of linkers with bulky groups next an ester carbonyl. A bulky group can be a methyl group, an ethyl group, a phenyl group, a ring, or an isopropyl group, or any group that provides steric bulk. In some cases, the steric bulk can be provided by the drug itself, such as by ketorolac when conjugated via its carboxylic acid. The rate of hydrolysis of the linker can be tuned according to the residency time of the conjugate in the cartilage. For example, when a peptide is cleared from the cartilage relatively quickly, the linker can be tuned to rapidly hydrolyze. In contrast, for example, when a peptide has a longer residence time in the cartilage, a slower hydrolysis rate can allow for extended delivery of an active agent. This can be important when the peptide is used to deliver a drug to the cartilage. "Programmed hydrolysis in designing paclitaxel prodrug for nanocarrier assembly" Sci Rep 2015, 5, 12023 Fu et al., provides an example of modified hydrolysis rates.

Peptide Stability

A peptide of the present disclosure can be stable in various biological conditions. For example, any peptide of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 can exhibit resistance to reducing agents, proteases, oxidative conditions, or acidic conditions.

In some cases, biologic molecules (such as peptides and proteins) can provide therapeutic functions, but such therapeutic functions are decreased or impeded by instability caused by the in vivo environment. (Moroz et al. Adv Drug Deliv Rev 101:108-21 (2016), Mitragotri et al. Nat Rev Drug Discov 13(9):655-72 (2014), Bruno et al. Ther Deliv (11):1443-67 (2013), Sinha et al. Crit Rev Ther Drug Carrier Syst. 24(1):63-92 (2007), Hamman et al. BioDrugs 19(3): 165-77 (2005)). For instance, the GI tract can contain a region of low pH (e.g. pH~1), a reducing environment, or a protease-rich environment that can degrade peptides and proteins. Proteolytic activity in other areas of the body, such as the mouth, eye, lung, intranasal cavity, joint, skin, vaginal tract, mucous membranes, and serum, can also be an obstacle to the delivery of functionally active peptides and polypeptides. Additionally, the half-life of peptides in serum can be very short, in part due to proteases, such that the peptide can be degraded too quickly to have a lasting therapeutic effect when administering reasonable dosing regimens. Likewise, proteolytic activity in cellular compartments such as lysosomes and reduction activity in lysosomes and the cytosol can degrade peptides and proteins such that they may be unable to provide a therapeutic function on intracellular targets. Therefore, peptides that are resistant to reducing agents, proteases, and low pH may be able to provide enhanced therapeutic effects or enhance the therapeutic efficacy of co-formulated or conjugated active agents in vivo.

Additionally, oral delivery of drugs can be desirable in order to target certain areas of the body (e.g., disease in the GI tract such as colon cancer, irritable bowel disorder, infections, metabolic disorders, and constipation) despite the obstacles to the delivery of functionally active peptides and polypeptides presented by this method of administration. For example, oral delivery of drugs can increase compliance by providing a dosage form that is more convenient for patients to take as compared to parenteral delivery. Oral delivery can be useful in treatment regimens that have a large therapeutic window. Therefore, peptides that are resistant to reducing agents, proteases, and low pH can allow for oral delivery of peptides without nullifying their therapeutic function.

Peptide Resistance to Reducing Agents

Peptides of this disclosure can contain one or more cysteines, which can participate in disulfide bridges that can be integral to preserving the folded state of the peptide. Exposure of peptides to biological environments with reducing agents can result in unfolding of the peptide and loss of functionality and bioactivity. For example, glutathione (GSH) is a reducing agent that can be present in many areas of the body and in cells, and can reduce disulfide bonds. As another example, a peptide can become reduced upon cellular internalization during trafficking of a peptide across the gastrointestinal epithelium after oral administration A peptide can become reduced upon exposure to various parts of the GI tract. The GI tract can be a reducing environment, which can inhibit the ability of therapeutic molecules with disulfide bonds to have optimal therapeutic efficacy, due to reduction of the disulfide bonds. A peptide can also be reduced upon entry into a cell, such as after internalization by endosomes or lysosomes or into the cytosol, or other cellular compartments. Reduction of the disulfide bonds and unfolding of the peptide can lead to loss of functionality or affect key pharmacokinetic parameters such as bioavailability, peak plasma concentration, bioactivity, and half-life. Reduction of the disulfide bonds can also lead to increased susceptibility of the peptide to subsequent degradation by proteases, resulting in rapid loss of intact peptide after administration. In some embodiments, a peptide that is resistant to reduction can remain intact and can impart a functional activity for a longer period of time in various compartments of the body and in cells, as compared to a peptide that is more readily reduced.

In certain embodiments, the peptides of this disclosure can be analyzed for the characteristic of resistance to reducing agents to identify stable peptides. In some embodiments, the peptides of this disclosure can remain intact after being exposed to different molarities of reducing agents such as 0.00001M-0.0001M, 0.0001M-0.001M, 0.001M-0.01M, 0.01 M-0.05 M, 0.05 M-0.1 M, for greater 15 minutes or more. In some embodiments, the reducing agent used to determine peptide stability can be dithiothreitol (DTT), Tris(2-carboxyethyl)phosphine HCl (TCEP), 2-Mercaptoethanol, (reduced) glutathione (GSH), or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a reducing agent.

Peptide Resistance to Proteases

The stability of peptides of this disclosure can be determined by resistance to degradation by proteases. Proteases, also referred to as peptidases or proteinases, can be enzymes that can degrade peptides and proteins by breaking bonds between adjacent amino acids. Families of proteases with specificity for targeting specific amino acids can include serine proteases, cysteine proteases, threonine proteases, aspartic proteases, glutamic proteases, esterases, serum proteases, and asparagine proteases. Additionally, metalloproteases, matrix metalloproteases, elastase, carboxypeptidases, Cytochrome P450 enzymes, and cathepsins can also digest peptides and proteins. Proteases can be present at high concentration in blood, in mucous membranes, lungs, skin, the GI tract, the mouth, nose, eye, and in compartments of the cell. Misregulation of proteases can also be present in various diseases such as rheumatoid arthritis and other immune disorders. Degradation by proteases can reduce bioavailability, biodistribution, half-life, and bioactivity of therapeutic molecules such that they are unable to perform their therapeutic function. In some embodiments, peptides that are resistant to proteases can better provide therapeutic activity at reasonably tolerated concentrations in vivo.

In some embodiments, peptides of this disclosure can resist degradation by any class of protease. In certain embodiments, peptides of this disclosure resist degradation by pepsin (which can be found in the stomach), trypsin (which can be found in the duodenum), serum proteases, or any combination thereof. In certain embodiments, peptides of this disclosure can resist degradation by lung proteases (e.g., serine, cysteinyl, and aspartyl proteases, metalloproteases, neutrophil elastase, alpha-1 antitrypsin, secretory leucoprotease inhibitor, elafin), or any combination thereof. In some embodiments, the proteases used to determine peptide stability can be pepsin, trypsin, chymotrypsin, or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a protease. Peptides of SEQ ID NO: 212, SEQ ID NO: 24, and SEQ ID NO: 111 can have particular structural qualities, which make them more resistant to protease degradation. For example, peptide of SEQ ID NO: 24 and SEQ ID NO: 112 exhibit the "hitchin" topology as described previously, which can be associated with resistance to protease and chemical degradation.

Peptide Stability in Acidic Conditions

Peptides of this disclosure can be administered in biological environments that are acidic. For example, after oral administration, peptides can experience acidic environmental conditions in the gastric fluids of the stomach and gastrointestinal (GI) tract. The pH of the stomach can range from −1-4 and the pH of the GI tract ranges from acidic to normal physiological pH descending from the upper GI tract to the colon. In addition, the vagina, late endosomes, and lysosomes can also have acidic pH values, such as less than pH 7. These acidic conditions can lead to denaturation of peptides and proteins into unfolded states. Unfolding of peptides and proteins can lead to increased susceptibility to subsequent digestion by other enzymes as well as loss of biological activity of the peptide.

In certain embodiments, the peptides of this disclosure can resist denaturation and degradation in acidic conditions and in buffers, which simulate acidic conditions. In certain embodiments, peptides of this disclosure can resist denaturation or degradation in buffer with a pH less than 1, a pH less than 2, a pH less than 3, a pH less than 4, a pH less than 5, a pH less than 6, a pH less than 7, or a pH less than 8. In some embodiments, peptides of this disclosure remain intact at a pH of 1-3. In certain embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH less than 1, a pH less than 2, a pH less than 3, a pH less than 4, a pH less than 5, a pH less than 6, a pH less than 7, or a pH less than 8. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH of 1-3. In other embodiments, the peptides of this disclosure can be resistant to denaturation or degradation in simulated gastric fluid (pH 1-2). In some embodiments, at least 5-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to simulated gastric fluid. In some embodiments, low pH solutions such as simulated gastric fluid or citrate buffers can be used to determine peptide stability.

Peptide Stability at High Temperatures

Peptides of this disclosure can be administered in biological environments with high temperatures. For example, after oral administration, peptides can experience high temperatures in the body. Body temperature can range from 36° C. to 40° C. High temperatures can lead to denaturation of peptides and proteins into unfolded states. Unfolding of peptides and proteins can lead to increased susceptibility to subsequent digestion by other enzymes as well as loss of biological activity of the peptide. In some embodiments, a peptide of this disclosure can remain intact at temperatures from 25° C. to 100° C. High temperatures can lead to faster degradation of peptides. Stability at a higher temperature can allow for storage of the peptide in tropical environments or areas where access to refrigeration is limited. In certain embodiments, 5%-100% of the peptide can remain intact after exposure to 25° C. for 6 months to 5 years. 5%-100% of a peptide can remain intact after exposure to 70° C. for 15 minutes to 1 hour. 5%-100% of a peptide can remain intact after exposure to 100° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 25° C. for 6 months to 5 years. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 70° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 100° C. for 15 minutes to 1 hour.

Pharmacokinetics of Peptides

The pharmacokinetics of any of the peptides of this disclosure can be determined after administration of the peptide via different routes of administration. For example, the pharmacokinetic parameters of a peptide of this disclosure can be quantified after intravenous, subcutaneous, intramuscular, rectal, aerosol, parenteral, ophthalmic, pulmonary, transdermal, vaginal, optic, nasal, oral, sublingual, inhalation, dermal, intrathecal, intranasal, intra-articular, peritoneal, buccal, synovial, or topical administration. Peptides of the present disclosure can be analyzed by using tracking agents such as radiolabels or fluorophores. For example, a radiolabeled peptides of this disclosure can be administered via various routes of administration. Peptide concentration or dose recovery in various biological samples such as plasma, urine, feces, any organ, skin, muscle, and other tissues can be determined using a range of methods including HPLC, fluorescence detection techniques (TECAN quantification, flow cytometry, iVIS), or liquid scintillation counting.

The methods and compositions described herein can relate to pharmacokinetics of peptide administration via any route to a subject. Pharmacokinetics can be described using methods and models, for example, compartmental models or noncompartmental methods. Compartmental models include but are not limited to monocompartmental model, the two compartmental model, the multicompartmental model or the like. Models can be divided into different compartments and can be described by the corresponding scheme. For example, one scheme is the absorption, distribution, metabolism and excretion (ADME) scheme. For another example, another scheme is the liberation, absorption, distribution, metabolism and excretion (LADME) scheme. In some aspects, metabolism and excretion can be grouped into one compartment referred to as the elimination compartment. For example, liberation can include liberation of the active portion of the composition from the delivery system, absorption includes absorption of the active portion of the composition by the subject, distribution includes distribution of the composition through the blood plasma and to different tissues, metabolism, which includes metabolism or inactivation of the composition and finally excretion, which includes excretion or elimination of the composition or the products of metabolism of the composition. Compositions administered intravenously to a subject can be subject to multiphasic pharmacokinetic profiles, which can include but are not limited to aspects of tissue distribution and metabolism/excretion. As such, the decrease in plasma or serum concentration of the composition is often biphasic, including, for example an alpha phase and a beta phase, occasionally a gamma, delta or other phase is observed Pharmacokinetics includes determining at least one parameter associated with administration of a peptide to a subject. In some aspects, parameters include at least the dose (D), dosing interval (τ), area under curve (AUC), maximum concentration ($C_{max}$), minimum concentration reached before a subsequent dose is administered ($C_{min}$), minimum time ($T_{min}$), maximum time to reach Cmax ($T_{max}$), volume of distribution ($V_d$), steady-state volume of distribution ($V_{ss}$), back-extrapolated concentration at time 0 ($C_0$), steady state concentration ($C_{ss}$), elimination rate constant ($k_e$), infusion rate ($k_{in}$), clearance (CL), bioavailability (f), fluctuation (% PTF) and elimination half-life ($t_{1/2}$).

In certain embodiments, the peptides of any of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 exhibit optimal pharmacokinetic parameters after oral administration. In other embodiments, the peptides of any of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 exhibit optimal pharmacokinetic parameters after any route of administration, such as oral administration, inhalation, intranasal administration, topical administration, intravenous administration, subcutaneous administration, intra-articular administration, intramuscular administration, intraperitoneal administration, or any combination thereof.

In some embodiments any peptide of SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 exhibits an average T. of 0.5-12 hours, or 1-48 hours at which the $C_{max}$ is reached, an average bioavailability in serum of 0.1%-10% in the subject after administering the peptide to the subject by an oral route, an average bioavailability in serum of less than 0.1% after oral administration to a subject for delivery to the GI tract, an average bioavailability in serum of 10-100% after parenteral administration, an average $t_{1/2}$ of 0.1 hours-168 hours, or 0.25 hours-48 hours in a subject after administering the peptide to the subject, an average clearance (CL) of 0.5-100 L/hour or 0.5-50 L/hour of the peptide after administering the peptide to a subject, an average volume of distribution ($V_d$) of 200-20,000 mL in the subject after systemically administering the peptide to the subject, or optionally no systemic uptake, any combination thereof.

Methods of Manufacture

Various expression vector/host systems can be utilized for the production of the recombinant expression of peptides described herein. Non-limiting examples of such systems include microorganisms such as bacteria transformed with recombinant bacteriophage DNA, plasmid DNA or cosmid DNA expression vectors containing a nucleic acid sequence encoding peptides or peptide fusion proteins/chimeric proteins described herein, yeast transformed with recombinant yeast expression vectors containing the aforementioned nucleic acid sequence, insect cell systems infected with recombinant virus expression vectors (e.g., baculovirus) containing the aforementioned nucleic acid sequence, plant cell systems infected with recombinant virus expression vectors (e.g., cauliflower mosaic virus (CaMV), tobacco mosaic virus (TMV) or transformed with recombinant plasmid expression vectors (e.g., Ti plasmid) containing the aforementioned nucleic acid sequence, or animal cell systems infected with recombinant virus expression vectors (e.g., adenovirus, vaccinia virus) including cell lines engineered to contain multiple copies of the aforementioned nucleic acid sequence, either stably amplified (e.g., CHO/dhfr, CHO/glutamine synthetase) or unstably amplified in double-minute chromosomes (e.g., murine cell lines). Disulfide bond formation and folding of the peptide could occur during expression or after expression or both.

A host cell can be adapted to express one or more peptides described herein. The host cells can be prokaryotic, eukaryotic, or insect cells. In some cases, host cells are capable of modulating the expression of the inserted sequences, or modifying and processing the gene or protein product in the specific fashion desired. For example, expression from certain promoters can be elevated in the presence of certain inducers (e.g., zinc and cadmium ions for metallothionine promoters). In some cases, modifications (e.g., phosphorylation) and processing (e.g., cleavage) of peptide products can be important for the function of the peptide. Host cells can have characteristic and specific mechanisms for the post-translational processing and modification of a peptide. In some cases, the host cells used to express the peptides secretes minimal amounts of proteolytic enzymes.

In the case of cell- or viral-based samples, organisms can be treated prior to purification to preserve and/or release a target polypeptide. In some embodiments, the cells are fixed using a fixing agent. In some embodiments, the cells are lysed. The cellular material can be treated in a manner that does not disrupt a significant proportion of cells, but which removes proteins from the surface of the cellular material, and/or from the interstices between cells. For example, cellular material can be soaked in a liquid buffer or, in the case of plant material, can be subjected to a vacuum, in order to remove proteins located in the intercellular spaces and/or in the plant cell wall. If the cellular material is a microorganism, proteins can be extracted from the microorganism culture medium. Alternatively, the peptides can be packed in inclusion bodies. The inclusion bodies can further be separated from the cellular components in the medium. In some embodiments, the cells are not disrupted. A cellular or viral peptide that is presented by a cell or virus can be used for the attachment and/or purification of intact cells or viral particles. In addition to recombinant systems, Peptides can also be synthesized in a cell-free system using a variety of known techniques employed in protein and peptide synthesis.

In some cases, a host cell produces a peptide that has an attachment point for a drug. An attachment point could comprise a lysine residue, an N-terminus, a cysteine residue, a cysteine disulfide bond, or a non-natural amino acid. The peptide could also be produced synthetically, such as by solid-phase peptide synthesis, or solution-phase peptide synthesis. The peptide could be folded (formation of disulfide bonds) during synthesis or after synthesis or both. Peptide fragments could be produced synthetically or recombinantly and then joined together synthetically, recombinantly, or via an enzyme.

Figure 9:
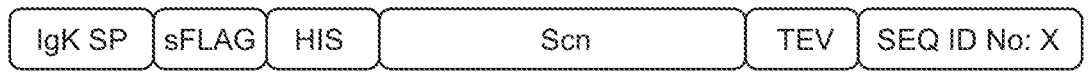
FIG. 9 illustrates an exemplary architecture of constructs expressing sequences of FIGS. 1A-1M and SEQ ID NO: X, where X can be any one of peptides of SEQ ID NO: 21-SEQ ID NO: 33.
Figure 10:
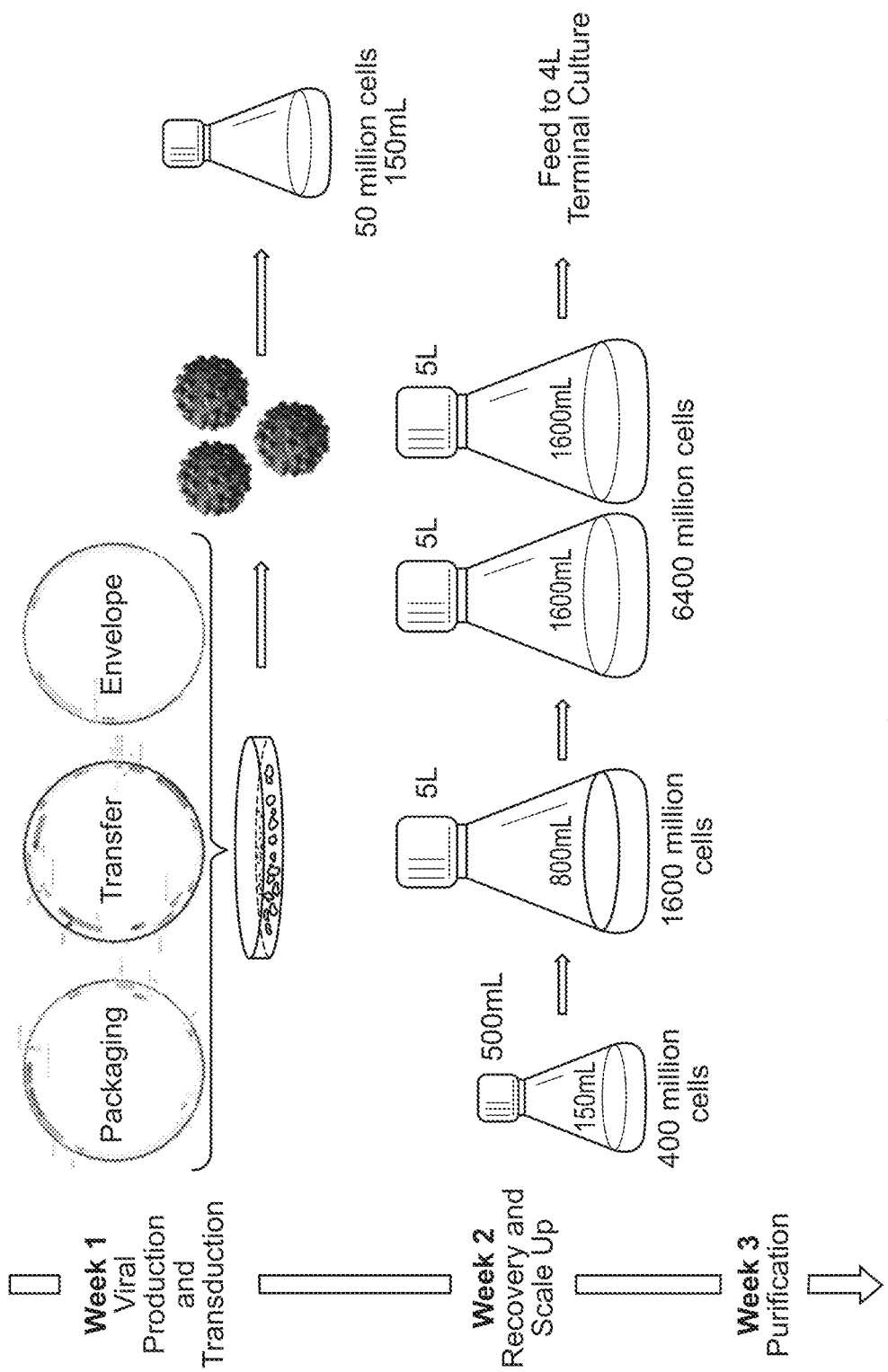
FIG. 10 illustrates a schematic of a method of manufacturing of a peptide of the disclosure.

FIG. 10 illustrates a schematic of a method of manufacturing a construct that expresses a peptide of the disclosure, such as the constructs illustrated in FIG. 9 and as described throughout the disclosure and in SEQ ID NO: 1-SEQ ID NO: 194, SEQ ID NO: 196, SEQ ID NO: 198-SEQ ID NO: 410, SEQ ID NO: 412, SEQ ID NO: 414-SEQ ID NO: 432 provided herein.

In other aspects, the peptides of the present disclosure can be prepared by conventional solid phase chemical synthesis techniques, for example according to the Fmoc solid phase peptide synthesis method ("Fmoc solid phase peptide synthesis, a practical approach," edited by W. C. Chan and P. D. White, Oxford University Press, 2000).

Pharmaceutical Compositions of Peptides

A pharmaceutical composition of the disclosure can be a combination of any peptide described herein with other chemical components, such as carriers, stabilizers, diluents, dispersing agents, suspending agents, thickening agents, antioxidants, solubilizers, buffers, osmolytes, salts, surfactants, amino acids, encapsulating agents, bulking agents, cryoprotectants, and/or excipients. The pharmaceutical composition facilitates administration of a peptide described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, sublingual, inhalation, dermal, intrathecal, intranasal, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduces the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously.

A peptide of the disclosure can be applied directly to an organ, or an organ tissue or cells, such as brain or brain tissue or cancer cells, during a surgical procedure. The recombinant peptides described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the peptide described herein described herein can be administered in pharmaceutical compositions to a subject suffering from a condition that affects the immune system. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a peptide described herein can be manufactured, for example, by expressing the peptide in a recombinant system, purifying the peptide, lyophilizing the peptide, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of peptides described herein comprising the compounds described herein include formulating the peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Administration of Pharmaceutical Compositions

A pharmaceutical composition of the disclosure can be a combination of any venom or toxin derived peptide described herein with other chemical components, such as carriers, stabilizers, diluents, dispersing agents, suspending agents, thickening agents, and/or excipients. The pharmaceutical composition facilitates administration of a peptide described herein to an organism. Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, inhalation, dermal, intra-articular, intrathecal, intranasal, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water-soluble form. Suspensions of peptides described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduces the aggregation of such peptides described herein to allow for the preparation of highly concentrated solutions. Alternatively, the peptides described herein can be lyophilized or in powder form for re-constitution with a suitable vehicle, e.g., sterile pyrogen-free water, before use. In some embodiments, a purified peptide is administered intravenously. A peptide described herein can be administered to a subject, home, target, migrates to, is retained by, and/or binds to, or be directed to an organ, e.g., the cartilage.

A peptide of the disclosure can be applied directly to an organ, or an organ tissue or cells, such as cartilage or cartilage tissue or cells, during a surgical procedure. The recombinant peptides described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of the peptide described herein described herein are administered in pharmaceutical compositions to a subject suffering from a condition. In some instances the pharmaceutical composition will affect the physiology of the animal, such as the immune system, inflammatory response, or other physiologic affect. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a peptide described herein can be manufactured, for example, by expressing the peptide in a recombinant system, purifying the peptide, lyophilizing the peptide, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of peptides described herein comprising the compounds described herein include formulating the peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

Use of Peptide in Imaging and Surgical Methods

The present disclosure generally relates to peptides that home, target, migrate to, are retained by, accumulate in, and/or bind to, or are directed to specific regions, tissues, structures, or cells within the body and methods of using such peptides. These peptides have the ability to contact the cartilage, which makes them useful for a variety of applications. In particular, the peptides can have applications in site-specific modulation of biomolecules to which the peptides are directed to. End uses of such peptides can include, for example, imaging, research, therapeutics, theranostics, pharmaceuticals, chemotherapy, chelation therapy, targeted drug delivery, and radiotherapy. Some uses can include targeted drug delivery and imaging.

In some embodiments, the present disclosure provides a method for detecting a cancer, cancerous tissue, or tumor tissue, the method comprising the steps of contacting a tissue of interest with a peptide of the present disclosure, wherein the peptide is conjugated to a detectable agent and measuring the level of binding of the peptide, wherein an elevated level of binding, relative to normal tissue, is indicative that the tissue is a cancer, cancerous tissue or tumor tissue.

In some embodiments, the disclosure provides a method of imaging an organ or body region or region, tissue or structure of a subject, the method comprising administrating to the subject the peptide or a pharmaceutical composition disclosed herein and imaging the subject. In some embodiments such imaging is used to detect a condition associated with a function of the cartilage. In some cases the condition is an inflammation, a cancer, a degradation, a growth disturbance, genetic, a tear or an injury, or another suitable condition. In some cases the condition is a chondrodystrophy, a traumatic rupture or detachment, pain following surgery in regions of the body containing cartilage, costochondritis, herniation, polychondritis, arthritis, osteoarthritis, rheumatoid arthritis, ankylosing spondylitis (AS), Systemic Lupus Erythematosus (SLE or "Lupus"), Psoriatic Arthritis (PsA), gout, achondroplasia, or another suitable condition. In some case the condition is associated with a cancer or tumor of the cartilage. In some cases the condition is a type of chondroma or chondrosarcoma, whether metastatic or not, or another suitable condition. In some embodiments, such as those associated with cancers, the imaging may be associated with surgical removal of the diseased region, tissue, structure or cell of a subject.

Furthermore, the present disclosure provides methods for intraoperative imaging and resection of a diseased or inflamed tissue, cancer, cancerous tissue, or tumor tissue using a peptide of the present disclosure conjugated with a detectable agent. In some embodiments, the diseased or inflamed tissue, cancer, cancerous tissue, or tumor tissue is detectable by fluorescence imaging that allows for intraoperative visualization of the cancer, cancerous tissue, or tumor tissue using a peptide of the present disclosure. In some embodiments, the peptide of the present disclosure is conjugated to one or more detectable agents. In a further embodiment, the detectable agent comprises a fluorescent moiety coupled to the peptide. In another embodiment, the detectable agent comprises a radionuclide. In some embodiments, imaging is achieved during open surgery. In further embodiments, imaging is accomplished using endoscopy or other non-invasive surgical techniques.

Treatment of Cartilage Disorders

The term "effective amount," as used herein, can refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case can be determined using techniques, such as a dose escalation study.

The methods, compositions, and kits of this disclosure can comprise a method to prevent, treat, arrest, reverse, or ameliorate the symptoms of a condition. The treatment can comprise treating a subject (e.g., an individual, a domestic animal, a wild animal or a lab animal afflicted with a disease or condition) with a peptide of the disclosure. In treating a disease, the peptide can contact the cartilage of a subject. The subject can be a human. A subject can be a human; a non-human primate such as a chimpanzee, or other ape or monkey species; a farm animal such as a cattle, horse, sheep, goat, swine; a domestic animal such as a rabbit, dog, and cat; a laboratory animal including a rodent, such as a rat, mouse and guinea pig, or the like. A subject can be of any age. A subject can be, for example, an elderly adult, adult, adolescent, pre-adolescens, child, toddler, infant, or fetus in utero.

Treatment can be provided to the subject before clinical onset of disease. Treatment can be provided to the subject after clinical onset of disease. Treatment can be provided to the subject after 1 day, 1 week, 6 months, 12 months, or 2 years or more after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment can also include treating a human in a clinical trial. A treatment can comprise administering to a subject a pharmaceutical composition, such as one or more of the pharmaceutical compositions described throughout the disclosure. A treatment can comprise a once daily dosing. A treatment can comprise delivering a peptide of the disclosure to a subject, either intravenously, subcutaneously, intramuscularly, by inhalation, dermally, intra-articular injection, orally, intrathecally, transdermally, intranasally, via a peritoneal route, or directly onto or into a joint, e.g., via topical, intra-articular injection route or injection route of application. A treatment can comprise administering a peptide-active agent complex to a subject, either intravenously, intra-articular injection, parenterally, orally, via a peritoneal route, or directly onto, near or into the cartilage.

Types of cartilage diseases or conditions that can be treated with a peptide of the disclosure can include inflammation, pain management, anti-infective, pain relief, anti-cytokine, cancer, injury, degradation, genetic basis, remodeling, hyperplasia, surgical injury/trauma, or the like. Examples of cartilage diseases or conditions that can be treated with a peptide of the disclosure include Costochondritis, Spinal disc herniation, Relapsing polychondritis, Injury to the articular cartilage, any manner of rheumatic disease (e.g., Rheumatoid Arthritis (RA), ankylosing spondylitis (AS), Systemic Lupus Erythematosus (SLE or "Lupus"), Psoriatic Arthritis (PsA), Osteoarthritis, Gout, and the like), Herniation, Achondroplasia, Benign or non-cancerous chondroma, Malignant or cancerous chondrosarcoma, Chondriodystrophies, Chondromalacia patella, Costochondritis, *Halus rigidus*, Hip labral tear, Osteochondritis dssecans, Osteochondrodysplasias, Torn meniscus, Pectus carinatum, Pectus excavatum, Chondropathy, Chondromalacia, Polychondritis, Relapsing Polychondritis, Slipped epiphysis, Osteochondritis Dissecans, Chondrodysplasia, Costochondritis, Perichondritis, Osteochondroma, Knee osteoarthritis, Finger osteoarthritis, Wrist osteoarthritis, Hip osteoarthritis, Spine osteoarthritis, Chondromalacia, Osteoarthritis Susceptibility, Ankle Osteoarthritis, Spondylosis, Secondary chondrosarcoma, Small and unstable nodules as seen in osteoarthritis, Osteochondroses, Primary chondrosarcoma, Cartilage disorders, scleroderma, collagen disorders, Chondrodysplasia, Tietze syndrome, Dermochondrocorneal dystrophy of Francois, Epiphyseal dysplasia multiple 1, Epiphyseal dysplasia multiple 2, Epiphyseal dysplasia multiple 3, Epiphyseal dysplasia multiple 4, Epiphyseal dysplasia multiple 5, Ossified Ear cartilages with Mental deficiency, Muscle Wasting and Bony Changes, Periosteal chondrosarcoma, Carpotarsal osteochondromatosis, Achondroplasia, Genochondromatosis II, Genochondromatosis, Chondrodysplasia—disorder of sex development, Chondroma, Chordoma, Atelosteogenesis, type 1, Atelosteogenesis Type III, Atelosteogenesis, type 2, Pyknoachondrogenesis, Osteoarthropathy of fingers familial, Dyschondrosteosis—nephritis, Coloboma of Alar-nasal cartilages with telecanthus, Alar cartilages hypoplasia—coloboma—telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Jequier-Kozlowski-skeletal dysplasia, Chondrodystrophy, Cranio osteoarthropathy, Tietze's syndrome, Hip dysplasia—ecchondromata, Bessel-Hagen disease, Chondromatosis (benign), Enchondromatosis (benign), Chondrocalcinosis due to apatite crystal deposition, Meyenburg-Altherr-Uehlinger syndrome, Enchondromatosis-dwarfism-deafness, premature growth plate closure (e.g., due to dwarfism, injury, therapy such as retinoid therapy for adolescent acne, or ACL repair), Astley-Kendall syndrome, Synovial osteochondromatosis, Severe achondroplasia with developmental delay and acanthosis *nigricans*, Chondrocalcinosis, Stanescu syndrome, Familial osteochondritis dissecans, Achondrogenesis type 1A, Achondrogenesis type 2, Achondrogenesis, Langer-Saldino Type, Achondrogenesis type 1B, Achondrogenesis type 1A and 1B, Type II Achondrogenesis-Hypochondrogenesis, Achondrogenesis, Achondrogenesis type 3, Achondrogenesis type 4, Chondrocalcinosis 1, Chondrocalcinosis 2, Chondrocalcinosis familial articular, Diastrophic dysplasia, Fibrochondrogenesis, Hypochondroplasia, Keutel syndrome, Maffucci Syndrome, Osteoarthritis Susceptibility 6, Osteoarthritis Susceptibility 5, Osteoarthritis Susceptibility 4, Osteoarthritis Susceptibility 3, Osteoarthritis Susceptibility 2, Osteoarthritis Susceptibility 1, Pseudoachondroplasia, Cauliflower ear, Costochondritis, Growth plate fractures, Pectus excavatum, septic arthritis, gout, pseudogout (calcium pyrophosphate deposition disease or CPPD), gouty arthritis, bacterial, viral, or fungal infections in or near the joint, bursitis, tendinitis, arthropathies, or another cartilage or joint disease or condition.

In some embodiments, a peptide or peptide conjugate of this disclosure can be administered to a subject in order to target, an arthritic joint. In other embodiments, a peptide or peptide conjugate of this disclosure can be administered to a subject in order to treat an arthritic joint.

In some embodiments, the present disclosure provides a method for treating a cancer, the method comprising administering to a subject in need thereof an effective amount of a peptide of the present disclosure.

In some embodiments, the present disclosure provides a method for treating a cancer, the method comprising administering to a patient in need thereof an effective amount of a pharmaceutical composition comprising a peptide of the present disclosure and a pharmaceutically acceptable carrier.

In some embodiments, the peptides of the present disclosure can be used to treat chondrosarcoma. Chondrosarcoma is a cancer of cartilage producing cells and is often found in bones and joints. It falls within the family of bone and soft-tissue sarcomas. In certain embodiments, administration of a peptide or peptide conjugate of the present disclosure can be used to image and diagnose or target and treat a subject with chondrosarcoma. The administration of a peptide or peptide conjugate of the present disclosure can be used in combination with ablative radiotherapy or proton therapy to treat chondrosarcoma. The subject can be a human or an animal.

In some embodiments, a peptide or peptide conjugate of this disclosure can be used to treat Chordoma. In certain embodiments, administration of a peptide or peptide conjugate of the present disclosure can be used to image and diagnose or target and treat a subject with chordoma. The administration of a peptide or peptide conjugate of the present disclosure can be used in combination with a tyrosine kinase inhibitor, such as imatinib mesylate, and ablative radiotherapy or proton therapy to treat chordoma. The administration of a peptide or peptide conjugate of the present disclosure can be used in combination with an antivascular agent such as bevacizumab and an epidermal growth factor receptor inhibitor such as erlotinib to treat chordoma. The subject can be a human or an animal.

In some embodiments, the present disclosure provides a method for inhibiting invasive activity of cells, the method comprising administering an effective amount of a peptide of the present disclosure to a subject.

In some embodiments, the peptides of the present disclosure are conjugated to one or more therapeutic agents. In further embodiments, the therapeutic agent is a chemotherapeutic, anti-cancer drug, or anti-cancer agent selected from, but are not limited to: anti-inflammatories, such as for example a glucocorticoid, a corticosteroid, a protease inhibitor, such as for example collagenase inhibitor or a matrix metalloprotease inhibitor (i.e., MMP-13 inhibitor), an amino sugar, vitamin (e.g., Vitamin D), and antibiotics, antiviral, or antifungal, a statin, an immune modulator, radioisotopes, toxins, enzymes, sensitizing drugs, nucleic acids, including interfering RNAs, antibodies, anti-angiogenic agents, cisplatin, anti-metabolites, mitotic inhibitors, growth factor inhibitors, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine, and their equivalents, as well as photo-ablation. Some of these active agents induce programmed cell death such as apoptosis in target cells and thereby improve symptoms or ameliorate disease. Apoptosis can be induced by many active agents, including, for example, chemotherapeutics, anti-inflammatories, corticosteroids, NSAIDS, tumor necrosis factor alpha (TNF-α) modulators, tumor necrosis factor receptor (TNFR) family modulators. In some embodiments, peptides of this disclosure can be used to target active agents to pathways of cell death or cell killing, such as caspases, apoptsis activators and inhibitors, XBP-1, Bcl-2, Bcl-X1, Bcl-w, and other disclosed herein. In other embodiments, the therapeutic agent is any nonsteroidal anti-inflammatory drug (NSAID). The NSAID can be any heterocyclic acetic acid derivatives such as ketorolac, indomethacin, etodolac, or tolemetin, any propionic acid derivatives such as naproxen, any enolic acid derivatives, any anthranilic acid derivatives, any selective COX-2 inhibitors such as celecoxib, any sulfonanilides, any salicylates, aceclofenac, nabumetone, sulindac, diclofenac, or ibuprofen. In other embodiments, the therapeutic agent is any steroid, such as dexamethasone, budesonide, triamcinolone, cortisone, prednisone, rednisolone, triamcinolone hexacetonide, or methylprednisolone. In other embodiments, the therapeutic agent is a pain reliever, such as acetaminophen, opioids, local anesthetics, antidepressants, glutamate receptor anatagonists, adenosine, or neuropetides. In some embodiments, a treatment consists of administering a combination of any of the above therapeutic agents and a peptide conjugate, such as a treatment in which both a dexamethasone-peptide conjugate and an NSAID are administered to a patient. Peptides of the current disclosure that target the cartilage can be used to treat the diseases conditions as described herein, for example, any diseases or conditions including tears, injuries (i.e., sports injuries), genetic factors, degradation, thinning, inflammation, cancer or any other disease or condition of the cartilage or to target therapeutically-active substances to treat these diseases amongst others. In other cases, a peptide of the disclosure can be used to treat traumatic rupture, detachment, chostochondritis, spinal disc herniation, relapsing and non-relapsing polychondritis, injury to the articular cartilage, osteoarthritis, arthritis or achondroplasia. In some cases, the peptide or peptide-active agent can be used to target cancer in the cartilage, for example benign chondroma or malignant chondrosarcoma, by contacting the cartilage by diffusion into chondrocytes and then having antitumor function, targeted toxicity, inhibiting metastases, etc. As well, such peptide or peptide-active agent can be used to label, detect, or image such cartilage lesions, including tumors and metastases amongst other lesions, which may be removed through various surgical techniques or by targeting with peptide-active agents that induce programmed cell death or kill cells.

Venom or toxin derived peptide(s), peptides, modified peptides, labeled peptides, peptide-active agent conjugates and pharmaceutical compositions described herein can be administered for prophylactic and/or therapeutic treatments. In therapeutic applications, the composition can be administered to a subject already suffering from a disease or condition, in an amount sufficient to cure or at least partially arrest the symptoms of the disease or condition, or to cure, heal, improve, or ameliorate the condition. Such peptides described herein can also be administered to prevent (either in whole or in part), lessen a likelihood of developing, contracting, or worsening a condition. Amounts effective for this use can vary based on the severity and course of the disease or condition, previous therapy, the subject's health status, weight, response to the drugs, and the judgment of the treating physician. Venom or toxin derived peptide(s), peptides, modified peptides, labeled peptides, peptide-active agent conjugates and pharmaceutical compositions described herein can allow for targeted homing of the peptide and local delivery of any conjugate. For example, a peptide conjugated to a steroid allows for local delivery of the steroid, which is significantly more effective and less toxic than traditional systemic steroids. A peptide conjugated to an NSAID is another example. In this case, the peptide conjugated to an NSAID allows for local delivery of the NSAID, which allows for administration of a lower NSAID dose and is subsequently less toxic. By delivering an active agent to the joint, pain relief can be more rapid, may be more long lasting, and can be obtained with a lower systemic dose and off-site undesired effects than with systemic dosing without targeting.

Peptides of the current disclosure that target the cartilage can be used to treat or manage pain associated with a cartilage injury or disorder, or any other cartilage or joint condition as described herein. The peptides can be used either directly or as carriers of active drugs, peptides, or molecules. For example, since ion channels can be associated with pain and can be activated in disease states such as arthritis, peptides that interact with ion channels can be used directly to reduce pain. In another embodiment, the peptide is conjugated to an active agent with anti-inflammatory activity, in which the peptide acts as a carrier for the local delivery of the active agent to reduce pain.

In some embodiments, the peptides described herein provide a method of treating a cartilage condition of a subject, the method comprising administering to the subject a therapeutically-effective amount of a peptide comprising the sequence SEQ ID NO: 1 or fragment thereof. In some embodiments, the peptides described herein provide a method of treating a cartilage condition of a subject, the method comprising administering to the subject a peptide of any one of SEQ ID NO: 2-SEQ ID NO: 194, SEQ ID NO: 196, SEQ ID NO: 198-SEQ ID NO: 410, SEQ ID NO: 412, SEQ ID NO: 414-SEQ ID NO: 432 or fragment thereof.

Multiple peptides described herein can be administered in any order or simultaneously. In some cases, multiple functional fragments of peptides derived from toxins or venom can be administered in any order or simultaneously. If simultaneously, the multiple peptides described herein can be provided in a single, unified form, such as an intravenous injection, or in multiple forms, such as subsequent intravenous dosages.

Peptides can be packaged as a kit. In some embodiments, a kit includes written instructions on the use or administration of the peptides.

EXAMPLES

The following examples are included to further describe some embodiments of the present disclosure, and should not be used to limit the scope of the disclosure.

Example 1

Manufacture of Peptides

This example provides a method for generating knottin peptides. Peptides derived from knottin peptides of scorpions and spiders were generated in mammalian cell culture using a published methodology. (A. D. Bandaranayke, C. Correnti, B. Y. Ryu, M. Brault, R. K. Strong, D. Rawlings. 2011. Daedalus: a robust, turnkey platform for rapid production of decigram quantities of active recombinant proteins in human cell lines using novel lentiviral vectors. Nucleic Acids Research. (39)21, e143).

The peptide sequence was reverse-translated into DNA, synthesized, and cloned in-frame with siderocalin using standard molecular biology techniques. (M. R. Green, Joseph Sambrook. Molecular Cloning. 2012 Cold Spring Harbor Press.). The resulting construct was packaged into a lentivirus, transfected into HEK293 cells, expanded, isolated by immobilized metal affinity chromatography (IMAC), cleaved with tobacco etch virus protease, and purified to homogeneity by reverse-phase chromatography. Following purification, each peptide was lyophilized and stored frozen.

Example 2

Radiolabeling of Peptide

This example describes radiolabelling of knottin peptides. Several knottins (some sequences derived from spiders and scorpions) were radiolabeled by reductive methylation with $^{14}C$ formaldehyde and sodium cyanoborohydride with standard techniques. See J Biol Chem. 254(11):4359-65 (1979). The sequences were engineered to have the amino acids, "G" and "S" at the N terminus. See Methods in Enzymology V91:1983 p. 570 and Journal of Biological Chemistry 254 (11):1979 p. 4359. An excess of formaldehyde was used to ensure complete methylation (dimethylation of every free amine). The labeled peptides were isolated via solid-phase extraction on Strata-X columns (Phenomenex 8B-S100-AAK), rinsed with water with 5% methanol, and recovered in methanol with 2% formic acid. Solvent was subsequently removed in a blowdown evaporator with gentle heat and a stream of nitrogen gas.

Example 3

Dosing of Peptide with Kidney Ligation

This example describes a dosing scheme for administering knottin peptides to mice in conjunction with kidney ligation. Different dosages of the peptides were administered to Female Harlan athymic nude mice, weighing 20 g-25 g, via tail vein injection (n=2 mice per knottin). The sequence of thirteen cartilage homing peptides of SEQ ID NO: 21-SEQ ID NO: 33 are shown in TABLE 1. The experiment was done in duplicates. The kidneys were ligated to prevent renal filtration of the peptides. Each peptide was radiolabeled by methylating lysines and the N-terminus, so the actual binding agent may contain methyl or dimethyl lysine (s) and a methylated or dimethylated amino terminus.

A target dosage of 50-100 nmol of each peptide carrying 10-25 uCi of $^{14}C$ was administered to Female Harlan athymic nude mice while anesthetized. Each peptide was allowed to freely circulate within the animal before the animals were euthanized and sectioned.

Example 4

Peptide Homing with Kidney Ligation

This example illustrates peptide homing to cartilage of mice with kidneys that were ligated prior to peptide administration. At the end of the dosing period in EXAMPLE 3, mice were frozen in a hexane/dry ice bath and then frozen in a block of carboxymethylcellulose. Whole animal sagittal slices were prepared that resulted in thin frozen sections being available for imaging. Thin, frozen sections of animal including imaging of tissues such as brain, tumor, liver, kidney, lung, heart, spleen, pancreas, muscle, adipose, gall bladder, upper gastrointestinal tract, lower gastrointestinal tract, bone, bone marrow, reproductive track, eye, cartilage, stomach, skin, spinal cord, bladder, salivary gland, and other types of tissues were obtained with a microtome, allowed to desiccate in a freezer, and exposed to phosphoimager plates for about ten days.

Figure 2:
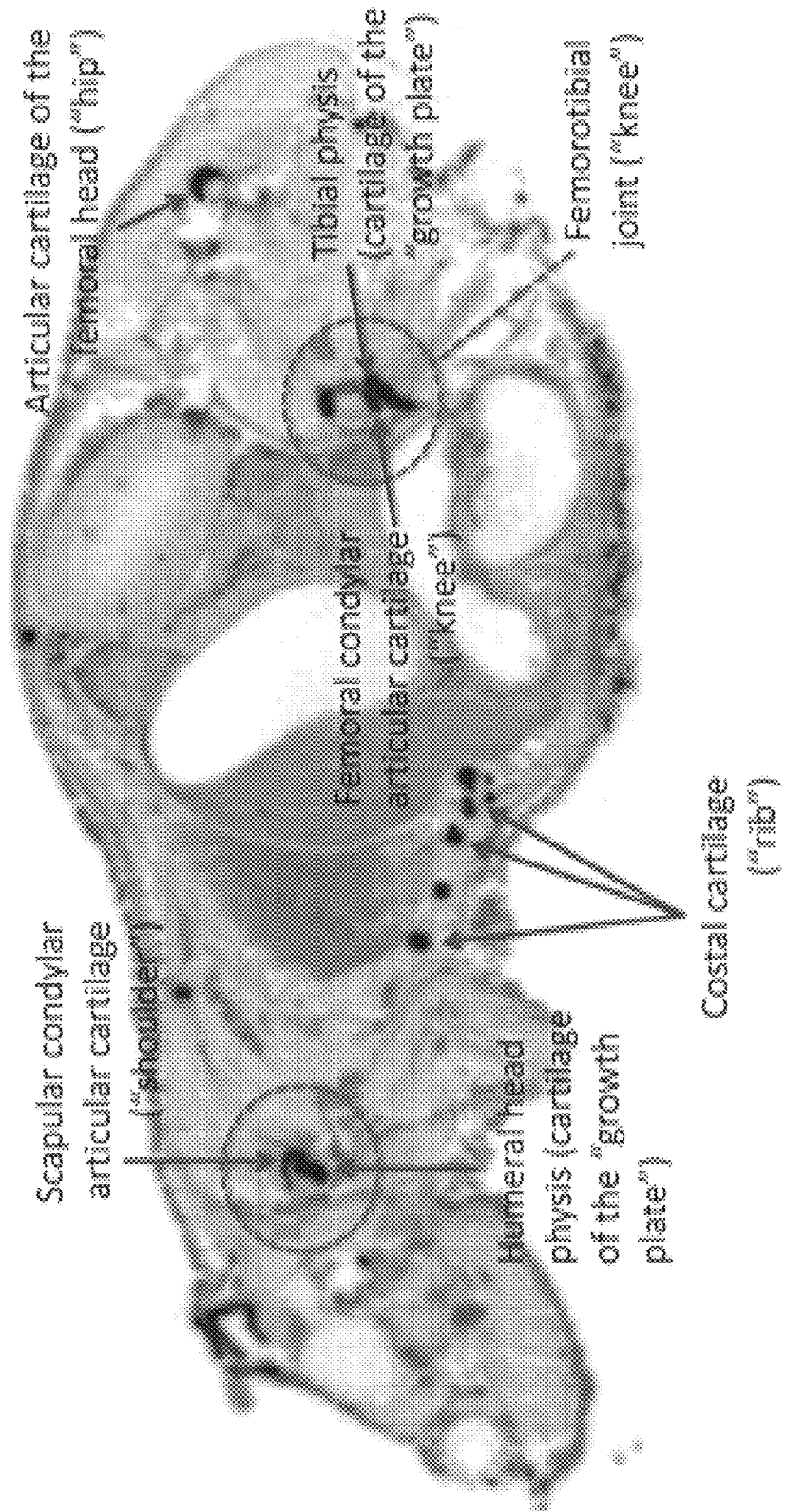
FIG. 2 illustrates the identification of the $^{14}$C signal in the joint and other cartilage of an animal treated with the peptide of SEQ ID NO: 24.
Figure 3:
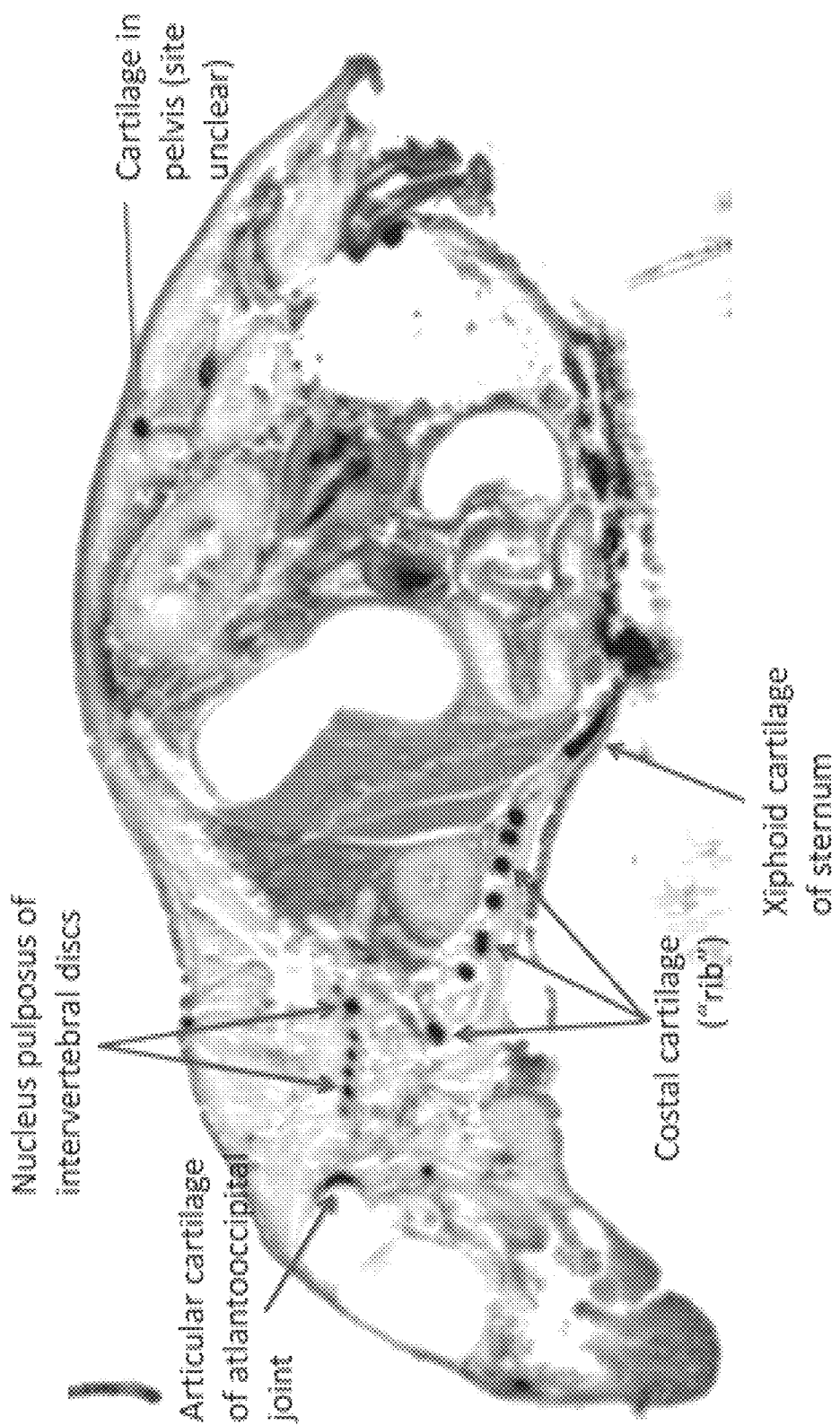
FIG. 3 illustrates the identification of the $^{14}$C signal in rib, spinal, and other cartilage of an animal treated with the peptide of SEQ ID NO: 24.
Figure 4:
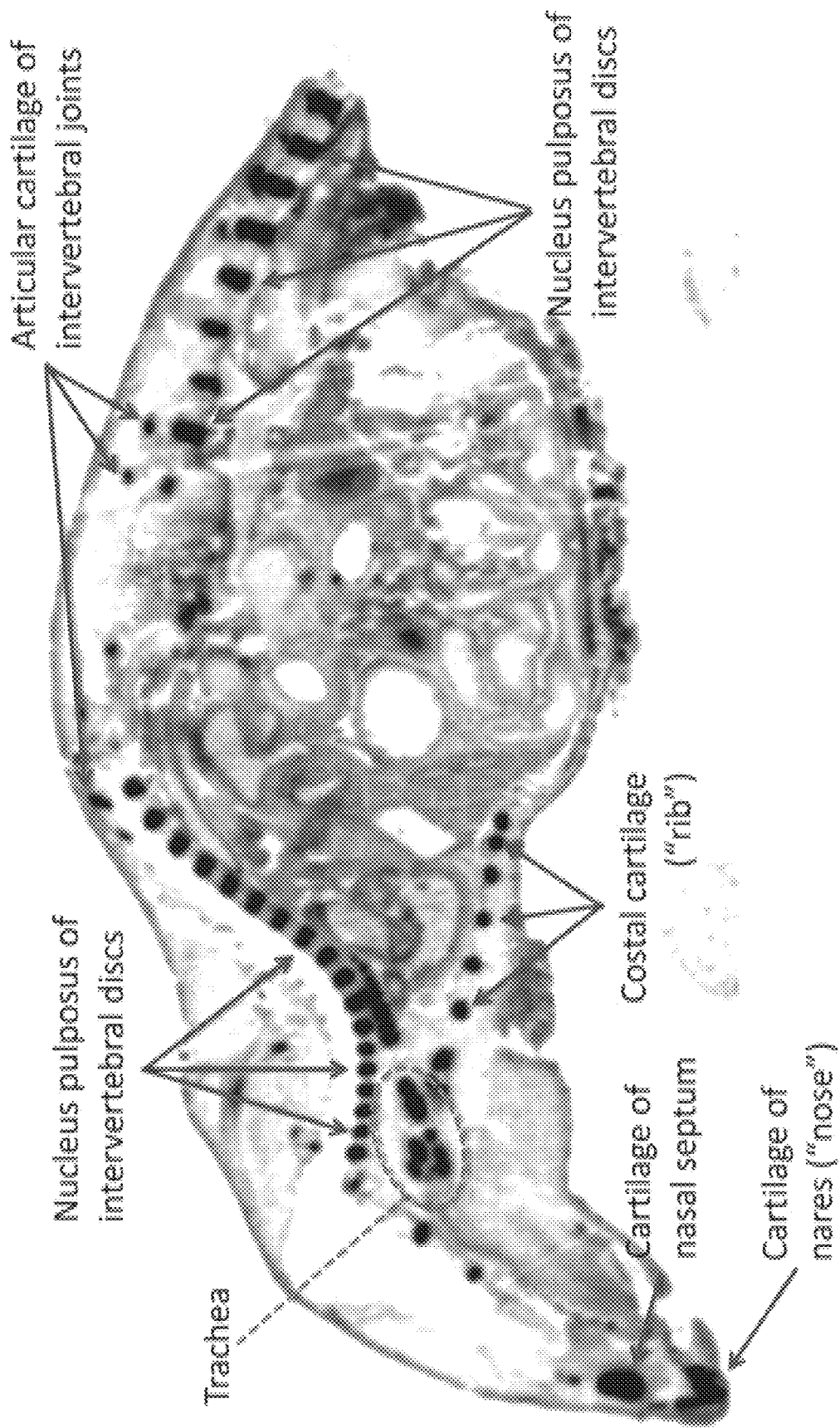
FIG. 4 illustrates the identification of locations the $^{14}$C signal in the nasal, spinal, tracheal, and other cartilage of an animal treated with the peptide of SEQ ID NO: 24.

These plates were developed, and the signal (densitometry) from each organ was normalized to the signal found in the heart blood of each animal. A signal in tissue darker than the signal expected from blood in that tissue indicates peptide accumulation in a region, tissue, structure or cell. For instance, the cartilage is avascular and contains minute amounts of blood. A ratio of at least 170% signal in the cartilage versus heart ventricle was chosen as a reference level for significant targeting to cartilage, which also correlated with clear accumulation in cartilaginous tissues in the images of the slices. FIG. 1 illustrates the tissue distribution in the cartilage for the peptides SEQ ID NO: 21-SEQ ID NO: 33, 3 hours after administration in animals with ligated kidneys. FIG. 2 identifies the locations of the SEQ ID NO: 24 peptide distribution in joint and other cartilage. FIG. 3 identifies the locations of the SEQ ID NO: 24 peptide distribution in rib, spinal, and other cartilage. FIG. 4 identifies the locations of the SEQ ID NO: 24 peptide distribution in nasal, spinal, tracheal, and other cartilage. FIGS. 3-4 illustrate the homing of SEQ ID NO: 24 to hyaline cartilage such as articular cartilage and physeal cartilage, as well as fibrocartilage.

Figure 5:
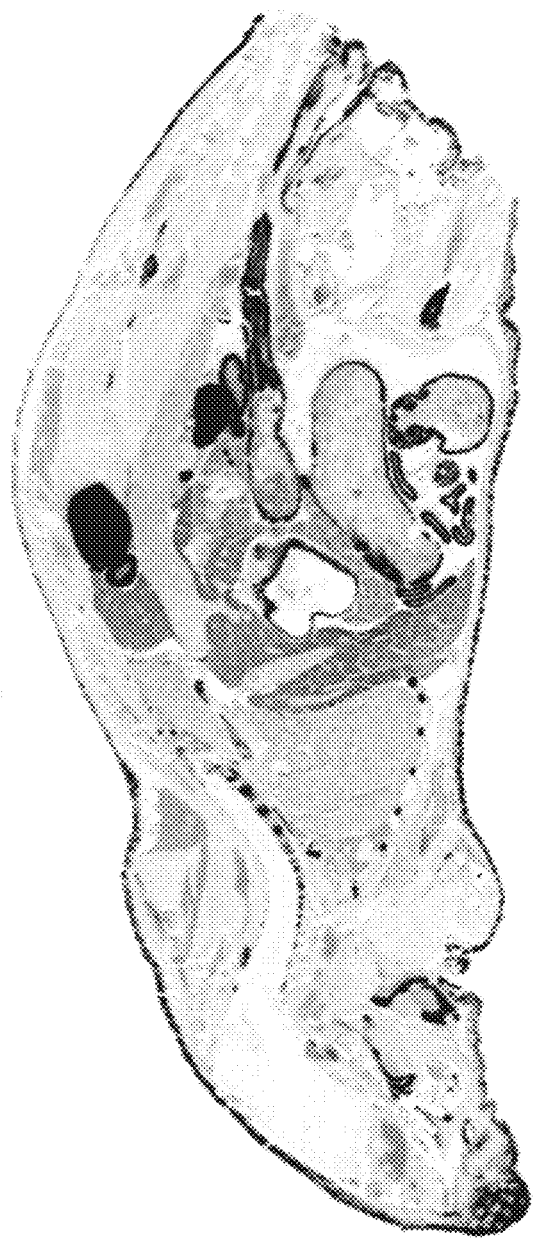
FIG. 5 illustrates the $^{14}$C signal in the cartilage of an animal with intact kidneys 24 hours after treatment with a peptide of SEQ ID NO: 24.

Additionally, the peptide can be retained in cartilage for hours after treatment. The SEQ ID NO: 24 peptide was radiolabeled as in Example 3 and 100 nmol of peptide was injected into a mouse with intact kidneys. FIG. 5 illustrates the retention of and the tissue distribution in the cartilage of a peptide of SEQ ID NO: 24, 24 hours after administration. For comparison, FIG. 11 shows white light and corresponding autoradiographic images from a section of a mouse 24 hours after administration of 100 nmol of radiolabeled SEQ ID NO: 433 peptide, which did not home to cartilage and was seen in the bone marrow. FIG. 11A illustrates a white light image of a frozen section of a mouse 24 hours after administration of 100 nmol of SEQ ID NO: 433. FIG. 11B shows an autoradiographic image corresponding to FIG. 11A in which the $^{14}C$ signal identifies the radiolabeled SEQ ID NO: 433 peptide.

TABLE 2 summarizes the net charge at neutral pH and migration of the peptides of SEQ ID NO: 21-SEQ ID NO: 33 to the cartilage (C) and muscle (M) compared to the level in the blood 3 hours after administration. The "cartilage"

entries reflect the percentage of signal in the cartilage compared to the blood signal in the heart ventricle within the tissue slices. Peptides that are cartilage homers have a cartilage signal of >170%, peptides that are efficient cartilage homers can have a cartilage signal of >300%, and peptides that are strong cartilage homers have a cartilage signal of >500%. SEQ ID NO: 484 corresponds to an amino acid sequence of GSECLGFGKGCNPSNDQCCK-SSNLVCSRKHRWCKYEIGK.

TABLE 2

| SEQ ID NO | Charge | Cartilage (C) | Muscle (M) |
|---|---|---|---|
| 21 | 8.7 | 270 | 36 |
| 22 | 7 | 337 | 27 |
| 23 | 6 | 497 | 26 |
| 24 | 6 | 624 | 34 |
| 25 | 5.7 | 358 | 24 |
| 26 | 5.7 | 413 | 38 |
| 27 | 4.7 | 448 | 31 |
| 28 | 4.7 | 361 | 17 |
| 29 | 4 | 243 | 26 |
| 30 | 4 | 221 | 26 |
| 31 | 3.7 | 306 | 68 |
| 32 | 2 | 194 | 44 |
| 33 | 3.7 | 179 | 28 |
| 196 | 6 | 291 | 30 |
| 198 | 4 | 276 | 26 |
| 483 | 1 | 67 | 24 |
| 485 | 2.7 | 92 | 21 |
| 484 | 4 | 93 | 20 |
| 433 | 3 | 156 | 20 |

As shown in TABLE 2, sequences with significant positive charge at physiological pH exhibited higher accumulation in cartilage. Many of these sequences share common elements. These common elements may represent parts of the sequence that confer cartilage homing to the peptide by locating positive charge or other binding elements into certain parts of the three dimensional structure of the folded peptide. For instance, K or R residues might be preferentially located in certain parts of the sequence in order to locate positive charge on the correct surface areas for homing, especially with respect to the C residues which determine folding and loop location of the folded peptide. However, only parts of these sequences may be important for homing or other aspects of the sequences may be important for homing.

Two example sequences containing common elements are GSXVXXXVKCXGSKQCXXPCK-RXXGXRXGKCINKKXCKCYXXX (SEQ ID NO: 9) and GSXXXGCVXXXXKCRPGXKXCCXPXKRCSRRFGX XXXKKCKXXXXXX (SEQ ID NO: 10), where X can independently be any number of any amino acid or no amino acid. FIG. 12 shows a sequence alignment of SEQ ID NO: 9 with the peptide sequences from which the common element sequences were based on and a sequence alignment of SEQ ID NO: 10 with the peptide sequences from which the common element sequences were based on. Sequence GSXVXXXVKCXGSKQCXXPCK-RXXGXRXGKCINKKXCKCYXXX (SEQ ID NO: 9) is a sequence based on the most common elements found in the following sequences: GSGVPINVKCRGSRD-CLDPCKKA-GMRFGKCINSK-CHCTP-- (SEQ ID NO: 24), GS-VRIPVSCKHSGQCLKPCKDA-GMRFGKCMNGK-CDCTPK- (SEQ ID NO: 23), GSQVQTNVKCQGGS-CASVCRREIGVAAGKCINGK-CVCYRN- (SEQ ID NO: 27), GS-----ISCTG-SKQCYDPCKRKTGCPNAKCMNKS-CKCYGCG (SEQ ID NO: 26), GSEV---IRCSG-SKQCYGPCKQQTGCTNSKCMNKV-CKCYGCG (SEQ ID NO: 28), GSAVCVYRT------CDKDCKRR-GYRSGK-CINNA-CKCYPYG (SEQ ID NO: 25), GS----GIVC---KVCKIICGMQ-GKKVNICKAPIKCKCKKG- (SEQ ID NO: 21), and GSQIYTSKECNGSSECYSHCE-GITGKRSGKCINKK-CYCYR--(SEQ ID NO: 30). Sequence GSXXXGCVXXXXKCRPGXKXCCXPXKRCS RRFGXXXXKKCKXXXXXX (SEQ ID NO: 10) is a sequence based on the most common elements found in the following sequences: GS---ACKGVFDACTPGKNECC-PNRVCSDK-H----KWCKWKL- (SEQ ID NO: 29), GS---GCLEFWWKCNPNDDKCCRPKLKCSKLF-----KLCNFSFG (SEQ ID NO: 31), GSSEKDCIKHLQRCR-ENKDCC--SKKCSRR-GTNPEKRCR- (SEQ ID NO: 22), and GS---GCFGY--KCDYY-KGCCSGYV-CSPTW-----KWCVRPGPGR (SEQ ID NO: 33). A dash, "-," indicates that no amino acid is in that position. The following residues may be independently interchanged in SEQ ID NO: 9 or SEQ ID NO: 10: any K and any R; any M, any I, any L, and any V; any G and any A; any S and any T; and any Q and any N. These sets of interchangeable amino acids have similarities in properties that can allow for them to be interchangeable without inhibiting homing to cartilage. For example, any K can be interchanged with any R because K and R both provide a positive charge at physiological pH and thus may provide necessary charge for homing to cartilage, and any S can be interchanged with any T because S and T both have a hydroxyl group available for hydrogen bonding. The N-terminal GS sequence may or may not be included between the peptides of the present disclosure.

Particular fragments with common elements were also noted, such as the GKCINKKCKC (SEQ ID NO: 316) fragment with the internal fragments KCIN (SEQ ID NO: 317) and KKCK (SEQ ID NO: 318), PCKR (SEQ ID NO: 319), KRCSRR (SEQ ID NO: 320), and KQC (SEQ ID NO: 321). The following residues may be independently interchanged in SEQ ID NO: 101-SEQ ID NO: 105 or SEQ ID NO: 316-SEQ ID NO: 321: any K and any R; any M, any I, any L, and any V; and G and any A; any S and any T; and any Q and any N.

A predominance of R and K residues were noted in the C-terminal parts of the peptides as well as in the fragments, correlating with the high positive charge of the peptides.

The peptides of SEQ ID NO: 21 and SEQ ID NO: 33 in TABLE 1 are derived from a scorpion toxin (e.g., *Buthus martensii* Karsh) that was found to migrate specifically to a region, tissue, structure or cells in the cartilage, potentially by diffusion. FIGS. 6A and 6B illustrate the HPLC profiles of a peptide of SEQ ID NO: 23 and SEQ ID NO: 24.

Example 5

Peptide Homing with Therapeutic Agents

This example describes certain exemplary therapeutic agents that are conjugated to a knottin peptide. A peptide of the disclosure is expressed recombinantly or chemically synthesized and then is conjugated to an exemplary drug, such as paclitaxel or triamcinolone acetonide using techniques known in the art, such as those described in Bioconjugate Techniques by Greg Hermanson. One or more drugs is conjugated per peptide, or an average of less than one drug is conjugated per peptide.

Coupling of these drugs to a peptide of any of SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432 targets

Example 6

Treatment of Osteoarthritis

This example describes a method for treating osteoarthritis using peptides of the present disclosure. This method is used as a treatment for acute and/or chronic symptoms associated with osteoarthritis. A peptide of the present disclosure is expressed recombinantly or chemically synthesized and then is used directly or conjugated to an anti-inflammatory compound, such as triamcinolone acetonide and dexamethasone. The resulting peptide or peptide-drug conjugate is administered in a pharmaceutical composition subcutaneously, intravenously, or orally, or is injected directly into a joint of a patient and targeted to cartilage. The formulation can be modified physically or chemically to increase the time of exposure in the cartilage. The peptide is selected from SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432. One or more anti-inflammatory peptide conjugates are administered to a human or animal.

Example 7

Treatment of Cartilage Degradation

This example describes a method for treating and/or preventing cartilage degradation using a peptide of the present disclosure. This method is used as a treatment for acute and/or chronic symptoms associated with cartilage degradation. Progressive degradation or thinning of the cartilage is difficult to treat in part because molecules such as small molecule drugs and antibodies typically do not reach the avascular cartilage. A peptide of the present disclosure is used for its homing and/or native activity, or is mutated to generate activity such as MMP protease inhibition. It is expressed recombinantly or chemically synthesized and then is used directly or conjugated to an extracellular matrix targeting compound, such as an inhibitor of MMP activity (e.g., MMP13, collagenase (MMP-1), or other agent as described herein). The resulting peptide or peptide-drug conjugate is administered in a pharmaceutical composition subcutaneously, intravenously, or orally, or is injected directly into a joint of a patient and targeted to extracellular matrix. The peptide is selected from SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432. One or more extracellular matrix targeting conjugates are administered to a human or animal.

Example 8

Treatment of a Cartilage Injury

This example describes a method for treating a cartilage injury using a peptide of the present disclosure. A peptide of the present disclosure is expressed recombinantly or chemically synthesized and then is used directly or conjugated to a therapeutic compound, such as those described herein, including, but not limited to triamcinolone and dexamethasone. The resulting peptide or peptide-drug conjugate is administered in a pharmaceutical composition to a patient and targeted to cartilage. The peptide is selected from S SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432. One or more therapeutic compound-peptide conjugates are administered to a human or animal.

Example 9

Treatment of Rheumatoid Arthritis

This example describes a method for treating rheumatoid arthritis. This method is used as a treatment for acute and/or chronic symptoms associated with rheumatoid arthritis. A peptide of the present disclosure is expressed recombinantly or chemically synthesized and then is used directly, or is conjugated to an anti-inflammatory compound, such as triamcinolone and dexamethasone. When the peptide is used directly, the peptide can, for example, bind or inhibit ion channels such as Kv 1.3. The resulting peptide or peptide-drug conjugate is administered in a pharmaceutical composition to a patient and is targeted to cartilage. The peptide is selected from SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432. One or more anti-inflammatory compound-peptide conjugates are administered to a human or animal subcutaneously, intravenously, or orally, or is injected directly into a joint

Example 10

Treatment of Gout

This example describes a method for treating gout using peptides of the present disclosure. This method is used as a treatment for acute and/or chronic symptoms associated with gout. A peptide of the present disclosure is expressed and administered in a pharmaceutical composition to a patient as a therapeutic for gout. A peptide of the disclosure is recombinantly or 78566491.1 chemically synthesized and then is used directly or conjugated to a nonsteroidal anti-inflammatory drugs, colchicine, a steroid, or uricase. The peptide selected from SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432 is administered in a pharmaceutical composition to a patient and the peptide is targeted to the cartilage affected by gout. One or more peptides are administered to a human or animal subcutaneously, intravenously, or orally, or is injected directly into a joint.

Example 11

Treatment or Management of Pain

This example describes a method for treating or managing pain associated with a cartilage injury or disorder. This method is used as a treatment for acute and/or chronic symptoms associated with a cartilage injury or disorder. A peptide of the disclosure is expressed and administered in a pharmaceutical composition to a patient as a therapeutic for pain as a result of injury or other cartilage or joint condition as described herein. The peptide of the present disclosure inhibits ion channels, such as Nav 1.7. The peptide is expressed recombinantly or chemically synthesized, wherein the peptide selected from SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432. Alternatively, the peptides of SEQ ID NO: 21-SEQ ID NO: 194, SEQ ID NO: 196, SEQ ID NO: 198-SEQ ID NO: 216 or SEQ ID NO: 237-SEQ ID NO: 410, SEQ ID NO: 412, SEQ ID NO: 414-SEQ ID NO: 432 are mutated to maintain the cartilage homing function, but to add or increase ion channel inhibition, such as to Nav 1.7. Following expression or synthesis, the peptide is used directly or conjugated to an NSAID. Following administration of the peptide, the peptide targets to the cartilage affected by pain. One or more peptides are administered to a human or animal subcutaneously, intravenously, or orally, or is injected directly into a joint.

Example 12

Immunogenicity of Peptides

Figure 7:
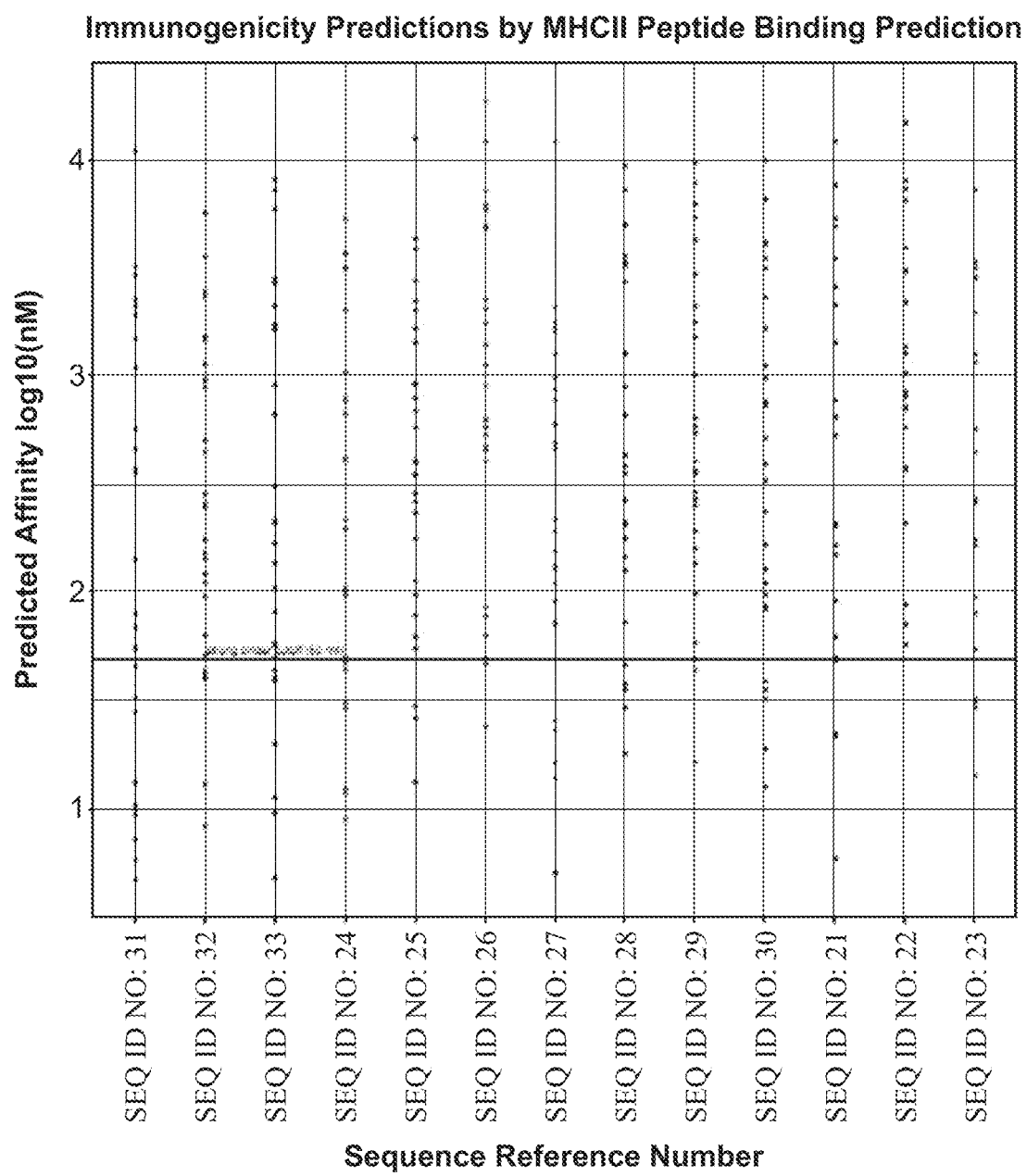
FIG. 7 illustrates the immunogenicity profiles of the peptides of SEQ ID NO: 21-SEQ ID NO: 33.

This example describes the evaluation of immunogenicity for certain peptides of the present disclosure. Immunogenicity was predicted using the network-based alignment algorithm ("NN-align. An artificial neural network-based alignment algorithm for MHC class II peptide biding prediction", Nielsen et. al. BMC Bioinformatics 2009 Vol 10, p 296). The algorithm was applied to intact knottin proteins with sequences SEQ ID NO: 21-SEQ ID NO: 33 against 24 alleles of HLA-DR, HLA-DP, HLA-DQ and H2-IAb MHCII classes. FIG. 7 shows the MHC class II peptide binding prediction of peptides with the sequences SEQ ID NO: 21-SEQ ID NO: 33 as listed in TABLE 1. The y-axis shows the predicted affinity of MHC class II peptide binding prediction for a peptide with units of log(nM), where affinity <50 nM predicts strong binding. Among the peptides with SEQ ID NO: 21-SEQ ID NO: 33, 82.3% (284/345) of the simulated bindings showed binding weaker than 50 nM between the peptide and MHC class II peptide. The high content of weak binders indicates that the peptides are predicted to have lower immunogenicity when administered to humans.

Immunogenicity was evaluated in silico for additional intact cartilage homing peptides. TABLE 3 illustrates the MHC class II peptide binding prediction of intact cartilage homing peptides sequences. The prediction values were obtained using network-based alignment algorithm. The algorithm was run using intact knottin peptides against 28 alleles of HLA-DR, HLA-DP, DLA-DQ, and H2-IAb MHC II classes. Some of the intact knottin peptides were predicted to be strong binders of MHC class II, however excluding certain sequences known to have high immunogenicity such as C-terminal proline in a peptide of SEQ ID NO: 111 or glycine in a peptide of SEQ ID NO: 199 reduced binding to MHC II alleles. As an example, peptides of SEQ ID NO: 209-SEQ ID NO: 210 have 90% homology to a peptide of SEQ ID NO: 111 and SEQ ID NO: 110, respectively, and are less immunogenic due to reduced binding to MHC II alleles. In another example, a peptide of SEQ ID NO: 211 has 83% homology to a peptide of SEQ ID NO: 114 and is less immunogenic due to reduced binding to MHC II alleles.

TABLE 3

| SEQ ID NO | Number of alleles that compounds bind at <50 nM | Number of alleles that compounds bind at <500 nM |
| --- | --- | --- |
| 111 | 7 | 11 |
| 199 | 10 | 12 |
| 109 | 2 | 11 |
| 110 | 8 | 11 |
| 114 | 6 | 12 |
| 200 | 2 | 5 |

Example 13

Ketorolac Peptide Conjugate

This example describes the conjugation of ketorolac to a knottin peptide using a lactic acid linker. As shown below in reaction scheme (I), a conjugate is produced from a mixture of (R,S)-ketorolac, lactic acid, and a knottin peptide:

The ketorolac-lactic acid linker conjugate depicted above is then reacted with a lysine or the N-terminus of a knottin peptide to create a ketorolac-lactic acid-peptide conjugate. The knottin peptide is selected from the peptides of SEQ ID NO: 21-SEQ ID NO: 194, SEQ ID NO: 196, SEQ ID NO:

198-SEQ ID NO: 216, SEQ ID NO: 237-SEQ ID NO: 410, SEQ ID NO: 412, or SEQ ID NO: 414-SEQ ID NO: 432.

Ketorolac is currently dosed as an enantiomeric mixture, in which enantiomers with a single racemic stereocenter are very difficult to separate. As in the reaction scheme (I), a diastereomer with two chiral centers is created by the addition of a chiral linker such as L-lactic acid. Since diastereomers are easily separated, the active enantiomer of ketorolac conjugated to the lactic acid linker can be purified prior to conjugation to a knottin peptide. The chemical synthesis can use any conjugation techniques known in the art, such as described in Bioconjugate Techniques by Greg Hermanson and in "Ketorolac-dextran conjugates: synthesis, in vitro, and in vivo evaluation:" Acta Pharm. 57 (2007) 441-450, Vyas, Trivedi, and Chaturvedi. The conjugate can display anti-inflammatory activity, or free ketorolac is released from the conjugate to provide anti-inflammatory activity. The free ketorolac can result from hydrolysis that occurs after administration, such as hydrolysis at the ester bond. By dosing the conjugate containing the cartilage homing peptide, a higher AUC of ketorolac delivery to the joint may be achieved than would be achieved by systemic dosing of ketorolac alone.

Example 14

Ibuprofen Peptide Conjugate

This example describes the conjugation of ibuprofen to a knottin peptide using a PEG linker. A conjugate is produced using ibuprofen and a PEG linker, which forms an ester bond that can hydrolyze as described in "In vitro and in vivo study of poly(ethylene glycol) conjugated ibuprofen to extend the duration of action," Scientia Pharmaceutica, 2011, 79:359-373, Nayak and Jain. Fischer esterification is used to conjugate ibuprofen with a short PEG, e.g., with triethylene glycol, to yield ibuprofen-ester-PEG-OH.

Following preparation of the PEG-ibuprofen conjugate as shown above, the hydroxyl moiety of PEG is activated with N,N'-disuccinimidyl carbonate (DSC) to form ibuprofen-ester-PEG-succinimidyl carbonate, which is then reacted with a lysine or the N-terminus of a knottin peptide to form an ibuprofen-ester-PEG-peptide conjugate. The knottin peptide is selected from any one of the peptides of sequence SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, or SEQ ID NO: 414-SEQ ID NO: 432. The conjugate can display anti-inflammatory activity, or free ibuprofen is released from the conjugate to provide anti-inflammatory activity. The free ibuprofen can result from hydrolysis that occurs after administration, such as hydrolysis at the ester bond.

Ibuprofen-peptide conjugates are administered to a subject in need thereof. The subject can be a human or a non-human animal.

Example 15

Dexamethasone Peptide Conjugate

This example describes different methods of conjugating dexamethasone with a peptide of this disclosure. A peptide of SEQ ID NO: 111 was recombinantly expressed. Dexamethasone was readily conjugated to a peptide of this disclosure using a dicarboxylic acid linker. The peptide-dexamethasone conjugate was made by first converting dexamethasone to a hemisuccinate by reacting it with succinic anhydride. The hemisuccinate was then converted to a succinate carboxylic acid containing an active ester, using dicyclohexyl carbodiimide (DCC) or 1-ethyl-3-(3-dimethylamninopropyl)carbodiimide (EDC) in the presence of N-hydroxy succinimide (NHS). This active ester was then reacted with a lysine or the N-terminus of a knottin peptide to create a dexamethasone-carboxylic acid-peptide conjugate. Methods such as those described in "Functionalized derivatives of hyaluronic acid oligosaccharides: drug carriers and novel biomaterials" Bioconjugate Chemistry 1994, 5, 339-347, Pouyani and Prestwich, and Bioconjugate Techniques by Greg Hermanson can be used.

Peptide-dexamethasone conjugates were prepared by coupling dexamethasone to the peptides of this disclosure using standard coupling-reagent chemistry. For example, dexamethasone conjugates were made by reacting dexamethasone hemigluterate with 1.05 molar equivalents of 1,1'-carbonyldiimidazole in anhydrous DMSO in an inert atmosphere. After 30 minutes, excess dexamethasone in anhydrous DMSO was added along with two molar equivalents of anhydrous trimethylamine. The N-hydroxysuccinimide ester of the peptide-dexamethasone conjugate was generated to form a shelf-stable intermediate for later reaction with an amine-containing carrier. The N-terminal dexamethasone-peptide conjugate (SEQ ID NO: 111B) was verified by electrospray mass spectrometry (ES-MS) within a 10 ppm error.

A knottin peptide of any of the sequences of this disclosure including SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, or SEQ ID NO: 414-SEQ ID NO: 432, are conjugated to dexamethasone using the methods described above.

Example 16

Peptide Conjugate Hydrolysis

This example describes preparation of knottin peptide conjugates having tunable hydrolysis rates. The dexamethasone conjugate described in EXAMPLE 15 is synthesized with the modification that instead of using succinic anhydride, other molecules are used to provide steric hindrance to hydrolysis at the carbon adjacent to the final hydrolyzable ester. In one exemplary conjugate, the dexamethasone conjugate is synthesized with tetramethyl succinic anhydride to generate hindered esters, which causes a decreased rate of hydrolysis. In another exemplary conjugate, one methyl group is present at the adjacent carbon. In another exemplary conjugate, two methyl groups are present at the adjacent carbon. In another exemplary conjugate, one ethyl group is present at the adjacent carbon. In another exemplary conjugate, two ethyl groups are present at the adjacent carbon. The rate of hydrolysis in these exemplary conjugates is therefore adjusted as compared to the conjugates in EXAMPLE 15, preventing premature cleavage and ensuring that the majority of peptide-dexamethasone conjugates accumulate in cartilage.

The resulting peptide conjugates are administered to a human or animal subcutaneously, intravenously, orally, or injected directly into a joint to treat disease.

Example 17

Effects of Peptide on Ion Channels

This example describes the interaction between knottin peptides of the present disclosure and ion channels. Ion channels can be associated with pain and can be activated in disease states such as arthritis. A peptide of the disclosure is expressed and administered in a pharmaceutical composition to a patient to treat a joint condition or disease associated with an ion channel and treatable by binding, blocking, or interacting with the ion channel. Ion channels, such as Nav 1.7, are inhibited by peptides of the present disclosure. A given peptide is expressed recombinantly or chemically synthesized, wherein the peptide selected from SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, or SEQ ID NO: 414-SEQ ID NO: 432. Following expression or synthesis, the peptide is used directly or conjugated to a therapeutic compound, such as those described herein. A peptide of the present disclosure selectively interacts with ion channels, or is mutated in order to interact with ion channels. For example, a peptide of this disclosure is bound to Nav 1.7 or Nav 1.7 is blocked by a peptide of this disclosure. When the peptide is administered to a human subject, Nav 1.7 signaling is reduced in the tissues in proximity to the joints, and pain relief is thereby provided.

Example 18

Dosing of Peptide without Kidney Ligation

This example describes a dosing scheme for administering knottin peptides to mice without kidney ligation. The peptide administered had the sequence of SEQ ID NO: 24 as shown in TABLE 1. The peptide was radiolabeled by methylating lysines and the N-terminus, so the actual binding agent may contain methyl or dimethyl lysine(s) and a methylated or dimethylated amino terminus.

A target dosage of 100 nmol of each peptide carrying 10-25 µCi of $^{14}$C was administered to Female Harlan athymic nude mice by a tail vein injection. Each peptide was allowed to freely circulate within the animal for either 4 hours or 24 hours before the animals were euthanized and sectioned.

Example 19

Peptide Homing with Intact Kidneys

This example illustrates peptide homing to cartilage in animals with intact kidneys. At the end of the 4 hour or 24 hour dosing periods in Example 18, mice were frozen in a hexane/dry ice bath and then frozen in a block of carboxymethylcellulose. Whole animal sagittal slices were prepared that resulted in thin frozen sections being available for imaging. Thin, frozen sections of animal including imaging of tissues such as brain, tumor, liver, kidney, lung, heart, spleen, pancreas, muscle, adipose, gall bladder, upper gastrointestinal track, lower gastrointestinal track, bone, bone marrow, reproductive track, eye, cartilage, stomach, skin, spinal cord, bladder, salivary gland, and other types of tissues were obtained with a microtome, allowed to desiccate in a freezer, and exposed to phosphoimager plates for about ten days.

These plates were developed. A signal in tissue darker than the signal expected from blood in that tissue indicates peptide accumulation in a region, tissue, structure or cell. For instance, the cartilage is avascular and contains minute amounts of blood. FIG. 13A illustrates a white light image of a frozen section of a mouse 4 hours after administration 100 nmol of radiolabeled SEQ ID NO: 24 peptide. FIG. 13B illustrates an autoradiographic image corresponding to FIG. 13A in which the $^{14}$C signal identifies the radiolabeled SEQ ID NO: 24 peptide distribution in the cartilage of a mouse 4 hours after administration of 100 nmol.

FIG. 14A illustrates a white light image of a frozen section of a mouse 24 hours after administration 100 nmol of radiolabeled SEQ ID NO: 24 peptide. FIG. 14B illustrates an autoradiographic image corresponding to FIG. 14A in which the $^{14}$C signal identifies the radiolabeled SEQ ID NO: 24 peptide distribution in the cartilage of a mouse 24 hours after administration of 100 nmol.

FIG. 15A illustrates a white light image of a frozen section of a hind limb of a mouse 4 hours after administration 100 nmol of radiolabeled SEQ ID NO: 24 peptide. FIG. 15B illustrates an autoradiographic image corresponding to FIG. 15A in which the $^{14}$C signal identifies the radiolabeled SEQ ID NO: 24 peptide distribution in the ankle and digit cartilage of a mouse 4 hours after administration of 100 nmol. FIG. 15C illustrates an autoradiographic image in which the $^{14}$C signal identifies the radiolabeled SEQ ID NO: 24 peptide distribution in the ankle and digit cartilage of a mouse 4 hours after administration of 100 nmol. FIG. 15D illustrates a white light image of a frozen section of a hind limb of a mouse 4 hours after administration 100 nmol of radiolabeled SEQ ID NO: 24 peptide. FIG. 15E illustrates an autoradiographic image corresponding to FIG. 15D in which the $^{14}$C signal identifies the radiolabeled SEQ ID NO: 24 peptide distribution in the ankle and digit cartilage of a mouse 4 hours after administration of 100 nmol. FIG. 15F illustrates a white light image of a frozen section of a hind limb of a mouse 4 hours after administration 100 nmol of radiolabeled SEQ ID NO: 24 peptide. FIG. 15G illustrates an autoradiographic image corresponding to FIG. 15F in which the $^{14}$C signal identifies the radiolabeled SEQ ID NO: 24 peptide distribution in the ankle and digit cartilage of a mouse 4 hours after administration of 100 nmol.

FIG. 16A illustrates a white light image of a frozen section of a hind limb of a mouse 24 hours after administration 100 nmol of radiolabeled SEQ ID NO: 24 peptide. FIG. 16B illustrates an autoradiographic image corresponding to FIG. 16A in which the $^{14}$C signal identifies the radiolabeled SEQ ID NO: 24 peptide distribution in the ankle and digit cartilage of a mouse 24 hours after administration of 100 nmol. FIG. 16C illustrates a white light image of a frozen section of a hind limb of a mouse 24 hours after administration 100 nmol of radiolabeled SEQ ID NO: 24 peptide. FIG. 16D illustrates an autoradiographic image corresponding to FIG. 16C in which the $^{14}$C signal identifies the radiolabeled SEQ ID NO: 24 peptide distribution in the ankle and digit cartilage of a mouse 24 hours after administration of 100 nmol. FIG. 16E illustrates a white light image of a frozen section of a hind limb of a mouse 24 hours after administration 100 nmol of radiolabeled SEQ ID NO: 24 peptide. FIG. 16F illustrates an autoradiographic image corresponding to FIG. 16E in which the $^{14}$C signal identifies the radiolabeled SEQ ID NO: 24 peptide distribution in the ankle and digit cartilage of a mouse 24 hours after administration of 100 nmol. FIG. 16G illustrates an autoradiographic image in which the $^{14}$C signal identifies the radiolabeled SEQ ID NO: 24 peptide distribution in the ankle and digit cartilage of a mouse 24 hours after administration of 100 nmol.

Example 20

Whole Body Fluorescence and Isolated Limb Fluorescence of Cartilage Homing Peptides This example illustrates peptide homing to cartilage mice after administration of a peptide fluorophore conjugate. A peptide of SEQ ID NO: 111 was chemically conjugated to one molecule of Cyanine 5.5, a near infrared fluorophore, at the N-terminus of the peptide via an active NHS ester on the dye. A dose of 10 nmol of each peptide of SEQ ID NO: 111 conjugated to a Cy5.5 fluorophore (SEQ ID NO: 111A) was administered to Female Haland athymic nude mice, weighing 20-25 g, and was administered via tail vein injection. Each experiment was done in duplicate (n=2 mice per group). The peptide of SEQ ID NO: 111 conjugated to a Cy5.5 fluorophore (SEQ ID NO: 111A) was allowed to freely circulate for the described time period before the mice were euthanized at various time points. Mice were evaluated for peptide distribution of the peptide of SEQ ID NO: 111 conjugated to a Cy5.5 fluorophore (SEQ ID NO: 111A) fluorescence in whole body imaging and in isolated hind limb imaging.

For Whole body fluorescence (WBF), at the end of the dosing period, mice were frozen in a hexane/dry ice bath and then embedded in a frozen block of carboxymethylcellulose. Whole animal sagittal slices were prepared that resulted in thin frozen sections for imaging. Thin frozen sections were obtained using a microtome and allowed visualization of tissues. Sections were allowed to desiccate in a freezer prior to imaging. WBF was then performed on fluorescent sections, which were scanned on a Li-Cor Odyssey scanner at a setting of 169 μm resolution, medium quality, 700 channel, L-2.0 intensity.

For isolated hind limb fluorescence studies, mice were euthanized by $CO_2$ asphyxiation at the end of the dosing period. The right hind limb was removed at the hip joint and imaged on a Sepctrum IVIS imager (ex/em: 675 nm. 720 nm) with a 1 second exposure length and a focal height of 0.5 cm. Limbs were imaged with skin removed and with muscle removed.

FIG. 17 shows white light images (left) and corresponding whole body fluorescence images (right) of a mouse 3 hours after administration of 10 nmol SEQ ID NO: 111 peptide conjugated to a Cy5.5 fluorophore (SEQ ID NO: 111A). This experiment and results were reproduced in a second mouse (images not shown).

FIG. 18 shows white light images (left) and corresponding whole body fluorescence images (right) of a mouse 24 hours after administration of 10 nmol SEQ ID NO: 111 peptide conjugated to a Cy5.5 fluorophore (SEQ ID NO: 111A). This experiment and results were reproduced in a second mouse (images not shown).

FIG. 19 shows white light images (left) and corresponding whole body fluorescence images (right) of a mouse 48 hours after administration of 10 nmol SEQ ID NO: 111 peptide conjugated to a Cy5.5 fluorophore (SEQ ID NO: 111A). This experiment and results were reproduced in a second mouse (images not shown). FIG. 20 shows white light images (left) and corresponding whole body fluorescence images (right) of a mouse 72 hours after administration of SEQ ID NO: 111 peptide conjugated to a Cy5.5 fluorophore (SEQ ID NO: 111A). This experiment and results were reproduced in a second mouse (images not shown). These WBF images showed SEQ ID NO: 112 peptide conjugated to a Cy5.5 fluorophore (SEQ ID NO: 111A) fluorescence distribution in intervertebral discs (IVD) and in joints and cartilaginous tissues at 3 hours and 24 hours.

FIG. 21 shows IVIS fluorescence imaging of an isolated hind limb from a first mouse and an isolated hind limb from a second mouse after administration of 10 nmol SEQ ID NO: 111 peptide conjugated to a Cy5.5 fluorophore (SEQ ID NO: 111A). FIG. 21A shows the right hind limb with skin removed from a first mouse and from a second mouse 3 hours after peptide administration. FIG. 21B shows the right hind limb with muscle removed from a first mouse and from a second mouse 3 hours after peptide administration. FIG. 21C shows the right hind limb with skin removed from a first mouse and from a second mouse 24 hours after peptide administration. FIG. 21D shows the right hind limb with muscle removed from a first moues and from a second mouse 24 hours after peptide administration. FIG. 21E shows the right hind limb with skin removed from a first mouse and from a second mouse 48 hours after peptide administration. FIG. 21F shows the right hind limb with muscle removed from a first mouse and from a second mouse 48 hours after peptide administration. FIG. 21G shows the right hind limb with skin removed from a first mouse and from a second mouse 72 hours after peptide administration. FIG. 21H shows the right hind limb with muscle removed from a first mouse and from a second mouse 72 hours after peptide administration. Peptide fluorescence was observed in the knee joints of isolated right hind limbs at all time points tested.

TABLE 4 summarizes fluorescence signal in IVD cartilage, at various time points after administration of SEQ ID NO: 111 peptide conjugated to a Cy5.5 fluorophore (SEQ ID NO: 111A) in mice.

TABLE 4

| SEQ ID NO | Signal Observed | Kidney Status | Duration |
| --- | --- | --- | --- |
| 111A | Yes | Intact | 3 hr |
| 111A | Yes | Intact | 24 hr |
| 111A | No | Intact | 48 hr |
| 111A | No | Intact | 72 hr |

Example 21

Whole Body Autoradiography of Cartilage Homing Peptides

This example illustrates peptide homing to cartilage mice 5 minutes to 48 hours after administration of a radiolabeled peptide. Signal from the radiolabeled peptides was found in all types of cartilage at each time point examined. Each peptide was radiolabeled by methylating lysines at the N-terminus as described in EXAMPLE 2. As such, the peptide may contain methyl or dimethyl lysines and a methylated or dimethylated amino terminus. A dose of 100 nmol radiolabeled peptide was administered via tail vein injection in Female Harlan athymic nude mice, weighing 20-25 g. The experiment was done in duplicate (n=2 animals per group). In some animals, kidneys were ligated to prevent renal filtration of the radiolabeled peptides and extend plasma half-life. Each radiolabeled peptide was allowed to freely circulate within the animal for the described time period before the animals were euthanized and sectioned.

Whole body autoradiography (WBA) sagittal sectioning was performed as follows. At the end of the dosing period, mice were frozen in a hexane/dry ice bath and then embedded in a frozen block of carboxymethylcellulose. Whole animal sagittal slices were prepared that resulted in thin frozen sections for imaging. Thin frozen sections were obtained using a microtome and allowed visualization of tissues such as brain, tumor, liver, kidney, lung, heart, spleen, pancreas, muscle, adipose, gall bladder, upper gastrointestinal tract, lower gastrointestinal tract, bone, bone marrow, reproductive tract, eye, cartilage, stomach, skin, spinal cord, bladder, salivary gland, and more. Sections were allowed to desiccate in a freezer prior to imaging.

For the autoradiography imaging, tape mounted thin sections were freeze dried and radioactive samples were exposed to phophoimager plates for 7 days. These plates were developed and the signal (densitometry) from each organ was normalized to the signal found in the cardiac blood of each animal. A signal in tissue darker than the signal expected from blood in that tissue indicates accumulation in a region, tissue, structure, or cell.

FIG. 22 illustrates a white light image and a corresponding autoradiography image of frozen sections of a mouse, 5 minutes after administration of 100 nmol of a radiolabeled peptide of SEQ ID NO: 111. FIG. 22A illustrates a white light image of a frozen section of a mouse, 5 minutes after administration of 100 nmol of a radiolabeled peptide of SEQ ID NO: 111. FIG. 22B illustrates the $^{14}C$ signal in a frozen section of a mouse, corresponding to the section shown in FIG. 22A, 5 minutes after administration of 100 nmol of a radiolabeled peptide of SEQ ID NO: 111. The $^{14}C$ signal identifies the radiolabeled peptide distribution in the cartilage of the mouse. FIG. 22C illustrates a white light image of a different frozen section of a mouse, 5 minutes after administration of 100 nmol of a radiolabeled peptide of SEQ ID NO: 111. FIG. 22D illustrates the $^{14}C$ signal in a frozen section of a mouse, corresponding to the section shown in FIG. 22C, 5 minutes after administration of 100 nmol of a radiolabeled peptide of SEQ ID NO: 111. The $^{14}C$ signal identifies the radiolabeled peptide distribution in the cartilage of the mouse. FIG. 22E illustrates a white light image of a different frozen section of a mouse, 5 minutes after administration of 100 nmol of a radiolabeled SEQ ID NO: 111. FIG. 22F illustrates the $^{14}C$ signal in a frozen section of a mouse, corresponding to the section shown in FIG. 22E, 5 minutes after administration of 100 nmol of a radiolabeled peptide of SEQ ID NO: 111. The $^{14}C$ signal identifies the radiolabeled peptide distribution in the cartilage of the mouse. FIG. 22G illustrates a white light image of a different frozen section of a mouse, 5 minutes after administration of 100 nmol of a radiolabeled peptide of a SEQ ID NO: 111. FIG. 22H illustrates the $^{14}C$ signal in a frozen section of a mouse, corresponding to the section shown in FIG. 22G, 5 minutes after administration of 100 nmol of a radiolabeled peptide of a SEQ ID NO: 111. The u signal identifies the radiolabeled peptide distribution in the cartilage of the mouse.

FIG. 23 illustrates a white light image and a corresponding autoradiography image of frozen sections of a mouse, 30 minutes after administration of 100 nmol of a radiolabeled peptide of SEQ ID NO: 111. FIG. 23A illustrates a white light image of a frozen section of a mouse, 30 minutes after administration of 100 nmol of a radiolabeled peptide of SEQ ID NO: 111. FIG. 23B illustrates the $^{14}C$ signal in a frozen section of a mouse, corresponding to the section shown in FIG. 23A, 30 minutes after administration of 100 nmol of a radiolabeled peptide of SEQ ID NO: 111. The $^{14}C$ signal identifies the radiolabeled peptide distribution in the cartilage of the mouse. FIG. 23C illustrates a white light image of a different frozen section of a mouse, 30 minutes after administration of 100 nmol of a radiolabeled peptide of SEQ ID NO: 111. FIG. 23D illustrates the $^{14}C$ signal in a frozen section of a mouse, corresponding to the section shown in FIG. 23C, 30 minutes after administration of 100 nmol of a radiolabeled peptide of SEQ ID NO: 111. The $^{14}C$ signal identifies the radiolabeled peptide distribution in the cartilage of the mouse. FIG. 23E illustrates a white light image of a different frozen section of the mouse, 30 minutes after administration of 100 nmol of a radiolabeled peptide of SEQ ID NO: 111. FIG. 23F illustrates the $^{14}C$ signal in a frozen section of the mouse, corresponding to the section shown in FIG. 23E, 30 minutes after administration of 100 nmol of a radiolabeled peptide of SEQ ID NO: 111. The $^{14}C$ signal identifies the radiolabeled peptide distribution in the cartilage of the mouse.

FIG. 24 illustrates a white light image and a corresponding autoradiography image of frozen sections from a mouse, 1 hour after administration of 100 nmol of a radiolabeled peptide of SEQ ID NO: 111. FIG. 24A illustrates a white light image of a frozen section of a mouse, 1 hour after administration of 100 nmol of a radiolabeled peptide of SEQ ID NO: 111. FIG. 24B illustrates the $^{14}C$ signal in a frozen section of a mouse, corresponding to the section shown in FIG. 24A, 1 hour after administration of 100 nmol of a radiolabeled peptide of SEQ ID NO: 111. The $^{14}C$ signal identifies the radiolabeled peptide distribution in the cartilage of the mouse. FIG. 24C illustrates a white light image of a different frozen section of a mouse, 1 hour after administration of 100 nmol of a radiolabeled peptide of SEQ ID NO: 111. FIG. 24D illustrates the $^{14}C$ signal in a frozen section of a mouse, corresponding to the section shown in FIG. 24C, 1 hour after administration of 100 nmol of a radiolabeled peptide of SEQ ID NO: 111. The $^{14}C$ signal identifies the radiolabeled peptide distribution in the cartilage of the mouse. FIG. 24E illustrates a white light image of a different frozen section of the mouse, 1 hour after administration of 100 nmol of a radiolabeled peptide of SEQ ID NO: 111. FIG. 24F illustrates the $^{14}C$ signal in a frozen section of a mouse, corresponding to the section shown in FIG. 24E, 1 hour after administration of 100 nmol of a radiolabeled peptide of SEQ ID NO: 111. The $^{14}C$ signal identifies the radiolabeled peptide distribution in the cartilage of the mouse. FIG. 24G illustrates a white light image of a different frozen section of the mouse, 1 hour after administration of 100 nmol of a radiolabeled peptide of SEQ ID NO: 111. FIG. 24H illustrates the $^{14}C$ signal in a frozen section of a mouse, corresponding to the section shown in FIG. 24G, 1 hour after administration of 100 nmol of a radiolabeled peptide of SEQ ID NO: 111. The $^{14}C$ signal identifies the radiolabeled peptide distribution in the cartilage of the mouse.

FIG. 25 illustrates a white light image and a corresponding autoradiography image of frozen sections from a mouse, 3 hours after administration of 100 nmol of a radiolabeled peptide of SEQ ID NO: 111. FIG. 25A illustrates a white light image of a frozen section of a mouse, 3 hours after administration of 100 nmol of a radiolabeled peptide of SEQ ID NO: 111. FIG. 25B illustrates the $^{14}C$ signal in a frozen section of the mouse, corresponding to the section shown in FIG. 25A, 3 hours after administration of 100 nmol of a radiolabeled peptide of SEQ ID NO: 111. The $^{14}C$ signal identifies the radiolabeled peptide distribution in the cartilage of the mouse. FIG. 56C illustrates a white light image of a different frozen section of a mouse, 3 hours after administration of 100 nmol of a radiolabeled peptide of SEQ ID NO: 111. FIG. 25D illustrates the $^{14}C$ signal in a different frozen section of the mouse, corresponding to the section shown in FIG. 25C, 3 hours after administration of 100 nmol of a radiolabeled peptide of SEQ ID NO: 111. The $^{14}C$ signal identifies the radiolabeled peptide distribution in the cartilage of the mouse. FIG. 25E illustrates the $^{14}C$ signal in a different frozen section of a mouse, 3 hours after administration of 100 nmol of a radiolabeled peptide of SEQ ID NO: 111. The $^{14}C$ signal identifies the radiolabeled peptide distribution in the cartilage of the mouse.

FIG. 26 illustrates a white light image and a corresponding autoradiography images of frozen sections from a mouse with ligated kidneys, 3 hours after administration of 100 nmol of a radiolabeled peptide of SEQ ID NO: 111. FIG. 26A illustrates a white light image of a frozen section of a mouse with ligated kidneys, 3 hours after administration of 100 nmol of a radiolabeled peptide of SEQ ID NO: 111. FIG. 26B illustrates the $^{14}$C signal in a frozen section of the mouse with ligated kidneys, corresponding to the section shown in FIG. 26A, 3 hours after administration of 100 nmol of a radiolabeled peptide of SEQ ID NO: 111. The $^{14}$C signal identifies the radiolabeled peptide distribution in the cartilage of the mouse. FIG. 26C illustrates a white light image of a different frozen section of the mouse with ligated kidneys, 3 hours after administration of 100 nmol of a radiolabeled peptide of SEQ ID NO: 111. FIG. 26D illustrates the $^{14}$C signal in a frozen section of the mouse with ligated kidneys, corresponding to the section shown in FIG. 26C, 3 hours after administration of 100 nmol of a radiolabeled peptide of SEQ ID NO: 111. The $^{14}$C signal identifies the radiolabeled peptide distribution in the cartilage of the mouse. FIG. 26E illustrates a white light image of a different frozen section of a mouse with ligated kidneys, 3 hours after administration of 100 nmol of a radiolabeled peptide of SEQ ID NO: 111. FIG. 26F illustrates the $^{14}$C signal in a frozen section of the mouse with ligated kidneys, corresponding to section shown in FIG. 26E, 3 hours after administration of 100 nmol of a radiolabeled peptide of SEQ ID NO: 111. The $^{14}$C signal identifies the radiolabeled peptide distribution in the cartilage of the mouse.

Figure 8:
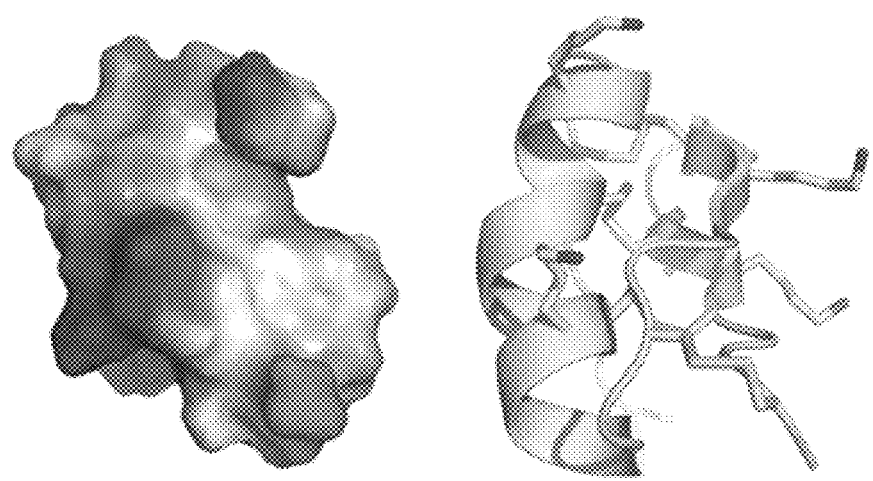
FIG. 8 illustrates a three-dimensional structure and a line structure of a peptide of FIG. 1B and SEQ ID NO: 28.

FIG. 27 illustrates a white light image and a corresponding autoradiography image of frozen sections from a mouse, 8 hours after administration of 100 nmol of a radiolabeled peptide of SEQ ID NO: 111. FIG. 27A illustrates a white light image of a frozen section of a mouse, 8 hours after administration of 100 nmol of a radiolabeled peptide of SEQ ID NO: 111. FIG. 27B illustrates the $^{14}$C signal in a frozen section of the mouse, corresponding to the section shown in FIG. 27A, 8 hours after administration of 100 nmol of a radiolabeled peptide of SEQ ID NO: 111. The $^{14}$C signal identifies the radiolabeled peptide distribution in the cartilage of the mouse. FIG. 27C illustrates an image of a different frozen section of a mouse, 8 hours after administration of 100 nmol of a radiolabeled peptide of SEQ ID NO: 111. FIG. 27D illustrates the $^{14}$C signal in a frozen section of the mouse, corresponding to the section shown in FIG. 27C, 8 hours after administration of 100 nmol of a radiolabeled peptide of SEQ ID NO: 111. The $^{14}$C signal identifies the radiolabeled peptide distribution in the cartilage of the mouse. FIG. 27E illustrates an image of a different frozen section of a mouse, 8 hours after administration of 100 nmol of a radiolabeled peptide of SEQ ID NO: 111. FIG. 27F illustrates the $^{14}$C signal in a frozen section of the mouse, corresponding to the section shown in FIG. 27E, 8 hours after administration of 100 nmol of a radiolabeled peptide of SEQ ID NO: 111. The $^{14}$C signal identifies the radiolabeled peptide distribution in the cartilage of the mouse. FIG. 27G illustrates a white light image of a different frozen section of a mouse, 8 hours after administration of 100 nmol of a radiolabeled peptide of SEQ ID NO: 111. FIG. 27H illustrates the $^{14}$C signal in a frozen section of a mouse, corresponding to the section shown in FIG. 27G, 8 hours after administration of 100 nmol of a radiolabeled peptide of SEQ ID NO: 111. The $^{14}$C signal identifies the radiolabeled peptide distribution in the cartilage of the mouse.

FIG. 28 illustrates a white light image and a corresponding autoradiography image of frozen sections from a mouse, 24 hours after administration of 100 nmol of a radiolabeled peptide of SEQ ID NO: 111. FIG. 28A illustrates a white light image of a frozen section of a mouse, 24 hours after administration of 100 nmol of a radiolabeled peptide of SEQ ID NO: 111. FIG. 28B illustrates the $^{14}$C signal in a frozen section of the mouse, corresponding to the section shown in FIG. 28A, 24 hours after administration of 100 nmol of a radiolabeled peptide of SEQ ID NO: 111. The $^{14}$C signal identifies the radiolabeled peptide distribution in the cartilage of the mouse. FIG. 28C illustrates a white light image of a different frozen section of a mouse, 24 hours after administration of 100 nmol of a radiolabeled peptide of SEQ ID NO: 111. FIG. 28D illustrates the $^{14}$C signal in a frozen section of the mouse, corresponding to the section shown in FIG. 28C, 24 hours after administration of 100 nmol of a radiolabeled peptide of SEQ ID NO: 111. The $^{14}$C signal identifies the radiolabeled peptide distribution in the cartilage of the mouse. FIG. 28E illustrates a white light image of a different frozen section of a mouse, 24 hours after administration of 100 nmol of a radiolabeled peptide of SEQ ID NO: 111. FIG. 28F illustrates the $^{14}$C signal in a frozen section of the mouse, corresponding to the section shown in FIG. 28E, 24 hours after administration of 100 nmol of a radiolabeled peptide of SEQ ID NO: 111. The $^{14}$C signal identifies the radiolabeled peptide distribution in the cartilage of the mouse.

FIG. 29 illustrates a white light image and a corresponding autoradiography image of frozen sections from a mouse, 48 hours after administration of 100 nmol of a radiolabeled peptide of SEQ ID NO: 111. FIG. 29A illustrates a white light image of a frozen section of a mouse, 48 hours after administration of 100 nmol of a radiolabeled peptide of SEQ ID NO: 111. FIG. 29B illustrates the $^{14}$C signal in a frozen section of the mouse, corresponding to the section shown in FIG. 29A, 48 hours after administration of 100 nmol of a radiolabeled peptide of SEQ ID NO: 111. The $^{14}$C signal identifies the radiolabeled peptide distribution in the cartilage of the mouse. FIG. 29C illustrates a white light image of a different frozen section of a mouse, 48 hours after administration of 100 nmol of a radiolabeled peptide of SEQ ID NO: 111. FIG. 29D illustrates the $^{14}$C signal in a frozen section of the mouse, corresponding to the section shown in FIG. 29C, 48 hours after administration of 100 nmol of a radiolabeled peptide of SEQ ID NO: 111. The $^{14}$C signal identifies the radiolabeled peptide distribution in the cartilage of the mouse. FIG. 29E illustrates a white light image of a different frozen section of the mouse, 48 hours after administration of 100 nmol of a radiolabeled peptide of SEQ ID NO: 111. FIG. 29F illustrates the $^{14}$C signal in a frozen section of the mouse, corresponding to the section shown in FIG. 29E, 48 hours after administration of 100 nmol of a radiolabeled peptide of SEQ ID NO: 111. The $^{14}$C signal identifies the radiolabeled peptide distribution in the cartilage of the mouse. FIG. 29G illustrates a white light image of a different frozen section of a mouse, 48 hours after administration of 100 nmol of a radiolabeled peptide of SEQ ID NO: 111. FIG. 29H illustrates the $^{14}$C signal in a frozen section of the mouse, corresponding to the section shown in FIG. 29G, 48 hours after administration of 100 nmol of a radiolabeled peptide of SEQ ID NO: 111. The $^{14}$C signal identifies the radiolabeled peptide distribution in the cartilage of the mouse.

TABLE 5 shows the signal of radiolabeled peptides of SEQ ID NO: 24 and SEQ ID NO: 111 in IVD and knee joints as a percentage of the blood. Because the peptides may arrive at the joint within five minutes, a therapeutic effect from the peptide or a conjugated active agent may begin quickly. A therapeutic effect could be long lasting, due to continued presence of detected agents at 48 hours and/or due to long lasting pharmacodynamics effects.

TABLE 5

| Hours | SEQ ID NO: 24 IVD | SEQ ID NO: 111 IVD | SEQ ID NO: 111 Knee |
|---|---|---|---|
| 0.08 | | 164 | 404 |
| 0.5 | | 369 | 510 |
| 1 | | 961 | 1114 |
| 3 | 1779 | 3213 | 4059 |
| 8 | | 3777 | 4990 |
| 24 | 833 | 5391 | 2137 |
| 48 | | 3320 | 843 |

A radiolabeled peptide of SEQ ID NO: 111 was observed in the intervertebral disc (IVD) and synovial joints at all time points (5 minutes-48 hours). The signal to background ratio in IVD peaked at 24 hours. The signal to background ratio in knee joints peaked at 8 hours. Signal in IVD was observed to progress from the periphery of the cartilage adjacent to the bone inwards.

FIG. 30 illustrates a white light image and a corresponding autoradiography image of frozen sections from a mouse, 3 hours after administration of 100 nmol of a radiolabeled peptide of SEQ ID NO: 109. FIG. 30A illustrates a white light image of a frozen section of a mouse, 3 hours after administration of 100 nmol of a radiolabeled peptide of SEQ ID NO: 109. FIG. 30B illustrates the $^{14}$C signal in a frozen section of a mouse, corresponding to the section shown in FIG. 30A, 3 hours after administration of 100 nmol of a radiolabeled peptide of SEQ ID NO: 109. The $^{14}$C signal identifies the radiolabeled peptide distribution in the cartilage of the mouse. FIG. 30C illustrates a white light image of a different frozen section of a mouse, 3 hours after administration of 100 nmol of a radiolabeled peptide of SEQ ID NO: 109. FIG. 30D illustrates the $^{14}$C signal in a frozen section of the mouse, corresponding to the section shown in FIG. 30C, 3 hours after administration of 100 nmol of a radiolabeled peptide of SEQ ID NO: 109. The $^{14}$C signal identifies the radiolabeled peptide distribution in the cartilage of the mouse. FIG. 30E illustrates a white light image of a different frozen section of a mouse, 3 hours after administration of 100 nmol of a radiolabeled peptide of SEQ ID NO: 109. FIG. 30F illustrates the $^{14}$C signal in a frozen section of the mouse, corresponding to the section shown in FIG. 30E, 3 hours after administration of 100 nmol of a radiolabeled peptide of SEQ ID NO: 109. The $^{14}$C signal identifies the radiolabeled peptide distribution in the cartilage of the mouse.

FIG. 31 illustrates a white light image and a corresponding autoradiography image of frozen sections from a mouse, 24 hours after administration of 100 nmol of a radiolabeled peptide of SEQ ID NO: 109. FIG. 31A illustrates a white light image of a frozen section of a mouse, 24 hours after administration of 100 nmol of a radiolabeled peptide of SEQ ID NO: 109. FIG. 31B illustrates the $^{14}$C signal in a frozen section of the mouse, corresponding to the section shown in FIG. 31A, 24 hours after administration of 100 nmol of a radiolabeled peptide of SEQ ID NO: 109. The $^{14}$C signal identifies the radiolabeled peptide distribution in the cartilage of the mouse. FIG. 31C illustrates a white light image of a different frozen section of the mouse, 24 hours after administration of 100 nmol of a radiolabeled peptide of SEQ ID NO: 109. FIG. 31D illustrates the $^{14}$C signal in a frozen section of the mouse, corresponding to the section shown in FIG. 31C, 24 hours after administration of 100 nmol of a radiolabeled peptide of SEQ ID NO: 109. The $^{14}$C signal identifies the radiolabeled peptide distribution in the cartilage of the mouse. FIG. 31E illustrates a white light image of a different frozen section of the mouse, 24 hours after administration of 100 nmol of a radiolabeled peptide of SEQ ID NO: 109. FIG. 31F illustrates the $^{14}$C signal in a frozen section of the mouse, corresponding to the section shown in FIG. 31E, 24 hours after administration of 100 nmol of a radiolabeled peptide of SEQ ID NO: 109. The $^{14}$C signal identifies the radiolabeled peptide distribution in the cartilage of the mouse.

FIG. 32 illustrates a white light image and a corresponding autoradiography image of frozen sections from a mouse 3 hours after administration of 100 nmol of a radiolabeled peptide of SEQ ID NO: 110. FIG. 32A illustrates a white light image of a frozen section of a mouse, 3 hours after administration of 100 nmol of a radiolabeled peptide of SEQ ID NO: 110. FIG. 32B illustrates the $^{14}$C signal in a frozen section of the mouse, corresponding to the section shown in FIG. 32A, 3 hours after administration of 100 nmol of a radiolabeled peptide of SEQ ID NO: 110. The $^{14}$C signal identifies the radiolabeled peptide distribution in the cartilage of the mouse. FIG. 32C illustrates a white light image of a different frozen section of a mouse, 3 hours after administration of 100 nmol of a radiolabeled peptide of SEQ ID NO: 110. FIG. 32D illustrates the $^{14}$C signal in a frozen section of the mouse, corresponding to the section shown in FIG. 32C, 3 hours after administration of 100 nmol of a radiolabeled peptide of SEQ ID NO: 110. The $^{14}$C signal identifies the radiolabeled peptide distribution in the cartilage of the mouse. FIG. 32E illustrates a white light image of a different frozen section of a mouse, 3 hours after administration of 100 nmol of a radiolabeled peptide of SEQ ID NO: 110. FIG. 32F illustrates the $^{14}$C signal in a frozen section of the mouse, corresponding to the section shown in FIG. 32E, 3 hours after administration of 100 nmol of a radiolabeled peptide of SEQ ID NO: 110. The $^{14}$C signal identifies the radiolabeled peptide distribution in the cartilage of the mouse. FIG. 32G illustrates a white light image of a different frozen section of a mouse, 3 hours after administration of 100 nmol of a radiolabeled peptide of SEQ ID NO: 110. FIG. 32H illustrates the $^{14}$C signal in a frozen section of the mouse, corresponding to the section shown in FIG. 32G, 3 hours after administration of 100 nmol of a radiolabeled peptide of SEQ ID NO: 110. The $^{14}$C signal identifies the radiolabeled peptide distribution in the cartilage of the mouse.

FIG. 33 illustrates a white light image and a corresponding autoradiography image of frozen sections from a mouse, 24 hours after administration of 100 nmol of a radiolabeled peptide of SEQ ID NO: 110. FIG. 33A illustrates a white light image of a frozen section of a mouse, 24 hours after administration of 100 nmol of a radiolabeled peptide of SEQ ID NO: 110. FIG. 33B illustrates the $^{14}$C signal in a frozen section of the mouse, corresponding to the section shown in FIG. 33A, 24 hours after administration of 100 nmol of a radiolabeled peptide of SEQ ID NO: 110. The $^{14}$C signal identifies the radiolabeled peptide distribution in the cartilage of the mouse. FIG. 33C illustrates a white light image of a different frozen section of the mouse, 24 hours after administration of 100 nmol of a radiolabeled peptide of SEQ ID NO: 110. FIG. 33D illustrates the $^{14}$C signal in a frozen section of the mouse, corresponding to the section shown in FIG. 33C, 24 hours after administration of 100 nmol of a radiolabeled peptide of SEQ ID NO: 110. The $^{14}$C signal identifies the radiolabeled peptide distribution in the cartilage of the mouse. FIG. 33E illustrates a white light image of a different frozen section of the mouse, 24 hours after administration of 100 nmol of a radiolabeled peptide of SEQ ID NO: 110. FIG. 33F illustrates the $^{14}$C signal in a frozen section of the mouse, corresponding to the section shown in FIG. 33E, 24 hours after administration of 100 nmol of a radiolabeled peptide of SEQ ID NO: 110. The $^{14}$C signal identifies the radiolabeled peptide distribution in the cartilage of the mouse.

FIG. 34 illustrates a white light image and a corresponding autoradiography image of frozen sections from a mouse 3 hours after administration of 100 nmol of a radiolabeled peptide of SEQ ID NO: 114. FIG. 34A illustrates a white light image of a frozen section of a mouse, 3 hours after administration of 100 nmol of a radiolabeled peptide of SEQ ID NO: 114. FIG. 34B illustrates the $^{14}$C signal in a frozen section of the mouse, corresponding to the section shown in FIG. 34A, 3 hours after administration of 100 nmol of a radiolabeled peptide of SEQ ID NO: 114. The $^{14}$C signal identifies the radiolabeled peptide distribution in the cartilage of the mouse. FIG. 34C illustrates a white light image of a different frozen section of a mouse, 3 hours after administration of 100 nmol of a radiolabeled peptide of SEQ ID NO: 114. FIG. 34D illustrates the $^{14}$C signal in a frozen section of a mouse, corresponding to the section shown in FIG. 34C, 3 hours after administration of 100 nmol of a radiolabeled peptide of SEQ ID NO: 114. The $^{14}$C signal identifies the radiolabeled peptide distribution in the cartilage of the mouse. FIG. 34E illustrates a white light image of a different frozen section of a mouse, 3 hours after administration of 100 nmol of a radiolabeled peptide of SEQ ID NO: 114. FIG. 34F illustrates the $^{14}$C signal in a frozen section of the mouse, corresponding to the section shown in FIG. 34E, 3 hours after administration of 100 nmol of a radiolabeled peptide of SEQ ID NO: 114. The $^{14}$C signal identifies the radiolabeled peptide distribution in the cartilage of the mouse.

FIG. 35 illustrates a white light image and a corresponding autoradiography image of frozen sections from a mouse, 24 hours after administration of 100 nmol of a radiolabeled peptide of SEQ ID NO: 114. FIG. 35A illustrates a white light image of a frozen section of a mouse, 24 hours after administration of 100 nmol of a radiolabeled peptide of SEQ ID NO: 114. FIG. 35B illustrates the $^{14}$C signal in a frozen section of the mouse, corresponding to the section shown in FIG. 35A, 24 hours after administration of 100 nmol of a radiolabeled peptide of SEQ ID NO: 114. The $^{14}$C signal identifies the radiolabeled peptide distribution in the cartilage of the mouse. FIG. 35C illustrates a white light image of a different frozen section of a mouse, 24 hours after administration of 100 nmol of a radiolabeled peptide of SEQ ID NO: 114. FIG. 35D illustrates the $^{14}$C signal in a frozen section of the mouse, corresponding to the section shown in FIG. 35C, 24 hours after administration of 100 nmol of a radiolabeled peptide of SEQ ID NO: 114. The $^{14}$C signal identifies the radiolabeled peptide distribution in the cartilage of the mouse. FIG. 35E illustrates a white light image of a different frozen section of a mouse, 24 hours after administration of 100 nmol of a radiolabeled peptide of SEQ ID NO: 114. FIG. 35F illustrates the $^{14}$C signal in a frozen section of the mouse, corresponding to the section shown in FIG. 35E, 24 hours after administration of 100 nmol of a radiolabeled peptide of SEQ ID NO: 114. The $^{14}$C signal identifies the radiolabeled peptide distribution in the cartilage of the mouse.

FIG. 36 illustrates a white light image and a corresponding autoradiography image of frozen sections from a mouse, 3 hours after administration of 100 nmol of a radiolabeled peptide of SEQ ID NO: 200. FIG. 36A illustrates a white light image of a frozen section of a mouse, 3 hours after administration of 100 nmol of a radiolabeled peptide of SEQ ID NO: 200. FIG. 36B illustrates the $^{14}$C signal in a frozen section of the mouse, corresponding to the section shown in FIG. 36A, 3 hours after administration of 100 nmol of a radiolabeled peptide of SEQ ID NO: 200. The $^{14}$C signal identifies the radiolabeled peptide distribution in the cartilage of the mouse. FIG. 36C illustrates a white light image of a different frozen section of a mouse, 3 hours after administration of 100 nmol of a radiolabeled peptide of SEQ ID NO: 200. FIG. 36D illustrates the $^{14}$C signal in a frozen section of the mouse, corresponding to the section shown in FIG. 36C, 3 hours after administration of 100 nmol of a radiolabeled peptide of SEQ ID NO: 200. The $^{14}$C signal identifies the radiolabeled peptide distribution in the cartilage of the mouse. FIG. 36E illustrates a white light image of a different frozen section of a mouse, 3 hours after administration of 100 nmol of a radiolabeled peptide of SEQ ID NO: 200. FIG. 36F illustrates the $^{14}$C signal in a frozen section of the mouse, corresponding to the section shown in FIG. 36E, 3 hours after administration of 100 nmol of a radiolabeled peptide of SEQ ID NO: 200. The $^{14}$C signal identifies the radiolabeled peptide distribution in the cartilage of the mouse.

FIG. 37 illustrates a white light image and a corresponding autoradiography image of frozen sections from a mouse, 24 hours after administration of 100 nmol of a radiolabeled peptide of SEQ ID NO: 200. FIG. 37A illustrates a white light image of a frozen section of a mouse, 24 hours after administration of 100 nmol of a radiolabeled peptide of SEQ ID NO: 200. FIG. 37B illustrates the $^{14}$C signal in a frozen section of the mouse, corresponding to the section shown in FIG. 37A, 24 hours after administration of 100 nmol of a radiolabeled peptide of SEQ ID NO: 200. The $^{14}$C signal identifies the radiolabeled peptide distribution in the cartilage of the mouse. FIG. 37C illustrates a white light image of a different frozen section of the mouse, 24 hours after administration of 100 nmol of a radiolabeled peptide of SEQ ID NO: 200. FIG. 37D illustrates the $^{14}$C signal in a frozen section of the mouse, corresponding to the section shown in FIG. 37C, 24 hours after administration of 100 nmol of a radiolabeled peptide of SEQ ID NO: 200. The $^{14}$C signal identifies the radiolabeled peptide distribution in the cartilage of the mouse. FIG. 37E illustrates a white light image of a different frozen section of the mouse, 24 hours after administration of 100 nmol of a radiolabeled peptide of SEQ ID NO: 200. FIG. 37F illustrates the $^{14}$C signal in a frozen section of the mouse, corresponding to the section shown in FIG. 37E, 24 hours after administration of 100 nmol of a radiolabeled peptide of SEQ ID NO: 200. The $^{14}$C signal identifies the radiolabeled peptide distribution in the cartilage of the mouse. FIG. 37G illustrates a white light image of a different frozen section of the mouse, 24 hours after administration of 100 nmol of a radiolabeled peptide of SEQ ID NO: 200. FIG. 37H illustrates the $^{14}$C signal in a frozen section of a mouse, corresponding to the section shown in FIG. 37G, 24 hours after administration of 100 nmol of a radiolabeled peptide of SEQ ID NO: 200. The $^{14}$C signal identifies the radiolabeled peptide distribution in the cartilage of the mouse.

TABLE 6 shows the signal, as a percentage of signal in blood, of radiolabeled peptides of SEQ ID NO: 109, SEQ ID NO: 110, SEQ ID NO: 114, and SEQ ID NO: 200 in synovial joints.

TABLE 6

| | SEQ ID NO: 109 | | SEQ ID NO: 110 | | SEQ ID NO: 114 | | SEQ ID NO: 200 | |
|---|---|---|---|---|---|---|---|---|
| | Average | Std. Dev. | Average | Std. Dev. | Average | Std. Dev. | Average | Std. Dev. |
| 3 hr | 5627 | 5121 | 3142 | 279 | 1175 | 366 | | |
| 24 hr | 5097 | 1874 | 981 | 326 | | | 4991 | 1764 |

TABLE 7 shows the signal of radiolabeled peptides of SEQ ID NO: 109, SEQ ID NO: 110, SEQ ID NO: 114, and SEQ ID NO: 200 in the intervertebral disc (IVD).

TABLE 7

| | SEQ ID NO: 109 | | SEQ ID NO: 110 | | SEQ ID NO: 114 | | SEQ ID NO: 200 | |
|---|---|---|---|---|---|---|---|---|
| | Average | Std. Dev. | Average | Std. Dev. | Average | Std. Dev. | Average | Std. Dev. |
| 3 hr | 2758 | 1905 | 2374 | 795 | 1075 | 169 | 1809 | 649 |
| 24 hr | 4367 | 1218 | 1327 | 460 | 191 | | 3542 | 848 |

Peptides signal for SEQ ID NO: 109, SEQ ID NO: 110, SEQ ID NO: 114, and SEQ ID NO: 200 all showed signal in cartilage and exhibited cartilage homing properties. All peptides shown in TABLE 6 and TABLE 7 were variants of other peptides of this disclosure in which all lysine (K) residues were mutated to arginine (R) residues. The peptide of SEQ ID NO: 109 is a K to R variant of a peptide of SEQ ID NO: 22, the peptide of SEQ ID NO: 110 is a K to R variant of a peptide of SEQ ID NO: 23, the peptide of SEQ ID NO: 114 is a K to R variant of a peptide of SEQ ID NO: 27, and the peptide of SEQ ID NO: 200 is a K to R variant of a peptide of SEQ ID NO: 86. These data show that K to R variants of cartilage homing peptides retain their cartilage homing properties. Radiolabeled peptide signals of SEQ ID NO: 109, SEQ ID NO: 110, SEQ ID NO: 114, and SEQ ID NO: 200 exhibited accumulation in the IVD and joint cartilage at 3 hours after radiolabeled peptide administration. Radiolabeled peptide signals from SEQ ID NO: 109 and SEQ ID NO: 200 were maintained or increased in IVD and joint cartilage between 3 and 24 hours. Radiolabeled peptide signal from SEQ ID NO: 110 decreased in joint and IVD cartilage between 3 and 24 hours. Radiolabeled peptide of SEQ ID NO: 114 exhibited reduced residence time with a signal near the limit of detection by 24 hours. SEQ ID NO: 110 was also present in the joint and IVD cartilage at 24 hours. SEQ ID NO: 109 exhibited the highest signal in cartilage, followed by SEQ ID NO: 200, SEQ ID NO: 110, and then SEQ ID NO: 114. The signal as a percentage of blood of a peptide of SEQ ID NO: 111 in the synovial joint (TABLE 5) at 3 hours and 24 hours ranked in intensity between peptides of SEQ ID NO: 200 and SEQ ID NO: 110 (TABLE 6). The signal as a percentage of blood of a peptide of SEQ ID NO: 111 in IVD (TABLE 5) at 3 hours and 24 hours was higher than any of the peptides of SEQ ID NO: 109, SEQ ID NO: 110, SEQ ID NO: 114, and SEQ ID NO: 200 (TABLE 7).

FIG. 38 illustrates a white light image and a corresponding autoradiography image of frozen sections from a mouse with ligated kidneys, 3 hours after administration of 100 nmol of a radiolabeled peptide of SEQ ID NO: 195 (GSNFKVEGACSKPCRKYCIDKGARNGKCIN-GRCHCYY). FIG. 38A illustrates a white light image of a frozen section of a mouse with ligated kidneys, 3 hours after administration of 100 nmol of a radiolabeled peptide of SEQ ID NO: 195. FIG. 38B illustrates the $^{14}$C signal in a frozen section of a mouse with ligated kidneys, corresponding to the section shown in FIG. 38A, 3 hours after administration of 100 nmol of a radiolabeled peptide of SEQ ID NO: 195. The $^{14}$C signal identifies the radiolabeled peptide distribution in the cartilage of the mouse. FIG. 38C illustrates a white light image of a different frozen section of the mouse with ligated kidneys, 3 hours after administration of 100 nmol of a radiolabeled peptide of SEQ ID NO: 195. FIG. 38D illustrates the $^{14}$C signal in a frozen section of the mouse with ligated kidneys, corresponding to the section shown in FIG. 38C, 3 hours after administration of 100 nmol of a radiolabeled peptide of SEQ ID NO: 195. The $^{14}$C signal identifies the radiolabeled peptide distribution in the cartilage of the mouse.

FIG. 39 illustrates a white light image and a corresponding autoradiography image of frozen sections from a mouse with ligated kidneys, 3 hours after administration of 100 nmol a radiolabeled peptide of SEQ ID NO: 196. FIG. 39A illustrates a white light image of a frozen section of a mouse with ligated kidneys, 3 hours after administration of 100 nmol a radiolabeled peptide of SEQ ID NO: 196. FIG. 39B illustrates the $^{14}$C signal in a frozen section of the mouse with ligated kidneys, corresponding to the section shown in FIG. 39A, 3 hours after administration of 100 nmol a radiolabeled peptide of SEQ ID NO: 196. The $^{14}$C signal identifies the radiolabeled peptide distribution in the cartilage of the mouse. FIG. 39C illustrates a white light image of a different frozen section of a mouse with ligated kidneys, 3 hours after administration of 100 nmol a radiolabeled peptide of SEQ ID NO: 196. FIG. 39D illustrates the $^{14}$C signal in a frozen section of the mouse with ligated kidneys, corresponding to the section shown in FIG. 39C, 3 hours after administration of 100 nmol a radiolabeled peptide of SEQ ID NO: 196. The $^{14}$C signal identifies the radiolabeled peptide distribution in the cartilage of the mouse.

FIG. 40 illustrates a white light image and a corresponding autoradiography image of frozen sections from a mouse with ligated kidneys, 3 hours after administration of 100 nmol a radiolabeled peptide of SEQ ID NO: 197 (GSDRDSCIDKSRCSKYGYYQECQDCCKK-AGHNGGTCMFFKCKCA). FIG. 40A illustrates a white light image of a frozen section of a mouse with ligated kidneys, 3 hours after administration of 100 nmol a radiolabeled peptide of SEQ ID NO: 197. FIG. 40B illustrates the $^{14}$C signal in a frozen section of a mouse with ligated kidneys, corresponding to the section shown in FIG. 40A, 3 hours after administration of 100 nmol a radiolabeled peptide of SEQ ID NO: 197. The $^{14}$C signal identifies the radiolabeled peptide distribution in the cartilage of the mouse. FIG. 40C illustrates a white light image of a different frozen section of the mouse with ligated kidneys, 3 hours after administration of 100 nmol a radiolabeled peptide of SEQ ID NO: 197. FIG. 40D illustrates the $^{14}$C signal in a frozen section of a mouse with ligated kidneys, corresponding to the section shown in FIG. 40C, 3 hours after administration of 100 nmol a radiolabeled peptide of SEQ ID NO: 197. The $^{14}$C signal identifies the radiolabeled peptide distribution in the cartilage of the mouse.

FIG. 41 illustrates a white light image and a corresponding autoradiography image of frozen sections from a mouse with ligated kidneys, 3 hours after administration of 100 nmol a radiolabeled peptide of SEQ ID NO: 198. FIG. 41A illustrates a white light image of a frozen section of a mouse with ligated kidneys, 3 hours after administration of 100 nmol a radiolabeled peptide of SEQ ID NO: 198. FIG. 41B illustrates the $^{14}$C signal in a frozen section of the mouse with ligated kidneys, corresponding to the section shown in FIG. 41A, 3 hours after administration of 100 nmol a radiolabeled peptide of SEQ ID NO: 198. The $^{14}$C signal identifies the radiolabeled peptide distribution in the cartilage of the mouse. FIG. 41C illustrates a white light image of a different frozen section of a mouse with ligated kidneys, 3 hours after administration of 100 nmol a radiolabeled peptide of SEQ ID NO: 198. FIG. 41D illustrates the $^{14}$C signal in a frozen section of a mouse with ligated kidneys, corresponding to the section shown in FIG. 41C, 3 hours after administration of 100 nmol a radiolabeled peptide of SEQ ID NO: 198. The $^{14}$C signal identifies the radiolabeled peptide distribution in the cartilage of the mouse.

SEQ ID NO: 434 is a linearized version of SEQ ID NO: 111, where the knotted scaffold of the peptide has been removed by mutating out the cysteine residues that form the disulfide bonds of the peptide to serine residues, but retaining the rest of the sequence. FIG. 42 illustrates a white light image and a corresponding autoradiography image of frozen sections from a mouse with ligated kidneys, 3 hours after administration of 100 nmol a radiolabeled linearized peptide of SEQ ID NO: 434. FIG. 42A illustrates a white light image of a frozen section of a mouse with ligated kidneys, 3 hours after administration of 100 nmol a radiolabeled linearized peptide of SEQ ID NO: 434. FIG. 42B illustrates the $^{14}$C signal in a frozen section of the mouse with ligated kidneys, corresponding to the section shown in FIG. 42A, 24 hours after administration of 100 nmol a radiolabeled linearized peptide of SEQ ID NO: 434. The $^{14}$C signal identifies the radiolabeled peptide distribution in the cartilage of the mouse. FIG. 42C illustrates a white light image of a different frozen section of the mouse with ligated kidneys, 3 hours after administration of 100 nmol a radiolabeled linearized peptide of SEQ ID NO: 434. FIG. 42D illustrates the $^{14}$C signal in a frozen section of the mouse with ligated kidneys, corresponding to the section shown in FIG. 42C, 3 hours after administration of 100 nmol a radiolabeled linearized peptide of SEQ ID NO: 434. The $^{14}$C signal identifies the radiolabeled peptide distribution in the cartilage of the mouse. FIG. 42E illustrates a white light image of a different frozen section of a mouse with ligated kidneys, 3 hours after administration of 100 nmol a radiolabeled linearized peptide of SEQ ID NO: 434. FIG. 42F illustrates the $^{14}$C signal in a frozen section of the mouse with ligated kidneys, corresponding to the section shown in FIG. 42E, 3 hours after administration of 100 nmol a radiolabeled linearized peptide of SEQ ID NO: 434. The $^{14}$C signal identifies the radiolabeled peptide distribution in the cartilage of the mouse. FIG. 42G illustrates a white light image of a different frozen section of the mouse with ligated kidneys, 3 hours after administration of 100 nmol a radiolabeled linearized peptide of SEQ ID NO: 434. FIG. 42H illustrates the $^{14}$C signal in a frozen section of the mouse with ligated kidneys, corresponding to the section shown in FIG. 42G, 3 hours after administration of 100 nmol a radiolabeled linearized peptide of SEQ ID NO: 434. The $^{14}$C signal identifies the radiolabeled peptide distribution in the cartilage of the mouse.

FIG. 43 illustrates a white light image and a corresponding autoradiography image of frozen sections from a mouse, 3 hours after administration of 100 nmol a radiolabeled linearized peptide of SEQ ID NO: 434. FIG. 43A illustrates a white light image of a frozen section of a mouse, 3 hours after administration of 100 nmol a radiolabeled linearized peptide of SEQ ID NO: 434. FIG. 43B illustrates the $^{14}$C signal in a frozen section of the mouse, corresponding to the section shown in FIG. 43A, 3 hours after administration of 100 nmol a radiolabeled linearized peptide of SEQ ID NO: 434. The $^{14}$C signal identifies the radiolabeled peptide distribution in the cartilage of the mouse. FIG. 43C illustrates a white light image of a different frozen section of a mouse, 3 hours after administration of 100 nmol a radiolabeled linearized peptide of SEQ ID NO: 434. FIG. 43D illustrates the $^{14}$C signal in a frozen section of the mouse, corresponding to the section shown in FIG. 43C, 3 hours after administration of 100 nmol a radiolabeled linearized peptide of SEQ ID NO: 434. The $^{14}$C signal identifies the radiolabeled peptide distribution in the cartilage of the mouse. FIG. 43E illustrates a white light image of a different frozen section of the mouse, 3 hours after administration of 100 nmol a radiolabeled linearized peptide of SEQ ID NO: 434. FIG. 43F illustrates the $^{14}$C signal in a frozen section of the mouse, corresponding to the section shown in FIG. 43E, 3 hours after administration of 100 nmol a radiolabeled linearized peptide of SEQ ID NO: 434. The $^{14}$C signal identifies the radiolabeled peptide distribution in the cartilage of the mouse. FIG. 43G illustrates a white light image of a different frozen section of a mouse, 3 hours after administration of 100 nmol a radiolabeled linearized peptide of SEQ ID NO: 434. FIG. 43H illustrates the $^{14}$C signal in a frozen section of a mouse, corresponding to the section shown in FIG. 43G, 3 hours after administration of 100 nmol a radiolabeled linearized peptide of SEQ ID NO: 434. The $^{14}$C signal identifies the radiolabeled peptide distribution in the cartilage of the mouse.

FIG. 44 illustrates a white light image and a corresponding autoradiography image of frozen sections from a mouse, 24 hours after administration of 100 nmol a radiolabeled linearized peptide of SEQ ID NO: 434. FIG. 44A illustrates a white light image of a frozen section of a mouse, 24 hours after administration of 100 nmol a radiolabeled linearized peptide of SEQ ID NO: 434. FIG. 44B illustrates the $^{14}$C signal in a frozen section of the mouse, corresponding to the section shown in FIG. 44A, 24 hours after administration of 100 nmol a radiolabeled linearized peptide of SEQ ID NO: 434. The $^{14}$C signal identifies the radiolabeled peptide distribution in the cartilage of the mouse. FIG. 44C illustrates a white light image of a different frozen section of a mouse, 24 hours after administration of 100 nmol a radiolabeled linearized peptide of SEQ ID NO: 434. FIG. 44D illustrates the $^{14}$C signal in a frozen section of the mouse, corresponding to the section shown in FIG. 44C, 24 hours after administration of 100 nmol a radiolabeled linearized peptide of SEQ ID NO: 434. The $^{14}$C signal identifies the radiolabeled peptide distribution in the cartilage of the mouse. FIG. 44E illustrates an image of a different frozen section of the mouse, 24 hours after administration of 100 nmol a radiolabeled linearized peptide of SEQ ID NO: 434. FIG. 44F illustrates the $^{14}$C signal in a frozen section of the mouse, corresponding to the section shown in FIG. 44E, 24 hours after administration of 100 nmol a radiolabeled linearized peptide of SEQ ID NO: 434. The $^{14}$C signal identifies the radiolabeled peptide distribution in the cartilage of the mouse. FIG. 44G illustrates a white light image of a different frozen section of a mouse, 24 hours after administration of 100 nmol a radiolabeled linearized peptide of SEQ ID NO: 434. FIG. 44H illustrates the $^{14}$C signal in a frozen section of the mouse, corresponding to the section shown in FIG. 44G, 24 hours after administration of 100 nmol a radiolabeled linearized peptide of SEQ ID NO: 434. The $^{14}$C signal identifies the radiolabeled peptide distribution in the cartilage of the mouse.

TABLE 8 shows quantification of signal as a percentage of signal in blood from a linearized radiolabeled SEQ ID NO: 434 peptide in intervertebral discs (IVD).

TABLE 8

|  | 3 hr Ligated Kidneys | 3 hr Intact Kidneys | 24 hr Intact Kidneys |
|---|---|---|---|
| IVD | 117 | 177 | 104 |

The peptide of SEQ ID NO: 434, a linearized version of the peptide of SEQ ID NO: 111, homed to cartilage to a much lesser extent than the folded knotted peptide (SEQ ID NO: 111). The signal of the folded knotted peptide of SEQ ID NO: 111 was ~20-fold greater at 3 hours and –50-fold greater at 24 hours (TABLE 5) as compared to the linearized peptide of SEQ ID NO: 434 (TABLE 8). These results indicate that in addition to changes in primary sequence or peptide charge, homing to cartilage can also be related to changes in conformation, or tertiary structure. Namely, in some cases, folded knottin peptides can be exemplary cartilage homers in comparison to unfolded, linearized peptides of the same primary sequence (except for the mutated cysteine residues).

Example 22

Budesonide Peptide Conjugates

This example describes conjugation of a peptide of this disclosure to budesonide. Budesonide is readily conjugated to any peptide disclosed herein via a dicarboxylic acid linker. The dicarboxylic acid linker is a linear dicarboxylic acid, such as succinic acid, or a related cyclic anhydride, such as succinic anhydride. Reactions with anhydrides can proceed under simple conditions. For example, the reaction of budesonide with five molar equivalents of glutaric anhydride is carried out in anhydrous pyridine at room temperature. Reactions with dicarboxylic acids can occur using standard carbodiimide coupling methods. For example, budesonide is reacted with one molar equivalent dimethylsuccinic acid, one molar equivalent 1-ethyl-3-(3-dimethylaminopropyl)carbodiimide (or another carbodiimide), and 0.2 molar equivalents of 40-dimethylamino pyridine.

The same methods as described in EXAMPLE 16 are used to adjust the rate of hydrolysis of peptide-budesonide conjugates, preventing premature cleavage and ensuring that the majority of peptide-budesonide conjugates accumulate in cartilage.

Peptide-budesonide conjugates are prepared by coupling budesonide to the peptides of this disclosure using standard coupling-reagent chemistry. The protocol for making the NHS succinic ester of budesonide is similar to that of dexamethasone, as described in EXAMPLE 15. The N-hydroxysuccinimide ester of the peptide-budesonide conjugate is generated to form a shelf-stable intermediate for later reaction with an amine-containing carrier.

The knottin peptide can be any peptide with the sequence selected from SEQ ID NO: 21-SEQ ID NO: 194, SEQ ID NO: 196, SEQ ID NO: 198-SEQ ID NO: 216 SEQ ID NO: 237-SEQ ID NO: 410, SEQ ID NO: 412, or SEQ ID NO: 414-SEQ ID NO: 432.

Example 23

Peptide Charge and Cartilage Homing

This example describes the charge of peptides of this disclosure and how it correlates to cartilage homing. TABLE 9 shows the number of lysines, and pI as calculated by various methods including Expasy pI and MYpI in peptides of this disclosure. The pI refers to the isoelectric point and is the pH at which the net charge of the peptide is zero.

TABLE 9

| SEQ ID NO | # Lysines | Expasy pI | Sillero pI |
|---|---|---|---|
| 483 | 2 | 7.78 | 7.756 |
| 433 | 3 | 8.66 | 8.385 |
| 28 | 5 | 8.9 | 8.59 |
| 22 | 6 | 9.5 | 9.689 |
| 24 | 5 | 9.34 | 9.23 |
| 23 | 6 | 9.3 | 9.22 |
| 32 | 3 | 8.34 | 8.121 |
| 485 | 2 | 8.52 | 8.206 |
| 33 | 3 | 8.87 | 8.603 |
| 27 | 3 | 9.15 | 8.885 |

Figure 45:
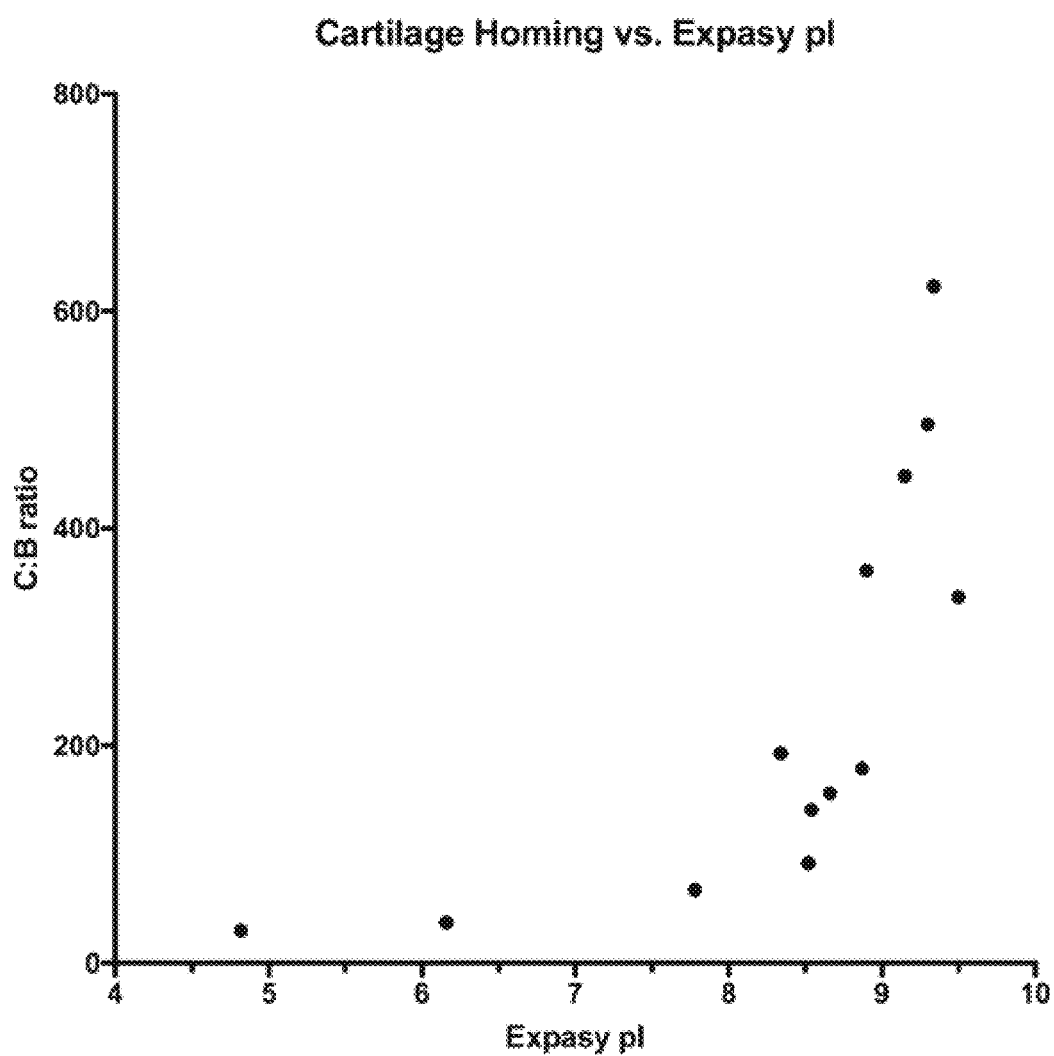
FIG. 45 illustrates the cartilage homing of various peptides of this disclosure plotted against the calculated Expasy pI.
Figure 46:
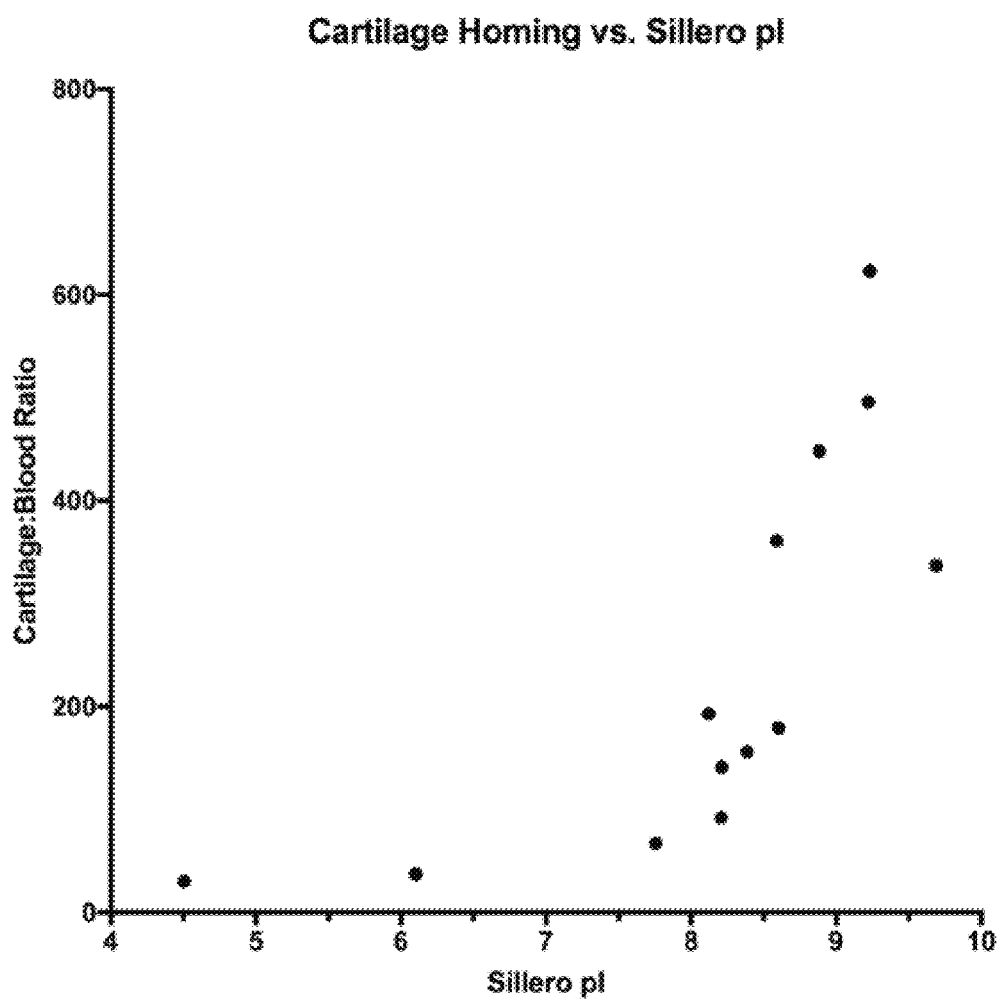
FIG. 46 shows cartilage homing of various peptides of this disclosure plotted against the calculated Sillero pI using R implementation.

FIG. 45 shows cartilage homing of various peptides of this disclosure plotted against the calculated Expasy pI (calculated as described in Bjellqvist et al. Electrophoresis. 14(10):1023-31 (1993) and Bjellqvist et al. Electrophoresis. 15(3-4):529-39 (1994)). The y-axis C:B ratio indicates the cartilage to blood ratio. FIG. 46 shows cartilage homing of various peptides of this disclosure plotted against the calculated Sillero pI using R implementation (calculated as described in Sillero et al. Comput Biol Med. 36(2): 157-66 (2006) and Rice et al. Trends Genet. 16(6): 276-7 (2000)). These figures show that a peptide with a pI in the range of ~8.5-9.5 by the Expasy or Sillero method can be desirable for cartilage homing.

A structure-based 3D modeling approach using a Poisson-Boltzmann distribution was also taken to identify the pI of various peptides of this disclosure. This approach identified the charge at biological pH (pH 7) and the overall pI, as summarized in TABLE 10, of peptides in their unfolded and folded state. The 3D structures of verified cartilage homers were determined by x-ray crystallography or modeled using various homolog-based approaches. The structures were analyzed using the PDB2PQR package (1) and the Adaptive Posisson-Boltzmann Solver software package (2). These structures are shown in FIG. 48, where they are rendered as electrostatic surfaces (also see, Dolinsky et al. Nucleic Acids Res July; 35(Web Server issue): W522-45 (2007) and Baker et al. Proc. Natl Acad Sci USA. 98(18): 10037-41 (2001)).

TABLE 10

| SEQ ID NO | Unfolded Peptide charge at pH 7 | Folded Peptide charge at pH 7 | Unfolded Peptide Overall pI | Folded Peptide Overall pI |
|---|---|---|---|---|
| 28 | 4.91 | 4.90 | 10.49 | 10.49 |
| 111 | 5.15 | 4.88 | 12.38 | 12.30 |
| 23 | 6.15 | 6.13 | 11.16 | 11.05 |
| 27 | 4.91 | 4.85 | 11.53 | 11.50 |

Example 24

Structure and Electrostatics of Cartilage Homing Peptides

Figure 47:
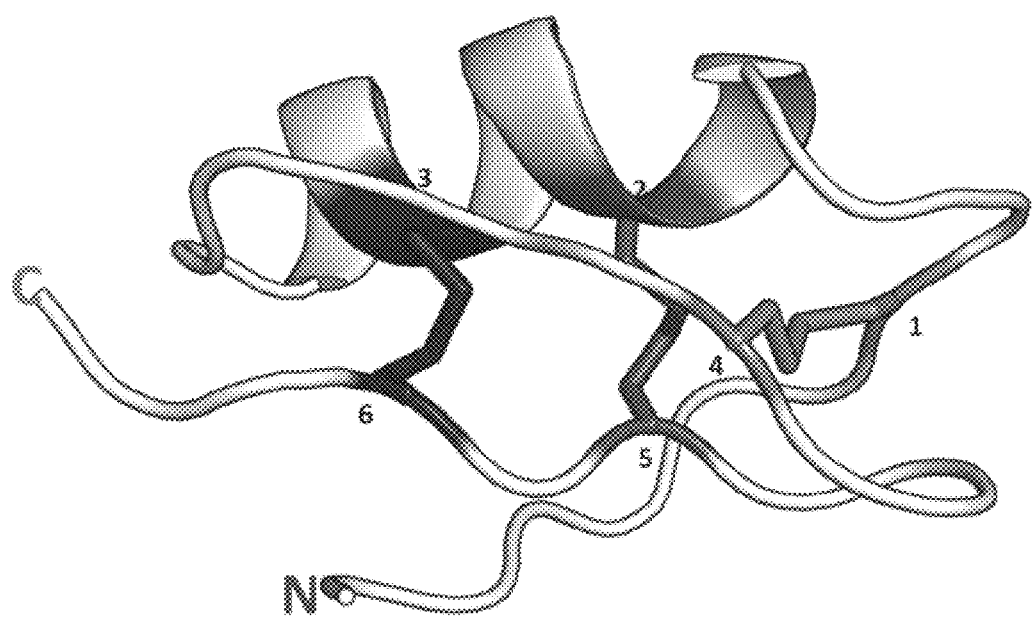
FIG. 47 depicts the topology of the "hitchins" class of cartilage homing peptides, with disulfide connectivity labeled as C1-C4, C2-C5, and C3-C6.

This example describes structural features and electrostatics of the cartilage homing peptides of this disclosure. Analysis of the primary sequences and predicted tertiary structure of multiple cartilage homing candidates (for example, SEQ ID NO: 23, SEQ ID NO: 24, SEQ ID NO: 27, and SEQ ID NO: 28) revealed interesting aspects of their structures that may be important for preserving biological function. Several cartilage homing candidates were grouped into a structural class identified herein as "hitchins." FIG. 47 depicts the topology of the "hitchins" class of cartilage homing peptides, with disulfide connectivity labeled as C1-C4, C2-O5, and C3-C6. Peptides of SEQ ID NO: 24, SEQ ID NO: 23, SEQ ID NO: 27, and SEQ ID NO: 28 are examples of the "hitchins" class of cartilage homing peptides. This information allowed for potential identification or prediction of cartilage homing proteins based on either primary sequence identity or similarly and/or structural homology. In addition to the "hitchins" peptides that were found to home to cartilage, other peptides such as the peptide of SEQ ID NO: 22 and SEQ ID NO: 205 home to cartilage and belong to a class of small proteins known as calcins. Data suggested that members of this calcin family may also home to cartilage despite having a distinct tertiary structure. Related members of this family include peptides of SEQ ID NO: 202-SEQ ID NO: 205 and SEQ ID NO: 22 and may also home to cartilage. Members of this family may also be able to modulate intracellular targets in cartilage, such as ion channels and ryanodine receptors.

Upon further structural analysis, it was identified that many of the cartilage homing proteins have a contiguous surface of positive charge that accounts for most of the solvent accessible surface area as shown in FIG. 48. Positions of the positively charged residues on the surface of the protein and their localization can be important for maintaining this function.

Other peptides that share the "hitchins" or calcin topology, that have large contiguous areas of positive surface charge, and/or that have pI values similar to other cartilage homing peptides as shown in EXAMPLE 24, may also be predicted to home to cartilage. For example, in some cases these include peptides of SEQ ID NO: 72-SEQ ID NO: 75, SEQ ID NO: 206, SEQ ID NO: 208-SEQ ID NO: 213, SEQ ID NO: 288-SEQ ID NO: 291, SEQ ID NO: 422, or SEQ ID NO: 424-SEQ ID NO: 429.

FIG. 49 illustrates HPLC chromatograms of peptides of SEQ ID NO: 24 and SEQ ID NO: 111 in different buffer conditions. FIG. 49A illustrates the HPLC trace of a peptide of SEQ ID NO: 24 in PBS. FIG. 49B illustrates the HPLC trace of a peptide of SEQ ID NO: 24 in DTT in PBS. FIG. 49C illustrates the HPLC trace of a peptide of SEQ ID NO: 24 in 50 U trypsin and 1 mg/ml inhibitor in PBS. FIG. 49D illustrates the HPLC trace of a peptide of SEQ ID NO: 24 in 50 U trypsin, 1 mg/ml inhibitor, and DTT in PBS. FIG. 49E illustrates the HPLC trace of a peptide of SEQ ID NO: 111 in PBS. FIG. 49F illustrates the HPLC trace of a peptide of SEQ ID NO: 111 in DTT in PBS. FIG. 49G illustrates the HPLC trace of a peptide of SEQ ID NO: 111 in 50 U trypsin and 1 mg/ml inhibitor in PBS. FIG. 49H illustrates the HPLC trace of a peptide of SEQ ID NO: 111 in 50 U trypsin, 1 mg/ml inhibitor, and DTT in PBS.

FIG. 71 illustrates HPLC chromatograms of two peptides after exposure to reducing agents, proteinases, and/or simulated gastric fluid conditions. FIG. 71A illustrates the HPLC trace of a peptide of SEQ ID NO: 24 incubated in PBS. FIG. 71B illustrates the HPLC trace of a peptide of SEQ ID NO: 24 incubated in DTT in PBS. FIG. 71C illustrates the HPLC trace of a peptide of SEQ ID NO: 24 incubated in simulated gastric fluid (SGF). FIG. 71D illustrates the HPLC trace of a peptide of SEQ ID NO: 24 incubated in 500 U pepsin in SGF. FIG. 71E illustrates the HPLC trace of a peptide of SEQ ID NO: 24 incubated in 500 U pepsin, 0.5 M Tris, and DTT in SGF. FIG. 71F illustrates the HPLC trace of a peptide of SEQ ID NO: 111 incubated in PBS. FIG. 71G illustrates the HPLC trace of a peptide of SEQ ID NO: 111 incubated in DTT in PBS. FIG. 71H illustrates the HPLC trace of a peptide of SEQ ID NO: 111 incubated in simulated gastric fluid (SGF). FIG. 71I illustrates the HPLC trace of a peptide of SEQ ID NO: 111 incubated in 500 U pepsin in SGF. FIG. 71J illustrates the HPLC trace of a peptide of SEQ ID NO: 111 incubated in 500 U pepsin, 0.5 M Tris, and DTT in SGF.

FIG. 72 illustrates HPLC chromatograms of peptides of SEQ ID NO: 111 and SEQ ID NO: 434 after exposure to a range of conditions including oxidative, reductive, and acidic conditions as well as after exposure to proteinases. The peptide of SEQ ID NO: 434 is a linearized version of the knottin peptide of SEQ ID NO: 111. The peptide of SEQ ID NO: 434 has the same amino acid sequence as the knottin peptide of SEQ ID NO: 111, but with all cysteines mutated to serines. FIG. 72A illustrates the HPLC trace of a peptide of SEQ ID NO: 111 under reducing and acidic conditions. FIG. 72B illustrates the HPLC trace of a peptide of SEQ ID NO: 111 under various combinations of reducing agents and proteases including 10 mM DTT in 500 U pepsin, 500 U pepsin, 10 mM DTT in 50 U trypsin, and 50 U trypsin. FIGS. 72A-B show that the peptide of SEQ ID NO: 111 is highly resistant to degradation at pH 1, reducing agents, trypsin, and pepsin. FIG. 72C illustrates the HPLC trace of a peptide of SEQ ID NO: 434 under various protease conditions including in 500 U pepsin, in 50 U trypsin, non-reducing (NR, oxidized conditions) in simulated gastric fluid (SGF) at pH 1.05, and NR. FIG. 72C shows that the linearized peptide is more susceptible to degradation at these different conditions. These data indicate that the knottin structure provided by the cysteine residues in the peptide of SEQ ID NO: 112 is an important factor in providing stability.

The structure of known cartilage homing peptides was also used to systematically vary key parameters and identify homologous sequences that are predicted to have cartilage homing properties using NCBI BLAST. Three criteria were modulated in NCBI BLAST to identify potential new sequences including setting the percentage of overall sequence identity, conservation of cysteines for preservation of disulfide bridges, and conservation of positively and/or negatively charged residues. Peptides of SEQ ID NO: 208-SEQ ID NO: 213 were identified as homologous to SEQ ID NO: 24 and are predicted to have cartilage homing properties.

Example 25

Peptide Localization in Chondrocytes

This example illustrates binding of peptides of this disclosure to chondrocytes within cartilage in animals with intact kidneys. In one embodiment, animals are dosed and are processed as described in EXAMPLE 20 and EXAMPLE 21. Whole animal sagittal slices are prepared that result in thin frozen sections being available for staining and imaging. At the end of the dosing period, animals are euthanized and cartilage is removed for use in staining and imaging procedures. One or more of the following cartilage components are identified in thin frozen sections or live cartilage explants using standard staining techniques: collagen fibrils, glycosaminoglycans, or chondrocytes. A peptide of this disclosure is found to localize to chondrocytes in cartilage. Localization is visualized and confirmed by microscopy.

In another embodiment, peptides or peptide-drug conjugates of this disclosure are administered in humans and are localized in chondrocytes in cartilage.

Example 26

Peptide Localization in Cartilage Extracellular Matrix

This example illustrates localization of peptides of this disclosure in cartilage extracellular matrix. Peptides of this disclosure are bound to extracellular matrix within cartilage in animals with intact kidneys. Thin frozen sections or live cartilage explants are acquired, stained, and visualized as described in EXAMPLE 25. A peptide of the present disclosure is found to localize to the extracellular matrix in cartilage. Localization is visualized and confirmed by microscopy.

In another embodiment, peptides or peptide-drug conjugates of this disclosure are administered in humans and are localized in cartilage extracellular matrix.

Example 27

Peptide Binding to Cartilage Explants

This example illustrates a peptide or peptide conjugation of this disclosure binding to human and animal cartilage explants in culture. A peptide is selected from any one of the peptides of SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, SEQ ID NO: 414-SEQ ID NO: 432. Peptides are recombinantly expressed or chemically synthesized and are used directly, after radiolabeling, or after conjugation to a fluorophore or therapeutic compound. A peptide of peptide conjugate of this disclosure is incubated with cartilage explants derived from humans or animals. Peptides of peptide conjugate are found to bind to cartilage explants. Binding is confirmed using various methods that include but are not limited to liquid scintillation counting, confocal microscopy, immunohistochemistry, HPLC, or LC/MS.

Example 28

Peptide Homing to an Arthritic Joint

This example illustrates peptide homing to cartilage in humans or animals with arthritis. A peptide of the present disclosure is expressed recombinantly or chemically synthesized and is used directly, after radiolabeling, or after conjugation to a fluorophore or therapeutic compound. A peptide is selected from any one of the peptides of SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, SEQ ID NO: 414-SEQ ID NO: 432. The peptide or peptide conjugate is administered to a human or animal subcutaneously, intravenously, or orally, or is injected directly into a joint. The peptide or peptide conjugate homes to cartilage.

Example 29

Peptide Homing to Cartilage in Non-Human Animals

This example illustrates a peptide or peptide conjugate of this disclosure homing to cartilage in non-human animals. Non-human animals include but are not limited to guinea pigs, rabbits, dog, cats, horses, and other non-human animals. A peptide of the present disclosure is recombinantly expressed or chemically synthesized and are used directly, after radiolabeling, or after conjugation to a fluorophore or therapeutic compound. The peptide is selected from any one of the peptides of SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, SEQ ID NO: 414-SEQ ID NO: 432. The resulting peptide or peptide conjugate is administered to a non-human animal subcutaneously, intravenously, or orally, or is injected directly into a joint. Biodistribution is assessed by LC/MS, autoradiography, positron emission tomography (PET), or fluorescence imaging. A peptide or peptide conjugate is homed to cartilage in non-human animals.

Example 30

Treatment of Chondrosarcoma

This example illustrates treatment of chondrosarcoma using peptides of the present disclosure. A peptide of the present disclosure is recombinantly expressed or chemically synthesized and are used directly, after radiolabeling, or after conjugation to a fluorophore or therapeutic compound, such as paclitaxel or monomethyl auristatin E. The peptide or peptide conjugate is administered in a pharmaceutical composition to a subject as a therapeutic for chondrosarcoma. The peptide is selected from any one of the peptides of SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, SEQ ID NO: 414-SEQ ID NO: 432. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by chondrosarcoma.

Example 31

Method to Determine Improved Peptide Variants

This example shows a method for determining ways to improve peptide variants by comparing and analyzing the primary sequences and tertiary structures of scaffold peptides. FIG. 50A-50C show sequences of SEQ ID NO: 486 aligned with SEQ ID NO: 239, SEQ ID NO: 486 aligned with SEQ ID NO: 487, and SEQ ID NO: 486 aligned with SEQ ID NO: 422. The sequence alignment of the two scaffolds was used to identify conserved positively charged residues (shown in boxes) that may be important for cartilage homing. A peptide of SEQ ID NO: 422 homes to cartilage and other peptides with positively charged residues in similar positions or cysteines in similar positions are also predicted to home to cartilage.

Many cartilage homing peptides that come from scorpions are predicted to modulate Kv ion channels. FIG. 51 shows sequences of SEQ ID NO: 243 aligned with SEQ ID NO: 423. The sequence alignment of the two scaffolds was used to identify the basic/aromatic dyad that may be involved in the interaction with the Kv ion channel (K27 and Y36 of SEQ ID NO: 423). The mutation of K27 to alanine, arginine, or glutamic acid destroyed activity against the squid Kv1A ion channel. K27 and Y36 may be desirable to maintain or add to a cartilage homing peptide of this disclosure to maintain or improve homing, to maintain or improve residence time in cartilage, or to maintain or improve modulation of an ion channel such as Kv. In contrast, K37 and &36 may be desirable to mutate out of a cartilage homing peptide to reduce interaction with an ion channel such as Kv. Disruption of either the basic or aromatic residue eliminates ion channel activity. In another example, D amino acids are expected to reduce or eliminate binding.

Example 32

Peptide-Fc Protein Fusions

This example illustrates making and using peptide-Fc protein fusions. A peptide of SEQ ID NO: 111 was recombinantly expressed with the sequence for the human IgG1 Fc protein in HEK293 cells to yield a sequence of SEQ ID NO: 435

(METDTLLLWVLLLWVPGSTGGSGVPINVRCRGSRDCLDPCRR

AGMREGRCINSRCHCTPGGSGGSDKTHTCPPCPAPELLGGPSV

FLEPPKPKDTLMISRTPEVTCVVVDVSHEDPEVKFNWYVDGVE

VHNAKTKPREEQYNSTYRVVSVLTVLHQDWLNGKEYKCKVSNK

ALPAPIEKTISKAKGQPREPQVYTLPPSRDELTKNQVSLTCLV

KGFYPSDIAVEWESNGQPENNYKTTPPVLDSDGSFFLYSKLTV

DKSRWQQGNVFSCSVMHEALHNHYTQKSLSLSPGK)

The sequence of any peptide of this disclosure is expressed as a fusion protein with either murine or human Fc by adding a secretion signal sequence to the N-terminus and an Fc sequence to the C-terminus. This creates a bivalent molecule with improved secretion properties. The larger peptide-Fc fusion is expressed in different mammalian or insect cell lines and is useful as a research reagent and a therapeutic.

Fc fusion to a peptide of SEQ ID NO: 111 to yield a sequence of SEQ ID NO: 435 extends half-life and improves biodistribution of the peptide to cartilage. Any peptide of this disclosure is co-expressed with Fc protein to yield Fc-fusion peptides with longer half-life and improved homing to cartilage. In SEQ ID NO: 435, the secretion signal sequence METDTLLLWVLLLWVPGSTG (SEQ ID NO: 485) is followed by the peptide of SEQ ID NO: 111, and is followed by the sequence for Fc protein. Cleaving can be imprecise, resulting in cleavage at position 20 or position 21 of SEQ ID NO: 435.

Example 33

Treatment of Chordoma

This example illustrates treatment of chordoma using peptides of the present disclosure. A peptide of the present disclosure is recombinantly expressed or chemically synthesized and are used directly, after radiolabeling, or after conjugation to a fluorophore or therapeutic compound, such as paclitaxel or monomethyl auristatin E. The peptide or peptide conjugate is administered in a pharmaceutical composition to a subject as a therapeutic for chordoma. The peptide is selected from any one of the peptides of SEQ ID NO: 21-SEQ ID NO: 194, SEQ ID NO: 196, SEQ ID NO: 198-SEQ ID NO: 216, SEQ ID NO: 237-SEQ ID NO: 410, SEQ ID NO: 412, SEQ ID NO: 414-SEQ ID NO: 432. One or more peptides or peptide conjugates of the present disclosure are administered to a subject. A subject can be a human or an animal. The pharmaceutical composition is administered subcutaneously, intravenously, orally, or injected directly into a joint. The peptides or peptide conjugates target cartilage affected by chordoma.

Example 34

Peptide Detectable Agent Conjugates

This example describes the dye labeling of peptides. A peptide of the disclosure is expressed recombinantly or chemically synthesized, and then the N-terminus of the peptide is conjugated to an detectable agent via an NHS ester using DCC or EDC to produce a peptide-detectable agent conjugate. The detectable agent is the fluorophore dye is a cyanine dye, such as Cy5.5 or an Alexa fluorophore, such as Alexa647.

The peptide detectable agent conjugates are administered to a subject. The subject can be a human or a non-human animal. After administration, the peptide detectable agent conjugates home to cartilage. The subject, or a biopsy from the subject, can be imaged to visualize localization of the peptide detectable agent conjugates to cartilage. In some aspects, visualization of the peptide detectable agent conjugates in cartilage after administration results in diagnosis of arthritis, cartilage damage, or any cartilage disorder.

Example 35

Peptide Conjugates with Cleavable Linkers

This example describes preparation of knottin peptide conjugates having cleavable linkers. A peptide of the disclosure is expressed recombinantly or chemically synthesized. The peptide is conjugated to a detectable agent or an active agent via a cleavable linker, such as an ester bond using standard 1-ethyl-3-(3-dimethylaminopropyl)carbodiimide (EDC) or dicylcohexylcarbodiimide (DCC) based chemistry or thionyl chloride or phosphorous chloride-based bioconjugation chemistries. The linker is cleaved by esterases, MMP, cathepsin B, a protease, or thrombin.

The resulting peptide conjugates are administered to a human or animal subcutaneously, intravenously, orally, or injected directly into a joint to treat disease. The peptide is cleaved from the detectable agent or active agent only by digestion by a cleaving agent.

Example 36

Intra-Articular Administration of Peptides and Peptide Conjugates

This example illustrates intra-articular administration of peptides or peptide conjugates of this disclosure. A peptide of this disclosure is expressed recombinantly or chemically synthesized. In some cases, the peptide is subsequently conjugated to a detectable agent or an active agent. The peptide or peptide conjugate is administered to a subject in need thereof via intra-articular administration. The cartilage is penetrated by the peptide or peptide conjugate due to the small size of the peptide or peptide conjugate, and due to binding of cartilage components by the peptide or peptide conjugate. The peptide or peptide conjugate is bound to cartilage and the residence time in the cartilage is longer due to this binding. Optionally, the injected material is aggregated, is crystallized, or complexes are formed, further extending the depot effect and contributing to longer residence time.

Example 37

Treatment for Rapid Pain Relief

This example illustrates rapid pain relief in patients treated for rheumatoid arthritis or osteoarthritis with the peptides or peptide conjugates of this disclosure. A peptide of this disclosure is expressed recombinantly or chemically synthesized, and then the N-terminus of the peptide is conjugated to an active agent via an NHS ester to produce a peptide-active agent conjugate. In some aspects the active agent is lidocaine. In some cases, the peptide alone is administered to the subject.

The peptide or peptide-active agent conjugate is administered to a subject in need thereof. The subject is a human or non-human animal. The subject in need thereof has rheumatoid arthritis or osteoarthritis. The peptide or peptide conjugate is delivered via intravenous administration. Upon administration, the peptide or peptide conjugate rapidly homes to cartilage. Rapid pain relief within five minutes to an hour is experienced by the subject, and pain relieve can last as long as over 3 hours.

Example 38

Selective Mutation of Residues to Produce Stable Peptides

This example illustrates selective mutations of residues to produce peptides with enhanced stability, such as enhanced stability during manufacturing or storage. A peptide of this disclosure is expressed recombinantly or chemically synthesized. Met residues are mutated to valine, Ala, Leu, or Ile to prevent oxidation. Asn-Pro sequences are mutated to any other residue (except cysteine) to avoid cleavage reactions. Asn-Gly or Asn-Ser, and/or Asn-Pro are replaced with any other residue (except cysteine) to reduce deamidation. Asp-Gly, Asp-Ser, or Asp-Pro are replaced with any other residue (except cysteine) to reduce cleavage reactions.

The above mutations in the primary sequence of peptides of this disclosure result in enhanced peptide stability during manufacturing, storage, and after administration to a subject in need thereof.

Example 39

Peptide Resistance to Pepsin Digestion

This example shows peptide resistance to pepsin. SEQ ID NO: 24 peptide and SEQ ID NO: 111 peptide were suspended in 500 µl of ddH$_2$O at a stock concentration of 2 mg/ml. Reactions were prepared with 12.5 µg peptide and 20 µg pepsin in simulated gastric fluid (pH 1.05) and incubated for 30 minutes at 37.5° C. Reactions were quenched with a final concentration of 100 mM Tris base and 10 mM dithiothreitol (DTT). Reversed phase HPLC (RP-HPLC) was run on samples using an Agilent 1260 HPLC equipped with a C-18 Poroshell 120B column. Sample were analyzed by a gradient method with a mobile phase of Solvent A (water with 0.1% TFA) and Solvent B (acetonitrile with 0.1% TFA). Solvent B was ramped up from 5%-45% of the mobile phase over a period of 10 minutes. Peptides were detected at an absorbance of 214 nm and 280 nm.

Figure 52:
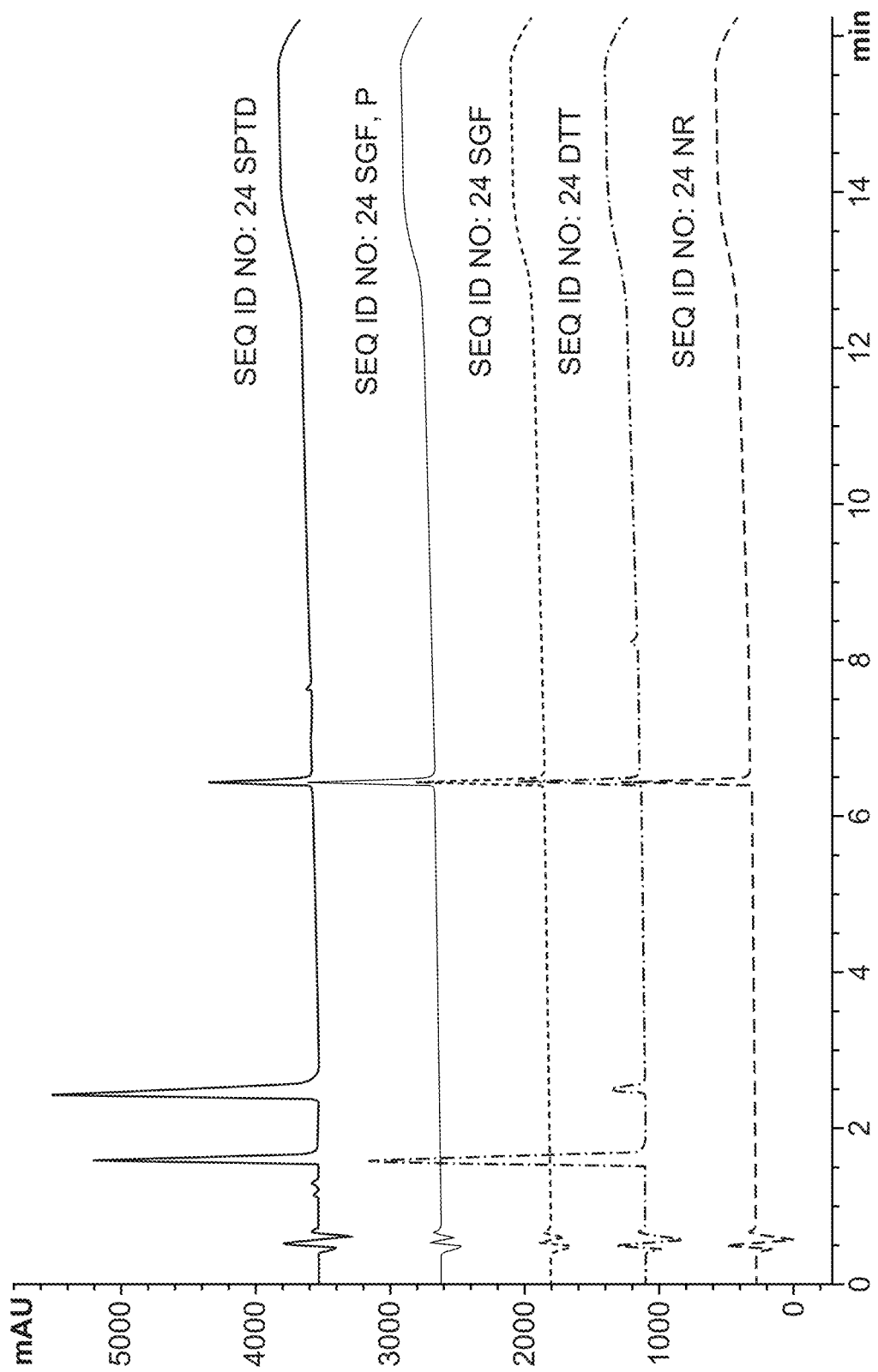
FIG. 52 shows HPLC chromatograms of 12.5 µg of a peptide of SEQ ID NO: 24 suspended in various solutions including SPTD, simulated gastric fluid (SGF) at pH 1.05 and 20 pepsin (P), SGF, Dithiothreitol (DTT), and non-reducing (NR) conditions using a Tris buffer.
Figure 53:
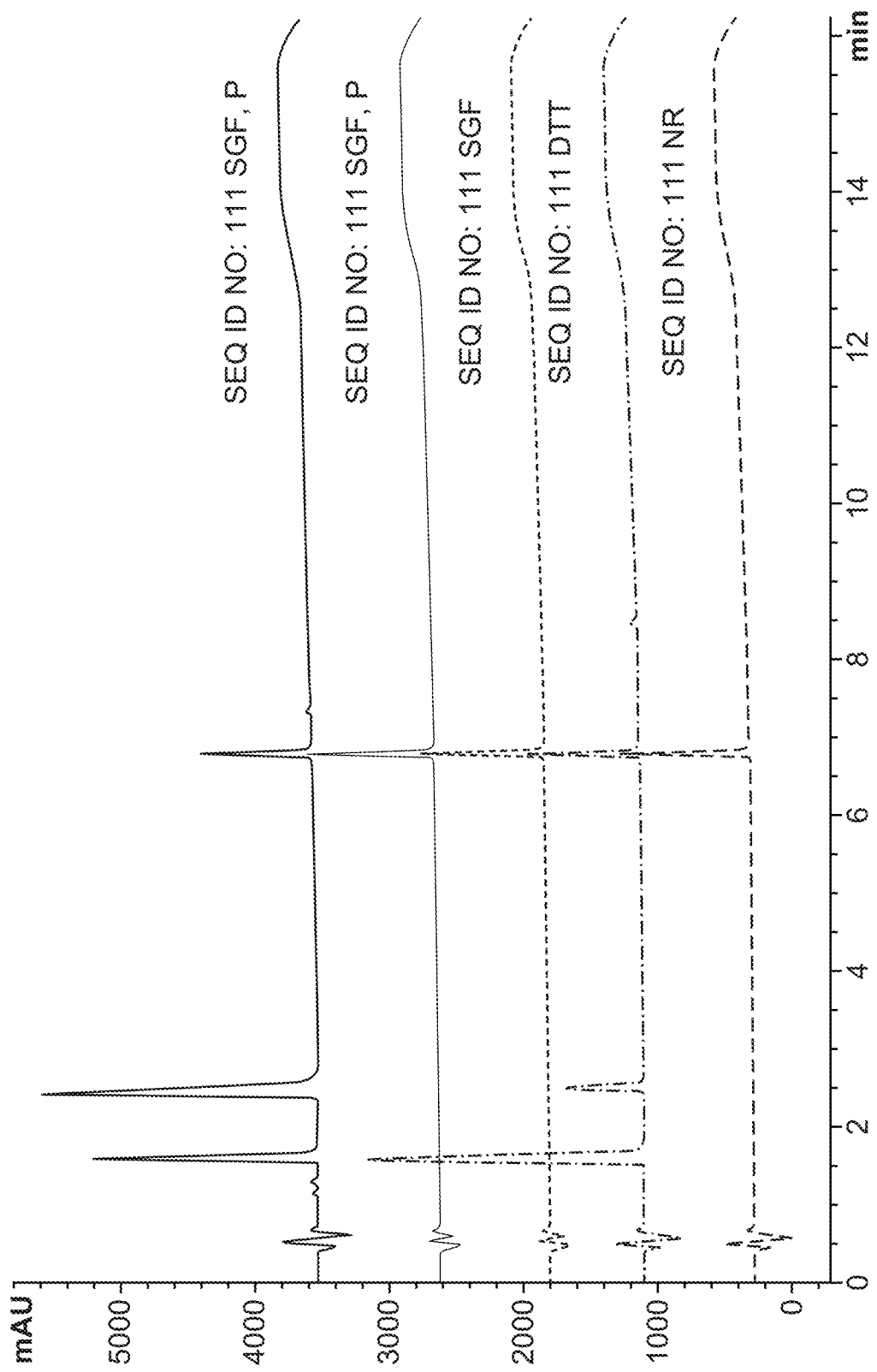
FIG. 53 shows HPLC chromatograms of 12.5 µg of a peptide of SEQ ID NO: 111 suspended in various solutions including SPTD, simulated gastric fluid (SGF) at pH 1.05 and 20 pepsin (P), SGF, Dithiothreitol (DTT), and non-reducing (NR) conditions using a Tris buffer.

FIG. 52 shows HPLC chromatograms of 12.5 µg of a peptide of SEQ ID NO: 24 suspended in various solutions including SPTD, simulated gastric fluid (SGF) at pH 1.05 and 20 pepsin (P), SGF, DTT, and non-reducing (NR) conditions. FIG. 53 shows HPLC chromatograms of 12.5 µg of a peptide of SEQ ID NO: 111 suspended in various solutions including SPTD, simulated gastric fluid (SGF) at pH 1.05 and 20 µg pepsin (P), SGF, DTT, and non-reducing (NR) conditions. FIG. 52 shows a peak eluting around 6.5 minutes, which was found to be the intact peptide of SEQ ID NO: 24, the peak eluting near 1.5 minutes was DTT, and the peak eluting near 2.5 minutes was oxidized DTT. Because an intact peptide peak was observed in the DTT solution, SGF solution, SGF and P solution, and the SPTD solution—it was determined that the peptide of SEQ ID NO: 24 was highly resistant to degradation. FIG. 53 showing a peptide of SEQ ID NO: 111 was also found to be similarly highly resistant in the various conditions tested.

Example 40

Peptide Resistance to Trypsin Digestion

This example shows peptide resistance to trypsin digestion. Various peptides were suspended in 500 µl of ddH$_2$O at a stock concentration of 2 mg/ml. Reactions were prepared with 12.5 µg peptide and 5 µg trypsin in 25 mM Tris/75 mM NaCl buffer (pH 7.0) and incubated for 30 minutes at 37.5° C. Reactions were quenched with 5 µg of soybean trypsin inhibitor and 10 mM dithiothreitol (DTT). Reversed phase HPLC (RP-HPLC) was run on samples using an Agilent 1260 HPLC equipped with a C-18 Poroshell 120B column. Sample were analyzed by a gradient method with a mobile phase of Solvent A (water with 0.1% TFA) and Solvent B (acetonitrile with 0.1% TFA). Solvent B was ramped up from 5%-45% of the mobile phase over a period of 10 minutes.

Figure 54:
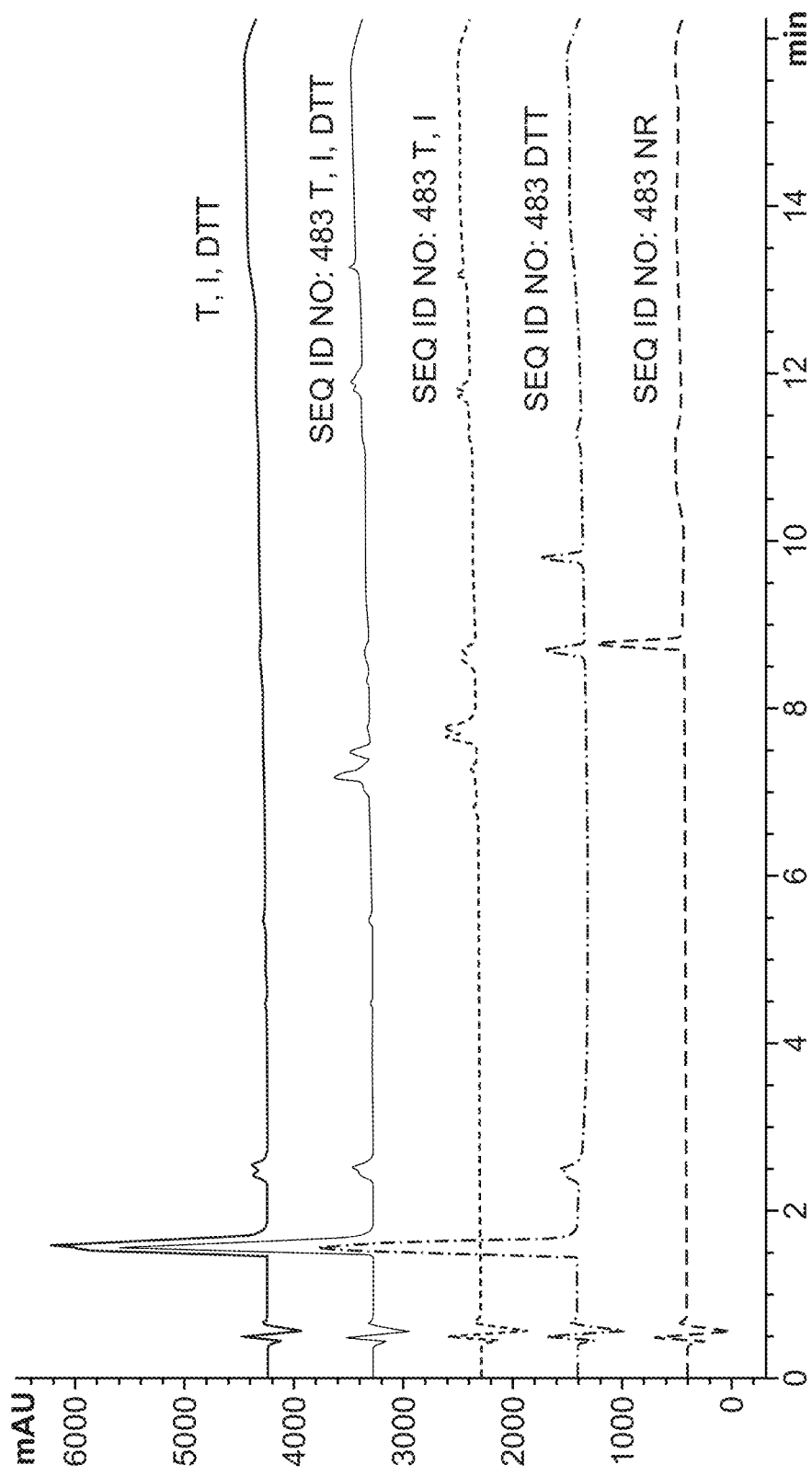
FIG. 54 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 483 (GSISIGIKCSPSIDL-CEGQCRIRKYFTGYCSGDTCHCSG) suspended in various solutions including (T, I, DTT), (T,I), DTT, and non-reducing (NR) conditions.
Figure 55:
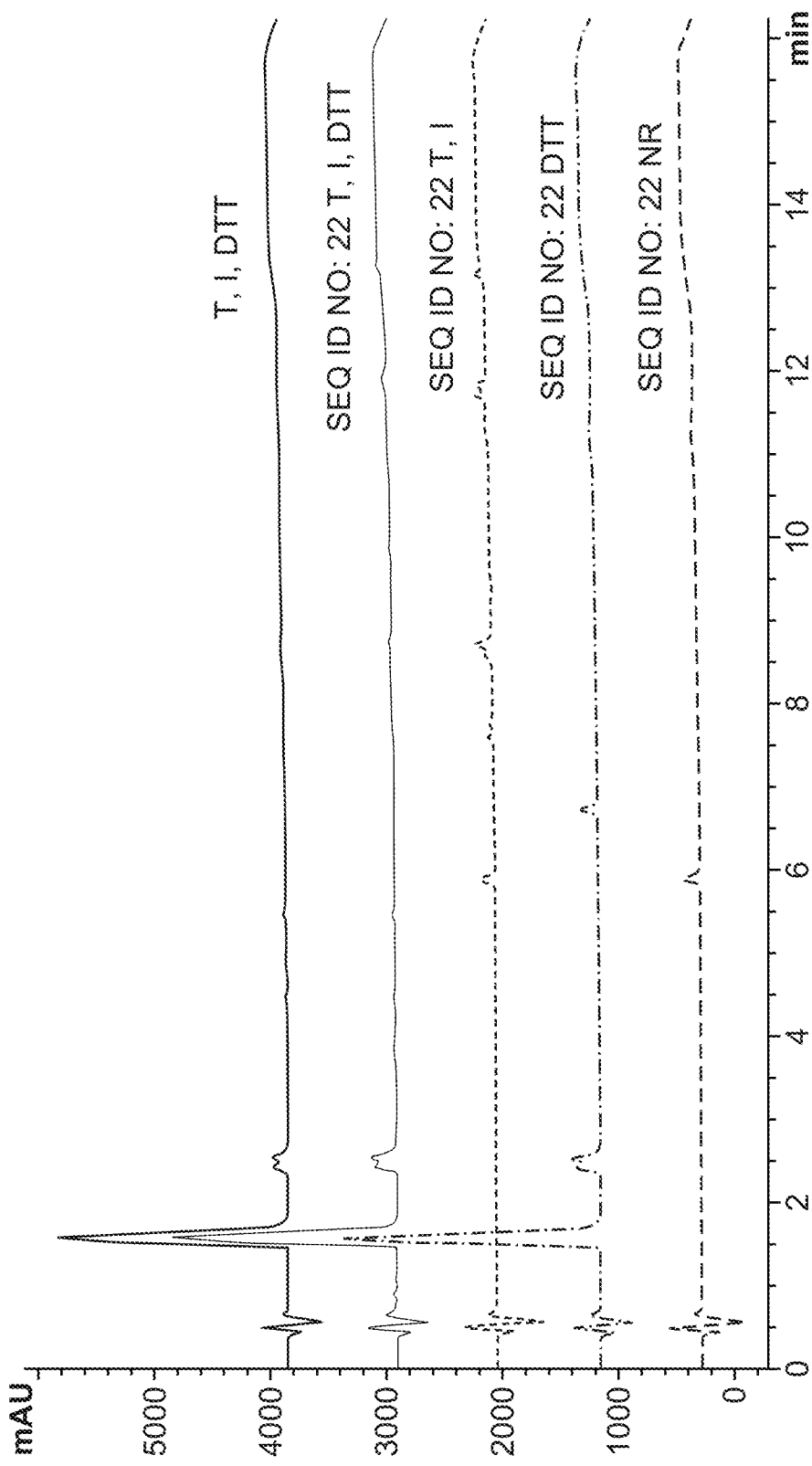
FIG. 55 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 22 suspended in various solutions including (T, I, DTT), (T,I), DTT, and non-reducing (NR) conditions.
Figure 56:
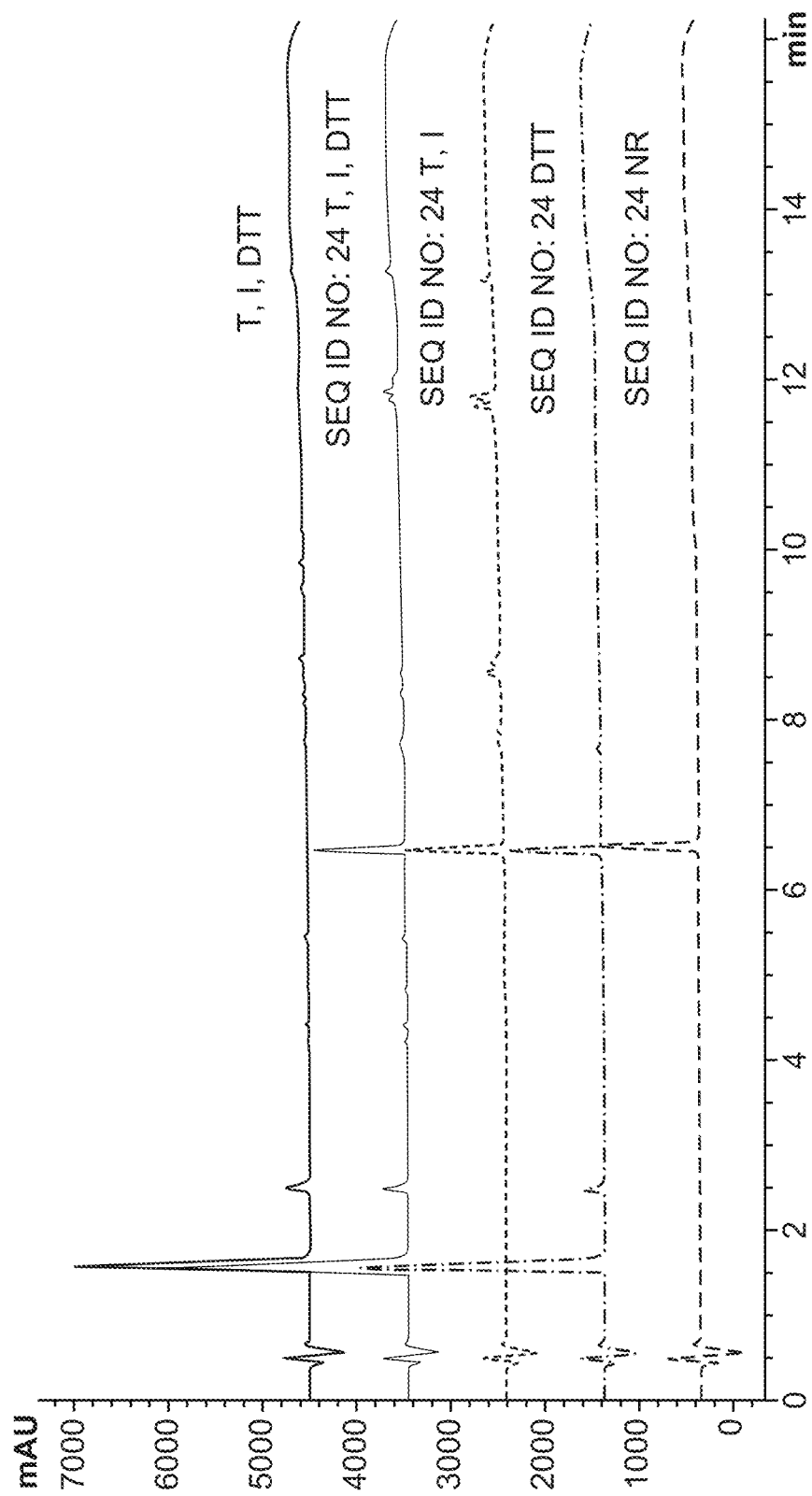
FIG. 56 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 24 suspended in various solutions including (T, I, DTT), (T,I), DTT, and non-reducing (NR) conditions.
Figure 57:
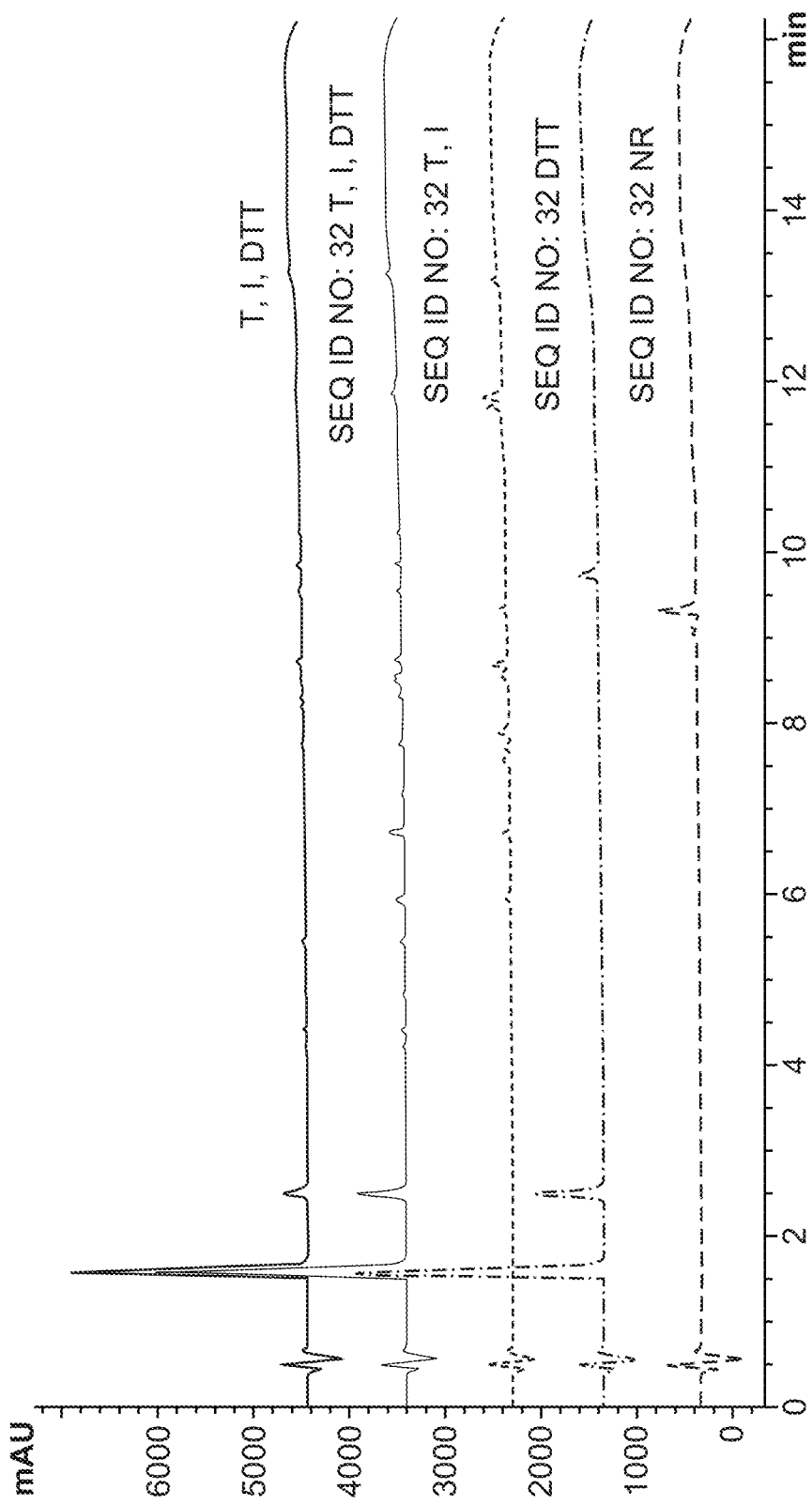
FIG. 57 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 32 suspended in various solutions including (T, I, DTT), (T,I), DTT, and non-reducing (NR) conditions.

FIG. 54 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 483 suspended in various solutions including (T, I, DTT), (T,I), DTT, and non-reducing (NR) conditions (starting peptide, no treatment with DTT, T, or I). DTT eluted near 1.5 minutes and 2.5 minutes (reduced and oxidized) and the NR trace shows that the intact peptide eluted near 8.75 minutes. The trace showing the peptide in a DTT solution shows intact peptide at 8.75 minutes and some reduced peptide near 10 minutes, showing that this peptide of SEQ ID NO: 483 is partially resistant to reduction by DTT. The trace showing the peptide with trypsin shows intact peptide and degraded peptide, again demonstrating that the peptide of SEQ ID NO: 483 was partially resistant to degradation by trypsin. FIG. 55 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 22 suspended in various solutions including (T, I, DTT), (T,I), DTT, and non-reducing (NR) conditions. FIG. 56 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 24 suspended in various solutions including (T, I, DTT), (T,I), DTT, and non-reducing (NR) conditions. FIG. 57 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 32 suspended in various solutions including (T, I, DTT), (T,I), DTT, and non-reducing (NR) conditions.

Figure 58:
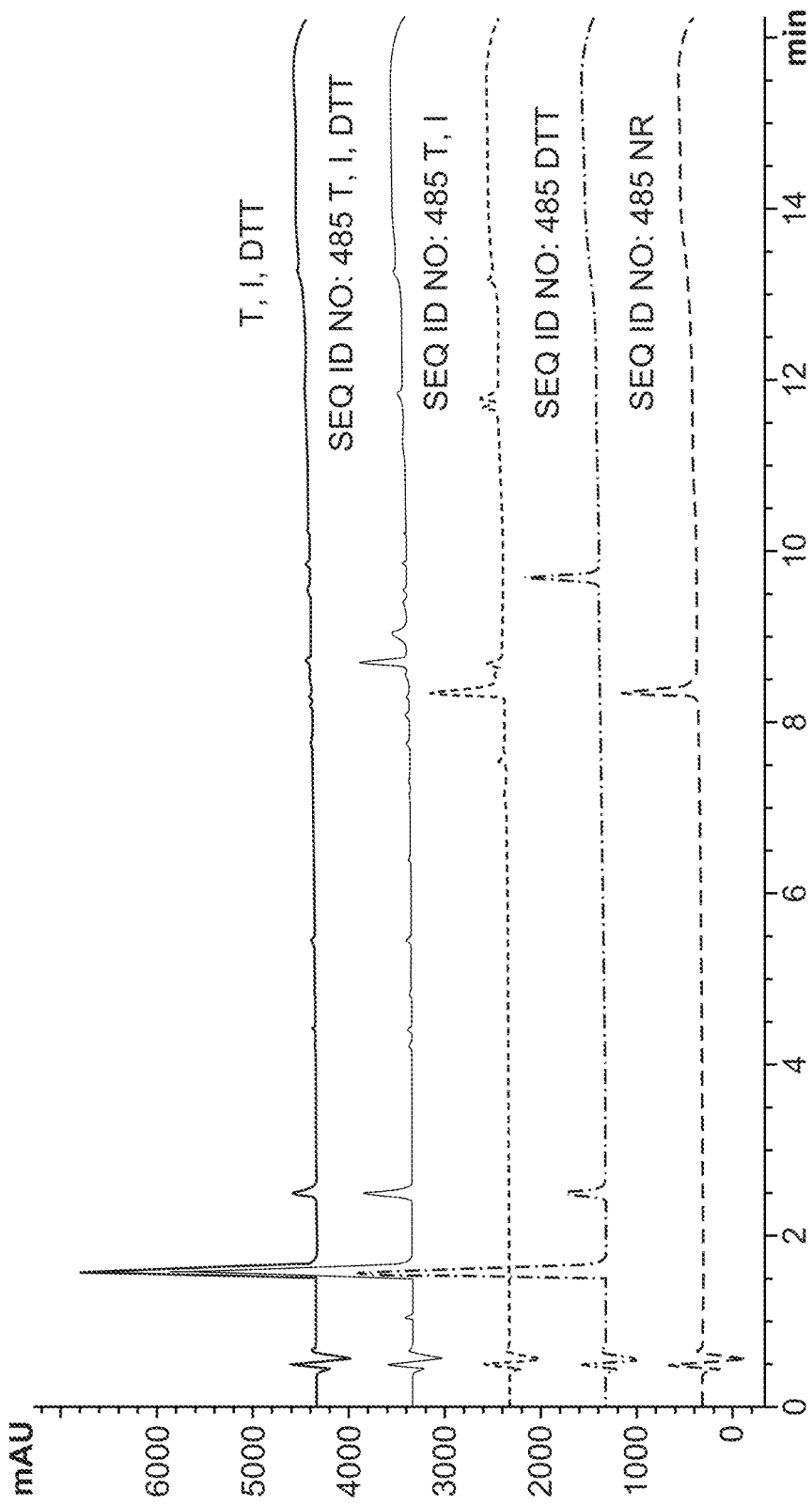
FIG. 58 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 485 (GSE-CLGFGKGCNPSNDQCCK-SSNLVCSRKHRWCKYEIGK) suspended in various solutions including (T, I, DTT), (T,I), DTT, and non-reducing (NR) conditions.
Figure 59:
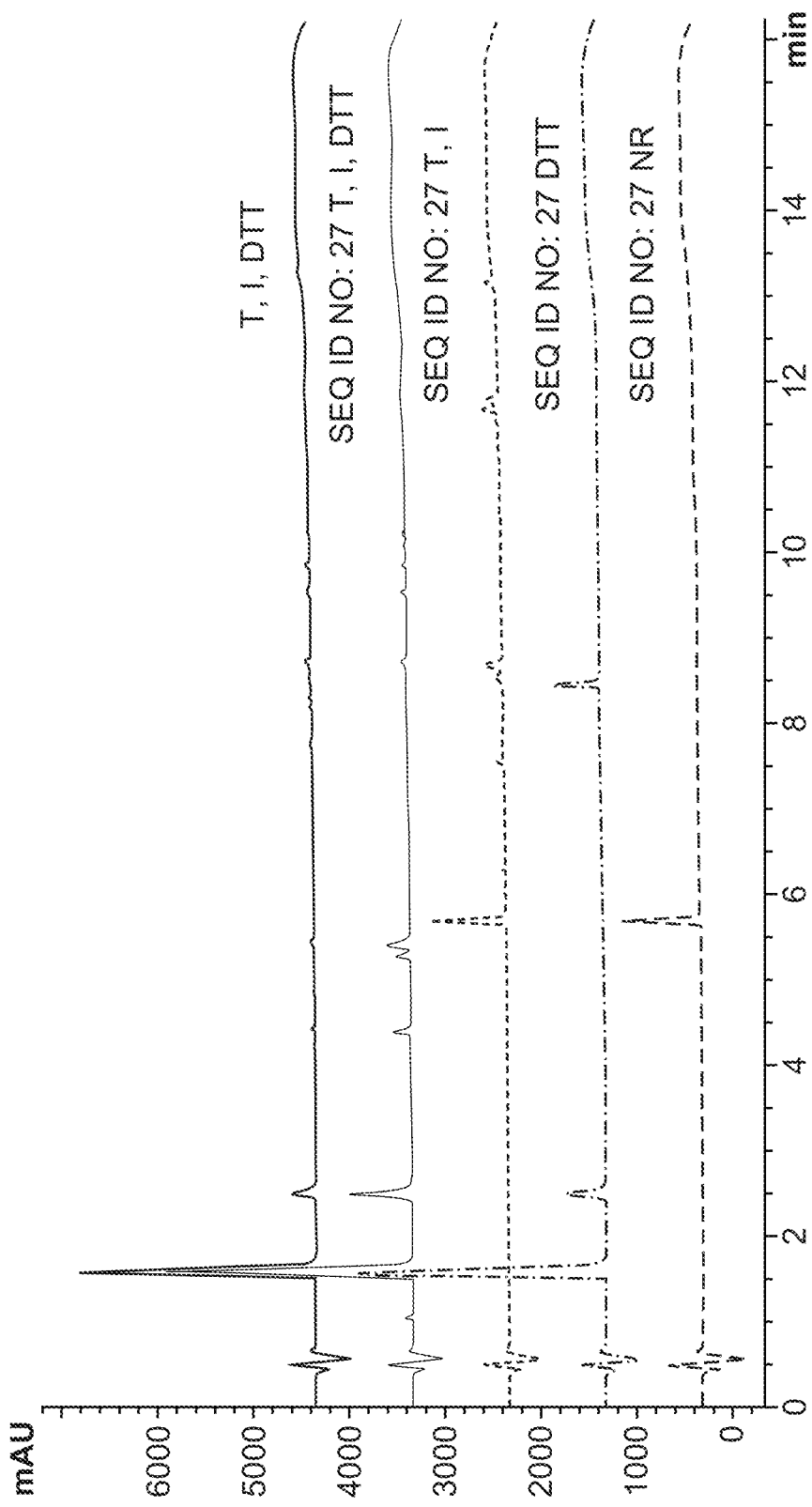
FIG. 59 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 27 suspended in various solutions including (T, I, DTT), (T,I), DTT, and non-reducing (NR) conditions.
Figure 60:
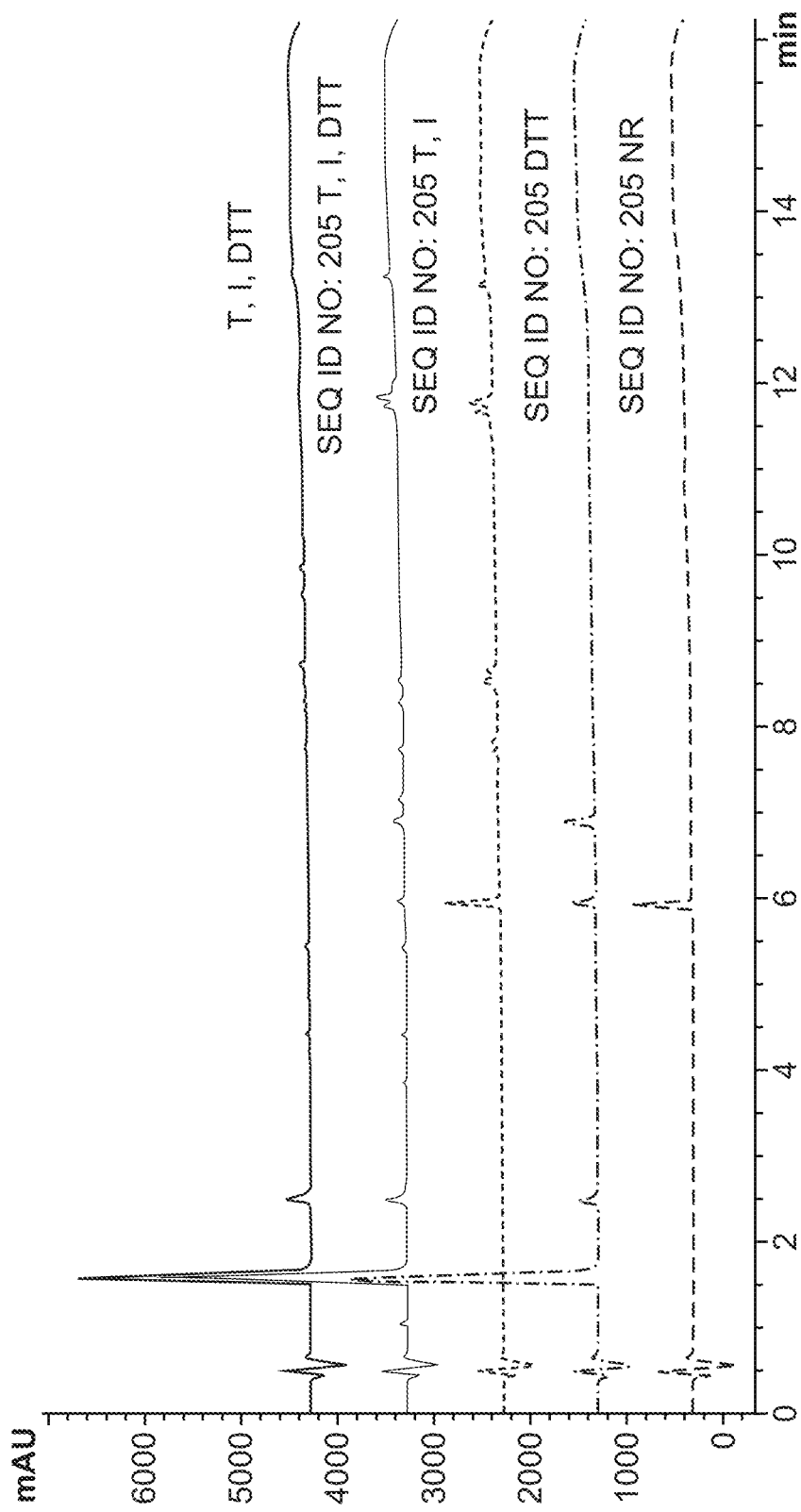
FIG. 60 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 205 suspended in various solutions including (T, I, DTT), (T,I), DTT, and non-reducing (NR) conditions.
Figure 61:
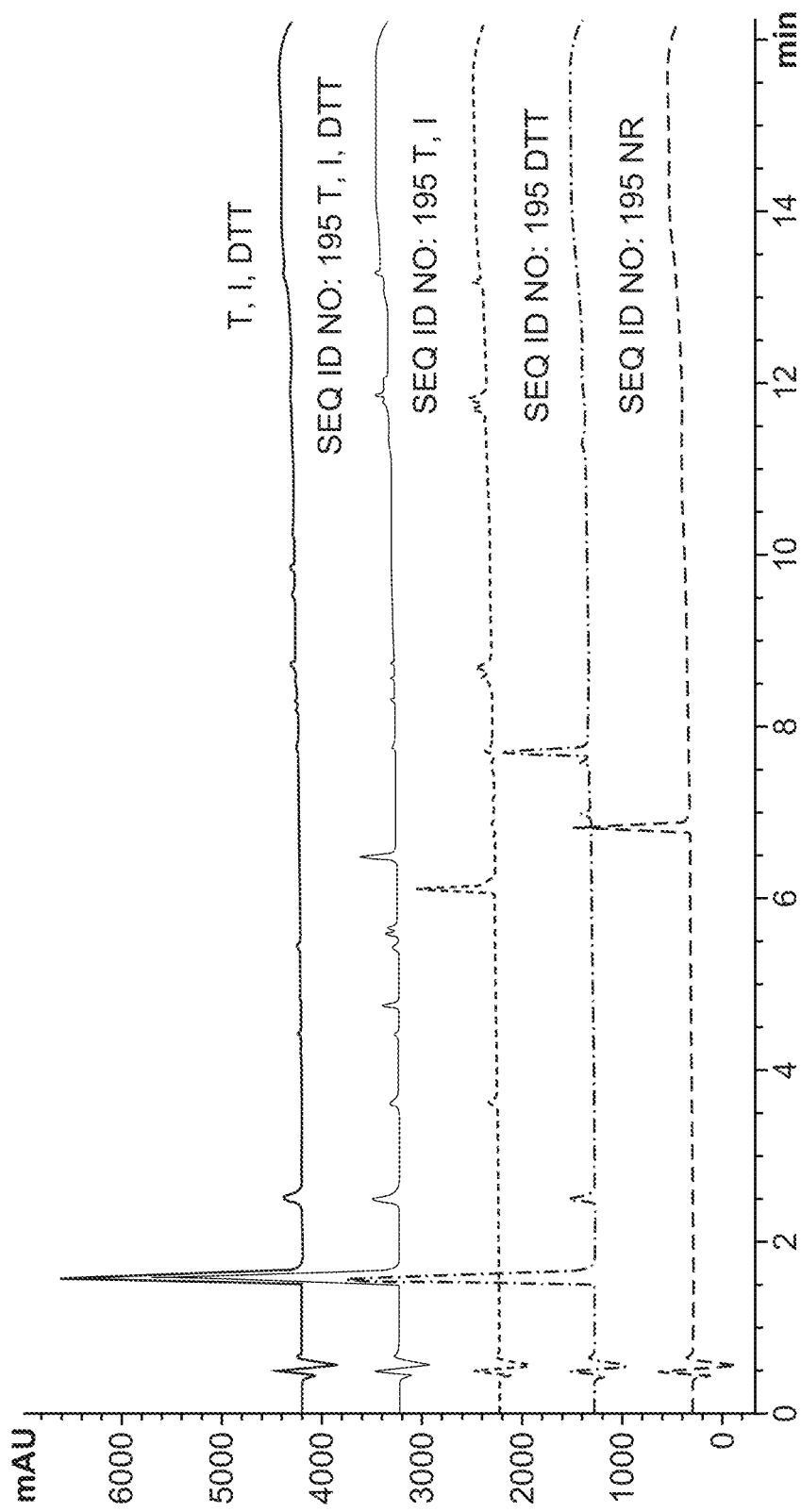
FIG. 61 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 195 suspended in various solutions including (T, I, DTT), (T,I), DTT, and non-reducing (NR) conditions.
Figure 62:
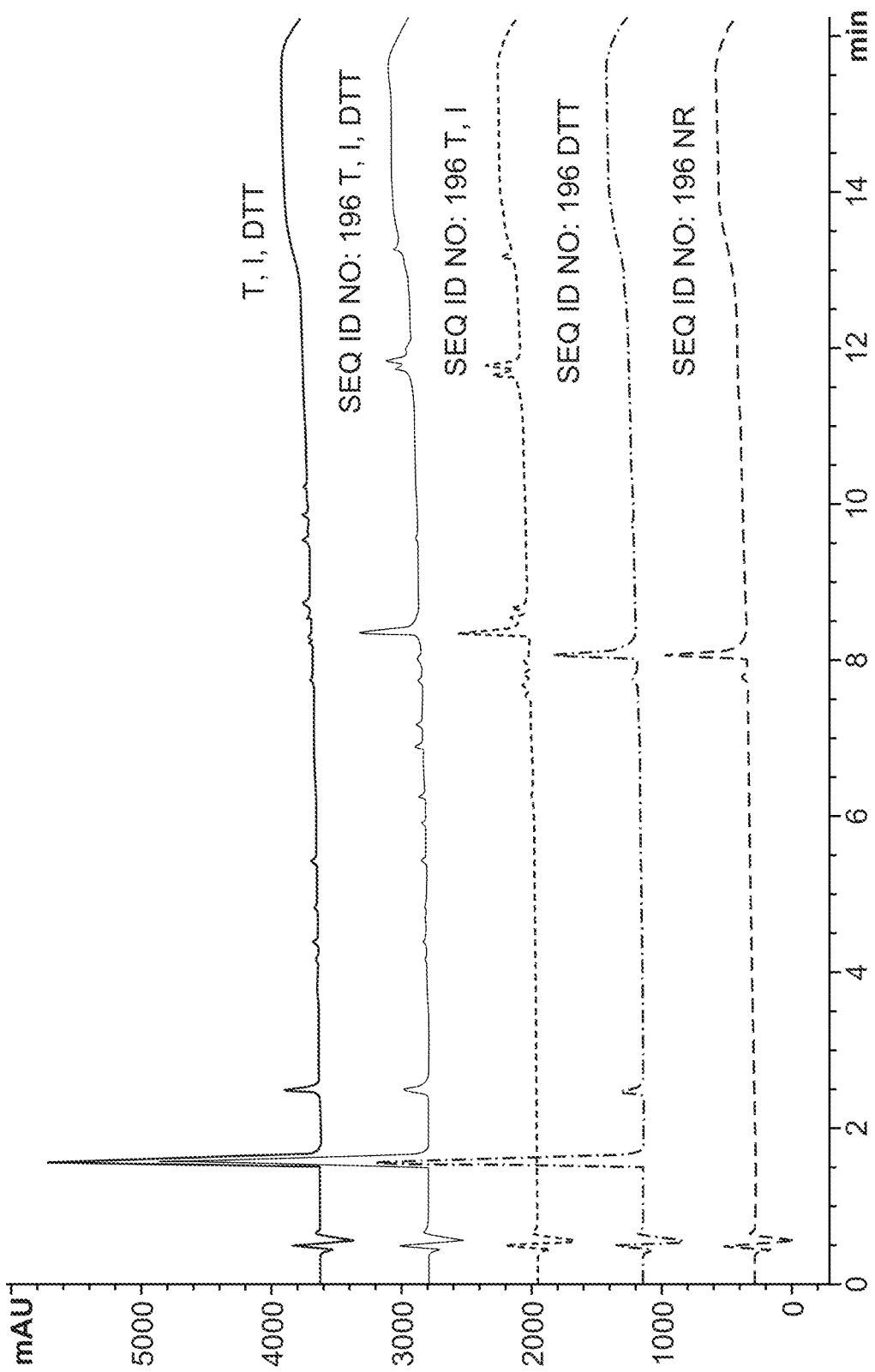
FIG. 62 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 196 suspended in various solutions including (T, I, DTT), (T,I), DTT, and non-reducing (NR) conditions.

FIG. 58 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 485 suspended in various solutions including (T, I, DTT), (T,I), DTT, and non-reducing (NR) conditions. FIG. 59 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 27 suspended in various solutions including (T, I, DTT), (T,I), DTT, and non-reducing (NR) conditions. FIG. 60 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 205 suspended in various solutions including (T, I, DTT), (T,I), DTT, and non-reducing (NR) conditions. FIG. 61 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 195 suspended in various solutions including (T, I, DTT), (T,I), DTT, and non-reducing (NR) conditions. FIG. 62 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 196 suspended in various solutions including (T, I, DTT), (T,I), DTT, and non-reducing (NR) conditions.

Figure 63:
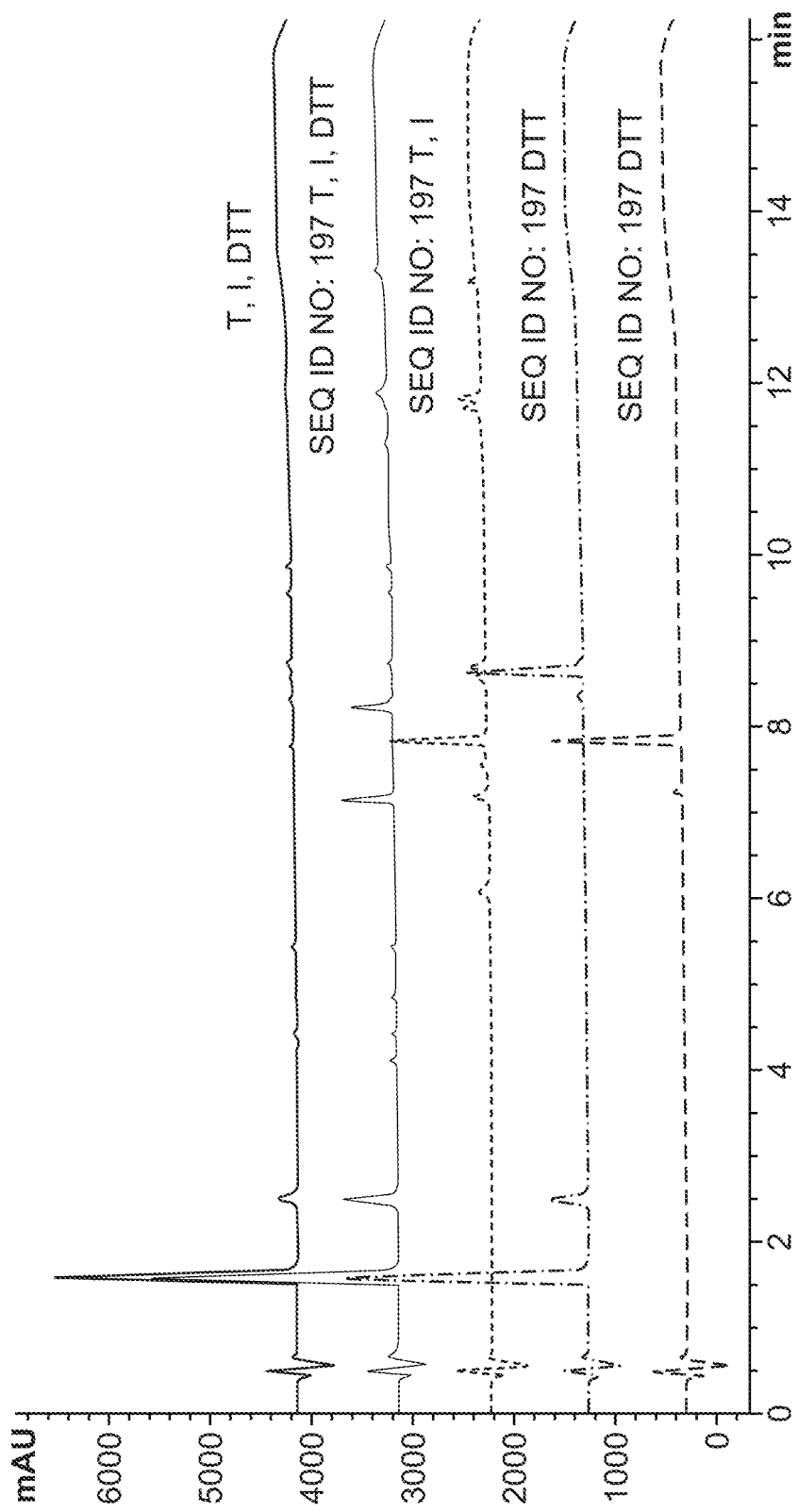
FIG. 63 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 197 suspended in various solutions including (T, I, DTT), (T,I), DTT, and non-reducing (NR) conditions.
Figure 64:
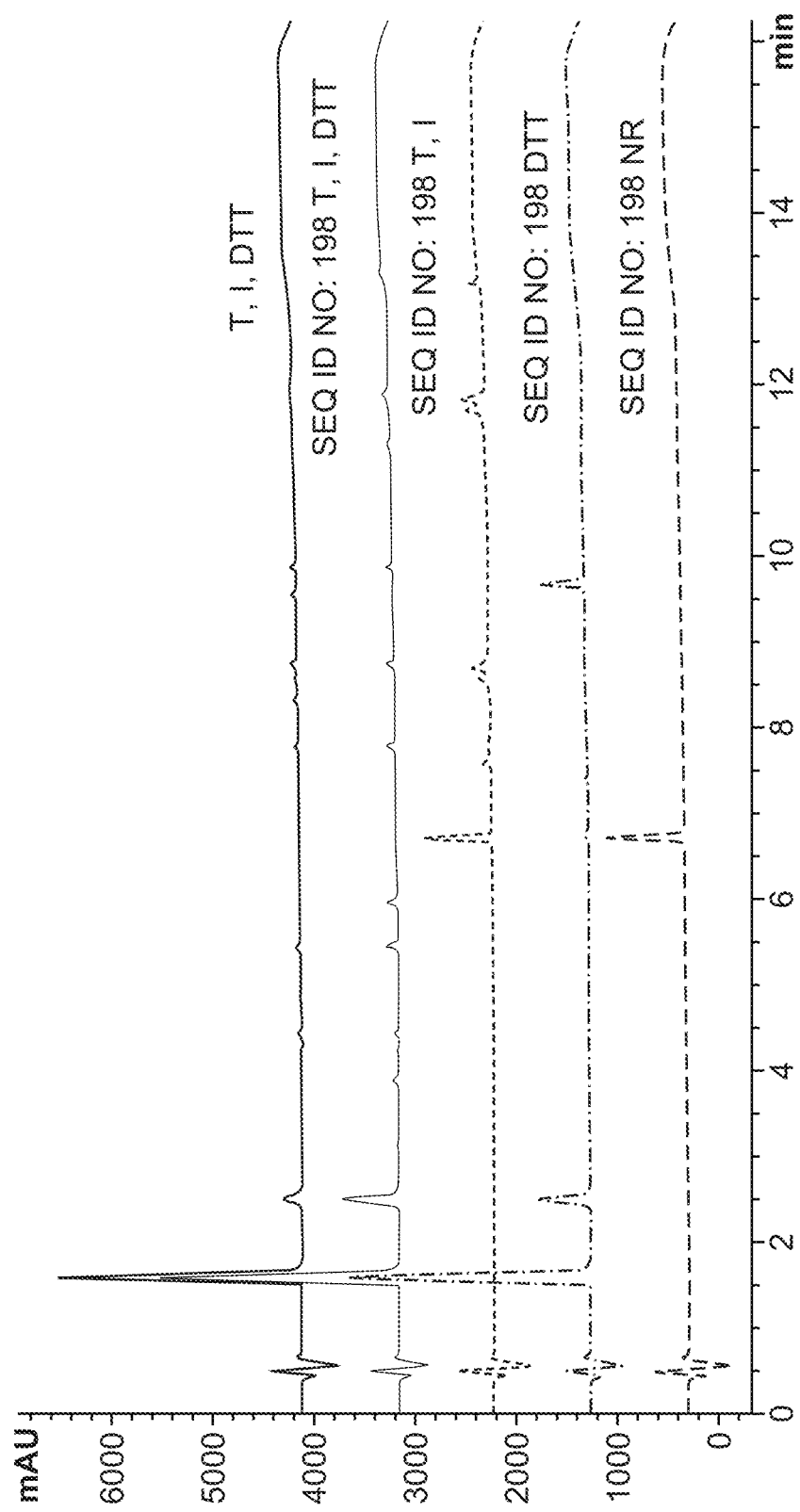
FIG. 64 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 198 suspended in various solutions including (T, I, DTT), (T,I), DTT, and non-reducing (NR) conditions.
Figure 65:
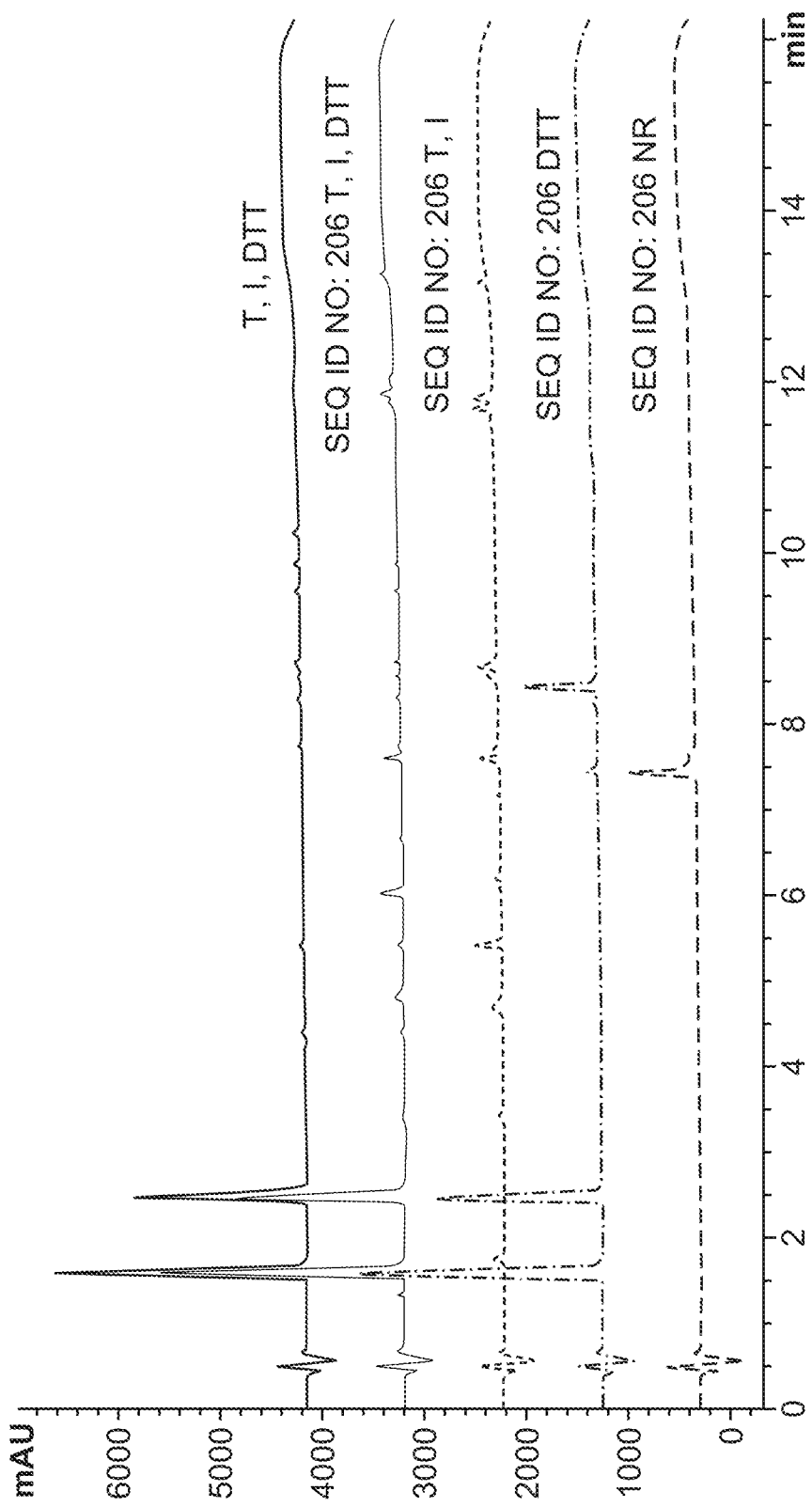
FIG. 65 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 206 suspended in various solutions including (T, I, DTT), (T,I), DTT, and non-reducing (NR) conditions.
Figure 66:
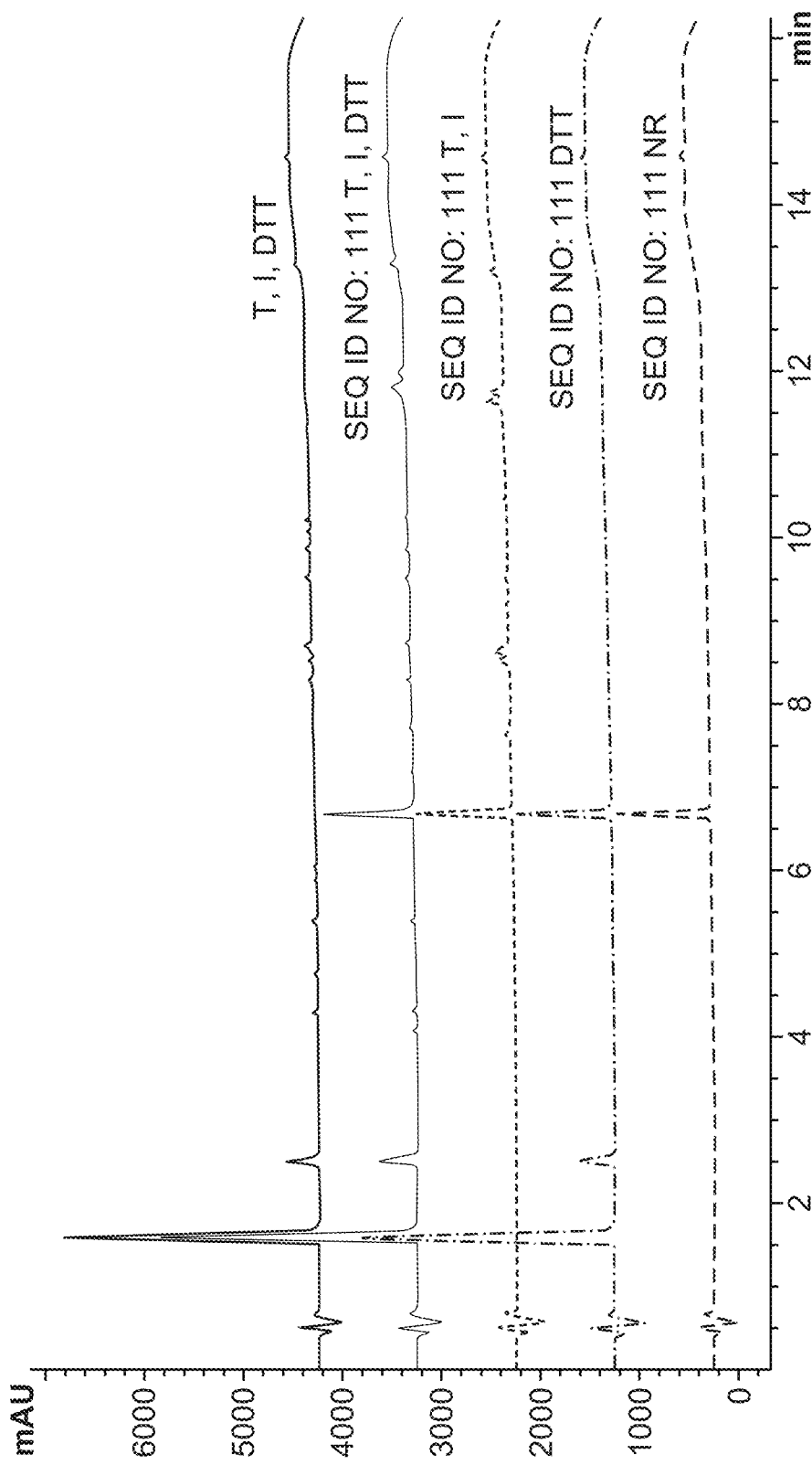
FIG. 66 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 111 suspended in various solutions including (T, I, DTT), (T,I), DTT, and non-reducing (NR) conditions.
Figure 67A:
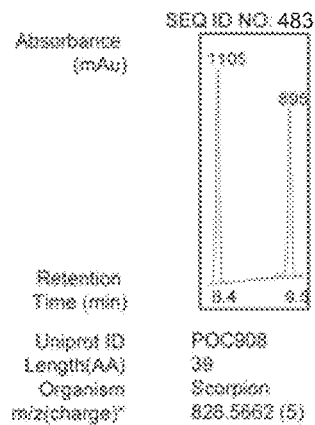
FIG. 67A shows the HPLC chromatogram and mass spectrometry results of a peptide of SEQ ID NO: 483. The peak near 9.5 minutes is the peptide under non-reducing conditions and the peak near 8.4 minutes shows reduced peptide.
Figure 67B:
FIG. 67B shows the HPLC chromatogram and mass spectrometry results of a peptide of SEQ ID NO: 22. The peak near 6.4 minutes is the peptide under non-reducing conditions and the peak near 5.4 minutes shows reduced peptide.
Figure 67C:
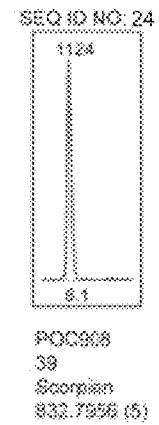
FIG. 67C shows the HPLC chromatogram and mass spectrometry results of a peptide of SEQ ID NO: 24. Peaks showing the peptide under non-reducing conditions and reducing conditions are overlapping.
Figure 67D:
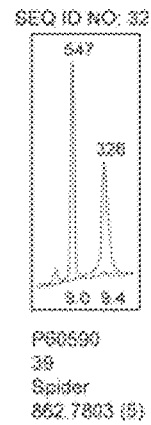
FIG. 67D shows the HPLC chromatogram and mass spectrometry results of a peptide of SEQ ID NO: 32. The peak near 9.4 minutes is the peptide under non-reducing conditions and the peak near 9.0 minutes shows reduced peptide.
Figure 67E:
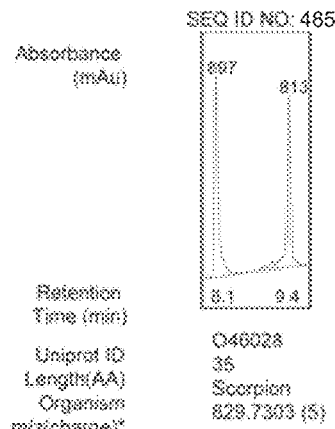
FIG. 67E shows the HPLC chromatogram and mass spectrometry results of a peptide of SEQ ID NO: 485. The peak near 9.4 minutes is the peptide under non-reducing conditions and the peak near 8.1 minutes shows reduced peptide.
Figure 67F:
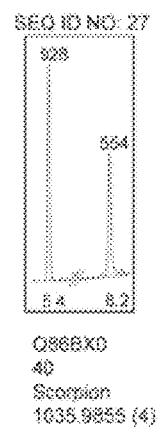
FIG. 67F shows the HPLC chromatogram and mass spectrometry results of a peptide of SEQ ID NO: 27. The peak near 8.2 minutes is the peptide under non-reducing conditions and the peak near 5.4 minutes shows reduced peptide.
Figure 67G:
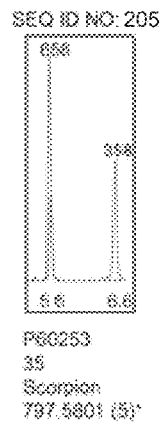
FIG. 67G shows the HPLC chromatogram and mass spectrometry results of a peptide of SEQ ID NO: 205. The peak near 6.6 minutes is the peptide under non-reducing conditions and the peak near 5.6 minutes shows reduced peptide.
Figure 67H:
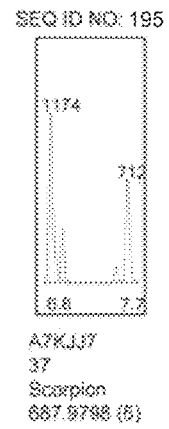
FIG. 67H shows the HPLC chromatogram and mass spectrometry results of a peptide of SEQ ID NO: 195. The peak near 9.5 minutes is the peptide under non-reducing conditions and the peak near 8.4 minutes shows reduced peptide.
Figure 67I:
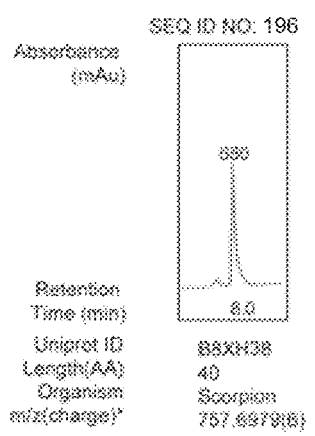
FIG. 67I shows the HPLC chromatogram and mass spectrometry results of a peptide of SEQ ID NO: 196. Peaks showing the peptide under non-reducing conditions and reducing conditions are overlapping.
Figure 67J:
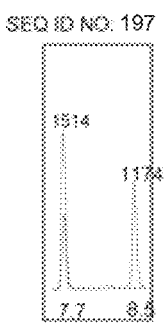
FIG. 67J shows the HPLC chromatogram and mass spectrometry results of a peptide of SEQ ID NO: 197. The peak near 8.5 minutes is the peptide under non-reducing conditions and the peak near 7.7 minutes shows reduced peptide.
Figure 67K:
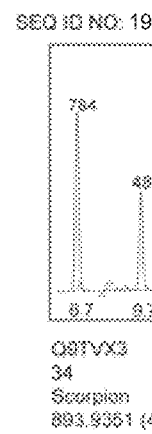
FIG. 67K shows the HPLC chromatogram and mass spectrometry results of a peptide of SEQ ID NO: 198. The peak near 9.7 minutes is the peptide under non-reducing conditions and the peak near 6.7 minutes shows reduced peptide.
Figure 67L:
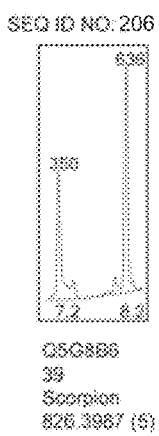
FIG. 67L shows the HPLC chromatogram and mass spectrometry results of a peptide of SEQ ID NO: 206. The peak near 8.2 minutes is the peptide under non-reducing conditions and the peak near 7.2 minutes shows reduced peptide.
Figure 67M:
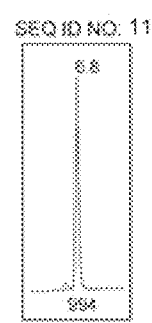
FIG. 67M shows the HPLC chromatogram of a peptide of SEQ ID NO: 111. Peaks showing the peptide under non-reducing conditions and reducing conditions are fully overlapping.

FIG. 63 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 197 suspended in various solutions including (T, I, DTT), (T,I), DTT, and non-reducing (NR) conditions. FIG. 64 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 198 suspended in various solutions including (T, I, DTT), (T,I), DTT, and non-reducing (NR) conditions. FIG. 65 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 206 suspended in various solutions including (T, I, DTT), (T,I), DTT, and non-reducing (NR) conditions. FIG. 66 shows an HPLC chromatogram of 5 µg trypsin in 25 mM Tris, 5 µg soybean trypsin inhibitor and 10 mM DTT (T, I, DTT) as well as HPLC chromatograms of 12.5 µg of a peptide of SEQ ID NO: 111 suspended in various solutions including (T, I, DTT), (T,I), DTT, and non-reducing (NR) conditions.

Example 41

Peptide Resistance to Reducing Agents

This example shows of peptide resistance to reducing agents. Several peptides were suspended in 500 µl of ddH$_2$O to a stock concentration of 2 mg/ml. Reactions were prepared by adding 12.5 µg peptide from the stock solution to a 10 mM solution of DTT in PBS and allowed to incubate at room temperature for 30 minutes. RP-HPLC was run on samples using an Agilent 1260 HPLC equipped with a C-18 Poroshell 120B column. Samples were analyzed by a gradient method with a mobile phase of Solvent A (water with 0.1% TFA) and Solvent B (acetonitrile with 0.1% TFA). Solvent B was ramped up from 5%-45% of the mobile phase over a period of 10 minutes.

FIG. 67 shows the HPLC chromatograms of various peptides and the mass spectrometry results of various peptides after direct-infusion electrospray mass spectrometry (ES-MS) on a Thermo Orbi Classic® mass spectrometer. Peptides were fractionated by HPLC and without any further sample prep, 5 µl of the sample was injected into the mass spectrometer at 1 mg/ml using a CTCPAL® autosampler. Alternatively, if peptides were provided as a lyophilized powder, the sample was dissolved in 100% water to a concentration of 1 mg/ml a Millipore Ziptip C18® column was used to desalt the peptides prior to injection for ES-MS. The mass spectrometer was calibrated using 5 pmol of mixture of five standard peptides to achieve a high accuracy of mass determination with less than a 10 ppm error. Confirmation of peptide disulfide bond formation was achieved by analyzing the m/z isotopic distribution and the exact charge. All peptides tested are shown under reducing and non-reducing conditions. Traces for peptides after DTT reduction that show some or all of the peptide eluting at the same retention time as under non-reducing conditions indicated that the peptide was resistant to reduction by DTT. FIG. 67A shows the HPLC chromatogram and mass spectrometry results of a peptide of SEQ ID NO: 483. The peak near 9.5 minutes is the peptide under non-reducing conditions and the peak near 8.4 minutes shows reduced peptide. FIG. 67B shows the HPLC chromatogram and mass spectrometry results of a peptide of SEQ ID NO: 22. The peak near 6.4 minutes is the peptide under non-reducing conditions and the peak near 5.4 minutes shows reduced peptide. FIG. 67C shows the HPLC chromatogram and mass spectrometry results of a peptide of SEQ ID NO: 24. Peaks showing the peptide under non-reducing conditions and reducing conditions are overlapping. FIG. 67D shows the HPLC chromatogram and mass spectrometry results of a peptide of SEQ ID NO: 32. The peak near 9.4 minutes is the peptide under non-reducing conditions and the peak near 9.0 minutes shows reduced peptide. FIG. 67E shows the HPLC chromatogram and mass spectrometry results of a peptide of SEQ ID NO: 485. The peak near 9.4 minutes is the peptide under non-reducing conditions and the peak near 8.1 minutes shows reduced peptide. FIG. 67F shows the HPLC chromatogram and mass spectrometry results of a peptide of SEQ ID NO: 27. The peak near 8.2 minutes is the peptide under non-reducing conditions and the peak near 5.4 minutes shows reduced peptide. FIG. 67G shows the HPLC chromatogram and mass spectrometry results of a peptide of SEQ ID NO: 205. The peak near 6.6 minutes is the peptide under non-reducing conditions and the peak near 5.6 minutes shows reduced peptide. FIG. 67H shows the HPLC chromatogram and mass spectrometry results of a peptide of SEQ ID NO: 195. The peak near 9.5 minutes is the peptide under non-reducing conditions and the peak near 8.4 minutes shows reduced peptide. FIG. 67I shows the HPLC chromatogram and mass spectrometry results of a peptide of SEQ ID NO: 196. Peaks showing the peptide under non-reducing conditions and reducing conditions are overlapping. FIG. 67J shows the HPLC chromatogram and mass spectrometry results of a peptide of SEQ ID NO: 197. The peak near 8.5 minutes is the peptide under non-reducing conditions and the peak near 7.7 minutes shows reduced peptide. FIG. 67K shows the HPLC chromatogram and mass spectrometry results of a peptide of SEQ ID NO: 198. The peak near 9.7 minutes is the peptide under non-reducing conditions and the peak near 6.7 minutes shows reduced peptide. FIG. 67L shows the HPLC chromatogram and mass spectrometry results of a peptide of SEQ ID NO: 206. The peak near 8.2 minutes is the peptide under non-reducing conditions and the peak near 7.2 minutes shows reduced peptide. FIG. 67M shows the HPLC chromatogram and mass spectrometry results of a peptide of SEQ ID NO: 111. Peaks showing the peptide under non-reducing conditions and reducing conditions are fully overlapping.

Example 42

Intravenous and Oral Administration of Peptides

This example describes intravenous and oral administration of peptides of this disclosure, including transit of the intact peptide through the GI tract and to the feces after oral administration. A radiolabeled peptide of SEQ ID NO: 24 was administered intravenously or orally to female Harlan athymic nude mice, 6-8 weeks of age. Radiolabeled peptides of SEQ ID NO: 24 was administered intravenously (IV) at a dose of 4.8 µCi/20 nmol. Radiolabeled peptide of SEQ ID NO: 24 was administered orally (PO) at a dose of 24 µCi/100 nmol. Mice were euthanized at various time points by $CO_2$ asphyxiation and biological fluids were collected, including blood, urine, and feces. Urine was collected be abdominal palpitation immediately before $CO_2$ asphyxiation. Blood was collected by cardiac puncture immediately after $CO_2$ asphyxiation and centrifuged to separate plasma. Feces was collected either before or after $CO_2$ asphyxiation by palpitation of the colon. Samples were analyzed by HPLC to quantify the concentration or dose of intact peptide recovered in plasma, urine, and feces. For HPLC analysis, urine samples were first diluted at a 1:20 ratio in water and plasma samples were diluted at a 1:5 ratio in water. Feces samples were dissolved in Tris buffer, centrifuged to remove the insoluble fraction, and supernatants were diluted at a 1:1 ratio in water.

TABLE 11 shows a summary of the study design.

TABLE 11

| Group | SEQ ID NO | Route | Peptide Dose | 14 C Dose | Time Points (hr) | Mice/time |
|---|---|---|---|---|---|---|
| 1 | 24 | IV | 20 nmol | 4.8 µCi | 0.08, 0.5, 1, 3, 8, 24, 48 | 3 |
| 2 | 24 | Oral | 100 nmol | 24 µCi | 0.08, 0.5, 1, 3, 8, 24, 48 | 3 |

FIG. 68 shows the concentration of a radiolabeled peptide of SEQ ID NO: 24 in plasma after administration to a mouse. FIG. 68A shows the concentration of peptide in plasma after intravenous (IV) administration of 20 nmol of a radiolabeled peptide of SEQ ID NO: 24 and oral (PO) administration of 100 nmol the radiolabeled peptide of SEQ ID NO: 24, as quantified by measuring the $^{14}C$ signal using liquid scintillation counting. The delivered dose of $^{14}C$ was 4.8 for intravenous administration and 24 µCi for oral administration. Time points examined included 0.08, 0.5, 1, 3, 8, 24, 48 hours and three mice were examined per time point. FIG. 68B shows the percent of administered peptide dose recovered in plasma after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 for intravenous administration and 24 µCi for oral administration. Time points examined included 0.08, 0.5, 1, 3, 8, 24, 48 hours and three mice were examined per time point. FIG. 68C shows the intensity of peptide and peptide fragment peaks in plasma as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 0.5, 1, and 3 hours. These data show detection of radioactive signal from the dosed peptide up to at least 50 hours in plasma, with plasma concentrations up to 10% of the dose by IV administration and plasma concentrations up to 1% of the dose by PO administration. The intact peptide was eluted near 6 minutes, whereas cleaved fragments—such as the N-terminal Gly residue—were eluted near 1 minute. Thus, nearly some of all of the radioactivity detected in plasma was due to fragments of the administered peptide.

FIG. 69 shows the concentration of a radiolabeled peptide of SEQ ID NO: 24 in urine after administration of the peptide to a mouse. FIG. 69A shows the concentration of peptide in urine after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 µCi for intravenous administration and 24 µCi for oral administration. Time points examined included 0.08, 0.5, 1, 3, 8, 24, 48 hours and three mice were examined per time point. FIG. 69B shows the intensity of peptide and peptide fragment peaks in urine as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 0.5, 1, 3, 8, 24, and 48 hours.

FIG. 70 shows the concentration of a radiolabeled peptide of SEQ ID NO: 24 in feces after administration of the peptide to a mouse. FIG. 70A shows the concentration of peptide in feces after intravenous (IV) administration of 20 nmol of a radiolabeled peptide of SEQ ID NO: 24 and oral (PO) administration of 100 nmol of a radiolabeled peptide of SEQ ID NO: 24, as quantified by measuring the $^{14}C$ signal using liquid scintillation counting. The delivered dose of $^{14}C$ was 4.8 µCi for intravenous administration and 24 µCi for oral administration. Time points examined included 0.08, 0.5, 1, 3, 8, 24, 48 hours and three mice were examined per time point. FIG. 70B shows the intensity of peptide and peptide fragment peaks in feces as measured by tandem HPLC and liquid scintillation counting after oral administration by gavage of 100 nmol of a radiolabeled peptide of SEQ ID NO: 24. The delivered dose of $^{14}C$ was 24 µCi for oral administration. Time points examined included 3 and 8 hours. These data showed that intact peptide of SEQ ID NO: 24 was detected in feces after oral dosing, indicating that some intact peptide transited through the GI tract.

Example 43

Sequence Alignment to pFam00451:Toxin_2 Family to Identify Cartilage Homing Peptides This example describes a method for identifying new cartilage homing peptides by sequence alignment to the pFam00451:toxin_2 structural class family. The pFam00451:toxin_2 structural class is a family of peptides related by similarities in sequence identity. FIG. 73 illustrates alignment of peptides within the pfam00451:toxin_2 structural class family of SEQ ID NO: 436-SEQ ID NO: 482. Boxed and bolded residues indicate relative conservation of sequence while non-boxed and non-bolded residues indicate areas of higher sequence variability. SEQ ID NO: 436 was identified as a cartilage homing candidate peptide based on its structural similarities with the pFam00451:toxin structural class family. FIG. 74 illustrates the sequence alignment of a peptide of SEQ ID NO: 436 from the pfam00451:toxin_2 structural class family with the sequence of SEQ ID NO: 24. Asterisks indicate positions with a single, fully conserved residue, a colon indicates conservation between groups of strongly similar properties (scoring >0.5 in the Gonnet point accepted mutation (PAM) 250 matrix), and a period indicates conservation between groups of weakly similar properties (scoring ≤0.5 in the Gonnet PAM 250 matrix). SEQ ID NO: 111 was also identified as a cartilage homing candidate based on its structural similarities with the pfam00451:toxin_2 structural class family of peptides.

The pFam00451:toxin_2 structural class family is used as a scaffold to identify variant peptides that have cartilage homing properties. Any member of the pFam00451:toxin_2 structural class family is used to predict new cartilage homing peptides based on homology, preserved residues, or a preserved cysteine residue.

Example 44

Temperature Stable Peptides

This example illustrates peptide stability at high temperatures. Peptides were first suspended in 500 µl of ddH$_2$O to a stock concentration of 2 mg/ml. Reactions were prepared by adding 6.25 µl of peptide from the stock solution with 95 µl ddH$_2$O and incubated at room temperature, 70° C., or 100° C. for one hour in a Thermocycler. RP-HPLC was then run on samples using an Agilent 1260 HPLC equipped with a C-18 Poroshell 120B column. Sample were analyzed by a gradient method with a mobile phase of Solvent A (water with 0.1% TFA) and Solvent B (acetonitrile with 0.1% TFA). Solvent B was ramped up from 5%-45% of the mobile phase over a period of 10 minutes.

Peptides of SEQ ID NO: 28 and SEQ ID NO: 483 were analyzed by HPLC after incubation at room temperature (25° C.), 70° C., or 100° C. for one hour. After incubation at 70° C. for 1 hour, peptides of SEQ ID NO: 483 and SEQ ID NO: 28 showed approximately the same HPLC elution time and peak height as the samples incubated at room temperature, indicating the peptides were resistant to heat-induced degradation. After incubation at 100° C. for 1 hour, peptides of SEQ ID NO: 483 and SEQ ID NO: 28 underwent various degrees of degradation as evidenced by the reduced amount of peptide eluting at the original elution time.

While preferred embodiments of the present disclosure have been shown and described herein, it will be apparent to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all embodiments of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

What is claimed:

1. A knotted peptide comprising a sequence having at least 90% sequence identity to SEQ ID NO: 325.

2. The knotted peptide of claim 1, wherein the knotted peptide comprises 4 or more cysteine residues and a plurality of disulfide bridges formed between cysteine residues.

3. The knotted peptide of claim 1, wherein the knotted peptide homes, targets, migrates to, accumulates in, binds to, is retained by, or is directed to a cartilage.

4. The knotted peptide of claim 1, wherein the knotted peptide comprises the sequence of SEQ ID NO: 325.

5. The knotted peptide of claim 1, wherein the knotted peptide is linked to an active agent.

6. The knotted peptide of claim 5, wherein the active agent comprises a therapeutic agent, a detectable agent, or a combination thereof.

7. The knotted peptide of claim 6, wherein the therapeutic agent comprises a therapeutic small molecule.

8. The knotted peptide of claim 6, wherein the therapeutic agent comprises an antibiotic, an anti-viral agent, an anti-fungal agent, an anti-inflammatory agent, a protease inhibitor, an immune modulator, an anti-cytokine agent, a tyrosine kinase inhibitor, a growth factor, a cytotoxic T-lymphocyte-associated protein 4 (CTLA4) inhibitor, a B-cell lymphoma 2 (BCL-2) family inhibitor, a tumor necrosis factor alpha (TNF-α) modulator, a tumor necrosis factor receptor (TNFR) family modulator, or any combination thereof.

9. The knotted peptide of claim 8, wherein the anti-inflammatory agent comprises a steroid or a nonsteroidal anti-inflammatory drug (NSAID).

10. The knotted peptide of claim 9, wherein the steroid is a corticosteroid or a glucocorticoid.

11. The knotted peptide of claim 9, wherein the steroid is triamcinolone acetonide, dexamethasone, budesonide, triamcinolone, cortisone, prednisone, rednisolone, triamcinolone hexacetonide, or methylprednisolone.

12. The knotted peptide of claim 9, wherein the NSAID is ibuprofen, naproxen, ketorolac, indomethacin, etodolac, tolemetin, celecoxib, aceclofenac, nabumetone, sulindac, or diclofenac.

13. The knotted peptide of claim 8, wherein the protease inhibitor is a matrix metalloprotease 13 (MMP13) inhibitor.

14. The knotted peptide of claim 6, wherein the therapeutic agent comprises imatinib mesylate or methotrexate.

15. The knotted peptide of claim 6, wherein the therapeutic agent comprises a therapeutic peptide.

16. The knotted peptide of claim 15, wherein the therapeutic peptide is a cytokine, an enzyme, a growth factor, a chemokine, a neurotransmitter, an Fc region, or any combination thereof.

17. The knotted peptide of claim 6, wherein the therapeutic agent comprises an antibody or an antibody fragment.

18. The knotted peptide of claim 6, wherein the detectable agent comprises a fluorophore, a metal, a metal chelate, an X-ray contrast agent, a PET agent, a radioisotope, a photosensitizer, a radiosensitizer, a radionuclide chelator, or any combination thereof.

19. A pharmaceutical composition comprising the knotted peptide of claim 1 and a pharmaceutically acceptable carrier.

20. The pharmaceutical composition of claim 19, wherein the pharmaceutical composition is formulated for inhalation, intranasal administration, oral administration, intravenous administration, subcutaneous administration, intra-articular administration, intramuscular administration, intraperitoneal administration, administration locally into an affected area, administration into a joint, or any combination thereof.

* * * * *

UNITED STATES PATENT AND TRADEMARK OFFICE
CERTIFICATE OF CORRECTION

PATENT NO. : 11,648,290 B2
APPLICATION NO. : 17/353447
DATED : May 16, 2023
INVENTOR(S) : James Olson et al.

Page 1 of 1

It is certified that error appears in the above-identified patent and that said Letters Patent is hereby corrected as shown below:

In the Claims

Claim 8, Column 393, Line 39, replace "(TNF-a)" with --(TNF-α)--

Signed and Sealed this
Twenty-ninth Day of August, 2023

Katherine Kelly Vidal
*Director of the United States Patent and Trademark Office*